US005593993A

United States Patent [19]

Morin, Jr. et al.

[11] Patent Number: 5,593,993
[45] Date of Patent: Jan. 14, 1997

[54] METHOD FOR INHIBITION OF HIV RELATED VIRUSES

[75] Inventors: John M. Morin, Jr., Brownsburg; Robert J. Ternansky, Indianapolis, both of Ind.; Rolf Noreen; Tomas Lind, both of Huddinge, Sweden

[73] Assignee: Medivir AB, Huddinge, Sweden

[21] Appl. No.: 395,702

[22] Filed: Feb. 28, 1995

Related U.S. Application Data

[60] Division of Ser. No. 11,940, Feb. 1, 1993, abandoned, which is a continuation-in-part of Ser. No. 921,890, Jul. 29, 1992, abandoned, which is a continuation-in-part of Ser. No. 739,927, Aug. 2, 1991, abandoned.

[51] Int. Cl.⁶ .................................................. A61K 31/425
[52] U.S. Cl. .......................... 514/247; 514/255; 514/332; 514/358; 514/371
[58] Field of Search .................................. 514/371, 332, 514/352, 255, 247

[56] References Cited

U.S. PATENT DOCUMENTS

| Re. 31,244 | 5/1983 | Peterson . |
|---|---|---|
| 3,061,640 | 10/1962 | Beaver et al. . |
| 3,705,903 | 12/1972 | Crank . |
| 3,809,755 | 5/1974 | Crank . |
| 3,891,769 | 6/1975 | Shea et al. . |
| 3,950,537 | 4/1976 | DeBenneville et al. . |
| 3,950,538 | 4/1976 | Shea . |
| 4,036,979 | 7/1977 | Asato . |
| 4,048,333 | 9/1977 | Galabov et al. . |
| 4,057,636 | 11/1977 | Peterson . |
| 4,066,695 | 1/1978 | Cohen et al. . |
| 4,096,276 | 6/1978 | Cohen et al. . |
| 4,113,776 | 9/1978 | Cohen et al. . |
| 4,150,138 | 4/1979 | Cohen et al. . |
| 4,169,154 | 9/1979 | Cohen et al. . |
| 4,367,226 | 1/1983 | Foye . |
| 4,656,026 | 4/1987 | Coffmann et al. . |
| 4,880,836 | 11/1989 | Elbaum . |
| 4,994,481 | 2/1991 | Zimmer et al. . |

FOREIGN PATENT DOCUMENTS

| 684412 | 6/1964 | Canada . |
|---|---|---|
| 929257 | 7/1961 | European Pat. Off. . |
| 0002259 | 6/1979 | European Pat. Off. . |
| 196185 | 10/1986 | European Pat. Off. . |
| 0297661 | 6/1988 | European Pat. Off. . |
| 0340709 | 11/1989 | European Pat. Off. . |
| 384522 | 8/1990 | European Pat. Off. . |
| 0392802 | 10/1990 | European Pat. Off. . |
| 1471681 | 3/1967 | France . |
| 819436 | 2/1975 | France . |
| 2350340 | 12/1977 | France . |
| 1518688 | 12/1965 | Germany . |
| 2036193 | 7/1970 | Germany . |
| 2132431 | 6/1971 | Germany . |
| 2136233 | 7/1971 | Germany . |
| 2137046 | 7/1971 | Germany . |
| 2137045 | 7/1971 | Germany . |
| 2241471 | 8/1972 | Germany . |
| 2453082 | 11/1974 | Germany . |
| 123466 | 12/1975 | Germany . |
| 2557438 | 12/1975 | Germany . |
| 2716838 | 10/1977 | Germany . |
| 2833073 | 7/1978 | Germany . |
| 1293303 | 10/1972 | United Kingdom . |
| 1354830 | 5/1974 | United Kingdom . |
| 9303022 | 2/1993 | WIPO . |

OTHER PUBLICATIONS

Indian J. Chem., vol. 10, pp. 686–690 (Jul., 1972).
Arch. Pharm. (Weinheim), vol. 323, pp. 971–975 (1990).
Jour. Pharm. Sci., vol. 51, No. 11, pp. 1031–1033 (Nov., 1962).
Indian J. Chem., vol. 21B, pp. 750–752, (Aug., 1982).
Chemical Abstracts, vol. 81, No. 21, (Nov. 25, 1974) Abstract No. 135582j and Zh. Org. Khim., vol. 10, No. 8, pp. 1661–1669 (1974).
Chemical Abstracts, vol. 83, No. 7, (Aug. 18, 1975) Abstract No. 53854b and Yakagaku Zasshi, vol. 95, No. 4, pp. 373–377 (1975).
Chemical Abstracts, vol. 70, No. 17 (Apr. 28, 1969) Abstract No. 77857n and Yakugaku Zasshi, vol. 88, No. 11, pp. 1428–1432 (1968).
Chemical Abstracts, vol. 62, No. 9 (Apr. 26, 1965) Abstract No. 10425d and Atti Accad. Sci. Lettere Arti Palermo, Pt. I, vol. 23, pp. 139–142 (1964).
Chemical Abstracts, vol. 65 (1966) Abstract No. 2907F and Bruce, M. et al. Cytokinin activity of some substituted ureas and thioureas, pp. 249–265 (Dec. 29, 1965).
Boll. Chim. Farm., F. Russo, vol. 100, pp. 252–256 (1961).
Indian Jour. Chem., Nagarajan, K. et al., vol. 23B, pp. 342–362 (Apr. 1984).
Jour. Med. Chem., vol. 15, No. 10, pp. 1082–1084 (1972).
Indian Jour. Chem., vol. 5, No. 4, pp. 145–146 (Apr. 1967).
Jour. Indian Chem. Soc., vol. 35, No. 4, pp. 245–248 (1961).
Indian Jour. Pharm. Sci., vol. 44, No. 1, pp. 83–85 (1982).
Kammuller et al., Int'l Jour. of Immunopharmacology, 997–1010 (1988).
Lombardino et al., Jour. of Medicinal Chemistry, 7, No. 1, 97–101 (Jan. 1964).

(List continued on next page.)

*Primary Examiner*—Robert Gerstl
*Attorney, Agent, or Firm*—Birch, Stewart, Kolasch & Birch, LLP

[57] ABSTRACT

Treatment of AIDS, inhibition of the replication of HIV and related viruses thereof, and formulations using thiourea derivative compounds or salts thereof is disclosed. Also disclosed are novel thiourea derivative compounds.

9 Claims, No Drawings

OTHER PUBLICATIONS

Ghomeim et al., Egypt. J. Pharm. Sci. 28, No. 1–4, 77–86 (1987).
Fujiwara et al., J. Chem. Soc. Perkin Trans. 2, 1573–1577 (1980).
Fujiwara et al., J. Chem. Soc. Perkin Trans. 2, 659–663 (1979).
Chemical Abstracts, 94, No. 17, pp. 766, Abstract No. 139811z (Apr. 27, 1981).
Chemical Abstracts, 90, No. 7, p. 107, Abstract No. 49009g (Feb. 12, 1979).
Nowak, Roczniki Chimii, 47, No. 12, 2377–2378 (1973).
Rahman et al., Bangladesh J. Biol. Science, 5, No. 1, 28–30 (1976).
Marx et al., J. of Medicinal Chem., 13, No. 6, 1179–1181 (1970).
Mammo et al., J. of Pharmacy and Pharmacology, 34, No. 11, 752–754 (1982).
Chemical Abstracts, 110, No. 9, p. 653, Abstract No. 75501n (Feb. 27, 1989).
Horn et al., J. of Chromatography, No. 180, 111–118 (1979).
Pataki, Chimia, 18, No. 1, 23–34 (1964).
Waite, Analytical Biochemistry, 192, No. 2, 429–433 (1991).
Lilova et al., Biological Chemistry Hoppe–Seyler, 367, No. 10, 1055–1059 (1986).
Attia et al., Bull. De L'Academie Polonaise Des Sciences, 24, No. 10, 781–790 (1976).
Korohoda et al., Polish J. of Pharmacology and Pharmacy, 28, No. 5, 423–427 (1976).
Weygand et al., European J. of Biochem., 20, 72–80 (1971).
Burrell et al., Australian J. of Chem., 28, No. 10, 2289–2298 (1975).
Mahachi et al., J. of Chromatography, No. 298, 279–288 (1984).
Miyano et al., Biomedical Chromatography, 2, No. 4, 139–144 (1987).
Chemical Abstracts, 60, No. 11, p. 1964, Abstract No. 13546f (May 25, 1964).
Knoppova et al., Collection of Czech. Chemical Comm., 39, No. 3, 773–778 (1974).
Epp, Analytical Chemistry, 29, No. 9, 1283–1287 (Aug. 23, 1957).
Solyom et al., Acta Chimica Academiae Scientarum Hungaricae, 68, No. 1–2, 93–132 (1971).
Chemical Abstracts, 76, No. 23, p. 46, Abstract No. 135847w (Jun. 5, 1972).
Chemical Abstracts, 111, No. 25, p. 854, Abstract No. 233511t (Dec. 18, 1989).
Chemical Abstracts, 112, No. 7, p. 14, Abstract No. 48249w (Feb. 12, 1990).
Chemical Abstracts, 95, No. 19, p. 731, Abstract No. 16907v (Nov. 9, 1981).
Martin et al., Archiv Der Pharmazie, 296, No. 10, 641–650 (Oct. 1963).
Birr et al., Angew. Chemie, 82, No. 18, 771–772 (1970).
Morikawa et al., Agricultural and Biological Chemistry, 55, No. 11, 2751–2756 (Nov. 1991).
A. Mohsen et al., J. Pharm. Sciences, vol. 73, No. 8 (1984) pp. 1166–1168.
Ware, E., Chem. Rev., 46, 436 (1950).
Central Patents Index Country Alerting Bulletin, Section B, 1979, Week B11, 27 Apr. 79, J5 4016–467.
H. Wilitzer et al., Pharmazie 33, H.1 (1978), pp. 30–38.
Chemical Abstracts, vol. 89, 1878, p. 644 (24221m).
Chemical Abstracts, vol. 94, 1981, p. 160 (26081t).
Chemical Abstracts, vol. 96, 1982, p. 52221 (52221Z).
Synthesis, May 1983, No. 5, pp. 391–392.

METHOD FOR INHIBITION OF HIV RELATED VIRUSES

This application is a divisional of application Ser. No. 08/011,940, filed on Feb. 1, 1993, abandoned, the entire contents of which are hereby incorporated by reference which is a continuation-in-part of application Ser. No. 07/921,890 filed Jul. 29, 1992, abandoned, which is a continuation-in-part of application Ser. No. 07/739,927, filed on Aug. 2, 1991, now abandoned.

FIELD OF THE INVENTION

The present invention relates to compounds and pharmaceutically acceptable salts thereof and processes for treating infections by HIV and related viruses and/or the treatment of Acquired Immune Deficiency Syndrome (AIDS). This invention also relates to pharmaceutical compositions containing the compounds and the method of use of the present compounds alone or in combination with other agents, for the treatment and inhibition of AIDS and viral infection from HIV.

BACKGROUND OF THE INVENTION

A retrovirus designated Human Immunodeficiency Virus (HIV) is believed to be the causative agent of the complex disease termed Acquired Immune Deficiency Syndrome (AIDS) and is a member of the lentivirus family of retroviruses (M. A. Gonda, F. Wong-Staal NR. C. Gallo, "Sequence Homology and Morphological Similarity of HTLV III and Visna Virus, A Pathogenic Lentivirus", *Science*, 227, 173, (1985); and P. Sonigo and N. Alizon, et al., "Nucleotide Sequence of the Visna Lentivirus: Relationship to the AIDS Virus", *Cell*, 42, 369, (1985)). The HIV virus (also referred to as the AIDS virus) was previously known as or referred to as LAV, HTLV-III, or ARV, and is now designated by HIV-1. Other closely related variants of HIV-1 include HIV-2 and SIV (simian immunodeficiency virus), and mutants thereof.

The complex disease AIDS includes progressive destruction of the immune system and degeneration of the central and peripheral nervous system. The HIV virus appears to preferentially attack helper T-cells (T-lymphocytes or OKT4-bearing T-cells) and also ocher human cells, e.g., certain cells within the brain. The helper T-cells are invaded by the virus and the T-cell becomes an HIV virus producer. The helper T-cells are quickly destroyed and their number in the human being is depleted to such an extent that the body's B-cells as well as other T-cells normally stimulated by helper T-cells no longer function normally or produce sufficient lymphokines and antibodies to destroy the invading virus or other invading microbes.

While the HIV virus does not necessarily cause death per se, it does cause the human's immune system to be so severely depressed that the human falls prey to various other diseases such as herpes, *Pneumocistis carinii*, toxoplasmosis, cytomegalovirus, Kaposi's sarcoma, and Epstein-Barr virus related lymphonmas among others. These secondary infections are separately treated using other medications as is conventional. Early during infection, humans with HIV virus seem to live on with little or no symptoms, but have persistent infections. Later in the disease, humans suffer mild immune system depression with various symptoms such as weight loss, malaise, fever, and swollen lymph nodes. These syndromes have been called persistent generalized lymphadenopathy syndrome (PGL) and AIDS related complex (ARC) and develop into AIDS.

In all cases, those infected with the AIDS virus are believed to be persistently infective to others. Further, AIDS and AIDS related complex is after some time fatal.

A description of the mechanism by which the virus infects its host is given in an article by R. Yarchoan, and S. Broder, "Development of Antiretroviral Therapy for the Acquired Immunodeficiency Syndrome and Related Disorders", *New England Journal of Medicine*, 316, 557–564 (Feb. 26, 1987).

Considerable efforts are being directed toward the control of HIV by means of inhibition of the reverse transcriptase of HIV, required for replication of the virus. (V. Merluzzi et al., "Inhibition of the HIV-1 Replication by a Nonnucleoside Reverse Transcriptase Inhibitor", *Science*, 25, 1411 (1990)). For example, a currently used therapeutic compound, AZT, is an inhibitor of the viral reverse transcriptase (U.S. Pat. No. 4,724,232). Unfortunately, many of the known compounds suffer from toxicity problems, lack of bioavailability or are short lived in vivo, viral resistance, or combinations thereof.

Therefore it is an object of the invention to provide compounds and pharmaceutically acceptable salts thereof to inhibit and/or treat HIV and AIDS.

Another object of the present invention is to provide therapeutic formulations that are of value in the inhibition and/or treatment of infection by HIV and the treatment or inhibition of the acquired immune deficiency syndrome.

Another object is to provide methods for the inhibition and/or treatment of infection by HIV and the resulting acquired immune deficiency syndrome.

Other objects, features, and advantages will become apparent to those skilled in the art from the following description and claims.

DESCRIPTION OF THE INVENTION

The present invention provides compounds useful for the inhibition and/or treatment of HIV and AIDS, either as compounds, pharmaceutically acceptable salts, pharmaceutical composition ingredients, whether or not in combination with other anti-virals, immunomodulators, antibiotics, or vaccines. Methods of treating or inhibiting AIDS, methods of inhibiting replication of HIV, and methods of treating or inhibiting HIV in humans are also disclosed.

The compounds used in the methods of the present invention are those of the formula (IA) below

in which $R_1$ is a stable saturated or unsaturated, substituted or unsubstituted, 3 to 8 membered organic monocyclic ring having 0 to 4 hetero atoms selected from S, O, and N; or $R_1$ is a stable, saturated or unsaturated, substituted or unsubstituted, 7 to 10 membered organic bicyclic ring having 0 to 5 hetero atoms selected from S, O, and N;

$R_2$ is a group of the formula

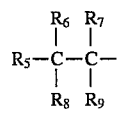

wherein R₅ is R₁ as defined above; or R₅ is a group of the formula

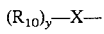

wherein y is 1 or 2; X is N, S, O and R₁₀ is R₁ as defined; or R₁₀ is hydrogen, C₁–C₆ alkyl, C₂–C₆ alkenyl, or C₂–C₆ alkynyl; or R₅ is hydrogen, halo, cyano, carboxy, amino, thio, hydroxy, C₁–C₄ alkoxy, C₁–C₆ alkyl, C₂–C₈ alkenyl, C₂–C₈ alkynyl, or C₂–C₈ alkenoxy;

R₆, R₇, R₈, and R₉ are independently C₃₋₈ cycloalkyl, hydrogen, C₁–C₆ alkyl, C₂–C₆ alkenyl, C₂–C₆ alkynyl, halo, amino, nitro, cyano, C₁–C₅ alkoxy, hydroxy, carboxy, hydroxymethyl, aminomethyl, carboxymethyl, C₁–C₄ alkylthio, C₁–C₄ alkanoyloxy, carbamoyl, or a halo substituted C₁–C₆ alkyl; or two of which, along with the carbons to which they are attached, combine to form a stable, saturated or unsaturated, substituted or unsubstituted, 3 to 7 membered organic monocylic ring having 0 to 4 hetero atoms selected from S, O, or N; or R₆ and R₈, or R₇ and R₉, along with the carbon to which they are attached, form a stable, saturated or unsaturated, substituted or unsubstituted, 3 to 7 membered organic monocyclic ring having 0 to 4 hetero atoms selected from S, O, or N;

R₃ and R₄ are independently hydrogen, hydroxy, C₁–C₆ alkyl, C₂–C₆ alkenyl, C₂–C₆ alkynyl, amino, cyano, nitro, C₁–C₅ alkoxy, carboxy, hydroxymethyl, aminomethyl, carboxymethyl, C₁–C₄ alkylthio, C₁–C₄ alkanoyloxy, halo-substituted (C₁–C₆)alkyl, or carbamoyl; or salts thereof;

or compounds of the formula

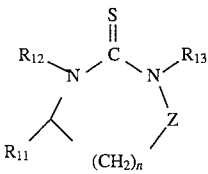 (IB)

wherein n is 0 to 4;

Z is

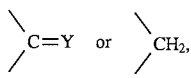

Y is 0 or S;

R₁₁ is of the formula

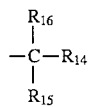

R₁₄ is a stable saturated or unsaturated, substituted or unsubstituted, 3 to 8 membered organic monocyclic ring having 0 to 4 hetero atoms selected from S, O, and N; or R₁₄ is a stable, saturated or unsaturated, substituted or unsubstituted, 7 to 10 membered organic bicyclic ring having 0 to 5 hetero atoms selected from S, O, and N; or R₁₄ is a group of the formula

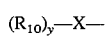

wherein y is 1 or 2; X is N, S, O and R₁₀ is a stable saturated or unsaturated, substituted or unsubstituted, 3 to 8 membered organic monocyclic ring having 0 to 4 hetero atoms selected from S, O, and N; or R₁₀ is a stable, saturated or unsaturated, substituted or unsubstituted, 7 to 10 membered organic bicyclic ring having 0 to 5 hetero atoms selected from S, O, and N; or R₁₀ is hydrogen, C₁–C₆ alkyl, C₂–C₆ alkenyl, or C₂–C₆ alkynyl; or R₁₄ is hydrogen, halo, cyano, carboxy, amino, thio, hydroxy, C₁–C₄ alkoxy, C₁–C₆ alkyl, C₂–C₈ alkenyl, C₂–C₈ alkynyl, or C₂–C₈ alkenoxy;

R₁₅ and R₁₆ are independently C₃–C₈ cycloalkyl, hydrogen, C₁–C₆ alkyl, C₂–C₆ alkenyl, halo, amino, nitro, cyano, C₁–C₅ alkoxy, hydroxy, carboxy, hydroxymethyl, aminomethyl, carboxymethyl, C₁–C₄ alkylthio, C₁–C₄ alkanoyloxy, carbamoyl, or a halo substituted C₁–C₆ alkyl;

R₁₂ is hydrogen, hydroxy, C₁–C₆ alkyl, C₂–C₆ alkenyl, amino, cyano, nitro, C₁–C₅ alkoxy, carboxy, hydroxymethyl, aminomethyl, carboxymethyl, C₁–C₄ alkylthio, C₁–C₄ alkanoyloxy, halo-substituted (C₁–C₆)alkyl, or carbamoyl;

R₁₃ is a stable saturated or unsaturated, substituted or unsubstituted, 3 to 8 membered organic monocyclic ring having 0 to 4 hetero atoms selected from S, O, and N; or R₁₃ is a stable, saturated or unsaturated, substituted or unsubstituted, 7 to 10 membered organic bicyclic ring having 0 to 5 hetero atoms selected from S, O, and N; or R₁₃ is R₁₁ as defined; or salts thereof.

The invention further encompasses compounds of the formula

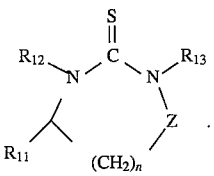 (IB)

wherein n is 0 to 4;

Z is

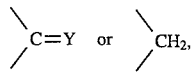

wherein Y is S or O;

R₁₁ is of the formula

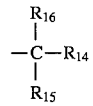

wherein R₁₄ is cyclo(C₃–C₈)alkyl, cyclo(C₃–C₈)alkenyl; isothiazolyl, substituted isothiazolyl, tetrazolyl, substituted tetrazolyl, triazolyl, substituted triazolyl, pyridyl, substituted pyridyl, imidazolyl, substituted imidazolyl, phenyl, substituted phenyl, naphthyl, substituted naphthyl, benzoxazolyl, substituted benzoxazolyl, benzimidazolyl, substituted benzimidazolyl,thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thiadiazolyl, substituted thiadiazolyl, benzotriazolyl, substituted benzotriazolyl, pyrrolyl, substituted pyrrolyl, indolyl, substituted indolyl, benzothienyl, substituted benzothienyl, thienyl, substituted thienyl, benzofuryl, substituted benzofuryl, furyl, substituted furyl, quinolinyl, substituted quinolinyl, isoquinolinyl, substituted isoquinolinyl, pyrazolyl, and substituted pyrazolyl; or $R_{14}$ is a group of the formula $$(R_{10})_y-X-$$

wherein y is 1 or 2; X is N, S, or O, and $R_{10}$ is cyclo($C_3$–$C_8$)alkyl, cyclo($C_3$–$C_8$)alkenyl; isothiazolyl, substituted isothiazolyl, tetrazolyl, substituted tetrazolyl, triazolyl, substituted triazolyl, pyridyl, substituted pyridyl, imidazolyl, substituted imidazolyl, phenyl, substituted phenyl, naphthyl, substituted naphthyl, benzoxazolyl, substituted benzoxazolyl, benzimidazolyl, substituted benzimidazolyl, thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thiadiazolyl, substituted thiadiazolyl, benzotriazolyl, substituted benzotriazolyl, pyrrolyl, substituted pyrrolyl, indolyl, substituted indolyl, benzothienyl, substituted benzothienyl, thienyl, substituted thienyl, benzofuryl, substituted benzofuryl, furyl, substituted furyl, quinolinyl, substituted quinolinyl, isoquinolinyl, substituted isoquinolinyl, pyrazolyl, and substituted pyrazolyl; or $R_{14}$ is halo, cyano, carboxy, amino, thio, hydroxy, $C_1$–$C_4$ alkoxy, $C_2$–$C_8$ alkonyl, $C_2$–$C_8$ alkynyl, or $C_2$–$C_8$ alkenoxy;

$R_{12}$ is hydrogen, hydroxy, $C_1$–$C_6$ alkyl, $C_2$–$C_6$ alkenyl, amino, cyano, nitro, $C_1$–$C_5$ alkoxy, carboxy, hydroxymethyl, aminomethyl, carboxymethyl, $C_1$–$C_4$ alkylthio, $C_1$–$C_4$ alkanoyloxy, halo substituted $C_1$–$C_6$ alkyl, or carbamoyl; and $R_{13}$ is cyclo($C_3$–$C_8$)alkyl, cyclo($C_3$–$C_8$)alkenyl; isothiazolyl, substituted isothiazolyl, tetrazolyl, substituted tetrazolyl, triazolyl, substituted triazolyl, pyridyl, substituted pyridyl, imidazolyl, substituted imidazolyl, phenyl, substituted phenyl, naphthyl, substituted naphthyl, benzoxazolyl, substituted benzoxazolyl, benzimidazolyl, substituted benzimidazolyl, thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thiadiazolyl, substituted thiadiazolyl, benzotriazolyl, substituted benzotriazolyl, pyrrolyl, substituted pyrrolyl, indolyl, substituted indolyl, benzothienyl, substituted benzothienyl, thienyl, substituted thienyl, benzofuryl, substituted benzofuryl, furyl, substituted furyl, quinolinyl, substituted quinolinyl, isoquinolinyl, substituted isoquinolinyl, pyrazolyl, and substituted pyrazolyl;

or $R_{13}$ is $R_{11}$ as defined;

$R_{15}$ and $R_{16}$ are independently $C_3$–$C_8$ cycloalkyl, hydrogen, $C_1$–$C_6$ alkyl, $C_2$–$C_6$ alkenyl, halo, amino, nitro, cyano, $C_1$–$C_5$ alkoxy, hydroxy, carboxy, hydroxymethyl, aminomethyl, carboxymethyl, $C_1$–$C_4$ alkylthio, $C_1$–$C_4$ alkanoyloxy, carbamoyl, or halo substituted ($C_1$–$C_6$)alkyl; and salts thereof, with the proviso that $R_{12}$ is not hydrogen when $R_{15}$ and $R_{16}$ are both hydrogen, $R_{14}$ is phenyl, $R_{13}$ is phenyl, Z is $$\diagdown_{\diagup}C=O,$$

and n is O.

The invention also encompasses compounds of the formula $$R_2-\underset{\underset{R_4}{|}}{N}-\overset{\overset{S}{\|}}{C}-\underset{\underset{R_3}{|}}{N}-R_1 \qquad (IA)$$

in which $R_1$ is a stable saturated or unsaturated, substituted or unsubstituted, 3 to 8 membered organic monocyclic ring having 0 to 4 hetero atoms selected from S, O, and N; or $R_1$ is a stable, saturated or unsaturated, substituted or unsubstituted, 7 to 10 membered organic bicyclic ring having 0 to 5 hetero atoms selected from S, O, and N;

$R_2$ is a group of the formula $$R_5-\underset{\underset{R_8}{|}}{\overset{\overset{R_6}{|}}{C}}-\underset{\underset{R_9}{|}}{\overset{\overset{R_7}{|}}{C}}-$$

wherein $R_5$ is $R_1$ as defined above; or $R_5$ is a group of the formula $$(R_{10})_y-X-$$

wherein y is 1 or 2; X is N, S, O and $R_{10}$ is $R_1$ as defined; or $R_{10}$ is hydrogen, $C_1$–$C_6$ alkyl, $C_2$–$C_6$ alkenyl, or $C_2$–$C_6$ alkynyl; or $R_5$ is hydrogen, $C_1$–$C_6$ alkyl, halo, cyano, carboxy, amino, thio, hydroxy, $C_1$–$C_4$ alkoxy, $C_2$–$C_8$ alkenyl, $C_2$–$C_8$ alkynyl, or $C_2$ to $C_8$ alkenoxy;

$R_6$ and $R_7$ are independently $C_3$–$C_8$ cycloalkyl, hydrogen, $C_1$–$C_6$ alkyl, $C_2$–$C_6$ alkenyl, $C_2$–$C_6$ alkynyl, halo, amino, nitro, cyano, $C_1$–$C_5$ alkoxy, hydroxy, carboxy, hydroxymethyl, aminomethyl, carboxymethyl, $C_1$–$C_4$ alkylthio, $C_1$–$C_4$ alkanoyloxy, carbamoyl, or a halo substituted $C_1$–$C_6$ alkyl;

$R_8$ and $R_9$, along with the carbons to which they are attached, combine to form a stable, saturated or 20 unsaturated, substituted or unsubstituted, 3 to 7 membered organic monocylic ring having 0 to 4 hetero atoms selected from S, O, or N;

$R_3$ and $R_4$ are independently hydrogen, hydroxy, $C_1$–$C_6$ alkyl, $C_2$–$C_6$ alkenyl, $C_2$–$C_6$ alkynyl, amino, cyano, nitro, $C_1$–$C_5$ alkoxy, carboxy, hydroxymethyl, aminomethyl, carboxymethyl, $C_1$–$C_4$ alkylthio, $C_1$–$C_4$ alkanoyloxy, halo-substituted ($C_1$–$C_6$)alkyl, or carbamoyl; or salts thereof.

The invention also encompasses compounds of the formula $$R_2-\underset{\underset{R_4}{|}}{N}-\overset{\overset{S}{\|}}{C}-\underset{\underset{R_3}{|}}{N}-R_1 \qquad (IA)$$

wherein $R_1$ is cyclo($C_3$–$C_8$)alkyl, cyclo($C_3$–$C_8$)alkenyl; isothiazolyl, substituted isothiazoyl, tetrazolyl, substituted tetrazolyl, triazolyl, substituted triazolyl, pyridyl, substituted pyridyl, imidazolyl, substituted imidazoiyl, phenyl, substituted phenyl, naphthyl, substituted naphthyl, benzoxazolyl, substituted benzoxazolyl, benzimidazolyl, substituted benzimidazolyl, thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thiadiazolyl, substituted thiadiazolyl, benzotriazolyl, substituted benzotriazolyl, pyrrolyl, substituted pyrrolyl, indolyl, substituted indolyl, benzothienyl, substituted benzothienyl, thienyl, substituted thienyl, benzofuryl, substituted benzofuryl, furyl, substituted furyl, quinolinyl, substituted quinolinyl, isoquinolinyl, substituted isoquinolinyl, pyrazolyl, and substituted pyrazolyl;

$R_2$ is a group of the formula

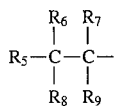

wherein $R_5$ is pyridyl, substituted pyridyl, phenyl, substituted phenyl, naphthyl, substituted naphthyl, cyclohexenyl, benzyl, or $R_5$ is a group of the formula

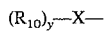

wherein y is 1 or 2; X is N, S, O and $R_{10}$ is $R_1$ as defined; or $R_{10}$ is hydrogen, $C_1$–$C_6$ alkyl, $C_2$–$C_6$ alkenyl, or $C_2$–$C_6$ alkynyl; or $R_5$ is hydrogen, $C_1$–$C_6$ alkyl, halo, cyano, carboxy, amino, thio, hydroxy, $C_1$–$C_4$ alkoxy, $C_2$–$C_8$ alkenyl, $C_2$–$C_8$ alkynyl, or $C_2$ to $C_8$ alkenoxy;

$R_6$, $R_7$, $R_8$, and $R_9$ are independently $C_3$–$C_8$ cycloalkyl, hydrogen, $C_1$–$C_6$ alkyl, $C_2$–$C_6$ alkenyl, $C_2$–$C_6$ alkynyl, halo, amino, nitro, cyano, $C_1$–$C_5$ alkoxy, hydroxy, carboxy, hydroxymethyl, aminomethyl, carboxymethyl, $C_1$–$C_4$ alkylthio, $C_1$–$C_4$ alkanoyloxy, carbamoyl, or a halo-substituted $C_1$–$C_6$ alkyl; or $R_6$ and $R_8$, or $R_7$ and $R_9$, along with the carbon to which they are attached, form a stable, saturated or unsaturated, substituted or unsubstituted, 3 to 7 membered organic monocylic ring having 0 to 4 hetero atoms selected from S, O, or N;

$R_3$ and $R_4$ are independently hydrogen, hydroxy, $C_1$–$C_6$ alkyl, $C_2$–$C_6$ alkenyl, $C_2$–$C_6$ alkynyl, amino, cyano, nitro, $C_1$–$C_5$ alkoxy, carboxy, hydroxymethyl, aminomethyl, carboxymethyl, $C_1$–$C_4$ alkylthio, $C_1$–$C_4$ alkanoyloxy, halo-substituted $C_1$–$C_6$ alkyl; or carbamoyl; or salts thereof, with the proviso that when $R_1$ is pyridyl or pyridyl monosubstituted with halogen, hydroxy, $C_1$–$C_6$ alkyl, or $C_1$–$C_6$ alkoxy; and $R_3$ and $R_4$ are hydrogen; and $R_6$, $R_7$, $R_8$, and $R_9$ are hydrogen;

$R_5$ is not non-substituted phenyl.

When referring to the above as formula (I), it is understood to encompass formulae (IA) and (IB). It should also be understood that when the term "HIV" is used, it includes HIV-1, components, mutant variations, subtypes, and serotypes thereof, and related viruses, components, mutant variations, subtypes, and serotypes thereof. When the term "inhibit" is used, its ordinary meaning is intended, which is to prohibit, hold in check, or discourage, and is not to be construed to be limited to a particular process, procedure, or mechanism of action.

The terms "stable, saturated or unsaturated, substituted or unsubstituted, 3 to 8 membered", or "3 to 7 membered organic monocyclic ring having 0 to 4 hetero atoms selected from S, O, and N" include those wherein the nitrogen and sulfur hetero atoms are optionally oxidized, and the nitrogen hetero atom optionally quaternized. The substituted ring may have 1–8 substituents independently selected from aryl, substituted aryl, halo, $C_1$–$C_6$ alkyl, $C_1$–$C_5$ alkoxy, $C_2$–$C_6$ alkenyl, $C_2$–$C_8$ alkynyl, $C_2$–$C_8$ alkenoxy, amino, nitro, cyano, carboxy, hydroxymethyl, aminomethyl, carboxymethyl, $C_1$–$C_4$ alkylthio, hydroxy, $C_1$–$C_4$ alkanoyloxy, carbamoyl, halo-substituted $C_1$–$C_6$ alkyl, $C_1$–$C_6$ alkoxy-substituted $C_1$–$C_6$ alkyl, a group of the formula

wherein $R_x$ is $C_1$–$C_6$ alkyl, aryl, substituted aryl, or amino; or a group of the formula

wherein $R_x$ is as defined above.

The term "stable, saturated or unsaturated, substituted or unsubstituted, 7 to 10 membered organic bicyclic rings having 0 to 5 hetero atoms selected from O, and N" includes those wherein the nitrogen and sulfur hetero atoms are optionally oxidized, and the nitrogen hetero atom(s) optionally quaternized. The bicyclic rings may be substituted 1 to 8 times, the substituents independently selected from those above listed for the monocyclic rings.

Examples of such monocyclic and bicyclic rings are cyclo($C_3$–$C_8$)alkyl, cyclo($C_3$–$C_8$)alkenyl; isothiazolyl, substituted isothiazolyl, tetrazolyl, substituted tetrazolyl, triazolyl, substituted triazolyl, pyridyl, substituted pyridyl, imidazolyl, substituted imidazolyl, phenyl, substituted phenyl, naphthyl, substituted naphthyl, benzoxazolyl, substituted benzoxazolyl, benzimidazolyl, substituted benzimidazolyl, thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thiadiazolyl, substituted thiadiazolyl, benzotriazolyl, substituted benzotriazolyl, pyrrolyl, substituted pyrrolyl, indolyl, substituted indolyl, benzothienyl, substituted benzothienyl, thienyl, substituted thienyl, benzofuryl, substituted benzofuryl, furyl, substituted furyl, quinolinyl, substituted quinolinyl, isoquinolinyl, substituted isoquinolinyl, pyrazolyl, and substituted pyrazolyl. Other examples of such ring systems may be found in J. Fletcher, O. Dermer, R. Fox, *Nomenclature of Organic Compounds*, pp. 20–63 (1974), and in the Examples herein.

The term "$C_1$–$C_6$ alkyl" includes such groups as methyl, ethyl, n-propyl, isopropyl, n-butyl, s-butyl, t-butyl, n-pentyl, n-hexyl, 3-methylpentyl, and the like.

The term "halo" and "halogen" refer to chloro, bromo, fluoro, and iodo.

"$C_1$–$C_5$ alkoxy" refers to those groups such as methoxy, ethoxy, propoxy, t-butoxy, and the like.

"$C_2$–$C_6$ alkenyl" refers to those groups such as vinyl, 1-propene-2-yl, 1-butene-4-yl, 1-pentene-5-yl, 1-butene-1-yl, and the like.

"$C_1$–$C_4$ alkylthio" refers to those groups such as methylthio, ethylthio, t-butylthio, and the like.

"$C_1$–$C_4$ alkanoyloxy" refers to those groups such as acetoxy, propionoxy, formyloxy, butyryloxy, and the like.

The term "$C_2$–$C_8$ alkenoxy" includes groups such as ethenyloxy, propenyloxy, iso-butoxy ethenyl, and the like.

The term "$C_2$–$C_8$ alkynyl" includes groups such as ethynyl, propynyl, pentynyl, butynyl, and the like.

The term halo-substituted $C_1$–$C_6$ alkyl includes alkyls substituted 1, 2, or 3 times by a halogen, including groups such as trifluoromethyl, 2-dichloroethyl, 3,3-difluoropropyl, and the like.

The term "aryl" includes 3 to 8 membered stable saturated or unsaturated organic monocyclic rings having 0 to 4 hereto atoms selected from S, O, and N; and 7 to 10 membered organic stable, saturated or unsaturated, bicyclic rings having 0 to 5 hetero atoms selected from S, O, N; both of which may be substituted by halo, $C_1$–$C_6$ alkyl, $C_1$–$C_5$ alkoxy, $C_2$–$C_6$ alkenyl, amino, nitro, cyano, carboxy, hydroxymethyl, aminomethyl, carboxymethyl, $C_1$–$C_4$ alkylthio, hydroxy, $C_1$–$C_4$ alkanoyloxy, carbamoyl, or halo-substituted $C_1$–$C_6$ alkyl.

The following are preferred compounds.

N-(2-phenethyl)-N'-(2-thiazolyl)thiourea
N-(2-phenethyl)-N'-[2-(4-methyl)thiazolyl]thiourea
N-(2-phenethyl)-N'-[2-(4,5-dimethyl)thiazolyl]thiourea
N-(2-phenethyl)-N'-[2-(4-cyano)thiazolyl]thiourea
N-(2-phenethyl)-N'-[2-(4-trifluoromethyl)thiazolyl]thiourea
N-(2-phenethyl)-N'-(2-benzothiazolyl)thiourea
N-(2-phenethyl)-N'-[2-(6-fluoro)benzothiazolyl]thiourea
N-(2-phenethyl)-N'-[2-(6-chloro)pyrazinyl]thiourea
N-(2-phenethyl)-N'-[2-(4-ethyl)thiazolyl]thiourea
N-(2-phenethyl)-N'-[2-(4-(3-pyridyl)thiazolyl)]thiourea
N-(2-phenethyl)-N'-[2-(4-(3-nitrophenyl)thiazolyl)]thiourea
N-(2-phenethyl)-N'-(2-pyridyl)thiourea
N-(2-phenethyl)-N'-[2-(6-bromo)pyridyl]thiourea
N-(2-phenethyl)-N'-[2-(6-chloro)pyridyl]thiourea
N-(2-phenethyl)-N'-[2-(6-methyl)pyridyl]thiourea
N-(2-phenethyl)-N'-[2-(5-methyl)pyridyl]thiourea
N-(2-phenethyl)-N'-[2-(6-trifluoromethyl)pyridyl]thiourea
N-(2-phenethyl)-N'-[2-(5-trifluoromethyl)pyridyl]thiourea
N-(2-phenethyl)-N'-[2-(6-ethyl)pyridyl]thiourea
N-(2-phenethyl)-N'-[2-(5-ethyl)pyridyl]thiourea
N-(2-phenethyl)-N'-[2-(6-bromo)pyrazinyl]thiourea
N-(2-phenethyl)-N'-[(3-(6-bromo)pyridazinyl)]thiourea
N-(2-phenethyl)-N'-[2-(6-cyano)pyridyl]thiourea
N-(2-phenethyl)-N'-[2-(5-cyano)pyridyl]thiourea
N-(2-phenethyl)-N'-[2-(5-cyano)pyrazinyl]thiourea
N-(2-phenethyl)-N'-[2-(6-cyano)pyrazinyl]thiourea
N-(2-phenethyl)-N'-[(3-(6-cyano)pyridazinyl)]thiourea
N-(2-phenethyl)-N'-(2-[1,3,4-thiadiazoyl])thiourea
N-(2-phenethyl)-N'-(2-benzimidazolyl)thiourea
N-(2-phenethyl)-N'-(2-imidazolyl)thiourea
N-(2-(2-methoxyphenyl)ethyl)-N'-(2-thiazolyl)thiourea
N-(2-(2-methoxyphenyl)ethyl)-N'-[2-(4-methyl)thiazolyl]thiourea
N-(2-(2-methoxyphenyl)ethyl)-N'-[2-(4,5-dimethyl)thiazolyl]thiourea
N-(2-(2-methoxyphenyl)ethyl)-N'-(2-benzothiazolyl)thiourea
N-(2-(2-methoxyphenyl)ethyl)-N'-[2-(6-fluoro)benzothiazolyl]thiourea
N-(2-(2-methoxyphenyl)ethyl)-N'-[2-(6-chloro)pyrazinyl]thiourea
N-(2-(2-methoxyphenyl)ethyl)-N'-[2-(4-(3-pyridyl)thiazolyl)]thiourea
N-(2-(2-methoxyphenyl)ethyl)-N'-[2-(4-(3-nitrophenyl)thiazolyl)]thiourea
N-(2-(2-methoxyphenyl)ethyl)-N'-(2-pyridyl)thiourea
N-(2-(2-methoxyphenyl)ethyl)-N'-[2-(6-bromo)pyridyl]thiourea
N-(2-(2-methoxyphenyl)ethyl)-N'-[2-(6-chloro)pyridyl]thiourea
N-(2-(2-methoxyphenyl)ethyl)-N'-[2-(6-methyl)pyridyl]thiourea
N-(2-(2-methoxyphenyl)ethyl)-N'-[2-(5-methyl)pyridyl]thiourea
N-(2-(2-methoxyphenyl)ethyl)-N'-[2-(6-trifluoromethyl)pyridyl]thiourea
N-(2-(2-methoxyphenyl)ethyl)-N'-[2-(5-trifluoromethyl)pyridyl]thiourea
N-(2-(2-methoxyphenyl)ethyl)-N'-[2-(6-ethyl)pyridyl]thiourea
N-(2-(2-methoxyphenyl)ethyl)-N'-[2-(5-ethyl)pyridyl]thiourea
N-(2-(2-methoxyphenyl)ethyl)-N'-[2-(6-bromo)pyrazinyl]thiourea
N-(2-(2-methoxyphenyl)ethyl)-N'-[(3-(6-bromo)pyridazinyl)]thiourea
N-(2-(2-methoxyphenyl)ethyl)-N'-[2-(6-cyano)pyridyl]thiourea
N-(2-(2-methoxyphenyl)ethyl)-N'-[2-(5-cyano)pyridyl]thiourea
N-(2-(2-methoxyphenyl)ethyl)-N'-[2-(5-cyano)pyrazinyl]thiourea
N-(2-(2-methoxyphenyl)ethyl)-N'-[2-(6-cyano)pyrazinyl]thiourea
N-(2-(2-methoxyphenyl)ethyl)-N'-[(3-(6-cyano)pyridazinyl)]thiourea
N-(2-(2-methoxyphenyl)ethyl)-N'-(2-[1,3,4-thiadiazoyl])thiourea
N-(2-(2-methoxyphenyl)ethyl)-N'-(2-benzimidazolyl)thiourea
N-(2-(2-methoxyphenyl)ethyl)-N'-(2-imidazolyl)thiourea
N-(2-(3-methoxyphenyl)ethyl)-N'-(2-thiazolyl)thiourea
N-(2-(3-methoxyphenyl)ethyl)-N'-[2-(4-methyl)thiazolyl]thiourea
N-(2-(3-methoxyphenyl)ethyl)-N'-[2-(4,5-dimethyl)thiazolyl]thiourea
N-(2-(3-methoxyphenyl)ethyl)-N'-(2-benzothiazolyl)thiourea
N-(2-(3-methoxyphenyl)ethyl)-N'-[2-(6-fluoro)benzothiazolyl]thiourea
N-(2-(3-methoxyphenyl)ethyl)-N'-[2-(6-chloro)pyrazinyl]thiourea
N-(2-(3-methoxyphenyl)ethyl)-N'-[2-(4-(3-pyridyl)thiazolyl)]thiourea
N-(2-(3-methoxyphenyl)ethyl)-N'-[2-(4-(3-nitrophenyl)thiazolyl)]thiourea
N-(2-(3-methoxyphenyl)ethyl)-N'-(2-pyridyl)thiourea
N-(2-(3-methoxyphenyl)ethyl)-N'-[2-(6-bromo)pyridyl]thiourea
N-(2-(3-methoxyphenyl)ethyl)-N'-[2-(6-chloro)pyridyl]thiourea
N-(2-(3-methoxyphenyl)ethyl)-N'-[2-(6-methyl)pyridyl]thiourea
N-(2-(3-methoxyphenyl)ethyl)-N'-[2-(5-methyl)pyridyl]thiourea
N-(2-(3-methoxyphenyl)ethyl)-N'-[2-(6-trifluoromethyl)pyridyl]thiourea
N-(2-(3-methoxyphenyl)ethyl)-N'-[2-(5-trifluoromethyl)pyridyl]thiourea
N-(2-(3-methoxyphenyl)ethyl)-N'-[2-(6-ethyl)pyridyl]thiourea
N-(2-(3-methoxyphenyl)ethyl)-N'-[2-(5-ethyl)pyridyl]thiourea
N-(2-(3-methoxyphenyl)ethyl)-N'-[2-(6-bromo)pyrazinyl]thiourea
N-(2-(3-methoxyphenyl)ethyl)-N'-[(3-(6-bromo)tryridazinyl)]thiourea
N-(2-(3-methoxyphenyl)ethyl)-N'-[2-(6-cyano)pyridyl]thiourea
N-(2-(3-methoxyphenyl)ethyl)-N'-[2-(5-cyano)pyridyl]thiourea
N-(2-(3-methoxyphenyl)ethyl)-N'-[2-(5-cyano)pyrazinyl]thiourea
N-(2-(3-methoxyphenyl)ethyl)-N'-[2-(6-cyano)pyrazinyl]thiourea
N-(2-(3-methoxyphenyl)ethyl)-N'-[(3-(6-cyano)pyridazinyl)]thiourea N-(2-(3-methoxyphenyl)ethyl)-N'-(2-[1,3,4-thiadiazoyl])thiourea
N-(2-(3-methoxyphenyl)ethyl)-N'-(2-benzimidazolyl)thiourea
N-(2-(3-methoxyphenyl)ethyl)-N'-(2-imidazolyl)thiourea
N-(2-(4-methoxyphenyl)ethyl)-N'-(2-thiazolyl)thiourea
N-(2-(4-methoxyphenyl)ethyl)-N'-[2-(4-methyl)thiazolyl]thiourea
N-(2-(4-methoxyphenyl)ethyl)-N'-[2-(4,5-dimethyl)thiazolyl]thiourea
N-(2-(4-methoxyphenyl)ethyl)-N'-[2-(4-cyano)thiazolyl]thiourea
N-(2-(4-methoxyphenyl)ethyl)-N'-[2-(4-trifluoromethyl)thiazolyl]thiourea
N-(2-(4-methoxyphenyl)ethyl)-N'-(2-benzothiazolyl)thiourea
N-(2-(4-methoxyphenyl)ethyl)-N'-[2-(6-fluoro)benzothiazolyl]thiourea
N-(2-(4-methoxyphenyl)ethyl)-N'-[2-(6-chloro)pyrazinyl]thiourea
N-(2-(4-methoxyphenyl)ethyl)-N'-[2-(4-ethyl)thiazolyl]thiourea
N-(2-(4-methoxyphenyl)ethyl)-N'-[2-(4-(3-pyridyl)thiazolyl)]thiourea
N-(2-(4-methoxyphenyl)ethyl)-N'-[2-(4-(3-nitrophenyl)thiazolyl)]thiourea
N-(2-(4-methoxyphenyl)ethyl)-N'-(2-pyridyl)thiourea
N-(2-(4-methoxyphenyl)ethyl)-N'-[2-(6-bromo)pyridyl]thiourea
N-(2-(4-methoxyphenyl)ethyl)-N'-[2-(5-bromo)pyridyl]thiourea
N-(2-(4-methoxyphenyl)ethyl)-N'-[2-(6-chloro)pyridyl]thiourea
N-(2-(4-methoxyphenyl)ethyl)-N'-[2-(5-chloro)pyridyl]thiourea
N-(2-(4-methoxyphenyl)ethyl)-N'-[2-(6-methyl)pyridyl]thiourea
N-(2-(4-methoxyphenyl)ethyl)-N'-[2-(5-methyl)pyridyl]thiourea
N-(2-(4-methoxyphenyl)ethyl)-N'-[2-(6-trifluoromethyl)pyridyl]thiourea
N-(2-(4-methoxyphenyl)ethyl)-N'-[2-(5-trifluoromethyl)pyridyl]thiourea
N-(2-(4-methoxyphenyl)ethyl)-N'-[2-(6-ethyl)pyridyl]thiourea
N-(2-(4-methoxyphenyl)ethyl)-N'-[2-(5-ethyl)pyridyl]thiourea
N-(2-(4-methoxyphenyl)ethyl)-N'-[2-(5-chloro)pyrazinyl]thiourea
N-(2-(4-methoxyphenyl)ethyl)-N'-[2-(6-bromo)pyrazinyl]thiourea
N-(2-(4-methoxyphenyl)ethyl)-N'-[2-(5-bromo)pyrazinyl]thiourea
N-(2-(4-methoxyphenyl)ethyl)-N'-[(3-(6-bromo)pyridazinyl)]thiourea
N-(2-(4-methoxyphenyl)ethyl)-N'-[(3-(6-chloro)pyridazinyl)]thiourea
N-(2-(4-methoxyphenyl)ethyl)-N'-[2-(6-cyano)pyridyl]thiourea
N-(2-(4-methoxyphenyl)ethyl)-N'-[2-(5-cyano)pyridyl]thiourea
N-(2-(4-methoxyphenyl)ethyl)-N'-[2-(5-cyano)pyrazinyl]thiourea
N-(2-(4-methoxyphenyl)ethyl)-N'-[2-(6-cyano)pyrazinyl]thiourea
N-(2-(4-methoxyphenyl)ethyl)-N'-[(3-(6-cyano)pyridazinyl)]thiourea
N-(2-(4-methoxyphenyl)ethyl)-N'-(2-[1,3,4-thiadiazoyl])thiourea
N-(2-(4-methoxyphenyl)ethyl)-N'-(2-benzimidazolyl)thiourea
N-(2-(4-methoxyphenyl)ethyl)-N'-(2-imidazolyl)thiourea
N-(2-(2-ethoxyphenyl)ethyl)-N'-(2-thiazolyl)thiourea
N-(2-(2-ethoxyphenyl)ethyl)-N'-[2-(4-methyl)thiazolyl]thiourea
N-(2-(2-ethoxyphenyl)ethyl)-N'-[2-(4,5-dimethyl)thiazolyl]thiourea
N-(2-(2-ethoxyphenyl)ethyl)-N'-(2-benzothiazolyl)thiourea
N-(2-(2-ethoxyphenyl)ethyl)-N'-[2-(6-fluoro)benzothiazolyl]thiourea
N-(2-(2-ethoxyphenyl)ethyl)-N'-[2-(6-chloro)pyrazinyl]thiourea
N-(2-(2-ethoxyphenyl)ethyl)-N'-[2-(4-(3-pyridyl)thiazolyl)]thiourea
N-(2-(2-ethoxyphenyl)ethyl)-N'-[2-(4-(3-nitrophenyl)thiazolyl)]thiourea
N-(2-(2-ethoxyphenyl)ethyl)-N'-(2-pyridyl)thiourea
N-(2-(2-ethoxyphenyl)ethyl)-N'-[2-(6-bromo)pyridyl]thiourea
N-(2-(2-ethoxyphenyl)ethyl)-N'-[2-(6-chloro)pyridyl]thiourea
N-(2-(2-ethoxyphenyl)ethyl)-N'-[2-(6-methyl)pyridyl]thiourea
N-(2-(2-ethoxyphenyl)ethyl)-N'-[2-(5-methyl)pyridyl]thiourea
N-(2-(2-ethoxyphenyl)ethyl)-N'-[2-(6-trifluoromethyl)pyridyl]thiourea
N-(2-(2-ethoxyphenyl)ethyl)-N'-[2-(5-trifluoromethyl)pyridyl]thiourea
N-(2-(2-ethoxyphenyl)ethyl)-N'-[2-(6-ethyl)pyridyl]thiourea
N-(2-(2-ethoxyphenyl)ethyl)-N'-[2-(5-ethyl)pyridyl]thiourea
N-(2-(2-ethoxyphenyl)ethyl)-N'-[2-(6-bromo)pyrazinyl]thiourea
N-(2-(2-ethoxyphenyl)ethyl)-N'-[(3-(6-bromo)pyridazinyl)]thiourea
N-(2-(2-ethoxyphenyl)ethyl)-N'-[2-(6-cyano)pyridyl]thiourea
N-(2-(2-ethoxyphenyl)ethyl)-N'-[2-(5-cyano)pyridyl]thiourea
N-(2-(2-ethoxyphenyl)ethyl)-N'-[2-(5-cyano)pyrazinyl]thiourea
N-(2-(2-ethoxyphenyl)ethyl)-N'-[2-(6-cyano)pyrazinyl]thiourea
N-(2-(2-ethoxyphenyl)ethyl)-N'-[(3-(6-cyano)pyridazinyl)]thiourea
N-(2-(2-ethoxyphenyl)ethyl)-N'-(2-[1,3,4-thiadiazoyl])thiourea
N-(2-(2-ethoxyphenyl)ethyl)-N'-(2-benzimidazolyl)thiourea
N-(2-(2-ethoxyphenyl)ethyl)-N'-(2-imidazolyl)thiourea
N-(2-(2-methylphenyl)ethyl)-N'-(2-thiazolyl)thiourea
N-(2-(2-methylphenyl)ethyl)-N'-[2-(4-methyl)thiazolyl]thiourea
N-(2-(2-methylphenyl)ethyl)-N'-[2-(4,5-dimethyl)thiazolyl]thiourea
N-(2-(2-methylphenyl)ethyl)-N'-(2-benzothiazolyl)thiourea
N-(2-(2-methylphenyl)ethyl)-N'-[2-(6-fluoro)benzothiazolyl]thiourea
N-(2-(2-methylphenyl)ethyl)-N'-[2-(6-chloro)pyrazinyl]thiourea
N-(2-(2-methylphenyl)ethyl)-N'-[2-(4-(3-pyridyl)thiazolyl)]thiourea
N-(2-(2-methylphenyl)ethyl)-N'-[2-(4-(3-nitrophenyl)thiazolyl)]thiourea N-(2-(2-methylphenyl)ethyl-N'-(2-pyridyl)thiourea
N-(2-(2-methylphenyl)ethyl-N'-[2-(6-bromo)pyridyl]thiourea
N-(2-(2-methylphenyl)ethyl-N'-[2-(5-chloro)pyridyl]thiourea
N-(2-(2-methylphenyl)ethyl-N'-[2-(6-methyl)pyridyl]thiourea
N-(2-(2-methylphenyl)ethyl-N'-[2-(5-methyl)pyridyl]thiourea
N-(2-(2-methylphenyl)ethyl)-N'-[2-(6-trifluoromethyl)pyridyl]thiourea
N-(2-(2-methylphenyl)ethyl)-N'-[2-(5-trifluoromethyl)pyridyl]thiourea
N-(2-(2-methylphenyl)ethyl)-N'-[2-(6-ethyl)pyridyl]thiourea
N-(2-(2-methylphenyl)ethyl)-N'-[2-(5-ethyl)pyridyl]thiourea
N-(2-(2-methylphenyl)ethyl)-N'-[2-(6-bromo)pyrazinyl]thiourea
N-(2-(2-methylphenyl)ethyl)-N'-[(3-(6-bromo)pyridazinyl)]thiourea
N-(2-(2-methylphenyl)ethyl)-N'-[2-(6-cyano)pyridyl]thiourea
N-(2-(2-methylphenyl)ethyl)-N'-[2-(5-cyano)pyridyl]thiourea
N-(2-(2-methylphenyl)ethyl)-N'-[2-(5-cyano)pyrazinyl]thiourea
N-(2-(2-methylphenyl)ethyl)-N'-[2-(6-cyano)pyrazinyl]thiourea
N-(2-(2-methylphenyl)ethyl)-N'-[(3-(6-cyano)pyridazinyl)]thiourea
N-(2-(2-methylphenyl)ethyl)-N'-(2-[1,3,4-thiadiazoyl])thiourea
N-(2-(2-methylphenyl)ethyl)-N'-(2-benzimidazolyl)thiourea
N-(2-(2-methylphenyl)ethyl)-N'-(2-imidazolyl)thiourea
N-(2-(3-methylphenyl)ethyl)-N'-(2-thiazolyl)thiourea
N-(2-(3-methylphenyl)ethyl)-N'-[2-(4-methyl)thiazolyl]thiourea
N-(2-(3-methylphenyl)ethyl)-N'-[2-(4,5-dimethyl)thiazolyl]thiourea
N-(2-(3-methylphenyl)ethyl)-N'-[2-(4-cyano)thiazolyl]thiourea
N-(2-(3-methylphenyl)ethyl)-N'-[2-(4-trifluoromethyl)thiazolyl]thiourea
N-(2-(3-methylphenyl)ethyl)-N'-(2-benzothiazolyl)thiourea
N-(2-(3-methylphenyl)ethyl)-N'-[2-(6-fluoro)benzothiazolyl]thiourea
N-(2-(3-methylphenyl)ethyl)-N'-[2-(6-chloro)pyrazinyl]thiourea
N-(2-(3-methylphenyl)ethyl)-N'-[2-(4-ethyl)thiazolyl]thiourea
N-(2-(3-methylphenyl)ethyl)-N'-[2-(4-(3-pyridyl)thiazolyl)]thiourea
N-(2-(3-methylphenyl)ethyl)-N'-[2-(4-(3-nitrophenyl)thiazolyl)]thiourea
N-(2-(3-methylphenyl)ethyl)-N'-(2-pyridyl)thiourea
N-(2-(3-methylphenyl)ethyl)-N'-[2-(6-bromo)pyridyl]thiourea
N-(2-(3-methylphenyl)ethyl)-N'-[2-(5-bromo)pyridyl]thiourea
N-(2-(3-methylphenyl)ethyl)-N'-[2-(6-chloro)pyridyl]thiourea
N-(2-(3-methylphenyl)ethyl)-N'-[2-(5-chloro)pyridyl]thiourea
N-(2-(3-methylphenyl)ethyl)-N'-[2-(6-methyl)pyridyl]thiourea
N-(2-(3-methylphenyl)ethyl)-N'-[2-(5-methyl)pyridyl]thiourea
N-(2-(3-methylphenyl)ethyl)-N'-[2-(6-trifluoromethyl)pyridyl]thiourea
N-(2-(3-methylphenyl)ethyl)-N'-[2-(5-trifluoromethyl)pyridyl]thiourea
N-(2-(3-methylphenyl)ethyl)-N'-[2-(6-ethyl)pyridyl]thiourea
N-(2-(3-methylphenyl)ethyl)-N'-[2-(5-ethyl)pyridyl]thiourea
N-(2-(3-methylphenyl)ethyl)-N'-[2-(5-chloro)pyrazinyl]thiourea
N-(2-(3-methylphenyl)ethyl)-N'-[2-(6-bromo)pyrazinyl]thiourea
N-(2-(3-methylphenyl)ethyl)-N'-[2-(5-bromo)pyrazinyl]thiourea
N-(2-(3-methylphenyl)ethyl)-N'-[(3-(6-bromo)pyridazinyl)]thiourea
N-(2-(3-methylphenyl)ethyl)-N'-[(3-(6-chloro)pyridazinyl)]thiourea
N-(2-(3-methylphenyl)ethyl)-N'-[2-(6-cyano)pyridyl]thiourea
N-(2-(3-methylphenyl)ethyl)-N'-[2-(5-cyano)pyridyl]thiourea
N-(2-(3-methylphenyl)ethyl)-N'-[2-(5-cyano)pyrazinyl]thiourea
N-(2-(3-methylphenyl)ethyl)-N'-[2-(6-cyano)pyrazinyl]thiourea
N-(2-(3-methylphenyl)ethyl)-N'-[(3-(6-cyano)pyridazinyl)]thiourea
N-(2-(3-methylphenyl)ethyl)-N'-(2-[1,3,4-thiadiazoyl])thiourea
N-(2-(3-methylphenyl)ethyl)-N'-(2-benzimidazolyl)thiourea
N-(2-(3-methylphenyl)ethyl)-N'-(2-imidazolyl)thiourea
N-(2-(2-fluorophenyl)ethyl)-N'-(2-thiazolyl)thiourea
N-(2-(2-fluorophenyl)ethyl)-N'-[2-(4-methyl)thiazolyl]thiourea
N-(2-(2-fluorophenyl)ethyl)-N'-[2-(4,5-dimethyl)thiazolyl]thiourea
N-(2-(2-fluorophenyl)ethyl)-N'-(2-benzothiazolyl)thiourea
N-(2-(2-fluorophenyl)ethyl)-N'-[2-(6-fluoro)benzothiazolyl]thiourea
N-(2-(2-fluorophenyl)ethyl)-N'-[2-(6-chloro)pyrazinyl]thiourea
N-(2-(2-fluorophenyl)ethyl)-N'-[2-(4-(3-pyridyl)thiazolyl)]thiourea
N-(2-(2-fluorophenyl)ethyl)-N'-[2-(4-(3-nitrophenyl)thiazolyl)]thiourea
N-(2-(2-fluorophenyl)ethyl)-N'-(2-pyridyl)thiourea
N-(2-(2-fluorophenyl)ethyl)-N'-[2-(6-bromo)pyridyl]thiourea
N-(2-(2-fluorophenyl)ethyl)-N'-[2-(6-chloro)pyridyl]thiourea
N-(2-(2-fluorophenyl)ethyl)-N'-[2-(6-methyl)pyridyl]thiourea
N-(2-(2-fluorophenyl)ethyl)-N'-[2-(5-methyl)pyridyl]thiourea
N-(2-(2-fluorophenyl)ethyl)-N'-[2-(6-trifluoromethyl)pyridyl]thiourea
N-(2-(2-fluorophenyl)ethyl)-N'-[2-(5-trifluoromethyl)pyridyl]thiourea
N-(2-(2-fluorophenyl)ethyl)-N'-[2-(6-ethyl)pyridyl]thiourea
N-(2-(2-fluorophenyl)ethyl)-N'-[2-(5-ethyl)pyridyl]thiourea
N-(2-(2-fluorophenyl)ethyl)-N'-[2-(6-bromo)pyrazinyl]thiourea
N-(2-(2-fluorophenyl)ethyl)-N'-[(3-(6-bromo)pyridazinyl)]thiourea N-(2-(2-fluorophenyl)ethyl)-N'-[2-(6-cyano)pyridyl]thiourea
N-(2-(2-fluorophenyl)ethyl)-N'-[2-(5-cyano)pyridyl]thiourea
N-(2-(2-fluorophenyl)ethyl)-N'-[2-(5-cyano)pyrazinyl]thiourea
N-(2-(2-fluorophenyl)ethyl)-N'-[2-(6-cyano)pyrazinyl]thiourea
N-(2-(2-fluorophenyl)ethyl)-N'-[(3-(6-cyano)pyridazinyl)]thiourea
N-(2-(2-fluorophenyl)ethyl)-N'-(2-[1,3,4-thiadiazoyl])thiourea
N-(2-(2-fluorophenyl)ethyl)-N'-(2-benzimidazolyl)thiourea
N-(2-(2-fluorophenyl)ethyl)-N'-(2-imidazolyl)thiourea
N-(2-(2,6-difluorophenyl)ethyl)-N'-[2-(4,5-dimethyl)thiazolyl]thiourea
N-(2-(2,6-difluorophenyl)ethyl)-N'-(2-benzothiazolyl)thiourea
N-(2-(2,6-difluorophenyl)ethyl)-N'-[2-(6-fluoro)benzothiazolyl]thiourea
N-(2-(2,6-difluorophenyl)ethyl)-N'-[2-(6-chloro)pyrazinyl]thiourea
N-(2-(2,6-difluorophenyl)ethyl)-N'-[2-(4-(3-pyridyl)thiazolyl)]thiourea
N-(2-(2,6-difluorophenyl)ethyl)-N'-[2-(4-(3-nitrophenyl)thiazolyl)]thiourea
N-(2-(2,6-difluorophenyl)ethyl)-N'-[2-(6-chloro)pyridyl]thiourea
N-(2-(2,6-difluorophenyl)ethyl)-N'-[2-(6-methyl)pyridyl]thiourea
N-(2-(2,6-difluorophenyl)ethyl)-N'-[2-(6-trifluoromethyl)pyridyl]thiourea
N-(2-(2,6-difluorophenyl)ethyl)-N'-[2-(6-ethyl)pyridyl]thiourea
N-(2-(2,6-difluorophenyl)ethyl)-N'-[2-(6-bromo)pyrazinyl]thiourea
N-(2-(2,6-difluorophenyl)ethyl)-N'-[(3-(6-bromo)pyridazinyl)]thiourea
N-(2-(2,6-difluorophenyl)ethyl)-N'-[2-(6-cyano)pyridyl]thiourea
N-(2-(2,6-difluorophenyl)ethyl)-N'-[2-(5-cyano)pyrazinyl]thiourea
N-(2-(2,6-difluorophenyl)ethyl)-N'-[2-(6-cyano)pyrazinyl]thiourea
N-(2-(2,6-difluorophenyl)ethyl)-N'-[(3-(6-cyano)pyridazinyl)]thiourea
N-(2-(2,6-difluorophenyl)ethyl)-N'-(2-[1,3,4-thiadiazoyl])thiourea
N-(2-(2,6-difluorophenyl)ethyl)-N'-(2-benzimidazolyl)thiourea
N-(2-(2,6-difluorophenyl)ethyl)-N'-(2-imidazolyl)thiourea
N-(2-(2-fluoro-6-methoxyphenyl)ethyl)-N'-(2-thiazolyl)thiourea
N-(2-(2-fluoro-6-methoxyphenyl)ethyl)-N'-[2-(4-methyl)thiazolyl]thiourea
N-(2-(2-fluoro-6-methoxyphenyl)ethyl)-N'-[2-(4,5-dimethyl)thiazolyl]thiourea
N-(2-(2-fluoro-6-methoxyphenyl)ethyl)-N'-(2benzothiazolyl)thiourea
N-(2-(2-fluoro-6-methoxyphenyl)ethyl)-N'-[2-(6-fluoro)benzothiazolyl]thiourea
N-(2-(2-fluoro-6-methoxyphenyl)ethyl)-N'-[2-(6-chloro)pyrazinyl]thiourea
N-(2-(2-fluoro-6-methoxyphenyl)ethyl)-N'-[2-(4-(3-pyridyl)thiazolyl)]thiourea
N-(2-(2-fluoro-6-methoxyphenyl)ethyl)-N'-[2-(4-(3-nitrophenyl)thiazolyl)]thiourea
N-(2-(2-fluoro-6-methoxyphenyl)ethyl)-N'-(2-pyridyl)thiourea
N-(2-(2-fluoro-6-methoxyphenyl)ethyl)-N'-[2-(6-bromo)pyridyl]thiourea
N-(2-(2-fluoro-6-methoxyphenyl)ethyl)-N'-[2-(6-chloro)pyridyl]thiourea
N-(2-(2-fluoro-6-methoxyphenyl)ethyl)-N'-[2-(6-methyl)pyridyl]thiourea
N-(2-(2-fluoro-6-methoxyphenyl)ethyl)-N'-[2-(5-methyl)pyridyl]thiourea
N-(2-(2-fluoro-6-methoxyphenyl)ethyl)-N'-[2-(6-trifluoromethyl)pyridyl]thiourea
N-(2-(2-fluoro-6-methoxyphenyl)ethyl)-N'-[2-(5-trifluoromethyl)pyridyl]thiourea
N-(2-(2-fluoro-6-methoxyphenyl)ethyl)-N'-[2-(6-ethyl)pyridyl]thiourea
N-(2-(2-fluoro-6-methoxyphenyl)ethyl)-N'-[2-(5-ethyl)pyridyl]thiourea
N-(2-(2-fluoro-6-methoxyphenyl)ethyl)-N'-[2-(6-bromo)pyrazinyl]thiourea
N-(2-(2-fluoro-6-methoxyphenyl)ethyl)-N'-[(3-(6-bromo)pyridazinyl)]thiourea
N-(2-(2-fluoro-6-methoxyphenyl)ethyl)-N'-[2-(6-cyano)pyridyl]thiourea
N-(2-(2-fluoro-6-methoxyphenyl)ethyl)-N'-[2-(5-cyano)pyridyl]thiourea
N-(2-(2-fluoro-6-methoxyphenyl)ethyl)-N'-[2-(5-cyano)pyrazinyl]thiourea
N-(2-(2-fluoro-6-methoxytphenyl)ethyl)-N'-[2-(6-cyano)pyrazinyl]thiourea
N-(2-(2-fluoro-6-methoxyphenyl)ethyl)-N'-[(3-(6-cyano)pyridazinyl)]thiourea
N-(2-(2-fluoro-6-methoxyphenyl)ethyl)-N'-(2-[1,3,4-thiadiazoyl])thiourea
N-(2-(2-fluoro-6-methoxyphenyl)ethyl)-N'-(2-benzimidazolyl)thiourea
N-(2-(2-fluoro-6-methoxyphenyl)ethyl)-N'-(2-imidazolyl)thiourea
N-(2-(2-fluoro-6-ethoxyphenyl)ethyl)-N'-(2-thiazolyl)thiourea
N-(2-(2-fluoro-6-ethoxyphenyl)ethyl)-N'-[2-(4-methyl)thiazolyl]thiourea
N-(2-(2-fluoro-6-ethoxyphenyl)ethyl)-N'-[2-(4,5-dimethyl)thiazolyl]thiourea
N-(2-(2-fluoro-6-ethoxyphenyl)ethyl)-N'-(2-benzothiazolyl)thiourea
N-(2-(2-fluoro-6-ethoxyphenyl)ethyl)-N'-[2-(6-fluoro)benzothiazolyl]thiourea
N-(2-(2-fluoro-6-ethoxyphenyl)ethyl)-N'-[2-(6-chloro)pyrazinyl]thiourea
N-(2-(2-fluoro-6-ethoxyphenyl)ethyl)-N'-[2-(4-(3-pyridyl)thiazolyl)]thiourea
N-(2-(2-fluoro-6-ethoxyphenyl)ethyl)-N'-[2-(4-(3-nitrophenyl)thiazolyl)]thiourea
N-(2-(2-fluoro-6-ethoxyphenyl)ethyl)-N'-(2-pyridyl)thiourea
N-(2-(2-fluoro-6-ethoxyphenyl)ethyl)-N'-[2-(6-bromo)pyridyl]thiourea
N-(2-(2-fluoro-6-ethoxyphenyl)ethyl)-N'-[2-(6-chloro)pyridyl]thiourea
N-(2-(2-fluoro-6-ethoxyphenyl)ethyl)-N'-[2-(6-methyl)pyridyl]thiourea
N-(2-(2-fluoro-6-ethoxyphenyl)ethyl)-N'-[2-(5-methyl)pyridyl]thiourea
N-(2-(2-fluoro-6-ethoxyphenyl)ethyl)-N'-[2-(6-trifluoromethyl)pyridyl]thiourea
N-(2-(2-fluoro-6-ethoxyphenyl)ethyl)-N'-[2-(5-trifluoromethyl)pyridyl]thiourea N-(2-(2-fluoro-6-ethoxyphenyl)ethyl)-N'-[2-(6-ethyl)pyridyl]thiourea
N-(2-(2-fluoro-6-ethoxyphenyl)ethyl)-N'-[2-(5-ethyl)pyridyl]thiourea
N-(2-(2-fluoro-6-ethoxyphenyl)ethyl)-N'-[2-(6-bromo)pyrazinyl]thiourea
N-(2-(2-fluoro-6-ethoxyphenyl)ethyl)-N'-[(3-(6-bromo)pyridazinyl)]thiourea
N-(2-(2-fluoro-6-ethoxyphenyl)ethyl)-N'-[2-(6-cyano)pyridyl]thiourea
N-(2-(2-fluoro-6-ethoxyphenyl)ethyl)-N'-[2-(5-cyano)pyridyl]thiourea
N-(2-(2-fluoro-6-ethoxyphenyl)ethyl)-N'-[2-(5-cyano)pyrazinyl]thiourea
N-(2-(2-fluoro-6-ethoxyphenyl)ethyl)-N'-[2-(6-cyano)pyrazinyl]thiourea
N-(2-(2-fluoro-6-ethoxyphenyl)ethyl)-N'-[(3-(6-cyano)pyridazinyl)]thiourea
N-(2-(2-fluoro-6-ethoxyphenyl)ethyl)-N'-(2-[1,3,4-thiadiazoyl])thiourea
N-(2-(2-fluoro-6-ethoxyphenyl)ethyl)-N'-(2-benzimidazolyl)thiourea
N-(2-(2-fluoro-6-ethoxyphenyl)ethyl)-N'-(2-imidazolyl)thiourea
N-(2-(2,3,5,6-tetrafluorophenyl)ethyl)-N'-(2-thiazolyl)thiourea
N-(2-(2,3,5,6-tetrafluorophenyl)ethyl)-N'-[2-(4-methyl)thiazolyl]thiourea
N-(2-(2,3,5,6-tetrafluorophenyl)ethyl)-N'-[2-(4,5-dimethyl)thiazolyl]thiourea
N-(2-(2,3,5,6-tetrafluorophenyl)ethyl)-N'-[2-(4-cyano)thiazolyl]thiourea
N-(2-(2,3,5,6-tetrafluorophenyl)ethyl)-N'-[2-(4-trifluoromethyl)thiazolyl]thiourea
N-(2-(2,3,5,6-tetrafluorophenyl)ethyl)-N'-[2-benzothiazolyl)thiourea
N-(2-(2,3,5,6-tetrafluorophenyl)ethyl)-N'-[2-(6-fluoro)benzothiazolyl]thiourea
N-(2-(2,3,5,6-tetrafluorophenyl)ethyl)-N'-[2-(6-chloro)pyrazinyl]thiourea
N-(2-(2,3,5,6-tetrafluorophenyl)ethyl)-N'-[2-(4-ethyl)thiazolyl]thiourea
N-(2-(2,3,5,6-tetrafluorophenyl)ethyl)-N'-[2-(4-(3-pyridyl)thiazolyl)]thiourea
N-(2-(2,3,5,6-tetrafluorophenyl)ethyl)-N'-[2-(4-(3-nitrophenyl)thiazolyl)]thiourea
N-(2-(2,3,5,6-tetrafluorophenyl)ethyl)-N'-(2-pyridyl)thiourea
N-(2-(2,3,5,6-tetrafluorophenyl)ethyl)-N'-[2-(6-bromo)pyridyl]thiourea
N-(2-(2,3,5,6-tetrafluorophenyl)ethyl)-N'-[2-(5-bromo)pyridyl]thiourea
N-(2-(2,3,5,6-tetrafluorophenyl)ethyl)-N'-[2-(6-chloro)pyridyl]thiourea
N-(2-(2,3,5,6-tetrafluorophenyl)ethyl)-N'-[2-(5-chloro)pyridyl]thiourea
N-(2-(2,3,5,6-tetrafluorophenyl)ethyl)-N'-[2-(6-methyl)pyridyl]thiourea
N-(2-(2,3,5,6-tetrafluorophenyl)ethyl)-N'-[2-(5-methyl)pyridyl]thiourea
N-(2-(2,3,5,6-tetrafluorophenyl)ethyl)-N'-[2-(6-trifluoromethyl)pyridyl]thiourea
N-(2-(2,3,5,6-tetrafluorophenyl)ethyl)-N'-[2-(5-trifluoromethyl)pyridyl]thiourea
N-(2-(2,3,5,6-tetrafluorophenyl)ethyl)-N'-[2-(6-ethyl)pyridyl]thiourea
N-(2-(2,3,5,6-tetrafluorophenyl)ethyl)-N'-[2-(5-ethyl)pyridyl]thiourea
N-(2-(2,3,5,6-tetrafluorophenyl)ethyl)-N'-[2-(5-chloro)pyrazinyl]thiourea
N-(2-(2,3,5,6-tetrafluorophenyl)ethyl)-N'-[2-(6-bromo)pyrazinyl]thiourea
N-(2-(2,3,5,6-tetrafluorophenyl)ethyl)-N'-[2-(5-bromo)pyrazinyl]thiourea
N-(2-(2,3,5,6-tetrafluorophenyl)ethyl)-N'-[(3-(6-bromo)pyridazinyl)]thiourea
N-(2-(2,3,5,6-tetrafluorophenyl)ethyl)-N'-[(3-(6-chloro)pyridazinyl)]thiourea
N-(2-(2,3,5,6-tetrafluorophenyl)ethyl)-N'-[2-(6-cyano)pyridyl]thiourea
N-(2-(2,3,5,6-tetrafluorophenyl)ethyl)-N'-[2-(5-cyano)pyridyl]thiourea
N-(2-(2,3,5,6-tetrafluorophenyl)ethyl)-N'-[2-(5-cyano)pyrazinyl]thiourea
N-(2-(2,3,5,6-tetrafluorophenyl)ethyl)-N'-[2-(6-cyano)pyrazinyl]thiourea
N-(2-(2,3,5,6-tetrafluorophenyl)ethyl)-N'-[(3-(6-cyano)pyridazinyl)]thiourea
N-(2-(2,3,5,6-tetrafluorophenyl)ethyl)-N'-(2-[1,3,4-thiadiazoyl])thiourea
N-(2-(2,3,5,6-tetrafluorophenyl)ethyl)-N'-(2-benzimidazolyl)thiourea
N-(2-(2,3,5,6-tetrafluorophenyl)ethyl)-N'-(2-imidazolyl)thiourea
N-(2-(2-chlorophenyl)ethyl)-N'-(2-thiazolyl)thiourea
N-(2-(2-chlorophenyl)ethyl)-N'-[2-(4-methyl)thiazolyl]thiourea
N-(2-(2-chlorophenyl)ethyl)-N'-[2-(4,5-dimethyl)thiazolyl]thiourea
N-(2-(2-chlorophenyl)ethyl)-N'-(2-benzothiazolyl)thiourea
N-(2-(2-chlorophenyl)ethyl)-N'-[2-(6-fluoro)benzothiazolyl]thiourea
N-(2-(2-chlorophenyl)ethyl)-N'-[2-(6-chloro)pyrazinyl]thiourea
N-(2-(2-chlorophenyl)ethyl)-N'-[2-(4-(3-pyridyl)thiazolyl)]thiourea
N-(2-(2-chlorophenyl)ethyl)-N'-[2-(4-(3-nitrophenyl)thiazolyl)]thiourea
N-(2-(2-chlorophenyl)ethyl)-N'-(2-pyridyl)thiourea
N-(2-(2-chlorophenyl)ethyl)-N'-[2-(6-bromo)pyridyl]thiourea
N-(2-(2-chlorophenyl)ethyl)-N'-[2-(6-chloro)pyridyl]thiourea
N-(2-(2-chlorophenyl)ethyl)-N'-[2-(6-methyl)pyridyl]thiourea
N-(2-(2-chlorophenyl)ethyl)-N'-[2-(5-methyl)pyridyl]thiourea
N-(2-(2-chlorophenyl)ethyl)-N'-[2-(6-trifluoromethyl)pyridyl]thiourea
N-(2-(2-chlorophenyl)ethyl)-N'-[2-(5-trifluoromethyl)pyridyl]thiourea
N-(2-(2-chlorophenyl)ethyl)-N'-[2-(6ethyl)pyridyl]thiourea
N-(2-(2-chlorophenyl)ethyl)-N'-[2-(5-ethyl)pyridyl]thiourea
N-(2-(2-chlorophenyl)ethyl)-N'-[2-(6-bromo)pyrazinyl]thiourea
N-(2-(2-chlorophenyl)ethyl)-N'-[(3-(6-bromo)pyridazinyl)]thiourea
N-(2-(2-chlorophenyl)ethyl)-N'-[2-(6-cyano)pyridyl]thiourea
N-(2-(2-chlorophenyl)ethyl)-N'-[2-(5-cyano)pyridyl]thiourea
N-(2-(2-chlorophenyl)ethyl-N'-[2-(5-cyano)pyrazinyl]thiourea
N-(2-(2-chlorophenyl)ethyl-N'-[2-(6-cyano)pyrazinyl]thiourea N-(2-(2-chlorophenyl)ethyl-N'-[(3-(6-cyano)pyridazinyl)]thiourea
N-(2-(2-chlorophenyl)ethyl-N'-(2-[1,3,4-thiadiazoyl])thiourea
N-(2-(2-chlorophenyl)ethyl)-N'-(2-benzimidazolyl)thiourea
N-(2-(2-chlorophenyl)ethyl)-N'-(2-imidazolyl)thiourea
N-(2-(3-chlorophenyl)ethyl)-N'-(2-thiazolyl)thiourea
N-(2-(3-chlorophenyl)ethyl)-N'-[2-(4-methyl)thiazolyl]thiourea
N-(2-(3-chlorophenyl)ethyl)-N'-[2-(4,5-dimethyl)thiazolyl]thiourea
N-(2-(3-chlorophenyl)ethyl)-N'-(2-benzothiazolyl)thiourea
N-(2-(3-chlorophenyl)ethyl)-N'-[2-(6-fluoro)benzothiazolyl]thiourea
N-(2-(3-chlorophenyl)ethyl)-N'-[2-(6-chloro)pyrazinyl]thiourea
N-(2-(3-chlorophenyl)ethyl)-N'-[2-(4-(3-pyridyl)thiazolyl)]thiourea
N-(2-(3-chlorophenyl)ethyl)-N'-[2-(4-(3-nitrophenyl)thiazolyl)]thiourea
N-(2-(3-chlorophenyl)ethyl)-N'-(2-pyridyl)thiourea
N-(2-(3-chlorophenyl)ethyl)-N'-[2-(6-bromo)pyridyl]thiourea
N-(2-(3-chlorophenyl)ethyl)-N'-[2-(6-chloro)pyridyl]thiourea
N-(2-(3-chlorophenyl)ethyl)-N'-[2-(6-methyl)pyridyl]thiourea
N-(2-(3-chlorophenyl)ethyl)-N'-[2-(5-methyl)pyridyl]thiourea
N-(2-(3-chlorophenyl)ethyl)-N'-[2-(6-trifluoromethyl)pyridyl]thiourea
N-(2-(3-chlorophenyl)ethyl)-N'-[2-(5-trifluoromethyl)pyridyl]thiourea
N-(2-(3-chlorophenyl)ethyl)-N'-[2-(6-ethyl)pryridyl]thiourea
N-(2-(3-chlorophenyl)ethyl)-N'-[2-(5-ethyl)pyridyl]thiourea
N-(2-(3-chlorophenyl)ethyl)-N'-[2-(6-bromo)pyrazinyl]thiourea
N-(2-(3-chlorophenyl)ethyl)-N'-[(3-(6-bromo)pyridazinyl)]thiourea
N-(2-(3-chlorophenyl)ethyl)-N'-[2-(6-cyano)pyridyl]thiourea
N-(2-(3-chlorophenyl)ethyl)-N'-[2-(5-cyano)pyridyl]thiourea
N-(2-(3-chlorophenyl)ethyl)-N'-[2-(5-cyano)pyrazinyl]thiourea
N-(2-(3-chlorophenyl)ethyl)-N'-[2-(6-cyano)pyrazinyl]thiourea
N-(2-(3-chlorophenyl)ethyl)-N'-[(3-(6cyano)pyridazinyl)]thiourea
N-(2-(3-chlorophenyl)ethyl)-N'-(2-[1,3,4-thiadiazoyl])thiourea
N-(2-(3-chlorophenyl)ethyl)-N'-(2-benzimidazolyl)thiourea
N-(2-(3-chlorophenyl)ethyl)-N'-(2-imidazolyl)thiourea
N-(2-(1-cyclohexenyl)ethyl)-N'-[2-(4,5-dimethyl)thiazolyl]thiourea
N-(2-(1-cyclohexenyl)ethyl)-N'-(2-benzothiazolyl)thiourea
N-(2-(1-cyclohexenyl)ethyl)-N'-[2-(6-fluoro)benzothiazolyl]thiourea
N-(2-(1-cyclohexenyl)ethyl)-N'-[2-(6-chloro)pyrazinyl]thiourea
N-(2-(1-cyclohexenyl)ethyl)-N'-[2-(4-(3-pyridyl)thiazolyl)]thiourea
N-(2-(1-cyclohexenyl)ethyl)-N'-[2-(4-(3-nitrophenyl)thiazolyl)]thiourea
N-(2-(1-cyclohexenyl)ethyl)-N'-[2-(6-bromo)pyridyl]thiourea
N-(2-(1-cyclohexenyl)ethyl)-N'-[2-(6-chloro)pyridyl]thiourea
N-(2-(1-cyclohexenyl)ethyl)-N'-[2-(6-methyl)pyridyl]thiourea
N-(2-(1-cyclohexenyl)ethyl)-N'-[2-(6-trifluoromethyl)pyridyl]thiourea
N-(2-(1-cyclohexenyl)ethyl)-N'-[2-(6-ethyl)pyridyl]thiourea
N-(2-(1-cyclohexenyl)ethyl)-N'-[2-(6-bromo)pyrazinyl]thiourea
N-(2-(1-cyclohexenyl)ethyl)-N'-[(3-(6-bromo)pyridazinyl)]thiourea
N-(2-(1-cyclohexenyl)ethyl)-N'-[2-(6-cyano)pyridyl]thiourea
N-(2-(1-cyclohexenyl)ethyl)-N'-[2-(6-cyano)pyrazinyl]thiourea
N-(2-(1-cyclohexenyl)ethyl)-N'-(2-[1,3,4-thiadiazoyl])thiourea
N-(2-(1-cyclohexenyl)ethyl)-N'-(2-benzimidazolyl)thiourea
N-(2-(1-cyclohexenyl)ethyl)-N'-(2-imidazolyl)thiourea
N-(2-(2-naphthyl)ethyl)-N'-(2-thiazolyl)thiourea
N-(2-(2-naphthyl)ethyl)-N'-[2-(4-methyl)thiazolyl]thiourea
N-(2-(2-naphthyl)ethyl)-N'-[2-(4,5-dimethyl)thiazolyl]thiourea
N-(2-(2-naphthyl)ethyl)-N'-[2-(4-cyano)thiazolyl]thiourea
N-(2-(2-naphthyl)ethyl)-N'-[2-(4-trifluoromethyl)thiazolyl]thiourea
N-(2-(2-naphthyl)ethyl)-N'-(2-benzothiazolyl)thiourea
N-(2-(2-naphthyl)ethyl)-N'-[2-(6-fluoro)benzothiazolyl]thiourea
N-(2-(2-naphthyl)ethyl)-N'-[2-(6-chloro)pyrazinyl]thiourea
N-(2-(2-naphthyl)ethyl)-N'-[2-(4-ethyl)thiazolyl]thiourea
N-(2-(2-naphthyl)ethyl)-N'-[2-(4-(3-pyridyl)thiazolyl)]thiourea
N-(2-(2-naphthyl)ethyl)-N'-[2-(4-(3-nitrophenyl)thiazolyl)]thiourea
N-(2-(2-naphthyl)ethyl)-N'-(2-pyridyl)thiourea
N-(2-(2-naphthyl)ethyl)-N'-[2-(6-bromo)pyridyl]thiourea
N-(2-(2-naphthyl)ethyl)-N'-[2-(5-bromo)pyridyl]thiourea
N-(2-(2-naphthyl)ethyl)-N'-[2-(6-chloro)pyridyl]thiourea
N-(2-(2-naphthyl)ethyl)-N'-[2-(5-chloro)pyridyl]thiourea
N-(2-(2-naphthyl)ethyl)-N'-[2-(6-methyl)pyridyl]thiourea
N-(2-(2-naphthyl)ethyl)-N'-[2-(5-methyl)pyridyl]thiourea
N-(2-(2-naphthyl)ethyl)-N'-[2-(6-trifluoromethyl)pyridyl]thiourea
N-(2-(2-naphthyl)ethyl)-N'-[2-(5-trifluoromethyl)pyridyl]thiourea
N-(2-(2-naphthyl)ethyl)-N'-[2-(6-ethyl)pyridyl]thiourea
N-(2-(2-naphthyl)ethyl)-N'-[2-(5-ethyl)pyridyl]thiourea
N-(2-(2-naphthyl)ethyl)-N'-[2-(5-chloro)pyrazinyl]thiourea
N-(2-(2-naphthyl)ethyl)-N'-[2-(6-bromo)pyrazinyl]thiourea
N-(2-(2-naphthyl)ethyl)-N'-[2-(5-bromo)pyrazinyl]thiourea
N-(2-(2-naphthyl)ethyl)-N'-[(3-(6-bromo)pyridazinyl)]thiourea
N-(2-(2-naphthyl)ethyl)-N'-[(3-(6-chloro)pyridazinyl)]thiourea
N-(2-(2-naphthyl)ethyl)-N'-[2-(6-cyano)pyridyl]thiourea
N-(2-(2-naphthyl)ethyl)-N'-[2-(5-cyano)pyridyl]thiourea
N-(2-(2-naphthyl)ethyl)-N'-[2-(5-cyano)pyrazinyl]thiourea
N-(2-(2-naphthyl)ethyl)-N'-[2-(6-cyano)pyrazinyl]thiourea
N-(2-(2-naphthyl)ethyl)-N'-[(3-(6-cyano)pyridazinyl)]thiourea
N-(2-(2-naphthyl)ethyl)-N'-(2-[1,3,4-thiadiazoyl])thiourea
N-(2-(2-naphthyl)ethyl)-N'-(2-benzimidazolyl)thiourea
N-(2-(2-naphthyl)ethyl)-N'-(2-imidazolyl)thiourea
N-(2-(2,5-dimethoxyphenyl)ethyl)-N'-(2-thiazolyl)thiourea
N-(2-(2,5-dimethoxyphenyl)ethyl)-N'-[2-(4-methyl)thiazolyl]thiourea N-(2-(2,5-dimethoxyphenyl)ethyl)-N'-[2-(4,5-dimethyl)thiazolyl]thiourea
N-(2-(2,5-dimethoxyphenyl)ethyl)-N'-(2-benzothiazolyl)thiourea
N-(2-(2,5-dimethoxyphenyl)ethyl)-N'-[2-(6-fluoro)benzothiazolyl]thiourea
N-(2-(2,5-dimethoxyphenyl)ethyl)-N'-[2-(6-chloro)pyrazinyl]thiourea
N-(2-(2,5-dimethoxyphenyl)ethyl)-N'-[2-(4-(3-pyridyl)thiazolyl)]thiourea
N-(2-(2,5-dimethoxyphenyl)ethyl)-N'-[2-(4-(3-nitrophenyl)thiazolyl)]thiourea
N-(2-(2,5-dimethoxyphenyl)ethyl)-N'-(2-pyridyl)thiourea
N-(2-(2,5-dimethoxyphenyl)ethyl)-N'-[2-(6-bromo)pyridyl]thiourea
N-(2-(2,5-dimethoxyphenyl)ethyl)-N'-[2-(6-chloro)pyridyl]thiourea
N-(2-(2,5-dimethoxyphenyl)ethyl)-N'-[2-(5-chloro)pyridyl]thiourea
N-(2-(2,5-dimethoxyphenyl)ethyl)-N'-[2-(6-methyl)pyridyl]thiourea
N-(2-(2,5-dimethoxyphenyl)ethyl)-N'-[2-(5-methyl)pyridyl]thiourea
N-(2-(2,5-dimethoxyphenyl)ethyl)-N'-[2-(6-trifluoromethyl)pyridyl]thiourea
N-(2-(2,5-dimethoxyphenyl)ethyl)-N'-[2-(5-trifluoromethyl)pyridyl]thiourea
N-(2-(2,5-dimethoxyphenyl)ethyl)-N'-[2-(6-ethyl)pyridyl]thiourea
N-(2-(2,5-dimethoxyphenyl)ethyl)-N'-[2-(5-ethyl)pyridyl]thiourea
N-(2-(2,5-dimethoxyphenyl)ethyl)-N'-[2-(6-bromo)pyrazinyl]thiourea
N-(2-(2,5-dimethoxyphenyl)ethyl)-N'-[(3-(6-bromo)pyridazinyl)]thiourea
N-(2-(2,5-dimethoxyphenyl)ethyl)-N'-[2-(6-cyano)pyridyl]thiourea
N-(2-(2,5-dimethoxyphenyl)ethyl)-N'-[2-(5-cyano)pyridyl]thiourea
N-(2-(2,5-dimethoxyphenyl)ethyl)-N'-[2-(5-cyano)pyrazinyl]thiourea
N-(2-(2,5-dimethoxyphenyl)ethyl)-N'-[2-(6-cyano)pyrazinyl]thiourea
N-(2-(2,5-dimethoxyphenyl)ethyl)-N'-[(3-(6-cyano)pyridazinyl)]thiourea
N-(2-(2,5-dimethoxyphenyl)ethyl)-N'-(2-[1,3,4-thiadiazoyl])thiourea
N-(2-(2,5-dimethoxyphenyl)ethyl)-N'-(2-benzimidazolyl)thiourea
N-(2-(2,5-dimethoxyphenyl)ethyl)-N'-(2-imidazolyl)thiourea
N-(2-(2-azidophenyl)ethyl)-N'-(2-thiazolyl)thiourea
N-(2-(2-azidophenyl)ethyl)-N'-[2-(4-methyl)thiazolyl]thiourea
N-(2-(2-azidophenyl)ethyl)-N'-[2-(4,5-dimethyl)thiazolyl]thiourea
N-(2-(2-azidophenyl)ethyl)-N'-[2-(4-cyano)thiazolyl]thiourea
N-(2-(2-azidophenyl)ethyl)-N'-[2-(4-trifluoromethyl)thiazolyl]thiourea
N-(2-(2-azidophenyl)ethyl)-N'-(2-benzothiazolyl)thiourea
N-(2-(2-azidophenyl)ethyl)-N'-[2-(6-fluoro)benzothiazolyl]thiourea
N-(2-(2-azidophenyl)ethyl)-N'-[2-(6-chloro)pyrazinyl]thiourea
N-(2-(2-azidophenyl)ethyl)-N'-[2-(4-ethyl)thiazolyl]thiourea
N-(2-(2-azidophenyl)ethyl)-N'-[2-(4-(3-pyridyl)thiazolyl)]thiourea
N-(2-(2-azidophenyl)ethyl)-N'-[2-(4-(3-nitrophenyl)thiazolyl)]thiourea
N-(2-(2-azidophenyl)ethyl)-N'-(2-pyridyl)thiourea
N-(2-(2-azidophenyl)ethyl)-N'-[2-(6-bromo)pyridyl]thiourea
N-(2-(2-azidophenyl)ethyl)-N'-[2-(5-bromo)pyridyl]thiourea
N-(2-(2-azidophenyl)ethyl)-N'-[2-(6-chloro)pyridyl]thiourea
N-(2-(2-azidophenyl)ethyl)-N'-[2-(5-chloro)pyridyl]thiourea
N-(2-(2-azidophenyl)ethyl)-N'-[2-(6-methyl)pyridyl]thiourea
N-(2-(2-azidophenyl)ethyl)-N'-[2-(5-methyl)pyridyl]thiourea
N-(2-(2-azidophenyl)ethyl)-N'-[2-(6-trifluoromethyl)pyridyl]thiourea
N-(2-(2-azidophenyl)ethyl)-N'-[2-(5-trifluoromethyl)pyridyl]thiourea
N-(2-(2-azidophenyl)ethyl)-N'-[2-(6-ethyl)pyridyl]thiourea
N-(2-(2-azidophenyl)ethyl)-N'-[2-(5-ethyl)pyridyl]thiourea
N-(2-(2-azidophenyl)ethyl)-N'-[2-(5-chloro)pyrazinyl]thiourea
N-(2-(2-azidophenyl)ethyl)-N'-[2-(6-bromo)pyrazinyl]thiourea
N-(2-(2-azidophenyl)ethyl)-N'-[2-(5-bromo)pyrazinyl]thiourea
N-(2-(2-azidophenyl)ethyl)-N'-[(3-(6-bromo)pyridazinyl)]thiourea
N-(2-(2-azidophenyl)ethyl)-N'-[(3-(6-chloro)pyridazinyl)]thiourea
N-(2-(2-azidophenyl)ethyl)-N'-[2-(6-cyano)pyridyl]thiourea
N-(2-(2-azidophenyl)ethyl)-N'-[2-(5-cyano)pyridyl]thiourea
N-(2-(2-azidophenyl)ethyl)-N'-[2-(5-cyano)pyrazinyl]thiourea
N-(2-(2-azidophenyl)ethyl)-N'-[2-(6-cyano)pyrazinyl]thiourea
N-(2-(2-azidophenyl)ethyl)-N'-[(3-(6-cyano)pyridazinyl)]thiourea
N-(2-(2-azidophenyl)ethyl)-N'-(2-[1,3,4-thiadiazoyl])thiourea
N-(2-(2-azidophenyl)ethyl)-N'-(2-benzimidazolyl)thiourea
N-(2-(2-azidophenyl)ethyl)-N'-(2-imidazolyl)thiourea
N-(2-(2,3,4-trifluorophenyl)ethyl)-N'-(2-thiazolyl)thiourea
N-(2-(2,3,4-trifluorophenyl)ethyl)-N'-[2-(4-methyl)thiazolyl]thiourea
N-(2-(2,3,4-trifluorophenyl)ethyl)-N'-[2-(4,5-dimethyl)thiazolyl]thiourea
N-(2-(2,3,4-trifluorophenyl)ethyl)-N'-[2-(4-cyano)thiazolyl]thiourea
N-(2-(2,3,4-trifluorophenyl)ethyl)-N'-[2-(4-trifluoromethyl)thiazolyl]thiourea
N-(2-(2,3,4-trifluorophenyl)ethyl)-N'-(2-benzothiazolyl)thiourea
N-(2-(2,3,4-trifluorophenyl)ethyl)-N'-[2-(6-fluoro)benzothiazolyl]thiourea
N-(2-(2,3,4-trifluorophenyl)ethyl)-N'-[2-(6-chloro)pyrazinyl]thiourea
N-(2-(2,3,4-trifluorophenyl)ethyl)-N'-[2-(4-ethyl)thiazolyl]thiourea
N-(2-(2,3,4-trifluorophenyl)ethyl)-N'-[2-(4-(3-pyridyl)thiazolyl)]thiourea
N-(2-(2,3,4-trifluorophenyl)ethyl)-N'-[2-(4-(3-nitrophenyl)thiazolyl)]thiourea N-(2-(2,3,4-trifluorophenyl)ethyl)-N'-(2-pyridyl)thiourea
N-(2-(2,3,4-trifluorophenyl)ethyl)-N'-[2-(6-bromo)pyridyl]thiourea
N-(2-(2,3,4-trifluorophenyl)ethyl)-N'-[2-(5-bromo)pyridyl]thiourea
N-(2-(2,3,4-trifluorophenyl)ethyl)-N'-[2-(6-chloro)pyridyl]thiourea
N-(2-(2,3,4-trifluorophenyl)ethyl)-N'-[2-(5-chloro)pyridyl]thiourea
N-(2-(2,3,4-trifluorophenyl)ethyl)-N'-[2-(6-methyl)pyridyl]thiourea
N-(2-(2,3,4-trifluorophenyl)ethyl)-N'-[2-(5-methyl)pyridyl]thiourea
N-(2-(2,3,4-trifluorophenyl)ethyl)-N'-[2-(6-trifluoromethyl)pyridyl]thiourea
N-(2-(2,3,4-trifluorophenyl)ethyl)-N'-[2-(5-trifluoromethyl)pyridyl]thiourea
N-(2-(2,3,4-trifluorophenyl)ethyl)-N'-[2-(6-ethyl)pyridyl]thiourea
N-(2-(2,3,4-trifluorophenyl)ethyl)-N'-[2-(5-ethyl)pyridyl]thiourea
N-(2-(2,3,4-trifluorophenyl)ethyl)-N'-[2-(5-chloro)pyrazinyl]thiourea
N-(2-(2,3,4-trifluorophenyl)ethyl)-N'-[2-(6-bromo)pyrazinyl]thiourea
N-(2-(2,3,4-trifluorophenyl)ethyl)-N'-[2-(5-bromo)pyrazinyl]thiourea
N-(2-(2,3,4-trifluorophenyl)ethyl)-N'-[(3-(6-bromo)pyridazinyl)]thiourea
N-(2-(2,3,4-trifluorophenyl)ethyl)-N'-[(3-(6-chloro)pyridazinyl)]thiourea
N-(2-(2,3,4-trifluorophenyl)ethyl)-N'-[2-(6-cyano)pyridyl]thiourea
N-(2-(2,3,4-trifluorophenyl)ethyl)-N'-[2-(5-cyano)pyridyl]thiourea
N-(2-(2,3,4-trifluorophenyl)ethyl)-N'-[2-(5-cyano)pyrazinyl]thiourea
N-(2-(2,3,4-trifluorophenyl)ethyl)-N'-[2-(6-cyano)pyrazinyl]thiourea
N-(2-(2,3,4-trifluorophenyl)ethyl)-N'-[(3-(6-cyano)pyridazinyl)]thiourea
N-(2-(2,3,4-trifluorophenyl)ethyl)-N'-(2-[1,3,4-thiadiazoyl])thiourea
N-(2-(2,3,4-trifluorophenyl)ethyl)-N'-(2-benzimidazolyl)thiourea
N-(2-(2,3,4-trifluorophenyl)ethyl)-N'-(2-imidazolyl)thiourea
N-(2-(2-fluoro-6-chlorophenyl)ethyl)-N'-(2-thiazolyl)thiourea
N-(2-(2-fluoro-6-chlorophenyl)ethyl)-N'-[2-(4-methyl)thiazolyl]thiourea
N-(2-(2-fluoro-6-chlorophenyl)ethyl)-N'-[2-(4,5-dimethyl)thiazolyl]thiourea
N-(2-(2-fluoro-6-chlorophenyl)ethyl)-N'-(2-benzothiazolyl)thiourea
N-(2-(2-fluoro-6-chlorophenyl)ethyl)-N'-[2-(6-fluoro)benzothiazolyl]thiourea
N-(2-(2-fluoro-6-chlorophenyl)ethyl)-N'-[2-(6-chloro)pyrazinyl]thiourea
N-(2-(2-fluoro-6-chlorophenyl)ethyl)-N'-[2-(4-(3-pyridyl)thiazolyl)]thiourea
N-(2-(2-fluoro-6-chlorophenyl)ethyl)-N'-[2-(4-(3-nitrophenyl)thiazolyl)]thiourea
N-(2-(2-fluoro-6-chlorophenyl)ethyl)-N'-(2-pyridyl)thiourea
N-(2-(2-fluoro-6-chlorophenyl)ethyl)-N'-[2-(6-bromo)pyridyl]thiourea
N-(2-(2-fluoro-6-chlorophenyl)ethyl)-N'-[2-(6-chloro)pyridyl]thiourea
N-(2-(2-fluoro-6-chlorophenyl)ethyl)-N'-[2-(6-methyl)pyridyl]thiourea
N-(2-(2-fluoro-6-chlorophenyl)ethyl)-N'-[2-(5-methyl)pyridyl]thiourea
N-(2-(2-fluoro-6-chlorophenyl)ethyl)-N'-[2-(6-trifluoromethyl)pyridyl]thiourea
N-(2-(2-fluoro-6-chlorophenyl)ethyl)-N'-[2-(5-trifluoromethyl)pyridyl]thiourea
N-(2-(2-fluoro-6-chlorophenyl)ethyl)-N'-[2-(6-ethyl)pyridyl]thiourea
N-(2-(2-fluoro-6-chlorophenyl)ethyl)-N'-[2-(5-ethyl)pyridyl]thiourea
N-(2-(2-fluoro-6-chlorophenyl)ethyl)-N'-[2-(6-bromo)pyrazinyl]thiourea
N-(2-(2-fluoro-6-chlorophenyl)ethyl)-N'-[(3-(6-bromo)pyridazinyl)]thiourea
N-(2-(2-fluoro-6-chlorophenyl)ethyl)-N'-[2-(6-cyano)pyridyl]thiourea
N-(2-(2-fluoro-6-chlorophenyl)ethyl)-N'-[2-(5-cyano)pyridyl]thiourea
N-(2-(2-fluoro-6-chlorophenyl)ethyl)-N'-[2-(5-cyano)pyrazinyl]thiourea
N-(2-(2-fluoro-6-chlorophenyl)ethyl)-N'-[2-(6-cyano)pyrazinyl]thiourea
N-(2-(2-fluoro-6-chlorophenyl)ethyl)-N'-[(3-(6-cyano)pyridazinyl)]thiourea
N-(2-(2-fluoro-6-chlorophenyl)ethyl)-N'-(2-[1,3,4-thiadiazoyl])thiourea
N-(2-(2-fluoro-6-chlorophenyl)ethyl)-N'-(2-benzimidazolyl)thiourea
N-(2-(2-fluoro-6-chlorophenyl)ethyl)-N'-(2-imidazolyl)thiourea
N-(2-(2,6-dimethoxyphenyl)ethyl)-N'-(2-thiazolyl)thiourea
N-(2-(2,6-dimethoxyphenyl)ethyl)-N'-[2-(4-methyl)thiazolyl]thiourea
N-(2-(2,6-dimethoxyphenyl)ethyl)-N'-[2-(4,5-dimethyl)thiazolyl]thiourea
N-(2-(2,6-dimethoxyphenyl)ethyl)-N'-(2-benzothiazolyl)thiourea
N-(2-(2,6-dimethoxyphenyl)ethyl)-N'-[2-(6-fluoro)benzothiazolyl]thiourea
N-(2-(2,6-dimethoxyphenyl)ethyl)-N'-[2-(6-chloro)pyrazinyl]thiourea
N-(2-(2,6-dimethoxyphenyl)ethyl)-N'-[2-(4-(3-pyridyl)thiazolyl)]thiourea
N-(2-(2,6-dimethoxyphenyl)ethyl)-N'-[2-(4-(3-nitrophenyl)thiazolyl)]thiourea
N-(2-(2,6-dimethoxyphenyl)ethyl)-N'-(2-pyridyl)thiourea
N-(2-(2,6-dimethoxyphenyl)ethyl)-N'-[2-(6-bromo)pyridyl]thiourea
N-(2-(2,6-dimethoxyphenyl)ethyl)-N'-[2-(6-chloro)pyridyl]thiourea
N-(2-(2,6-dimethoxyphenyl)ethyl)-N'-[2-(6-methyl)pyridyl]thiourea
N-(2-(2,6-dimethoxyphenyl)ethyl)-N'-[2-(5-methyl)pyridyl]thiourea
N-(2-(2,6-dimethoxyphenyl)ethyl)-N'-[2-(6-trifluoromethyl)pyridyl]thiourea
N-(2-(2,6-dimethoxyphenyl)ethyl)-N'-[2-(5-trifluoromethyl)pyridyl]thiourea
N-(2-(2,6-dimethoxyphenyl)ethyl)-N'-[2-(6-ethyl)pyridyl]thiourea
N-(2-(2,6-dimethoxyphenyl)ethyl)-N'-[2-(5-ethyl)pyridyl]thiourea
N-(2-(2,6-dimethoxyphenyl)ethyl)-N'-[2-(6-bromo)pyrazinyl]thiourea N-(2-(2,6-dimethoxyphenyl)ethyl)-N'-[(3-(6-bromo)pyridazinyl)]thiourea
N-(2-(2,6-dimethoxyphenyl)ethyl)-N'-[2-(6-cyano)pyridyl]thiourea
N-(2-(2,6-dimethoxyphenyl)ethyl)-N'-[2-(5-cyano)pyridyl]thiourea
N-(2-(2,6-dimethoxyphenyl)ethyl)-N'-[2-(5-cyano)pyrazinyl]thiourea
N-(2-(2,6-dimethoxyphenyl)ethyl)-N'-[2-(6-cyano)pyrazinyl]thiourea
N-(2-(2,6-dimethoxyphenyl)ethyl)-N'-[(3-(6-cyano)pyridazinyl)]thiourea
N-(2-(2,6-dimethoxyphenyl)ethyl)-N'-(2-[1,3,4-thiadiazoyl])thiourea
N-(2-(2,6-dimethoxyphenyl)ethyl)-N'-(2-benzimidazolyl)thiourea
N-(2-(2,6-dimethoxyphenyl)ethyl)-N'-(2-imidazolyl)thiourea
N-(2-(2,3,6-trichlorophenyl)ethyl)-N'-(2-thiazolyl)thiourea
N-(2-(2,3,6-trichlorophenyl)ethyl)-N'-[2-(4-methyl)thiazolyl]thiourea
N-(2-(2,3,6-trichlorophenyl)ethyl)-N'-[2-(4,5-dimethyl)thiazolyl]thiourea
N-(2-(2,3,6-trichlorophenyl)ethyl)-N'-[2-(4-cyano)thiazolyl]thiourea
N-(2-(2,3,6-trichlorophenyl)ethyl)-N'-[2-(4-trifluoromethyl)thiazolyl]thiourea
N-(2-(2,3,6-trichlorophenyl)ethyl)-N'-(2-benzothiazolyl)thiourea
N-(2-(2,3,6-trichlorophenyl)ethyl)-N'-[2-(6-fluoro)benzothiazolyl]thiourea
N-(2-(2,3,6-trichlorophenyl)ethyl)-N'-[2-(6-chloro)pyrazinyl]thiourea
N-(2-(2,3,6-trichlorophenyl)ethyl)-N'-[2-(4-ethyl)thiazolyl]thiourea
N-(2-(2,3,6-trichlorophenyl)ethyl)-N'-[2-(4-(3-pyridyl)thiazolyl)]thiourea
N-(2-(2,3,6-trichlorophenyl)ethyl)-N'-[2-(4-(3-nitrophenyl)thiazolyl)]thiourea
N-(2-(2,3,6-trichlorophenyl)ethyl)-N'-(2-pyridyl)thiourea
N-(2-(2,3,6-trichlorophenyl)ethyl)-N'-[2-(6-bromo)pyridyl]thiourea
N-(2-(2,3,6-trichlorophenyl)ethyl)-N'-[2-(5-bromo)pyridyl]thiourea
N-(2-(2,3,6-trichlorophenyl)ethyl)-N'-[2-(6-chloro)pyridyl]thiourea
N-(2-(2,3,6-trichlorophenyl)ethyl)-N'-[2-(5-chloro)pyridyl]thiourea
N-(2-(2,3,6-trichlorophenyl)ethyl)-N'-[2-(6-methyl)pyridyl]thiourea
N-(2-(2,3,6-trichlorophenyl)ethyl)-N'-[2-(5-methyl)pyridyl]thiourea
N-(2-(2,3,6-trichlorophenyl)ethyl)-N'-[2-(6-trifluoromethyl)pyridyl]thiourea
N-(2-(2,3,6-trichlorophenyl)ethyl)-N'-[2-(5-trifluoromethyl)pyridyl]thiourea
N-(2-(2,3,6-trichlorophenyl)ethyl)-N'-[2-(6-ethyl)pyridyl]thiourea
N-(2-(2,3,6-trichlorophenyl)ethyl)-N'-[2-(5-ethyl)pyridyl]thiourea
N-(2-(2,3,6-trichlorophenyl)ethyl)-N'-[2-(5-chloro)pyrazinyl]thiourea
N-(2-(2,3,6-trichlorophenyl)ethyl)-N'-[2-(6-bromo)pyrazinyl]thiourea
N-(2-(2,3,6-trichlorophenyl)ethyl)-N'-[2-(5-bromo)pyrazinyl]thiourea
N-(2-(2,3,6-trichlorophenyl)ethyl)-N'-[(3-(6-bromo)pyridazinyl)]thiourea
N-(2-(2,3,6-trichlorophenyl)ethyl)-N'-[(3-(6-chloro)pyridazinyl)]thiourea
N-(2-(2,3,6-trichlorophenyl)ethyl)-N'-[2-(6-cyano)pyridyl]thiourea
N-(2-(2,3,6-trichlorophenyl)ethyl)-N'-[2-(5-cyano)pyridyl]thiourea
N-(2-(2,3,6-trichlorophenyl)ethyl)-N'-[2-(5-cyano)pyrazinyl]thiourea
N-(2-(2,3,6-trichlorophenyl)ethyl)-N'-[2-(6-cyano)pyrazinyl]thiourea
N-(2-(2,3,6-trichlorophenyl)ethyl)-N'-[(3-(6-cyano)pyridazinyl)]thiourea
N-(2-(2,3,6-trichlorophenyl)ethyl)-N'-(2-[1,3,4-thiadiazoyl])thiourea
N-(2-(2,3,6-trichlorophenyl)ethyl)-N'-(2-benzimidazolyl)thiourea
N-(2-(2,3,6-trichlorophenyl)ethyl)-N'-(2-imidazolyl)thiourea
N-(2-(2,6-dichlorophenyl)ethyl)-N'-(2-thiazolyl)thiourea
N-(2-(2,6-dichlorophenyl)ethyl)-N'-[2-(4-methyl)thiazolyl]thiourea
N-(2-(2,6-dichlorophenyl)ethyl)-N'-[2-(4,5-dimethyl)thiazolyl]thiourea
N-(2-(2,6-dichlorophenyl)ethyl)-N'-(2-benzothiazolyl)thiourea
N-(2-(2,6-dichlorophenyl)ethyl)-N'-[2-(6-fluoro)benzothiazolyl]thiourea
N-(2-(2,6-dichlorophenyl)ethyl)-N'-[2-(6-chloro)pyrazinyl]thiourea
N-(2-(2,6-dichlorophenyl)ethyl)-N'-[2-(4-(3-pyridyl)thiazolyl)]thiourea
N-(2-(2,6-dichlorophenyl)ethyl)-N'-[2-(4-(3-nitrophenyl)thiazolyl)]thiourea
N-(2-(2,6-dichlorophenyl)ethyl)-N'-(2-pyridyl)thiourea
N-(2-(2,6-dichlorophenyl)ethyl)-N'-[2-(6-bromo)pyridyl]thiourea
N-(2-(2,6-dichlorophenyl)ethyl)-N'-[2-(6-chloro)pyridyl]thiourea
N-(2-(2,6-dichlorophenyl)ethyl)-N'-[2-(6-methyl)pyridyl]thiourea
N-(2-(2,6-dichlorophenyl)ethyl)-N'-[2-(5-methyl)pyridyl]thiourea
N-(2-(2,6-dichlorophenyl)ethyl)-N'-[2-(6-trifluoromethyl)pyridyl]thiourea
N-(2-(2,6-dichlorophenyl)ethyl)-N'-[2-(5-trifluoromethyl)pyridyl]thiourea
N-(2-(2,6-dichlorophenyl)ethyl)-N'-[2-(6-ethyl)pyridyl]thiourea
N-(2-(2,6-dichlorophenyl)ethyl)-N'-[2-(5-ethyl)pyridyl]thiourea
N-(2-(2,6-dichlorophenyl)ethyl)-N'-[2-(6-bromo)pyrazinyl]thiourea
N-(2-(2,6-dichlorophenyl)ethyl)-N'-[(3-(6-bromo)pyridazinyl)]thiourea
N-(2-(2,6-dichlorophenyl)ethyl)-N'-[2-(6-cyano)pyridyl]thiourea
N-(2-(2,6-dichlorophenyl)ethyl)-N'-[2-(5-cyano)pyridyl]thiourea
N-(2-(2,6-dichlorophenyl)ethyl)-N'-[2-(5-cyano)pyrazinyl]thiourea
N-(2-(2,6-dichlorophenyl)ethyl)-N'-[2-(6-cyano)pyrazinyl]thiourea
N-(2-(2,6-dichlorophenyl)ethyl)-N'-[(3-(6-cyano)pyridazinyl)]thiourea
N-(2-(2,6-dichlorophenyl)ethyl)-N'-(2-[1,3,4-thiadiazoyl])thiourea
N-(2-(2,6-dichlorophenyl)ethyl)-N'-(2-benzimidazolyl)thiourea N-(2-(2,6-dichlorophenyl)ethyl)-N'-(2-imidazolyl)thiourea
N-(2-(2,3,5-trichlorophenyl)ethyl)-N'-(2-thiazolyl)thiourea
N-(2-(2,3,5-trichlorophenyl)ethyl)-N'-[2-(4-methyl)thiazolyl]thiourea
N-(2-(2,3,5-trichlorophenyl)ethyl)-N'-[2-(4,5-dimethyl)thiazolyl]thiourea
N-(2-(2,3,5-trichlorophenyl)ethyl)-N'-[2-(4-cyano)thiazolyl]thiourea
N-(2-(2,3,5-trichlorophenyl)ethyl)-N'-[2-(4-trifluoromethyl)thiazolyl]thiourea
N-(2-(2,3,5-trichlorophenyl)ethyl)-N'-(2-benzothiazolyl)thiourea
N-(2-(2,3,5-trichlorophenyl)ethyl)-N'-[2-(6-fluoro)benzothiazolyl]thiourea
N-(2-(2,3,5-trichlorophenyl)ethyl)-N'-[2-(6-chloro)pyrazinyl]thiourea
N-(2-(2,3,5-trichlorophenyl)ethyl)-N'-[2-(4-ethyl)thiazolyl]thiourea
N-(2-(2,3,5-trichlorophenyl)ethyl)-N'-[2-(4-(3-pyridyl)thiazolyl)]thiourea
N-(2-(2,3,5-trichlorophenyl)ethyl)-N'-[2-(4-(3-nitrophenyl)thiazolyl)]thiourea
N-(2-(2,3,5-trichlorophenyl)ethyl)-N'-(2-pyridyl)thiourea
N-(2-(2,3,5-trichlorophenyl)ethyl)-N'-[2-(6-bromo)pyridyl]thiourea
N-(2-(2,3,5-trichlorophenyl)ethyl)-N'-[2-(5-bromo)pyridyl]thiourea
N-(2-(2,3,5-trichlorophenyl)ethyl)-N'-[2-(6-chloro)pyridyl]thiourea
N-(2-(2,3,5-trichlorophenyl)ethyl)-N'-[2-(5-chloro)pyridyl]thiourea
N-(2-(2,3,5-trichlorophenyl)ethyl)-N'-[2-(6-methyl)pyridyl]thiourea
N-(2-(2,3,5-trichlorophenyl)ethyl)-N'-[2-(5-methyl)pyridyl]thiourea
N-(2-(2,3,5-trichlorophenyl)ethyl)-N'-[2-(6-trifluoromethyl)pyridyl]thiourea
N-(2-(2,3,5-trichlorophenyl)ethyl)-N'-[2-(5-trifluoromethyl)pyridyl]thiourea
N-(2-(2,3,5-trichlorophenyl)ethyl)-N'-[2-(6-ethyl)pyridyl]thiourea
N-(2-(2,3,5-trichlorophenyl)ethyl)-N'-[2-(5-ethyl)pyridyl]thiourea
N-(2-(2,3,5-trichlorophenyl)ethyl)-N'-[2-(5-chloro)pyrazinyl]thiourea
N-(2-(2,3,5-trichlorophenyl)ethyl)-N'-[2-(6-bromo)pyrazinyl]thiourea
N-(2-(2,3,5-trichlorophenyl)ethyl)-N'-[2-(5-bromo)pyrazinyl]thiourea
N-(2-(2,3,5-trichlorophenyl)ethyl)-N'-[(3-(6-bromo)pyridazinyl)]thiourea
N-(2-(2,3,5-trichlorophenyl)ethyl)-N'-[(3-(6-chloro)pyridazinyl)]thiourea
N-(2-(2,3,5-trichlorophenyl)ethyl)-N'-[2-(6-cyano)pyridyl]thiourea
N-(2-(2,3,5-trichlorophenyl)ethyl)-N'-[2-(5-cyano)pyridyl]thiourea
N-(2-(2,3,5-trichlorophenyl)ethyl)-N'-[2-(5-cyano)pyrazinyl]thiourea
N-(2-(2,3,5-trichlorophenyl)ethyl)-N'-[2-(6-cyano)pyrazinyl]thiourea
N-(2-(2,3,5-trichlorophenyl)ethyl)-N'-[(3-(6-cyano)pyridazinyl)]thiourea
N-(2-(2,3,5-trichlorophenyl)ethyl)-N'-(2-[1,3,4-thiadiazoyl])thiourea
N-(2-(2,3,5-trichlorophenyl)ethyl)-N'-(2-benzimidazolyl)thiourea
N-(2-(2,3,5-trichlorophenyl)ethyl)-N'-(2-imidazolyl)thiourea
N-(2-(3,5-dichlorophenyl)ethyl)-N'-(2-thiazolyl)thiourea
N-(2-(3,5-dichlorophenyl)ethyl)-N'-[2-(4-methyl)thiazolyl]thiourea
N-(2-(3,5-dichlorophenyl)ethyl)-N'-[2-(4,5-dimethyl)thiazolyl]thiourea
N-(2-(3,5-dichlorophenyl)ethyl)-N'-[2-(4-cyano)thiazolyl]thiourea
N-(2-(3,5-dichlorophenyl)ethyl)-N'-[2-(4-trifluoromethyl)thiazolyl]thiourea
N-(2-(3,5-dichlorophenyl)ethyl)-N'-(2-benzothiazolyl)thiourea
N-(2-(3,5-dichlorophenyl)ethyl)-N'-[2-(6-fluoro)benzothiazolyl]thiourea
N-(2-(3,5-dichlorophenyl)ethyl)-N'-[2-(6-chloro)pyrazinyl]thiourea
N-(2-(3,5-dichlorophenyl)ethyl)-N'-[2-(4-ethyl)thiazolyl]thiourea
N-(2-(3,5-dichlorophenyl)ethyl)-N'-[2-(4-(3-pyridyl)thiazolyl)]thiourea
N-(2-(3,5-dichlorophenyl)ethyl)-N'-[2-(4-(3-nitrophenyl)thiazolyl)]thiourea
N-(2-(3,5-dichlorophenyl)ethyl)-N'-(2-pyridyl)thiourea
N-(2-(3,5-dichlorophenyl)ethyl)-N'-[2-(6-bromo)pyridyl]thiourea
N-(2-(3,5-dichlorophenyl)ethyl)-N'-[2-(5-bromo)pyridyl]thiourea
N-(2-(3,5-dichlorophenyl)ethyl)-N'-[2-(6-chloro)pyridyl]thiourea
N-(2-(3,5-dichlorophenyl)ethyl)-N'-[2-(5-chloro)pyridyl]thiourea
N-(2-(3,5-dichlorophenyl)ethyl)-N'-[2-(6-methyl)pyridyl]thiourea
N-(2-(3,5-dichlorophenyl)ethyl)-N'-[2-(5-methyl)pyridyl]thiourea
N-(2-(3,5-dichlorophenyl)ethyl)-N'-[2-(6-trifluoromethyl)pyridyl]thiourea
N-(2-(3,5-dichlorophenyl)ethyl)-N'-[2-(5-trifluoromethyl)pyridyl]thiourea
N-(2-(3,5-dichlorophenyl)ethyl)-N'-[2-(6-ethyl)pyridyl]thiourea
N-(2-(3,5-dichlorophenyl)ethyl)-N'-[2-(5-ethyl)pyridyl]thiourea
N-(2-(3,5-dichlorophenyl)ethyl)-N'-[2-(5-chloro)pyrazinyl]thiourea
N-(2-(3,5-dichlorophenyl)ethyl)-N'-[2-(6-bromo)pyrazinyl]thiourea
N-(2-(3,5-dichlorophenyl)ethyl)-N'-[2-(5-bromo)pyrazinyl]thiourea
N-(2-(3,5-dichlorophenyl)ethyl)-N'-[(3-(6-bromo)pyridazinyl)]thiourea
N-(2-(3,5-dichlorophenyl)ethyl)-N'-[(3-(6-chloro)pyridazinyl)]thiourea
N-(2-(3,5-dichlorophenyl)ethyl)-N'-[2-(6-cyano)pyridyl]thiourea
N-(2-(3,5-dichlorophenyl)ethyl)-N'-[2-(5-cyano)pyridyl]thiourea
N-(2-(3,5-dichlorophenyl)ethyl)-N'-[2-(5-cyano)pyrazinyl]thiourea
N-(2-(3,5-dichlorophenyl)ethyl)-N'-[2-(6-cyano)pyrazinyl]thiourea
N-(2-(3,5-dichlorophenyl)ethyl)-N'-[(3-(6-cyano)pyridazinyl)]thiourea
N-(2-(3,5-dichlorophenyl)ethyl)-N'-(2-[1,3,4-thiadiazoyl])thiourea
N-(2-(3,5-dichlorophenyl)ethyl)-N'-(2-benzimidazolyl)thiourea N-(2-(3,5-dichlorophenyl)ethyl)-N'-(2-imidazolyl)thiourea
N-(2-(3-fluorophenyl)ethyl)-N'-(2-thiazolyl)thiourea
N-(2-(3-fluorophenyl)ethyl)-N'-[2-(4-methyl)thiazolyl]thiourea
N-(2-(3-fluorophenyl)ethyl)-N'-[2-(4,5-dimethyl)thiazolyl]thiourea
N-(2-(3-fluorophenyl)ethyl)-N'-(2-benzothiazolyl)thiourea
N-(2-(3-fluorophenyl)ethyl)-N'-[2-(6-fluoro)benzothiazolyl]thiourea
N-(2-(3-fluorophenyl)ethyl)-N'-[2-(6-chloro)pyrazinyl]thiourea
N-(2-(3-fluorophenyl)ethyl)-N'-[2-(4-(3-pyridyl)thiazolyl)]thiourea
N-(2-(3-fluorophenyl)ethyl)-N'-[2-(4-(3-nitrophenyl)thiazolyl)]thiourea
N-(2-(3-fluorophenyl)ethyl)-N'-(2-pyridyl)thiourea
N-(2-(3-fluorophenyl)ethyl)-N'-[2-(6-bromo)pyridyl]thiourea
N-(2-(3-fluorophenyl)ethyl)-N'-[2-(6-chloro)pyridyl]thiourea
N-(2-(3-fluorophenyl)ethyl)-N'-[2-(6-methyl)pyridyl]thiourea
N-(2-(3-fluorophenyl)ethyl)-N'-[2-(5-methyl)pyridyl]thiourea
N-(2-(3-fluorophenyl)ethyl)-N'-[2-(6-trifluoromethyl)pyridyl]thiourea
N-(2-(3-fluorophenyl)ethyl)-N'-[2-(5-trifluoromethyl)pyridyl]thiourea
N-(2-(3-fluorophenyl)ethyl)-N'-[2-(6-ethyl)pyridyl]thiourea
N-(2-(3-fluorophenyl)ethyl)-N'-[2-(5-ethyl)pyridyl]thiourea
N-(2-(3-fluorophenyl)ethyl)-N'-[2-(6-bromo)pyrazinyl]thiourea
N-(2-(3-fluorophenyl)ethyl)-N'-[(3-(6-bromo)pyridazinyl)]thiourea
N-(2-(3-fluorophenyl)ethyl)-N'-[2-(6-cyano)pyridyl]thiourea
N-(2-(3-fluorophenyl)ethyl)-N'-[2-(5-cyano)pyridyl]thiourea
N-(2-(3-fluorophenyl)ethyl)-N'-[2-(5-cyano)pyrazinyl]thiourea
N-(2-(3-fluorophenyl)ethyl)-N'-[2-(6-cyano)pyrazinyl]thiourea
N-(2-(3-fluorophenyl)ethyl)-N'-[(3-(6-cyano)pyridazinyl)]thiourea
N-(2-(3-fluorophenyl)ethyl)-N'-(2-[1,3,4-thiadiazoyl])thiourea
N-(2-(3-fluorophenyl)ethyl)-N'-(2-benzimidazolyl)thiourea
N-(2-(3-fluorophenyl)ethyl)-N'-(2-imidazolyl)thiourea
N-(2-(2,4-dimethoxyphenyl)ethyl)-N'-(2-thiazolyl)thiourea
N-(2-(2,4-dimethoxyphenyl)ethyl)-N'-[2-(4-methyl)thiazolyl]thiourea
N-(2-(2,4-dimethoxyphenyl)ethyl)-N'-[2-(4,5-dimethyl)thiazolyl]thiourea
N-(2-(2,4-dimethoxyphenyl)ethyl)-N'-[2-(4-cyano)thiazolyl]thiourea
N-(2-(2,4-dimethoxyphenyl)ethyl)-N'-[2-(4-trifluoromethyl)thiazolyl]thiourea
N-(2-(2,4-dimethoxyphenyl)ethyl)-N'-(2-benzothiazolyl)thiourea
N-(2-(2,4-dimethoxyphenyl)ethyl)-N'-[2-(6-fluoro)benzothiazolyl]thiourea
N-(2-(2,4-dimethoxyphenyl)ethyl)-N'-[2-(6-chloro)pyrazinyl]thiourea
N-(2-(2,4-dimethoxyphenyl)ethyl)-N'-[2-(4-ethyl)thiazolyl]thiourea
N-(2-(2,4-dimethoxyphenyl)ethyl)-N'-[2-(4-(3-pyridyl)thiazolyl)]thiourea
N-(2-(2,4-dimethoxyphenyl)ethyl)-N'-[2-(4-(3-nitrophenyl)thiazolyl)]thiourea
N-(2-(2,4-dimethoxyphenyl)ethyl)-N'-(2-pyridyl)thiourea
N-(2-(2,4-dimethoxyphenyl)ethyl)-N'-[2-(6-bromo)pyridyl]thiourea
N-(2-(2,4-dimethoxyphenyl)ethyl)-N'-[2-(5-bromo)pyridyl]thiourea
N-(2-(2,4-dimethoxyphenyl)ethyl)-N'-[2-(6-chloro)pyridyl]thiourea
N-(2-(2,4-dimethoxyphenyl)ethyl)-N'-[2-(5-chloro)pyridyl]thiourea
N-(2-(2,4-dimethoxyphenyl)ethyl)-N'-[2-(6-methyl)pyridyl]thiourea
N-(2-(2,4-dimethoxy)phenyl)ethyl)-N'-[2-(5-methyl)pyridyl]thiourea
N-(2-(2,4-dimethoxyphenyl)ethyl)-N'-[2-(6-trifluoromethyl)pyridyl]thiourea
N-(2-(2,4-dimethoxyphenyl)ethyl)-N'-[2-(5-trifluoromethyl)pyridyl]thiourea
N-(2-(2,4-dimethoxyphenyl)ethyl)-N'-[2-(6-ethyl)pyridyl]thiourea
N-(2-(2,4-dimethoxyphenyl)ethyl)-N'-[2-(5-ethyl)pyridyl]thiourea
N-(2-(2,4-dimethoxyphenyl)ethyl)-N'-[2-(5-chloro)pyrazinyl]thiourea
N-(2-(2,4-dimethoxyphenyl)ethyl)-N'-[2-(6-bromo)pyrazinyl]thiourea
N-(2-(2,4-dimethoxyphenyl)ethyl)-N'-[2-(5-bromo)pyrazinyl]thiourea
N-(2-(2,4-dimethoxyphenyl)ethyl)-N'-[(3-(6-bromo)pyridazinyl)]thiourea
N-(2-(2,4-dimethoxyphenyl)ethyl)-N'-[(3-(6-chloro)pyridazinyl)]thiourea
N-(2-(2,4-dimethoxyphenyl)ethyl)-N'-[2-(6-cyano)pyridyl]thiourea
N-(2-(2,4-dimethoxyphenyl)ethyl)-N'-[2-(5-cyano)pyridyl]thiourea
N-(2-(2,4-dimethoxyphenyl)ethyl)-N'-[2-(5-cyano)pyrazinyl]thiourea
N-(2-(2,4-dimethoxyphenyl)ethyl)-N'-[2-(6-cyano)pyrazinyl]thiourea
N-(2-(2,4-dimethoxyphenyl)ethyl)-N'-[(3-(6-cyano)pyridazinyl)]thiourea
N-(2-(2,4-dimethoxyphenyl)ethyl)-N'-(2-[1,3,4-thiadiazoyl])thiourea
N-(2-(2,4-dimethoxyphenyl)ethyl)-N'-(2-benzimidazolyl)thiourea
N-(2-(2,4-dimethoxyphenyl)ethyl)-N'-(2-imidazolyl)thiourea
N-[(4-methyl)-3-pentenyl]-N'-(2-thiazolyl)thiourea
N-[(4-methyl)-3-pentenyl]-N'-[2-(4-methyl)thiazolyl]thiourea
N-[(4-methyl)-3-pentenyl]-N'-[2-(4,5-dimethyl)thiazolyl]thiourea
N-[(4-methyl)-3-pentenyl]-N'-[2-(4-cyano)thiazolyl]thiourea
N-[(4-methyl)-3-pentenyl]-N'-[2-(4-trifluoromethyl)thiazolyl]thiourea
N-[(4-methyl)-3-pentenyl]-N'-(2-benzothiazolyl)thiourea
N-[(4-methyl)-3-pentenyl]-N'-[2-(6-fluoro)benzothiazolyl]thiourea
N-[(4-methyl)-3-pentenyl]-N'-[2-(6-chloro)pyrazinyl]thiourea
N-[(4-methyl)-3-pentenyl]-N'-[2-(4-ethyl)thiazolyl]thiourea
N-[(4-methyl)-3-pentenyl]-N'-[2-(4-(3-pyridyl)thiazolyl)]thiourea
N-[(4-methyl)-3-pentenyl]-N'-[2-(4-(3-nitrophenyl)thiazolyl)]thiourea N-[(4-methyl)-3-pentenyl]-N'-(2-pyridyl)thiourea
N-[(4-methyl)-3-pentenyl]-N'-[2-(6-bromo)pyridyl]thiourea
N-[(4-methyl)-3-pentenyl]-N'-[2-(5-bromo)pyridyl]thiourea
N-[(4-methyl)-3-pentenyl]-N'-[2-(6-chloro)pyridyl]thiourea
N-[(4-methyl)-3-pentenyl]-N'-[2-(5-chloro)pyridyl]thiourea
N-[(4-methyl)-3-pentenyl]-N'-[2-(6-methyl)pyridyl]thiourea
N-[(4-methyl)-3-pentenyl]-N'-[2-(5-methyl)pyridyl]thiourea
N-[(4-methyl)-3-pentenyl]-N'-[2-(6-trifluoromethyl)pyridyl]thiourea
N-[(4-methyl)-3-pentenyl]-N'-[2-(5-trifluoromethyl)pyridyl]thiourea
N-[(4-methyl)-3-pentenyl]-N'-[2-(6-ethyl)pyridyl]thiourea
N-[(4-methyl)-3-pentenyl]-N'-[2-(5-ethyl)pyridyl]thiourea
N-[(4-methyl)-3-pentenyl]-N'-[2-(5-chloro)pyrazinyl]thiourea
N-[(4-methyl)-3-pentenyl]-N'-[2-(6-bromo)pyrazinyl]thiourea
N-[(4-methyl)-3-pentenyl]-N'-[2-(5-bromo)pyrazinyl]thiourea
N-[(4-methyl)-3-pentenyl]-N'-[(3-(6-bromo)pyridazinyl)]thiourea
N-[(4-methyl)-3-pentenyl]-N'-[(3-(6-chloro)pyridazinyl)]thiourea
N-[(4-methyl)-3-pentenyl]-N'-[2-(6-cyano)pyridyl]thiourea
N-[(4-methyl)-3-pentenyl]-N'-[2-(5-cyano)pyridyl]thiourea
N-[(4-methyl)-3-pentenyl]-N'-[2-(5-cyano)pyrazinyl]thiourea
N-[(4-methyl)-3-pentenyl]-N'-[2-(6-cyano)pyrazinyl]thiourea
N-[(4-methyl)-3-pentenyl]-N'-[(3-(6-cyano)pyridazinyl)-]thiourea
N-[(4-methyl)-3-pentenyl]-N'-(2-[1,3,4-thiadiazoyl])thiourea
N-[(4-methyl)-3-pentenyl]-N'-(2-benzimidazolyl)thiourea
N-[(4-methyl)-3-pentenyl]-N'-(2-imidazolyl)thiourea
N-(2-cis-phenylcyclopropyl)-N'-[2-(4-methyl)thiazolyl]thiourea
N-(2-cis-phenylcyclopropyl)-N'-[2-(4,5-dimethyl)thiazolyl]thiourea
N-(2-cis-phenylcyclopropyl)-N'-(2-benzothiazolyl)thiourea
N-(2-cis-phenylcyclopropyl)-N'-[2-(6-fluoro)benzothiazolyl]thiourea
N-(2-cis-phenylcyclopropyl)-N'-[2-(6-chloro)pyrazinyl]thiourea
N-(2-cis-phenylcyclopropyl)-N'-[2-(4-(3-pyridyl)thiazolyl)]thiourea
N-(2-cis-phenylcyclopropyl)-N'-[2-(4-(3-nitrophenyl)thiazolyl)]thiourea
N-(2-cis-phenylcyclopropyl)-N'-[2-(6-bromo)pyridyl]thiourea
N-(2-cis-phenylcyclopropyl)-N'-[2-(6-chloro)pyridyl]thiourea
N-(2-cis-phenylcyclopropyl)-N'-[2-(6-methyl)pyridyl]thiourea
N-(2-cis-phenylcyclopropyl)-N'-[2-(6-trifluoromethyl)pyridyl]thiourea
N-(2-cis-phenylcyclopropyl)-N'-[2-(6-ethyl)pyridyl]thiourea
N-(2-cis-phenylcyclopropyl)-N'-[2-(6-bromo)pyrazinyl]thiourea
N-(2-cis-phenylcyclopropyl)-N'-[2-(6-cyano)pyridyl]thiourea
N-(2-cis-phenylcyclopropyl)-N'-[2-(5-cyano)pyrazinyl]thiourea
N-(2-cis-phenylcyclopropyl)-N'-[2-(6-cyano)pyrazinyl]thiourea
N-(2-cis-phenylcyclopropyl)-N'-[(3-(6-cyano)pyridazinyl)]thiourea
N-(2-cis-phenylcyclopropyl)-N'-(2-[1,3,4-thiadiazoyl])thiourea
N-(2-cis-phenylcyclopropyl)-N'-(2-benzimidazolyl)thiourea
N-(2-cis-phenylcyclopropyl)-N'-(2-imidazolyl)thiourea
N-[(2-methyl)-2-(2,6-dichlorophenyl)ethyl]-N'-(2-thiazolyl)thiourea
N-[(2-methyl)-2-(2,6-dichlorophenyl)ethyl]-N'-[2-(4-methyl)thiazolyl]thiourea
N-[(2-methyl)-2-(2,6-dichlorophenyl)ethyl]-N'-[2-(4,5-dimethyl)thiazolyl]thiourea
N-[(2-methyl)-2-(2,6-dichlorophenyl)ethyl]-N'-[2-(4-cyano)thiazolyl]thiourea
N-[(2-methyl)-2-(2,6-dichlorophenyl)ethyl]-N'-[2-(4-trifluoromethyl)thiazolyl]thiourea
N-[(2-methyl)-2-(2,6-dichlorophenyl)ethyl]-N'-(2-benzothiazolyl)thiourea
N-[(2-methyl)-2-(2,6-dichlorophenyl)ethyl]-N'-[2-(6-fluoro)benzothiazolyl]thiourea
N-[(2-methyl)-2-(2,6-dichlorophenyl)ethyl]-N'-[2-(6-chloro)pyrazinyl]thiourea
N-[(2-methyl)-2-(2,6-dichlorophenyl)ethyl]-N'-[2-(4-ethyl)thiazolyl]thiourea
N-[(2-methyl)-2-(2,6-dichlorophenyl)ethyl]-N'-[2-(4-(3-pyridyl)thiazolyl)]thiourea
N-[(2-methyl)-2-(2,6-dichlorophenyl)ethyl]-N'-[2-(4-(3-nitrophenyl)thiazolyl)]thiourea
N-[(2-methyl)-2-(2,6-dichlorophenyl)ethyl]-N'-(2-pyridyl)thiourea
N-[(2-methyl)-2-(2,6-dichlorophenyl)ethyl]-N'-[2-(6-bromo)pyridyl]thiourea
N-[(2-methyl)-2-(2,6-dichlorophenyl)ethyl]-N'-[2-(5-bromo)pyridyl]thiourea
N-[(2-methyl)-2-(2,6-dichlorophenyl)ethyl]-N'-[2-(6-chloro)pyridyl]thiourea
N-[(2-methyl)-2-(2,6-dichlorophenyl)ethyl]-N'-[2-(5-chloro)pyridyl]thiourea
N-[(2-methyl)-2-(2,6-dichlorophenyl)ethyl]-N'-[2-(6-methyl)pyridyl]thiourea
N-[(2-methyl)-2-(2,6-dichlorophenyl)ethyl]-N'-[2-(5-methyl)pyridyl]thiourea
N-[(2-methyl)-2-(2,6-dichlorophenyl)ethyl]-N'-[2-(6-trifluoromethyl)pyridyl]thiourea
N-[(2-methyl)-2-(2,6-dichlorophenyl)ethyl]-N'-[2-(5-trifluoromethyl)pyridyl]thiourea
N-[(2-methyl)-2-(2,6-dichlorophenyl)ethyl]-N'-[2-(6-ethyl)pyridyl]thiourea
N-[(2-methyl)-2-(2,6-dichlorophenyl)ethyl]-N'-[2-(5-ethyl)pyridyl]thiourea
N-[(2-methyl)-2-(2,6-dichlorophenyl)ethyl]-N'-[2-(5-chloro)pyrazinyl]thiourea
N-[(2-methyl)-2-(2,6-dichlorophenyl)ethyl]-N'-[2-(6-bromo)pyrazinyl]thiourea
N-[(2-methyl)-2-(2,6-dichlorophenyl)ethyl]-N'-[2-(5-bromo)pyrazinyl]thiourea
N-[(2-methyl)-2-(2,6-dichlorophenyl)ethyl]-N'-[(3-(6-bromo)pyridazinyl)]thiourea
N-[(2-methyl)-2-(2,6-dichlorophenyl)ethyl]-N'-[(3-(6-chloro)pyridazinyl)]thiourea
N-[(2-methyl)-2-(2,6-dichlorophenyl)ethyl]-N'-[2-(6-cyano)pyridyl]thiourea
N-[(2-methyl)-2-(2,6-dichlorophenyl)ethyl]-N'-[2-(5-cyano)pyridyl]thiourea
N-[(2-methyl)-2-(2,6-dichlorophenyl)ethyl]-N'-[2-(5-cyano)pyrazinyl]thiourea
N-[(2-methyl)-2-(2,6-dichlorophenyl)ethyl]-N'-[2-(6-cyano)pyrazinyl]thiourea N-[(2-methyl)-2-(2,6-dichlorophenyl)ethyl]-N'-[(3-(6-cyano)pyridazinyl)]thiourea
N-[(2-methyl)-2-(2,6-dichlorophenyl)ethyl]-N'-(2-1,3,4-thiadiazoyl])thiourea
N-[(2-methyl)-2-(2,6-dichlorophenyl)ethyl]-N'-(2-benzimidazolyl)thiourea
N-[(2-methyl)-2-(2,6-dichlorophenyl)ethyl]-N'-(2-imidazolyl)thiourea
N-[(2,2-dimethyl)-2-(2-fluoro-6-chlorophenyl)ethyl]-N'-(2-thiazolyl)thiourea
N-[(2,2-dimethyl)-2-(2-fluoro-6-chlorophenyl)ethyl]-N'-[2-(4-methyl)thiazolyl]thiourea
N-[(2,2-dimethyl)-2-(2-fluoro-6-chlorophenyl)ethyl]-N'-[2-(4,5-dimethyl)thiazolyl]thiourea
N-[(2,2-dimethyl)-2-(2-fluoro-6-chlorophenyl)ethyl]-N'-[2-(4-cyano)thiazolyl]thiourea
N-[(2,2-dimethyl)-2-(2-fluoro-6-chlorophenyl)ethyl]-N'-[2-(4-trifluoromethyl)thiazolyl]thiourea
N-[(2,2-dimethyl)-2-(2-fluoro-6-chlorophenyl)ethyl]-N'-(2-benzothiazolyl)thiourea
N-[(2,2-dimethyl)-2-(2-fluoro-6-chlorophenyl)ethyl]-N'-[2-(6-fluoro)benzothiazolyl]thiourea
N-[(2,2-dimethyl)-2-(2-fluoro-6-chlorophenyl)ethyl]-N'-[2-(6-chloro)pyrazinyl]thiourea
N-[(2,2-dimethyl)-2-(2-fluoro-6-chlorophenyl)ethyl]-N'-[2-(4-ethyl)thiazolyl]thiourea
N-[(2,2-dimethyl)-2-(2-fluoro-6-chlorophenyl)ethyl]-N'-[2-(4-(3-pyridyl)thiazolyl)]thiourea
N-[(2,2-dimethyl)-2-(2-fluoro-6-chlorophenyl)ethyl]-N'-[2-(4-(3-nitrophenyl)thiazolyl)]thiourea
N-[(2,2-dimethyl)-2-(2-fluoro-6-chlorophenyl)ethyl]-N'-(2-pyridyl)thiourea
N-[(2,2-dimethyl)-2-(2-fluoro-6-chlorophenyl)ethyl]-N'-[2-(6-bromo)pyridyl]thiourea
N-[(2,2-dimethyl)-2-(2-fluoro-6-chlorophenyl)ethyl]-N'-[2-(5-bromo)pyridyl]thiourea
N-[(2,2-dimethyl)-2-(2-fluoro-6-chlorophenyl)ethyl]-N'-[2-(6-chloro)pyridyl]thiourea
N-[(2,2-dimethyl)-2-(2-fluoro-6-chlorophenyl)ethyl]-N'-[2-(5-chloro)pyridyl]thiourea
N-[(2,2-dimethyl)-2-(2-fluoro-6-chlorophenyl)ethyl]-N'-[2-(6-methyl)pyridyl]thiourea
N-[(2,2-dimethyl)-2-(2-fluoro-6-chlorophenyl)ethyl]-N'-[2-(5-methyl)pyridyl]thiourea
N-[(2,2-dimethyl)-2-(2-fluoro-6-chlorophenyl)ethyl]-N'-[2-(6-trifluoromethyl)pyridyl]thiourea
N-[(2,2-dimethyl)-2-(2-fluoro-6-chlorophenyl)ethyl]-N'-[2-(5-trifluoromethyl)pyridyl]thiourea
N-[(2,2-dimethyl)-2-(2-fluoro-6-chlorophenyl)ethyl]-N'-[2-(6-ethyl)pyridyl]thiourea
N-[(2,2-dimethyl)-2-(2-fluoro-6-chlorophenyl)ethyl]-N'-[2-(5-ethyl)pyridyl]thiourea
N-[(2,2-dimethyl)-2-(2-fluoro-6-chlorophenyl)ethyl]-N'-[2-(5-chloro)pyrazinyl]thiourea
N-[(2,2-dimethyl)-2-(2-fluoro-6-chlorophenyl)ethyl]-N'-[2-(6-bromo)pyrazinyl]thiourea
N-[(2,2-dimethyl)-2-(2-fluoro-6-chlorophenyl)ethyl]-N'-[2-(5-bromo)pyrazinyl]thiourea
N-[(2,2-dimethyl)-2-(2-fluoro-6-chlorophenyl)ethyl]-N'-[(3-(6-bromo)pyridazinyl)]thiourea
N-[(2,2-dimethyl)-2-(2-fluoro-6-chlorophenyl)ethyl]-N'-[(3-(6-chloro)pyridazinyl)]thiourea
N-[(2,2-dimethyl)-2-(2-fluoro-6-chlorophenyl)ethyl]-N'-[2-(6-cyano)pyridyl]thiourea
N-[(2,2-dimethyl)-2-(2-fluoro-6-chlorophenyl)ethyl]-N'-[2-(5-cyano)pyridyl]thiourea
N-[(2,2-dimethyl)-2-(2-fluoro-6-chlorophenyl)ethyl]-N'-[2-(5-cyano)pyrazinyl]thiourea
N-[(2,2-dimethyl)-2-(2-fluoro-6-chlorophenyl)ethyl]-N'-[2-(6-cyano)pyrazinyl]thiourea
N-[(2,2-dimethyl)-2-(2-fluoro-6-chlorophenyl)ethyl]-N'-[(3-(6-cyano)pyridazinyl)]thiourea
N-[(2,2-dimethyl)-2-(2-fluoro-6-chlorophenyl)ethyl]-N'-(2-[1,3,4-thiadiazoyl])thiourea
N-[(2,2-dimethyl)-2-(2-fluoro-6-chlorophenyl)ethyl]-N'-(2-benzimidazolyl)thiourea
N-[(2,2-dimethyl)-2-(2-fluoro-6-chlorophenyl)ethyl]-N'-(2-imidazolyl)thiourea
N-[2-(2-pyridyl)ethyl]-N'-[2-(4,5-dimethyl)thiazolyl]thiourea
N-[2-(2-pyridyl)ethyl]-N'-(2-benzothiazolyl)thiourea
N-[2-(2-pyridyl)ethyl]-N'-[2-(6-fluoro)benzothiazolyl]thiourea
N-[2-(2-pyridyl)ethyl]-N'-[2-(6-chloro)pyrazinyl thiourea
N-[2-(2-pyridyl)ethyl]-N'-[2-(4-(3-pyridyl)thiazolyl)]thiourea
N-[2-(2-pyridyl)ethyl]-N'-[2-(4-(3-nitrophenyl)thiazolyl)]thiourea
N-[2-(2-pyridyl)ethyl]-N'-[2-(6-bromo)pyrazinyl]thiourea
N-[2-(2-pyridyl)ethyl]-N'-[2-(6-cyano)pyridyl]thiourea
N-[2-(2-pyridyl)ethyl]-N'-[2-(6-cyano)pyrazinyl]thiourea
N-[2-(2-pyridyl)ethyl]-N'-(2-[1,3,4-thiadiazoyl])thiourea
N-[2-(2-pyridyl)ethyl]-N'-(2-benzimidazolyl)thiourea
N-[2-(2-pyridyl)ethyl]-N'-(2-imidazolyl)thiourea
N-[2-(2-(6-methoxy)pyridyl)ethyl]-N'-[2-(4,5-dimethyl)thiazolyl]thiourea
N-[2-(2-(6-methoxy)pyridyl)ethyl]-N'-(2-benzothiazolyl)thiourea
N-[2-(2-(6-methoxy)pyridyl)ethyl]-N'-[2-(6-fluoro)benzothiazolyl]thiourea
N-[2-(2-(6-methoxy)pyridyl)ethyl]-N'-[2-(6-chloro)pyrazinyl]thiourea
N-[2-(2-(6-methoxy)pyridyl)ethyl]-N'-[2-(4-(3-pyridyl)thiazolyl)]thiourea
N-[2-(2-(6-methoxy)pyridyl)ethyl]-N'-[2-(4-(3-nitrophenyl)thiazolyl)]thiourea
N-[2-(2-(6-methoxy)pyridyl)ethyl]-N'-[2-(6-bromo)pyridyl]thiourea
N-[2-(2-(6-methoxy)pyridyl)ethyl]-N'-[2-(6-chloro)pyridyl]thiourea
N-[2-(2-(6-methoxy)pyridyl)ethyl]-N'-[2-(6-methyl)pyridyl]thiourea
N-[2-(2-(6-methoxy)pyridyl)ethyl]-N'-[2-(6-trifluoromethyl)pyridyl]thiourea
N-[2-(2-(6-methoxy)pyridyl)ethyl]-N'-[2-(6-ethyl)pyridyl]thiourea
N-[2-(2-(6-methoxy)pyridyl)ethyl]-N'-[2-(5-ethyl)pyridyl]thiourea
N-[2-(2-(6-methoxy)pyridyl)ethyl]-N'-[2-(6-bromo)pyrazinyl]thiourea
N-[2-(2-(6-methoxy)pyridyl)ethyl]-N'-[(3-(6-bromo)pyridazinyl)]thiourea
N-[2-(2-(6-methoxy)pyridyl)ethyl]-N'-[2-(6-cyano)pyridyl]thiourea
N-[2-(2-(6-methoxy)pyridyl)ethyl]-N'-[2-(5-cyano)pyridyl]thiourea
N-[2-(2-(6-methoxy)pyridyl)ethyl]-N'-[2-(5-cyano)pyrazinyl]thiourea
N-[2-(2-(6-methoxy)pyridyl)ethyl]-N'-[2-(6-cyano)pyrazinyl]thiourea
N-[2-(2-(6-methoxy)pyridyl)ethyl]-N'-[(3-(6-cyano)pyridazinyl)]thiourea
N-[2-(2-(6-methoxy)pyridyl)ethyl]-N'-(2-[1,3,4-thiadiazoyl])thiourea
N-[2-(2-(6-methoxy)pyridyl)ethyl]-N'-(2-benzimidazolyl)thiourea N-[2-(2-(6-methoxy)pyridyl)ethyl]-N'-(2-imidazolyl)thiourea
N-[2-(2-(6-ethoxy)pyridyl)ethyl]-N'-[2-(4,5-dimethyl)thiazolyl]thiourea
N-[2-(2-(6-ethoxy)pyridyl)ethyl]-N'-(2-benzothiazolyl)thiourea
N-[2-(2-(6-ethoxy)pyridyl)ethyl]-N'-[2-(6-fluoro)benzothiazolyl]thiourea
N-[2-(2-(6-ethoxy)pyridyl)ethyl]-N'-[2-(6-chloro)pyrazinyl]thiourea
N-[2-(2-(6-ethoxy)pyridyl)ethyl]-N'-[2-(4-(3-pyridyl)thiazolyl)]thiourea
N-[2-(2-(6-ethoxy)pyridyl)ethyl]-N'-[2-(4-(3-nitrophenyl)thiazolyl)]thiourea
N-[2-(2-(6-ethoxy)pyridyl)ethyl]-N'-[2-(6-bromo)pyridyl]thiourea
N-[2-(2-(6-ethoxy)pyridyl)ethyl]-N'-[2-(6-chloro)pyridyl]thiourea
N-[2-(2-(6-ethoxy)pyridyl)ethyl]-N'-[2-(6-methyl)pyridyl]thiourea
N-[2-(2-(6-ethoxy)pyridyl)ethyl]-N'-[2-(6-trifluoromethyl)pyridyl]thiourea
N-[2-(2-(6-ethoxy)pyridyl)ethyl]-N'-[2-(6-ethyl)pyridyl]thiourea
N-[2-(2-(6-ethoxy)pyridyl)ethyl]-N'-[2-(5-ethyl)pyridyl]thiourea
N-[2-(2-(6-ethoxy)pyridyl)ethyl]-N'-[2-(6-bromo)pyrazinyl]thiourea
N-[2-(2-(6-ethoxy)pyridyl)ethyl]-N'-[(3-(6-bromo)pyridazinyl)]thiourea
N-[2-(2-(6-ethoxy)pyridyl)ethyl]-N'-[2-(6-cyano)pyridyl]thiourea
N-[2-(2-(6-ethoxy)pyridyl)ethyl]-N'-[2-(5-cyano)pyrazinyl]thiourea
N-[2-(2-(6-ethoxy)pyridyl)ethyl]-N'-[2-(6-cyano)pyrazinyl]thiourea
N-[2-(2-(6-ethoxy)pyridyl)ethyl]-N'-[(3-(6-cyano)pyridazinyl)]thiourea
N-[2-(2-(6-ethoxy)pyridyl)ethyl]-N'-(2-[1,3,4-thiadiazoyl])thiourea
N-[2-(2-(6-ethoxy)pyridyl)ethyl]-N'-(2-benzimidazolyl)thiourea
N-[2-(2-(6-ethoxy)pyridyl)ethyl]-N'-(2-imidazolyl)thiourea
N-[2-(2-(6-fluoro)pyridyl)ethyl]-N'-[2-(4,5-dimethyl)thiazolyl]thiourea
N-[2-(2-(6-fluoro)pyridyl)ethyl]-N'-(2-benzothiazolyl)thiourea
N-[2-(2-(6-fluoro)pyridyl)ethyl]-N'-[2-(6-fluoro)benzothiazolyl]thiourea
N-[2-(2-(6-fluoro)pyridyl)ethyl]-N'-[2-(6-chloro)pyrazinyl]thiourea
N-[2-(2-(6-fluoro)pyridyl)ethyl]-N'-[2-(4-(3-pyridyl)thiazolyl)]thiourea
N-[2-(2-(6-fluoro)pyridyl)ethyl]-N'-[2-(4-(3-nitrophenyl)thiazolyl)]thiourea
N-[2-(2-(6-fluoro)pyridyl)ethyl]-N'-[2-(6-bromo)pyridyl]thiourea
N-[2-(2-(6-fluoro)pyridyl)ethyl]-N'-[2-(6-chloro)pyridyl]thiourea
N-[2-(2-(6-fluoro)pyridyl)ethyl]-N'-[2-(6-methyl)pyridyl]thiourea
N-[2-(2-(6-fluoro)pyridyl)ethyl]-N'-[2-(6-trifluoromethyl)pyridyl]thiourea
N-[2-(2-(6-fluoro)pyridyl)ethyl]-N'-[2-(6-bromo)pyrazinyl]thiourea
N-[2-(2-(6-fluoro)pyridyl)ethyl]-N'-[(3-(6-bromo)pyridazinyl)]thiourea
N-[2-(2-(6-fluoro)pyridyl)ethyl]-N'-[2-(6-cyano)pyridyl]thiourea
N-[2-(2-(6-fluoro)pyridyl)ethyl]-N'-[2-(5-cyano)pyrazinyl]thiourea
N-[2-(2-(6-fluoro)pyridyl)ethyl]-N'-[2-(6-cyano)pyrazinyl]thiourea
N-[2-(2-(6-fluoro)pyridyl)ethyl]-N'-[(3-(6-cyano)pyridazinyl)]thiourea
N-[2-(2-(6-fluoro)pyridyl)ethyl]-N'-(2-[1,3,4-thiadiazoyl])thiourea
N-[2-(2-(6-fluoro)pyridyl)ethyl]-N'-(2-benzimidazolyl)thiourea
N-[2-(2-(6-fluoro)pyridyl)ethyl]-N'-(2-imidazolyl)thiourea
N-[2-(2-(5-fluoro)pyridyl)ethyl]-N'-(2-thiazolyl)thiourea
N-[2-(2-(5-fluoro)pyridyl)ethyl]-N'-[2-(4-methyl)thiazolyl]thiourea
N-[2-(2-(5-fluoro)pyridyl)ethyl]-N'-[2-(4,5-dimethyl)thiazolyl]thiourea
N-[2-(2-(5-fluoro)pyridyl)ethyl]-N'-[2-(4-cyano)thiazolyl]thiourea
N-[2-(2-(5-fluoro)pyridyl)ethyl]-N'-[2-(4-trifluoromethyl)thiazolyl]thiourea
N-[2-(2-(5-fluoro)pyridyl)ethyl]-N'-(2-benzothiazolyl)thiourea
N-[2-(2-(5-fluoro)pyridyl)ethyl]-N'-[2-(6-fluoro)benzothiazolyl]thiourea
N-[2-(2-(5-fluoro)pyridyl)ethyl]-N'-[2-(6-chloro)pyrazinyl]thiourea
N-[2-(2-(5-fluoro)pyridyl)ethyl]-N'-[2-(4-ethyl)thiazolyl]thiourea
N-[2-(2-(5-fluoro)pyridyl)ethyl]-N'-[2-(4-(3-pyridyl)thiazolyl)]thiourea
N-[2-(2-(5-fluoro)pyridyl)ethyl]-N'-[2-(4-(3-nitrophenyl)thiazolyl)]thiourea
N-[2-(2-(5-fluoro)pyridyl)ethyl]-N'-(2-pyridyl)thiourea
N-[2-(2-(5-fluoro)pyridyl)ethyl]-N'-[2-(6-bromo)pyridyl]thiourea
N-[2-(2-(5-fluoro)pyridyl)ethyl]-N'-[2-(5-bromo)pyridyl]thiourea
N-[2-(2-(5-fluoro)pyridyl)ethyl]-N'-[2-(6-chloro)pyridyl]thiourea
N-[2-(2-(5-fluoro)pyridyl)ethyl]-N'-[2-(5-chloro)pyridyl]thiourea
N-[2-(2-(5-fluoro)pyridyl)ethyl]-N'-[2-(6-methyl)pyridyl]thiourea
N-[2-(2-(5-fluoro)pyridyl)ethyl]-N'-[2-(5-methyl)pyridyl]thiourea
N-[2-(2-(5-fluoro)pyridyl)ethyl]-N'-[2-(6-trifluoromethyl)pyridyl]thiourea
N-[2-(2-(5-fluoro)pyridyl)ethyl]-N'-[2-(5-trifluoromethyl)pyridyl]thiourea
N-[2-(2-(5-fluoro)pyridyl)ethyl]-N'-[2-(6-ethyl)pyridyl]thiourea
N-[2-(2-(5-fluoro)pyridyl)ethyl]-N'-[2-(5-ethyl)pyridyl]thiourea
N-[2-(2-(5-fluoro)pyridyl)ethyl]-N'-[2-(5-chloro)pyrazinyl]thiourea
N-[2-(2-(5-fluoro)pyridyl)ethyl]-N'-[2-(6-bromo)pyrazinyl]thiourea
N-[2-(2-(5-fluoro)pyridyl)ethyl]-N'-[2-(5-bromo)pyrazinyl]thiourea
N-[2-(2-(5-fluoro)pyridyl)ethyl]-N'-[(3-(6-bromo)pyridazinyl)]thiourea
N-[2-(2-(5-fluoro)pyridyl)ethyl]-N'-[(3-(6-chloro)pyridazinyl)]thiourea
N-[2-(2-(5-fluoro)pyridyl)ethyl]-N'-[2-(6-cyano)pyridyl]thiourea N-[2-(2-(5-fluoro)pyridyl)ethyl]-N'-[2-(5-cyano)pyridyl]thiourea
N-[2-(2-(5-fluoro)pyridyl)ethyl]-N'-[2-(5-cyano)pyrazinyl]thiourea
N-[2-(2-(5-fluoro)pyridyl)ethyl]-N'-[2-(6-cyano)pyrazinyl]thiourea
N-[2-(2-(5-fluoro)pyridyl)ethyl]-N'-[(3-(6-cyano)pyridazinyl)]thiourea
N-[2-(2-(5-fluoro)pyridyl)ethyl]-N'-(2-[1,3,4-thiadiazoyl])thiourea
N-[2-(2-(5-fluoro)pyridyl)ethyl]-N'-(2-benzimidazolyl)thiourea
N-[2-(2-(5-fluoro)pyridyl)ethyl]-N'-(2-imidazolyl)thiourea
N-[2-(2-(4-fluoro)pyridyl)ethyl]-N'-(2-thiazolyl)thiourea
N-[2-(2-(4-fluoro)pyridyl)ethyl]-N'-[2-(4-methyl)thiazolyl]thiourea
N-[2-(2-(4-fluoro)pyridyl)ethyl]-N'-[2-(4,5-dimethyl)thiazolyl]thiourea
N-[2-(2-(4-fluoro)pyridyl)ethyl]-N'-[2-(4-cyano)thiazolyl]thiourea
N-[2-(2-(4-fluoro)pyridyl)ethyl]-N'-[2-(4-trifluoromethyl)thiazolyl]thiourea
N-[2-(2-(4-fluoro)pyridyl)ethyl]-N'-(2-benzothiazolyl)thiourea
N-[2-(2-(4-fluoro)pyridyl)ethyl]-N'-[2-(6-fluoro)benzothiazolyl]thiourea
N-[2-(2-(4-fluoro)pyridyl)ethyl]-N'-[2-(6-chloro)pyrazinyl]thiourea
N-[2-(2-(4-fluoro)pyridyl)ethyl]-N'-[2-(4-ethyl)thiazolyl]thiourea
N-[2-(2-(4-fluoro)pyridyl)ethyl]-N'-[2-(4-(3-pyridyl)thiazolyl)]thiourea
N-[2-(2-(4-fluoro)pyridyl)ethyl]-N'-[2-(4-(3-nitrophenyl)thiazolyl)]thiourea
N-[2-(2-(4-fluoro)pyridyl)ethyl]-N'-(2-pyridyl)thiourea
N-[2-(2-(4-fluoro)pyridyl)ethyl]-N'-[2-(6-bromo)pyridyl]thiourea
N-[2-(2-(4-fluoro)pyridyl)ethyl]-N'-[2-(5-bromo)pyridyl]thiourea
N-[2-(2-(4-fluoro)pyridyl)ethyl]-N'-[2-(6-chloro)pyridyl]thiourea
N-[2-(2-(4-fluoro)pyridyl)ethyl]-N'-[2-(5-chloro)pyridyl]thiourea
N-[2-(2-(4-fluoro)pyridyl)ethyl]-N'-[2-(6-methyl)pyridyl]thiourea
N-[2-(2-(4-fluoro)pyridyl)ethyl]-N'-[2-(5-methyl)pyridyl]thiourea
N-[2-(2-(4-fluoro)pyridyl)ethyl]-N'-[2-(6-trifluoromethyl)pyridyl]thiourea
N-[2-(2-(4-fluoro)pyridyl)ethyl]-N'-[2-(5-trifluoromethyl)pyridyl]thiourea
N-[2-(2-(4-fluoro)pyridyl)ethyl]-N'-[2-(6-ethyl)pyridyl]thiourea
N-[2-(2-(4-fluoro)pyridyl)ethyl]-N'-[2-(5-ethyl)pyridyl]thiourea
N-[2-(2-(4-fluoro)pyridyl)ethyl]-N'-[2-(5-chloro)pyrazinyl]thiourea
N-[2-(2-(4-fluoro)pyridyl)ethyl]-N'-[2-(6-bromo)pyrazinyl]thiourea
N-[2-(2-(4-fluoro)pyridyl)ethyl]-N'-[2-(5-bromo)pyrazinyl]thiourea
N-[2-(2-(4-fluoro)pyridyl)ethyl]-N'-[(3-(6-bromo)pyridazinyl)]thiourea
N-[2-(2-(4-fluoro)pyridyl)ethyl]-N'-[(3-(6-chloro)pyridazinyl)]thiourea
N-[2-(2-(4-fluoro)pyridyl)ethyl]-N'-[2-(6-cyano)pyridyl]thiourea
N-[2-(2-(4-fluoro)pyridyl)ethyl]-N'-[2-(5-cyano)pyridyl]thiourea
N-[2-(2-(4-fluoro)pyridyl)ethyl]-N'-[2-(5-cyano)pyrazinyl]thiourea
N-[2-(2-(4-fluoro)pyridyl)ethyl]-N'-[2-(6-cyano)pyrazinyl]thiourea
N-[2-(2-(4-fluoro)pyridyl)ethyl]-N'-[(3-(6-cyano)pyridazinyl)]thiourea
N-[2-(2-(4-fluoro)pyridyl)ethyl]-N'-(2-[1,3,4-thiadiazoyl])thiourea
N-[2-(2-(4-fluoro)pyridyl)ethyl]-N'-(2-benzimidazolyl)thiourea
N-[2-(2-(4-fluoro)pyridyl)ethyl]-N'-(2-imidazolyl)thiourea
N-[2-(2-(3-fluoro)pyridyl)ethyl]-N'-(2-thiazolyl)thiourea
N-[2-(2-(3-fluoro)pyridyl)ethyl]-N'-[2-(4-methyl)thiazolyl]thiourea
N-[2-(2-(3-fluoro)pyridyl)ethyl]-N'-[2-(4,5-dimethyl)thiazolyl]thiourea
N-[2-(2-(3-fluoro)pyridyl)ethyl]-N'-(2-benzothiazolyl)thiourea
N-[2-(2-(3-fluoro)pyridyl)ethyl]-N'-[2-(6-fluoro)benzothiazolyl]thiourea
N-[2-(2-(3-fluoro)pyridyl)ethyl]-N'-[2-(6-chloro)pyrazinyl]thiourea
N-[2-(2-(3-fluoro)pyridyl)ethyl]-N'-[2-(4-(3-pyridyl)thiazolyl)]thiourea
N-[2-(2-(3-fluoro)pyridyl)ethyl]-N'-[2-(4-(3-nitrophenyl)thiazolyl)]thiourea
N-[2-(2-(3-fluoro)pyridyl)ethyl]-N'-(2-pyridyl)thiourea
N-[2-(2-(3-fluoro)pyridyl)ethyl]-N'-[2-(6-bromo)pyridyl]thiourea
N-[2-(2-(3-fluoro)pyridyl)ethyl]-N'-[2-(6-chloro)pyridyl]thiourea
N-[2-(2-(3-fluoro)pyridyl)ethyl]-N'-[2-(6-methyl)pyridyl]thiourea
N-[2-(2-(3-fluoro)pyridyl)ethyl]-N'-[2-(5-methyl)pyridyl]thiourea
N-[2-(2-(3-fluoro)pyridyl)ethyl]-N'-[2-(6-trifluoromethyl)pyridyl]thiourea
N-[2-(2-(3-fluoro)pyridyl)ethyl]-N'-[2-(5-trifluoromethyl)pyridyl]thiourea
N-[2-(2-(3-fluoro)pyridyl)ethyl]-N'-[2-(6-ethyl)pyridyl]thiourea
N-[2-(2-(3-fluoro)pyridyl)ethyl]-N'-[2-(5-ethyl)pyridyl]thiourea
N-[2-(2-(3-fluoro)pyridyl)ethyl]-N'-[2-(6-bromo)pyrazinyl]thiourea
N-[2-(2-(3-fluoro)pyridyl)ethyl]-N'-[(3-(6-bromo)pyridazinyl)]thiourea
N-[2-(2-(3-fluoro)pyridyl)ethyl]-N'-[2-(6-cyano)pyridyl]thiourea
N-[2-(2-(3-fluoro)pyridyl)ethyl]-N'-[2-(5-cyano)pyridyl]thiourea
N-[2-(2-(3-fluoro)pyridyl)ethyl]-N'-[2-(5-cyano)pyrazinyl]thiourea
N-[2-(2-(3-fluoro)pyridyl)ethyl]-N'-[2-(6-cyano)pyrazinyl]thiourea
N-[2-(2-(3-fluoro)pyridyl)ethyl]-N'-[(3-(6-cyano)pyridazinyl)]thiourea
N-[2-(2-(3-fluoro)pyridyl)ethyl]-N'-(2-[1,3,4-thiadiazoyl])thiourea
N-[2-(2-(3-fluoro)pyridyl)ethyl]-N'-(2-benzimidazolyl)thiourea
N-[2-(2-(3-fluoro)pyridyl)ethyl]-N'-(2-imidazolyl)thiourea
N-[2-(2-(6-chloro)pyridyl)ethyl]-N'-(2-thiazolyl)thiourea
N-[2-(2-(6-chloro)pyridyl)ethyl]-N'-[2-(4-methyl)thiazolyl]thiourea N-[2-(2-(6-chloro)pyridyl)ethyl]-N'-[2-(4,5-dimethyl)thiazolyl]thiourea
N-[2-(2-(6-chloro)pyridyl)ethyl]-N'-(2-benzothiazolyl)thiourea
N-[2-(2-(6-chloro)pyridyl)ethyl]-N'-[2-(6-fluoro)benzothiazolyl]thiourea
N-[2-(2-(6-chloro)pyridyl)ethyl]-N'-[2-(6-chloro)pyrazinyl]thiourea
N-[2-(2-(6-chloro)pyridyl)ethyl]-N'-[2-(4-(3-pyridyl)thiazolyl)]thiourea
N-[2-(2-(6-chloro)pyridyl)ethyl]-N'-[2-(4-(3-nitrophenyl)thiazolyl)]thiourea
N-[2-(2-(6-chloro)pyridyl)ethyl]-N'-(2-pyridyl)thiourea
N-[2-(2-(6-chloro)pyridyl)ethyl]-N'-[2-(6-bromo)pyridyl]thiourea
N-[2-(2-(6-chloro)pyridyl)ethyl]-N'-[2-(6-chloro)pyridyl]thiourea
N-[2-(2-(6-chloro)pyridyl)ethyl]-N'-[2-(6-methyl)pyridyl]thiourea
N-[2-(2-(6-chloro)pyridyl)ethyl]-N'-[2-(5-methyl)pyridyl]thiourea
N-[2-(2-(6-chloro)pyridyl)ethyl]-N'-[2-(6-trifluoromethyl)pyridyl]thiourea
N-[2-(2-(6-chloro)pyridyl)ethyl]-N'-[2-(5-trifluoromethyl)pyridyl]thiourea
N-[2-(2-(6-chloro)pyridyl)ethyl]-N'-[2-(6-ethyl)pyridyl]thiourea
N-[2-(2-(6-chloro)pyridyl)ethyl]-N'-[2-(5-ethyl)pyridyl]thiourea
N-[2-(2-(6-chloro)pyridyl)ethyl]-N'-[2-(6-bromo)pyrazinyl]thiourea
N-[2-(2-(6-chloro)pyridyl)ethyl]-N'-[(3-(6-bromo)pyridazinyl)]thiourea
N-[2-(2-(6-chloro)pyridyl)ethyl]-N'-[2-(6-cyano)pyridyl]thiourea
N-[2-(2-(6-chloro)pyridyl)ethyl]-N'-[2-(5-cyano)pyridyl]thiourea
N-[2-(2-(6-chloro)pyridyl)ethyl]-N'-[2-(5-cyano)pyrazinyl]thiourea
N-[2-(2-(6-chloro)pyridyl)ethyl]-N'-[2-(6-cyano)pyrazinyl]thiourea
N-[2-(2-(6-chloro)pyridyl)ethyl]-N'-[(3-(6-cyano)pyridazinyl)]thiourea
N-[2-(2-(6-chloro)pyridyl)ethyl]-N'-(2-[1,3,4-thiadiazoyl])thiourea
N-[2-(2-(6-chloro)pyridyl)ethyl]-N'-(2-benzimidazolyl)thiourea
N-[2-(2-(6-chloro)pyridyl)ethyl]-N'-(2-imidazolyl)thiourea
N-[2-(2-(5-chloro)pyridyl)ethyl]-N'-(2-thiazolyl)thiourea
N-[2-(2-(5-chloro)pyridyl)ethyl]-N'-[2-(4-methyl)thiazolyl]thiourea
N-[2-(2-(5-chloro)pyridyl)ethyl]-N'-[2-(4,5-dimethyl)thiazolyl]thiourea
N-[2-(2-(5-chloro)pyridyl)ethyl]-N'-[2-(4-cyano)thiazolyl]thiourea
N-[2-(2-(5-chloro)pyridyl)ethyl]-N'-[2-(4-trifluoromethyl)thiazolyl]thiourea
N-[2-(2-(5-chloro)pyridyl)ethyl]-N'-(2-benzothiazolyl)thiourea
N-[2-(2-(5-chloro)pyridyl)ethyl]-N'-[2-(6-fluoro)benzothiazolyl]thiourea
N-[2-(2-(5-chloro)pyridyl)ethyl]-N'-[2-(6-chloro)pyrazinyl]thiourea
N-[2-(2-(5-chloro)pyridyl)ethyl]-N'-[2-(4-ethyl)thiazolyl]thiourea
N-[2-(2-(5-chloro)pyridyl)ethyl]-N'-[2-(4-(3-pyridyl)thiazolyl)]thiourea
N-[2-(2-(5-chloro)pyridyl)ethyl]-N'-[2-(4-(3-nitrophenyl)thiazolyl)]thiourea
N-[2-(2-(5-chloro)pyridyl)ethyl]-N'-(2-pyridyl)thiourea
N-[2-(2-(5-chloro)pyridyl)ethyl]-N'-[2-(6-bromo)pyridyl]thiourea
N-[2-(2-(5-chloro)pyridyl)ethyl]-N'-[2-(5-bromo)pyridyl]thiourea
N-[2-(2-(5-chloro)pyridyl)ethyl]-N'-[2-(6-chloro)pyridyl]thiourea
N-[2-(2-(5-chloro)pyridyl)ethyl]-N'-[2-(5chloro)pyridyl]thiourea
N-[2-(2-(5-chloro)pyridyl)ethyl]-N'-[2-(6-methyl)pyridyl]thiourea
N-[2-(2-(5-chloro)pyridyl)ethyl]-N'-[2-(5-methyl)pyridyl]thiourea
N-[2-(2-(5-chloro)pyridyl)ethyl]-N'-[2-(6-trifluoromethyl)pyridyl]thiourea
N-[2-(2-(5-chloro)pyridyl)ethyl]-N'-[2-(5-trifluoromethyl)pyridyl]thiourea
N-[2-(2-(5-chloro)pyridyl)ethyl]-N'-[2-(6-ethyl)pyridyl]thiourea
N-[2-(2-(5-chloro)pyridyl)ethyl]-N'-[2-(5-ethyl)pyridyl]thiourea
N-[2-(2-(5-chloro)pyridyl)ethyl]-N'-[2-(5-chloro)pyrazinyl]thiourea
N-[2-(2-(5-chloro)pyridyl)ethyl]-N'-[2-(6-bromo)pyrazinyl]thiourea
N-[2-(2-(5-chloro)pyridyl)ethyl]-N'-[2-(5-bromo)pyrazinyl]thiourea
N-[2-(2-(5-chloro)pyridyl)ethyl]-N'-[(3-(6-bromo)pyridazinyl)]thiourea
N-[2-(2-(5-chloro)pyridyl)ethyl]-N'-[(3-(6-chloro)pyridazinyl)]thiourea
N-[2-(2-(5-chloro)pyridyl)ethyl]-N'-[2-(6-cyano)pyridyl]thiourea
N-[2-(2-(5-chloro)pyridyl)ethyl]-N'-[2-(5-cyano)pyridyl]thiourea
N-[2-(2-(5-chloro)pyridyl)ethyl]-N'-[2-(5-cyano)pyrazinyl]thiourea
N-[2-(2-(5-chloro)pyridyl)ethyl]-N'-[2-(6-cyano)pyrazinyl]thiourea
N-[2-(2-(5-chloro)pyridyl)ethyl]-N'-[(3-(6-cyano)pyridazinyl)]thiourea
N-[2-(2-(5-chloro)pyridyl)ethyl]-N'-(2-[1,3,4-thiadiazoyl])thiourea
N-[2-(2-(5-chloro)pyridyl)ethyl]-N'-(2-benzimidazolyl)thiourea
N-[2-(2-(5-chloro)pyridyl)ethyl]-N'-(2-imidazolyl)thiourea
N-[2-(2-(4-chloro)pyridyl)ethyl]-N'-(2-thiazolyl)thiourea
N-[2-(2-(4-chloro)pyridyl)ethyl]-N'-[2-(4-methyl)thiazolyl]thiourea
N-[2-(2-(4-chloro)pyridyl)ethyl]-N'-[2-(4,5-dimethyl)thiazolyl]thiourea
N-[2-(2-(4-chloro)pyridyl)ethyl]-N'-[2-(4-cyano)thiazolyl]thiourea
N-[2-(2-(4-chloro)pyridyl)ethyl]-N'-[2-(4-trifluoromethyl)thiazolyl]thiourea
N-[2-(2-(4-chloro)pyridyl)ethyl]-N'-(2-benzothiazolyl)thiourea
N-[2-(2-(4-chloro)pyridyl)ethyl]-N'-[2-(6-fluoro)benzothiazolyl]thiourea
N-[2-(2-(4-chloro)pyridyl)ethyl]-N'-[2-(6-chloro)pyrazinyl]thiourea
N-[2-(2-(4-chloro)pyridyl)ethyl]-N'-[2-(4-ethyl)thiazolyl]thiourea
N-[2-(2-(4-chloro)pyridyl)ethyl]-N'-[2-(4-(3-pyridyl)thiazolyl)]thiourea N-[2-(2-(4-chloro)pyridyl)ethyl]-N'-[2-(4-(3-nitrophenyl)thiazolyl)]thiourea
N-[2-(2-(4-chloro)pyridyl)ethyl]-N'-(2-pyridyl)thiourea
N-[2-(2-(4-chloro)pyridyl)ethyl]-N'-[2-(6-bromo)pyridyl]thiourea
N-[2-(2-(4-chloro)pyridyl)ethyl]-N'-[2-(5-bromo)pyridyl]thiourea
N-[2-(2-(4-chloro)pyridyl)ethyl]-N'-[2-(6-chloro)pyridyl]thiourea
N-[2-(2-(4-chloro)pyridyl)ethyl]-N'-[2-(5-chloro)pyridyl]thiourea
N-[2-(2-(4-chloro)pyridyl)ethyl]-N'-[2-(6-methyl)pyridyl]thiourea
N-[2-(2-(4-chloro)pyridyl)ethyl]-N'-[2-(5-methyl)pyridyl]thiourea
N-[2-(2-(4-chloro)pyridyl)ethyl]-N'-[2-(6-trifluoromethyl)pyridyl]thiourea
N-[2-(2-(4-chloro)pyridyl)ethyl]-N'-[2-(5-trifluoromethyl)pyridyl]thiourea
N-[2-(2-(4-chloro)pyridyl)ethyl]-N'-[2-(6-ethyl)pyridyl]thiourea
N-[2-(2-(4-chloro)pyridyl)ethyl]-N'-[2-(5-ethyl)pyridyl]thiourea
N-[2-(2-(4-chloro)pyridyl)ethyl]-N'-[2-(5-chloro)pyrazinyl]thiourea
N-[2-(2-(4-chloro)pyridyl)ethyl]-N'-[2-(6-bromo)pyrazinyl]thiourea
N-[2-(2-(4-chloro)pyridyl)ethyl]-N'-[2-(5-bromo)pyrazinyl]thiourea
N-[2-(2-(4-chloro)pyridyl)ethyl]-N'-[(3-(6-bromo)pyridazinyl)]thiourea
N-[2-(2-(4-chloro)pyridyl)ethyl]-N'-[(3-(6-chloro)pyridazinyl)]thiourea
N-[2-(2-(4-chloro)pyridyl)ethyl]-N'-[2-(6-cyano)pyridyl]thiourea
N-[2-(2-(4-chloro)pyridyl)ethyl]-N'-[2-(5-cyano)pyridyl]thiourea
N-[2-(2-(4-chloro)pyridyl)ethyl]-N'-[2-(5-cyano)pyrazinyl]thiourea
N-[2-(2-(4-chloro)pyridyl)ethyl]-N'-[2-(6-cyano)pyrazinyl]thiourea
N-[2-(2-(4-chloro)pyridyl)ethyl]-N'-[(3-(6-cyano)pyridazinyl)]thiourea
N-[2-(2-(4-chloro)pyridyl)ethyl]-N'-(2-[1,3,4-thiadiazoyl])thiourea
N-[2-(2-(4-chloro)pyridyl)ethyl]-N'-(2-benzimidazolyl)thiourea
N-[2-(2-(4-chloro)pyridyl)ethyl]-N'-(2-imidazolyl)thiourea
N-[2-(2-(3-chloro)pyridyl)ethyl]-N'-(2-thiazolyl)thiourea
N-[2-(2-(3-chloro)pyridyl)ethyl]-N'-[2-(4-methyl)thiazolyl]thiourea
N-[2-(2-(3-chloro)pyridyl)ethyl]-N'-[2-(4,5-dimethyl)thiazolyl]thiourea
N-[2-(2-(3-chloro)pyridyl)ethyl]-N'-[2-(4-cyano)thiazolyl]thiourea
N-[2-(2-(3-chloro)pyridyl)ethyl]-N'-[2-(4-trifluoromethyl)thiazolyl]thiourea
N-[2-(2-(3-chloro)pyridyl)ethyl]-N'-(2-benzothiazolyl)thiourea
N-[2-(2-(3-chloro)pyridyl)ethyl]-N'-[2-(6-fluoro)benzothiazolyl]thiourea
N-[2-(2-(3-chloro)pyridyl)ethyl]-N'-[2-(6-chloro)pyrazinyl]thiourea
N-[2-(2-(3-chloro)pyridyl)ethyl]-N'-[2-(4-ethyl)thiazolyl]thiourea
N-[2-(2-(3-chloro)pyridyl)ethyl]-N'-[2-(4-(3-pyridyl)thiazolyl)]thiourea
N-[2-(2-(3-chloro)pyridyl)ethyl]-N'-[2-(4-(3-nitrophenyl)thiazolyl)]thiourea
N-[2-(2-(3-chloro)pyridyl)ethyl]-N'-(2-pyridyl)thiourea
N-[2-(2-(3-chloro)pyridyl)ethyl]-N'-[2-(6-bromo)pyridyl]thiourea
N-[2-(2-(3-chloro)pyridyl)ethyl]-N'-[2-(5-bromo)pyridyl]thiourea
N-[2-(2-(3-chloro)pyridyl)ethyl]-N'-[2-(6-chloro)pyridyl]thiourea
N-[2-(2-(3-chloro)pyridyl)ethyl]-N'-[2-(5-chloro)pyridyl]thiourea
N-[2-(2-(3-chloro)pyridyl)ethyl]-N'-[2-(6-methyl)pyridyl]thiourea
N-[2-(2-(3-chloro)pyridyl)ethyl]-N'-[2-(5-methyl)pyridyl]thiourea
N-[2-(2-(3-chloro)pyridyl)ethyl]-N'-[2-(6-trifluoromethyl)pyridyl]thiourea
N-[2-(2-(3-chloro)pyridyl)ethyl]-N'-[2-(5-trifluoromethyl)pyridyl]thiourea
N-[2-(2-(3-chloro)pyridyl)ethyl]-N'-[2-(6-ethyl)pyridyl]thiourea
N-[2-(2-(3-chloro)pyridyl)ethyl]-N'-[2-(5-ethyl)pyridyl]thiourea
N-[2-(2-(3-chloro)pyridyl)ethyl]-N'-[2-(5-chloro)pyrazinyl]thiourea
N-[2-(2-(3-chloro)pyridyl)ethyl]-N'-[2-(6-bromo)pyrazinyl]thiourea
N-[2-(2-(3-chloro)pyridyl)ethyl]-N'-[2-(5-bromo)pyrazinyl]thiourea
N-[2-(2-(3-chloro)pyridyl)ethyl]-N'-[(3-(6-bromo)pyridazinyl)]thiourea
N-[2-(2-(3-chloro)pyridyl)ethyl]-N'-[(3-(6-chloro)pyridazinyl)]thiourea
N-[2-(2-(3-chloro)pyridyl)ethyl]-N'-[2-(6-cyano)pyridyl]thiourea
N-[2-(2-(3-chloro)pyridyl)ethyl]-N'-[2-(5-cyano)pyridyl]thiourea
N-[2-(2-(3-chloro)pyridyl)ethyl]-N'-[2-(5-cyano)pyrazinyl]thiourea
N-[2-(2-(3-chloro)pyridyl)ethyl]-N'-[2-(6-cyano)pyrazinyl]thiourea
N-[2-(2-(3-chloro)pyridyl)ethyl]-N'-[(3-(6-cyano)pyridazinyl)-]thiourea
N-[2-(2-(3-chloro)pyridyl)ethyl]-N'-(2-[1,3,4-thiadiazoyl])thiourea
N-[2-(2-(3-chloro)pyridyl)ethyl]-N'-(2-benzimidazolyl)thiourea
N-[2-(2-(3-chloro)pyridyl)ethyl]-N'-(2-imidazolyl)thiourea
N-[2-(2-(5-methoxy-6-fluoro)pyridyl)ethyl]-N'-(2-thiazolyl)thiourea
N-[2-(2-(5-methoxy-6-fluoro)pyridyl)ethyl]-N'-[2-(4-methyl)thiazolyl]thiourea
N-[2-(2-(5-methoxy-6-fluoro)pyridyl)ethyl]-N'-[2-(4,5-dimethyl)thiazolyl]thiourea
N-[2-(2-(5-methoxy-6-fluoro)pyridyl)ethyl]-N'-[2-(4-cyano)thiazolyl]thiourea
N-[2-(2-(5-methoxy-6-fluoro)pyridyl)ethyl]-N'-[2-(4-trifluoromethyl)thiazolyl]thiourea
N-[2-(2-(5-methoxy-6-fluoro)pyridyl)ethyl]-N'-(2-benzothiazolyl)thiourea
N-[2-(2-(5-methoxy -6-fluoro)pyridyl)ethyl]-N'-[2-(6-fluoro)benzothiazolyl]thiourea
N-[2-(2-(5-methoxy-6-fluoro)pyridyl)ethyl]-N'-[2-(6-chloro)pyrazinyl]thiourea
N-[2-(2-(5-methoxy-6-fluoro)pyridyl)ethyl]-N'-[2-(4-ethyl)thiazolyl]thiourea
N-[2-(2-(5-methoxy-6-fluoro)pyridyl)ethyl]-N'-[2-(4-(3-pyridyl)thiazolyl)]thiourea N-[2-(2-(5-methoxy-6-fluoro)pyridyl)ethyl]-N'-[2-(4-(3-nitrophenyl)thiazolyl)]thiourea
N-[2-(2-(5-methoxy-6-fluoro)pyridyl)ethyl]-N'-(2-pyridyl)thiourea
N-[2-(2-(5-methoxy-6-fluoro)pyridyl)ethyl]-N'-[2-(6-bromo)pyridyl]thiourea
N-[2-(2-(5-methoxy-6-fluoro)pyridyl)ethyl]-N'-[2-(5-bromo)pyridyl]thiourea
N-[2-(2-(5-methoxy-6-fluoro)pyridyl)ethyl]-N'-[2-(6-chloro)pyridyl]thiourea
N-[2-(2-(5-methoxy-6-fluoro)pyridyl)ethyl]-N'-[2-(5-chloro)pyridyl]thiourea
N-[2-(2-(5-methoxy-6-fluoro)pyridyl)ethyl]-N'-[2-(6-methyl)pyridyl]thiourea
N-[2-(2-(5-methoxy-6-fluoro)pyridyl)ethyl]-N'-[2-(5-methyl)pyridyl]thiourea
N-[2-(2-(5-methoxy-6-fluoro)pyridyl)ethyl]-N'-[2-(6-trifluoromethyl)pyridyl]thiourea
N-[2-(2-(5-methoxy-6-fluoro)pyridyl)ethyl]-N'-[2-(5-trifluoromethyl)pyridyl]thiourea
N-[2-(2-(5-methoxy-6-fluoro)pyridyl)ethyl]-N'-[2-(6-ethyl)pyridyl]thiourea
N-[2-(2-(5-methoxy-6-fluoro)pyridyl)ethyl]-N'-[2-(5-ethyl)pyridyl]thiourea
N-[2-(2-(5-methoxy-6-fluoro)pyridyl)ethyl]-N'-[2-(5-chloro)pyrazinyl]thiourea
N-[2-(2-(5-methoxy-6-fluoro)pyridyl)ethyl]-N'-[2-(6-bromo)pyrazinyl]thiourea
N-[2-(2-(5-methoxy-6-fluoro)pyridyl)ethyl]-N'-[2-(5-bromo)pyrazinyl]thiourea
N-[2-(2-(5-methoxy-6-fluoro)pyridyl)ethyl]-N'-[(3-(6-bromo)pyridazinyl)]thiourea
N-[2-(2-(5-methoxy-6-fluoro)pyridyl)ethyl]-N'-[(3-(6-chloro)pyridazinyl)]thiourea
N-[2-(2-(5-methoxy-6-fluoro)pyridyl)ethyl]-N'-[2-(6-cyano)pyridyl]thiourea
N-[2-(2-(5-methoxy-6-fluoro)pyridyl)ethyl]-N'-[2-(5-cyano)pyridyl]thiourea
N-[2-(2-(5-methoxy-6-fluoro)pyridyl)ethyl]-N'-[2-(5-cyano)pyrazinyl]thiourea
N-[2-(2-(5-methoxy-6-fluoro)pyridyl)ethyl]-N'-[2-(6-cyano)pyrazinyl]thiourea
N-[2-(2-(5-methoxy-6-fluoro)pyridyl)ethyl]-N'-[(3-(6-cyano)pyridazinyl)]thiourea
N-[2-(2-(5-methoxy-6-fluoro)pyridyl)ethyl]-N'-(2-[1,3,4-thiadiazoyl])thiourea
N-[2-(2-(5-methoxy-6-fluoro)pyridyl)ethyl]-N'-(2-benzimidazolyl)thiourea
N-[2-(2-(5-methoxy-6-fluoro)pyridyl)ethyl]-N'-(2-imidazolyl)thiourea
N-[2-(2-(3-methoxy-6-fluoro)pyridyl)ethyl]-N'-(2-thiazolyl)thiourea
N-[2-(2-(3-methoxy-6-fluoro)pyridyl)ethyl]-N'-[2-(4,5-dimethyl)thiazolyl]thiourea
N-[2-(2-(3-methoxy-6-fluoro)pyridyl)ethyl]-N'-(2-benzothiazolyl)thiourea
N-[2-(2-(3-methoxy-6-fluoro)pyridyl)ethyl]-N'-[2-(6-fluoro)benzothiazolyl]thiourea
N-[2-(2-(3-methoxy-6-fluoro)pyridyl)ethyl]-N'-[2-(6-chloro)pyrazinyl]thiourea
N-[2-(2-(3-methoxy-6-fluoro)pyridyl)ethyl]-N'-[2-(4-(3-pyridyl)thiazolyl)]thiourea
N-[2-(2-(3-methoxy-6-fluoro)pyridyl)ethyl]-N'-[2-(4-(3-nitrophenyl)thiazolyl)]thiourea
N-[2-(2-(3-methoxy-6-fluoro)pyridyl)ethyl]-N'-[2-(6-bromo)pyridyl]thiourea
N-[2-(2-(3-methoxy-6-fluoro)pyridyl)ethyl]-N'-[2-(6-chloro)pyridyl]thiourea
N-[2-(2-(3-methoxy-6-fluoro)pyridyl)ethyl]-N'-[2-(6-methyl)pyridyl]thiourea
N-[2-(2-(3-methoxy-6-fluoro)pyridyl)ethyl]-N'-[2-(5-methyl)pyridyl]thiourea
N-[2-(2-(3-methoxy-6-fluoro)pyridyl)ethyl]-N'-[2-(6-trifluoromethyl)pyridyl]thiourea
N-[2-(2-(3-methoxy-6-fluoro)pyridyl)ethyl]-N'-[2-(5-trifluoromethyl)pyridyl]thiourea
N-[2-(2-(3-methoxy-6-fluoro)pyridyl)ethyl]-N'-[2-(6-ethyl)pyridyl]thiourea
N-[2-(2-(3-methoxy-6-fluoro)pyridyl)ethyl]-N'-[2-(5-ethyl)pyridyl]thiourea
N-[2-(2-(3-methoxy-6-fluoro)pyridyl)ethyl]-N'-[2-(6-bromo)pyrazinyl]thiourea
N-[2-(2-(3-methoxy-6-fluoro)pyridyl)ethyl]-N'-[(3-(6-bromo)pyridazinyl)]thiourea
N-[2-(2-(3-methoxy-6-fluoro)pyridyl)ethyl]-N'-[2-(6-cyano)pyridyl]thiourea
N-[2-(2-(3-methoxy-6-fluoro)pyridyl)ethyl]-N'-[2-(5-cyano)pyridyl]thiourea
N-[2-(2-(3-methoxy-6-fluoro)pyridyl)ethyl]-N'-[2-(5-cyano)pyrazinyl]thiourea
N-[2-(2-(3-methoxy-6-fluoro)pyridyl)ethyl]-N'-[2-(6-cyano)pyrazinyl]thiourea
N-[2-(2-(3-methoxy-6-fluoro)pyridyl)ethyl]-N'-[(3-(6-cyano)pyridazinyl)]thiourea
N-[2-(2-(3-methoxy-6-fluoro)pyridyl)ethyl]-N'-(2-[1,3,4-thiadiazoyl])thiourea
N-[2-(2-(3-methoxy-6-fluoro)pyridyl)ethyl]-N'-(2-benzimidazolyl)thiourea
N-[2-(2-(3-methoxy-6-fluoro)pyridyl)ethyl]-N'-(2-imidazolyl)thiourea
N-[2-(2-(6-methoxy-3-fluoro)pyridyl)ethyl]-N'-(2-thiazolyl)thiourea
N-[2-(2-(6-methoxy-3-fluoro)pyridyl)ethyl]-N'-[2-(4-methyl)thiazolyl]thiourea
N-[2-(2-(6-methoxy-3-fluoro)pyridyl)ethyl]-N'-[2-(4,5-dimethyl)thiazolyl]thiourea
N-[2-(2-(6-methoxy-3-fluoro)pyridyl)ethyl]-N'-[2-(4-cyano)thiazolyl]thiourea
N-[2-(2-(6-methoxy-3-fluoro)pyridyl)ethyl]-N'-[2-(4-trifluoromethyl)thiazolyl]thiourea
N-[2-(2-(6-methoxy-3-fluoro)pyridyl)ethyl]-N'-(2-benzothiazolyl)thiourea
N-[2-(2-(6-methoxy-3-fluoro)pyridyl)ethyl]-N'-[2-(6-fluoro)benzothiazolyl]thiourea
N-[2-(2-(6-methoxy-3-fluoro)pyridyl)ethyl]-N'-[2-(6-chloro)pyrazinyl]thiourea
N-[2-(2-(6-methoxy-3-fluoro)pyridyl)ethyl]-N'-[2-(4-ethyl)thiazolyl]thiourea
N-[2-(2-(6-methoxy-3-fluoro)pyridyl)ethyl]-N'-[2-(4-(3-pyridyl)thiazolyl)]thiourea
N-[2-(2-(6-methoxy-3-fluoro)pyridyl)ethyl]-N'-[2-(4-(3-nitrophenyl)thiazolyl)]thiourea
N-[2-(2-(6-methoxy-3-fluoro)pyridyl)ethyl]-N'-(2-pyridyl)thiourea
N-[2-(2-(6-methoxy-3-fluoro)pyridyl)ethyl]-N'-[2-(6-bromo)pyridyl]thiourea
N-[2-(2-(6-methoxy-3-fluoro)pyridyl)ethyl]-N'-[2-(5-bromo)pyridyl]thiourea
N-[2-(2-(6-methoxy-3-fluoro)pyridyl)ethyl]-N'-[2-(6-chloro)pyridyl]thiourea
N-[2-(2-(6-methoxy-3-fluoro)pyridyl)ethyl]-N'-[2-(5-chloro)pyridyl]thiourea
N-[2-(2-(6-methoxy-3-fluoro)pyridyl)ethyl]-N'-[2-(6-methyl)pyridyl]thiourea
N-[2-(2-(6-methoxy-3-fluoro)pyridyl)ethyl]-N'-[2-(5-methyl)pyridyl]thiourea N-[2-(2-(6-methoxy-3-fluoro)pyridyl)ethyl]-N'-[2-(6-trifluoromethyl)pyridyl]thiourea
N-[2-(2-(6-methoxy-3-fluoro)pyridyl)ethyl]-N'-[2-(5-trifluoromethyl)pyridyl]thiourea
N-[2-(2-(6-methoxy-3-fluoro)pyridyl)ethyl]-N'-[2-(6-ethyl)pyridyl]thiourea
N-[2-(2-(6-methoxy-3-fluoro)pyridyl)ethyl]-N'-[2-(5-ethyl)pyridyl]thiourea
N-[2-(2-(6-methoxy-3-fluoro)pyridyl)ethyl]-N'-[2-(5-chloro)pyrazinyl]thiourea
N-[2-(2-(6-methoxy-3-fluoro)pyridyl)ethyl]-N'-[2-(6-bromo)pyrazinyl]thiourea
N-[2-(2-(6-methoxy-3-fluoro)pyridyl)ethyl]-N'-[2-(5-bromo)pyrazinyl]thiourea
N-[2-(2-(6-methoxy-3-fluoro)pyridyl)ethyl]-N'-[(3-(6-bromo)pyridazinyl)]thiourea
N-[2-(2-(6-methoxy-3-fluoro)pyridyl)ethyl]-N'-[(3-(6-chloro)pyridazinyl)]thiourea
N-[2-(2-(6-methoxy-3-fluoro)pyridyl)ethyl]-N'-[2-(6-cyano)pyridyl]thiourea
N-[2-(2-(6-methoxy-3-fluoro)pyridyl)ethyl]-N'-[2-(5-cyano)pyridyl]thiourea
N-[2-(2-(6-methoxy-3-fluoro)pyridyl)ethyl]-N'-[2-(5-cyano)pyrazinyl]thiourea
N-[2-(2-(6-methoxy-3-fluoro)pyridyl)ethyl]-N'-[2-(6-cyano)pyrazinyl]thiourea
N-[2-(2-(6-methoxy-3-fluoro)pyridyl)ethyl]-N'-[(3-(6-cyano)pyridazinyl)]thiourea
N-[2-(2-(6-methoxy-3-fluoro)pyridyl)ethyl]-N'-(2-[1,3,4-thiadiazoyl])thiourea
N-[2-(2-(6-methoxy-3-fluoro)pyridyl)ethyl]-N'-(2-benzimidazolyl)thiourea
N-[2-(2-(6-methoxy-3-fluoro)pyridyl)ethyl]-N'-(2-imidazolyl)thiourea
N-[2-(2-(5-ethoxy-6-fluoro)pyridyl)ethyl]-N'-(2-thiazolyl)thiourea
N-[2-(2-(5-ethoxy-6-fluoro)pyridyl)ethyl]-N'-[2-(4-methyl)thiazolyl]thiourea
N-[2-(2-(5-ethoxy-6-fluoro)pyridyl)ethyl]-N'-[2-(4,5-dimethyl)thiazolyl]thiourea
N-[2-(2-(5-ethoxy-6-fluoro)pyridyl)ethyl]-N'-(2-benzothiazolyl)thiourea
N-[2-(2-(5-ethoxy-6-fluoro)pyridyl)ethyl]-N'-[2-(6-fluoro)benzothiazolyl]thiourea
N-[2-(2-(5-ethoxy-6-fluoro)pyridyl)ethyl]-N'-[2-6-chloro)pyrazinyl]thiourea
N-[2-(2-(5-ethoxy-6-fluoro)pyridyl)ethyl]-N'-[2-(4-(3-pyridyl)thiazolyl)]thiourea
N-[2-(2-(5-ethoxy-6-fluoro)pyridyl)ethyl]-N'-[2-(4-(3-nitrophenyl)thiazolyl)]thiourea
N-[2-(2-(5-ethoxy-6-fluoro)pyridyl)ethyl]-N'-(2-pyridyl)thiourea
N-[2-(2-(5-ethoxy-6-fluoro)pyridyl)ethyl]-N'-[2-(6-bromo)pyridyl]thiourea
N-[2-(2-(5-ethoxy-6-fluoro)pyridyl)ethyl]-N'-[2-(6-chloro)pyridyl]thiourea
N-[2-(2-(5-ethoxy-6-fluoro)pyridyl)ethyl]-N'-[2-(6-methyl)pyridyl]thiourea
N-[2-(2-(5-ethoxy-6-fluoro)pyridyl)ethyl]-N'-[2-(5-methyl)pyridyl]thiourea
N-[2-(2-(5-ethoxy-6-fluoro)pyridyl)ethyl]-N'-[2-(6-trifluoromethyl)pyridyl]thiourea
N-[2-(2-(5-ethoxy-6-fluoro)pyridyl)ethyl]-N'-[2-(5-trifluoromethyl)pyridyl]thiourea
N-[2-(2-(5-ethoxy-6-fluoro)pyridyl)ethyl]-N'-[2-(6-ethyl)pyridyl]thiourea
N-[2-(2-(5-ethoxy-6-fluoro)pyridyl)ethyl]-N'-[2-(5-ethyl)pyridyl]thiourea
N-[2-(2-(5-ethoxy-6-fluoro)pyridyl)ethyl]-N'-[2-(6-bromo)pyrazinyl]thiourea
N-[2-(2-(5-ethoxy-6-fluoro)pyridyl)ethyl]-N'-[(3-(6-bromo)pyridazinyl)]thiourea
N-[2-(2-(5-ethoxy-6-fluoro)pyridyl)ethyl]-N'-[2-(6-cyano)pyridyl]thiourea
N-[2-(2-(5-ethoxy-6-fluoro)pyridyl)ethyl]-N'-[2-(5-cyano)pyridyl]thiourea
N-[2-(2-(5-ethoxy-6-fluoro)pyridyl)ethyl]-N'-[2-(5-cyano)pyrazinyl]thiourea
N-[2-(2-(5-ethoxy-6-fluoro)pyridyl)ethyl]-N'-[2-(6-cyano)pyrazinyl]thiourea
N-[2-(2-(5-ethoxy-6-fluoro)pyridyl)ethyl]-N'-[(3-(6-cyano)pyridazinyl)]thiourea
N-[2-(2-(5-ethoxy-6-fluoro)pyridyl)ethyl]-N'-(2-[1,3,4-thiadiazoyl])thiourea
N-[2-(2-(5-ethoxy-6-fluoro)pyridyl)ethyl]-N'-(2-benzimidazolyl)thiourea
N-[2-(2-(5-ethoxy-6-fluoro)pyridyl)ethyl]-N'-(2-imidazolyl)thiourea
N-[2-(2-(3-ethoxy-6-fluoro)pyridyl)ethyl]-N'-(2-thiazolyl)thiourea
N-[2-(2-(3-ethoxy-6-fluoro)pyridyl)ethyl]-N'-[2-(4-methyl)thiazolyl]thiourea
N-[2-(2-(3-ethoxy-6-fluoro)pyridyl)ethyl]-N'-[2-(4,5-dimethyl)thiazolyl]thiourea
N-[2-(2-(3-ethoxy-6-fluoro)pyridyl)ethyl]-N'-(2-benzothiazolyl)thiourea
N-[2-(2-(3-ethoxy-6-fluoro)pyridyl)ethyl]-N'-[2-(6-fluoro)benzothiazolyl]thiourea
N-[2-(2-(3-ethoxy-6-fluoro)pyridyl)ethyl]-N'-[2-(6-chloro)pyrazinyl]thiourea
N-[2-(2-(3-ethoxy-6-fluoro)pyridyl)ethyl]-N'-[2-(4-(3-pyridyl)thiazolyl)]thiourea
N-[2-(2-(3-ethoxy-6-fluoro)pyridyl)ethyl]-N'-[2-(4-(3-nitrophenyl)thiazolyl)]thiourea
N-[2-(2-(3-ethoxy-6-fluoro)pyridyl)ethyl]-N'-[2-pyridyl)thiourea
N-[2-(2-(3-ethoxy-6-fluoro)pyridyl)ethyl]-N'-[2-(6-bromo)pyridyl]thiourea
N-[2-(2-(3-ethoxy-6-fluoro)pyridyl)ethyl]-N'-[2-(6-chloro)pyridyl]thiourea
N-[2-(2-(3-ethoxy-6-fluoro)pyridyl)ethyl]-N'-[2-(6-methyl)pyridyl]thiourea
N-[2-(2-(3-ethoxy-6-fluoro)pyridyl)ethyl]-N'-[2-(5-methyl)pyridyl]thiourea
N-[2-(2-(3-ethoxy-6-fluoro)pyridyl)ethyl]-N'-[2-(6-trifluoromethyl)pyridyl]thiourea
N-[2-(2-(3-ethoxy-6-fluoro)pyridyl)ethyl]-N'-[2-(5-trifluoromethyl)pyridyl]thiourea
N-[2-(2-(3-ethoxy-6-fluoro)pyridyl)ethyl]-N'-[2-(6-ethyl)pyridyl]thiourea
N-[2-(2-(3-ethoxy-6-fluoro)pyridyl)ethyl]-N'-[2-(5-ethyl)pyridyl]thiourea
N-[2-(2-(3-ethoxy-6-fluoro)pyridyl)ethyl]-N'-[2-(6-bromo)pyrazinyl]thiourea
N-[2-(2-(3-ethoxy-6-fluoro)pyridyl)ethyl]-N'-[(3-(6-bromo)pyridazinyl)]thiourea
N-[2-(2-(3-ethoxy-6-fluoro)pyridyl)ethyl]-N'-[2-(6-cyano)pyridyl]thiourea
N-[2-(2-(3-ethoxy-6-fluoro)pyridyl)ethyl]-N'-[2-(5-cyano)pyridyl]thiourea
N-[2-(2-(3-ethoxy-6-fluoro)pyridyl)ethyl]-N'-[2-(5-cyano)pyrazinyl]thiourea
N-[2-(2-(3-ethoxy-6-fluoro)pyridyl)ethyl]-N'-[2-(6-cyano)pyrazinyl]thiourea
N-[2-(2-(3-ethoxy-6-fluoro)pyridyl)ethyl]-N'-[(3-(6-cyano)pyridazinyl)]thiourea N-[2-(2-(3-ethoxy-6-fluoro)pyridyl)ethyl]-N'-(2-[1,3,4-thiadiazoyl])thiourea
N-[2-(2-(3-ethoxy-6-fluoro)pyridyl)ethyl]-N'-(2-benzimidazolyl)thiourea
N-[2-(2-(3-ethoxy-6-fluoro)pyridyl)ethyl]-N'-(2-imidazolyl)thiourea
N-[2-(2-(6-ethoxy-3-fluoro)pyridyl)ethyl]-N'-(2-thiazolyl)thiourea
N-[2-(2-(6-ethoxy-3-fluoro)pyridyl)ethyl]-N'-[2-(4-methyl)thiazolyl]thiourea
N-[2-(2-(6-ethoxy-3-fluoro)pyridyl)ethyl]-N'-[2-(4,5-dimethyl)thiazolyl]thiourea
N-[2-(2-(6-ethoxy-3-fluoro)pyridyl)ethyl]-N'-[2-(4-cyano)thiazolyl]thiourea
N-[2-(2-(6-ethoxy-3-fluoro)pyridyl)ethyl]-N'-[2-(4-trifluoromethyl)thiazolyl]thiourea
N-[2-(2-(6-ethoxy-3-fluoro)pyridyl)ethyl]-N'-(2-benzothiazolyl)thiourea
N-[2-(2-(6-ethoxy-3-fluoro)pyridyl)ethyl]-N'-[2-(6-fluoro)benzothiazolyl]thiourea
N-[2-(2-(6-ethoxy-3-fluoro)pyridyl)ethyl]-N'-[2-(6-chloro)pyrazinyl]thiourea
N-[2-(2-(6-ethoxy-3-fluoro)pyridyl)ethyl]-N'-[2-(4-ethyl)thiazolyl]thiourea
N-[2-(2-(6-ethoxy-3-fluoro)pyridyl)ethyl]-N'-[2-(4-(3-pyridyl)thiazolyl)]thiourea
N-[2-(2-(6-ethoxy-3-fluoro)pyridyl)ethyl]-N'-[2-(4-(3-nitrophenyl)thiazolyl)]thiourea
N-[2-(2-(6-ethoxy-3-fluoro)pyridyl)ethyl]-N'-(2-pyridyl)thiourea
N-[2-(2-(6-ethoxy-3-fluoro)pyridyl)ethyl]-N'-[2-(6-bromo)pyridyl]thiourea
N-[2-(2-(6-ethoxy-3-fluoro)pyridyl)ethyl]-N'-[2-(5-bromo)pyridyl]thiourea
N-[2-(2-(6-ethoxy-3-fluoro)pyridyl)ethyl]-N'-[2-(6-chloro)pyridyl]thiourea
N-[2-(2-(6-ethoxy-3-fluoro)pyridyl)ethyl]-N'-[2-(5-chloro)pyridyl]thiourea
N-[2-(2-(6-ethoxy-3-fluoro)pyridyl)ethyl]-N'-[2-(6-methyl)pyridyl]thiourea
N-[2-(2-(6-ethoxy-3-fluoro)pyridyl)ethyl]-N'-[2-(5-methyl)pyridyl]thiourea
N-[2-(2-(6-ethoxy-3-fluoro)pyridyl)ethyl]-N'-[2-(6-trifluoromethyl)pyridyl]thiourea
N-[2-(2-(6-ethoxy-3-fluoro)pyridyl)ethyl]-N'-[2-(5-trifluoromethyl)pyridyl]thiourea
N-[2-(2-(6-ethoxy-3-fluoro)pyridyl)ethyl]-N'-[2-(6-ethyl)pyridyl]thiourea
N-[2-(2-(6-ethoxy-3-fluoro)pyridyl)ethyl]-N'-[2-(5-ethyl)pyridyl]thiourea
N-[2-(2-(6-ethoxy-3-fluoro)pyridyl)ethyl]-N'-[2-(5-chloro)pyrazinyl]thiourea
N-[2-(2-(6-ethoxy-3-fluoro)pyridyl)ethyl]-N'-[2-(6-bromo)pyrazinyl]thiourea
N-[2-(2-(6-ethoxy-3-fluoro)pyridyl)ethyl]-N'-[2-(5-bromo)pyrazinyl]thiourea
N-[2-(2-(6-ethoxy-3-fluoro)pyridyl)ethyl]-N'-[(3-(6-bromo)pyridazinyl)]thiourea
N-[2-(2-(6-ethoxy-3-fluoro)pyridyl)ethyl]-N'-[(3-(6-chloro)pyridazinyl)]thiourea
N-[2-(2-(6-ethoxy-3-fluoro)pyridyl)ethyl]-N'-[2-(6-cyano)pyridyl]thiourea
N-[2-(2-(6-ethoxy-3-fluoro)pyridyl)ethyl]-N'-[2-(5-cyano)pyridyl]thiourea
N-[2-(2-(6-ethoxy-3-fluoro)pyridyl)ethyl]-N'-[2-(5-cyano)pyrazinyl]thiourea
N-[2-(2-(6-ethoxy-3-fluoro)pyridyl)ethyl]-N'-[2-(6-cyano)pyrazinyl]thiourea
N-[2-(2-(6-ethoxy-3-fluoro)pyridyl)ethyl]-N'-[(3-(6-cyano)pyridazinyl)]thiourea
N-[2-(2-(6-ethoxy-3-fluoro)pyridyl)ethyl]-N'-(2-[1,3,4-thiadiazoyl])thiourea
N-[2-(2-(6-ethoxy-3-fluoro)pyridyl)ethyl]-N'-(2-benzimidazolyl)thiourea
N-[2-(2-(6-ethoxy-3-fluoro)pyridyl)ethyl]-N'-(2-imidazolyl)thiourea
N-[2-(5,6-fluoro)pyridyl)ethyl]-N'-(2-thiazolyl)thiourea
N-[2-(5,6-fluoro)pyridyl)ethyl]-N'-[2-(4-methyl)thiazolyl]thiourea
N-[2-(5,6-fluoro)pyridyl)ethyl]-N'-[2-(4,5-dimethyl)thiazolyl]thiourea
N-[2-(5,6-fluoro)pyridyl)ethyl]-N'-[2-(4-cyano)thiazolyl]thiourea
N-[2-(5,6-fluoro)pyridyl)ethyl]-N'-[2-(4-trifluoromethyl)thiazolyl]thiourea
N-[2-(5,6-fluoro)pyridyl)ethyl]-N'-(2-benzothiazolyl)thiourea
N-[2-(5,6-fluoro)pyridyl)ethyl]-N'-[2-(6-fluoro)benzothiazolyl]thiourea
N-[2-(5,6-fluoro)pyridyl)ethyl]-N'-[2-(6-chloro)pyrazinyl]thiourea
N-[2-(5,6-fluoro)pyridyl)ethyl]-N'-[2-(4-ethyl)thiazolyl]thiourea
N-[2-(5,6-fluoro)pyridyl)ethyl]-N'-[2-(4-(3-pyridyl)thiazolyl)]thiourea
N-[2-(5,6-fluoro)pyridyl)ethyl]-N'-[2-(4-(3-nitrophenyl)thiazolyl)]thiourea
N-[2-(5,6-fluoro)pyridyl)ethyl]-N'-(2-pyridyl)thiourea
N-[2-(5,6-fluoro)pyridyl)ethyl]-N'-[2-(6-bromo)pyridyl]thiourea
N-[2-(5,6-fluoro)pyridyl)ethyl]-N'-[2-(5-bromo)pyridyl]thiourea
N-[2-(5,6-fluoro)pyridyl)ethyl]-N'-[2-(6-chloro)pyridyl]thiourea
N-[2-(5,6-fluoro)pyridyl)ethyl]-N'-[2-(5-chloro)pyridyl]thiourea
N-[2-(5,6-fluoro)pyridyl)ethyl]-N'-[2-(6-methyl)pyridyl]thiourea
N-[2-(5,6-fluoro)pyridyl)ethyl]-N'-[2-(5-methyl)pyridyl]thiourea
N-[2-(5,6-fluoro)pyridyl)ethyl]-N'-[2-(6-trifluoromethyl)pyridyl]thiourea
N-[2-(5,6-fluoro)pyridyl)ethyl]-N'-[2-(5-trifluoromethyl)pyridyl]thiourea
N-[2-(5,6-fluoro)pyridyl)ethyl]-N'-[2-(6-ethyl)pyridyl]thiourea
N-[2-(5,6-fluoro)pyridyl)ethyl]-N'-[2-(5-ethyl)pyridyl]thiourea
N-[2-(5,6-fluoro)pyridyl)ethyl]-N'-[2-(5-chloro)pyrazinyl]thiourea
N-[2-(5,6-fluoro)pyridyl)ethyl]-N'-[2-(6-bromo)pyrazinyl]thiourea
N-[2-(5,6-fluoro)pyridyl)ethyl]-N'-[2-(5-bromo)pyrazinyl]thiourea
N-[2-(5,6-fluoro)pyridyl)ethyl]-N'-[(3-(6-bromo)pyridazinyl)]thiourea
N-[2-(5,6-fluoro)pyridyl)ethyl]-N'-[(3-(6-chloro)pyridazinyl)]thiourea
N-[2-(5,6-fluoro)pyridyl)ethyl]-N'-[2-(6-cyano)pyridyl]thiourea
N-[2-(5,6-fluoro)pyridyl)ethyl]-N'-[2-(5-cyano)pyridyl]thiourea
N-[2-(5,6-fluoro)pyridyl)ethyl]-N'-[2-(5-cyano)pyrazinyl]thiourea
N-[2-(5,6-fluoro)pyridyl)ethyl]-N'-[2-(6-cyano)pyrazinyl]thiourea N-[2-(5,6-fluoro)pyridyl)ethyl]-N'-[3-(6-cyano)pyridazinyl)]thiourea
N-[2-(5,6-fluoro)pyridyl)ethyl]-N'-(2-[1,3,4-thiadiazoyl])thiourea
N-[2-(5,6-fluoro)pyridyl)ethyl]-N'-(2-benzimidazolyl)thiourea
N-[2-(5,6-fluoro)pyridyl)ethyl]-N'-(2-imidazolyl)thiourea
N-[2-(2-(5,6-difluoro)pyridyl)ethyl]-N'-(2-thiazolyl)thiourea
N-[2-(2-(5,6-difluoro)pyridyl)ethyl]-N'-[2-(4-methyl)thiazolyl]thiourea
N-[2-(2-(5,6-difluoro)pyridyl)ethyl]-N'-[2-(4,5-dimethyl)thiazolyl]thiourea
N-[2-(2-(5,6-difluoro)pyridyl)ethyl]-N'-[2-(4-cyano)thiazolyl]thiourea
N-[2-(2-(5,6-difluoro)pyridyl)ethyl]-N'-[2-(4-trifluoromethyl)thiazolyl]thiourea
N-[2-(2-(5,6-difluoro)pyridyl)ethyl]-N'-[2-benzothiazolyl]thiourea
N-[2-(2-(5,6-difluoro)pyridyl)ethyl]-N'-[2-(6-fluoro)benzothiazolyl]thiourea
N-[2-(2-(5,6-difluoro)pyridyl)ethyl]-N'-[2-(6-chloro)pyrazinyl]thiourea
N-[2-(2-(5,6-difluoro)pyridyl)ethyl]-N'-[2-(4-ethyl)thiazolyl]thiourea
N-[2-(2-(5,6-difluoro)pyridyl)ethyl]-N'-[2-(4-(3-pyridyl)thiazolyl)]thiourea
N-[2-(2-(5,6-difluoro)pyridyl)ethyl]-N'-[2-(4-(3-nitrophenyl)thiazolyl)]thiourea
N-[2-(2-(5,6-difluoro)pyridyl)ethyl]-N'-(2-pyridyl)thiourea
N-[2-(2-(5,6-difluoro)pyridyl)ethyl]-N'-[2-(6-bromo)pyridyl]thiourea
N-[2-(2-(5,6-difluoro)pyridyl)ethyl]-N'-[2-(5-bromo)pyridyl]thiourea
N-[2-(2-(5,6-difluoro)pyridyl)ethyl]-N'-[2-(6-chloro)pyridyl]thiourea
N-[2-(2-(5,6-difluoro)pyridyl)ethyl]-N'-[2-(5-chloro)pyridyl]thiourea
N-[2-(2-(5,6-difluoro)pyridyl)ethyl]-N'-[2-(6-methyl)pyridyl]thiourea
N-[2-(2-(5,6-difluoro)pyridyl)ethyl]-N'-[2-(5-methyl)pyridyl]thiourea
N-[2-(2-(5,6-difluoro)pyridyl)ethyl]-N'-[2-(6-trifluoromethyl)pyridyl]thiourea
N-[2-(2-(5,6-difluoro)pyridyl)ethyl]-N'-[2-(5-trifluoromethyl)pyridyl]thiourea
N-[2-(2-(5,6-difluoro)pyridyl)ethyl]-N'-[2-(6-ethyl)pyridyl]thiourea
N-[2-(2-(5,6-difluoro)pyridyl)ethyl]-N'-[2-(5-ethyl)pyridyl]thiourea
N-[2-(2-(5,6-difluoro)pyridyl)ethyl]-N'-[2-(5-chloro)pyrazinyl]thiourea
N-[2-(2-(5,6-difluoro)pyridyl)ethyl]-N'-[2-(6-bromo)pyrazinyl]thiourea
N-[2-(2-(5,6-difluoro)pyridyl)ethyl]-N'-[2-(5-bromo)pyrazinyl]thiourea
N-[2-(2-(5,6-difluoro)pyridyl)ethyl]-N'-[(3-(6-bromo)pyridazinyl)]thiourea
N-[2-(2-(5,6-difluoro)pyridyl)ethyl]-N'-[(3-(6-chloro)pyridazinyl)]thiourea
N-[2-(2-(5,6-difluoro)pyridyl)ethyl]-N'-[2-(6-cyano)pyridyl]thiourea
N-[2-(2-(5,6-difluoro)pyridyl)ethyl]-N'-[2-(5-cyano)pyridyl]thiourea
N-[2-(2-(5,6-difluoro)pyridyl)ethyl]-N'-[2-(5-cyano)pyrazinyl]thiourea
N-[2-(2-(5,6-difluoro)pyridyl)ethyl]-N'-[2-(6-cyano)pyrazinyl]thiourea
N-[2-(2-(5,6-difluoro)pyridyl)ethyl]-N'-[(3-(6-cyano)pyridazinyl)]thiourea
N-[2-(2-(5,6-difluoro)pyridyl)ethyl]-N'-(2-[1,3,4-thiadiazoyl])thiourea
N-[2-(2-(5,6-difluoro)pyridyl)ethyl]-N'-(2-benzimidazolyl)thiourea
N-[2-(2-(5,6-difluoro)pyridyl)ethyl]-N'-(2-imidazolyl)thiourea
N-[2-(2-(3,6-difluoro)pyridyl)ethyl]-N'-(2-thiazolyl)thiourea
N-[2-(2-(3,6-difluoro)pyridyl)ethyl]-N'-[2-(4-methyl)thiazolyl]thiourea
N-[2-(2-(3,6-difluoro)pyridyl)ethyl]-N'-[2-(4,5-dimethyl)thiazolyl]thiourea
N-[2-(2-(3,6-difluoro)pyridyl)ethyl]-N'-[2-benzothiazolyl]thiourea
N-[2-(2-(3,6-difluoro)pyridyl)ethyl]-N'-[2-(6-fluoro)benzothiazolyl]thiourea
N-[2-(2-(3,6-difluoro)pyridyl)ethyl]-N'-[2-(6-chloro)pyrazinyl]thiourea
N-[2-(2-(3,6-difluoro)pyridyl)ethyl]-N'-[2-(4-(3-pyridyl)thiazolyl)]thiourea
N-[2-(2-(3,6-difluoro)pyridyl)ethyl]-N'-[2-(4-(3-nitrophenyl)thiazolyl)]thiourea
N-[2-(2-(3,6-difluoro)pyridyl)ethyl]-N'-(2-pyridyl)thiourea
N-[2-(2-(3,6-difluoro)pyridyl)ethyl]-N'-[2-(6-bromo)pyridyl]thiourea
N-[2-(2-(3,6-difluoro)pyridyl)ethyl]-N'-[2-(6-chloro)pyridyl]thiourea
N-[2-(2-(3,6-difluoro)pyridyl)ethyl]-N'-[2-(6-methyl)pyridyl]thiourea
N-[2-(2-(3,6-difluoro)pyridyl)ethyl]-N'-[2-(5-methyl)pyridyl]thiourea
N-[2-(2-(3,6-difluoro)pyridyl)ethyl]-N'-[2-(6-trifluoromethyl)pyridyl]thiourea
N-[2-(2-(3,6-difluoro)pyridyl)ethyl]-N'-[2-(5-trifluoromethyl)pyridyl]thiourea
N-[2-(2-(3,6-difluoro)pyridyl)ethyl]-N'-[2-(6-ethyl)pyridyl]thiourea
N-[2-(2-(3,6-difluoro)pyridyl)ethyl]-N'-[2-(5-ethyl)pyridyl]thiourea
N-[2-(2-(3,6-difluoro)pyridyl)ethyl]-N'-[2-(6-bromo)pyrazinyl]thiourea
N-[2-(2-(3,6-difluoro)pyridyl)ethyl]-N'-[(3-(6-bromo)pyridazinyl)]thiourea
N-[2-(2-(3,6-difluoro)pyridyl)ethyl]-N'-[2-(6-cyano)pyridyl]thiourea
N-[2-(2-(3,6-difluoro)pyridyl)ethyl]-N'-[2-(5-cyano)pyridyl]thiourea
N-[2-(2-(3,6-difluoro)pyridyl)ethyl]-N'-[2-(5-cyano)pyrazinyl]thiourea
N-[2-(2-(3,6-difluoro)pyridyl)ethyl]-N'-[2-(6-cyano)pyrazinyl]thiourea
N-[2-(2-(3,6-difluoro)pyridyl)ethyl]-N'-[(3-(6-cyano)pyridazinyl)]thiourea
N-[2-(2-(3,6-difluoro)pyridyl)ethyl]-N'-(2-[1,3,4-thiadiazoyl])thiourea
N-[2-(2-(3,6-difluoro)pyridyl)ethyl]-N'-(2-benzimidazolyl)thiourea
N-[2-(2-(3,6-difluoro)pyridyl)ethyl]-N'-(2-imidazolyl)thiourea
N-[2-(2-(5,6-dichloro)pyridyl)ethyl]-N'-(2-thiazolyl)thiourea
N-[2-(2-(5,6-dichloro)pyridyl)ethyl]-N'-[2-(4-methyl)thiazolyl]thiourea
N-[2-(2-(5,6-dichloro)pyridyl)ethyl]-N'-[2-(4,5-dimethyl)thiazolyl]thiourea N-[2-(2-(5,6-dichloro)pyridyl)ethyl]-N'-[2-(4-cyano)thiazolyl]thiourea
N-[2-(2-(5,6-dichloro)pyridyl)ethyl]-N'-[2-(4-trifluoromethyl)thiazolyl]thiourea
N-[2-(2-(5,6-dichloro)pyridyl)ethyl]-N'-(2-benzothiazolyl)thiourea
N-[2-(2-(5,6-dichloro)pyridyl)ethyl]-N'-[2-(6-fluoro)benzothiazolyl]thiourea
N-[2-(2-(5,6-dichloro)pyridyl)ethyl]-N'-[2-(6-chloro)pyrazinyl]thiourea
N-[2-(2-(5,6-dichloro)pyridyl)ethyl]-N'-[2-(4-ethyl)thiazolyl]thiourea
N-[2-(2-(5,6-dichloro)pyridyl)ethyl]-N'-[2-(4-(3-pyridyl)thiazolyl)]thiourea
N-[2-(2-(5,6-dichloro)pyridyl)ethyl]-N'-[2-(4-(3-nitrophenyl)thiazolyl)]thiourea
N-[2-(2-(5,6-dichloro)pyridyl)ethyl]-N'-(2-pyridyl)thiourea
N-[2-(2-(5,6-dichloro)pyridinyl)ethyl]-N'-[2-(6-bromo)pyridyl]thiourea
N-[2-(2-(5,6-dichloro)pyridyl)ethyl]-N'-[2-(5-bromo)pyridyl]thiourea
N-[2-(2-(5,6-dichloro)pyridyl)ethyl]-N'-[2-(6-chloro)pyridyl]thiourea
N-[2-(2-(5,6-dichloro)pyridyl)ethyl]-N'-[2-(5-chloro)pyridyl]thiourea
N-[2-(2-(5,6-dichloro)pyridyl)ethyl]-N'-[2-(6-methyl)pyridyl]thiourea
N-[2-(2-(5,6-dichloro)pyridyl)ethyl]-N'-[2-(5-methyl)pyridyl]thiourea
N-[2-(2-(5,6-dichloro)pyridyl)ethyl]-N'-[2-(6-trifluoromethyl)pyridyl]thiourea
N-[2-(2-(5,6-dichloro)pyridyl)ethyl]-N'-[2-(5-trifluoromethyl)pyridyl]thiourea
N-[2-(2-(5,6-dichloro)pyridyl)ethyl]-N'-[2-(6-ethyl)pyridyl]thiourea
N-[2-(2-(5,6-dichloro)pyridyl)ethyl]-N'-[2-(5-ethyl)pyridyl]thiourea
N-[2-(2-(5,6-dichloro)pyridyl)ethyl]-N'-[2-(5-chloro)pyrazinyl]thiourea
N-[2-(2-(5,6-dichloro)pyridyl)ethyl]-N'-[2-(6-bromo)pyrazinyl]thiourea
N-[2-(2-(5,6-dichloro)pyridyl)ethyl]-N'-[2-(5-bromo)pyrazinyl]thiourea
N-[2-(2-(5,6-dichloro)pyridyl)ethyl]-N'-[(3-(6-bromo)pyridazinyl)]thiourea
N-[2-(2-(5,6-dichloro)pyridyl)ethyl]-N'-[(3-(6-chloro)pyridazinyl)]thiourea
N-[2-(2-(5,6-dichloro)pyridyl)ethyl]-N'-[2-(6-cyano)pyridyl]thiourea
N-[2-(2-(5,6-dichloro)pyridyl)ethyl]-N'-[2-(5-cyano)pyridyl]thiourea
N-[2-(2-(5,6-dichloro)pyridyl)ethyl]-N'-[2-(5-cyano)pyrazinyl]thiourea
N-[2-(2-(5,6-dichloro)pyridyl)ethyl]-N'-[2-(6-cyano)pyrazinyl]thiourea
N-[2-(2-(5,6-dichloro)pyridyl)ethyl]-N'-[(3-(6-cyano)pyridazinyl)]thiourea
N-[2-(2-(5,6-dichloro)pyridyl)ethyl]-N'-(2-[1,3,4-thiadiazoyl])thiourea
N-[2-(2-(5,6-dichloro)pyridyl)ethyl]-N'-(2-benzimidazolyl)thiourea
N-[2-(2-(5,6-dichloro)pyridyl)ethyl]-N'-(2-imidazolyl)thiourea
N-[2-(2-(3,6-dichloro)pyridyl)ethyl]-N'-(2-thiazolyl)thiourea
N-[2-(2-(3,6-dichloro)pyridyl)ethyl]-N'-[2-(4-methyl)thiazolyl]thiourea
N-[2-(2-(3,6-dichloro)pyridyl)ethyl]-N'-[2-(4,5-dimethyl)thiazolyl]thiourea
N-[2-(2-(3,6-dichloro)pyridyl)ethyl]-N'-[2-(4-cyano)thiazolyl]thiourea
N-[2-(2-(3,6-dichloro)pyridyl)ethyl]-N'-[2-(4-trifluoromethyl)thiazolyl]thiourea
N-[2-(2-(3,6-dichloro)pyridyl)ethyl]-N'-(2-benzothiazolyl)thiourea
N-[2-(2-(3,6-dichloro)pyridyl)ethyl]-N'-[2-(6-fluoro)benzothiazolyl]thiourea
N-[2-(2-(3,6-dichloro)pyridyl)ethyl]-N'-[2-(6-chloro)pyrazinyl]thiourea
N-[2-(2-(3,6-dichloro)pyridyl)ethyl]-N'-[2-(4-ethyl)thiazolyl]thiourea
N-[2-(2-(3,6-dichloro)pyridyl)ethyl]-N'-[2-(4-(3-pyridinyl)thiazolyl)]thiourea
N-[2-(2-(3,6-dichloro)pyridyl)ethyl]-N'-[2-(4-(3-nitrophenyl)thiazolyl)]thiourea
N-[2-(2-(3,6-dichloro)pyridyl)ethyl]-N'-(2-pyridyl)thiourea
N-[2-(2-(3,6-dichloro)pyridyl)ethyl]-N'-[2-(6-bromo)pyridyl]thiourea
N-[2-(2-(3,6-dichloro)pyridyl)ethyl]-N'-[2-(5-bromo)pyridyl]thiourea
N-[2-(2-(3,6-dichloro)pyridyl)ethyl]-N'-[2-(6-chloro)pyridyl]thiourea
N-[2-(2-(3,6-dichloro)pyridyl)ethyl]-N'-[2-(5-chloro)pyridyl]thiourea
N-[2-(2-(3,6-dichloro)pyridyl)ethyl]-N'-[2-(6-methyl)pyridyl]thiourea
N-[2-(2-(3,6-dichloro)pyridyl)ethyl]-N'-[2-(5-methyl)pyridyl]thiourea
N-[2-(2-(3,6-dichloro)pyridyl)ethyl]-N'-[2-(6-trifluoromethyl)pyridyl]thiourea
N-[2-(2-(3,6-dichloro)pyridyl)ethyl]-N'-[2-(5-trifluoromethyl)pyridyl]thiourea
N-[2-(2-(3,6-dichloro)pyridyl)ethyl]-N'-[2-(6-ethyl)pyridyl]thiourea
N-[2-(2-(3,6-dichloro)pyridyl)ethyl]-N'-[2-(5-ethyl)pyridyl]thiourea
N-[2-(2-(3,6-dichloro)pyridyl)ethyl]-N'-[2-(5-chloro)pyrazinyl]thiourea
N-[2-(2-(3,6-dichloro)pyridyl)ethyl]-N'-[2-(6-bromo)pyrazinyl]thiourea
N-[2-(2-(3,6-dichloro)pyridyl)ethyl]-N'-[2-(5-bromo)pyrazinyl]thiourea
N-[2-(2-(3,6-dichloro)pyridyl)ethyl]-N'-[(3-(6-bromo)pyridazinyl)]thiourea
N-[2-(2-(3,6-dichloro)pyridyl)ethyl]-N'-[(3-(6-chloro)pyridazinyl)]thiourea
N-[2-(2-(3,6-dichloro)pyridyl)ethyl]-N'-[2-(6-cyano)pyridyl]thiourea
N-[2-(2-(3,6-dichloro)pyridyl)ethyl]-N'-[2-(5-cyano)pyridyl]thiourea
N-[2-(2-(3,6-dichloro)pyridyl)ethyl]-N'-[2-(5-cyano)pyrazinyl]thiourea
N-[2-(2-(3,6-dichloro)pyridyl)ethyl]-N'-[2-(6-cyano)pyrazinyl]thiourea
N-[2-(2-(3,6-dichloro)pyridyl)ethyl]-N'-[(3-(6-cyano)pyridazinyl)]thiourea
N-[2-(2-(3,6-dichloro)pyridyl)ethyl]-N'-(2-[1,3,4-thiadiazoyl])thiourea
N-[2-(2-(3,6-dichloro)pyridyl)ethyl]-N'-(2-benzimidazolyl)thiourea
N-[2-(2-(3,6-dichloro)pyridyl)ethyl]-N'-(2-imidazolyl)thiourea
N-[2-(cis-2-pyridyl)cyclopropyl]-N'-(2-thiazolyl)thiourea
N-[2-(cis-2-pyridyl)cyclopropyl]-N'-[2-(4-methyl)thiazolyl]thiourea N-[2-(cis-2-pyridyl)cyclopropyl]-N'-[2-(4,5-dimethyl)thiazolyl]thiourea
N-[2-(cis-2-pyridyl)cyclopropyl]-N'-[2-benzothiazolyl]thiourea
N-[2-(cis-2-pyridyl)cyclopropyl]-N'-[2-(6-fluoro)benzothiazolyl]thiourea
N-[2-(cis-2-pyridyl)cyclopropyl]-N'-[2-(6-chloro)pyrazinyl]thiourea
N-[2-(cis-2-pyridyl)cyclopropyl]-N'-[2-(4-(3-pyridyl)thiazolyl)]thiourea
N-[2-(cis-2-pyridyl)cyclopropyl]-N'-[2-(4-(3-nitrophenyl)thiazolyl)]thiourea
N-[2-(cis-2-pyridyl)cyclopropyl]-N'-[2-(6-bromo)pyridyl]thiourea
N-[2-(cis-2-pyridyl)cyclopropyl]-N'-[2-(6-chloro)pyridyl]thiourea
N-[2-(cis-2-pyridyl)cyclopropyl]-N'-[2-(6-methyl)pyridyl]thiourea
N-[2-(cis-2-pyridyl)cyclopropyl]-N'-[2-(6-trifluoromethyl)pyridyl]thiourea
N-[2-(cis-2-pyridyl)cyclopropyl]-N'-[2-(6-ethyl)pyridyl]thiourea
N-[2-(cis-2-pyridyl)cyclopropyl]-N'-[2-(6-bromo)pyrazinyl]thiourea
N-[2-(cis-2-pyridyl)cyclopropyl]-N'-[(3-(6-bromo)pyridazinyl)]thiourea
N-[2-(cis-2-pyridyl)cyclopropyl]-N'-[2-(6-cyano)pyridyl]thiourea
N-[2-(cis-2-pyridyl)cyclopropyl]-N'-[2-(5-cyano)pyridyl]thiourea
N-[2-(cis-2-pyridyl)cyclopropyl]-N'-[2-(5-cyano)pyrazinyl]thiourea
N-[2-(cis-2-pyridyl)cyclopropyl]-N'-[2-(6-cyano)pyrazinyl]thiourea
N-[2-(cis-2-pyridyl)cyclopropyl]-N'-[(3-(6-cyano)pyridazinyl)]thiourea
N-[2-(cis-2-pyridyl)cyclopropyl]-N'-(2-[1,3,4-thiadiazoyl])thiourea
N-[2-(cis-2-pyridyl)cyclopropyl]-N'-(2-benzimidazolyl)thiourea
N-[2-(cis-2-pyridyl)cyclopropyl]-N'-(2-imidazolyl)thiourea
N-[2-(cis-2-(6-fluoro)pyridyl)cyclopropyl]-N'-(2-thiazolyl)thiourea
N-[2-(cis-2-(6-fluoro)pyridyl)cyclopropyl]-N'-[2-(4-methyl)thiazolyl]thiourea
N-[2-(cis-2-(6-fluoro)pyridyl)cyclopropyl]-N'-[2-(4,5-dimethyl)thiazolyl]thiourea
N-[2-(cis-2-(6-fluoro)pyridyl)cyclopropyl]-N'-[2-benzothiazolyl]thiourea
N-[2-(cis-2-(6-fluoro)pyridyl)cyclopropyl]-N'-[2-(6-fluoro)benzothiazolyl]thiourea
N-[2-(cis-2-(6-fluoro)pyridyl)cyclopropyl]-N'-[2-(6-chloro)pyrazinyl]thiourea
N-[2-(cis-2-(6-fluoro)pyridyl)cyclopropyl]-N'-[2-(4-(3-pyridyl)thiazolyl)]thiourea
N-[2-(cis-2-(6-fluoro)pyridyl)cyclopropyl]-N'-[2-(4-(3-nitrophenyl)thiazolyl)]thiourea
N-[2-(cis-2-(6-fluoro)pyridyl)cyclopropyl]-N'-[2-(6-bromo)pyridyl]thiourea
N-[2-(cis-2-(6-fluoro)pyridyl)cyclopropyl]-N'-[2-(6-chloro)pyridyl]thiourea
N-[2-(cis-2-(6-fluoro)pyridyl)cyclopropyl]-N'-[2-(6-methyl)pyridyl]thiourea
N-[2-(cis-2-(6-fluoro)pyridyl)cyclopropyl]-N'-[2-(6-trifluoromethyl)pyridyl]thiourea
N-[2-(cis-2-(6-fluoro)pyridyl)cyclopropyl]-N'-[2-(5-trifluoromethyl)pyridyl]thiourea
N-[2-(cis-2-(6-fluoro)pyridyl)cyclopropyl]-N'-[2-(6-ethyl)pyridyl]thiourea
N-[2-(cis-2-(6-fluoro)pyridyl)cyclopropyl]-N'-[2-(5-ethyl)pyridyl]thiourea
N-[2-(cis-2-(6-fluoro)pyridyl)cyclopropyl]-N'-[2-(6-bromo)pyrazinyl]thiourea
N-[2-(cis-2-(6-fluoro)pyridyl)cyclopropyl]-N'-[(3-(6-bromo)pyridazinyl)]thiourea
N-[2-(cis-2-(6-fluoro)pyridyl)cyclopropyl]-N'-[2-(6-cyano)pyridyl]thiourea
N-[2-(cis-2-(6-fluoro)pyridyl)cyclopropyl]-N'-[2-(5-cyano)pyridyl]thiourea
N-[2-(cis-2-(6-fluoro)pyridyl)cyclopropyl]-N'-[2-(5-cyano)pyrazinyl]thiourea
N-[2-(cis-2-(6-fluoro)pyridyl)cyclopropyl]-N'-[2-(6-cyano)pyrazinyl]thiourea
N-[2-(cis-2-(6-fluoro)pyridyl)cyclopropyl]-N'-[(3-(6-cyano)pyridazinyl)]thiourea
N-[2-(cis-2-(6-fluoro)pyridyl)cyclopropyl]-N'-(2-[1,3,4-thiadiazoyl])thiourea
N-[2-(cis-2-(6-fluoro)pyridyl)cyclopropyl]-N'-(2-benzimidazolyl)thiourea
N-[2-(cis-2-(6-fluoro)pyridyl)cyclopropyl]-N'-(2-imidazolyl)thiourea
N-[2-(cis-2-(6-chloro)pyridyl)cyclopropyl]-N'-(2-thiazolyl)thiourea
N-[2-(cis-2-(6-chloro)pyridyl)cyclopropyl]-N'-[2-(4-methyl)thiazolyl]thiourea
N-[2-(cis-2-(6-chloro)pyridyl)cyclopropyl]-N'-[2-(4,5-dimethyl)thiazolyl]thiourea
N-[2-(cis-2-(6-chloro)pyridyl)cyclopropyl]-N'-[2-(4-cyano)thiazolyl]thiourea
N-[2-(cis-2-(6-chloro)pyridyl)cyclopropyl]-N'-[2-(4-trifluoromethyl)thiazolyl]thiourea
N-[2-(cis-2-(6-chloro)pyridyl)cyclopropyl]-N'-(2-benzothiazolyl)thiourea
N-[2-(cis-2-(6-chloro)pyridyl)cyclopropyl]-N'-[2-(6-fluoro)benzothiazolyl]thiourea
N-[2-(cis-2-(6-chloro)pyridyl)cyclopropyl]-N'-[2-(6-chloro)pyrazinyl]thiourea
N-[2-(cis-2-(6-chloro)pyridyl)cyclopropyl]-N'-[2-(4-ethyl)thiazolyl]thiourea
N-[2-(cis-2-(6-chloro)pyridyl)cyclopropyl]-N'-[2-(4-(3-pyridyl)thiazolyl)]thiourea
N-[2-(cis-2-(6-chloro)pyridyl)cyclopropyl]-N'-[2-(4-(3-nitrophenyl)thiazolyl)]thiourea
N-[2-(cis-2-(6-chloro)pyridyl)cyclopropyl]-N'-(2-pyridinyl)thiourea
N-[2-(cis-2-(6-chloro)pyridyl)cyclopropyl]-N'-[2-(6-bromo)pyridyl]thiourea
N-[2-(cis-2-(6-chloro)pyridyl)cyclopropyl]-N'-[2-(5-bromo)pyridyl]thiourea
N-[2-(cis-2-(6-chloro)pyridyl)cyclopropyl]-N'-[2-(6-chloro)pyridyl]thiourea
N-[2-(cis-2-(6-chloro)pyridyl)cyclopropyl]-N'-[2-(5-chloro)pyridyl]thiourea
N-[2-(cis-2-(6-chloro)pyridyl)cyclopropyl]-N'-[2-(6-methyl)pyridyl]thiourea
N-[2-(cis-2-(6-chloro)pyridyl)cyclopropyl]-N'-[2-(5-methyl)pyridyl]thiourea
N-[2-(cis-2-(6-chloro)pyridyl)cyclopropyl]-N'-[2-(6-trifluoromethyl)pyridyl]thiourea
N-[2-(cis-2-(6-chloro)pyridyl)cyclopropyl]-N'-[2-(5-trifluoromethyl)pyridyl]thiourea
N-[2-(cis-2-(6-chloro)pyridyl)cyclopropyl]-N'-[2-(6-ethyl)pyridyl]thiourea
N-[2-(cis-2-(6-chloro)pyridyl)cyclopropyl]-N'-[2-(5-ethyl)pyridyl]thiourea N-[2-(cis-2-(6-chloro)pyridyl)cyclopropyl]-N'-[2-(5-chloro)pyrazinyl]thiourea
N-[2-(cis-2-(6-chloro)pyridyl)cyclopropyl]-N'-[2-(6-bromo)pyrazinyl]thiourea
N-[2-(cis-2-(6-chloro)pyridyl)cyclopropyl]-N'-[2-(5-bromo)pyrazinyl]thiourea
N-[2-(cis-2-(6-chloro)pyridyl)cyclopropyl]-N'-[(3-(6-bromo)pyridazinyl)]thiourea
N-[2-(cis-2-(6-chloro)pyridyl)cyclopropyl]-N'-[(3-(6-chloro)pyridazinyl)]thiourea
N-[2-(cis-2-(6-chloro)pyridyl)cyclopropyl]-N'-[2-(6-cyano)pyridyl]thiourea
N-[2-(cis-2-(6-chloro)pyridyl)cyclopropyl]-N'-[2-(5-cyano)pyridyl]thiourea
N-[2-(cis-2-(6-chloro)pyridyl)cyclopropyl]-N'-[2-(5-cyano)pyrazinyl]thiourea
N-[2-(cis-2-(6-chloro)pyridyl)cyclopropyl]-N'-[2-(6-cyano)pyrazinyl]thiourea
N-[2-(cis-2-(6-chloro)pyridyl)cyclopropyl]-N'-[(3-(6-cyano)pyridazinyl)]thiourea
N-[2-(cis-2-(6-chloro)pyridyl)cyclopropyl]-N'-(2-[1,3,4-thiadiazoyl])thiourea
N-[2-(cis-2-(6-chloro)pyridyl)cyclopropyl]-N'-(2-benzimidazolyl)thiourea
N-[2-(cis-2-(6-chloro)pyridyl)cyclopropyl]-N'-(2-imidazolyl)thiourea
N-[2-(cis-2-(6-methoxy)pyridyl)cyclopropyl]-N'-(2-thiazolyl)thiourea
N-[2-(cis-2-(6-methoxy)pyridyl)cyclopropyl]-N'-[2-(4-methyl)thiazolyl]thiourea
N-[2-(cis-2-(6-methoxy)pyridyl)cyclopropyl]-N'-[2-(4,5-dimethyl)thiazolyl]thiourea
N-[2-(cis-2-(6-methoxy)pyridyl)cyclopropyl]-N'-(2-benzothiazolyl)thiourea
N-[2-(cis-2-(6-methoxy)pyridyl)cyclopropyl]-N'-[2-(6-fluoro)benzothiazolyl]thiourea
N-[2-(cis-2-(6-methoxy)pyridyl)cyclopropyl]-N'-[2-(6-chloro)pyrazinyl]thiourea
N-[2-(cis-2-(6-methoxy)pyridyl)cyclopropyl]-N'-[2-(4-(3-pyridyl)thiazolyl)]thiourea
N-[2-(cis-2-(6-methoxy)pyridyl)cyclopropyl]-N'-[2-(4-(3-nitrophenyl)thiazolyl)]thiourea
N-[2-(cis-2-(6-methoxy)pyridyl)cyclopropyl]-N'-(2-pyridyl)thiourea
N-[2-(cis-2-(6-methoxy)pyridyl)cyclopropyl]-N'-[2-(6-bromo)pyridyl]thiourea
N-[2-(cis-2-(6-methoxy)pyridyl)cyclopropyl]-N'-[2-(6-chloro)pyridyl]thiourea
N-[2-(cis-2-(6-methoxy)pyridinyl)cyclopropyl]-N'-[2-(6-methyl)pyridyl]thiourea
N-[2-(cis-2-(6-methoxy)pyridyl)cyclopropyl]-N'-[2-(5-methyl)pyridyl]thiourea
N-[2-(cis-2-(6-methoxy)pyridyl)cyclopropyl]-N'-[2-(6-trifluoromethyl)pyridyl]thiourea
N-[2-(cis-2-(6-methoxy)pyridyl)cyclopropyl]-N'-[2-(5-trifluoromethyl)pyridyl]thiourea
N-[2-(cis-2-(6-methoxy)pyridyl)cyclopropyl]-N'-[2-(6-ethyl)pyridyl]thiourea
N-[2-(cis-2-(6-methoxy)pyridyl)cyclopropyl]-N'-[2-(5-ethyl)pyridyl]thiourea
N-[2-(cis-2-(6-methoxy)pyridyl)cyclopropyl]-N'-[2-(6-bromo)pyrazinyl]thiourea
N-[2-(cis-2-(6-methoxy)pyridyl)cyclopropyl]-N'-[(3-(6-bromo)pyridazinyl)]thiourea
N-[2-(cis-2-(6-methoxy)pyridyl)cyclopropyl]-N'-[2-(6-cyano)pyridyl]thiourea
N-[2-(cis-2-(6-methoxy)pyridyl)cyclopropyl]-N'-[2-(5-cyano)pyridyl]thiourea
N-[2-(cis-2-(6-methoxy)pyridyl)cyclopropyl]-N'-[2-(5-cyano)pyrazinyl]thiourea
N-[2-(cis-2-(6-methoxy)pyridyl)cyclopropyl]-N'-[2-(6-cyano)pyrazinyl]thiourea
N-[2-(cis-2-(6-methoxy)pyridyl)cyclopropyl]-N'-[(3-(6-cyano)pyridazinyl)]thiourea
N-[2-(cis-2-(6-methoxy)pyridyl)cyclopropyl]-N'-(2-[1,3,4-thiadiazoyl])thiourea
N-[2-(cis-2-(6-methoxy)pyridyl)cyclopropyl]-N'-(2-benzimidazolyl)thiourea
N-[2-(cis-2-(6-methoxy)pyridyl)cyclopropyl]-N'-(2-imidazolyl)thiourea
N-[2-(cis-2-(6-ethoxy)pyridyl)cyclopropyl]-N'-(2-thiazolyl)thiourea
N-[2-(cis-2-(6-ethoxy)pyridyl)cyclopropyl]-N'-[2-(4-methyl)thiazolyl]thiourea
N-[2-(cis-2-(6-ethoxy)pyridyl)cyclopropyl]-N'-[2-(4,5-dimethyl)thiazolyl]thiourea
N-[2-(cis-2-(6-ethoxy)pyridyl)cyclopropyl]-N'-(2-benzothiazolyl)thiourea
N-[2-(cis-2-(6-ethoxy)pyridyl)cyclopropyl]-N'-[2-(6-fluoro)benzothiazolyl]thiourea
N-[2-(cis-2-(6-ethoxy)pyridyl)cyclopropyl]-N'-[2-(6-chloro)pyrazinyl]thiourea
N-[2-(cis-2-(6-ethoxy)pyridyl)cyclopropyl]-N'-[2-(4-(3-pyridyl)thiazolyl)]thiourea
N-[2-(cis-2-(6-ethoxy)pyridyl)cyclopropyl]-N'-[2-(4-(3-nitrophenyl)thiazolyl)]thiourea
N-[2-(cis-2-(6-ethoxy)pyridyl)cyclopropyl]-N'-(2-pyridyl)thiourea
N-[2-(cis-2-(6-ethoxy)pyridyl)cyclopropyl]-N'-[2-(6-bromo)pyridyl]thiourea
N-[2-(cis-2-(6-ethoxy)pyridyl)cyclopropyl]-N'-[2-(6-chloro)pyridyl]thiourea
N-[2-(cis-2-(6-ethoxy)pyridyl)cyclopropyl]-N'-[2-(6-methyl)pyridyl]thiourea
N-[2-(cis-2-(6-ethoxy)pyridyl)cyclopropyl]-N'-[2-(5-methyl)pyridyl]thiourea
N-[2-(cis-2-(6-ethoxy)pyridyl)cyclopropyl]-N'-[2-(6-trifluoromethyl)pyridyl]thiourea
N-[2-(cis-2-(6-ethoxy)pyridyl)cyclopropyl]-N'-[2-(5-trifluoromethyl)pyridyl]thiourea
N-[2-(cis-2-(6-ethoxy)pyridyl)cyclopropyl]-N'-[2-(6-ethyl)pyridyl]thiourea
N-[2-(cis-2-(6-ethoxy)pyridyl)cyclopropyl]-N'-[2-(5-ethyl)pyridyl]thiourea
N-[2-(cis-2-(6-ethoxy)pyridyl)cyclopropyl]-N'-[2-(6-bromo)pyrazinyl]thiourea
N-[2-(cis-2-(6-ethoxy)pyridyl)cyclopropyl]-N'-[(3-(6-bromo)pyridazinyl)]thiourea
N-[2-(cis-2-(6-ethoxy)pyridyl)cyclopropyl]-N'-[2-(6-cyano)pyridyl]thiourea
N-[2-(cis-2-(6-ethoxy)pyridyl)cyclopropyl]-N'-[2-(5-cyano)pyridyl]thiourea
N-[2-(cis-2-(6-ethoxy)pyridyl)cyclopropyl]-N'-[2-(5-cyano)pyrazinyl]thiourea
N-[2-(cis-2-(6-ethoxy)pyridyl)cyclopropyl]-N'-[2-(6-cyano)pyrazinyl]thiourea
N-[2-(cis-2-(6-ethoxy)pyridyl)cyclopropyl]-N'-[(3-(6-cyano)pyridazinyl)]thiourea
N-[2-(cis-2-(6-ethoxy)pyridyl)cyclopropyl]-N'-(2-[1,3,4-thiadiazoyl])thiourea
N-[2-(cis-2-(6-ethoxy)pyridyl)cyclopropyl]-N'-(2-benzimidazolyl)thiourea
N-[2-(cis-2-(6-ethoxy)pyridyl)cyclopropyl]-N'-(2-imidazolyl)thiourea
N-[2-(2-[1,3-pyrimidyl])ethyl]-N'-(2-thiazolyl)thiourea N-[2-(2-[1,3-pyrimidyl])ethyl]-N'-[2-(4-methyl)thiazolyl]thiourea
N-[2-(2-[1,3-pyrimidyl])ethyl]-N'-[2-(4,5-dimethyl)thiazolyl]thiourea
N-[2-(2-[1,3-pyrimidyl])ethyl]-N'-[2-(4-cyano)thiazolyl]thiourea
N-[2-(2-[1,3-pyrimidyl])ethyl]-N'-[2-(4-trifluoromethyl)thiazolyl]thiourea
N-[2-(2-[1,3-pyrimidyl])ethyl]-N'-(2-benzothiazolyl)thiourea
N-[2-(2-[1,3-pyrimidyl])ethyl]-N'-[2-(6-fluoro)benzothiazolyl]thiourea
N-[2-(2-[1,3-pyrimidyl])ethyl]-N'-[2-(6-chloro)pyrazinyl]thiourea
N-[2-(2-[1,3-pyrimidyl])ethyl]-N'-[2-(4-ethyl)thiazolyl]thiourea
N-[2-(2-[1,3-pyrimidyl])ethyl]-N'-[2-(4-(3-pyridyl)thiazolyl)]thiourea
N-[2-(2-[1,3-pyrimidyl])ethyl]-N'-[2-(4-(3-nitrophenyl)thiazolyl)]thiourea
N-[2-(2-[1,3-pyrimidyl])ethyl]-N'-(2-pyridyl)thiourea
N-[2-(2-[1,3-pyrimidyl])ethyl]-N'-[2-(6-bromo)pyridyl]thiourea
N-[2-(2-[1,3-pyrimidyl])ethyl]-N'-[2-(5-bromo)pyridyl]thiourea
N-[2-(2-[1,3-pyrimidyl])ethyl]-N'-[2-(6-chloro)pyridyl]thiourea
N-[2-(2-[1,3-pyrimidyl])ethyl]-N'-[2-(5-chloro)pyridyl]thiourea
N-[2-(2-[1,3-pyrimidyl])ethyl]-N'-[2-(6-methyl)pyridyl]thiourea
N-[2-(2-[1,3-pyrimidyl])ethyl]-N'-[2-(5-methyl)pyridyl]thiourea
N-[2-(2-[1,3-pyrimidyl])ethyl]-N'-[2-(6-trifluoromethyl)pyridyl]thiourea
N-[2-(2-[1,3-pyrimidyl])ethyl]-N'-[2-(5-trifluoromethyl)pyridyl]thiourea
N-[2-(2-[1,3-pyrimidyl])ethyl]-N'-[2-(6-ethyl)pyridyl]thiourea
N-[2-(2-[1,3-pyrimidyl])ethyl]-N'-[2-(5-ethyl)pyridyl]thiourea
N-[2-(2-[1,3-pyrimidyl])ethyl]-N'-[2-(5-chloro)pyrazinyl]thiourea
N-[2-(2-[1,3-pyrimidyl])ethyl]-N'-[2-(6-bromo)pyrazinyl]thiourea
N-[2-(2-[1,3-pyrimidyl])ethyl]-N'-[2-(5-bromo)pyrazinyl]thiourea
N-[2-(2-[1,3-pyrimidyl])ethyl]-N'-[(3-(6-bromo)pyridazinyl)]thiourea
N-[2-(2-[1,3-pyrimidyl])ethyl]-N'-[(3-(6-chloro)pyridazinyl)]thiourea
N-[2-(2-[1,3-pyrimidyl])ethyl]-N'-[2-(6-cyano)pyridyl]thiourea
N-[2-(2-[1,3-pyrimidyl])ethyl]-N'-[2-(5-cyano)pyridyl]thiourea
N-[2-(2-[1,3-pyrimidyl])ethyl]-N'-[2-(5-cyano)pyrazinyl]thiourea
N-[2-(2-[1,3-pyrimidyl])ethyl]-N'-[2-(6-cyano)pyrazinyl]thiourea
N-[2-(2-[1,3-pyrimidyl])ethyl]-N'-[(3-(6-cyano)pyridazinyl)]thiourea
N-[2-(2-[1,3-pyrimidyl])ethyl]-N'-(2-[1,3,4-thiadiazoyl])thiourea
N-[2-(2-[1,3-pyrimidyl])ethyl]-N'-(2-benzimidazolyl)thiourea
N-[2-(2-[1,3-pyrimidyl])ethyl]-N'-(2-imidazolyl)thiourea
N-[2-(2-pyrazinyl)ethyl]-N'-(2-thiazolyl)thiourea
N-[2-(2-pyrazinyl)ethyl]-N'-[2-(4-methyl)thiazolyl]thiourea
N-[2-(2-pyrazinyl)ethyl]-N'-[2-(4,5-dimethyl)thiazolyl]thiourea
N-[2-(2-pyrazinyl)ethyl]-N'-[2-(4-cyano)thiazolyl]thiourea
N-[2-(2-pyrazinyl)ethyl]-N'-[2-(4-trifluoromethyl)thiazolyl]thiourea
N-[2-(2-pyrazinyl)ethyl]-N'-(2-benzothiazolyl)thiourea
N-[2-(2-pyrazinyl)ethyl]-N'-[2-(6-fluoro)benzothiazolyl]thiourea
N-[2-(2-pyrazinyl)ethyl]-N'-[2-(6-chloro)pyrazinyl]thiourea
N-[2-(2-pyrazinyl)ethyl]-N'-[2-(4-ethyl)thiazolyl]thiourea
N-[2-(2-pyrazinyl)ethyl]-N'-[2-(4-(3-pyridyl)thiazolyl)]thiourea
N-[2-(2-pyrazinyl)ethyl]-N'-[2-(4-(3-nitrophenyl)thiazolyl)]thiourea
N-[2-(2-pyrazinyl)ethyl]-N'-(2-pyridyl)thiourea
N-[2-(2-pyrazinyl)ethyl]-N'-[2-(6-bromo)pyridyl]thiourea
N-[2-(2-pyrazinyl)ethyl]-N'-[2-(5-bromo)pyridyl]thiourea
N-[2-(2-pyrazinyl)ethyl]-N'-[2-(6-chloro)pyridyl]thiourea
N-[2-(2-pyrazinyl)ethyl]-N'-[2-(5-chloro)pyridyl]thiourea
N-[2-(2-pyrazinyl)ethyl]-N'-[2-(6-methyl)pyridyl]thiourea
N-[2-(2-pyrazinyl)ethyl]-N'-[2-(5-methyl)pyridyl]thiourea
N-[2-(2-pyrazinyl)ethyl]-N'-[2-(6-trifluoromethyl)pyridyl]thiourea
N-[2-(2-pyrazinyl)ethyl]-N'-[2-(5-trifluoromethyl)pyridyl]thiourea
N-[2-(2-pyrazinyl)ethyl]-N'-[2-(6-ethyl)pyridyl]thiourea
N-[2-(2-pyrazinyl)ethyl]-N'-[2-(5-ethyl)pyridyl]thiourea
N-[2-(2-pyrazinyl)ethyl]-N'-[2-(5-chloro)pyrazinyl]thiourea
N-[2-(2-pyrazinyl)ethyl]-N'-[2-(6-bromo)pyrazinyl]thiourea
N-[2-(2-pyrazinyl)ethyl]-N'-[2-(5-bromo)pyrazinyl]thiourea
N-[2-(2-pyrazinyl)ethyl]-N'-[(3-(6-bromo)pyridazinyl)]thiourea
N-[2-(2-pyrazinyl)ethyl]-N'-[(3-(6-chloro)pyridazinyl)]thiourea
N-[2-(2-pyrazinyl)ethyl]-N'-[2-(6-cyano)pyridyl]thiourea
N-[2-(2-pyrazinyl)ethyl]-N'-[2-(5-cyano)pyridyl]thiourea
N-[2-(2-pyrazinyl)ethyl]-N'-[2-(5-cyano)pyrazinyl]thiourea
N-[2-(2-pyrazinyl)ethyl]-N'-[2-(6-cyano)pyrazinyl]thiourea
N-[2-(2-pyrazinyl)ethyl]-N'-[(3-(6-cyano)pyridazinyl)]thiourea
N-[2-(2-pyrazinyl)ethyl]-N'-(2-[1,3,4-thiadiazoyl])thiourea
N-[2-(2-pyrazinyl)ethyl]-N'-(2-benzimidazolyl)thiourea
N-[2-(2-pyrazinyl)ethyl]-N'-(2-imidazolyl)thiourea
N-[2-(3-pyridazinyl)ethyl]-N'-(2-thiazolyl)thiourea
N-[2-(3-pyridazinyl)ethyl]-N'-[2-(4-methyl)thiazolyl]thiourea
N-[2-(3-pyridazinyl)ethyl]-N'-[2-(4,5-dimethyl)thiazolyl]thiourea
N-[2-(3-pyridazinyl)ethyl]-N'-[2-(4-cyano)thiazolyl]thiourea
N-[2-(3-pyridazinyl)ethyl]-N'-[2-(4-trifluoromethyl)thiazolyl]thiourea
N-[2-(3-pyridazinyl)ethyl]-N'-(2-benzothiazolyl)thiourea
N-[2-(3-pyridazinyl)ethyl]-N'-[2-(6-fluoro)benzothiazolyl]thiourea
N-[2-(3-pyridazinyl)ethyl]-N'-[2-(6-chloro)pyrazinyl]thiourea
N-[2-(3-pyridazinyl)ethyl]-N'-[2-(4-ethyl)thiazolyl]thiourea
N-[2-(3-pyridazinyl)ethyl]-N'-[2-(4-(3-pyridyl)thiazolyl)]thiourea
N-[2-(3-pyridazinyl)ethyl]-N'-[2-(4-(3-nitrophenyl)thiazolyl)]thiourea
N-[2-(3-pyridazinyl)ethyl]-N'-(2-pyridyl)thiourea
N-[2-(3-pyridazinyl)ethyl]-N'-[2-(6-bromo)pyridyl]thiourea N-[2-(3-pyridazinyl)ethyl]-N'-[2-(5-bromo)pyridyl]thiourea
N-[2-(3-pyridazinyl)ethyl]-N'-[2-(6-chloro)pyridyl]thiourea
N-[2-(3-pyridazinyl)ethyl]-N'-[2-(5-chloro)pyridyl]thiourea
N-[2-(3-pyridazinyl)ethyl]-N'-[2-(6-methyl)pyridyl]thiourea
N-[2-(3-pyridazinyl)ethyl]-N'-[2-(5-methyl)pyridyl]thiourea
N-[2-(3-pyridazinyl)ethyl]-N'-[2-(6-trifluoromethyl)pyridyl]thiourea
N-[2-(3-pyridazinyl)ethyl]-N'-[2-(5-trifluoromethyl)pyridyl]thiourea
N-[2-(3-pyridazinyl)ethyl]-N'-[2-(6-ethyl)pyridyl]thiourea
N-[2-(3-pyridazinyl)ethyl]-N'-[2-(5-ethyl)pyridyl]thiourea
N-[2-(3-pyridazinyl)ethyl]-N'-[2-(5-chloro)pyrazinyl]thiourea
N-[2-(3-pyridazinyl)ethyl]-N'-[2-(6-bromo)pyrazinyl]thiourea
N-[2-(3-pyridazinyl)ethyl]-N'-[2-(5-bromo)pyrazinyl]thiourea
N-[2-(3-pyridazinyl)ethyl]-N'-[(3-(6-bromo)pyridazinyl)]thiourea
N-[2-(3-pyridazinyl)ethyl]-N'-[(3-(6-chloro)pyridazinyl)]thiourea
N-[2-(3-pyridazinyl)ethyl]-N'-[2-(6-cyano)pyridyl]thiourea
N-[2-(3-pyridazinyl)ethyl]-N'-[2-(5-cyano)pyridyl]thiourea
N-[2-(3-pyridazinyl)ethyl]-N'-[2-(5-cyano)pyrazinyl]thiourea
N-[2-(3-pyridazinyl)ethyl]-N'-[2-(6-cyano)pyrazinyl]thiourea
N-[2-(3-pyridazinyl)ethyl]-N'-[(3-(6-cyano)pyridazinyl)]thiourea
N-[2-(3-pyridazinyl)ethyl]-N'-(2-[1,3,4-thiadiazoyl])thiourea
N-[2-(3-pyridazinyl)ethyl]-N'-(2-benzimidazolyl)thiourea
N-[2-(3-pyridazinyl)ethyl]-N'-(2-imidazolyl)thiourea
N-[2-(2,6-difluoro-3-methoxyphenyl)ethyl]-N'-(2-thiazolyl)thiourea
N-[2-(2,6-difluoro-3-methoxyphenyl)ethyl]-N'-[2-(4-methyl)thiazolyl]thiourea
N-[2-(2,6-difluoro-3-methoxyphenyl)ethyl]-N'-[2-(4,5-dimethyl)thiazolyl]thiourea
N-[2-(2,6-difluoro-3-methoxyphenyl)ethyl]-N'-[2-(4-cyano)thiazolyl]thiourea
N-[2-(2,6-difluoro-3-methoxyphenyl)ethyl]-N'-[2-(4-trifluoromethyl)thiazolyl]thiourea
N-[2-(2,6-difluoro-3-methoxyphenyl)ethyl]-N'-(2-benzothiazolyl)thiourea
N-[2-(2,6-difluoro-3-methoxyphenyl)ethyl]-N'-[2-(6-fluoro)benzothiazolyl]thiourea
N-[2-(2,6-difluoro-3-methoxyphenyl)ethyl]-N'-[2-(6-chloro)pyrazinyl]thiourea
N-[2-(2,6-difluoro-3-methoxyphenyl)ethyl]-N'-[2-(4-ethyl)thiazolyl]thiourea
N-[2-(2,6-difluoro-3-methoxyphenyl)ethyl]-N'-[2-(4-(3-pyridyl)thiazolyl)]thiourea
N-[2-(2,6-difluoro-3-methoxyphenyl)ethyl]-N'-[2-(4-(3-nitrophenyl)thiazolyl)]thiourea
N-[2-(2,6-difluoro-3-methoxyphenyl)ethyl]-N'-(2-pyridyl)thiourea
N-[2-(2,6-difluoro-3-methoxyphenyl)ethyl]-N'-[2-(6-bromo)pyridyl]thiourea
N-[2-(2,6-difluoro-3-methoxyphenyl)ethyl]-N'-[2-(6-chloro)pyridyl]thiourea
N-[2-(2,6-difluoro-3-methoxyphenyl)ethyl]-N'-[2-(5-chloro)pyridyl]thiourea
N-[2-(2,6-difluoro-3-methoxyphenyl)ethyl]-N'-[2-(6-methyl)pyridyl]thiourea
N-[2-(2,6-difluoro-3-methoxyphenyl)ethyl]-N'-[2-(5-methyl)pyridyl]thiourea
N-[2-(2,6-difluoro-3-methoxyphenyl)ethyl]-N'-[2-(6-trifluoromethyl)pyridyl]thiourea
N-[2-(2,6-difluoro-3-methoxyphenyl)ethyl]-N'-[2-(5-trifluoromethyl)pyridyl]thiourea
N-[2-(2,6-difluoro-3-methoxyphenyl)ethyl]-N'-[2-(6-ethyl)pyridyl]thiourea
N-[2-(2,6-difluoro-3-methoxyphenyl)ethyl]-N'-[2-(5-ethyl)pyridyl]thiourea
N-[2-(2,6-difluoro-3-methoxyphenyl)ethyl]-N'-[2-(5-chloro)pyrazinyl]thiourea
N-[2-(2,6-difluoro-3-methoxyphenyl)ethyl]-N'-[2-(6-bromo)pyrazinyl]thiourea
N-[2-(2,6-difluoro-3-methoxyphenyl)ethyl]-N'-[2-(5-bromo)pyrazinyl]thiourea
N-[2-(2,6-difluoro-3-methoxyphenyl)ethyl]-N'-[2-(3-[6-bromo]pyridazinyl)]thiourea
N-[2-(2,6-difluoro-3-methoxyphenyl)ethyl]-N'-[2-(3-[6-chloro]pyridazinyl)]thiourea
N-[2-(2,6-difluoro-3-methoxyphenyl)ethyl]-N'-[2-(6-cyano)pyridyl]thiourea
N-[2-(2,6-difluoro-3-methoxyphenyl)ethyl]-N'-[2-(5-cyano)pyridyl]thiourea
N-[2-(2,6-difluoro-3-methoxyphenyl)ethyl]-N'-[2-(5-cyano)pyrazinyl]thiourea
N-[2-(2,6-difluoro-3-methoxyphenyl)ethyl]-N'-[2-(6-cyano)pyrazinyl]thiourea
N-[2-(2,6-difluoro-3-methoxyphenyl)ethyl]-N'-[2-(3-[6-cyano]pyridazinyl)]thiourea
N-[2-(2,6-difluoro-3-methoxyphenyl)ethyl]-N'-(2-[1,3,4-thiadiazoyl])thiourea
N-[2-(2,6-difluoro-3-methoxyphenyl)ethyl]-N'-(2-benzimidazolyl)thiourea
N-[2-(2,6-difluoro-3-methoxyphenyl)ethyl]-N'-(2-imidazolyl)thiourea
N-[2-(2,6-difluoro-3-ethoxyphenyl)ethyl]-N'-(2-thiazolyl)thiourea
N-[2-(2,6-difluoro-3-ethoxyphenyl)ethyl]-N'-[2-(4-methyl)thiazolyl]thiourea
N-[2-(2,6-difluoro-3-ethoxyphenyl)ethyl]-N'-[2-(4,5-dimethyl)thiazolyl]thiourea
N-[2-(2,6-difluoro-3-ethoxyphenyl)ethyl]-N'-[2-(4-cyano)thiazolyl]thiourea
N-[2-(2,6-difluoro-3-ethoxyphenyl)ethyl]-N'-[2-(4-trifluoromethyl)thiazolyl]thiourea
N-[2-(2,6-difluoro-3-ethoxyphenyl)ethyl]-N'-(2-benzothiazolyl)thiourea
N-[2-(2,6-difluoro-3-ethoxyphenyl)ethyl]-N'-[2-(6-fluoro)benzothiazolyl]thiourea
N-[2-(2,6-difluoro-3-ethoxyphenyl)ethyl]-N'-[2-(6-chloro)pyrazinyl]thiourea
N-[2-(2,6-difluoro-3-ethoxyphenyl)ethyl]-N'-[2-(4-ethyl)thiazolyl]thiourea
N-[2-(2,6-difluoro-3-ethoxyphenyl)ethyl]-N'-[2-(4-(3-pyridyl)thiazolyl)]thiourea
N-[2-(2,6-difluoro-3-ethoxyphenyl)ethyl]-N'-[2-(4-(3-nitrophenyl)thiazolyl)]thiourea
N-[2-(2,6-difluoro-3-ethoxyphenyl)ethyl]-N'-(2-pyridyl)thiourea
N-[2-(2,6-difluoro-3-ethoxyphenyl)ethyl]-N'-[2-(6-bromo)pyridyl]thiourea
N-[2-(2,6-difluoro-3-ethoxyphenyl)ethyl]-N'-[2-(5-bromo)pyridyl]thiourea
N-[2-(2,6-difluoro-3-ethoxyphenyl)ethyl]-N'-[2-(6-chloro)pyridyl]thiourea
N-[2-(2,6-difluoro-3-ethoxyphenyl)ethyl]-N'-[2-(5-chloro)pyridyl]thiourea N-[2-(2,6-difluoro-3-ethoxyphenyl)ethyl]-N'-[2-(6-methyl)pyridyl]thiourea
N-[2-(2,6-difluoro-3-ethoxyphenyl)ethyl]-N'-[2-(5-methyl)pyridyl]thiourea
N-[2-(2,6-difluoro-3-ethoxyphenyl)ethyl]-N'-[2-(6-trifluoromethyl)pyridyl]thiourea
N-[2-(2,6-difluoro-3-ethoxyphenyl)ethyl]-N'-[2-(5-trifluoromethyl)pyridyl]thiourea
N-[2-(2,6-difluoro-3-ethoxyphenyl)ethyl]-N'-[2-(6-ethyl)pyridyl]thiourea
N-[2-(2,6-difluoro-3-ethoxyphenyl)ethyl]-N'-[2-(5-ethyl)pyridyl]thiourea
N-[2-(2,6-difluoro-3-ethoxyphenyl)ethyl]-N'-[2-(5-chloro)pyrazinyl]thiourea
N-[2-(2,6-difluoro-3-ethoxyphenyl)ethyl]-N'-[2-(6-bromo)pyrazinyl]thiourea
N-[2-(2,6-difluoro-3-ethoxyphenyl)ethyl]-N'-[2-(5-bromo)pyrazinyl]thiourea
N-[2-(2,6-difluoro-3-ethoxyphenyl)ethyl]-N'-[2-(3-[6-bromo]pyridazinyl)]thiourea
N-[2-(2,6-difluoro-3-ethoxyphenyl)ethyl]-N'-[2-(3-[6-chloro]pyridazinyl)]thiourea
N-[2-(2,6-difluoro-3-ethoxyphenyl)ethyl]-N'-[2-(6-cyano)pyridyl]thiourea
N-[2-(2,6-difluoro-3-ethoxyphenyl)ethyl]-N'-[2-(5-cyano)pyridyl]thiourea
N-[2-(2,6-difluoro-3-ethoxyphenyl)ethyl]-N'-[2-(5-cyano)pyrazinyl]thiourea
N-[2-(2,6-difluoro-3-ethoxyphenyl)ethyl]-N'-[2-(6-cyano)pyrazinyl]thiourea
N-[2-(2,6-difluoro-3-ethoxyphenyl)ethyl]-N'-[2-(3-[6-cyano]pyridazinyl)]thiourea
N-[2-(2,6-difluoro-3-ethoxyphenyl)ethyl]-N'-(2-[1,3,4-thiadiazoyl])thiourea
N-[2-(2,6-difluoro-3-ethoxyphenyl)ethyl]-N'-(2-benzimidazolyl)thiourea
N-[2-(2,6-difluoro-3-ethoxyphenyl)ethyl]-N'-(2-imidazolyl)thiourea
N-[2-(2,6-difluoro-4-methoxyphenyl)ethyl]-N'-(2-thiazolyl)thiourea
N-[2-(2,6-difluoro-4-methoxyphenyl)ethyl]-N'-[2-(4-methyl)thiazolyl]thiourea
N-[2-(2,6-difluoro-4-methoxyphenyl)ethyl]-N'-[2-(4,5-dimethyl)thiazolyl]thiourea
N-[2-(2,6-difluoro-4-methoxyphenyl)ethyl]-N'-[2-(4-cyano)thiazolyl]thiourea
N-[2-(2,6-difluoro-4-methoxyphenyl)ethyl]-N'-[2-(4-trifluoromethyl)thiazolyl]thiourea
N-[2-(2,6-difluoro-4-methoxyphenyl)ethyl]-N'-(2-benzothiazolyl)thiourea
N-[2-(2,6-difluoro-4-methoxyphenyl)ethyl]-N'-[2-(6-fluoro)benzothiazolyl]thiourea
N-[2-(2,6-difluoro-4-methoxyphenyl)ethyl]-N'-[2-(6-chloro)pyrazinyl]thiourea
N-[2-(2,6-difluoro-4-methoxyphenyl)ethyl]-N'-[2-(4-ethyl)thiazolyl]thiourea
N-[2-(2,6-difluoro-4-methoxyphenyl)ethyl]-N'-[2-(4-(3-pyridyl)thiazolyl)]thiourea
N-[2-(2,6-difluoro-4-methoxyphenyl)ethyl]-N'-[2-(4-(3-nitrophenyl)thiazolyl)]thiourea
N-[2-(2,6-difluoro-4-methoxyphenyl)ethyl]-N'-(2-pyridyl)thiourea
N-[2-(2,6-difluoro-4-methoxyphenyl)ethyl]-N'-[2-(6-bromo)pyridyl]thiourea
N-[2-(2,6-difluoro-4-methoxyphenyl)ethyl]-N'-[2-(5-bromo)pyridyl]thiourea
N-[2-(2,6-difluoro-4-methoxyphenyl)ethyl]-N'-[2-(6-chloro)pyridyl]thiourea
N-[2-(2,6-difluoro-4-methoxyphenyl)ethyl]-N'-[2-(5-chloro)pyridyl]thiourea
N-[2-(2,6-difluoro-4-methoxyphenyl)ethyl]-N'-[2-(6-methyl)pyridyl]thiourea
N-[2-(2,6-difluoro-4-methoxyphenyl)ethyl]-N'-[2-(5-methyl)pyridyl]thiourea
N-[2-(2,6-difluoro-4-methoxyphenyl)ethyl]-N'-[2-(6-trifluoromethyl)pyridyl]thiourea
N-[2-(2,6-difluoro-4-methoxyphenyl)ethyl]-N'-[2-(5-trifluoromethyl)pyridyl]thiourea
N-[2-(2,6-difluoro-4-methoxyphenyl)ethyl]-N'-[2-(6-ethyl)pyridyl]thiourea
N-[2-(2,6-difluoro-4-methoxyphenyl)ethyl]-N'-[2-(5-ethyl)pyridyl]thiourea
N-[2-(2,6-difluoro-4-methoxyphenyl)ethyl]-N'-[2-(5-chloro)pyrazinyl]thiourea
N-[2-(2,6-difluoro-4-methoxyphenyl)ethyl]-N'-[2-(6-bromo)pyrazinyl]thiourea
N-[2-(2,6-difluoro-4-methoxyphenyl)ethyl]-N'-[2-(5-bromo)pyrazinyl]thiourea
N-[2-(2,6-difluoro-4-methoxyphenyl)ethyl]-N'-[2-(3-[6-bromo]pyridazinyl)]thiourea
N-[2-(2,6-difluoro-4-methoxyphenyl)ethyl]-N'-[2-(3-[6-chloro]pyridazinyl)]thiourea
N-[2-(2,6-difluoro-4-methoxyphenyl)ethyl]-N'-[2-(6-cyano)pyridyl]thiourea
N-[2-(2,6-difluoro-4-methoxyphenyl)ethyl]-N'-[2-(5-cyano)pyridyl]thiourea
N-[2-(2,6-difluoro-4-methoxyphenyl)ethyl]-N'-[2-(5-cyano)pyrazinyl]thiourea
N-[2-(2,6-difluoro-4-methoxyphenyl)ethyl]-N'-[2-(6-cyano)pyrazinyl]thiourea
N-[2-(2,6-difluoro-4-methoxyphenyl)ethyl]-N'-[2-(3-[6-cyano]pyridazinyl)]thiourea
N-[2-(2,6-difluoro-4-methoxyphenyl)ethyl]-N'-(2-[1,3,4-thiadiazoyl])thiourea
N-[2-(2,6-difluoro-4-methoxyphenyl)ethyl]-N'-(2-benzimidazolyl)thiourea
N-[2-(2,6-difluoro-4-methoxyphenyl)ethyl]-N'-(2-imidazolyl)thiourea
N-[2-(2,6-difluoro-4-ethoxyphenyl)ethyl]-N'-(2-thiazolyl)thiourea
N-[2-(2,6-difluoro-4-ethoxyphenyl)ethyl]-N'-[2-(4-methyl)thiazolyl]thiourea
N-[2-(2,6-difluoro-4-ethoxyphenyl)ethyl]-N'-[2-(4,5-dimethyl)thiazolyl]thiourea
N-[2-(2,6-difluoro-4-ethoxyphenyl)ethyl]-N'-[2-(4-cyano)thiazolyl]thiourea
N-[2-(2,6-difluoro-4-ethoxyphenyl)ethyl]-N'-[2-(4-trifluoromethyl)thiazolyl]thiourea
N-[2-(2,6-difluoro-4-ethoxyphenyl)ethyl]-N'-(2-benzothiazolyl)thiourea
N-[2-(2,6-difluoro-4-ethoxyphenyl)ethyl]-N'-[2-(6-fluoro)benzothiazolyl]thiourea
N-[2-(2,6-difluoro-4-ethoxyphenyl)ethyl]-N'-[2-(6-chloro)pyrazinyl]thiourea
N-[2-(2,6-difluoro-4-ethoxyphenyl)ethyl]-N'-[2-(4-ethyl)thiazolyl]thiourea
N-[2-(2,6-difluoro-4-ethoxyphenyl)ethyl]-N'-[2-(4-(3-pyridyl)thiazolyl)]thiourea
N-[2-(2,6-difluoro-4-ethoxyphenyl)ethyl]-N'-[2-(4-(3-nitrophenyl)thiazolyl)]thiourea
N-[2-(2,6-difluoro-4-ethoxyphenyl)ethyl]-N'-(2-pyridyl)thiourea
N-[2-(2,6-difluoro-4-ethoxyphenyl)ethyl]-N'-[2-(6-bromo)pyridyl]thiourea
N-[2-(2,6-difluoro-4-ethoxyphenyl)ethyl]-N'-[2-(5-bromo)pyridyl]thiourea N-[2-(2,6-difluoro-4-ethoxyphenyl)ethyl]-N'-[2-(6-chloro)pyridyl]thiourea
N-[2-(2,6-difluoro-4-ethoxyphenyl)ethyl]-N'-[2-(5-chloro)pyridyl]thiourea
N-[2-(2,6-difluoro-4-ethoxyphenyl)ethyl]-N'-[2-(6-methyl)pyridyl]thiourea
N-[2-(2,6-difluoro-4-ethoxyphenyl)ethyl]-N'-[2-(5-methyl)pyridyl]thiourea
N-[2-(2,6-difluoro-4-ethoxyphenyl)ethyl]-N'-[2-(6-trifluoromethyl)pyridyl]thiourea
N-[2-(2,6-difluoro-4-ethoxyphenyl)ethyl]-N'-[2-(5-trifluoromethyl)pyridyl]thiourea
N-[2-(2,6-difluoro-4-ethoxyphenyl)ethyl]-N'-[2-(6-ethyl)pyridyl]thiourea
N-[2-(2,6-difluoro-4-ethoxyphenyl)ethyl]-N'-[2-(5-ethyl)pyridyl]thiourea
N-[2-(2,6-difluoro-4-ethoxyphenyl)ethyl]-N'-[2-(5-chloro)pyrazinyl]thiourea
N-[2-(2,6-difluoro-4-ethoxyphenyl)ethyl]-N'-[2-(6-bromo)pyrazinyl]thiourea
N-[2-(2,6-difluoro-4-ethoxyphenyl)ethyl]-N'-[2-(5-bromo)pyrazinyl]thiourea
N-[2-(2,6-difluoro-4-ethoxyphenyl)ethyl]-N'-[2-(3-[6-bromo]pyridazinyl)]thiourea
N-[2-(2,6-difluoro-4-ethoxyphenyl)ethyl]-N'-[2-(3-[6-chloro]pyridazinyl)]thiourea
N-[2-(2,6-difluoro-4-ethoxyphenyl)ethyl]-N'-[2-(6-cyano)pyridyl]thiourea
N-[2-(2,6-difluoro-4-ethoxyphenyl)ethyl]-N'-[2-(5-cyano)pyridyl]thiourea
N-[2-(2,6-difluoro-4-ethoxyphenyl)ethyl]-N'-[2-(5-cyano)pyrazinyl]thiourea
N-[2-(2,6-difluoro-4-ethoxyphenyl)ethyl]-N'-[2-(6-cyano)pyrazinyl]thiourea
N-[2-(2,6-difluoro-4-ethoxyphenyl)ethyl]-N'-[2-(3-[6-cyano]pyridazinyl)]thiourea
N-[2-(2,6-difluoro-4-ethoxyphenyl)ethyl]-N'-(2-[1,3,4-thiadiazoyl])thiourea
N-[2-(2,6-difluoro-4-ethoxyphenyl)ethyl]-N'-(2-benzimidazolyl)thiourea
N-[2-(2,6-difluoro-4-ethoxyphenyl)ethyl]-N'-(2-imidazolyl)thiourea
N-[2-(2-(3-ethoxy)pyridyl)ethyl]-N'-[2-(5-bromo)pyridyl]thiourea
N-[2-(2-(3-methoxy)pyridyl)ethyl]-N'-[2-(5-bromo)pyridyl]thiourea
N-(2-phenethyl)-N'-[2-(3-ethyl)pyridyl]thiourea
N-[2-(2,6-difluorophenyl)ethyl]-N'-[3-(6-methoxy)pyridazinyl]thiourea
N-[2-(2,6-difluoro-3-N-methylcarboxamidephenyl)ethyl]-N'-[2-(5-bromo)pyridyl]thiourea
N-[2-(2-fluoro-6-chlorophenyl)ethyl]-N'-(2-thiazolyl)thiourea
N-[2-(2-pyridyl)ethyl]-N'-[2-(5-nitro)pyridyl]thiourea
N-[2-(3-bromo-6-methoxyphenyl)ethyl]-N'-(2-thiazolyl)thiourea
(±)N-[2-[(2,6-difluorophenyl)-2-(methyl)]ethyl]-N'-(2-thiazolyl)thiourea
N-[2-(3-ethoxyphenyl)ethyl]-N'-(2-thiazolyl)thiourea
N-[2-(3-bromo-6-ethoxyphenyl)ethyl]-N'-(2-thiazolyl)thiourea
N-[2-(cis-(2-fluoro)phenyl)cyclopropyl]-N'-(2-thiazolyl)thiourea
N-[2-(3-(2-fluoro)pyridyl)ethyl]-N'-[2-(5-bromo)pyridyl]thiourea
(±)N-[cis-2-(3-chlorophenyl)cyclopropyl]-N'-[2-(5-chloro)pyridyl]thiourea
(±)N-[cis-2-(3-fluorophenyl)cyclopropyl]-N'-[2-(5-chloro)pyridyl]thiourea
N-[2-(2-vinyl)phenethyl]-N'-[2-(5-bromo)pyridyl]thiourea
N-[2-(3-vinyl)phenethyl]-N'-[2-(5-bromo)pyridyl]thiourea
N-[2-(3-methoxycarbonyl)phenethyl]-N'-[2-(5-bromo)pyridyl]thiourea
N-[2-(5,6-dimethylbenzotriazolyl)ethyl]-N'-[2-(5-bromo)pyridyl]thiourea
N-[2-(1-cyclohexenyl)ethyl]-N'-[2-(5,6-dichloro-4-azabenzimidazolyl)]thiourea
N-[2-(2,3-difluoro-6-methoxyphenyl)ethyl]-N'-[2-(5-bromo)pyridyl]thiourea
(±)N-[cis-2-(4-methylphenyl)cyclopropyl]-N'-[2-(5-chloro)pyridyl]thiourea
(±)N-[cis-2-(2-fluorophenyl)cyclopropyl]-N'-[2-(5-chloro)pyridyl]thiourea
(±)N-[cis-2-(3-cyanophenyl)cyclopropyl]-N'-[2-(5-chloro)pyridyl]thiourea
(±)N-[cis-2-(2,6-difluoro-3-cyanophenyl)cyclopropyl]-N'-[2-(5-chloro)pyridyl]thiourea
(±)-cis-N-(3,4-benzo-cis-bicyclo-[3.1.0]-hexen-6-yl)-N'-[2-(5-chloro)pyridyl]thiourea
N-[2-(3-ethynylphenyl)ethyl]-N'-[2-(5-bromo)pyridyl]thiourea
N-[2-(2,5-diethoxyphenyl)ethyl]-N'-[2-(5-bromo)pyridyl]thiourea
N-[2-(2-methoxyphenyl)ethyl]-N'-[4-(6-aminopyrimidinyl)]thiourea
N-[2-(2-methoxyphenyl)ethyl]-N'-(4-pyrimidinyl)thiourea
(±)N-[2-(cis-2-pyridyl)]-N'-[2-(3-pyridazinyl)]thiourea
(±)N-[2-(cis-2-pyridyl)]-N'-[2-(3-(6-methyl)pyridazinyl)]thiourea
(±)N-[2-(cis-2-pyridyl)]-N'-(2-pyrazinyl)]thiourea
(±)N-[2-(cis-2-pyridyl)]-N'-[2-(5-methyl)pyrazinyl)]thiourea
(±)N-[2-(cis-2-(3-fluoro)pyridyl)]-N'-[2-(3-pyridazinyl)]thiourea
(±)N-[2-(cis-2-(3-fluoro)pyridyl)]-N'-[2-(3-(6-methyl)pyridazinyl)]thiourea
(±)N-[2-(cis-2-(3-fluoro)pyridyl)]-N'-(2-pyrazinyl)]thiourea
(±)N-[2-(cis-2-(3-fluoro)pyridyl)]-N'-[2-(5-methyl)pyrazinyl)]thiourea
N-(2-cis-phenylcyclopropyl)-N'-[2-(3-pyridazinyl)]thiourea
N-(2-cis-phenylcyclopropyl)-N'-[2-(3-(6-methyl)pyridazinyl)]thiourea
N-(2-cis-phenylcyclopropyl)-N'-(2-pyrazinyl)]thiourea
N-(2-cis-phenylcyclopropyl)-N'-[2-(5-methyl)pyrazinyl)]thiourea
N-[2-(cis-2-fluorophenyl)cyclopropyl)]-N'-[2-(3-pyridazinyl)]thiourea
N-[2-(cis-2-fluorophenyl)cyclopropyl)]-N'-[2-(3-(6-methyl)pyridazinyl)]thiourea
N-[2-(cis-2-fluorophenyl)cyclopropyl)]-N'-(2-pyrazinyl)]thiourea
N-[2-(cis-2-fluorophenyl)cyclopropyl)]-N'-[2-(5-methyl)pyrazinyl)]thiourea
N-[2-(cis-2,6-difluorophenyl)cyclopropyl)]-N'-[2-(3-pyridazinyl)]thiourea
N-[2-(cis-2,6-difluorophenyl)cyclopropyl)]-N'-[2-(3-(6-methyl)pyridazinyl)]thiourea
N-[2-(cis-2,6-difluorophenyl)cyclopropyl)]-N'-(2-pyrazinyl)]thiourea
N-[2-(cis-2,6-difluorophenyl)cyclopropyl)]-N'-[2-(5-methyl)pyrazinyl)]thiourea
N-[2-(cis-3-methoxyphenyl)cyclopropyl)]-N'-[2-(3-pyridazinyl))]thiourea
N-[2-(cis-3-methoxyphenyl)cyclopropyl)]-N'-[2-(3-(6-methyl)pyridazinyl)]thiourea N-[2-(cis-3-methoxyphenyl)cyclopropyl)]-N'-(2-pyrazinyl)]thiourea
N-[2-(cis-3-methoxyphenyl)cyclopropyl)]-N'-[2-(5methyl)pyrazinyl)]thiourea

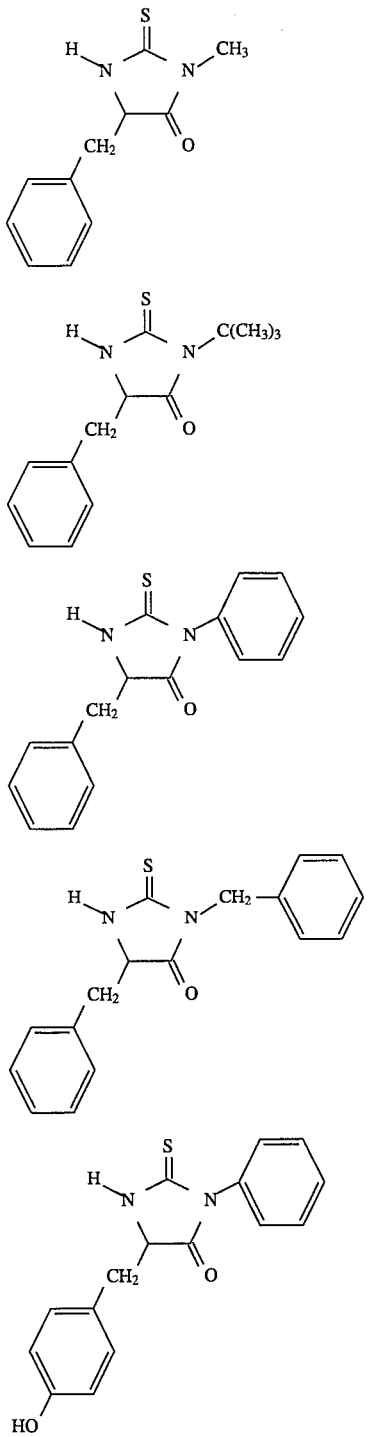

The following are more preferred compounds.
N-(2-phenethyl)-N'-[2-(5-bromo)pyridyl]thiourea
N-(2-phenethyl)-N'-[2-(5-chloro)pyridyl]thiourea
N-(2-phenethyl)-N'-[2-(5-chloro)pyrazinyl]thiourea
N-(2-phenethyl)-N'-[2-(5-bromo)pyrazinyl]thiourea
N-(2-phenethyl)-N'-[(3-(6-chloro)pyridazinyl)]thiourea
N-(2-(2-methoxyphenyl)ethyl)-N'-[2-(5-chloro)pyrazinyl]thiourea
N-(2-(2-methoxyphenyl)ethyl)-N'-[2-(5-bromo)pyrazinyl]thiourea
N-(2-(2-methoxyphenyl)ethyl)-N'-[(3-(6-chloro)pyridazinyl)]thiourea
N-(2-(3-methoxyphenyl)ethyl)-N'-[2-(5-chloro)pyrazinyl]thiourea
N-(2-(3-methoxyphenyl)ethyl)-N'-[2-(5-bromo)pyrazinyl]thiourea
N-(2-(3-methoxyphenyl)ethyl)-N'-[(3-(6-chloro)pyridazinyl)]thiourea
N-(2-(2-ethoxyphenyl)ethyl)-N'-[2-(4-cyano)thiazolyl]thiourea
N-(2-(2-ethoxyphenyl)ethyl)-N'-[2-(4-trifluoromethyl)thiazolyl]thiourea
N-(2-(2-ethoxyphenyl)ethyl)-N'-[2-(4-ethyl)thiazolyl]thiourea
N-(2-(2-ethoxyphenyl)ethyl)-N'-[2-(5-chloro)pyrazinyl]thiourea
N-(2-(2-ethoxyphenyl)ethyl)-N'-[2-(5-bromo)pyrazinyl]thiourea
N-(2-(2-ethoxyphenyl)ethyl)-N'-[(3-(6-chloro)pyridazinyl)]thiourea
N-(2-(2-methylphenyl)ethyl)-N'-[2-(4-cyano)thiazolyl]thiourea
N-(2-(2-methylphenyl ethyl)-N'-[2-(4-trifluoromethyl)thiazolyl)thiourea
N-(2-(2-methylphenyl ethyl)-N'-[2-(4-ethyl)thiazolyl]thiourea
N-(2-(2-methylphenyl ethyl)-N'-[2-(5-bromo)pyridyl]thiourea
N-(2-(2-methylphenyl ethyl)-N'-[2-(6-chloro)pyridyl]thiourea
N-(2-(2-methylphenyl ethyl)-N'-[2-(5-chloro)pyrazinyl]thiourea
N-(2-(2-methylphenyl ethyl)-N'-[2-(5-bromo)pyrazinyl]thiourea
N-(2-(2-methylphenyl)ethyl)-N'-[(3-(6-chloro)pyridazinyl)]thiourea
N-(2-(2-fluorophenyl)ethyl)-N'-[2-(4-cyano)thiazolyl]thiourea
N-(2-(2-fluorophenyl)ethyl)-N'-[2-(4-trifluoromethyl)thiazolyl]thiourea
N-(2-(2-fluorophenyl)ethyl)-N'-[2-(4-ethyl)thiazolyl]thiourea
N-(2-(2-fluorophenyl)ethyl)-N'-[2-(5-bromo)pyridyl]thiourea
N-(2-(2-fluorophenyl)ethyl)-N'-[2-(5-chloro)pyridyl]thiourea
N-(2-(2-fluorophenyl)ethyl)-N'-[2-(5-chloro)pyrazinyl]thiourea
N-(2-(2-fluorophenyl)ethyl)-N'-[2-(5-bromo)pyrazinyl]thiourea
N-(2-(2-fluorophenyl)ethyl)-N'-[(3-(6-chloro)pyridazinyl)]thiourea
N-(2-(2,6-difluorophenyl)ethyl)-N'-(2-thiazolyl)thiourea
N-(2-(2,6-difluorophenyl)ethyl)-N'-[2-(4-methyl)thiazolyl]thiourea
N-(2-(2,6-difluorophenyl)ethyl)-N'-(2-pyridyl)thiourea
N-(2-(2,6-difluorophenyl)ethyl)-N'-[2-(6-bromo)pyridyl]thiourea
N-(2-(2,6-difluorophenyl)ethyl)-N'-[2-(5-methyl)pyridyl]thiourea
N-(2-(2,6-difluorophenyl)ethyl)-N'-[2-(5-trifluoromethyl)pyridyl]thiourea
N-(2-(2,6-difluorophenyl)ethyl)-N'-[2-(5-ethyl)pyridyl]thiourea
N-(2-(2,6-difluorophenyl)ethyl)-N'-[2-(5-chloro)pyrazinyl]thiourea N-(2-(2,6-difluorophenyl)ethyl)-N'-[2-(5-cyano)pyridyl]thiourea
N-(2-(2-fluoro-6-methoxyphenyl)ethyl)-N'-[2-(4-cyano)thiazolyl]thiourea
N-(2-(2-fluoro-6-methoxyphenyl)ethyl)-N'-[2-(4-trifluoromethyl)thiazolyl]thiourea
N-(2-(2-fluoro-6-methoxyphenyl)ethyl)-N'-[2-(4-ethyl)thiazolyl]thiourea
N-(2-(2-fluoro-6-methoxyphenyl)ethyl)-N'-[2-(5-chloro)pyrazinyl]thiourea
N-(2-(2-fluoro-6-methoxyphenyl)ethyl)-N'-[2-(5-bromo)pyrazinyl]thiourea
N-(2-(2-fluoro-6-methoxyphenyl)ethyl)-N'-[(3-(6-chloro)pyridazinyl)]thiourea
N-(2-(2-fluoro-6-ethoxyphenyl)ethyl)-N'-[2-(4-cyano)thiazolyl]thiourea
N-(2-(2-fluoro-6-ethoxyphenyl)ethyl)-N'-[2-(4-trifluoromethyl)thiazolyl]thiourea
N-(2-(2-fluoro-6-ethoxyphenyl)ethyl)-N'-[2-(4-ethyl)thiazolyl]thiourea
N-(2-(2-fluoro-6-ethoxyphenyl)ethyl)-N'-[2-(5-bromo)pyridyl]thiourea
N-(2-(2-fluoro-6-ethoxyphenyl)ethyl)-N'-[2-(5-chloro)pyridyl]thiourea
N-(2-(2-fluoro-6-ethoxyphenyl)ethyl)-N'-[2-(5-chloro)pyrazinyl]thiourea
N-(2-(2-fluoro-6-ethoxyphenyl)ethyl)-N'-[2-(5-bromo)pyrazinyl]thiourea
N-(2-(2-fluoro-6-ethoxyphenyl)ethyl)-N'-[(3-(6-chloro)pyridazinyl)]thiourea
N-(2-(2-chlorophenyl)ethyl)-N'-[2-(4-trifluoromethyl)thiazolyl]thiourea
N-(2-(2-chlorophenyl)ethyl)-N'-[2-(5-chloro)pyrazinyl]thiourea
N-(2-(2-chlorophenyl)ethyl)-N'-[2-(5-bromo)pyrazinyl]thiourea
N-(2-(2-chlorophenyl)ethyl)-N'-[(3-(6-chloro)pyridazinyl)]thiourea
N-(2-(3-chlorophenyl)ethyl)-N'-[2-(4-trifluoromethyl)thiazolyl]thiourea
N-(2-(3-chlorophenyl)ethyl)-N'-[2-(5-chloro)pyrazinyl]thiourea
N-(2-(3-chlorophenyl)ethyl)-N'-[2-(5-bromo)pyrazinyl]thiourea
N-(2-(3-chlorophenyl)ethyl)-N'-[(3-(6-chloro)pyridazinyl)]thiourea
N-(2-(1-cyclohexenyl)ethyl)-N'-(2-thiazolyl)thiourea
N-(2-(1-cyclohexenyl)ethyl)-N'-[2-(4-methyl)thiazolyl]thiourea
N-(2-(1-cyclohexenyl)ethyl)-N'-(2-pyridyl)thiourea
N-(2-(1-cyclohexenyl)ethyl)-N'-[2-(5-methyl)pyridyl]thiourea
N-(2-(1-cyclohexenyl)ethyl)-N'-[2-(5-trifluoromethyl)pyridyl]thiourea
N-(2-(1-cyclohexenyl)ethyl)-N'-[2-(5-ethyl)pyridyl]thiourea
N-(2-(1-cyclohexenyl)ethyl)-N'-[2-(5-chloro)pyrazinyl]thiourea
N-(2-(1-cyclohexenyl)ethyl)-N'-[2-(5-bromo)pyrazinyl]thiourea
N-(2-(1-cyclohexenyl)ethyl)-N'-[2-(5-cyano)pyridyl]thiourea
N-(2-(1-cyclohexenyl)ethyl)-N'-[2-(5-cyano)pyrazinyl]thiourea
N-(2-(1-cyclohexenyl)ethyl)-N'-[(3-(6-cyano)pyridazinyl)]thiourea
N-(2-(2,5-dimethoxyphenyl)ethyl)-N'-[2-(4-cyano)thiazolyl]thiourea
N-(2-(2,5-dimethoxyphenyl)ethyl)-N'-[2-(4-trifluoromethyl)thiazolyl]thiourea
N-(2-(2,5-dimethoxyphenyl)ethyl)-N'-[2-(4-ethyl)thiazolyl]thiourea
N-(2-(2,5-dimethoxyphenyl)ethyl)-N'-[2-(5-bromo)pyridyl]thiourea
N-(2-(2,5-dimethoxyphenyl)ethyl)-N'-[(3-(6-chloro)pyridazinyl)]thiourea
N-(2-(2-fluoro-6-chlorophenyl)ethyl)-N'-[2-(4-cyano)thiazolyl]thiourea
N-(2-(2-fluoro-6-chlorophenyl)ethyl)-N'-[2-(4-trifluoromethyl)thiazolyl]thiourea
N-(2-(2-fluoro-6-chlorophenyl)ethyl)-N'-[2-(4-ethyl)thiazolyl]thiourea
N-(2-(2-fluoro-6-chlorophenyl)ethyl)-N'-[2-(5-bromo)pyridyl]thiourea
N-(2-(2-fluoro-6-chlorophenyl)ethyl)-N'-[2-(5-chloro)pyridyl]thiourea
N-(2-(2-fluoro-6-chlorophenyl)ethyl)-N'-[2-(5-chloro)pyrazinyl]thiourea
N-(2-(2-fluoro-6-chlorophenyl)ethyl)-N'-[2-(5-bromo)pyrazinyl]thiourea
N-(2-(2-fluoro-6-chlorophenyl)ethyl)-N'-[(3-(6-chloro)pyridazinyl)]thiourea
N-(2-(2,6-dimethoxyphenyl)ethyl)-N'-[2-(4-cyano)thiazolyl]thiourea
N-(2-(2,6-dimethoxyphenyl)ethyl)-N'-[2-(4-trifluoromethyl)thiazolyl]thiourea
N-(2-(2,6-dimethoxyphenyl)ethyl)-N'-[2-(4-ethyl)thiazolyl]thiourea
N-(2-(2,6-dimethoxyphenyl)ethyl)-N'-[2-(5-bromo)pyridyl]thiourea
N-(2-(2,6-dimethoxyphenyl)ethyl)-N'-[2-(5-chloro)pyridyl]thiourea
N-(2-(2,6-dimethoxyphenyl)ethyl)-N'-[2-(5-chloro)pyrazinyl]thiourea
N-(2-(2,6-dimethoxyphenyl)ethyl)-N'-[2-(5-bromo)pyrazinyl]thiourea
N-(2-(2,6-dimethoxyphenyl)ethyl)-N'-[(3-(6-chloro)pyridazinyl)]thiourea
N-(2-(2,6-dichlorophenyl)ethyl)-N'-[2-(4-cyano)thiazolyl]thiourea
N-(2-(2,6-dichlorophenyl)ethyl)-N'-[2-(4-trifluoromethyl)thiazolyl]thiourea
N-(2-(2,6-dichlorophenyl)ethyl)-N'-[2-(4-ethyl)thiazolyl]thiourea
N-(2-(2,6-dichlorophenyl)ethyl)-N'-[2-(5-bromo)pyridyl]thiourea
N-(2-(2,6-dichlorophenyl)ethyl)-N'-[2-(5-chloro)pyridyl]thiourea
N-(2-(2,6-dichlorophenyl)ethyl)-N'-[2-(5-chloro)pyrazinyl]thiourea
N-(2-(2,6-dichlorophenyl)ethyl)-N'-[2-(5-bromo)pyrazinyl]thiourea
N-(2-(2,6-dichlorophenyl)ethyl)-N'-[(3-(6-chloro)pyridazinyl)]thiourea
N-(2-(3-fluorophenyl)ethyl)-N'-[2-(4-cyano)thiazolyl]thiourea
N-(2-(3-fluorophenyl)ethyl)-N'-[2-(4-trifluoromethyl)thiazolyl]thiourea
N-(2-(3-fluorophenyl)ethyl)-N'-[2-(4-ethyl)thiazolyl]thiourea
N-(2-(3-fluorophenyl)ethyl)-N'-[2-(5-bromo)pyridyl]thiourea
N-(2-(3-fluorophenyl)ethyl)-N'-[2-(5-chloro)pyridyl]thiourea
N-(2-(3-fluorophenyl)ethyl)-N'-[2-(5-chloro)pyrazinyl]thiourea N-(2-(3-fluorophenyl)ethyl)-N'-[2-(5-bromo)pyrazinyl]thiourea
N-(2-(3-fluorophenyl)ethyl)-N'-[(3-(6-chloro)pyridazinyl)]thiourea
N-(2-cis-phenylcyclopropyl)-N'-(2-thiazolyl)thiourea
N-(2-cis-phenylcyclopropyl)-N'-[2-(4-cyano)thiazolyl]thiourea
N-(2-cis-phenylcyclopropyl)-N'-[2-(4-trifluoromethyl)thiazolyl]thiourea
N-(2-cis-phenylcyclopropyl)-N'-[2-(5-methyl)pyridyl]thiourea
N-(2-cis-phenylcyclopropyl)-N'-[2-(4-ethyl)thiazolyl]thiourea
N-(2-cis-phenylcyclopropyl)-N'-(2-pyridyl)thiourea
N-(2-cis-phenylcyclopropyl)-N'-[2-(5-trifluoromethyl)pyridyl]thiourea
N-(2-cis-phenylcyclopropyl)-N'-[2-(5-ethyl)pyridyl]thiourea
N-(2-cis-phenylcyclopropyl)-N'-[2-(5-chloro)pyrazinyl]thiourea
N-(2-cis-phenylcyclopropyl)-N'-[2-(5-bromo)pyrazinyl]thiourea
N-(2-cis-phenylcyclopropyl)-N'-[(3-(6-bromo)pyridazinyl)]thiourea
N-(2-cis-phenylcyclopropyl)-N'-[(3-(6-chloro)pyridazinyl)]thiourea
N-(2-cis-phenylcyclopropyl)-N'-[2-(5-cyano)pyridyl]thiourea
N-[2-(2-pyridyl)ethyl]-N'-(2-thiazolyl)thiourea
N-[2-(2-pyridyl)ethyl]-N'-[2-(4-methyl)thiazolyl]thiourea
N-[2-(2-pyridyl)ethyl]-N'-[2-(4-cyano)thiazolyl]thiourea
N-[2-(2-pyridyl)ethyl]-N'-[2-(4-trifluoromethyl)thiazolyl]thiourea
N-[2-(2-pyridyl)ethyl]-N'-[2-(4-ethyl)thiazolyl]thiourea
N-[2-(2-pyridyl)ethyl]-N'-(2-pyridyl)thiourea
N-[2-(2-pyridyl)ethyl]-N'-[2-(6-bromo)pyridyl]thiourea
N-[2-(2-pyridyl)ethyl]-N'-[2-(6-chloro)pyridyl]thiourea
N-[2-(2-pyridyl)ethyl]-N'-[2-(6-methyl)pyridyl]thiourea
N-[2-(2-pyridyl)ethyl]-N'-[2-(5-methyl)pyridyl]thiourea
N-[2-(2-pyridyl)ethyl]-N'-[2-(6-trifluoromethyl)pyridyl]thiourea
N-[2-(2-pyridyl)ethyl]-N'-[2-(6-ethyl)pyridyl]thiourea
N-[2-(2-pyridyl)ethyl]-N'-[2-(5-chloro)pyrazinyl]thiourea
N-[2-(2-pyridyl)ethyl]-N'-[2-(5-bromo)pyrazinyl]thiourea
N-[2-(2-pyridyl)ethyl]-N'-[(3-(6-bromo)pyridazinyl)]thiourea
N-[2-(2-pyridyl)ethyl]-N'-[(3-(6-chloro)pyridazinyl)]thiourea
N-[2-(2-pyridyl)ethyl]-N'-[2-(5-cyano)pyridyl]thiourea
N-[2-(2-pyridyl)ethyl]-N'-[2-(5-cyano)pyrazinyl]thiourea
N-[2-(2-pyridyl)ethyl]-N'-[(3-(6-cyano)pyridazinyl)]thiourea
N-[2-(2-(6-methoxy)pyridyl)ethyl]-N'-(2-thiazolyl)thiourea
N-[2-(2-(6-methoxy)pyridyl)ethyl]-N'-[2-(4-methyl)thiazolyl]thiourea
N-[2-(2-(6-methoxy)pyridyl)ethyl]-N'-[2-(4-cyano)thiazolyl]thiourea
N-[2-(2-(6-methoxy)pyridyl)ethyl]-N'-[2-(4-trifluoromethyl)thiazolyl]thiourea
N-[2-(2-(6-methoxy)pyridyl)ethyl]-N'-[2-(4-ethyl)thiazolyl]thiourea
N-[2-(2-(6-methoxy)pyridyl)ethyl]-N'-(2-pyridyl)thiourea
N-[2-(2-(6-methoxy)pyridyl)ethyl]-N'-[2-(5-methyl)pyridyl]thiourea
N-[2-(2-(6-methoxy)pyridyl)ethyl]-N'-[2-(5-trifluoromethyl)pyridyl]thiourea
N-[2-(2-(6-methoxy)pyridyl)ethyl]-N'-[2-(5-chloro)pyrazinyl]thiourea
N-[2-(2-(6-methoxy)pyridyl)ethyl]-N'-[2-(5-bromo)pyrazinyl]thiourea
N-[2-(2-(6-methoxy)pyridyl)ethyl]-N'-[(3-(6-chloro)pyridazinyl)]thiourea
N-[2-(2-(6-ethoxy)pyridyl)ethyl]-N'-(2-thiazolyl)thiourea
N-[2-(2-(6-ethoxy)pyridyl)ethyl]-N'-[2-(4-methyl)thiazolyl]thiourea
N-[2-(2-(6-ethoxy)pyridyl)ethyl]-N'-[2-(4-cyano)thiazolyl]thiourea
N-[2-(2-(6-ethoxy)pyridyl)ethyl]-N'-[2-(4-trifluoromethyl)thiazolyl]thiourea
N-[2-(2-(6-ethoxy)pyridyl)ethyl]-N'-[2-(4-ethyl)thiazolyl]thiourea
N-[2-(2-(6-ethoxy)pyridyl)ethyl]-N'-(2-pyridyl)thiourea
N-[2-(2-(6-ethoxy)pyridyl)ethyl]-N'-[2-(5-methyl)pyridyl]thiourea
N-[2-(2-(6-ethoxy)pyridyl)ethyl]-N'-[2-(5-trifluoromethyl)pyridyl]thiourea
N-[2-(2-(6-ethoxy)pyridyl)ethyl]-N'-[2-(5-chloro)pyrazinyl]thiourea
N-[2-(2-(6-ethoxy)pyridyl)ethyl]-N'-[2-(5-bromo)pyrazinyl]thiourea
N-[2-(2-(6-ethoxy)pyridyl)ethyl]-N'-[(3-(6-chloro)pyridazinyl)]thiourea
N-[2-(2-(6-ethoxy)pyridyl)ethyl]-N'-[2-(5-cyano)pyridyl]thiourea
N-[2-(2-(6-fluoro)pyridyl)ethyl]-N'-(2-thiazolyl)thiourea
N-[2-(2-(6-fluoro)pyridyl)ethyl]-N'-[2-(4-methyl)thiazolyl]thiourea
N-[2-(2-(6-fluoro)pyridyl)ethyl]-N'-[2-(4-cyano)thiazolyl]thiourea
N-[2-(2-(6-fluoro)pyridyl)ethyl]-N'-[2-(4-trifluoromethyl)thiazolyl]thiourea
N-[2-(2-(6-fluoro)pyridyl)ethyl]-N'-[2-(4-ethyl)thiazolyl]thiourea
N-[2-(2-(6-fluoro)pyridyl)ethyl]-N'-(2-pyridyl)thiourea
N-[2-(2-(6-fluoro)pyridyl)ethyl]-N'-[2-(5-methyl)pyridyl]thiourea
N-[2-(2-(6-fluoro)pyridyl)ethyl]-N'-[2-(5-trifluoromethyl)pyridyl]thiourea
N-[2-(2-(6-fluoro)pyridyl)ethyl]-N'-[2-(6-ethyl)pyridyl]thiourea
N-[2-(2-(6-fluoro)pyridyl)ethyl]-N'-[2-(5-ethyl)pyridyl]thiourea
N-[2-(2-(6-fluoro)pyridyl)ethyl]-N'-[2-(5-chloro)pyrazinyl]thiourea
N-[2-(2-(6-fluoro)pyridyl)ethyl]-N'-[2-(5-bromo)pyrazinyl]thiourea
N-[2-(2-(6-fluoro)pyridyl)ethyl]-N'-[(3-(6-chloro)pyridazinyl)]thiourea
N-[2-(2-(6-fluoro)pyridyl)ethyl]-N'-[2-(5-cyano)pyridyl]thiourea
N-[2-(2-(3-fluoro)pyridyl)ethyl]-N'-[2-(4-cyano)thiazolyl]thiourea
N-[2-(2-(3-fluoro)pyridyl)ethyl]-N'-[2-(4-trifluoromethyl)thiazolyl]thiourea
N-[2-(2-(3-fluoro)pyridyl)ethyl]-N'-[2-(4-ethyl)thiazolyl]thiourea
N-[2-(2-(3-fluoro)pyridyl)ethyl]-N'-[2-(5-chloro)pyrazinyl]thiourea
N-[2-(2-(3-fluoro)pyridyl)ethyl]-N'-[2-(5-bromo)pyrazinyl]thiourea
N-[2-(2-(3-fluoro)pyridyl)ethyl]-N'-[(3-(6-chloro)pyridazinyl)]thiourea
N-[2-(2-(6-chloro)pyridyl)ethyl]-N'-[2-(4-cyano)thiazolyl]thiourea
N-[2-(2-(6-chloro)pyridyl)ethyl]-N'-[2-(4-trifluoromethyl)thiazolyl]thiourea N-[2-(2-(6-chloro)pyridyl)ethyl]-N'-[2-(4-ethyl)thiazolyl]thiourea
N-[2-(2-(6-chloro)pyridyl)ethyl]-N'-[2-(5-chloro)pyrazinyl]thiourea
N-[2-(2-(6-chloro)pyridyl)ethyl]-N'-[2-(5-bromo)pyrazinyl]thiourea
N-[2-(2-(6-chloro)pyridyl)ethyl]-N'-[(3-(6-chloro)pyridazinyl)]thiourea
N-[2-(2-(3-methoxy-6-fluoro)pyridyl)ethyl]-N'-[2-(4-methyl)thiazolyl]thiourea
N-[2-(2-(3-methoxy-6-fluoro)pyridyl)ethyl]-N'-[2-(4-cyano)thiazolyl]thiourea
N-[2-(2-(3-methoxy-6-fluoro)pyridyl)ethyl]-N'-[2-(4-trifluoromethyl)thiazolyl]thiourea
N-[2-(2-(3-methoxy-6-fluoro)pyridyl)ethyl]-N'-[2-(4-ethyl)thiazolyl]thiourea
N-[2-(2-(3-methoxy-6-fluoro)pyridyl)ethyl]-N'-(2-pyridinyl)thiourea
N-[2-(2-(3-methoxy-6-fluoro)pyridyl)ethyl]-N'-[2-(5-chloro)pyrazinyl]thiourea
N-[2-(2-(3-methoxy-6-fluoro)pyridyl)ethyl]-N'-[2-(5-bromo)pyrazinyl]thiourea
N-[2-(2-(3-methoxy-6-fluoro)pyridyl)ethyl]-N'-[(3-(6-chloro)pyridazinyl)]thiourea
N-[2-(2-(5-ethoxy-6-fluoro)pyridyl)ethyl]-N'-[2-(4-cyano)thiazolyl]thiourea
N-[2-(2-(5-ethoxy-6-fluoro)pyridyl)ethyl]-N'-[2-(4-trifluoromethyl)thiazolyl]thiourea
N-[2-(2-(5-ethoxy-6-fluoro)pyridyl)ethyl]-N'-[2-(4-ethyl)thiazolyl]thiourea
N-[2-(2-(5-ethoxy-6-fluoro)pyridyl)ethyl]-N'-[2-(5-chloro)pyrazinyl]thiourea
N-[2-(2-(5-ethoxy-6-fluoro)pyridyl)ethyl]-N'-[2-(5-bromo)pyrazinyl]thiourea
N-[2-(2-(5-ethoxy-6-fluoro)pyridyl)ethyl]-N'-[(3-(6-chloro)pyridazinyl)]thiourea
N-[2-(2-(3-ethoxy-6-fluoro)pyridyl)ethyl]-N'-[2-(4-cyano)thiazolyl]thiourea
N-[2-(2-(3-ethoxy-6-fluoro)pyridyl)ethyl]-N'-[2-(4-trifluoromethyl)thiazolyl]thiourea
N-[2-(2-(3-ethoxy-6-fluoro)pyridyl)ethyl]-N'-[2-(4-ethyl)thiazolyl]thiourea
N-[2-(2-(3-ethoxy-6-fluoro)pyridyl)ethyl]-N'-[2-(5-chloro)pyrazinyl]thiourea
N-[2-(2-(3-ethoxy-6-fluoro)pyridyl)ethyl]-N'-[2-(5-bromo)pyrazinyl]thiourea
N-[2-(2-(3-ethoxy-6-fluoro)pyridyl)ethyl]-N'-[(3-(6-chloro)pyridazinyl)]thiourea
N-[2-(2-(3,6-difluoro)pyridyl)ethyl]-N'-[2-(4-cyano)thiazolyl]thiourea
N-[2-(2-(3,6-difluoro)pyridyl)ethyl]-N'-[2-(4-trifluoromethyl)thiazolyl]thiourea
N-[2-(2-(3,6-difluoro)pyridyl)ethyl]-N'-[2-(4-ethyl)thiazolyl]thiourea
N-[2-(2-(3,6-difluoro)pyridyl)ethyl]-N'-[2-(5-chloro)pyrazinyl]thiourea
N-[2-(2-(3,6-difluoro)pyridyl)ethyl]-N'-[2-(5-bromo)pyrazinyl]thiourea
N-[2-(2-(3,6-difluoro)pyridyl)ethyl]-N'-[(3-(6-chloro)pyridazinyl)]thiourea
N-[2-(cis-2-pyridyl)cyclopropyl]-N'-[2-(4-cyano)thiazolyl]thiourea
N-[2-(cis-2-pyridyl)cyclopropyl]-N'-[2-(4-trifluoromethyl)thiazolyl]thiourea
N-[2-(cis-2-pyridyl)cyclopropyl]-N'-[2-(4-ethyl)thiazolyl]thiourea
N-[2-(cis-2-pyridyl)cyclopropyl]-N'-(2-pyridyl)thiourea
N-[2-(cis-2-pyridyl)cyclopropyl]-N'-[2-(5-methyl)pyridyl]thiourea
N-[2-(cis-2-pyridyl)cyclopropyl]-N'-[2-(5-trifluoromethyl)pyridyl]thiourea
N-[2-(cis-2-pyridyl)cyclopropyl]-N'-[2-(5-ethyl)pyridyl]thiourea
N-[2-(cis-2-pyridyl)cyclopropyl]-N'-[2-(5-chloro)pyrazinyl]thiourea
N-[2-(cis-2-pyridyl)cyclopropyl]-N'-[2-(5-bromo)pyrazinyl]thiourea
N-[2-(cis-2-pyridyl)cyclopropyl]-N'-[(3-(6-chloro)pyridazinyl)]thiourea
N-[2-(cis-2-(6-fluoro)pyridyl)cyclopropyl]-N'-[2-(4-cyano)thiazolyl]thiourea
N-[2-(cis-2-(6-fluoro)pyridyl)cyclopropyl]-N'-[2-(4-trifluoromethyl)thiazolyl]thiourea
N-[2-(cis-2-(6-fluoro)pyridyl)cyclopropyl]-N'-[2-(4-ethyl)thiazolyl]thiourea
N-[2-(cis-2-(6-fluoro)pyridyl)cyclopropyl]-N'-(2-pyridyl)thiourea
N-[2-(cis-2-(6-fluoro)pyridyl)cyclopropyl]-N'-[2-(5-methyl)pyridyl]thiourea
N-[2-(cis-2-(6-fluoro)pyridyl)cyclopropyl]-N'-[2-(5-chloro)pyrazinyl]thiourea
N-[2-(cis-2-(6-fluoro)pyridyl)cyclopropyl]-N'-[2-(5-bromo)pyrazinyl]thiourea
N-[2-(cis-2-(6-fluoro)pyridyl)cyclopropyl]-N'-[(3-(6-chloro)pyridazinyl)]thiourea
N-[2-(cis-2-(6-methoxy)pyridyl)cyclopropyl]-N'-[2-(4-cyano)thiazolyl]thiourea
N-[2-(cis-2-(6-methoxy)pyridyl)cyclopropyl]-N'-[2-(4-trifluoromethyl)thiazolyl]thiourea
N-[2-(cis-2-(6-methoxy)pyridyl)cyclopropyl]-N'-[2-(4-ethyl)thiazolyl]thiourea
N-[2-(cis-2-(6-methoxy)pyridyl)cyclopropyl]-N'-[2-(5-chloro)pyrazinyl]thiourea
N-[2-(cis-2-(6-methoxy)pyridyl)cyclopropyl]-N'-[2-(5-bromo)pyrazinyl]thiourea
N-[2-(cis-2-(6-methoxy)pyridyl)cyclopropyl]-N'-[(3-(6-chloro)pyridazinyl)]thiourea
N-[2-(cis-2-(6-ethoxy)pyridyl)cyclopropyl]-N'-[2-(4-cyano)thiazolyl]thiourea
N-[2-(cis-2-(6-ethoxy)pyridyl)cyclopropyl]-N'-[2-(4-trifluoromethyl)thiazolyl]thiourea
N-[2-(cis-2-(6-ethoxy)pyridyl)cyclopropyl]-N'-[2-(4-ethyl)thiazolyl]thiourea
N-[2-(cis-2-(6-ethoxy)pyridyl)cyclopropyl]-N'-[2-(5-chloro)pyrazinyl]thiourea
N-[2-(cis-2-(6-ethoxy)pyridyl)cyclopropyl]-N'-[2-(5-bromo)pyrazinyl]thiourea
N-[2-(cis-2-(6-ethoxy)pyridyl)cyclopropyl]-N'-[(3-(6-chloro)pyridazinyl)]thiourea The following are most preferred compounds.
N-(2-(2-methoxyphenyl)ethyl)-N'-[2-(4-cyano)thiazolyl]thiourea
N-(2-(2-methoxyphenyl)ethyl)-N'-[2-(4-trifluoromethyl)thiazolyl]thiourea
N-(2-(2-methoxyphenyl)ethyl)-N'-[2-(4-ethyl)thiazolyl]thiourea
N-(2-(2-methoxyphenyl)ethyl)-N'-[2-(5-bromo)pyridyl]thiourea
N-(2-(2-methoxyphenyl)ethyl)-N'-[2-(5-chloro)pyridyl]thiourea
N-(2-(3-methoxyphenyl)ethyl)-N'-[2-(4-cyano)thiazolyl]thiourea
N-(2-(3-methoxyphenyl)ethyl)-N'-[2-(4-trifluoromethyl)thiazolyl]thiourea N-(2-(3-methoxyphenyl)ethyl)-N'-[2-(4-ethyl)thiazolyl]thiourea
N-(2-(3-methoxyphenyl)ethyl)-N'-[2-(5-bromo)pyridyl]thiourea
N-(2-(3-methoxyphenyl)ethyl)-N'-[2-(5-chloro)pyridyl]thiourea
N-(2-(2-ethoxyphenyl)ethyl)-N'-[2-(5-bromo)pyridyl]thiourea
N-(2-(2-ethoxyphenyl)ethyl)-N'-[2-(5-chloro)pyridyl]thiourea
N-(2-(2,6-difluorophenyl)ethyl)-N'-[2-(4-cyano)thiazolyl]thiourea
N-(2-(2,6-difluorophenyl)ethyl)-N'-[2-(4-trifluoromethyl)thiazolyl]thiourea
N-(2-(2,6-difluorophenyl)ethyl)-N'-[2-(4-ethyl)thiazolyl]thiourea
N-(2-(2,6-difluorophenyl)ethyl)-N'-[2-(5-bromo)pyridyl]thiourea
N-(2-(2,6-difluorophenyl)ethyl)-N'-[2-(5-chloro)pyridyl]thiourea
N-(2-(2,6-difluorophenyl)ethyl)-N'-[2-(5-bromo)pyrazinyl]thiourea
N-(2-(2,6-difluorophenyl)ethyl)-N'-[(3-(6-chloro)pyridazinyl)]thiourea
N-(2-(2-fluoro-6-methoxyphenyl)ethyl)-N'-[2-(5-bromo)pyridyl]thiourea
N-(2-(2-fluoro-6-methoxyphenyl)ethyl)-N'-[2-(5-chloro)pyridyl]thiourea
N-(2-(2-chlorophenyl)ethyl)-N'-[2-(4-cyano)thiazolyl]thiourea
N-(2-(2-chlorophenyl)ethyl)-N'-[2-(4-ethyl)thiazolyl]thiourea
N-(2-(2-chlorophenyl)ethyl)-N'-[2-(5-bromo)pyridyl]thiourea
N-(2-(2-chlorophenyl)ethyl)-N'-[2-(5-chloro)pyridyl]thiourea
N-(2-(3-chlorophenyl)ethyl)-N'-[2-(4-cyano)thiazolyl]thiourea
N-(2-(3-chlorophenyl)ethyl)-N'-[2-(4-ethyl)thiazolyl]thiourea
N-(2-(3-chlorophenyl)ethyl)-N'-[2-(5-bromo)pyridyl]thiourea
N-(2-(3-chlorophenyl)ethyl)-N'-[2-(5-chloro)pyridyl]thiourea
N-(2-(1-cyclohexenyl)ethyl)-N'-[2-(4-cyano)thiazolyl]thiourea
N-(2-(1-cyclohexenyl)ethyl)-N'-[2-(4-trifluoromethyl)thiazolyl]thiourea
N-(2-(1-cyclohexenyl)ethyl)-N'-[2-(4-ethyl)thiazolyl]thiourea
N-(2-(1-cyclohexenyl)ethyl)-N'-[2-(5-bromo)pyridyl]thiourea
N-(2-(1-cyclohexenyl)ethyl)-N'-[2-(5-chloro)pyridyl]thiourea
N-(2-(1-cyclohexenyl)ethyl)-N'-[(3-(6-chloro)pyridazinyl)]thiourea
N-(2-(2,5-dimethoxyphenyl)ethyl)-N'-[2-(5-chloro)pyrazinyl]thiourea
N-(2-(2,5-dimethoxyphenyl)ethyl)-N'-[2-(5-bromo)pyrazinyl]thiourea
N-(2-cis-phenylcyclopropyl)-N'-[2-(5-bromo)pyridyl]thiourea
N-(2-cis-phenylcyclopropyl)-N'-[2-(5-chloro)pyridyl]thiourea
N-[2-(2-pyridyl)ethyl]-N'-[2-(5-bromo)pyridyl]thiourea
N-[2-(2-pyridyl)ethyl]-N'-[2-(5-chloro)pyridyl]thiourea
N-[2-(2-pyridyl)ethyl]-N'-[2-(5-trifluoromethyl)pyridyl]thiourea
N-[2-(2-pyridyl)ethyl]-N'-[2-(5-ethyl)pyridyl]thiourea
N-[2-(2-pyridyl)ethyl]-N'-[2-(5-methyl)pyridyl]thiourea
N-[2-(2-(6-methoxy)pyridyl)ethyl]-N'-[2-(5-bromo)pyridyl]thiourea
N-[2-(2-(6-methoxy)pyridyl)ethyl]-N'-[2-(5-chloro)pyridyl]thiourea
N-[2-(2-(6-ethoxy)pyridyl)ethyl]-N'-[2-(5-bromo)pyridyl]thiourea
N-[2-(2-(6-ethoxy)pyridyl)ethyl]-N'-[2-(5-chloro)pyridyl]thiourea
N-[2-(2-(6-fluoro)pyridyl)ethyl]-N'-[2-(5-bromo)pyridyl]thiourea
N-[2-(2-(6-fluoro)pyridyl)ethyl]-N'-[2-(5-chloro)pyridyl]thiourea
N-[2-(2-(3-fluoro)pyridyl)ethyl]-N'-[2-(5-bromo)pyridyl]thiourea
N-[2-(2-(3-fluoro)pyridyl)ethyl]-N'-[2-(5-chloro)pyridyl]thiourea
N-[2-(2-(6-chloro)pyridyl)ethyl]-N'-[2-(5-bromo)pyridyl]thiourea
N-[2-(2-(6-chloro)pyridyl)ethyl]-N'-[2-(5-chloro)pyridyl]thiourea
N-[2-(2-(3-methoxy-6-fluoro)pyridyl)ethyl]-N'-[2-(5-bromo)pyridyl]thiourea
N-[2-(2-(3-methoxy-6-fluoro)pyridyl)ethyl]-N'-[2-(5-chloro)pyridyl]thiourea
N-[2-(2-(5-ethoxy-6-fluoro)pyridyl)ethyl]-N'-[2-(5-bromo)pyridyl]thiourea
N-[2-(2-(5-ethoxy-6-fluoro)pyridyl)ethyl]-N'-[2-(5-chloro)pyridyl]thiourea
N-[2-(2-(3-ethoxy-6-fluoro)pyridyl)ethyl]-N'-[2-(5-bromo)pyridyl]thiourea
N-[2-(2-(3-ethoxy-6-fluoro)pyridyl)ethyl]-N'-[2-(5-chloro)pyridyl]thiourea
N-[2-(2-(3,6-difluoro)pyridyl)ethyl]-N'-[2-(5-bromo)pyridyl]thiourea
N-[2-(2-(3,6-difluoro)pyridyl)ethyl]-N'-[2-(5-chloro)pyridyl]thiourea
N-[2-cis-2-pyridyl)cyclopropyl]-N'-[2-(5-bromo)pyridyl]thiourea
N-[2-cis-2-pyridyl)cyclopropyl]-N'-[2-(5-chloro)pyridyl]thiourea
N-[2-(cis-2-(6-fluoro)pyridyl)cyclopropyl]-N'-[2-(5-bromo)pyridyl]thiourea
N-[2-(cis-2-6-fluoro)pyridyl)cyclopropyl]-N'-[2-(5-chloro)pyridyl]thiourea
N-[2-(cis-2-(6-methoxy)pyridyl)cyclopropyl]-N'-[2-(5-bromo)pyridyl]thiourea
N-[2-(cis-2-(6-methoxy)pyridinyl)cyclopropyl]-N'-[2-(5-chloro)pyridyl]thiourea
N-[2-(cis-2-(6-ethoxy)pyridyl)cyclopropyl]-N'-[2-(5-bromo)pyridyl]thiourea
N-[2-(cis-2-6-ethoxy)pyridyl)cyclopropyl]-N'-[2-(5-chloro)pyridyl]thiourea
N-[2-(2,6-difluoro-3-methoxyphenyl)ethyl]-N'-[2-(5-bromo)pyridyl]thiourea Especially preferred is N-[2-(2-pyridyl)ethyl]-N'-[2-(5-bromo)pyridyl]thiourea, and its hydrochloride salt.

As mentioned above, the invention includes pharmaceutically acceptable salts of the compounds defined by the above formula (I). Although generally neutral, a particular compound of this invention can possess a sufficiently acidic, a sufficiently basic, or both, functional groups, and accordingly react with any of a number of nontoxic inorganic bases, and nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid and the like, and organic acids such as p-toluene sulfonic, methanesulfonic acid, oxalic acid, p-bromophenylsulfonic acid, carbonic acid, succinic acid, citric acid, benzoic acid, acetic acid, and the Like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberase, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, naphthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium bicarbonate, calcium hydroxide, calcium carbonate, and the like.

The pharmaceutically acceptable salts of the invention are typically formed by reacting a compound as defined with an equimolar or excess amount of acid or base. The reactants are generally combined in a mutual solvent such as diethyl ether or benzene, for acid addition salts, or water or alcohols for base addition salts, and the salts normally precipitate out of solution within about one hour to about ten days and can be isolated by filtration or other conventional methods. The salts of the compounds of the invention will convert to the compound per se after administration and are thus prodrugs. All prodrugs are administered in an amount sufficient to generate an effective amount of the compound to contact the virus and interact with it (e.g. inhibit replication thereof).

The compounds of the present invention also include racemates, racemic mixtures, and individual enantiomers or diastereomers. All asymmetric forms, individual isomers and combinations thereof are within the scope of the present invention.

As noted, the optically active diastereomers of the compounds of Formula 1 are considered part of this invention and such optically active isomers may be prepared from their respective optically active precursors by the procedures described herein, or by resolving the racemic mixtures. The resolution can be carried out in the presence of a resolving agent, by chromatography, by repeated crystallization or by some combination of these techniques which are known to those skilled in the art. Further details regarding resolutions can be found in Jacques, et al., *Enantiomers, Racemates, and Resolutions*, John Wiley & Sons 1981.

The compounds of the present invention, or their precursors, are prepared using procedures known to those of ordinary skill in art. More particularly, the compounds of Formula (1) are prepared according to the procedures shown below in Schemes I, II, and III, and as described following the Schemes.

SCHEME I

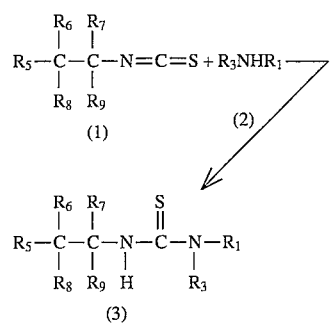

In Scheme I, a derivative of isothiocyanate (1) is reacted with an amino group (2) in approximately 1:1 molar ratio, in an inert organic solvent such as N,N-dimethyl formamide and stirred at an appropriate temperature of between about 0°–150° C. for a period of time between about 1 and 72 hours. The time and temperature used depends upon the reactivity of the individual reagents. The product (3) may be isolated by conventional techniques.

Scheme II

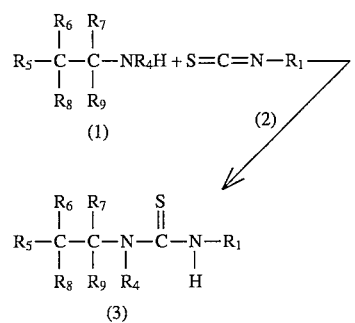

Scheme II is run under the same general reaction conditions as Scheme I.

Scheme III

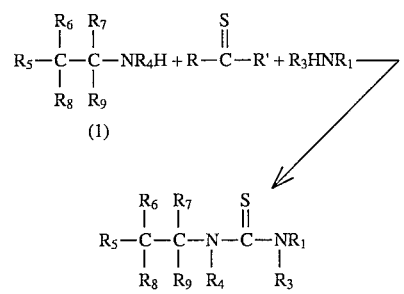

Scheme III is a process analogous to that described in *J. Org. Chem.* Vol. 49, 4123 (1984) herein incorporated by reference.

The compounds employed as initial starting materials in the synthesis of the compounds of this invention are well known and, to the extent not commercially available, are readily synthesized by standard procedures commonly employed by those or ordinary skill in the art.

Other teaching for preparing the compounds of the invention may be found in *Organic Synthesis,* 45, 69 (1965); *Synthesis,* 289 (1974); *Journal of the American Chem. Society,* 79, 1236 (1957); and *Organic Synthesis,* 20, 69, (1940), and *Synthesis,* May 1983, p. 391, incorporated herein by reference.

Tests with the above compounds of Formula 1 have indicated activity as inhibitors of HIV. While not being bound by theory, it is believed that the compounds act as reverse transcriptase inhibitors, and thereby act to inhibit replication of the virus.

The following is a description of the test systems used in analyzing compounds in effectiveness against HIV.

Tests A, B, C, and D (XTT)

MT4 cells in a medium of RPMI 1640, 5% FCS, penicillin/streptomycin are adjusted to $2\times10^5$ cells/ml and seeded into microplates (96 wells/plate) 100 ml cell suspension/well giving $2\times10^4$ cells/well. The compound to be tested is made into a 10 mg/ml mixture in DMSO and stored at $-20°$ C. The compound in DMSO is diluted with medium containing 10% DMSO in a 10-fold dilution series to give 1 mg/ml, 10 mg/ml, and 100 mg/ml solutions. Further dilutions to 400, 40, 4 and 0.4 mg/ml are made in medium containing microplates. Fifty ml of the 400, 40, and 4 mg/ml are transferred to the cell-containing microplates with a multi-channel pipette (final concentration: 100, 10, and 1 mg/ml). Finally, 50 ml of virus suspension is added to each well (with a repetitive "Eppendorf" multipipett). Each plate has at least six wells with the following: [Test A: HIV virus; Test B: HIV(II) virus; Test C: SIV virus; Test D: No virus]; with no drug (virus control) and six wells without virus (medium control). The plate is put into a plastic bag and incubated for six days in $CO_2$ atmosphere. To each well in the plate is added 50 ml of XTT ((2,3-bis[2-methoxy-4-nitro-5-sulfophenyl]-5-[(phenylamino)carbonyl]-2H-tetrazolium hydroxide), (1 mg/ml 0.01–0.02 mM N-methylphenazonium methosulfate). After six hours of incubation in $CO_2$ atmosphere the plates are covered with adhesive plate sealers and gently mixed on a vortex. Optical densities are determined at a wavelength of 450 nm and a reference wavelength of 650 nm. The percent reduction of cytotoxocity caused by the virus infection is calculated as follows:

$$\frac{OD_{450} \text{ compound} - OD_{450} \text{ inf cells}}{OD_{450} \text{ uninf cells} - OD_{450} \text{ inf cells}} \times 100$$

Tests E, F, G, H (HIV-IRT, HIV-2RT, SIVRT, no virus)

MT-4/H9-cells are adjusted to $2\times10^5$ cels/ml medium (RPMI 1640, 5% FCS, penicillin/streptomycin) and seeded into microplates (96 wells/plate) 100 ml cell suspension/well giving $2\times10^4$ cells/well. The compound to be tested is made 10 mg/ml in DMSO=stock solution (stored at $-20\infty$ C.). The compound dissolved in DMSO is diluted 25 times in medium to give 400 mg/ml. Further dilutions to 40 mg/ml and 4 mg/ml are made in microplates.

50 ml of the dilutions 400 mg/ml, 40 mg/ml and 4 mg/ml are transferred to the "cell-containing" microplate with a multichannel pipette. (Final concentration: 100, 10 and 1 mg/ml).

Finally 50 ml of virus suspension is added to each well (with a repetitive "Eppendorf multipett"). [Test E-HIV-1; Test F-HIV-2; Test G-SIV; Test H-no virus].

Each plate has at least four wells with virus but no drug (virus control) and two wells without virus (medium control). The plate is put into a plastic bag to avoid evaporation and incubated for six days in $CO_2$-atmosphere. 10 ml supernatant from each well is transferred with a multichannel pipette into a new microplate to which 40 ml VDB, (50 mM Tris-HCl pH=7.6, 35 mM KCl, 4 mM DTT, 1 mM EDTA, 1.3% Triton X-100), have been added to each well. The addition of 50 ml RT-reaction mix, (10 ml culture supernatant, 40 ml VDB and 50 ml reaction mixture giving a final concentration of: 100 mM Tris-HCl pH=7.6, 100 mM KCl, 4 mM $MgCl_2$, 4 mM DTT, 275 mg/ml BSA/ml, 5 mg $(rA)_n(dT)_{12-18}$/ml and 0.3 mM $^3$H dTTP (specific activity 18.000 cpm/pmol)) gives a final volume of 100 ml/well. After 60 minutes of incubation the whole assay volume is transferred by use of a cell harvester to a filter mat prewetted with 5% TCA. The filter is washed in 5% TCA and rinsed once in ethanol. After drying the filter mat at $60\infty$ C. for 30 min. each filter (96/mat) is punched out and put into counting vials 2 ml of scintillation fluid is added and the samples are counted (1 min) or the whole filter mat is put into a plastic bag, 10 ml of scintillation fluid is added and the filter man is counted in a Beckman Betaplate counter. Percent reduction of RT activity is determined by comparing RT activity for virus control with the RT activity measured for each dilution of the compound.

Test I (HIVRT (rAdt))

The compounds were tested for direct inhibitory activity on HIV-RT in a volume of 100 ml recombinant HIV-RT (diluted in virus disruption buffer to give 200.000 cpm).

100 mM Tris-HCl pH 7.6, 100 mM KCl, 4 mM $MgCl_2$, 4 mM DTT, 275 mg/ml BSA, 0.5 mg $(rA)n(dT)_{12-18}$ and 0.3 mM $^3$H-=dTTP (specific activity 18.000 cpm/mol). After 60 minutes of incubation 40 ml in duplicate were spotted on paper discs and washed in 5% TCA. After rinsing the paper discs in ethanol they were dried and counted in scintillation fluid.

The following Tables illustrate activities of compounds in the above-described tests. The numbers represent % inhibition.

TABLE A1

| Test | 100 µg/ml | 10 µg | 1 µg/ml | 0.1 µg/ml |
|---|---|---|---|---|
| A | — | 99 | 41 | 13 |
| A | — | 100 | 100 | 2 |
| A | 48 | 100 | 80 | 4 |
| A | — | 70 | 62 | 8 |
| A | 58 | 100 | 78 | 4 |
| A | 64 | 98 | 77 | 0 |
| D | 45 | 33 | 18 | 31 |
| B | 50 | 28 | 48 | 0 |
| B | 20 | 84 | 0 | 10 |
| B | 0 | 0 | 0 | 19 |
| C | 6 | 0 | 0 | — |
| C | 9 | 75 | 0 | 0 |
| C | 22 | 40 | 8 | 0 |
| C | 65 | 17 | 2 | 1 |
| E | 99 | 99 | 99 | 10 |
| E | 99 | 99 | 99 | 1 |
| F | 95 | 57 | 75 | 43 |
| F | 86 | 76 | 79 | 43 |

TABLE A2

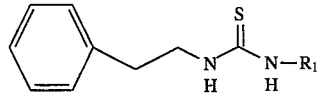

| R1 | Test | 100 μg/ml | 10 μg/ml | 1 μg/ml | 0.1 μg/ml |
|---|---|---|---|---|---|
| 2-methylthiazol-4-yl with CF₃ substituent | A | 66 | 24 | 100 | — |
| " | A | 4 | 16 | 75 | 62 |
| " | A | 31 | 31 | 84 | 84 |
| " | D | 68 | 75 | 46 | 0 |
| " | C | 43 | 5 | 11 | 9 |
| " | I | — | 73 | 73 | 63 |
| " | I | — | 75 | 75 | 68 |
| " | E | 97 | 96 | 97 | 98 |
| " | F | 96 | 98 | 95 | 56 |
| " | B | 19 | 38 | 100 | 21 |
| 2-methylthiazol-4-yl with C(CH₃)₃ substituent | A | 0 | 9 | 0 | 0 |
| " | I | — | 15 | 8 | 8 |
| 2-methylthiazol-4-yl with CH₃, CH₃ substituents | A | 99 | 85 | 71 | — |
| " | A | 100 | 88 | 6 | 7 |
| " | D | 0 | 0 | — | — |
| " | I | — | 38 | 39 | 34 |
| " | C | 0 | 1 | 0 | — |
| " | E | 94 | 91 | 23 | 1 |
| " | F | 93 | 61 | 92 | 1 |
| " | B | 85 | 100 | 100 | 13 |
| 2-methylthiazol-4-yl with CN substituent | A | 0 | 0 | 63 | — |
| " | A | 0 | 0 | 51 | 84 |
| " | D | 93 | 70 | 53 | 0 |
| " | C | 0 | 2 | 5 | 11 |
| " | I | — | 94 | 93 | 72 |
| " | I | — | 95 | 95 | 73 |
| " | E | 98 | 98 | 98 | 99 |
| " | F | 96 | 94 | 91 | 67 |
| " | B | 0 | 0 | 90 | 74 |
| 2-methylthiazol-4-yl with C(=O)C(=O)OCH₃ substituent | A | 0 | 0 | 0 | — |
| " | I | — | 13 | 1 | 1 |
| 2-methylthiazol-5-yl with 4-chlorophenyl | A | 18 | 0 | 0 | — |
| " | I | — | 1 | 1 | 1 |
| 2-methylthiazol-4-yl with 4-bromophenyl | A | 30 | 0 | 0 | — |
| " | I | — | 1 | 1 | 1 |
| 2-methylthiazol-4-yl with pyridin-4-yl | A | 30 | 51 | 32 | — |
| " | A | 14 | 65 | 46 | — |
| 2-methylthiazol-4-yl with C₁₄H₂₉ and 4-chlorophenyl | A | 33 | 0 | 0 | — |
| " | I | — | 1 | 1 | 1 |
| phenyl | A | 0 | 25 | 0 | — |
| " | I | — | 16 | 16 | 1 |
| 4-chlorophenyl | A | 0 | 67 | 17 | — |
| " | I | — | 35 | 29 | 4 |
| 4-fluorophenyl | A | — | 41 | 5 | 0 |
| " | A | 0 | 32 | 5 | — |
| 2-chlorophenyl | A | 0 | 52 | 0 | — |
| " | I | — | 50 | 31 | 5 |
| 4-SO₂NH₂-phenyl | A | — | 22 | 0 | 3 |
| 4-CO₂nBu-phenyl | A | — | 0 | 0 | 0 |
| pyridin-2-yl | A | 6 | 2 | 0 | — |
| pyrimidin-2-yl | A | 22 | 23 | 0 | — |

81
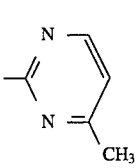
| | | | | | |
|---|---|---|---|---|---|
| | I | — | 6 | 12 | 5 |
| | A | 100 | 64 | 42 | — |
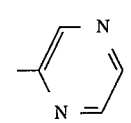
| | | | | | |
|---|---|---|---|---|---|
| | I | — | 9 | 15 | 9 |
| | B | 100 | 27 | 0 | — |
| | C | 0 | 0 | 0 | — |
| | A | 100 | 100 | 4 | — |
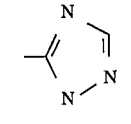
| | | | | | |
|---|---|---|---|---|---|
| | I | — | 36 | 27 | 1 |
| | C | 100 | 20 | 2 | — |
| | A | 10 | 0 | 0 | — |
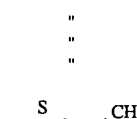
| | | | | | |
|---|---|---|---|---|---|
| | A | 45 | 27 | 11 | — |
| | I | — | 14 | 14 | 12 |
| | C | 15 | 8 | 5 | — |
| | D | 0 | 33 | 33 | 15 |
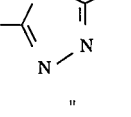
| | | | | | |
|---|---|---|---|---|---|
| | A | 20 | 38 | 3 | — |
| | I | — | 18 | 21 | 1 |
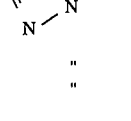
| | | | | | |
|---|---|---|---|---|---|
| | A | 17 | 7 | 0 | — |
| | I | — | 11 | 53 | 12 |
| | I | — | 17 | 9 | 12 |
| | I | — | 14 | 14 | 12 |
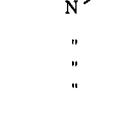
| | | | | | |
|---|---|---|---|---|---|
| | A | 100 | 100 | 100 | — |
| | C | 0 | 17 | 0 | — |
| | B | 96 | 57 | 100 | — |
| | A | 100 | 100 | 94 | — |
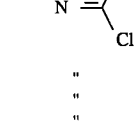
| | | | | | |
|---|---|---|---|---|---|
| | A | 38 | 49 | 37 | — |
| | B | 26 | 16 | 8 | — |
| | B | 100 | 60 | 55 | — |
| | A | — | 0 | 0 | 0 |
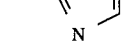
82
| | | | | | |
|---|---|---|---|---|---|
| | A | — | 0 | 0 | 0 |
| | A | 0 | 0 | 0 | — |
| | I | — | 38 | 8 | 1 |
| | A | 0 | 71 | 0 | — |
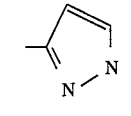
| | | | | | |
|---|---|---|---|---|---|
| | A | — | 7 | 10 | 3 |
| | I | — | 10 | 12 | 7 |
| | A | 100 | 100 | 63 | — |
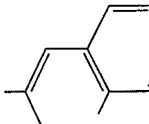
| | | | | | |
|---|---|---|---|---|---|
| | D | 23 | 27 | 32 | — |
| | C | 8 | 1 | 0 | — |
| | I | — | 40 | 36 | 39 |
| | A | 41 | 99 | 53 | 0 |
| | E | 95 | 96 | 77 | 1 |
| | F | 96 | 84 | 87 | 1 |
| | B | 50 | 100 | 99 | 17 |
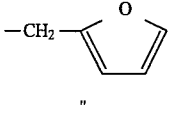
| | | | | | |
|---|---|---|---|---|---|
| | A | 50 | 28 | 8 | — |
| | I | — | 24 | 12 | 12 |
| | A | 100 | 19 | 4 | — |
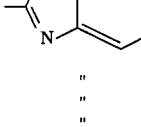
| | | | | | |
|---|---|---|---|---|---|
| | E | 97 | 8 | 11 | — |
| | F | 93 | 72 | 6 | 1 |
| | B | 36 | 100 | 22 | 18 |
| | I | — | 1 | 6 | 9 |
| | C | 17 | 2 | 0 | — |
| | G | 87 | 1 | 1 | — |
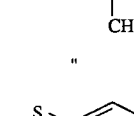
| | | | | | |
|---|---|---|---|---|---|
| | A | 33 | 5 | 0 | — |
| | I | — | 8 | 5 | 1 |
| | A | 68 | 63 | 0 | — |
| | A | 49 | 67 | 0 | — |
| | E | 96 | 51 | 1 | — |
| | F | 98 | 79 | 1 | — |
| | I | — | 18 | 18 | 12 |
| | B | 27 | 67 | 9 | 24 |
| | C | 21 | 0 | 0 | — |
| | G | 90 | 12 | 1 | — |

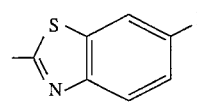

| | TEST | 100 | 100 | 100 | — |
|---|---|---|---|---|---|
| " | A | 100 | 100 | 100 | — |
| " | A | 100 | 100 | 100 | — |
| " | D | 0 | 28 | 5 | — |
| " | C | 19 | 5 | 2 | — |
| " | I | — | 39 | 38 | 33 |
| " | E | 95 | 16 | 51 | 1 |
| " | F | 97 | 62 | 77 | 4 |
| " | B | 93 | 12 | 40 | 4 |
| " | A | 72 | 21 | 3 | — |

TABLE A3

Ph-CH2-CH2-NH-C(=S)-$R_x$

| $R_x$ | TEST | 100 µg/ml | 10 µg/ml | 1 µg/ml | 0.1 µg/ml |
|---|---|---|---|---|---|
| −N(tetrahydroquinoline) | A | — | 0 | 0 | 0 |
| " | A | — | 0 | 0 | 25 |
| −N(piperidine) | A | — | 0 | 0 | 0 |
| −N(N-methylpiperazine) | A | 0 | 0 | 0 | — |
| −N(morpholine) | A | — | 9 | 13 | 0 |

TABLE A4

$R_5$-CH2-CH2-NH-C(=S)-NH-C(=S)-(pyrrolyl)

| $R_5$ | TEST | 100 µg/ml | 10 µg/ml | 1 µg/ml | 0.1 µg/ml |
|---|---|---|---|---|---|
| 3,4-(MeO)2-C6H3 | A | 0 | 54 | 4 | — |
| " | A | 0 | 58 | 44 | — |
| 4-Cl-C6H4 | A | 73 | 79 | 5 | — |

TABLE A4-continued $R_5$-CH2-CH2-NH-C(=S)-NH-C(=S)-(pyrrolyl)

| $R_5$ | TEST | 100 µg/ml | 10 µg/ml | 1 µg/ml | 0.1 µg/ml |
|---|---|---|---|---|---|
| " | A | 71 | 93 | 22 | — |
| 2-Cl-6-F-C6H3 | A | 100 | 100 | 100 | — |
| " | A | 16 | 52 | 98 | — |
| " | I | — | 92 | 77 | 43 |
| 2-OC2H5-C6H4 | A | 100 | 100 | 96 | — |
| " | B | 100 | 91 | 100 | — |
| " | C | 0 | 5 | 0 | — |
| " | I | — | 33 | 30 | 12 |

TABLE A5

Thiohydantoin structure with $R_{11}$, $R_{13}$

| $R_{11}$ | $R_{13}$ | TEST | 100 | 10 | 1 | 0.1 |
|---|---|---|---|---|---|---|
| Ph, Ph | H | A | — | 0 | 0 | 0 |
| Ph, Ph | Ph | A | — | 0 | 0 | 0 |
| Ph | Ph | A | — | 0 | 0 | 0 |
| Ph | Ac | A | — | 0 | 0 | 0 |
| CH2Ph | H | A | — | 28 | 5 | 8 |
| CH2Ph | CH3 | A | 100 | 24 | 0 | — |
| " | " | " | 100 | 34 | 0 | — |
| " | " | E | 94 | 7 | 13 | — |
| " | " | F | 98 | 1 | 1 | 1 |
| " | " | B | 100 | 63 | 0 | 34 |
| " | " | C | 100 | 26 | 0 | — |
| CH2Ph | nBu | A | 100 | 20 | 0 | — |
| CH2Ph | nBu | A | 100 | 31 | 5 | — |
| " | " | " | 100 | 52 | 0 | — |
| " | " | E | 98 | 9 | 11 | — |
| " | " | F | 98 | 1 | 1 | — |
| " | " | B | 100 | 82 | 20 | 1 |
| " | " | C | 100 | 22 | 3 | — |
| CH2Ph | Ac | A | — | 26 | 5 | 6 |
| " | " | B | 100 | 0 | 16 | — |
| " | " | C | 100 | 6 | 7 | — |
| CH2Ph-pCl | Ac | A | 18 | 3 | 5 | — |
| CH2Ph | Ph | A | 100 | 16 | 2 | — |
| " | " | C | 100 | 12 | 0 | — |
| " | " | D | 3 | 0 | 0 | — |
| " | " | A | 99 | 12 | 0 | — |
| " | " | E | 98 | 63 | 41 | — |
| " | " | F | 95 | 1 | 33 | 42 |
| " | " | B | 80 | 48 | 37 | 24 |
| CH2Ph | CH2Ph | A | 100 | 46 | 0 | — |
| " | " | " | 100 | 29 | 4 | — |

TABLE A5-continued

[Structure: thiohydantoin-like with H-N-C(=S)-N(R13)-C(R11)-C(=O)]

| $R_{11}$ | $R_{13}$ | TEST | 100 | 10 | 1 | 0.1 |
|---|---|---|---|---|---|---|
| " | " | E | 98 | 9 | 1 | — |
| " | " | F | 98 | 59 | 1 | 1 |
| " | " | B | 58 | 100 | 35 | 0 |
| " | " | C | 100 | 20 | 2 | — |
| " | " | G | 93 | 1 | 1 | — |
| $CH_2Ph$-p-OH | H | A | — | 0 | 0 | 0 |
| $CH_2Ph$-p-OH | Ph | A | — | 34 | 4 | 1 |
| $CH_2Ph$-p-OH | Ph | A | 99 | 19 | 44 | — |
| " | " | B | 100 | 12 | 0 | — |
| " | " | C | 100 | 28 | 6 | — |

A feature of this invention also disclosed is a method of administering to a human in need thereof the compounds of the invention or their pharmaceutically acceptable salts to treat or inhibit HIV/AIDS, to inhibit the replication of the HIV/AIDS virus in infected human cells and to inhibit AIDS from developing in humans infected with the HIV/AIDS virus or carrying antibodies to the HIV/AIDS virus.

The present invention also discloses the compounds of the invention and their salts for use in the treatment of the condition referred to above, as well as the use of such compounds in the preparation of pharmaceutical formulations for the treatment of such conditions.

In general for the treatment as described above, a suitable effective dose of the compound or its pharmaceutically acceptable salt will be in the range of 0.5 to 250 mg per kilogram bodyweight of recipient per day. Administration may be by any suitable route including oral, rectal, nasal, topical (including buccal and sublingual), vaginal or parenteral (including subcutaneous, intramuscular, intravenous and intradermal) administration. It will be appreciated that the preferred route may vary with, for example, the condition, age, and weight of the recipient.

The administered ingredients may be used as a therapy in conjunction with other therapeutic agents, (other anti-virals, anti-bacterials, compounds useful for preventing resulting secondary or contemporaneous afflictions associated with HIV/AIDS) such as AZT, ddI, ddC, 9-[[2-hydroxy-1-(hydroxymethyl)ethoxy]methyl]guanine, 9-(2-hydroxyethoxymethyl)guanine(acyclovir), 2-amino-9-(2-hydroxyethoxymethyl)purine, suramin, ribavarin, antimoniotungstate (HPA-23), interferon, e.g., a interferon, interleukin II, and phosphonoformate (Foscarnet) or in conjunction with other immune modulators including bone marrow or lymphocyte transplants or other medications such as levamisol or thymosin which would increase lymphocyte numbers and/or function as is appropriate.

For example, in an evaluation of the combination of AZT and a compound of the formula

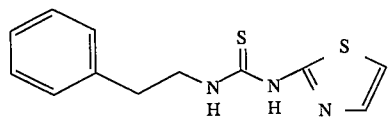

a synergistic effect was observed. The combination was evaluated against HIV-1 in CEM cells using the technique of Prichard and Shipman (*Antiviral Research*, 14, 181–206 (1990)). The peak of synergy was observed at 0.5 µg/ml of the compound of the formula above and 0.005 µg/ml of AZT.

While it is possible for the administered ingredients to be administered alone, it is preferable to present them as part of a pharmaceutical formulation. The formulations of the present invention comprise at least one administered ingredient, as above-defined together with one or more acceptable carriers thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, in ravenous and intradermal) administration. The formulations may conveniently be presented in unit dosage form, e.g., tablets and sustained release capsules, and may be prepared by any methods well known in the art of pharmacy.

Such methods include the step of bringing into association the to be administered ingredients with the carrier which constitutes one or more accessory ingredients. In general, the formulations are prepared by uniformly and intimately bringing into association the active ingredients with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion and as a bolus, etc.

With regard to compositions for oral administration (e.g. tablets and capsules), the term "suitable vehicle" means common excipients such as binding agents, for example, syrup, acacia, gelatin, sorbitol, tragacanth, polyvinylpyrrolidine (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; disintegrators such as microcrystalline cellulose, corn starch, sodium starch glycolate, alginic acid; and lubricants such as magnesium stearate and other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more aesthetically pleasing in appearance or to help identify the product. The tablets may also be coated by methods well known in the art.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered and a pharmaceutically acceptable carrier. An exemplary topical delivery system is a transdermal patch containing the ingredient to be administered.

Formulations for rectal administration may be presented as a suppository with a suitable base comprising, for example, cocoa butter or a salicylate.

Formulations suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams, or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, or example water for injections, immediately prior to use. Extemporaneous injection solutions and suspensions may be prepared from sterile powders, granules, and tablets of the kind previously described.

Preferred unit dosage formulations are those containing a daily dose or unit, daily sub-dose, as herein above recited, or an appropriate fraction thereof, of the administered ingredient.

The antiviral compounds of Formula I can be used as surface disinfectants. Solutions containing as little as 0.1 percent by weight of the antiviral compound maybe effective for disinfecting purposes. Preferably, such solutions also can contain a detergent or other cleansing agent. The solutions maybe useful for disinfecting objects such as glassware, dental and surgical instruments, and surfaces such as walls, floors, and tables in areas where maintenance of sterile conditions is important, for example, hospitals, food-preparation areas, and the like.

In practicing the method for treating or inhibiting HIV and/or AIDS, the antiviral can be administered in a single daily dose or in multiple doses per day. The treatment regime may require administration over extended periods of time, e.g., for several days or for several months or years. The amount administered per dose or the total amount administered will depend on such factors as the nature and severity of the infection, the age and general health of the patient, the tolerance of both the patient and the microorganism or microorganisms involved in the infection to the antiviral compound.

The following formulation examples represent specific pharmaceutical formulations employing compounds comprehended by the present method. The formulations may employ as active compounds any of the compounds of Formula I or a pharmaceutically acceptable salt thereof. The examples are illustrative only and are not intended to limit the scope of the invention in any way.

Formulation 1

Hard gelatin capsules are prepared using the following ingredients:

|  | Quantity (mg/capsule) |
| --- | --- |
| Compound | 1250 |
| Starch dried | 200 |
| Magnesium stearate | 10 |

The above ingredients are mixed and filled into hard gelatin capsules in 460 mg quantities.

Formulation 2

A tablet formula is prepared using the ingredients below:

|  | Quantity (mg/tablet) |
| --- | --- |
| Compound | 250 |
| Cellulose, microcrystalline | 400 |
| Silicon dioxide, fumed | 10 |
| Stearic acid | 5 |
| Magnesium stearate | 10 |

The components are blended and compressed to form tablets each weighing 675 mg.

Formulation 3

An aerosol solution is prepared containing the following components:

|  | Weight |
| --- | --- |
| Compound | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then placed in a stainless steel container and diluted with the remainder of the propellant. The valve units are then fitted to the container.

Formulation 4

Tablets each containing 60 mg of active ingredient are made up as follows:

| Compound | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |

89

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 40°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| Compound | 80 mg |
|---|---|
| Starch | 59 mg |
| Microcrystalline cellulose | 59 mg |
| Silicone fluid | 2 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of medicament are made as follows:

| Compound | 225 mg |
|---|---|
| Saturated fatty acid glycerides | 2 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

As intravenous formulation is prepared as follows:

| Compound | 100 mg |
|---|---|
| Isotonic saline | 1000 ml |

The solution of the above ingredients is administered intravenously at a rate of 1 ml/minute to a mammal in need of treatment.

It should be understood that in addition to the ingredients particularly mentioned above the formulations of this invention may include other agents conventional in the art having regard to the type of formulation in question.

The following examples further illustrate the compounds of the present invention and methods for the synthesis. The examples are not intended to be limiting to the scope of the invention in any respect and should not be so construed.

EXAMPLES AND PROCEDURES

The following are experimentals illustrating methods for preparing the compounds of the invention.

90

Example 1

N-(2-Phenethyl)-N'-[2(1,3,4-thiadiazolyl)]thiourea

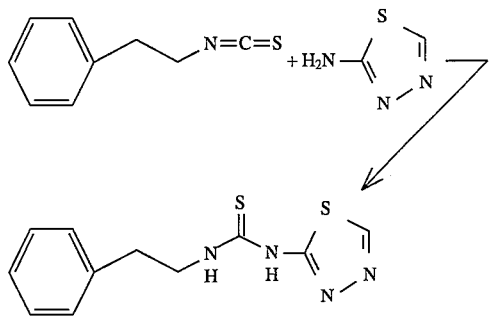

A solution of 2-phenethyl isothiocyanate (3.26 g, 20 mmol, 3.0 mL) and 2-amino-1,3,4-thiadiazole (2.02 g, mmol) in N,N-dimethylformamide (50 mL) was heated to 100° C. After 68 h, the reaction was cooled to room temperature and poured into ethyl acetate. The organic phase was washed with 1N hydrochloric acid, saturated sodium bicarbonate solution, and water. The organic layer was filtered and the solid obtained (2.24 g) triturated with ethyl acetate to provide 1.9 g (36%) of the title product:

mp 210°–211.5° C.;

IR (KBr, cm$^{-1}$) 3320, 2924, 2869, 2685, 1645, 1543, 1453, 1384, 1344, 1278, 762, 749, 700, 650;

$^1$H NMR (300 MHz, DMSO-d$_6$) δ12.35 (br s, 1H), 8.92 (s, 1H), 8.78 (br s, 1H), 7.38–7.18 (m, 5H), 3.84–3.72 (m, 2H), 2.92 (t, J=6 Hz, 2H);

MS (FD) m/e 264 (M+);

UV (EtOH) 277 nm, 253 nm, 205 nm.

Anal. Calcd for $C_{11}H_{12}N_4S_2$: Theory: C, 49.98; H, 4.57; N, 21.19. Found: C, 50.07; H, 4.66; N, 21.48.

Example 2

N-(2-Phenethyl)-N'-[4,5-dimethyl-(2-thiazolyl)]thiourea

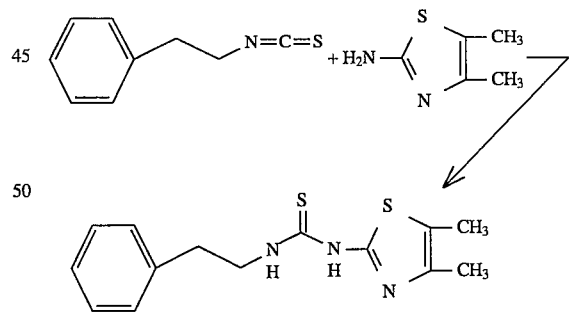

2-Amino-4,5-dimethylthiazole hydrochloride (3.3 g, 20 mmol) was slurried with methylene chloride and shaken with saturated sodium bicarbonate solution. The layers were separated and the aqueous washed with methylene chloride (2×). The combined organics were dried over magnesium sulfate, filtered and concentrated. To the resulting solid was added 2-phenethyl isothiocyanate (3.26 g, 20 mmol, 3.0 mL) and N,N-dimethylformamide (50 mL). The resulting solution was heated to 100° C. After 95.25 h, the reaction was cooled to room temperature and poured into ethyl acetate. The organic phase was washed with 1N hydrochloric acid, saturated sodium bicarbonate solution, and water (2x). The organic layer was filtered and the solid obtained (3.9 g) recrystallized from ethyl acetate to provide 3.3 g (57%) of the title product:

mp 186°–7° C.;

IR (KBr, cm$^{-1}$) 3166, 3022, 1523, 1502, 1289, 1215, 737, 695;

$^1$H NMR (300 MHz, DMSO-d$_6$) δ11.42 (br s, 1H), 9.83 (br s, 1H), 7.36–7.16 (m, 5H), 3.86–3.73 (m, 2H), 2.91 (t, J=7 Hz, 2H), 2.19 (s, 3H), 2.08 (s, 3H);

MS (FD) m/e 291 (M+);

UV (EtOH) 298 nm (ε=17987), 257 nm (ε=9939), 204 nm (ε=20802).

Anal. Calcd for C$_{14}$H$_{17}$N$_3$S$_2$: Theory: C, 57.70; H, 5.80; N, 14.42. Found: C, 57.41; H, 5.85; N, 14.39.

Example 3

N-[2-(4-Methyl)-1-phenethyl]-N'-(2-thiazolyl)thiourea

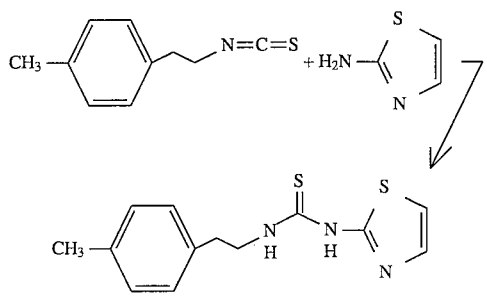

A solution of 2-(4-methylphenethyl) isothiocyanate (820 mg, 4.6 mmol) and 2-aminothiazole (565 mg, 5.65 mmol) in N,N-dimethylformamide (15 mL) was heated to 100° C. After 20.5 h, the reaction was cooled to room temperature and poured into ethyl acetate. The organic phase was washed with iN hydrochloric acid (2x), saturated sodium bicarbonate solution, and brine. The organic layer was dried over magnesium sulfate, filtered and concentrated. The solid obtained (1.1 g) was purified by flash chromatography on silica gel (1% ethyl acetate in methylene chloride) to provide 570 mg (45%) of the titled compound. A sample was recrystallized from ethyl acetate:

mp 132°–3° C.;

IR (KBr, cm$^{-1}$) 3168, 2990, 1560, 1513, 1166, 808,705;

$^1$H NMR (300 MHz, DMSO-d$_6$) δ11.62 (br s, 1H), 9.69 (br s, 1H), 7.36 (d, J=4 Hz, 1H), 7.20–7.06 (m, 5H), 3.83–3.73 (m, 2H), 2.87 (t, J=7 Hz, 2H), 2.30 (s, 3H);

MS (FD) m/e 277 (M+);

UV (EtOH) 288 nm (ε=18773), 257 nm (ε=11948), 212 nm (ε=14509).

Anal. Calcd for C$_{13}$H$_{15}$N$_3$S$_2$: Theory: C, 56.29; H, 5.45; N, 15.15. Found: C, 56.55; H, 5.52; N, 15.04.

Example 4

N-(2-phenethyl)-N'-(2-pyridyl)thiourea

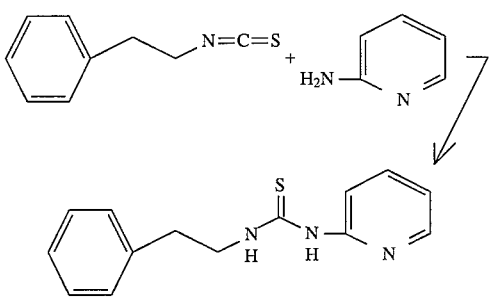

A solution of 2-phenethyl isothiocyanate (3.26 g, 20 mmol, 3.0 mL) and 2-aminopyridine (1.90 g, 20 mmol) in N,N-dimethylformamide (50 mL) was heated to 100° C. After 4 h, the reaction was cooled to room temperature and poured into ethyl acetate. The organic solution was washed with water (3x). The organic layer was dried over sodium sulfate, filtered and concentrated. The resulting white solid was recrystallized from ethyl acetate to provide 1.86 g (36%) of the titled product:

mp 153°–154° C.;

IR (KBr, cm$^{-1}$) 3232, 1536, 1477, 1319, 775;

$^1$H NMR (300 MHz, CDCl$_3$) δ11.72 (br s, 1H), 8.59 (br s, 1H), 7.97 (d, J=4.2 Hz, 1H), 7.64(dt, J=1.7,8.2 Hz, 1H), 7.37–7.26 (m, 5H), 6.92 (dd, J=7.2,5.1 Hz, 1H), 6.74 (d, J=8.2 Hz, 1H), 4.06 (m, J=6.8 Hz, 2H), 3.04 (t, J=6.9 Hz, 2H);

MS (FD) m/e 257 (M$^+$);

UV (EtOH) 293 nm (ε=12040), 266 nm (ε=12961), 247 nm (ε=11912) 202 nm (ε=12963).

Anal. Calcd for C$_{14}$H$_{15}$N$_3$S: Theory: C, 65.35; H, 5.87; N, 16.33. Found: C, 65.46; H, 5.82; N, 16.24

Example 5

N-(2-phenethyl)-N'-(4-pyridyl)thiourea

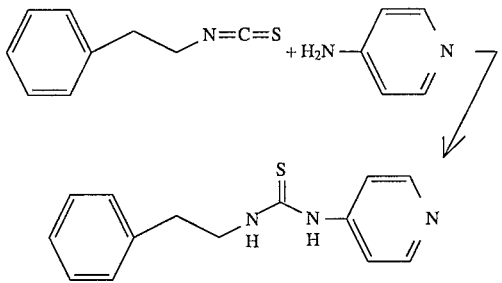

A solution of 2-phenethyl isothiocyanate (3.26 g, 20 mmol, 3.0 mL) and 4-aminopyridine (1.92 g, 20 mmol) in N,N-dimethylformamide (50 mL) was heated to 100° C. After 4.5 h, the reaction was cooled to room temperature and poured into ethyl acetate. The organic solution was washed with water (2x) and brine. The organic layer was dried over sodium sulfate, filtered and concentrated. The oil obtained was purified by flash chromatography on silica gel (5% methanol in ethyl acetate to 10% methanol in ethyl acetate). This material was recrystallized from ethyl acetate yielding 1.85 g (36%) of the title product:

mp 154.5° C.;

IR (KBr, cm$^{-1}$) 3142, 1579, 1518, 1328, 1276, 750;

$^1$H NMR (300 MHz, CDCl$_3$) δ8.42 (dd, J=1,5 Hz, 2H), 7.94 (br s, 1H), 7.39–7.23 (m, 5H), 6.81 (d, J=5 Hz, 2H), 6.38 (br s, 1H), 3.99 (m, J=6 Hz, 2H), 3.02 (t, J=6 Hz, 2H):

MS (FD) m/e 258 (M+1);

UV (EtOH) 281 nm (ε=16486), 255 nm (ε=21182), 208 nm (ε=25744).

Anal. Calcd for C$_{14}$H$_{15}$N$_3$S: Theory: C, 65.34; H, 5.87; N, 16.33. Found: C, 65.43; H, 5.97; N, 16.17.

Example 6

N-(2-phenethyl)-N'-[2-(6-fluoro)-benzothiazolyl]thiourea

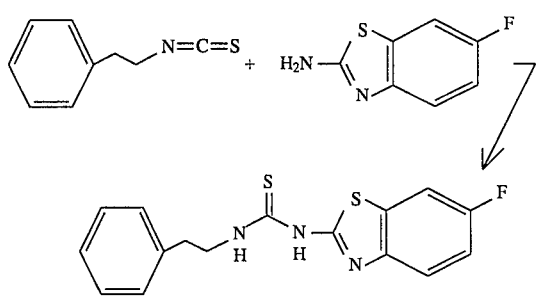

A solution of 2-phenethyl isothiocyanate (3.26 g, 20 mmol, 3.0 mL) and 2-amino-6-fluoro-benzothiazole (3.36 g, 20 mmol) in dimethylsulfoxide (10 mL) was heated to 150° C. After 5 h, the reaction was cooled to room temperature and filtered. The filtrate was poured into ethyl acetate, washed with water (5×) and brine (2×). The organic layer was concentrated and recrystallized from ethyl acetate to provide 729.5 mg (11%) of the titled product:

mp 212°–213° C.;

IR (KBr, cm$^{-1}$) 3175, 3025, 1561, 1534, 1461, 1249, 1215;

$^1$H NMR (300 MHz, CDCl$_3$) δ11.81 (br s, 1H), 9.83 (br s, 1H), 7.77 (dd, J=8.7, 2.4 Hz, 1H), 7.52 (br s, 1H), 7.31–7.15 (m, 6H), 3.79 (m, 2H), 2.90 (t, J=6.6 Hz, 2H);

MS (FD) m/e 331 (M$^+$);

UV (EtOH) 310 nm, 289 nm, 245 nm, 208 nm, 201 nm.

Anal. Calcd for C$_{16}$H$_{14}$N$_3$S$_2$F: Theory: C, 57.98; H, 4.26; N, 12.68. Found: C, 57.74; H, 4.39; N, 12.53.

Example 7

N-(2-phenethyl)-N'-[2-(4-phenyl-5-tetradecyl)-thiazolyl]thiourea

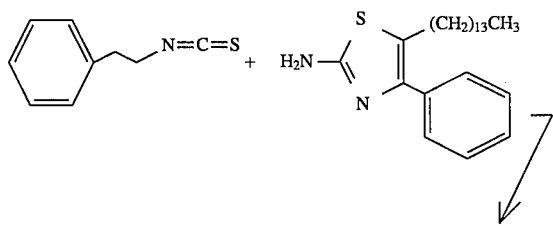

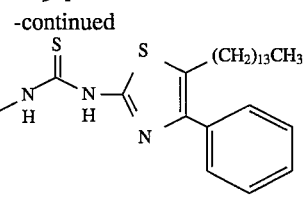

A solution of 2-phenethyl isothiocyanate (3.26 g, 20 mmol, 3 mL) and 2-amino-4-phenyl-5-tetradecylthiazole (7.45 g, 20 mmol) in N,N-dimethylformamide (50 mL) was heated to 100° C. After 24 h, the reaction was cooled room temperature and poured into ethyl acetate. The organic solution was washed with 1N hydrochloric acid, saturated sodium bicarbonate solution, water (3×) and brine. The organic layer was dried over sodium sulfate, filtered and concentrated. The material was recrystallized from ethyl acetate (once) and hexanes (once) to provide 4.93 g (46%) of the title product:

mp 108.5°–109° C.;

IR (KBr, cm$^{-1}$) 3166, 3022, 2915, 1850, 1574, 1523, 1502, 1215, 695;

$^1$H NMR (300 MHz, CDCl$_3$) δ10.87 (br s, 1H), 9.28 (br s, 1H), 7.55–7.16 (m, 10H), 4.00–3.95 (m, 2H), 2.99 (t, J=7 Hz, 2H), 2.79 (t, J=9Hz, 2H), 1.65–1.00 (m, 24H), 0.86 (t, J=6 Hz, 3H);

MS (FD) m/e 535 (M$^+$);

UV (EtOH) 299 nm (ε=19199), 261 nm (ε=17809), 203 nm (ε=31542).

Anal. Calcd for C$_{32}$H$_{45}$N$_3$S$_2$: Theory: C, 71.73; H, 8.46; N, 7.84. Found: C, 71.93; H, 8.75; N, 7.92.

Example 8

N-[2-(3,4-dimethoxy)-phenethyl]-N'-(2-thiazolyl)thiourea

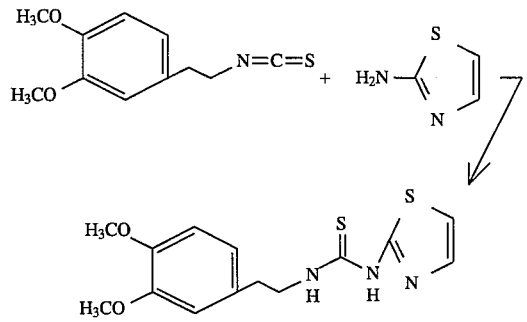

A solution of 2-(3,4-dimethoxyphenethyl) isothio-cyanate (0.52 g, 2.33 mmol) and 2-aminothiazole (233 mg, 2.33 mmol) in N,N-dimethylformamide (10 mL) was heated to 100° C. After 24 h, the reaction was cooled to room temperature and poured into ethyl acetate. The organic solution was washed with 1N hydrochloric acid, saturated sodium bicarbonate solution, water (3×) and brine. The organic layer was dried over sodium sulfate, filtered and concentrated. The oil was recrystallized from toluene to provide 129 mg (17%) of the title product:

mp 139° C.;

IR (KBr, cm$^{-1}$) 3168, 3112, 3013, 1572, 1550, 1516, 1461, 1263, 1237, 1183;

$^1$H NMR (300 MHz, DMSO-d$_6$) δ11.55 (br s, 1H), 9.80–9.62 (br s, 1H), 7.35 (m, 1H), 7.15 (br s, 1H), 6.90–6.75 (m, 3H), 3.80–3.70 (m, 2H), 3.72 (s, 6H), 2.84 (t, J=6 Hz, 2H);

MS (FD) m/e 323 (M+);

UV (EtOH) 287 nm (ε=21678), 258 nm (ε=11828), 228 nm (ε=11401), 205 nm (ε=36669).

Anal. Calcd for C$_{14}$H$_{17}$N$_3$O$_2$S$_2$: Theory: C, 51.99; H, 5.30; N, 12.99. Found: C, 51.96; H, 5.51; N, 13.02.

Example 9

N-(2-phenethyl)-N'-[2-(4-(4-bromophenyl))thiazolyl]thiourea

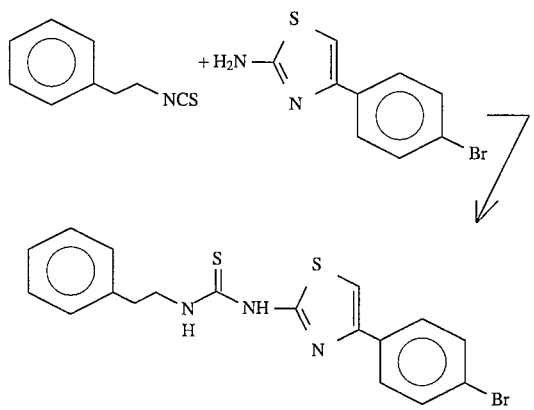

A solution of 2-phenethyl isothiocyanate (3.26 g, 20 mmol, 3 mL) and 2-amino-4-(4-bromophenyl)thiazole (5.15 g, 20 mmol) in N,N-dimethylformamide (50 mL) was heated to 100° C. After 65 h, the reaction was cooled to room temperature and poured into ethyl acetate. The organic solution was washed with 1N hydrochloric acid, saturated sodium bicarbonate solution, water (3×) and brine. The organic layer contained as solid which was filtered. The filtrate was dried over sodium sulfate, filtered and concentrated and added to the filtered solid. The combined material was recrystallized from ethyl acetate to provide 12.04 g (24%) of the title product:

mp 215.5°–216.5° C.;

IR (KBr, cm$^{-1}$) 3166, 3022, 1574, 1523, 1502, 737, 695;

$^1$H NMR (300 MHz, DMSO-d$_6$) δ11.70 (br s, 1H), 9.40 (br s, 1H), 7.74–7.54 (m, 5H), 7.36–7.18 (m, 5H), 3.90–3.81 (m, 2H), 2.96 (t, J=6 Hz, 2H);

MS (FD) m/e 419 (M$^+$1);

UV (EtOH) 287 nm (ε=28740), 268 nm (ε=24574), 246 nm (ε=18009), 203 nm (ε=35813).

Anal. Calcd for C$_{18}$H$_{16}$N$_3$S$_2$Br: Theory: C, 51.68; H, 3.86; N, 10.04. Found: C, 51.39; H, 3.77; N, 9.77.

Example 10

N-[2-(4-Chloro)-phenethyl]-N'-(2-thiazolyl)thiourea

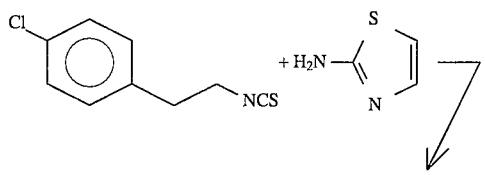

-continued

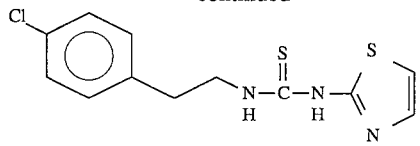

A solution of 2-(4-chloro)-phenethyl isothiocyanate (657 mg, 3.3 mmol) and 2-aminothiazole (335 mg, 3.3 mmol) in N,N-dimethylformamide (10 mL) was heated to 100° C. After 20.5 h, the reaction was cooled to room temperature and poured into ethyl acetate. The organic solution was washed with 1N hydrochloric acid, saturated sodium bicarbonate solution, and water (3×). The organic layer was dried over sodium sulfate, filtered and concentrated. The material was recrystallized from ethyl acetate (2×) to provide 136 mg (14%) of title product:

mp 154°–155° C.;

IR (KBr, cm$^{-1}$) 3090, 2991, 1561, 1515, 1490, 1176;

$^1$H NMR (300 MHz, DMSO-d$_6$) δ11.58 (br s, 1H), 9.78–9.60 (br s, 1H), 7.40–7.28 (m, 5H), 7.12 (br s, 1H), 3.81–3.72 (m, 2H), 2.92 (t, J=6 Hz, 2H);

MS (FD) m/e 297 (M$^+$);

UV (EtOH) 289 nm (ε=19572), 257 nm (ε=12071), 220 nm (ε=15393), 202 nm (ε=22079).

Anal. Calcd for C$_{12}$H$_{12}$N$_3$S$_2$Cl: Theory: C, 48.40; H, 4.06; N, 14.11. Found: C, 48.17; H, 4.02; N, 13.83.

Example 11

N-(1-phenethyl)-N'-[2-(4,5-dihydro)thiazolyl]thiourea

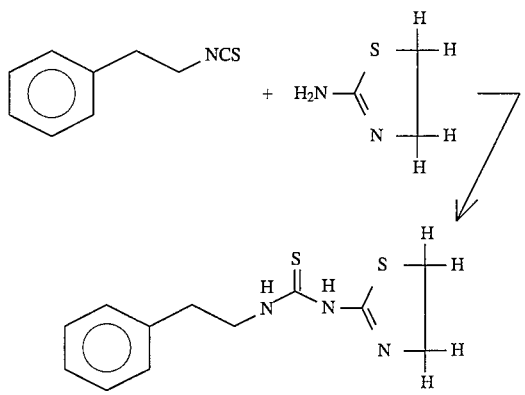

A solution of 2-phenethyl isothiocyanate (1.63 g, 10 mmol, 1.5 mL) and 2-amino-4,5-dihydrothiazole (1.02 g, 10 mmol) in dimethylsulfoxide (10 mL) was heated to 100° C. After 2.5 h, the reaction was cooled to room temperature and poured into ethyl acetate. The organic phase was washed with 1N hydrochloric acid (2×), water (4×), and brine. The organic layer was dried over sodium sulfate, filtered and concentrated. The solid obtained was recrystallized from ethyl acetate to provide 1.48 g (56%) of title product as a white crystalline solid. A sample was recrystallized a second time from ethyl acetate:

mp 132°–134° C.;

IR (KBr, cm$^{-1}$) 3161, 3027, 2945, 2852, 1630, 1574, 1552, 1221, 1033;

$^1$H NMR (300 MHZ, CDCl$_3$) δ11.11 (br s, 1H), 8.36 (s, 1H), 7.32 –7.14 (m, 5H), 4.05–3.97 (m, 2H), 3.90–3.83 (m, 2H), 3.30–3.22 (m, 2H), 2.94 (t, J=7.1 Hz, 2H);

MS (EI) m/e 265 (M+);

UV (EtOH) 269 nm (ε=18349), 206 nm (ε=18745).

Anal. Calcd for C$_{12}$H$_{15}$N$_3$S$_2$: Theory: C, 54.31; H, 5.70; N, 15.83. Found: C, 54.36; H, 5.66; N, 15.78.

Example 12

N-(2-Phenethyl)-N'-[2-(4-methylthiazolyl)]thiourea

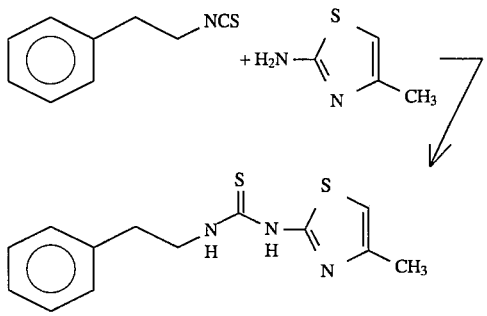

A solution of 2-phenethyl isothiocyanate (1.63 g, 10 mmol, 1.5 mL), 2-amino-4-methylthiazole hydrochloride (1.51 g, 10 mmol) and N,N-diisopropylethylamine (1.29 g, 10 mmol, 1.74 mL) in dimethylsulfoxide (10 mL) was heated to 100° C. After 21 h, the reaction was cooled to room temperature and poured into ethyl acetate. The organic phase was washed with 1N hydrochloric acid, saturated sodium bicarbonate solution, water (3×), and brine. The organic layer was dried over sodium sulfate, filtered and concentrated. The solid obtained was purified by flash chromatography on silica gel (1% ethyl acetate in dichloromethane), followed by recrystallization from ethyl acetate to provide 1.05 g (38%) of the title product as a very light green crystalline solid:

mp 190°–192° C.;

IR (KBr, cm$^{-1}$) 3456, 3169, 3084, 3024, 1565, 1533, 1506, 1214;

$^1$H NMR (300 MHZ, CDCl$_3$) δ10.92 (s, 1H), 10.08 (s, 1H), 7.33–7.20 (m, 5H), 6.31 (s, 1H), 4.04–3.98 (m, 2H), 3.01 (t, J=6.9 Hz, 2H), 2.17 (s, 3H);

MS (EI) m/e 277 (M+);

UV (EtOH) 293 nm (ε=18119), 258 nm (ε=10137), 204 nm (ε=18979).

Anal. Calcd. for C$_{13}$H$_{15}$N$_3$S$_2$: Theory: C, 56.29; H, 5.45; N, 15.15. Found: C, 56.53; H, 5.53; N, 15.18.

Example 13

N-(2-Phenethyl)-N'-[2-(4-(ethylglyoxylate)thiazolyl)]

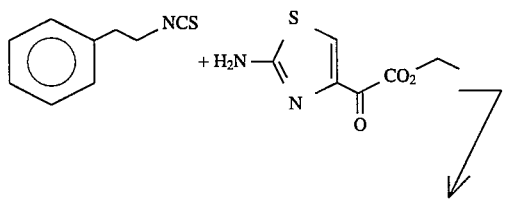

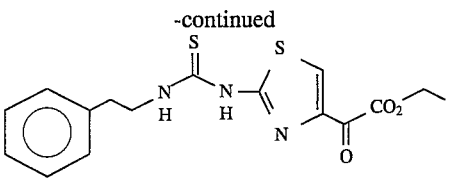

A solution of 2-phenethyl isothiocyanate (3.25 g, 20 mmol, 3.0 mL) and ethyl 2-amino-4-thiazoleglyoxylate (4.0 g, 20 mmol) in dimethylsulfoxide (20 mL) was heated to 110° C. After 68 h, the reaction was cooled to room temperature and poured into ethyl acetate. The organic phase was washed with 1N hydrochloric acid, water (5×), and brine. The organic layer was dried over sodium sulfate, filtered and concentrated. The solid obtained was purified by flash chromatography on silica gel (10% ethyl acetate in dichloromethane) and treated with decolorizing carbon to provide 2.37 g (33%) of the title product as a light yellow solid. A sample was recrystallized from ethyl acetate:

mp 168°–169° C.;

IR (KBr, cm$^{-1}$) 3174, 3029, 1724, 1685, 1558, 1530, 1215, 1133, 1054;

$^1$H NMR (300 MHZ, CDCl$_3$) δ10.67 (s, 1H), 8.21 (s, 1H), 7.34–7.17 (m, 5H), 4.39 (q, J=7.1 Hz, 2H), 3.96–3.85 (m, 2H), 3.09–2.93 (m, 2H), 1.40 (t, J=7.1 Hz, 3H);

MS (FD) m/e 363 (M+);

UV (EtOH) 284 nm (ε=18549), 255 nm (ε=17141), 204 nm (ε=23447).

Anal. Calcd for C$_{16}$H$_{17}$N$_3$O$_3$S$_2$: Theory: C, 52.87; H, 4.71; N, 11.56. Found: C, 53.08; H, 4.80; N, 11.55.

Example 14

N-(2-Phenethyl)-N'-[2-(5,6-dimethylbenzothiazolyl)]thiourea

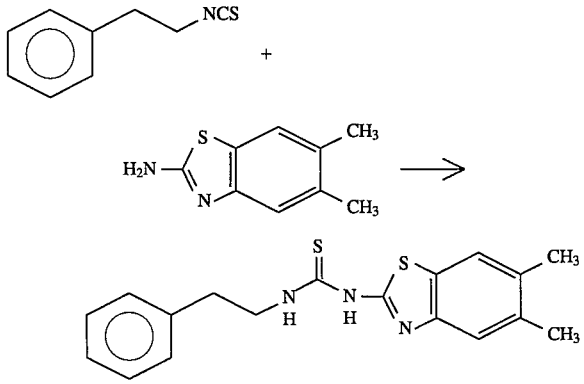

A solution of 2-phenethyl isothiocyanate (3.26 g, 20 mmol, 3.0 mL ) and 2 -amino-5,6 -dimethylbenzothiazolyl (3.57 g, 20 mmol) in N,N-dimethyl-formamide (50 mL) was heated to 100° C. After 24 h, the reaction was cooled to room temperature and poured into ethyl acetate, with formation of a precipitate. The organic phase was washed with 1N hydrochloric acid, saturated sodium bicarbonate solution, water (2×) and brine. The organic layer was filtered and the solid obtained (3.0 g) triturated with 20% ethanol in ethyl acetate to provide 2.91 g (43%) of the title product as a pale yellow solid:

mp 226°–228° C.;

IR (KBr, cm$^{-1}$) 3178, 3047, 1557, 1530, 1462, 1254, 1220;

$^1$H NMR (300 MHZ, DMSO-d$_6$) δ11.69 (s, 1H), 10.30 (s, 1H), 7.55 (s, 1H), 7.35–7.16 (m, 6H), 3.80–3.73 (m, 2H), 2.90 (t, J=7.0 Hz, 2H), 2.25 (s, 3H), 2.23 (s, 3H);

MS (EI) m/e 341 (M+);

UV (EtOH) 307 nm, 253 nm, 204 nm.

Anal. Calcd for C$_{18}$H$_{19}$N$_3$S$_2$: Theory: C, 63.31; H, 5.61; N, 12.31. Found: C, 63.15; H, 5.63; N, 12.14.

Example 15

N-(2-Phenethyl)-N'-[2-(6-methoxybenzothiazolyl)]thiourea

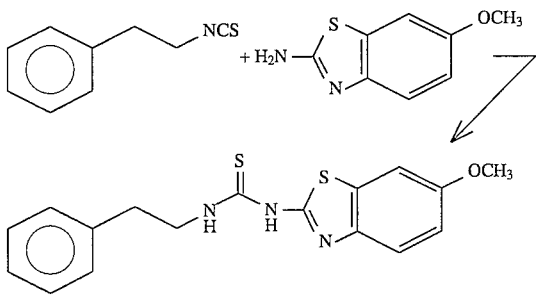

A solution of 2-phenethyl isothiocyanate (3.26 g, 20 mmol, 3.0 mL) and 2-amino-6-methoxybenzothiazole (3.60 g, 20 mmol) in N,N-dimethylformamide (50 mL) was heated to 100° C. After 16 h, the reaction was cooled to room temperature and poured into ethyl acetate. The organic phase was washed wish 1N hydrochloric acid, saturated sodium bicarbonate solution, water (3×) and brine. The organic layer was filtered to provide 550 mg of the title product. The filtrate was concentrated and the resulting solid recrystallized from ethyl acetate to provide another 830 mg of the title product. Total yield: 1.38 g (20%) of the title product as a fluffy white solid:

mp 217°–218° C.;

IR (KBr, cm$^{-1}$) 3182, 3050, 1556, 1534, 1473, 1437, 1221, 1055;

$^1$H NMR (300 MHZ, CDCl$_3$) δ10.99 (s, 1H), 9.29 (s, 1H), 7.46–6.99 (m, 8H), 4.12–4.06 (m, 2H), 3.86 (s, 3H), 3.08 (t, J=6.8 Hz, 2H);

MS (FD) m/e 343 (M+);

UV (EtOH) 312 nm (ε=22725), 251 nm (ε=11152), 204 nm (ε=26183).

Anal. Calcd for C$_{17}$H$_{17}$N$_3$OS$_2$: Theory: C, 59.45; H, 4.99; N, 12.23. Found: C, 59.21; H, 4.97; N, 12.19.

Example 16

2-Amino-4-cyanothiazole

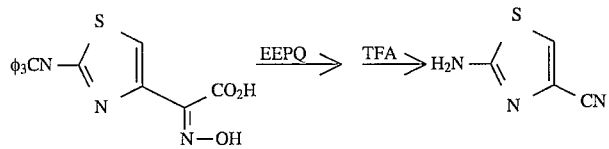

Ethyl 1,2-dihydro-2-ethoxy-1-quinolinecarboxylate (6.68 g, 27.0 mmol) was added to a solution of ethyl [2-(tritylamino)thiazol-4-yl]-(Z)-hydroxyiminoacetate (11.46 g, 26.7 mmol) in N,N-dimethylformamide (100 mL) and stirred for 6 h at room temperature. The reaction was poured into ethyl acetate, washed with 1N hydrochloric acid (2×), water (3×) and brine, dried over sodium sulfate, filtered and concentrated. The resulting white foam (9.9 g) was dissolved in dichloromethane (300 mL), treated with triethylsilane (12.44 g, 107 mmol, 17 mL) and trifluoroacetic acid (25 mL) and stirred for 2.5 h at room temperature. The reaction was concentrated in vacuo, dissolved in ethyl acetate, washed with saturated sodium bicarbonate solution and brine, dried over sodium sulfate, filtered and concentrated. The solid obtained was purified by flash chromatography on silica gel (1:1 ethyl acetate and hexanes) to provide 2.75 g (82%) of the title product as a white solid:

mp 154°–156° C.;

IR (KBr, cm$^{-1}$) 3416, 3291, 3118, 2234, 1638, 1547, 1315, 1108;

$^1$H NMR (300 MHZ, CDCl$_3$) δ7.23 (s, 1H), 5.19 (br s, 2H);

MS (FD) m/e 125 (M+);

UV (EtOH) 278 nm (ε=4359), 235 nm (ε=4047), 210 nm (ε=16728).

Anal. Calcd for C$_4$H$_3$N$_3$S: Theory: C, 38.39; H, 2.42; N, 33.57. Found: C, 38.65; H, 2.46; N, 33.24.

Example 17

N-(3-Phenylpropyl)-N'-(2-thiazolyl)thiourea

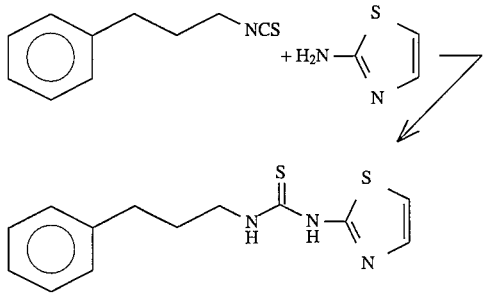

A solution of 3-phenylpropyl isothiocyanate (500 mg, 2.82 mmol) and 2-aminothiazole (300 mg, 3.0 mmol) in N,N-dimethylformamide (10 mL) was heated to 100° C. After 20 h, the reaction was cooled to room temperature and poured into ethyl acetate. The organic phase was washed with 1N hydrochloric acid, water (3×), and brine. The organic layer was dried over sodium sulfate, filtered and concentrated. The solid obtained was purified by flash chromatography on silica gel (1% ethyl acetate in dichloromethane) and then recrystallized from ethyl acetate to provide 129 mg of the title product. A second crop was recrystallized from 1:1 ethyl acetate/hexanes to provide another 110 mg of the title product. Total yield of the title product: 239 mg (30%) as an off-white solid. A sample was recrystallized again from ethyl acetate:

mp 126.5°–127.5° C.;

IR (KBr, cm$^{-1}$) 3166, 3022, 1574, 1523, 1502, 1215, 1166;

$^1$H NMR (300 MHZ, CDCl$_3$) δ10.88 (s, 1H), 10.42 (s, 1H), 7.37 –7.15 (m, 6H), 6.82 (d, J=3.6 Hz, 1H), 3.82 –3.71 (m, 2H), 2.74 (t, J=7.7 Hz, 2H), 2.12 –2.01 (m, 2H);

MS (FD) m/e 277 (M+);

UV (EtOH) 288 nm (ε=19598), 256 nm (ε=11329), 206 nm (ε=19259).

Anal. Calcd for C$_{13}$H$_{15}$N$_3$S$_2$: Theory: C, 56.29; H, 5.45; N, 15.15. Found: C, 56.29; H, 5.38; N, 15.00.

Example 18

N-(2-Phenethyl)-N'-[2-(6-ethoxybenzothiazolyl)]thiourea

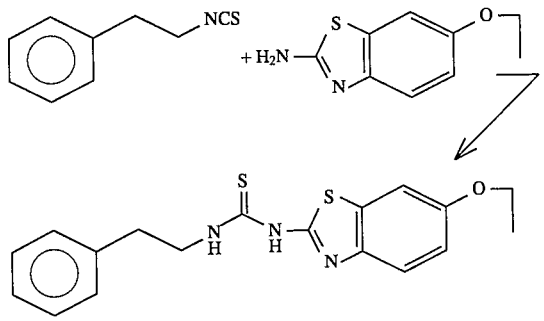

A solution of 2-phenethyl isothiocyanate (3.26 g, 20 mmol, 3.0 mL) and 2-amino-6-ethoxy-benzothiazole (3.88 g, 20 mmol) in N,N-dimethylformamide (50 mL) was heated to 100° C. After 20 h, the reaction was cooled to room temperature and poured into ethyl acetate. The organic phase was washed with 1N hydrochloric acid, saturated sodium bicarbonate solution, water (3×) and brine. The organic layer was dried over sodium sulfate, filtered and concentrated. The solid obtained was recrystallized from ethyl acetate to provide 649 mg (9%) of the title product as a tan solid:

mp 204–205° C.;

IR (KBr, cm$^{-1}$) 3166, 3022, 1574, 1523, 1502, 1435, 1215;

$^1$H NMR (300 MHZ, CDCl$_3$) δ11.01 (s, 1H), 9.77 (s, 1H), 7.43–6.95 (m, 8H), 4.08–4.01 (m, 4H), 3.06 (t, J=6.6 Hz, 2H), 1.43 (t, J=6.8 Hz, 3H);

MS (FD) m/e 357 (M+);

UV (EtOH) 312 nm (ε=23035), 251 nm (ε=11355), 204 nm (ε=26891).

Anal. Calcd for C$_{18}$H$_{19}$N$_3$OS$_2$: Theory: C, 60.48; H, 5.36; N, 11.75. Found: C, 60.2!; H, 5.10; N, 11.52.

Example 19

N-(2-Phenethyl)-N'-[2-(4-tert-butylthiazolyl)]thiourea

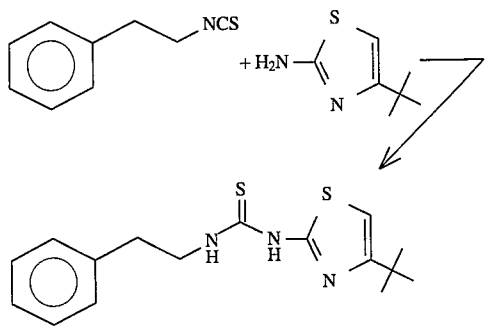

A solution off 2-phenethyl isothiocyanate (3.26 g, 20 mmol, 3.0 mL) and 2-amino-4-tert-butylthiazole (3.13 g, 20 mmol) in N,N-dimethylformamide (50 mL) was heated to 100° C. After 64 h, the reaction was cooled to room temperature and poured into ethyl acetate. The organic phase was washed with 1N hydrochloric acid, saturated sodium bicarbonate solution, water (2×) and brine. The organic layer was dried over sodium sulfate, filtered and concentrated. The solid obtained was recrystallized from ethyl acetate to provide 2.98 g (47%) of the title product as an off-white crystalline solid:

mp 173.5°–175° C.;

IR (KBr, cm$^{-1}$) 3173, 2960, 1576, 1514, 1465, 1348, 1204, $^1$H NMR (300 MHZ, CDCl$_3$) δ11.14 (s, 1H), 10.26 (s, 1H), 7.31–7.18 (m, 5H), 6.33 (s, 1H), 4.05–3.99 (m, 2H), 3.04 (t, J=7.1 Hz, 2H), 1.14 (s, 9H);

MS (FD) m/e 319 (M+);

UV (EtOH) 292 nm (ε=20804), 257 nm (ε=10502), 203 nm (ε=19085).

Anal. Calcd for C$_{16}$H$_{21}$N$_3$S$_2$: Theory: C, 60.15; H, 6.63; N, 13.15. Found: C, 59.95; H, 6.66; N, 13.15.

Example 20

N-(2-Phenethyl)-N'-[2-(4-trifluoromethylthiazolyl)]thiourea

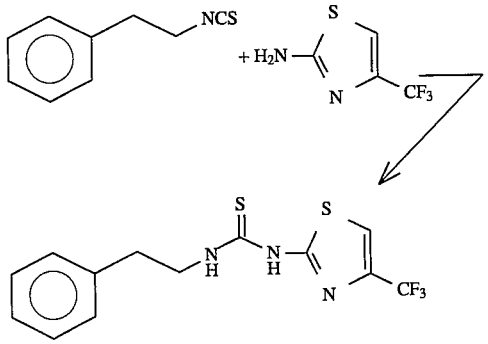

A solution of 2-phenethyl isothiocyanate (3.26 g, 20 mmol, 3.0 mL) and 2-amino-4-trifluoromethylthiazole (3.84 g, 22.8 mmol) in N,N-dimethyl-formamide (50 mL) was heated to 100° C. After 20 h, the reaction was cooled to room temperature and poured into ethyl acetate. The organic phase was washed with 1N hydrochloric acid, water (3×) and brine. The organic layer was dried over sodium sulfate, filtered and concentrated. The solid obtained was recrystallized from 1:1 ethyl acetate/hexanes to provide mg (13%) of the title product as a white solid:

mp 162°–163° C.;

IR (KBr, cm$^{-1}$) 3156, 3033, 1562, 1516, 1469, 1242, 1126;

$^1$H NMR (300 MHZ, CDCl$_3$) δ10.49 (s, 1H), 10.31 (s, 1H), 7.33–7.19 (m, 6H), 4.01–3.95 (m, 2H), 3.02 (t, J=6.9 Hz, 2H);

MS (FD) m/e 331 (M+);

UV (EtOH) 286 nm (ε=14352), 258 nm (ε=14149), 205 nm (ε=24571).

Anal. Calcd for C$_{13}$H$_{12}$F$_3$N$_3$S$_2$: Theory: C, 47.12; H, 3.65; N, 12.68. Found: C, 47.34; H, 3.85; N, 12.72.

Example 21

N-(2-Phenethyl)-N',N'-dimethyl thiourea

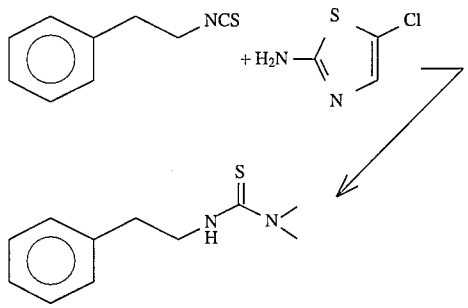

A solution of 2-phenethyl isothiocyanate (3.26 g, 20 mmol, 3.0 mL) and 2-amino-5-chlorothiazole (2.69 g, 20 mmol) in N,N-dimethylformamide (50 mL) was heated to 100° C. After 20 h, the reaction was cooled to room temperature and poured into ethyl acetate. The organic phase was washed with 1N hydrochloric acid and brine (3×). The organic layer was dried over sodium sulfate, filtered and concentrated. The solid obtained was purified by flash chromatography on silica gel (1% ethyl acetate in dichloromethane) and then recrystallized twice from ethyl acetate to provide 606 mg (14%) of the title product as an off-white crystalline solid:

mp 104.5°–105.5° C.;

IR (KBr, cm$^{-1}$) 3284, 1536, 1452, 1347, 901;

$^1$H NMR (300 MHZ, CDCl$_3$) δ7.33–7.19 (m, 5H), 5.37 (br s, 1H), 3.93–3.87 (m, 2H), 3.16 (s, 6H), 2.93 (t, J=6.8 Hz, 2H);

MS (FD) m/e 208 (M+);

UV (EtOH) 242 nm (ε=12899), 210 nm (ε=21286).

Anal. Calcd for C$_{11}$H$_{16}$N$_2$S: Theory: C, 63.42; H, 7.74; N, 13.45. Found: C, 63.39; H, 7.80; N, 13.67.

Example 22

N-(2-Phenyethyl)-N'-[2-(4-cyanothiazolyl)thiourea

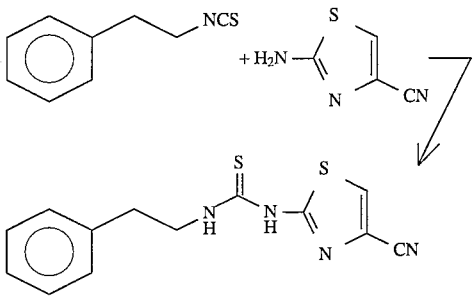

A solution of 2-phenethyl isothiocyanate (3.26 g, 20 mmol, 3.0 mL) and 2-amino-4-cyanothiazole (2.50 g, 20 mmol) in N,N-dimethylformamide (50 mL) was heated to 100° C. After 20 h, the reaction was cooled to room temperature and poured into ethyl acetate. The organic phase was washed with saturated sodium bicarbonate solution, water (3×), and brine. The organic layer was dried over sodium sulfate, filtered and concentrated. The solid obtained was purified by flash chromatography on silica gel (1% ethyl acetate in dichloromethane) and then recrystallized from 1:1 ethyl acetate/hexanes to provide 132 mg of the title product (2%) as a white solid:

mp 169°–1700° C.;

IR (KBr, cm$^{-1}$) 3166, 3022, 1574, 1523, 1502, 1215, 1166;

$^1$H NMR (300 MHZ, CDCl$_3$) δ10.88 (s, 1H), 10.09 (s, 1H), 7.50 (s, 1H), 7.39–7.23 (m, 5H), 4.00–3.93 (m, 2H), 3.02 (t, J=6.9 Hz, 2H);

MS (FD) m/e 288 (M+);

UV (EtOH) 288 nm (ε=11104), 258 nm (ε=17433), 208 nm (ε=31355).

Anal. Calcd for C$_{13}$H$_{12}$N$_4$S$_2$: Theory: C, 54.14; H, 4.19; N, 19.43. Found: C, 54.04; H, 4.23; N, 19.73.

Example 23

N-(2-Phenethyl)-N'-2-[4-(4-pyridyl)-thiazolyl]thiourea

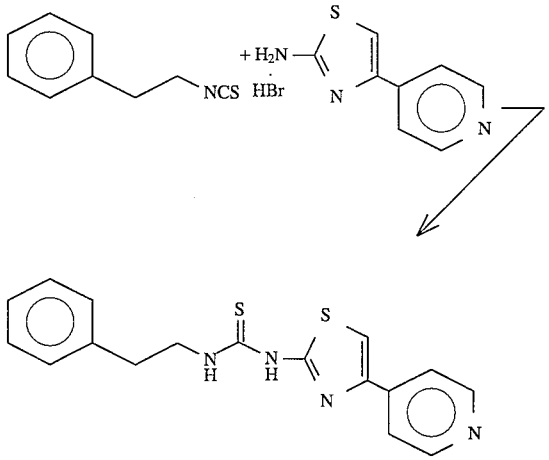

2-Amino-4-(4-pyridyl)thiazole hydrobromide[1,2] was slurried with methylene chloride and shaken with saturated sodium bicarbonate solution. The layers were separated and the aqueous washed with methylene chloride and ethyl acetate. The combined organic layers were concentrated. To the solid (1.0 g, 5.6 mmol) was added 2-phenethyl isothiocyanate (0.91 g, 5.6 mmol, 0.83 mL) in N,N-dimethylformamide (12.5 mL). The resulting suspension was heated to 100° C. After 20.5 h, the reaction was cooled to room temperature and poured into ethyl acetate. The organic phase was washed with water (4×) and brine. The organic layer was dried over sodium sulfate, filtered and concentrated. The resulting solid was recrystallized from ethyl acetate (3×) to provide 133 mg (7%) of the title product:

mp 196.5° C.;

IR (KBr, cm$^{-1}$) 3250, 2939, 1723, 1604, 1506, 1223, 670, 664;

$^1$H NMR (300 MHz, DMSO-$d_6$) δ11.72 (s, 1H), 9.21 (br s, 1H), 8.54 (d, J=6 Hz, 2H), 7.82 (s, 1H), 7.63 (d, J=6 Hz, 2H), 7.30–7.15 (m, 5H), 3.84–3.77 (m, 2H), 2.89 (t, J=7 Hz, 2H);

MS (FD) m/e 340 (M+);

HRMS (FAB) m/e (M+) calcd 341.0895, obs 341.0909;

UV (EtOH) 294 nm (ε=23935), 231 nm (ε=16356), 203 nm (ε=25793).

(1) Nielsen, A. T. and Platt, E. N. *Heterocyclic Chem.*, 1969, vol 6 p 896.
(2) Brown, Cowden, Grigg, Kavulak Aust. *J. Chem.* 1980, 33, 2291.

Example 24

N-(2-phenethyl)-N'-[2-(4-(4-biphenyl)-thiazolyl]thiourea

100° C. After 19.5 h, the reaction was cooled to room temperature and poured into ethyl acetate. The organic solution was washed with 1N hydrochloric acid. The mixture was filtered and the filtrate was separated and the organic phase washed with saturated sodium bicarbonate solution, water (4×) and brine. The organic layer was dried over sodium sulfate, filtered and concentrated. The material was purified by flash chromatography on silica gel (1% ethyl acetate in dichloromethane to 2% ethyl acetate in dichloromethane) to provide 372 mg of the title product (18%). The yellow solid was recrystallized from ethyl acetate:

mp 208.5°–209° C.;

IR (KBr, cm$^{-1}$) 3437, 3172, 3029, 1570, 1553, 1511, 1211, 1060, 738;

$^1$H NMR (300 MHz, DMSO-$d_6$) δ11.72 (s, 1H), 9.54 (br s, 1H), 7.86–7.80 (m, 2H), 7.78–7.68 (m, 4H), 7.58 (s, 1H), 7,52–7.44 (m, 2H), 7.41–7.35 (m, 1H), 7.34–7.29 (m, 4H), 7.27–7.20 (m, 1H), 3.92–3.84 (m, 2H), 2.98 (t, J=3 Hz, 2H);

MS (FD) m/e 415 (M+);

UV (EtOH) 293 nm, 212 nm.

Anal. Calcd for $C_{24}H_{21}N_3S_2$: Theory: C, 69.36; H, 5.09; N, 10.11. Found: C, 69.08; H, 5.10; N, 9.99.

Example 25

N-(2-Phenethyl)-N'-2-[4-(1-(1-ethyoxycarbonlyl)-(3-t-butoxycarbonylmethoxy)imino)-thiazolyl]thiourea

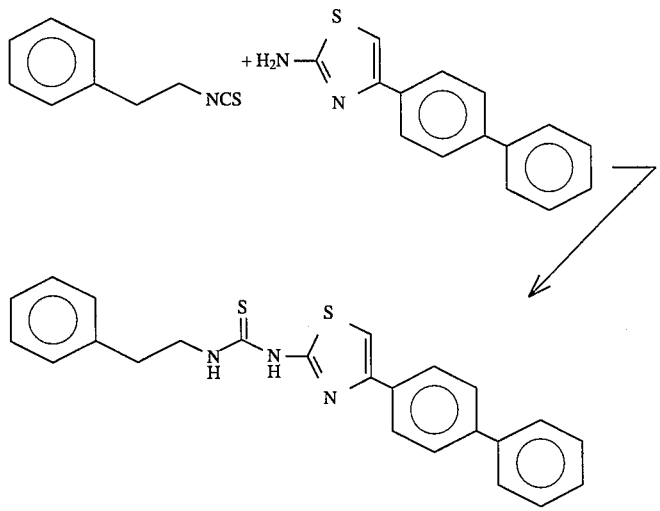

A solution of 2-phenethyl isothiocyanate (0.82 g, 5 mmol, 0.75 mL) and 2-amino-4-(4-biphenyl)thiazole (1.26 g, 5 mmol) in N,N-dimethylformamide (12.5 mL) was heated to

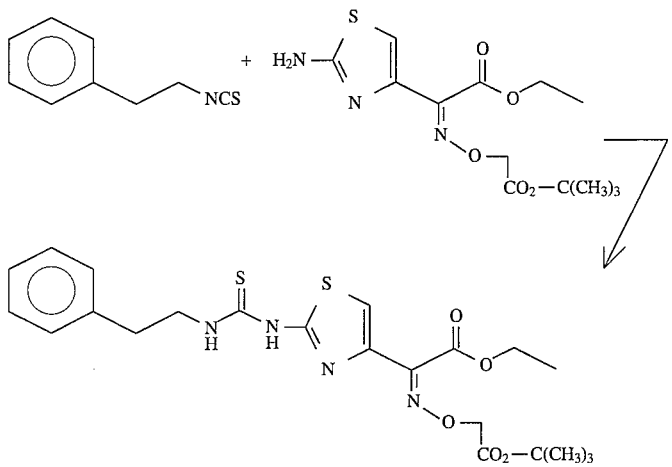

2-Amino-4-(1-(1-ethoxycarbonyl)-(3-t-butoxy-carbonyl-methoxy)imino)thiazole (2.64 g, 8 mmol) and 2-phenethyl isothiocyanate (1.31 g, 8 mmol, 1.2 mL) in N,N-dimethylformamide (20 mL) were heated to 100° C. After 24 h, the reaction was cooled to room temperature and poured into ethyl acetate. The organic phase was washed with 1N hydrochloric acid, saturated sodium bicarbonate solution, water (3x) and brine. The organic layer was dried over sodium sulfate, filtered and concentrated. The resulting solid was triturated with ethyl acetate to provide 801 mg (20%) of the title product:

mp 188.5° C.;

IR (KBr, cm$^{-1}$) 3293, 2975, 1749, 1594, 1543, 1453, 1382, 1231, 1154, 1054, 748, 698;

$^1$H NMR (300 MHz, DMSO-d$_6$) δ11.85 (s, 1H), 8.46 (br s,1H), 7.29–7.17 (m, 5H), 4.59 (s, 2H), 4.31–4.24 (q, J=7.1 Hz, 2H), 3.70–3.64 (m, 2H), 2.82 (t, J=7.1 Hz, 2H), 1.36 (s, 9H), 1.23 (t, J=7.1 Hz, 3H);

MS (FD) m/e 492 (M+);

UV (EtOH) 292 nm, 257 nm (ε=16356), 203 nm.

Anal. Calcd for C$_{22}$H$_{28}$N$_4$O$_5$S$_2$: Theory: C, 53.64; H, 5.73; N, 11.37. Found: C, 53.67; H, 5.83; N, 11.34.

Example 26

N-(2-Phenethyl)-N'-2-[4-t-butyl-5-methylthiazolyl]thiourea

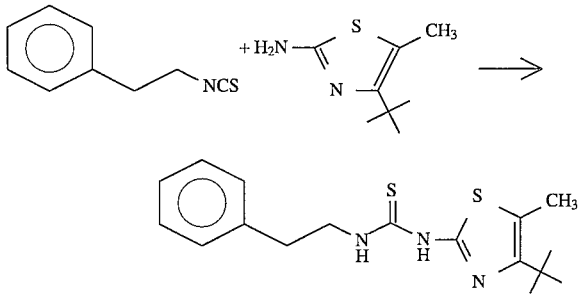

2-Amino-4-t-butyl-5-methylthiazole (1.87 g, 11 mmol) and 2-phenethyl isothiocyanate (1.80 g, 11 mmol, 1.64 mL) in N,N-dimethylformamide (25 mL) were heated to 100° C. After 18.5 h, the reaction was cooled to room temperature and poured into ethyl acetate. The organic phase was washed with 1N hydrochloric acid, saturated sodium bicarbonate solution, water (3x) and brine. The organic layer was dried over sodium sulfate, filtered and concentrated. The resulting solid was triturated with ether to provide 1.02 g (28%) of the title product:

mp 153°–153.5° C.;

IR (KBr, cm$^{-1}$) 3171, 2966, 1474, 1534, 1510, 1455, 1346, 1221, 1186, 755, 704;

$^1$H NMR (300 MHz, DMSO-d$_6$) δ11.28 (BR S, 1H), 9.90 (BR S, 1H), 7.28–7.14 (M, 5H), 3.78–3.34 (M, 2H), 2.84 (T, J=7 Hz, 2H), 2.27 (s, 3H), 1.16 (s, 9H);

MS (FD) m/e 333 (M+);

UV (EtOH) 297 nm (ε=19835), 257 nm (ε=9954), 202 nm (ε=21059).

Anal. Calcd for C$_{17}$H$_{23}$N$_3$S$_2$: Theory: C, 61.22; H, 6.95; N, 12.60. Found: C, 61.42; H, 6.92; N, 12.55.

Example 27

N-(2-Phenethyl)-N'-[5-methyl-[2-(1,3,4-thiadiazolyl)]]thiourea

A solution of 2-amino-5-methyl 1,3,4-thiadiazole (2.30 g, 20 mmol) and 2-phenethyl isothiocyanate (3.26 g, 20 mmol, 3.0 mL) in N,N-dimethylformamide (50 mL) was heated to 100° C. for 18 h. The reaction was cooled to room temperature and the solvent was removed in vacuo. The resultant solid was crystallized from ethyl acetate to provide 1.86 g (33%) of the title product as a white solid:

IR (KBr, cm$^{-1}$) 3323, 3031, 1640, 1540, 1444, 1385, 781, 697,652;

$^1$H NMR (300 MHz, DMSO-d$_6$) δ12.4 (br s, 1H), 8.75 (br s, 1H), 7.4–7.2 (m, 5H), 3.85–3.75 (m, 2H), 2.9 (t, J=7 Hz, 2H), 2.54 (s, 3H);

MS (FD) m/e 278 (M+);

UV (EtOH) 280 nm (ε=10188), 253 nm (ε=11849), 205 nm (ε=19724).

Example 28

N-(2-phenethyl)-N'-(2-pyridinyl)thiourea

A solution of 2-aminopyridine (1.90 g, 20 mmol) and 2-phenethyl isothiocyanate (3.26 g, 20 mmol, 3.0 mL) in N,N-dimethylformamide (50 mL) was heated to 120° C. for 40 h. The reaction was cooled to room temperature and the solvent was removed in vacuo. The resultant solid was recrystallized twice from ethyl acetate to provide 0.90 g (17%) of the title product as white needles:

IR (KBr, cm$^{-1}$) 3325, 1588, 1524, 1434, 1415, 1333, 1228, 1154, 797;

$^1$H NMR (300 MHz, DMSO-d$_6$) δ11.25 (br s, 1H), 10.65 (br s, 1H), 8.6 (d, J=5 HZ, 2H) 7.4–7.2 (m, 6H), 3.85–3.75 (m, 2H), 2.9 (t, J=7 Hz, 2H);

MS (FD) m/e 258 (M+);

UV (EtOH) 286 nm (ε=17644), 267 nm (ε=15834), 244 nm (ε=12312), 205 nm (ε=21839).

Anal. Calcd for C$_{13}$H$_{14}$N$_4$S: Theory: C, 60.44; H, 5.46; N, 21.69. Found: C, 60.15; H, 5.48; N, 21.89.

Example 29

N-(2-Phenethyl)-N'-[2-(4-(4-chlorophenyl)thiazolyl)]thiourea

A solution of 2-phenethyl isothiocyanate (0.77 g, 4.75 mmol) and 2-amino-4-(4-chlorophenyl)thiazole (1.0 g, 4.75 mmol) in N,N-dimethylformamide (10 mL) was heated to 120° C. 20 h. The solvent was removed in vacuo. The resultant solid was recrystallized from ethyl acetate to provide 0.30 g (17%) of the title product as a yellow solid:

IR (KBr, cm$^{-1}$) 3176, 3029, 1579, 1515, 1231, 737,698;

$^1$H NMR (300 MHz, DMSO-d$_6$) δ11.70 (br s, 1H), 9.40 (br s, 1H), 7.74–7.54 (m, 5H), 7.36–7.18 (m, 5H), 3.9–3.8 (m, 2H), 2.96 (t, J=6 Hz, 2H);

MS (FD) m/e 373 (M$^+$);

UV (EtOH) 273 nm (ε=35089), 247 nm (ε=21894), 202 nm (ε=22213).

Anal. Calcd for C$_{18}$H$_{16}$N$_3$S$_2$Cl: Theory: C, 57.82; H, 4.31; N, 11.24. Found: C, 57.55; H, 4.24; N, 11.26.

Example 30

N-(2-phenethyl)-N'-[2-(6-chloro)benzothiazolyl]thiourea

A solution of 2-phenethyl isothiocyanate (3.26 g, 20 mmol) and 2-amino-6-chlorobenzothiazole (3.69 g, 20 mmol) in N,N-dimethylformamide (50 mL) was heated to 120° C. for 24 h. The solvent was removed in vacuo. The resultant solid was recrystallized from ethyl acetate to provide 3.68 g (53%) of the title product as a white solid:

IR (KBr, cm$^{-1}$) 3165, 3021, 1574, 1522, 1501, 1289, 1215;

$^1$H NMR (300 MHz, CDCl$_3$) δ12.0 (br s, 1H), 9.8 (br s, 1H), 8.1–7.2 (m, 8H), 3.85 (m, 2H), 2.95 (t, J=7 Hz, 2H);

MS (FD) m/e 347 (M$^+$);

UV (EtOH) 304 nm, 292 nm, 248 nm, 220 nm, 205 nm.

Example 31

N-(2-Phenethyl)-N'-[5-ethyl-[2-(1,3,4-thiadiazolyl)]]thiourea

A solution of 2-amino-5-ethyl-1,3,4-thiadiazole (2.58 g, 20 mmol) and 2-phenethyl isothiocyanate (3.26 g, 0 mmol, 3.0 mL) in N,N-dimethylformamide (50 mL) was heated to 120° C. for 8 h. The reaction was cooled to room temperature and the solvent was removed in vacuo. The resultant solid was crystallized from ethyl acetate to provide 2.45 g (33%) of the title product as a white solid:

IR (KBr, cm$^{-1}$) 3317, 1645, 1536, 1448, 1384, 783,693, 651;

$^1$H NMR (300 MHz, DMSO-d$_6$) δ12.4 (br s, 1H), 8.75 (br s, 1H), 7.4–7.2 (m, 5H), 3.85–3.75 (m, 2H), 3.0–2.8 (m, 4H), 1.25 (t, J=7 Hz, 3H);

MS (FD) m/e 292 (M+);

UV (EtOH) 281 nm (ε=13028), 253 nm (ε=13615), 206 nm (ε=23674).

Example 32

N-(2-Phenethyl)-N'-[4-chlorophenyl]thiourea

A solution of 4-chloroaniline (2.55 g, 20 mmol) and 2-phenethyl isothiocyanate (3.26 g, 20 mmol, 3.0 mL) in N,N-dimethylformamide (50 mL) was heated to 120° C. for 18 h. The reaction was cooled to room temperature and the solvent was removed in vacuo. The resultant solid was crystallized from ethyl acetate to provide 1.50 g (26%) of the title product as a yellow solid:

IR (KBr, cm$^{-1}$) 3166, 3021, 1523, 1501, 1289, 1079, 802, 737,695;

$^1$H NMR (300 MHz, DMSO-d$_6$) δ9.6 (br s, 1H), 7.9 (br s, 1H), 7.5–7.2 (m, 9H), 3.8–3.65 (m, 2H), 3.0–2.8 (t, J=7 Hz, 2H);

MS (FD) m/e 290 (M+);

UV (EtOH) 270 nm (ε14107), 247 nm (ε=18128), 206 nm (ε=27795).

Anal. Calcd for C$_{15}$H$_{15}$N$_2$SCl: Theory: C, 61.95; H, 5.20; N, 9.63. Found: C, 62.19; H, 5.46; N, 9.87.

Example 33

N-(2-Phenethyl)-N'-[3-chlorophenyl]thiourea

A solution of 3-chloroaniline (2.55 g, 20 mmol) and 2-phenethyl isothiocyanate (3.26 g, 20 mmol, 3.0 mL) in N,N-dimethylformamide (50 mL) was heated to 120° C. for 20 h. The reaction was cooled to room temperature and the solvent was removed in vacuo. The resultant yellow oil was purified by HPLC on silica gel to provide 0.95 g (16%) of the title product as a white solid:

IR (KBr, cm$^{-1}$) 3310, 1591, 1542, 1495;

$^1$H NMR (300 MHz, DMSO-d$_6$) δ9.85 (br s, 1H), 7.9 (br s, 1H), 7.65–7.2 (m, 9H), 3.8–3.65 (m, 2H), 3.0–2.8 (t, J=7 Hz, 2H);

MS (FD) m/e 290 (M+);

UV (EtOH) 250 nm (ε=17296), 209 nm (ε=29630).

Anal. Calcd for C$_{15}$H$_{15}$N$_2$SCl: Theory: C, 61.95; H, 5.20; N, 9.63. Found: C, 61.65; H, 5.44; N, 9.84.

Example 34

N-(n-Propyl)-N'-[2-thiazoyl]thiourea

A solution of 2-aminothiazole (2.0 g, 20 mmol) and n-propyl isothiocyanate (2.0 g, 20 mmol) in dimethylformamide (50 mL) was heated to 120° C. for 20 h. The reaction was cooled to room temperature and the solvent was removed in vacuo. The resultant yellow oil was recrystallized twice from ethyl acetate to provide 0.42 g (10%) of the title product as a white solid:

IR (KBr, cm$^{-1}$) 3179, 1556, 1514, 1471, 680;

¹H NMR (300 MHz, DMSO-d₆) δ11.55 (br s, 1H), 9.7 (br s, 1H), 7.4 (d, J=5 Hz, 1H), 7.1 (d, J=5 Hz, 1H), 3.5 (m, 2H), 1.6 (m, 2H), 0.95 (t, J=7 Hz, 3H);

MS (FD) m/e 201 (M+);

UV (EtOH) 288 nm (ε=19469), 256 nm (ε=10151), 202 nm (ε=11550).

Anal. Calcd for $C_7H_{11}N_3S_2$: Theory: C, 41.77; H, 5.51; N, 20.87. Found: C, 42.02; H, 5.61; N, 20.93.

Example 35

N-(2-phenethyl)-N'-[2-(4,5,6,7-tetrahydrobenzothiazolyl)]thiourea

A solution of 2-phenethyl isothiocyanate (1.63 g, 10 mmol) and 2-amino-4,5,6,7-tetrahydrobenzothiazole (1.54 g, 10 mmol) in N,N-dimethylformamide (25 mL) was heated to 120° C. for 48 h. The solvent was removed in vacuo. The resultant solid was recrystallized from ethyl acetate to provide 0.32 g (11%) of the title product as a white solid:

IR (KBr, cm⁻¹) 3165, 3021, 2923, 1601, 1529, 1501, 1261, 1225;

¹H NMR (300 MHz, DMSO-d₆) δ11.5 (br s, 1H), 10.0 (br s, 1H), 7.4–7.2 (m, 5H), 3.85 (m, 2H), 2.95 (t, J=7 Hz, 2H), 2.6–2.4 (m, 4H), 1.75 (m, 4H);

MS (FD) m/e 317 (M⁺);

UV (EtOH) 299 nm (ε=11440), 258 nm (ε=6011), 207 nm (ε=10579).

Example 36

N-(2-phenethyl)-N'-[2-benzothiazolyl]thiourea

A solution of 2-phenethyl isothiocyanate (3.26 g, 20 mmol, 3.0 mL) and 2-aminobenzothiazole (3.0 g, 20 mmol) in toluene (50 mL) was heated to reflux. After 5 h, the reaction was cooled to room temperature and poured into ethyl acetate, washed with water, 1N aqueous HCl, water, saturated sodium bicarbonate, and brine. The organic layer was concentrated and the residue recrystallized from ethyl acetate to provide 1.8 g (29%) of the title product:

mp 203°–207° C.;

IR (KBr, cm⁻¹) 3181, 3045, 1697, 1557, 1523, 1451, 1440, 1244, 749;

¹H NMR (300 MHz, CDCl₃/DMSO-d₆) δ11.7 (br s, 1H), 10.6 (br s, 1H), 7.8–7.2 (m, 9H), 3.95 (m, 2H), 3.05 (t, J=7 Hz, 2H);

MS (FD) m/e 313 (M⁺);

UV (EtOH) 300 nm (ε=24241), 207 nm (ε=28964).

Anal. Calcd for $C_{16}H_{15}N_3S_2$: Theory: C, 61.31; H, 4.82; N, 13.41. Found: C, 61.03; H, 4.67; N, 13.19.

Example 37

N-(2-phenethyl)-N'-[2-(4-methyl)benzothiazolyl]thiourea

A solution of 2-phenethyl isothiocyanate (3.26 g, 20 mmol, 3.0 mL) and 2-amino-4-methylbenzothiazole (3.3 g, 20 mmol) in toluene (50 mL) was heated to reflux. After 5 h, the reaction was cooled t6 room temperature and poured into ethyl acetate, washed with water, 1N aqueous HCl, water, saturated sodium bicarbonate, and brine. The organic layer was concentrated and the residue recrystallized from ethyl acetate to provide 1.68 g (26%) of the title product:

mp 185°–188° C.;

IR (KBr, cm⁻¹) 3170, 3024, 1571, 1525, 1219, 767, 742, 698;

¹H NMR (300 MHz, CDCl₃/DMSO-d₆) δ11.4 (br s, 1H), 10.9 (br s, 1H), 7.6–7.1 (m, 8H), 4.05 (m, 2H), 3.05 (t, J=7 Hz, 2H), 2.37 (s, 3H);

MS (FD) m/e 327 (M⁺);

UV (EtOH) 303 nm (ε=27416), 204 nm (ε=30294).

Anal. Calcd for $C_{17}H_{17}N_3S_2$: Theory: C, 62.35; H, 5.23; N, 12.83.

Found: C, 62.56; H, 5.37; N, 12.77.

Example 38

N-(2-phenethyl)-N'-[2-(4-methoxy)benzothiazolyl]thiourea

A solution of 2-phenethyl isothiocyanate (3.26 g, 20 mmol, 3.0 mL) and 2-amino-4-methoxybenzothiazole (3.2 g, 20 mmol) in N,N-dimethylformamide (20 mL) was heated at 115° C. for 24 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 0.97 g (14%) of the title product:

mp 205°–207° C.;

IR (KBr, cm⁻¹) 3165, 3021, 1574, 1522, 1215, 736, 695, 655;

¹H NMR (300 MHz, DMSO-d₆) δ12.4 (br s, 1H), 9.9 (br s, 1H), 7.6–7.0 (m, 8H), 3.9 (s, 1H), 3.85 (m, 2H), 2.95 (t, J=7 Hz, 2H);

MS (FD) m/e 343 (M⁺);

UV (EtOH) 293 nm (ε=20046), 248 nm (ε=15731), 210 nm (ε=38172).

Example 39

N-(2-phenethyl)-N'-[2-(4-chloro)benzothiazolyl]thiourea

A solution of 2-phenethyl isothiocyanate (3.26 g, 20 mmol, 3.0 mL) and 2-amino-4-chlorobenzothiazole (3.7 g, 20 mmol) in N,N-dimethylformamide (20 mL) was heated at 115° C. for 24 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 2.56 g (37%) of the title product:

mp 216°–217° C.;

IR (KBr, cm⁻¹) 3166, 2940, 1568, 1527, 766, 733, 673;

¹H NMR (300 MHz, DMSO-d₆) δ12.2 (br s, 1H), 9.3 (br s, 1H), 7.6–7.0 (m, 8H), 3.85 (m, 2H), 2.95 (t, J=7 Hz, 2H);

MS (FD) m/e 347 (M⁺);

UV (EtOH) 301 nm (ε=20231), 249 nm (ε=17615), 211 nm (ε=31440).

Example 40

N-(2-Phenethyl)-N'-[3-(1,2,4-triazolyl)]thiourea

A solution of 3-amino-1,2,4-triazole (1.70 g, 20 mmol) and 2-phenethyl isothiocyanate (3.26 g, 20 mmol, 3.0 mL) in N,N-dimethylformamide (20 mL) was heated to 115° C. for 24 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 0.99 g (20%) of the title product:

mp 160°–162° C.;

IR (KBr, cm$^{-1}$) 3160, 3061, 2872, 1581, 1535, 1467, 1167, 977, 743, 681;

$^1$H NMR (300 MHz, DMSO-d$_6$) δ13.9 (br s, 1H), 10.85 (br s, 1H), 10.0 (br s, 1H), 7.4–7.2 (m, 6H), 3.85 (m, 2H), 2.95 (t, J=7 Hz, 2H);

MS (FD) m/e 247 (M$^+$);

UV (EtOH) 261 nm (ε=21785), 229 nm (ε=11918), 206 nm (ε=17437).

Anal. Calcd for C$_{11}$H$_{13}$N$_5$S: Theory: C, 53.42 H, 5.30; N, 28.32. Found: C, 53.69; H, 5.50; N, 28.07.

Example 41

N-(2-Phenethyl)-N'-[3-quinolinyl]thiourea

A solution of 3-aminoquinoline (2.90 g, 20 mmol) and 2-phenethyl isothiocyanate (3.26 g, 20 mmol, 3.0 mL) in N,N-dimethylformamide (20 mL) was heated to 90° C. for 72 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 3.62 g (59%) of the title product:

mp 162°–164° C.;

IR (KBr, cm$^{-1}$) 3143, 1537, 1493, 1350, 1283, 1239, 749, 705;

$^1$H NMR (300 MHz, DMSO-d$_6$) δ9.9 (br s, 1H), 8.87 (d, J=4 Hz), 1H), 8.35 (br s, 1H), 8.0 (d, J=8 Hz, 1H), 7.9 (d, J=8 Hz, 1H), 7.7–7.2 (m, 8H), 3.8 (m, 2H), 2.95 (t, J=7 Hz, 2H);

MS (FD) m/e 308 (M$^+$);

UV (EtOH) 331 nm (ε=5945), 257 nm (ε=27215), 247 nm (ε=28319), 212 nm (ε=37613).

Example 42

N-(2-Phenethyl)-N'-[2-(4-methyl)pyrimidine]thiourea

A solution of 2-aminopyridine (1.90 g, 20 mmol) and 2-phenethyl isothiocyanate (3.26 g, 20 mmol, 3.0 mL) in N,N-dimethylformamide (20 mL) was heated to 115° C. for 24 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 1.21 g (22%) of the title product:

mp 174°–176° C.;

IR (KBr, cm$^{-1}$) 3184, 3034, 1561, 1409, 1344, 1291, 1165, 1030, 836, 792;

$^1$H NMR (300 MHz, DMSO-d$_6$) δ11.3 (br s, 1H), 10.45 (br s, 1H), 8.4 (d, J=5 Hz, 2H) 7.4–7.2 (m, 5H), 7.0 (d, J=5 Hz, 1H), 3.85–3.75 (m, 2H), 2.9 (t, J=7 Hz, 2H), 2.3 (s, 3H);

MS (FD) m/e 272 (M+);

UV (EtOH) 274 nm (ε=25263), 248 nm (ε=15528), 203 nm (ε=17107).

Anal. Calcd for C$_{14}$H$_{16}$N$_4$S: Theory: C, 61.74; H, 5.92; N, 20.57. Found: C, 61.44; H, 6.11; N, 20.38.

Example 43

N-(2-phenethyl)-N'-[2-(4-(4-fluorophenyl))thiazolyl]thiourea

A solution of 2-phenethyl isothiocyanate (1.63 g, 10 mmol ), triethylamine (1.01 g, 10 mmol), and 2-amino-4-(4-fluorophenyl)thiazole hydroiodide (3.2 g, 10 mmol) in N,N-dimethylformamide (20 mL) was heated to 100° C. for 24 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 1.06 g (30%) of the title product:

mp 224°–228° C.;

IR (KBr, cm$^{-1}$) 3178, 3030, 1553, 840, 737, 670;

$^1$H NMR (300 MHz, DMSO-d$_6$) δ11.70 (br s, 1H), 9.50 (br s, 1H), 7.8–7.2 (m, 10H), 3.90–3.81 (m, 2H), 2.95 (t, J=6 Hz, 2H);

MS (FD) m/e 357 (M$^+$);

UV (EtOH) 282 nm (ε=15755), 264 nm (ε=17277), 239 nm (ε=13046), 209 nm (ε=18271).

Anal. Calcd for C$_{18}$H$_{16}$N$_3$S$_2$F: Theory: C, 60.42; H, 4.48; N, 11.74. Found: C, 60.79; H, 4.48; N, 11.63.

Example 44

N-(2-phenethyl)-N'-[2-(4-thiazolylacetic acid]thiourea methyl ester

A solution of 2-phenethyl isothiocyanate (0.82 g, 5 mmol) and 2-aminothiazoleacetic acid methyl ester (0.85 g, 5 mmol) in N,N-dimethylformamide (20 mL) was heated to 100° C. for 72 h, the reaction was cooled to room temperature and poured into ethyl acetate, washed with water, 1N aqueous HCl, water, saturated sodium bicarbonate, and brine. The organic layer was concentrated and the residue recrystallized from ethyl acetate to provide 0.52 g (31% ) of the title product:

mp 125°–127° C.;

IR (KBr, cm$^{-1}$) 3168, 3085, 1740, 1557, 1524,;

$^1$H NMR (300 MHz, DMSO-d$_6$) δ11.6 (br s, 1H), 9.4 (br s, 1H), 7.4–7.2 (m, 5H), 6.85 (s, 1H), 3.8 (m, 2H), 3.65 (s, 2H), 3.6 (s, 3H), 2.9 (t, J=7 Hz, 2H);

MS (FD) m/e 335 (M$^+$);

UV (EtOH) 291 nm (ε=19133), 258 nm (ε=10917), 202 nm (ε=21433).

Anal. Calcd for C$_{15}$H$_{17}$N$_3$S$_2$O$_2$: Theory: C, 53.71; H, 5.11; N, 12.53. Found: C, 53.96; H, 5.16; N, 12.79.

Example 45

N-(2-phenethyl)-N'-[2-thiazolyl]thiourea

A solution of 2-phenethyl isothiocyanate (7.5 g, 45.9 mmol) and 2-aminothiazole (4.6 g, 45.9 mmol) in N,N-dimethylformamide (100 mL) was heated at 115° C. for 12 h. The reaction was cooled to room temperature, poured into ethyl acetate, washed with water, 1N aqueous HCl, water, saturated sodium bicarbonate, and brine. The organic layer was concentrated and the residue recrystallized twice from ethyl acetate to provide 5.7 g (47%) of the title product:

IR (KBr, cm$^{-1}$) 3187, 3033, 2978, 1569, 1515, 1470, 1454, 1216, 1170, 1063;

¹H NMR (300 MHz, DMSO-d₆) δ11.6 (br s, 1H), 9.7 (br s, 1H), 7.4–7.2 (m, 6H), 7.1 (d, J=3 Hz, 1H), 3.8 (m, 2H), 2.9 (t, J=7 Hz, 2H);

MS (FD) m/e 263 (M⁺);

UV (EtOH) 288 nm (ε=19656), 257 nm (ε=11658), 203 nm (ε=20054).

Anal. Calcd for $C_{12}H_{13}N_3S_2$: Theory: C, 54.72 H, 4.97; N, 15.95. Found: C, 54.63; H, 5.02; N, 15.85.

Example 46

N-(2-[1-cyclohexenyl]ethyl)-N'-[2-thiazolyl]thiourea

A solution of 2-(1-cyclohexenyl)ethyl isothiocyanate (3.3 g, 20 mmol) and 2-aminothiazole (2.0 g, 20 mmol) in N,N-dimethylformamide (20 mL) was heated at 100° C. for 24 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 2.66 g (50%) of the title product:

mp 147°–148° C.;

IR (KBr, cm⁻¹) 3170, 3118, 2989, 1566, 1513, 1180, 706;

¹H NMR (300 MHz, DMSO-d₆) δ11.6 (br s, 1H), 9.7 (br s, 1H), 7.38 (d, J=3 Hz, 1H), 7.1 (d, J=3 Hz, 1H), 5.45 (br s, 1H), 3.65 (m, 2H), 2.25 (t, J=7 Hz, 2H), 1.9 (m, 4H), 1.5 (m, 4H);

MS (FD) m/e 267 (M⁺);

UV (EtOH) 288 nm (ε=19663), 256 nm (ε=10534), 201 nm (ε=14819).

Anal. Calcd for $C_{12}H_{13}N_3S_2$: Theory: C, 53.89 H, 6.41; N, 15.71. Found: C, 54.15; H, 6.52; N, 15.84.

Example 47

N-(2-phenethyl)-N'-[2-(4-thiazolylacetic acid]thiourea ethyl ester

A solution of 2-phenethyl isothiocyanate (3.62 g, 20 mmol) and 2-aminothiazoleacetic acid ethyl ester (3.72 g, 20 mmol) in N,N-dimethylformamide (20 mL) was heated to 100° C. for 24 h, the reaction was cooled to room temperature and poured into ethyl acetate, washed with water, 1N aqueous HCl, water, saturated sodium bicarbonate, and brine. The organic layer was concentrated and the residue was purified by HPLC on silica gel to provide 1.7 g (24%) of the title product:

mp 80°–83° C.;

IR (KBr, cm⁻¹) 3184, 3109, 1730, 1580, 704,;

¹H NMR (300 MHz, DMSO-d₆) δ11.6 (br s, 1H), 9.4 (br s, 1H), 7.4–7.2 (m, 5H), 6.85 (s, 1H), 4.1 (q, J=7 Hz, 2H), 3.8 (m, 2H), 3.65 (s, 2H), 2.9 (t, J=7 Hz, 2H), 1.2 (t, J=7 Hz, 3H);

MS (FD) m/e 349 (M⁺);

UV (EtOH) 291 nm (ε=15025), 250 nm (ε=10893), 203 nm (ε=24071).

Anal. Calcd for $C_{16}H_{19}N_3S_2O_2$: Theory: C, 54.99; H, 5.48; N, 12.02. Found: C, 55.24; H, 5.62; N, 11.96.

Example 48

N-(2-phenethyl)-N'-[2-(4-thiazolylacetic acid]thiourea

A solution of N-(2-phenethyl)-N'-[2-(4-thiazolylacetic acid]thiourea ethyl ester (0.7 g, 2.0 mmol) and 1N NaOH (2.5 mL, 2.5 mmol) in 50 mL of 1/1 acetonitrile-water was stirred at room temperature for 24 h. The reaction was poured into ethyl acetate and washed with saturated sodium bicarbonate. The aqueous layer was acidified to pH 2 with 1N HCl and extracted with ethyl acetate. The organic extracts were washed with brine and concentrated. The residue was crystallized from ethyl acetate to provide 0.29 g (45%) of the title product:

mp 188°–190° C.;

IR (KBr, cm⁻¹) 3200–2800 (br), 1659, 1586, 1377, 671,;

¹H NMR (300 MHz, DMSO-d₆) δ12.0 (br s, 2H), 9.6 (br s, 1H), 7.4–7.2 (m, 5H), 6.85 (s, 1H), 3.8 (m, 2H), 3.65 (s, 2H), 2.9 (t, J=7 Hz, 2H);

MS (FD) m/e 322 (M⁺);

UV (EtOH) 291 nm (ε=19464), 257 nm (ε=10601), 202 nm (ε=20396).

Anal. Calcd for $C_{14}H_{15}N_3S_2O_2$: Theory: C, 52.32; H, 4.70; N, 13.07. Found: C, 52.58; H, 4.88; N, 13.34.

Example 49

N-(benzyl)-N'-[2-thiazolyl]thiourea

A solution of benzyl isothiocyanate (1.5 g, 10 mmol) and 2-aminothiazole (1.0 g, 10 mmol) in N,N-dimethylformamide. (25 mL) was heated at 100° C. for 12 h. The reaction was cooled to room temperature, poured into ethyl acetate, washed with water, 1N aqueous HCl, water, saturated sodium bicarbonate, and brine. The organic layer was concentrated and the residue recrystallized twice from ethyl acetate to provide 1.15 g (46%) of the title product:

mp 165°–167° C.;

IR (KBr, cm⁻¹) 3171, 3038, 1560, 1509, 1451, 1183, 972, 691;

¹H NMR (300 MHz, DMSO-d₆) δ11.7 (br s, 1H), 9.9 (br s, 1H), 7.4–7.2 (m, 6H), 7.05 (d, J=3 Hz, 1H), 4.8 (m, 2H);

MS (FD) m/e 249 (M⁺);

UV (EtOH) 289 nm (ε=19103), 257 nm (ε=12196), 204 nm (ε=21328).

Anal. Calcd for $C_{11}H_{11}N_3S_2$: Theory: C, 52.99 H, 4.47; N, 16.85. Found: C, 53.09; H, 4.50; N, 16.77.

Example 50

N-(2-Phenethyl)-N'-(2-pyrazinyl)thiourea

A solution of 2-aminopyrazine (1.90 g, 20 mmol) and 2-phenethyl isothiocyanate (3.26 g, 20 mmol, 3.0 mL) in N,N-dimethylformamide (50 mL) was heated to 100° C. for 17 h. The reaction was cooled to room temperature, poured into ethyl acetate, washed with water, 1N aqueous HCl, water, saturated sodium bicarbonate, and brine. The organic layer was concentrated and the residue recrystallized twice from ethyl acetate to provide 0.95 g (18%) of the title product:

mp 142°–143° C.;

IR (KBr, cm⁻¹) 3181, 3049, 1606, 1533, 1472, 1314, 1221, 862, 725;

¹H NMR (300 MHz, DMSO-d₆) δ11.02 (br s, 1H), 10.95 (br s, 1H), 8.5 (s, 1H), 8.18 (d, J=2 Hz, 1H), 8.05 (d, J=2 Hz, 1H), 7.4–7.2 (m, 5H), 3.85–3.75 (m, 2H), 2.9 (t, J=7 Hz, 2H);

MS (FD) m/e 258 (M+);

UV (EtOH) 318 nm (ε=10579), 263 nm (ε=17922), 202 nm (ε=15887).

Anal. Calcd for $C_{13}H_{14}N_4S$: Theory: C, 60.44; H, 5.46; N, 21.69. Found: C, 60.45; H, 5.63; N, 22.02.

Example 51

N-(2-Phenethyl)-N'-(3-pyrazolyl)thiourea

A solution of 3-aminopyrazole (1.66 g, 20 mmol) and 2-phenethyl isothiocyanate (3.26 g, 20 mmol, 3.0 mL) in N,N-dimethylformamide (50 mL) was heated to 100° C. for 18.5 h. The reaction was cooled to room temperature, poured into ethyl acetate, washed with water, 1N aqueous HCl, water, saturated sodium bicarbonate, and brine. The organic layer was concentrated and the residue recrystallized twice from ethyl acetate to provide 2.38 g (48%) of the title product:

mp 142°–144° C.;

IR (KBr, cm$^{-1}$) 3397, 3207, 3078, 1576, 1537, 1255, 1182, 751;

$^1$H NMR (300 MHz, DMSO-d$_6$) δ12.4 (br s, 1H), 10.35 (br s, 1H), 9.85 (br s, 1H), 7.6 (s, 1H), 7.4–7.2 (m, 5H), 5.83 (s, 1H), 3.75 (m, 2H), 2.85 (t, J=7 Hz, 2H);

MS (FD) m/e 246 (M+);

UV (EtOH) 264 nm (ε=21473), 204 nm (ε=17842).

Anal. Calcd for $C_{12}H_{14}N_4S$: Theory: C, 58.51; H, 5.73; N, 22.74. Found: C, 58.80; H, 5.83; N, 23.00.

Example 52

Preparation of N-(2-Phenethyl)-N'-(phenyl)thiourea

A solution of aniline (1.86 g, 20 mmol) and 2-phenethyl isothiocyanate (3.26 g, 20 mmol, 3.0 mL) in N,N-dimethylformamide (50 mL) was heated to 100° C. for 18 h. The reaction was cooled to room temperature, poured into ethyl acetate, washed with water, 1N aqueous HCl, water, saturated sodium bicarbonate, and brine. The organic layer was concentrated and the residue recrystallized from ethyl ether/hexanes to provide 2.88 g (56%) of the title product:

mp 102°–104° C.;

IR (KBr, cm$^{-1}$) 3375, 1592, 1542, 1493, 1250, 1000, 695;

$^1$H NMR (300 MHz, CDCl$_3$) δ7.85 (br s, 1H), 7.5–7.0 (m, 10H), 6.0 (br s, 1H), 3.9 (m, 2H), 2.9 (t, J=7 Hz, 2H);

MS (FD) m/e 256 (M+);

UV (EtOH) 248 nm (ε=15081), 206 nm (ε=25573).

Anal. Calcd for $C_{15}H_{16}N_2S$: Theory: C, 70.28; H, 6.29; N, 10.93. Found: C, 70.14; H, 6.37; N, 10.97.

Example 53

N-(ethyl)-N'-(2-thiazolyl)thiourea

A solution of ethyl isothiocyanate (1.74 g, 20 mmol) and 2-aminothiazole (2.0 g, 20 mmol) in N,N-dimethylformamide (50 mL) was heated at 100° C. for 23 h. The reaction was cooled to room temperature, poured into ethyl acetate, washed with water, 1N aqueous HCl, water, saturated sodium bicarbonate, and brine. The organic layer was concentrated and the residue recrystallized twice from ethyl acetate to provide 0.48 g (13%) of the title product:

mp 135°–136° C.;

IR (KBr, cm$^{-1}$) 3165, 3021, 1574, 1501, 1435, 1366, 1215, 1179, 695;

$^1$H NMR (300 MHz, DMSO-d$_6$) δ10.4 (br s, 2H), 7.4 (d, J=3 Hz, 1H), 6.8 (d, J=3 Hz, 1H), 3.7 (m, 2H), 1.4 (t, J=7 Hz, 3H);

MS (FD) m/e 187 (M$^+$);

UV (EtOH) 287 nm (ε=19544), 256 nm (ε=10213), 202 nm (ε=11588).

Anal. Calcd for $C_6H_9N_3S_2$: Theory: C, 38.48 H, 4.84; N, 22.44. Found: C, 38.71; H, 4.92; N, 22.66.

Example 54

N-(2-Phenethyl)-N'-(2-chlorophenyl)thiourea

A solution of 2-chloroaniline (2.55 g, 20 mmol) and 2-phenethyl isothiocyanate (3.26 g, 20 mmol, 3.0 mL) in N,N-dimethylformamide (50 mL) was heated to 100° C. for 17 h. The reaction was cooled to room temperature, poured into ethyl acetate, washed with water, 1N aqueous HCl, water, saturated sodium bicarbonate, and brine. The organic layer was concentrated and the residue was purified by HPLC on silica gel to provide 1.18 g (20%) of the title product as a white solid:

IR (KBr, cm$^{-1}$) 3378, 3167, 1540, 1499, 1470, 1250, 1060, 758, 685;

$^1$H NMR (300 MHz, DMSO-d$_6$) δ7.55 (br s, 1H), 7.5–7.2 (m, 9H), 5.9 (br s, 1H), 3.9 (m, 2H), 2.9 (t, J=7 Hz, 2H);

MS (FD) m/e 290 (M+);

UV (EtOH) 245 nm (ε=16042), 209 nm (ε=29276).

Anal. Calcd for $C_{15}H_{15}N_2SCl$: Theory: C, 61.95; H, 5.20; N, 9.63. Found: C, 61.69; H, 5.28; N, 9.84.

Example 55

N-(benzyl)-N'-[2-(5-chloro)thiazolyl]thiourea

A solution of benzyl isothiocyanate (3.0 g, 20 mmol) and 2-amino-5-chlorothiazole (2.69 g, 20 mmol) in N,N-dimethylformamide (25 mL) was heated at 100° C. for 20 h. The reaction was cooled to room temperature, poured into ethyl acetate, washed with water, 1N aqueous HCl, water, saturated sodium bicarbonate, and brine. The organic layer was concentrated and the residue purified by HPLC on silica gel to provide 0.86 g (15%) of the title product:

mp 162°–164° C.;

IR (KBr, cm$^{-1}$) 3154, 3003, 2958, 1588, 1515, 1421, 1231, 1192, 726;

$^1$H NMR (300 MHz, DMSO-d$_6$) δ8.8 (br s, 1H), 7.45 (s 1H), 7.4–7.2 (m, 5H), 4.7 (m, 2H);

MS (EI) m/e 283 (M$^+$);

UV (EtOH) 295 nm (ε=6457), 259 nm (ε=5741), 208 nm (ε=11042).

Example 56

N-(3-Phenylpropyl)-N'-[2-(5-chloro)thiazolyl]thiourea

A solution of 3-phenylpropyl isothiocyanate (3.54 g, 20 mmol) and 2-amino-5-chlorothiazole (2.69 g, 20 mmol) in N,N-dimethylformamide (50 mL) was heated to 100° C. After 18 h, the reaction was cooled to room temperature, poured into ethyl acetate, washed with water, 1N aqueous HCl, water, saturated sodium bicarbonate, and brine. The organic layer was concentrated and the residue purified by HPLC on silica gel to provide 0.29 g (5%) of the title product:

mp 121°–130° C.;

IR (KBr, cm$^{-1}$) 3160, 3100, 2949, 1565, 1517, 1493, 698;

$^1$H NMR (300 MHZ, DMSO-d$_6$) δ10.8 (s, 1H), 8.5 (br s, 1H), 7.4 (s, 1H), 7.3 (m, 5H), 3.5 (m, 2H), 2.6 (t, J=7.7 Hz, 2H), 1.8 (m, 2H);

MS (FD) m/e 311 (M+);

UV (EtOH) 295 nm (ε=14069), 259 nm (ε=12092), 205 nm (ε=27316).

Anal. Calcd for C$_{13}$H$_{14}$N$_3$S$_2$Cl: Theory: C, 50.07; H, 4.52; N, 13.47. Found: C, 50.17; H, 4.51; N, 13.42.

Example 57

N-(2-Phenethyl)-N'-(5-tetrazolyl)thiourea

A solution of 5-aminotetrazole monohydrate (2.06 g, 20 mmol) and 2-phenethyl isothiocyanate (3.26 g, 20 mmol, 3.0 mL) in N,N-dimethylformamide (50 mL) was heated to 100° C. for 21 h. The reaction was cooled to room temperature, poured into ethyl acetate, washed with water, 1N aqueous HCl, water, saturated sodium bicarbonate, and brine. The organic layer was concentrated and the residue recrystallized twice from ethyl acetate to provide 0.59 g (12%) of impure title product:

mp 161°–177° C.;

IR (KBr, cm$^{-1}$) 3451, 3235, 3148, 1547, 1511, 1169, 697;

$^1$H NMR (300 MHz, DMSO-d$_6$) δ10.8 (s, 1H), 10.4 (m, 1H), 8.6 (br s, 1H), 7.2–7.0 (m, 5H), 3.8 (m, 2H), 2.8 (t, J=7 Hz, 2H);

MS (FD) m/e 248 (M+);

UV (EtOH) 258 nm (ε=13630), 234 nm (ε=15631), 204 nm (ε=15594).

Example 58

N-(2-phenethyl)-N'-[2-(4-methyl-5-acetyl)thiazolyl]thiourea

A solution of 2-phenethyl isothiocyanate (1.14 g, 7 mmol) and 2-amino-4-methyl-5-acetylthiazole (1.09 g, 7 mmol) in N,N-dimethylformamide (50 mL) was heated at 100° C. for 23 h. The reaction was cooled to room temperature, poured into ethyl acetate, washed with water, 1N aqueous HCl, water, saturated sodium bicarbonate, and brine. The organic layer was concentrated and the residue recrystallized twice from ethyl acetate to provide 0.21 g (9%) of the title product:

IR (KBr, cm$^{-1}$) 3314, 3060, 1694, 1610, 1555, 1507, 1372, 1233, 980, 667;

$^1$H NMR (300 MHz, DMSO-d$_6$) δ12.5(br s, 1H), 8.8 (br s, 1H), 7.4–7.2 (m, 5H), 3.8 (m, 2H), 2.9 (t, J=7 Hz, 2H) 2.4 (s, 3H), 2.3 (s, 3H);

MS (FD) m/e 319 (M+);

UV (EtOH) 319 nm (ε=16944), 230 nm (ε=13216), 201 nm (ε=18476).

Example 59

N-(2-Phenethyl)-N'-[2-(6-chloro)pyrazinyl]thiourea

A solution of 2-amino-6-chloropyrazine (2.59 g, 20 mmol) and 2-phenethyl isothiocyanate (3.26 g, 20 mmol, 3.0 mL) in N,N-dimethylformamide (50 mL) was heated to 100° C. for 35 h. The reaction was cooled to room temperature, poured into ethyl acetate, washed with water, 1N aqueous HCl, water, saturated sodium bicarbonate, and brine. The organic layer was concentrated and the residue purified by HPLC on silica gel to provide 0.23 g (4%) of the title product:

mp 194°–195° C.;

IR (KBr, cm$^{-1}$) 3171, 2932, 1575, 1517, 1465, 1359, 1270, 1169, 707;

$^1$H NMR (300 MHz, DMSO-d$_6$) δ11.2 (s, 1H), 10.2 (br s, 1H), 8.5 (s, 1H), 8.3 (s, 1H), 7.4–7.2 (m, 5H), 3.85–3.75 (m, 2H), 2.9 (t, J=7 Hz, 2H);

MS (FD) m/e 292 (M+);

UV (EtOH) 328 nm (ε=12858), 265 nm (ε=17945), 201 nm (ε=17746).

Example 60

N-(2-phenbutyl)-N'-[2-thiazolyl]thiourea

A solution of 2-phenbutyl isothiocyanate (3.8 g, 20 mmol) and 2-aminothiazole (2.0 g, 20 mmol) in N,N-dimethylformamide (50 mL) was heated at 100° C. for 26 h. The reaction was cooled to room temperature, poured into ethyl acetate, washed with water, 1N aqueous HCl, water, saturated sodium bicarbonate, and brine. The organic layer was concentrated and the residue recrystallized from ethyl ether to provide 2.3 g (39%) of the title product:

mp 105°–107° C.

IR (KBr, cm$^{-1}$) 3171, 2932, 1575, 1517, 1465, 1359, 1169, 1064, 707;

$^1$H NMR (300 MHz, DMSO-d$_6$) δ11.5 (br s, 1H), 9.7 (br s, 1H), 7.4–7.1 (m, 7H), 3.6 (m, 2H), 2.6 (m, 2H), 1.6 (m, 4H);

MS (FD) m/e 291 (M+);

UV (EtOH) 288 nm (ε=19013), 256 nm (ε=10681), 203 nm (ε=18908).

Anal. Calcd for C$_{14}$H$_{17}$N$_3$S$_2$: Theory: C, 57.70; H, 5.88; N, 14.42. Found: C, 57.60; H, 6.08; N, 14.56.

Example 61

N-(2-Phenethyl)-N'-[2-(4-(3-nitro)phenyl)thiazoly]thiourea

A solution of 2-phenethyl isothiocyanate (0.74 g, 4.5 mmol) and 2-amino-4-[(3-nitro)phenyl]-thiazole (1.0 g, 4.5 mmol) in N,N-dimethylformamide (50 mL) was heated to 100° C. for 120 h. The reaction was cooled to room temperature, poured into ethyl acetate, washed with water, 1N aqueous HCl, water, saturated sodium bicarbonate, and brine. The organic layer was concentrated and the residue purified by HPLC on silica gel to provide 0.07 g (4%) of the title product:

mp 192°–196° C.;

IR (KBr, cm$^{-1}$) 3165, 3023, 1571, 1517, 1352, 1217, 1166;

$^1$H NMR (300 MHz, DMSO-d$_6$) δ11.7 (br s, 1H), 9.0 (br s, 1H), 8.6 (s, 1H), 8.2 (m, 2H), 7.75 (s, 1H), 7.6 (t, J=6 Hz, 1H), 7.4–7.2 (m, 5H), 3.8 (m, 2H), 2.95 (t, J=6 Hz, 2H);

MS (FD) m/e 384 (M+);

UV (EtOH) 286 nm (ε=21349), 264 nm (ε=22766), 237 nm (ε=18307), 202 nm (ε=28514).

Anal. Calcd for C$_{18}$H$_{16}$N$_4$S$_2$O$_2$: Theory: C, 56.23; H, 4.19; N, 14.57. Found: C, 56.12; H, 4.24; N, 14.47.

Example 62

N-(n-Propyl)-N'-[2-(5-chlorothiazolyl)]thiourea

A solution of 2-amino-5-chlorothiazole (2.69 g, 20 mmol) and n-propyl isothiocyanate (2.0 g, 20 mmol) in N,N-dimethylformamide (50 mL) was heated to 100° C. for 19 h. The reaction was cooled to room temperature, poured into ethyl acetate, washed with water, 1N aqueous HCl, water, saturated sodium bicarbonate, and brine. The organic layer was concentrated and the residue purified by HPLC on silica gel to provide 0.17 g (4%) of the title product:

mp 128°–133° C.;

IR (KBr, cm$^{-1}$) 3170, 2958, 1560, 1487, 1187, 691;

$^1$H NMR (300 HHz, DMSO-d$_6$) δ11.5 (br s, 1H), 8.4 (br s, 1H), 7.4 (s 1H), 3.4 (m, 2H), 1.6 (m, 2H), 0.95 (t, J=7 Hz, 3H);

MS (FD) m/e 235 (M+);

UV (EtOH) 294 nm (ε=12928), 259 nm (ε=10257), 204 nm (ε=16979).

Anal. Calcd for C$_7$H$_{10}$N$_3$S$_2$Cl: Theory: C, 35.66; H, 4.28; N, 19.82. Found: C, 35.85; H, 4.19; N, 19.78.

Example 63

N-(2-Phenethyl) -N'-[2-(4-(2',2'-diphenyl-2'-cyano)ethyl)thiazolyl]thiourea

A solution of 2-amino(4-(2',2'-diphenyl-2'-cyano)ethyl)thiazole (0.91 g, 3 mmol) and 2-phenethyl isothiocyanate (0.49 g, 3 mmol ) in N,N-dimethylformamide (50 mL) was heated to 100° C. for 91 h. The reaction was cooled to room temperature, poured into ethyl acetate, washed with water, 1N aqueous HCl, water, saturated sodium bicarbonate, and brine. The organic layer was concentrated and the residue purified by HPLC on silica gel to provide 0.28 g (20%) of the title product:

IR (KBr, cm$^{-1}$) 3179, 3024, 2238, 1562, 1250, 698;

$^1$H NMR (300 MHz, DMSO-d$_6$) δ11.5 (s, 1H), 10.4 (br s, 1H), 7.5–7.2 (m, 15H), 6.6 (s, 1H), 3.85 (s, 2H), 3.8 (m, 2H), 2.8 (t, J=7 Hz, 2H);

MS (FD) m/e 468 (M$^+$);

UV (EtOH) 292 nm (ε=12023), 259 nm (ε=5862), 202 nm (ε=25516).

Anal. Calcd for C$_{27}$H$_{24}$N$_4$S$_2$: Theory: C, 69.20; H, 5.16; N, 11.95. Found: C, 69.05; H, 5.33; N, 11.76.

Example 64

N-(2-[1-cyclohexenyl]ethyl)-N'-[2-benzothiazolyl]thiourea

A solution of 2-(1-cyclohexenyl)ethyl isothiocyanate (3.3 g, 20 mmol) and 2-aminobenzothiazole (3.0 g, 20 mmol) in N,N-dimethylformamide (50 mL) was heated at 100° C. for 17.5 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 2.57 g (40%) of the title product:

mp 185°–186° C.;

IR (KBr, cm$^{-1}$) 3179, 3044, 2921, 2830, 1556, 1523, 1441, 1196;

$^1$H NMR (300 MHz, DMSO-d$_6$) d 11.8 (br s, 1H), 10.2 (br s, 1H), 8.0–7.2 (m, 4H), 5.45 (s, 1H), 3.65 (m, 2H), 2.3 (t, J=7 Hz, 2H), 1.9 (m, 4H), 1.5 (m, 4H);

MS (FD) m/e 317 (M$^+$);

UV (EtOH) 287 nm (ε=20679), 201 nm (ε=25939).

Anal. Calcd for C$_{16}$H$_{19}$N$_3$S$_2$: Theory.: C, 60.53; H, 6.03; N, 13.24. Found: C, 60.29; H, 5.94; N, 13.49.

Example 65

N-(2-phenethyl)-N'-[2-(4-ethyl)thiazolyl]thiourea

A solution of 2-phenethyl isothiocyanate (1.63 g, 10 mmol) and 2-amino-4-ethylthiazole (1.28 g, 10 mmol) in N,N-dimethylformamide (50 mL) was heated at 100° C. for 23 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 0.84 g (29%) of the title product:

mp 145°–146° C.;

IR (KBr, cm$^{-1}$) 3199, 3049, 2962, 1591, 1275, 685;

$^1$H NMR (300 MHz, DMSO-d$_6$) δ11.5 (br s, 1H), 9.8 (br s, 1H), 7.4–7.2 (m, 5H), 6.6 (s, 1H), 3.8 (m, 2H), 2.9 (t, J=7 Hz, 2H), 2.45 (q, J=7 Hz, 2H), 1.1 (t, J=7 Hz, 3H);

MS (FD) m/e 291 (M$^+$);

UV (EtOH) 292 nm (ε=19382), 257 nm (ε=10362), 202 nm (ε=20282).

Anal. Calcd for C$_{14}$H$_{17}$N$_3$S$_2$: Theory: C, 57.70; H, 5.88; N, 14.42. Found: C, 57.47; H, 5.91; N, 14.51.

Example 66

1-[(2-benzothiazolyl)thiocarbamoyl]imidazole

A solution of 1,1'-thiocarbonyldiimidazole (8.9 g, 50 mmol) and 2-aminobenzothiazole (7.5 g, 50 mmol) in acetonitrile (125 mL) was stirred at room temperature for 20 h. The resulting precipitate was collected by filtration to provide 5.75 g (44%) of the title product:

IR (KBr, cm$^{-1}$) 3199, 3049, 2962, 1628, 1461, 738;

$^1$H NMR (300 MHz, DMSO-d$_6$) δ8.85 (s, 1H), 8.1 (br s, 1H), 7.9–7.0 (m, 6H);

MS (FD) m/e 261 (M$^+$);

UV (EtOH) 366 nm (ε=13072), 305 nm (ε=11556), 213 nm (ε=35893).

Anal. Calcd for C$_{11}$H$_8$N$_4$S$_2$: Theory: C, 50.75; H, 3.10; N, 21.52. Found: C, 50.50; H, 3.02; N, 21.49.

Example 67

N-[2-(2-chlorophenyl)ethyl]-N'-[2-benzothiazolyl]thiourea

A solution of 1-[(2-benzothiazolyl)thiocarbamoyl]imidazole (2.1 g, 8 mmol) and 2-(2-chlorophenyl)-ethylamine (1.25 g, 8 mmol) in N,N-dimethylformamide (30 mL) was stirred at 100° C. for 1.5 h, the reaction was cooled to room temperature and the solvent removed in vacuo. The residue was crystallized from ethyl acetate to provide 1.6 g (57%) of the title product:

IR (KBr, cm$^{-1}$) 3181, 3050, 1587, 1527, 1231, 753;

$^1$H NMR (300 MHz, DMSO-d$_6$) δ11.9 (br s, 1H), 10.0 (br s, 1H), 7.8–7.2 (m, 8H), 3.95 (m, 2H), 3.1 (t, J=7 Hz, 2H);

MS (FD) m/e 347 (M$^+$);

UV (EtOH) 301 nm (ε=23050), 202 nm (ε=30924).

Example 68

N-[2-(3-chlorophenyl)ethyl]-N'-[2-benzothiazolyl]thiourea

A solution of 1-[(2-benzothiazolyl)thiocarbamoyl]imidazole (1.04 g, 4 mmol) and 2-(3-chlorophenyl)ethylamine (0.63 g, 4 retool) in N,N-dimethylformamide (15 mL) was stirred at 100° C. for 1 h, the reaction was cooled to room temperature and the solvent removed in vacuo. The residue was crystallized from ethyl acetate to provide 0.88 g (63%) of the title product:

IR (KBr, cm$^{-1}$) 3180, 2997, 1569, 1527, 1209, 755;

$^1$H NMR (300 MHz, DMSO-d$_6$) δ11.9 (br s, 1H), 10.1 (br s, 1H), 7.8–7.2 (m, 8H), 3.9 (m, 2H), 3.0 (t, J=7 Hz, 2H);

MS (FD) m/e 347 (M$^+$);

UV (EtOH) 301 nm (ε=25367), 202 nm (ε=31735).

Anal. Calcd for C$_{16}$H$_{14}$N$_3$S$_2$Cl: Theory: C, 55.24; H, 4.06; N, 12.08. Found: C, 55.05; H, 4.05; N, 12.03.

Example 69

N-[2-(4-chlorophenyl)ethyl]-N'-[2-benzothiazolyl]thiourea

A solution of 1-[(2-benzothiazolyl)thiocarbamoyl]imidazole (1.04 g, 4 mmol) and 2-(4-chlorophenyl)ethylamine (0.63 g, 4 mmol) in N,N-dimethylformamide (15 mL) was stirred at 100° C. for 1 h, the reaction was cooled to room temperature and the solvent removed in vacuo. The residue was crystallized from ethyl acetate to provide 0.89 g (64%) of the title product:

IR (KBr, cm$^{-1}$) 3180, 2997, 1569, 1527, 1257, 755;

$^1$H NMR (300 MHz, DMSO-d$_6$) δ12.0 (br s, 1H), 10.0 (br s, 1H), 7.9–7.2 (m, 8H), 3.85 (m, 2H), 2.95 (t, J=7 Hz, 2H);

MS (FD) m/e 347 (M$^+$);

UV (EtOH) 301 nm (ε=25731), 218 nm (ε=29376), 202 nm (ε=28033).

Anal. Calcd for C$_{16}$H$_{14}$N$_3$S$_2$Cl: Theory: C, 55.24; H, 4.06; N, 12.08. Found: C, 55.27; H, 4.02; N, 12.10.

Example 70

N-[2-(2-methoxyphenyl)ethyl]-N'-[2-benzothiazolyl]thiourea

A solution of 1-[(2-benzothiazolyl)thiocarbamoyl]imidazole (1.04 g, 4 mmol) and 2- (2-methoxyphenyl)ethylamine (0.62 g, 4 mmol) in N,N-dimethylformamide (15 mL) was stirred at 100° C. for 1 h, the reaction was cooled to room temperature and the solvent removed in vacuo. The residue was crystallized from ethyl acetate to provide 0.9 g (66%) of the title product:

IR (KBr, cm$^{-1}$) 3180, 1672, 1539, 1437, 1202, 1137, 783;

$^1$H NMR (300 MHz, DMSO-d$_6$) δ12.0 (br s, 1H), 10.0 (br s, 1H), 7.9–7.0 (m, 8H), 3.85 (m, 2H), 3.75 (s, 3H), 2.9 (t, J=7 Hz, 2H);

MS (FD) m/e 343 (M$^+$);

UV (EtOH) 301 nm (ε=25894), 218 nm (ε=28357), 202 nm (ε=32552).

Anal. Calcd for C$_{17}$H$_{17}$N$_3$OS$_2$: Theory: C, 59.45; H, 4.99; N, 12.23. Found: C, 59.70; H, 5.01; N, 11.99.

Example 71

N-[2-(3-methoxyphenyl)ethyl]-N'-[2-benzothiazolyl]thiourea

A solution of 1-[(2-benzothiazolyl)thiocarbamoyl]imidazole (1.04 g, 4 mmol) and 2-(3-methoxyphenyl)ethyl-amine (0.62 g, 4 mmol) in N,N-dimethylformamide (15 mL) was stirred at 100° C. for 1 h, the reaction was cooled to room temperature and the solvent removed in vacuo. The residue was crystallized from ethyl acetate to provide 0.77 g (56%) of the title product:

IR (KBr, cm$^{-1}$) 3180, 1670, 1543, 1479, 1205, 1136, 718;

$^1$H NMR (300 MHz, DMSO-d$_6$) δ11.9 (br s, 1H), 10.05 (br s, 1H), 7.9–6.8 (m, 8H), 3.87 (m, 2H), 3.75 (s, 3H), 2.95 (t, J=7 Hz, 2H);

MS (FD) m/e 343 (M$^+$);

UV (EtOH) 301 nm (ε=24893), 216 nm (ε=28250), 203 nm (ε=33504).

Anal. Calcd for C$_{17}$H$_{17}$N$_3$OS$_2$: Theory: C, 59.45; H, 4.99; N, 12.23. Found: C, 59.36; H, 5.02; N, 12.00.

Example 72

N-[2-(4-methoxyphenyl)ethyl]-N'-[2-benzothiazolyl]thiourea

A solution of 1-[(2-benzothiazolyl)thiocarbamoyl]imidazole (1.04 g, 4 mmol) and 2-(4-methoxyphenyl)ethylamine (0.62 g, 4 mmol) in N,N-dimethylformamide (15 mL) was stirred at 100° C. for 1 h, the reaction was cooled to room temperature and the solvent removed in vacuo. The residue was crystallized from ethyl acetate to provide 0.85 g (62%) of the title product:

IR (KBr, cm$^{-1}$) 3162, 1610, 1572, 1255, 1208, 1106, 761;

$^1$H NMR (300 MHz, DMSO-d$_6$) δ11.9 (br s, 1H), 10.05 (br s, 1H), 7.9–6.8 (m, 8H), 3.85 (m, 2H), 3.75 (s, 3H), 2.9 (t, J=7 Hz, 2H);

MS (FD) m/e 343 (M$^+$);

UV (EtOH) 301 nm (ε=22113), 218 nm (ε=23878), 201 nm (ε=28098).

Anal. Calcd for C$_{17}$H$_{17}$N$_3$OS$_2$: Theory: C, 59.45; H, 4.99; N, 12.23. Found: C, 59.33; H, 5.06; N, 12.04.

Example 73

1-[(2-[4,5-dimethyl]thiazolyl)thiocarbamoyl]imidazole

A solution of 1,1'-thiocarbonyldiimidazole (1.8 g, 10 mmol), 2-amino-4,5-dimethylthiazole hydrochloride (1.65 g, 10 mmol) and triethylamine (1.01 g, 10 mmol) in acetonitrile (40 mL) was stirred at room temperature for 7 h. The solvent was removed in vacuo to afford crude of the title product as a yellow solid used in the next step without purification.

Example 74

N-[2-(2-chlorophenyl)ethyl]-N'-[2-(4,5-dimethyl)thiazolyl]thiourea

A solution of 1-[(2-[4,5-dimethyl]thiazolyl)thio-carbamoyl]imidazole (10 mmol) and 2-(2-chlorophenyl)-ethylamine (1.55 g, 10 mmol) in N,N-dimethylformamide (30 mL) was stirred at 90° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 2.1 g (65%) of the title product:

IR (KBr, cm$^{-1}$) 3171, 3013, 1583, 1549, 1510, 1216, 759;

$^1$H NMR (300 MHz, DMSO-d$_6$) δ11.45 (br s, 1H), 9.75 (br s, 1H), 7.5–7.2 (m, 4H), 3.85 (m, 2H), 3.05 (t, J=7 Hz, 2H), 2.2 (s, 3H), 2.05 (s, 3H);

MS (FD) m/e 325 (M$^+$);

UV (EtOH) 297 nm (ε=9209), 257 nm (ε=5133), 201 nm (ε=14635).

Example 75

N-[2-(3-chlorophenyl)ethyl]-N'-[2-(4,5-dimethyl)thiazolyl]thiourea

A solution of 1-[(2-[4,5-dimethyl]thiazolyl)thio-carbamoyl]imidazole (10 mmol) and 2-(3-chlorophenyl)ethylamine (1.55 g, 10 mmol in N,N-dimethylformamide (30 mL) was stirred at 90° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 2.2 g (67%) of the title product:

IR (KBr, cm$^{-1}$) 3182, 3018, 1584, 1549, 1511, 1215, 788;

$^1$H NMR (300 MHz, DMSO-d$_6$) δ11.45 (br s, 1H), 9.8 (br s, 1H), 7.4–7.2 (m, 4H), 3.85 (m, 2H), 2.9 (t, J=7 Hz, 2H), 2.2 (s, 3H), 2.05 (s, 3H);

MS (FD) m/e 325 (M$^+$);

UV (EtOH) 297 nm (ε=6543), 257 nm (ε=3650).

Anal. Calcd for C$_{14}$H$_{16}$N$_3$S$_2$Cl: Theory: C, 51.60; H, 4.95; N, 12.89. Found: C, 51.73; H, 4.99; N, 13.16.

Example 76

N-[2-(2-methoxythenyl)ethyl]-N'-[2-(4,5-dimethyl)thiazolyl]thiourea

A solution of 1-[(2-[4,5-dimethyl]thiazolyl)thio-carbamoyl]imidazole (47) (10 mmol) and 2-(2-methoxyphenyl)ethylamine (1.51 g, 10 mmol) in N,N-dimethylformamide (30 mL) was stirred at 90° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 1.9 g (65%) of the title product:

mp 178°–180° C.;

IR (KBr, cm$^{-1}$) 3175, 2998, 1598, 1495, 1213, 760, 707;

$^1$H NMR (300 MHz, DMSO-d$_6$) δ11.4 (br s, 1H), 9.75 (br s, 1H), 7.25–6.8 (m, 4H), 3.8 (s, 3H), 3.78 (m, 2H), 2.87 J=7 Hz, 2H), 2.2 (s, 3H), 2.05 (s, 3H);

MS (FD) m/e 321 (M$^+$);

UV (EtOH) 297 nm (ε=18573), 258 nm (ε=10587), 202 nm (ε=28862).

Anal. Calcd for C$_{15}$H$_{19}$N$_3$OS$_2$: Theory: C, 56.04; H, 5.96; N, 13.09. Found: C, 56.29; H, 6.19; N, 13.27.

Example 77

N-[2-(3-methoxyphenyl)ethyl]-N'-[2-(4,5-dimethyl)thiazolyl]thiourea

A solution of 1-[(2-[4,5-dimethyl]thiazolyl)thiocarbamoyl]imidazole (10 mmol) and 2-(3-methoxyphenyl)ethylamine (1.51 g, 10 mmol) in N,N-dimethylformamide (30 mL) was stirred at 90° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 2.2 g (69%) of the title product:

mp 146°–148° C.;

IR (KBr, cm$^{-1}$) 3179, 3035, 1587, 1551, 1214, 701, 682;

$^1$H NMR (300 MHz, DMSO-d$_6$) δ11.45 (br s, 1H), 9.8 (br s, 1H), 7.25–6.8 (m, 4H), 3.8 (m, 2H), 3.75 (s, 3H), 2.85 (t, J=7 Hz, 2H), 2.2 (s, 3H), 2.05 (s, 3H);

MS (FD) m/e 321 (M$^+$);

UV (EtOH) 297 nm (ε=16992), 258 nm (ε=9639), 202 nm (ε=27993).

Anal. Calcd for C$_{15}$H$_{19}$N$_3$OS$_2$: Theory: C, 56.04; H, 5.96; N, 13.09. Found: C, 56.01; H, 5.96; N, 13.30.

Example 78

N-[2-(4-methoxyphenyl)ethyl]-N'-[2-(4,5-dimethyl)thiazolyl]thiourea

A solution of 1-[(2-[4,5-dimethyl]thiazolyl)thiocarbamoyl]imidazole (10 mmol) and 2-(4-methoxyphenyl)ethylamine (1.51 g, 10 mmol) in N,N-dimethylformamide (30 mL) was stirred at 90° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 2.2 g (69%) of the title product:

mp 178°–180° C.;

IR (KBr, cm$^{-1}$) 3174, 3024, 1590, 1552, 1214, 688;

$^1$H NMR (300 MHz, DMSO-d$_6$) δ11.45 (br s, 1H), 9.8 (br s, 1H), 7.2(d, J=8 Hz, 2H), 6.85 (d, J=8 Hz, 2H), 3.78 (m, 2H), 3.75 (s, 3H), 2.85 (t, J=7 Hz, 2H), 2.2 (s, 3H), 2.05 (s, 3H);

MS (FD) m/e 321 (M$^+$);

UV (EtOH) 297 nm (ε=8102), 258 nm (ε=4813), 223 nm (ε=6614).

Example 79

N-(2-phenethyl)-N'-(5-[3-methyl]isothiazolyl)thiourea

A solution of 2-phenethyl isothiocyanate (3.26 g, 20 mmol, 3.0 mL) and 5-amino-3-methylisothiazole (3.0 g, 20 mmol) in N,N-dimethylformamide (30 mL) was heated at 100° C. 24 h, the reaction was cooled to room temperature and poured into ethyl acetate, washed with water, 1N aqueous HCl, water, saturated sodium bicarbonate, and brine. The organic layer was concentrated and the residue recrystallized from ethyl acetate to provide 5.5 g (100%) of the title product:

mp 213°–216° C.;

IR (KBr, cm$^{-1}$) 3188, 2744, 1593, 1525, 1495, 1423, 1313, 1248, 829, 777, 752, 705, 670, 522;

$^1$H NMR (300 MHz, DMSO-d$_6$) δ9.3 (br s, 1H), 7.4–7.2 (m, 5H), 6.85 (br s, 1H), 3.7(m, 2H), 2.9 (t, J=7 Hz, 2H), 2.45 (s, 3H);

MS (FD) m/e 278 (M$^+$);

UV (EtOH) 286 nm (ε=12263), 247 nm (ε=14257), 206 nm (ε=27381).

Example 80

1-[(2-[6-fluoro]benzothiazolyl)thiocarbamoyl]imidazole

A solution of 1,1'-thiocarbonyldiimidazole (17.8 g, 100 mmol) and 2-amino-6-fluorobenzothiazole (16.8 g, 100 mmol) in acetonitrile (700 mL) was stirred at room temperature for 20 h, then at 40° C. for 6 h. The resulting precipitate was collected by filtration to provide 19.5 g (70%) of the title product:

IR (KBr, cm$^{-1}$) 3200, 3050, 2558, 1595, 1560, 1461, 1331, 1216, 1088, 1040, 948, 740, 648, 627;

$^1$H NMR (300 MHz, DMSO-d$_6$) δ12.0 (br s, 1H), 8.85 (s, 1H), 8.1 (br s, 1H), 7.9–7.0 (m, 4H);

MS (FD) m/e 279 (M$^+$H);

UV (EtOH) 364 nm (ε=7372), 306 nm (ε=13593), 213 nm (ε=31325).

Anal. Calcd for C$_{11}$H$_7$N$_4$S$_2$F: Theory: C, 47.47; H, 2.54; N, 20.13. Found: C, 47.72; H, 2.66; N, 20.09.

Example 81

N-[2-(2-chlorophenyl)ethyl]-N'-(2-[6-fluoro]benzothiazolyl)thiourea

A solution of 1-[(2-[6-fluoro]benzothiazolyl)thio-carbamoyl]imidazole (2.1 g, 8 mmol) and 2-(2-chlorophenyl)ethylamine (1.25 g, 8 mmol) in N,N-dimethylformamide (30 mL) was stirred at 100° C. for 1.5 h, the reaction was cooled to room temperature and the solvent removed in vacuo. The residue was crystallized from ethyl acetate to provide 1.6 g (57%) of the title product:

mp 188°–189° C.;

IR (KBr, cm$^{-1}$) 3166, 3014, 1560, 1538, 1460, 1217, 1198, 853;

$^1$H NMR (300 MHz, DMSO-d$_6$) δ11.6 (br s, 1H), 9.8 (br s, 1H), 7.9–7.2 (m, 7H), 3.9 (m, 2H), 3.1 (t, J=7 Hz, 2H);

MS (FD) m/e 365 (M$^+$);

UV (EtOH) 301 nm (ε=22535), 216 nm (ε=27344), 201 nm (ε=28624).

Anal. Calcd for C$_{16}$H$_{13}$N$_3$S$_2$ClF: Theory: C, 52.53; H, 3.58; N, 11.49. Found: C, 52.79; H, 3.72; N, 11.76.

Example 82

N-[2-(3-chlorophenyl)ethyl]-N'-(2-[6-fluoro]benzothiazolyl)thiourea

A solution of 1-[(2-[6-fluoro]benzothiazolyl)thiocarbamoyl]imidazole (2.1 g, 8 mmol) and 2-(3-chlorophenyl)ethylamine (1.25 g, 8 mmol) in N,N-dimethylformamide (30 mL) was stirred at 100° C. for 1.5 h, the reaction was cooled to room temperature and the solvent removed in vacuo. The residue was crystallized from ethyl acetate to provide 1.6 g (57%) of the title product:

mp 193°–194° C.;

IR (KBr, cm$^{-1}$) 3171, 3015, 1557, 1526, 1460, 1229, 1201, 866;

$^1$H NMR (300 MHz, DMSO-d$_6$) d 11.9 (br s, 1H), 9.9 (br s, 1H), 7.9–7.2 (m, 7H), 3.85 (m, 2H), 3.0 (t, J=7 Hz, 2H);

MS (FD) m/e 365 (M$^+$);

UV (EtOH) 301 nm (ε=24232), 217 nm (ε=30020), 201 nm (ε=31875).

Anal. Calcd for C$_{16}$H$_{13}$N$_3$S$_2$ClF: Theory: C, 52.53; H, 3.58; N, 11.49. Found: C, 52.50; H, 3.67; N, 11.38.

Example 83

N-[2-(4-chlorophenyl)ethyl]-N'-(2-[6-fluoro]benzothiazolyl)thiourea

A solution of 1-[(2-[6-fluoro]benzothiazolyl)thio-carbamoyl]imidazole (2.1 g, 8 mmol) and 2-(4-chlorophenyl)ethylamine (1.25 g, 8 mmol) in N,N-dimethylformamide (30 mL) was stirred at 100° C. for 1.5 h, the reaction was cooled to room temperature and the solvent removed in vacuo. The residue was crystallized from ethyl acetate to provide 1.6 g (57%) of the title product:

mp 217°–218° C.;

IR (KBr, cm$^{-1}$) 3168, 3033, 1559, 1532, 1491, 1462, 1230, 1143, 809;

$^1$H NMR (300 MHz, DMSO-d$_6$) d 11.85 (br s, 1H), 9.8 (br s, 1H), 7.9–7.2 (m, 7H), 3.85 (m, 2H), 2.95 (t, J=7 Hz, 2H);

MS (FD) m/e 365 (M$^+$);

UV (EtOH) 301 nm (ε=24527), 220 nm (ε=31031).

Anal. Calcd for C$_{16}$H$_{13}$N$_3$S$_2$ClF: Theory: C, 52.53; H, 3.58; N, 11.49. Found: C, 52.80; H, 3.70; N, 11.34.

Example 84

N-[2-(2-methoxyphenyl)ethyl]-N'-(2-[6-fluoro]benzothiazolyl)thiourea

A solution of 1-[(2-[6-fluoro]benzothiazolyl)thiocarbamoyl]imidazole (2.1 g, 8 mmol) and 2-(2-methoxyphenyl)ethylamine (1.25 g, 8 mmol) in N,N-dimethylformamide (30 mL) was stirred at 100° C. for 1.5 h, the reaction was cooled to room temperature and the solvent removed in vacuo. The residue was crystallized from ethyl acetate to provide 1.6 g (57%) of the title product:

mp 208°–209° C.;

IR (KBr, cm$^{-1}$) 3168, 3034, 1562, 1536, 1462, 1242, 1198, 852;

$^1$H NMR (300 MHz, DMSO-d$_6$) d 11.85 (br s, 1H), 9.8 (br s, 1H), 7.9–7.0 (m, 7H), 3.85 (m, 2H), 3.8 (s, 3H), 2.9 (t, J=7 Hz, 2H);

MS (FD) m/e 361 (M$^+$);

UV (EtOH) 300 nm (ε=24273), 218 nm (ε=28369), 201 nm (ε=34036).

Anal. Calcd for C$_{17}$H$_{16}$N$_3$OS$_2$CF: Theory: C, 56.49; H, 4.46; N, 11.63. Found: C, 56.56; H, 4.59; N, 11.66.

Example 85

N-[2-(3-methoxyphenyl)ethyl]-N'-(2-[6-fluoro]benzothiazolyl)thiourea

A solution of 1-[(2-[6-fluoro]benzothiazolyl)thiocarbamoyl]imidazole (2.1 g, 8 mmol) and 2-(3-methoxyphenyl)ethylamine (1.25 g, 8 mmol) in N,N-dimethylformamide (30 mL) was stirred at 100° C. for 1.5 h, the reaction was cooled to room temperature and the solvent removed in vacuo. The residue was crystallized from ethyl acetate to provide 1.6 g (57%) of the title product:

mp 190°–192° C.;

IR (KBr, cm$^{-1}$) 3050, 1536, 1460, 1302, 1221, 1060, 674;

$^1$H NMR (300 MHz, DMSO-d$_6$) d 11.9 (br s, 1H), 9.9 (br s, 1H), 7.9–7.0 (m, 7H), 3.85 (m, 2H), 3.75 (s, 3H), 2.95 J=7 Hz, 2H);

MS (FD) m/e 361 (M$^+$);

UV (EtOH) 301 nm (ε=24608), 218 nm (ε=28535), 201 nm (ε=37337).

Anal. Calcd for $C_{17}H_{16}N_3OS_2CF$: Theory: C, 56.49; H, 4.46; N, 11.63. Found: C, 56.21; H, 4.54; N, 11.40.

Example 86

N-[2-(4-methoxyphenyl)ethyl]-N'-(2-[6-fluoro]benzothiazolyl)thiourea

A solution of 1-[(2-[6-fluoro]benzothiazolyl)thio-carbamoyl]imidazole (54) (2.1 g, 8 mmol) and 2-(4-methoxyphenyl)ethylamine (1.25 g, 8 mmol) in N,N-dimethylformamide (30 mL) was stirred at 100° C. for 1.5 h, the reaction was cooled to room temperature and the solvent removed in vacuo. The residue was crystallized from ethyl acetate to provide 1.6 g (57%) of the title product:

mp 203°–204.5° C.;

IR (KBr, cm$^{-1}$) 3001, 1561, 1539, 1458, 1251, 860, 818;

$^1$H NMR (300 MHz, DMSO-d$_6$) d 11.85 (br s, 1H), 9.85 (br s, 1H), 7.9–6.9 (m, 7H), 3.85 (m, 2H), 3.75 (s, 3H), 2.9 (t, J=7 Hz, 2H);

MS (FD) m/e 361 (M$^+$);

UV (EtOH) 301 nm (ε=23562), 222 nm (ε=28328).

Anal. Calcd for $C_{17}H_{16}N_3OS_2CF$: Theory: C, 56.49; H, 4.46; N, 11.63. Found: C, 56.70; H, 4.42; N, 11.79.

Example 87

1-[(2-[5-chloro]thiazolyl)thiocarbamoyl]imidazole

A solution of 1,1'-thiocarbonyldiimidazole (25 g, 140 mmol) and 2-amino-5-chlorothiazole (18.8 g, 140 mmol) in acetonitrile (300 mL) was stirred at room temperature for 23 h. The resulting precipitate was collected by filtration to provide 21.2 g (62%) of the title product:

$^1$H NMR (300 MHz, DMSO-d$_6$) δ9.5 (s, 1H), 8.2 (s, 1H), 7.6 (s, 1H), 7.5 (s, 1H);

MS (FD) m/e 176 (M$^+$-C$_3$H$_3$N$_2$).

Example 88

N-[2-(2-chlorophenyl)ethyl]-N'-[2-(5-chloro)thiazolyl]thiourea

A solution of 1-[(2-[5-chloro]thiazolyl)thiocarbamoyl]imidazole (0.68 g, 2.8 mmol) and 2-(2-chlorophenyl)ethylamine (0.43 g, 2.8 mmol) in N,N-dimethylformamide (15 mL) was stirred at 100° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 0.68 g (73%) of the title product:

mp 172°–174° C.;

IR (KBr, cm$^{-1}$) 3318, 2873, 1606, 1526, 1513, 1436, 1351, 1237, 747;

$^1$H NMR (300 MHz, DMSO-d$_6$) δ10.7 (br s, 1H), 8.5 (br s, 1H), 7.4 (s, 1H), 7.4–7.2 (m, 4H), 3.8 (m, 2H), 2.9 (t, J=7 Hz, 2H);

MS (FD) m/e 331 (M$^+$);

UV (EtOH) 295 nm (ε=11804), 259 nm (ε=10397), 202 nm (ε=27067).

Anal. Calcd for $C_{12}H_{11}N_3S_2Cl_2$: Theory: C, 43.38; H, 3.34; N, 12.65. Found: C, 43.61; H, 3.57; N, 12.57.

Example 89

N-[2-(3-chlorophenyl)ethyl]-N'-[2-(5-chloro)thiazolyl]thiourea

A solution of 1-[(2-[5-chloro]thiazolyl)thiocarbamoyl]imidazole (1.22 g, 5 mmol) and 2-(3-chlorophenyl)ethylamine (0.78 g, 5 mmol) in N,N-dimethylformamide (20 mL) was stirred at 100° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl ether to provide 0.9 g (54%) of the title product:

mp 154°–155° C.;

IR (KBr, cm$^{-1}$) 3178, 3044, 1557, 1520, 1458, 1346, 1196, 784, 755;

$^1$H NMR (300 MHz, DMSO-d$_6$) δ11.6 (br s, 1H), 8.4 (br s, 1H), 7.4 (s, 1H), 7.4–7.2 (m, 4H), 3.7 (m, 2H), 2.8 (t, J=7 Hz, 2H);

MS (FD) m/e 331 (M$^+$);

UV (EtOH) 296 nm (ε=14281), 259 nm (ε=12090), 205 nm (ε=29809).

Example 90

N-[2-(4-chlorophenyl)ethyl]-N'-[2-(5-chloro)thiazolyl]thiourea

A solution of 1-[(2-[5-chloro]thiazolyl)thiocarbamoyl]imidazole (1.22 g, 5 mmol) and 2-(4-chlorophenyl)ethylamine (0.78 g, 5 mmol) in N,N-dimethylformamide (20 mL) was stirred at 100° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 1.1 g (66%) of the title product:

mp 178°–180° C.;

IR (KBr, cm$^{-1}$) 3180, 2927, 1610, 1536, 1492, 1325, 1256, 1181, 1088, 1014, 811, 747, 643, 508;

$^1$H NMR (300 MHz, DMSO-d$_6$) δ11.6 (br s, 1H), 8.4 (br s, 1H), 7.4 (s, 1H), 7.32 (d, J=8 Hz, 2H), 7.22 (d, J=8 Hz, 2H), 3.7 (m, 2H), 2.8 (t, J=7 Hz, 2H);

MS (FD) m/e 331 (M$^+$);

UV (EtOH) 295 nm (ε=13675), 259 nm (ε=12330), 202 nm (ε=27524).

Anal. Calcd for $C_{12}H_{11}N_3S_2Cl_2$: Theory: C, 43.38; H, 3.34; N, 12.65. Found: C, 43.61; H, 3.46; N, 12.85.

Example 91

N-(2-(1-methyl)-2-pyrrolylethyl)-N'-(2-thiazolyl)thiourea

An isothiocyanate of 2-(2-aminoethyl)-1-methylpyrrole was prepared according to Ann 657, 104–107 (1962). $^1$H-NMR (CDCl$_3$) δ2.95 (t, 2H), 3.55 (s, 1H), 3.65 (t, 2H), 5.9–5.95 (m, 1H), 6.05 (t, 1H), 6.55 (t, 1H). This isothiocyanate was dissolved in DMF (4 ml). To this solution was added 200 mg (2 mmol) of 2-aminothiazole and the solution was heated at 100° C. for about 16 h. EtOAc was added and the organic phase was washed with sat. NH$_4$Cl-solution and brine. After drying (Na$_2$SO$_4$), the product was purified on a silica gel column, using EtOAc/Hexane 1:1, as eluent. This gave almost pure titled product. Recrystallization from toluene/hexanes gave 150 mg of the titled product.

Mp: 183°–184° C. (dec).

$^1$H-NMR (DMSO-$d_6$) δ2.86 (t, 2H), 3.55 (s, 3H), 3.75 (q, 2H), 5.85–5.90 (m, 2H), 6.62 (s, 1H), 7.09 (d, 1H), 7.36 (d, 1H ), 9.74 (broad s, 1H ), 11.65 (broad s, 1H ).

$^{13}$C-NMR (DMSO-$d_6$) δ25.03, 33.31, 43.92, 106.24, 106.31, 112.03, 121.55, 129.33, 136.71, 161.68, 178.25.

Example 92

N-(2-1-piperazinylethyl))-N'-(2-thiazolyl)thiourea 1.78 g Thiocarbonyldiimidazole (10 mmol) was added to a solution of 1.29 g 1-(2-aminoethyl)piperazine (10 mmol) in 5 ml methylene chloride at 0° C. The reaction mixture was warmed to room temperature, and stirred for 30 minutes. The methylene chloride was evaporated, and 40 ml dimethylformamide together with 10.01 g 2-aminothiazole were added. The mixture was stirred 17 h at 100° C. The product was purified by chromatography on a silica gel column eluted with mixtures of methanol and chloroform. Crystallization of the salt with oxalic acid gave further purification.

$^1$H-NMR (oxalate in $D_2O$): 2.8–3.7 ppm (m), 6.75 ppm (d), 7.1 ppm (d).

Example 93

N-(2-(2-chloro)phenethyl)-N'-(2-thiazolyl)thiourea

Thiocarbonyldiimidazolide (980 mg, 5.5 mmole) was dissolved in 20 ml methylene chloride. To the solution was added dropwise 2-chlorophenethylamine (0.69 ml, 5 mmole) in 20 ml methylene chloride at 0° C. After reaction for 30 min at 0° C., it was warmed up to room temperature, and then concentrated to small volume in vacuo. To the residue was added 20 ml DMF and 2-aminothiazole (700 mg, 7 mmole). It was kept at 100° C. for 3 hours. After cooling to room temperature, it was poured into 1N HCl solution (100 ml) and extracted with ethyl acetate (2×100 ml); the organic phase was washed with brine and dried over magnesium sulfate. The solution was concentrated in vacuo and separated by silica gel column chromatography. Yield= 440 mg (30%).

$^1$H-NMR (CDCl$_3$) δ7.38–7.17 (m, 5H, CPh, thiazol) 6.81 (d, J=3.7 Hz, 1H, thiazole), 4,02 (q, J=7 Hz, 2H, CH$_2$NH), 3.17 (t, J=7.1 Hz, CH$_2$).

$^{13}$C-NMR (CDCl$_3$) δ177.5 (C=S), 161 (thiazol), 137.5 (thiazol), 136.0 (ClPh), 134.1 (ClPh), 131.1 (ClPh), 129.5 (ClPh), 128.0 (ClPh) and 126.7 (ClPh) 111.1 (thiazol), 44.8 (CH$_2$) and 32.3 (CH$_2$).

Example 94

N-(2-(2-methoxy)phenethyl)-N'-(2-thiazolyl)thiourea

To a solution of 1.8 g (10 mmol) 1,1'-thiocarbonyldiimidazole in CH$_2$Cl$_2$ (30 ml) at 0° C. was added 1.46 ml (10 mmol) of 2-methoxyphenethylamine. The solution was then stirred for 1 hour. After the addition of hexane, the reaction mixture was filtered and evaporated. The residue was dissolved in DMF (8 ml) and 1.0 g (10 mmol) 2-aminothiazole (Merck) was added. The reaction mixture was heated at 100° C. for about 16 h. Thereafter, EtOAc and diluted HCl-solution were added. The organic phase was separated and washed with diluted HCl-solution, sat. NH$_4$Cl-solution and water (× 2), respectively. After drying over Na$_2$SO$_4$, the product was purified on a silica gel column, using hexanes/ EtOAc (2:1) as eluent, to give 0.77 g crude product. Recrystallization from toluene gave 0.54 g of still crude titled product. A final purification was achieved by the use of a Al$_2$O$_3$ column eluted with CHCl$_3$ (containing 0.5% EtOH) as the eluent. This gave 85 mg of the titled product.

Mp: 126.0°–127.5° C.

$^1$H-NMR (CDCl$_3$) δ3.03 (t, 2H), 3.82 (s, 3H), 3.96 (q, 2H), 6.79–6.93 (m, 3H), 7.20–7.26 (m, 3H), 10.35 (broad s, 1H), 10.73 (broad s, 1H).

$^{13}$C-NMR (CDCl$_3$) δ29.59, 45.69, 55.19, 110.22, 110.97, 120.40, 126.75, 127.96, 130.78, 137.72, 157.62, 161.58, 177.34.

Example 95

N-(2-(4-fluoro)phenethyl)-N'-(2-thiazolyl)thiourea

In a manner analogous to Example 94, using 4-fluorophenethylamine, the titled product resulted.

Analyses: Calculated: C 51.22, H 4.30, N 14.93. Found: C 51.0, H 4.35, N 14.8.

Mp: 124.5°–126.0° C.

$^1$H-NMR (CDCl$_3$) δ3.0 (m, 3H), 4.0 (q, 3H), 6.86 (d, 1H), 7.0–7.3 (m, 5H).

$^{13}$C-NMR (CDCl$_3$) δ34.05, 46.82, 111.35, 115.38 (d, 2C), 130.39 (d, 2C), 134.20 (d, 1C), 137.46, 161.74 (d, 1C), 161.83, 177.52.

Example 96

N-(2-(4-nitro)phenethyl)-N'-(2-thiazolyl)thiourea

In a manner analogous to Example 93, using 4-nitrophenethylamine, the titled product resulted.

$^1$H-NMR (CDCl$_3$) δ8.17 (d, J=8.6 Hz, 2H, O$_2$NPh), 7.45 (d, J=8.6 Hz, 2H, O$_2$NPh), 7.21 (d, J=3.7 Hz, 1H, thiazole), 6.84 (d, J=3.7 Hz, 1H, thiazole), 4.01 (q, J=5.7 Hz, 2H, CH$_2$NH ), 3.15 (t, J=7.2 Hz, 2H, CH$_2$).

$^{13}$C-NMR (CDCl$_3$+CD$_3$OD) δ179 (C=S), 161 (thiazole), 146.4 (O$_2$NPh), 136.9 (thiazole), 129 (O2NPh), 123.4 (O$_2$NPh), 111.1 (thiazole), 45.3 (CH$_2$), 34.3 (CH$_2$).

Example 97

N-(2-(4-amino)phenethyl)-N'-(2-thiazolyl)thiourea

The titled product was prepared by reduction of the product from Example 96 with iron and hydrochloric acid using the literature procedure (Vogel, *Textbook of Practical Organic Chemistry*, 4th ed., p.657, Longman 1978).

$^1$H-NMR (CDCl$_3$) δ7.23 (d, J=3.8 Hz, 1H, thiazole), 7.07 (d, J=8.3 Hz, 2H, H$_2$NPh ), 6.79 (d, J=3.7 Hz, 1H, thiazole), 6.65 (d, J=8.3 Hz, 2H, H$_2$NPh), 3.91 (q, 2H, CH$_2$NH), 2.91 (t, J=7.1 Hz, 2H, CH$_2$).

$^{13}$C-NMR (CDCl$_3$+CD$_3$OD) δ177 (C=S), 161 (thiazole), 144 (H$_2$NPh), 137.3 (thiazole), 129.5 (H$_2$NPh), 128.6 (H$_2$NPh), 115.4 (H$_2$NPh), 110.9 (thiazole), 46.7 (CH$_2$), 33.6 (CH$_2$).

Example 98

N-(2-(4-methoxy)phenethyl)-N'-(2-thiazolyl)thiourea

In a manner analogous to Example 93, using 4-methoxyphenethylamine, the titled product resulted.

¹H-NMR (CDCl₃) δ7.22–7.18 (t, 3H, MeOPh and thiazole), 6.85 (d, J=8.5 Hz, 2H, MeOPh), 6.81 (d, J=3.7 Hz, 1H, thiazole), 3.94 (q, J=7.1 Hz, 2H, CH₂NH), 3.79 (s, 3H, MeO), 2.96 (t, 7.1 Hz, 2H, CH₂).

¹³C-NMR (CDCl₃) δ177.3 (C=s), 161.6 (thiazole) 158.2 (MeOPh), 137.4 (thiazole), 130.4 (MeOPh), 129.7 (MeOPh), 113.8 (MeOPh), 111.0 (thiazole), 55.1 (MeO), 47.0 (CH₂), 33.8 (CH₂).

Example 99

N-(2-(4-hydroxy)phenethyl)-N'-(2-thiazolyl)thiourea

The titled product was prepared by treatment of the product of Example 98 with iodotrimethyl silane in dichloroethane according to literature procedure (H. Sakurai, *Synthesis*, p. 740, 1979) (Example 97).

¹H-NMR (CDCl₃) δ7.22 (d, J=3.6 Hz, 1H, thiazole), 7.14 (d, J=8.4Hz, 2H, HOPh), 6.81–6.77 (t, 2H, thiazole, HOPh), 3.94 (q, 2H, CH₂NH₂), 2.94 (t, J=7.2 Hz, 2H, CH₂).

¹³C-NMR (CDCl₃) δ177.4 (C=S), 161.4 (thiazole), 154.1 (HOPh), 137.6 (thiazole), 130.5 (HOPh), 129.9 (HOPh), 115.3 (HOPh), 110.9 (thiazole), 47.1 (CH₂), 33.7 (CH₂).

Example 100

N-(2-(4-bromo)phenethyl)-N'-(2-thiazolyl)thiourea

In a manner analogous to Example 93, using 4-bromophenethylamine, the titled product resulted.

¹H-NMR (CDCl₃+CD₃OD) δ7.43 (d, J=6.4 Hz, 2H, BrPh), 7.22 (d, J=3.6 Hz, 1H, thiazole), 7.15 (d, J=6.3 Hz, 2H, BrPh), 6.83 (d, J=3.7 Hz, 1H, thiazole), 3.95 (t, J=7.1 Hz, 2H, CH₂NH), 2.94 (t, J=7 Hz, 2H, CH₂). ¹³C-NMR (CDCl₃+CD₃OD) δ177.5 (C=S), 161.5 (thiazole), 137.4 (thiazole), 131.5 (BrPh), 130.5 (BrPh), 120.3 (BrPh), 111.1 (thiazole), 46.2 (CH₂), 34.0 (CH₂).

Example 101

N-(2-(1-piperidinyl)ethyl)-N'-(2-thiazolyl)thiourea

In a manner analogous to Example 93, using 1-piperidinylethylamine, the titled product resulted.

¹H-NMR (CDCl₃) δ7.32 (d, J=3.7 Hz, 1H, thiazole), 6.84 (d, J=3.7 Hz, 1H, thiazole), 3.80 (t, 2H, CH₂NH), 2.62 (t, J=6.4 Hz, 2H, CH₂), 2.48 (m, 2H, pip), 1.62 (m, 2H, pip), 1.46 (m, 1H, pip).

¹³C-NMR (CDCl₃+CD₃OD): 177.3 (C=S), 161 (thiazole), 137.3 (thiazole), 111.1 (thiazole), 56.1 (CH₂), 54.1 (pip), 42.2 (CH₂), 25.6 (pip), 24.0 (pip).

Example 102

N-(2-morpholinoethyl)-N'-(2-thiazolyl)thiourea

In a manner analogous to Example 91, using morpholinoethylamine, the title product resulted.

¹H-NMR (250 MHz, CDCl₃) δ7.38 (d, 1H, CH=CH), 6.86 (d, 1H, CH=CH), 3.82 (q, 2H, CH₂—NH), 3.86–3.71 (m, 4H, CH₂—O—CH₂), 2.67 (t, 2H,CH₂—N (ring)), 2.62–2.52 (m, 4H, CH₂—N—CH₂).

¹³C-NMR (250 MHz, CDCl₃) δ178, 163, 138, 112, 67, 57, 53, 42.

Mp: 150.5°–151.5° C.

Example 103

1-(2-Aminothiazole)-1'-imidazole thiocarbonyl 8.90 g Thiocarbonyldiimidazole (50 mmole) and 5.0 g 2-aminothiazole (50 mmole) was added to 50 ml acetonitrile. The mixture was heated to 40° C., and stirred for 2 hours at this temperature. The mixture was cooled to 0° C., and the solid was filtrated off, and washed with 300 ml cold acetonitrile. The yield of pure product after drying was 9.7 g (46 mmole).

Elemental anal: Found; C=39.3, H=2.8, N=26.2; Calc: C=40.0, H=2.87, N=26.6.

¹H-NMR (250 MHz, DMSO) δ8.68 (s, 1H, N=CH—N), 7.97 (s, 1H, N—CH=CH—N), 7.76 (d, 1H, S—CH=CH—N), 7.33 (d, 1H, S—CH=CH—N), 7.08 (s, 1H, N—CH=CH—N).

Example 104

N-(2-Phenethyl)-N'-[2-(6-hydroxy)pyridyl]thiourea

A stirred solution of phenethyl isothiocyanate (1.63 g, 10 mmol, 1.5 mL) and 2-amino-6-hydroxypyridine (1.10 g, 10 mmol) in N-methylpyrrolidinone (20 mL) was heated to 100° C. After 87.25 h, the reaction was cooled to room temperature and poured into ethyl acetate. The organic phase was washed with water (4×) and brine. The organic layer was dried over sodium sulfate, filtered and concentrated. The solid obtained was purified by flash chromatography on silica gel (10% ethyl acetate/dichloromethane to 15% ethyl acetate), followed by trituration with ethyl acetate to provide 1.15 g of the titled product (42%) as an off-white solid:

mp 196°–197° C.;

IR (KBr, cm⁻¹) 2937, 1668, 1595, 1475, 1428, 1365, 1219, 1158, 1023;

¹H NMR (300 MHZ, DMSO-d₆) δ11.49 (br s, 1H), 10.82 (s, 1H), 10.33 (s, 1H), 7.52 (t, J=7.9 Hz, 1H), 7.25–7.14 (m, 5H), 6.53 (d, J=7.9 Hz, 1H), 6.19 (d, J=8.0 Hz, 1H), 3.80–3.73 (m, 2H), 2.92 (t, J=7.7 Hz, 2H);

MS (FD) m/e 273 (M+);

UV (EtOH) 305 nm (ε=20692), 262 nm (ε=13737), 247 nm (ε=8743), 203 nm (ε=19201).

Anal. Calcd for C₁₄H₁₅N₃OS: C, 61.52; H, 5.53; N, 15.37. Found: C, 61.73; H, 5.72; N, 15.57.

Example 105

N-(2-(2-naphthyl)ethyl)-N'-(2-thiazolyl)thiourea

2-Naphthalenethylamine (256 mg, 1.5 mmole) and the product from Example 103 (400 mg, 1.9 mmole) was suspended in DMF (5 ml). The reaction mixture was heated to 110° C. and it became a clear solution in a few minutes. After 1 hour, the reaction mixture was cooled to room temperature, and 20 ml methylene chloride was added. The organic solution was washed successively with 0.5N HCl solution (70 ml), brine (50 ml) and water (50 ml). The organic solution was dried over magnesium sulfate, and then dried in vacuo. The product was purified by silica gel column chromatography (chloroform/cyclohexane=1/1 v/v).

Yield=324 mg (69%).

¹H-NMR (CDCl₃) δ7.82–7.39 (m, 7H, naph), 6.98 (d, J=3.6 Hz, 1H, thiazol), 6.73 (d, J=3.1 Hz, 1H, thiazol), 4.07 (q, J=7 Hz, 2H, CH₂NH), 3.28 (t, J=7 Hz, 2H, CH₂).

$^{13}$C-NMR (CDCl$_3$+CD$_3$OD) δ177 (C=S), 161 (thiazol), 137 (thiazol), 134.5 (naph), 133.6 (naph), 131.7 (naph), 128.5 (naph), 127.2 (naph), 126.8 (naph), 125.9 (naph), 125.5 (naph), 125.2 (naph), 123.6 (naph), 110.9 (thiazol), 45.8 (CH$_2$), 31.7 (CH).

Example 106

N-(1-(4-pentenyl)-N'-(2-thiazolyl)thiourea

A mixture of 4-pentenol (3.04 g, 35.3 mmole), pyridine (2.79 g, 35.3 mmole) and 25 ml diethyl ether was cooled to −60° C. Trifluoromethanesulfonic anhydride (10 g, 35.4 mmol) was added dropwise at −60° C. (5 min). The reaction was heated slowly (30 min) to room temperature, and the salt formed was filtered off.

The filtrate was added dropwise to a mixture of 10 ml diethyl ether and 30 ml liquid ammonia kept at ca −30° C. The ammonia was evaporated while the remaining solution was allowed to reach room temperature. The ether solution was extracted with 10 ml 10M aqueous sodium hydroxide. Distillation at atmosphere pressure gave 4-pentenylamine (2.35 g, 27.6 mmole).

0.85 g (10 mmole) of this amine was condensed with 2.1 g of the product of Example 103 using the method as described in Example 105. Crystallization from a mixture of n-hexane and toluene gave pure product.

$^1$H-NMR (CDCl$_3$) δ1.85 ppm (m), 2.20 ppm (m), 3.7 ppm (m), 5.0–5.15 ppm (m), 5.75–5.95 ppm (m), 6.85 ppm (d), 7.30 ppm (d).

$^{13}$C-NMR (CDCl$_3$) δ177, 162, 137, 137, 116, 111, 45, 31, 28 ppm.

Example 107

N-(2-(3-trifluoromethyl)phenethyl)-N'-(2-thiazolyl)thiourea

In a manner analogous to Example 106, using 1-trifluoromethyl-3-ethanolbenzene, the titled product resulted.

$^1$H-NMR (CDCl$_3$) δ3.0 (t, PhCH$_2$, 2H), 4.0 (q, CH$_2$N, 2H), 6.8 (d, thiazole, 1H), 7.2 (d, thiazole, 1H), 7.4–7.6 (mult. o, m and p, 4H).

Example 108

N-(cis-3-Hexenyl))-N'-(2-thiazolyl)thiourea

In a manner analogous to Example 106, using 3-cis-hexenol, the titled product resulted.

$^1$H-NMR (CDCl$_3$) δ7.30 (d, J=3.9 Hz, 1H, thiazol), 6.83 (d, J=3.8 Hz, 1H, thiazole), 5.56 and 5.40 (m, 2H, H—C=C—H), 3.75 (q, 2H, CH$_2$NH), 2.47 (q, 2H, CH$_2$), 2.09 (p, 2H, CH$_2$), 0.95 (t, J=5.4 Hz, 3H, CH$_3$).

$^{13}$C-NMR (CDCl$_3$) δ 177 (C=S), 161 (thiazole), 137.5 (thiazole), 134.8 (C=C), 124.6 (C=C), 111.0 (thiazole), 45.4 (CH$_2$NH), 26.3 (CH$_2$), 20.6 (CH$_2$), 14.1 (CH$_3$).

Example 109

N-(2-(1-naphthyl)ethyl)-N'-(2-thiazolyl)thiourea

In a manner analogous to Example 106, using (1-naphthyl)-2-ethanol, the titled product resulted.

$^1$H-NMR (CDCl$_3$+CD$_3$OD) δ8.24–7.40 (m, 7H, naph), 7.16 (d, J=3.7 Hz, 1H, thiazole), 6.80 (d, J=3.7 Hz, 1H, thiazole), 4.10 (t, J=7.5 Hz, 2H, CH$_2$NH), 3.49 (t, J=7.5 Hz, 2H, CH$_2$).

Example 110

N-(2-(2-fluoro)-phenethyl)-N'-(2-thiazolyl)thiourea

In a manner analogous to Example 106, using 1-fluoro-2-ethanolbenzene, the titled product resulted.

$^1$H-NMR (CDCl$_3$) δ7.28–7.03 (m, 5H, thiazole, FPh), 6.81 (d, J=3.8 Hz, 1H, thiazole), 3.99 (q, J=7.1 Hz, 2H, CH$_2$NH), 3.08 (t, J=7 Hz, 2H, CH$_2$).

$^{13}$C-NMR (CDCl$_3$) δ 178 (C=S), 161 (thiazole), 137.4 (thiazole), 131 (d, C-F coupling, FPh), 128 (d, C-F coupling, FPh), 124 (FPh), 115.4 (FPh), 115 (FPh), 111 (thiazole), 45.3 (CH$_2$), 28.1 (CH$_2$).

Example 111

N-(2-(2-trifluoromethyl)phenethyl)-N'-(2-thiazolyl)thiourea

In a manner analogous for Example 106, using 1-trifluoromethyl-2-ethanolbenzene, the title product resulted.

$^1$H-NMR (CDCl$_3$) δ7.66 (d, 1H, TFMPh), 7.51 (m, 2H, TFMPh), 7.34 (m, 1H, TFMPh), 7.26 (d, J=3.6 Hz, 1H, thiazole), 6.84 (d, J=3.8 Hz, 1H, thiazole), 3.99 (q, J=6.3 Hz, 2H, CH$_2$NH), 3.23 (t, J=7.6 Hz, 2H, CH$_2$).

$^{13}$C-NMR (CDCl$_3$) δ177.7 (C=S), 161.5 (thiazole), 137.6 (thiazole), 136.9 (TFMPh), 131.8 (TFMPh), 131.6 (TFMPh), 129 (q, C-F coupling, CF$_3$), 126.6 (TFMPh), 125.9 (d, TFMPh), 111.1 (thiazole), 46.3 (CH$_2$), 31.4 (CH$_2$).

Example 112

N-N-(3-pentynyl)-N'-(2-thiazolyl)thiourea

The starting material, 3-pentynylamine, was synthesized from 3-pentyn-1-ol. 3-pentynylamine Trifluoromethanesulfonic anhydride (4.0 ml; 23.8 mmol) was added to a solution of 3-pentyn-1-ol (2.0 g; 23.8 mmol) and pyridine (1.92 ml; 23.8 mmol) in diethyl ether (50 ml) at −45° C. The mixture was stirred for 15 min at the same temperature and filtered cold into diethyl ether (−10 ml) saturated with NH$_3$ at −45° C. with stirring. The precipitate was washed with cold diethyl ether. The reaction mixture was stirred at RT for 3 h and evaporated to give yellow crystals (2.0 g, 36 %) as a salt of 3-pentynylamine and trifluoromethane sulfonic acid.

$^1$H-NMR (250 MHz, D$_2$O) δ3.12 (m, 2H, CH$_2$-NH$^+$3), 2.55 (m, 2H, CH$_2$—C≡C), 178 (t, 3H,CH$_3$—C≡C).

$^{13}$C-NMR (250 MHz, D$_2$O) δ126, 83, 77, 41, 20, 5.

The titled product was then prepared in a manner analogous to Example 106.

$^1$H-NMR (250 MHz, CDCl$_3$) δ7.33 (d, 1H, CH=CH ), 6.87 (d, 1H, CH=CH), 3.86 (q, 2H, CH$_2$—NH), 2.56 (H, 2H, CH$_2$—C≡C), 1.81 (t, 3H, CH$_3$—C≡C).

$^{13}$C-NMR (250 MHz, CDCl$_3$) δ178, 162, 138, 111, 45, 19, 4.

Mp: 118.5°–119.5° C.

Example 113

3-(2-Phenethyl)-2-thioxo-1,2,3,4-tetrahydroquinazoline

2-Nitrobenzaldehyde (10.0 g, 66 mmol) and 2-phenylethylamine (8.3 ml, 66 mmol) was dissolved in acetonitrile (200 ml). pH was adjusted to 6.0 with acetic acid.

Sodium cyanoborohydride (4.15 g, 66 mol) was added in small portions. The solution was stirred 40 min. The solution was diluted with water (400 ml) and extracted with ether.

Acid-base partitioning [aq. HCl, $NH_4OH$ (aq.)] and evaporation gave an oil. The oil was suspended in water (200 ml) and iron dust (10 g, 180 mmol) was added. The mixture was heated to reflux and HCl (conc. aq.) (10 ml) was slowly added. Reflux was continued for 40 minutes. The solution was cooled, basified with sodium hydroxide 40 (aq.) to pH 14. The solution was stirred with toluene (700 ml) and filtered through a pad of celite.

Acid-base partitioning [(HCl (a.q.) $NH_4OH$ (a.q.)] and evaporation afforded an oil. The oil was dissolved in acetonitrile (20 ml) and N,N-thiocarbonyldiimidazole (0.7 g, 6.6 mmol) was added. The solution was stirred for 78 hours at ambient temperature, heated to 75° C. for 40 minutes and evaporated. The residue was purified by flash-chromatography on silica gel by elution with ethyl acetate-cyclohexane (1:3). The product crystallized spontaneously from the pure fractions forming long needles.

$^1$H-NMR (CDCl$_3$) $\delta$3.0 (t, PhCH$_2$, 2H), 4.1 (t, PhCH$_2$CH$_2$N, 2H), 4.4 (s, PhCH$_2$N, 2H), 6.7–7.5 (mult., C$_6$H$_5$, $\underline{C_6H_4}$, 9H), 8.7 (Broad singlet NH, 1H).

Example 114

N-(2-Phenethyl)-N'-[2-(3-methyl)-pyridyl]thiourea

A stirred solution of 2-phenethyl isothiocyanate (1.63 g, 10 mmol, 1.5 mL) and 2-amino-3-methylpyridine (1.08 g, 10 mmol) in N-methylpyrrolidinone (20 mL) was heated to 100° C. After 16.5 h, the reaction was cooled to room temperature and poured into ethyl acetate. The organic phase was washed with water (4×) and brine. The organic layer was dried over sodium sulfate, filtered and concentrated. The solid obtained was purified by flash chromatography on silica gel (2% ethyl acetate/dichloromethane) to provide 1.77 g of the titled product (65%). This material was recrystallized from ethyl acetate/hexanes to provide 878 mg of the titled product as a pale yellow crystalline solid:

mp 82°–84° C.; IR (KBr, cm$^{-1}$) 3430, 2945, 1594, 1555, 1454, 1268, 1243, 1161;

$^1$H NMR (300 MHZ, DMSO-d$_6$) $\delta$11.62 (br s, 1H), 8.66 (s, 1H), 7.90 (d, J=4.1 Hz, 1H), 7.59 (d, J=7.2 Hz, 1H), 7.28–7.15 (m, 5H), 6.96 (dd, J=7.4, 5.0 Hz, 1H), 3.84–3.78 (m, 2H), 2.89 (t, J=7.0 Hz, 2H), 2.23 (s, 3H);

MS (FD) m/e 271 (M+); UV (EtOH) 293 nm ($\epsilon$=17290), 265 nm ($\epsilon$=14634), 244 nm ($\epsilon$=16338), 202 nm ($\epsilon$=19784).

Anal. Calcd for C$_{15}$H$_{17}$N$_3$S: C, 66.39; H, 6.31; N, 15.48. Found: C, 66.66; H, 6.32; N, 15.73.

Example 115

N-(2-(2-thienyl)ethyl)-N'-(2-thiazolyl)thiourea 6.4 g 2-(2-thienyl)ethanol (50 mmoles) was dissolved in 50 ml diethyl ether together with 3.95 g pyridine (50 mmoles).

The mixture was cooled to −30° C., and 5.7 g methanesulfonylchloride (50 moles) was added dropwise under stirring. The reaction mixture was then heated and kept at reflux temperature for 30 minutes. The mixture was then cooled to room temperature and filtered. The filtrate was transferred to an autoclave together with 100 ml of a solution of ammonia in methanol (saturated at 0° C.). The autoclave was sealed and heated to 150° C. for 17 hours. The solvent was removed by evaporation in vacuo, and 100 ml 5M sodium hydroxide in water was added. The mixture was extracted twice with 100 ml methylene chloride to give a solution of 2-(2-thienyl)ethylamine together with some secondary amine.

The pure primary amine was obtained by fractional crystallization from methanol of the salts with oxalic acid, followed by addition of aqueous sodium hydroxide and extraction with methylene chloride.

500 mg of the pure 2-(2-thienyl)ethylamine (3.93 mole) was added to a solution of 800 mg thiocarbonyldiimidazole (4.5 mole) in 5 ml methylene chloride at 0° C. The mixture was stirred at 0° C. for 15 minutes, and then 1 hour at 20° C. The solvent was removed in vacuo, and 5 ml dimethylformamide and 500 mg 2-aminothiazole was added. This mixture was allowed to react 17 hours at 110° C. After evaporation of solvent in vacuo 100 ml ethyl acetate was added, and the mixture was heated to 50° C. The warm mixture was washed twice with 20 ml 1M HCl, and once with 20 ml H$_2$O. Evaporation of solvent to a small volume gave crystals of the desired product. Recrystallization twice from ethyl acetate gave 340 mg of very pure product.

$^{13}$C-NMR (CDCl$_3$+DMSO-d$_6$) $\delta$178, 162, 141, 137, 127, 125, 124, 111, 46, 29 PPM.

$^1$H-NMR (CDCl$_3$+DMSO-d$_6$) $\delta$3.3 ppm (t), 3.9 ppm (m), 6.85 ppm (d), 6.90 ppm (m), 7.20 ppm (d), 7.25 ppm (d).

Example 116

N-(2-(2-fluoro-6-chloro)phenethyl)-N'-(2-thiazolyl)thiourea

2-Chloro-6-fluorophenylacetonitrile (2.5 g, 14.7 mmol) was dissolved in 30 ml diethyl ether. Lithium aluminium hydride (1.5 g) was added in small portions over a period of 10 minutes. The mixture was then heated to reflux for 15 minutes. After cooling to room temperature, 1.5 ml water, 1.5 ml aqueous sodium hydroxide, and 4 ml water was added slowly. The ether solution containing the product 2-chloro-6-fluorophenethylamine was decanted off and the solvent was removed in vacuo.

The amine formed was condensed with the product of Example 103 using the method as described in Examples 104 and 105 to give 270 mg of the titled product after recrystallization from ethanol.

$^1$H-NMR (DMSO-d$_6$) $\delta$3.1 ppm (t), 3.85 ppm (m), 7.1 ppm (d), 7.15–7.30 ppm (m), 7.40 ppm (d).

Example 117

N-(2-(3-Methoxy)-phenethyl)-N'-(2-thiazolyl)thiourea

In a manner analogous to Example 105, the product of Example 103 was condensed with 3-methoxyphenethylamine to give the titled product.

$^1$H-NMR (DMSO-d$_6$) $\delta$2.9 (t, Ph, CH$_2$, 2H), 3.75 (s, OCH$_3$, 3H), 3,9 (q, CH$_2$N, 2H), 6.8 (mult. o and p, 4H), 7.1 (d, thiazole, 1H), 7.2 (t, m, 1H), 7.4 (d, thiazole, 1H).

Example 118

N-(2-Phenethyl)-N-[2-(5-methyl)pyridyl]thiourea

A stirred solution of 2-phenethyl isothiocyanate (1.63 g, 10 mmol, 1.5 mL) and 2-amino-5-methylpyridine (1.08 g, 10 mmol) in N-methylpyrrolidinone (20 mL) was heated to 125° C. After 16.5 h, the reaction was cooled to room temperature and poured into ethyl acetate. The organic phase was washed with water (4×) and brine. The organic layer was dried over sodium sulfate, filtered and concentrated. The solid obtained was purified by flash chromatography on silica gel (2% ethyl acetate/dichloromethane) to provide 2.01 g of the titled product (74%). This material was recrystallized from ethyl acetate/hexanes to provide 1.72 g of titled product as a white crystalline solid:

mp 153°–154° C.; IR (KBr,cm$^{-1}$) 3235, 2939, 1613, 1559, 1534, 1493, 1300, 1188;

$^1$H NMR (300 MHZ, DMSO-d$_6$) δ11.56 (br s, 1H), 10.42 (s, 1H), 7.84 (d, J=1.3 Hz, 1H), 7.52 (dd, J=8.5, 2.1 Hz, 1H), 7.31–7.16 (m, 5H), 6.99 (d, J=8.5 Hz, 1H), 3.82–3.75 (m, 2H), 2.87 (t, J=7.0 Hz, 2H), 2.16 (s, 3H);

MS (FD) m/e 271 (M+);

UV (EtOH) 298 nm (ε=14080), 268 nm (ε=21638), 248 nm (ε=15905), 201 nm (ε=18504).

Anal. Calcd for $C_{15}H_{17}N_3S$: C, 66.39; H, 6.31; N, 15.48. Found: C, 66.33; H, 6.26; N, 15.33.

Example 119

N-Methyl-N-(2-phenethyl)-N'-(2-thiazolyl)thiourea

In a manner analogous to Example 105, the product of Example 103 was condensed with N-methylphenethylamine, to give the titled product.

$^1$H-NMR (DMSO-d$_6$) δ2.9 (t,PhCH$_2$,2H), 3.2 (s,NCH$_3$, 3H) 4.0 (t, CH$_2$N, 2H), 6.8 (d, thiazole, 1H), 7.2 (m, thiazole, 1H), 7.3 (mult., C$_6$H$_5$, 5H)

Example 120

N-(2-Indanyl)-N'-(2'-thiazolyl)thiourea

In a manner analogous to Example 105, the product of Example 103 was condensed with 2-indanylamine, to give the titled product.

$^1$H-NMR (DMSO-d$_6$) δ2.4 (q, CH$_2$, 2H), 3.3 (q, CH$_2$, 2H), 4.8 (q, CHN, 1H), 7.0 (d, thiazole, 1H), 7.1–7.3 (mult., C$_6$H$_4$, 4H), 7.4 (d, thiazole, 1H).

Example 121

N-(2-(2-Azido)-phenethyl)-N'-(2-thiazolyl)thiourea

2-Aminophenethylalcohol (Aldrich) (0.8 g, 5.8 mmol) was dissolved in 15 ml H$_2$O at 0° C. Trifluoroacetic acid (1.2 ml ) was added. Sodium nitrite (0.41 g, 0.6 mmol) dissolved in cold water (2.0 ml) was added. The solution was stirred at 0° C. for 10 minutes.

Lithium azide (0.59 g, 12 mmol) in water (2.0 ml) was added slowly. The solution was brought up to ambient temperature. The solution was extracted with diethyl ether (3×50 ml), the organic phase was washed with 1N HCl (aq.) (2×20 ml), dried with Na$_2$SO$_4$, filtered and evaporated.

The residue was dissolved in dichloromethane (20 ml) under a nitrogen atmosphere. The solution was cooled to −10° C. and ethyldiisopropylamine (1.1 ml, 6.4 mmol) was added.

Trifluoromethanesulfonic anhydride (0.87 ml, 5.17 mmol) was added dropwise. The solution was stirred at 0° for 20 minutes and then added to a solution of NH$_3$ (g) in methanol (50 ml sat. at 0° C.) under vigouros stirring. The solution was stirred for 40 minutes at ambient temperature. The solution was diluted with water (100 ml) and extracted with dichloromethane (2×50 ml). Acid-base partitioning [NH$_4$OH (aq)-HCl (aq) [and evaporation gave 2-azidophenethylamine.

In a manner analogous to Examples 104 and 105, the product of Example 103 was condensed with 2-azidophenethylamine, to give the titled product.

$^1$H-NMR (DMSO-d6) δ2.9 (t, PhCH$_2$, 2H), 3.8 (q, CH$_2$N, 2H), 7.0–7.4 (m, Ph-o, m, p, thiazole, 6H).

Example 122

N-(2-(3-Fluoro)phenethyl)-N'-(2-thiazolyl)thiourea

In a manner analogous to Example 105, the product of Example 103 was condensed with 3-fluorophenethylamine to give the titled product.

$^1$H-NMR (DMSO-d6) δ2.9 (t, PhCH$_2$, 2H), 3.8 (q, CH$_2$N, 2H), 7.0–7.4 (m, Ph-o,m,p, thiazole, 6H).

Example 123

N-(2-(Benzenesulfonamide-4-ethyl))-N'-(2-thiazolyl)thiourea

In a manner analogous to Example 105, the product of Example 103 was condensed with 4-(2-aminoethyl)benzenesulfonamide to give the titled product.

$^1$H-NMR (DMSO-d$_6$) δ3.0(t), 3.8(m), 7.1(d), 7.35(m), 7.45(d), 7.80(d).

$^{13}$C-NMR (DMSO-d$_6$) δ178, 162, 143, 142, 137, 129, 126, 112, 45, 34.

Example 124

N-(2-(3,4-Dimethoxy)phenethyl)-N'-(2-thiazolyl)thiourea

In a manner analogous to Example 105, the product of Example 103 was condensed with 3,4-dimethoxyphenethylamine to give the titled product.

$^1$H-NMR (DMSO-d$_6$-CDCl$_3$) δ2.95 (t), 3.70 (t), 3,85 (s), 3.90 (s), 6.80 (s), 6.90 (d), 7.40 (d).

Example 125

N-(Phenylpropan-1-ol-2-yl)-N'-(2-thiazolyl)thiourea

In a manner analogous to Example 105, the product of Example 103 was condensed with norephedrine to give the titled product.

$^1$H-NMR (DMSO-d$_6$) δ0.95 (d), 4.25 (m), 4.95 (d), 7.1–7.5 (m).

Example 126

N-(2-(2-Pridyl)ethyl)-N'-(2-thiazolyl)thiourea

In a manner analogous to Example 105, the product of Example 103 was condensed with 2-(2-aminoethyl)pyridine to give the titled product.

$^1$H-NMR (DMSO-d$_6$) δ3.1 (t), 4.0 (m), 7.1 (d), 7.2–7.4 (m), 7.7 (m), 8.5 (d), 9.8 (s), 11.7 (s).

Example 127

N-(2-(2,5-Dimethoxy)phenethyl)-N'-(2-thiazolyl)thiourea

In a manner analogous to Example 105, the product of Example 103 was condensed with 2,6-dimethoxyphenethylamine to give the titled product.

$^1$H-NMR (CDCl$_3$) δ3.00 (t), 3.73 (s), 3.77 (s), 3.97 (m), 6.70–6.85 (m), 7.24 (d), 10.80 (s).

$^{13}$C-NMR (CDCl$_3$) δ177, 162, 153, 152, 138, 128, 117 112, 111, 111, 56, 56, 46, 30.

Example 128

N-(1-(2phenyl)propanyl)-N'-(2-thiazolyl)thiourea

In a manner analogous to Example 105, the product of Example 103 was condensed with 1-amino-2-phenylpropane to give the titled product.

$^1$H-NMR (DMSO-d6) δ1.20 (d), 3.13 (q), 3.70 (t), 7.09 (d), 7.20–7.50 (m).

Broad peaks δ8.14, 9.33, 9.75 and 10.57.

Example 129

N-(2-(3-Indol)ethyl)-N'-(2-thiazolyl)thiourea

In a manner analogous to Example 105, the product of Example 103 was condensed with tryptamine to give the titled product.

$^1$H-NMR (CDCl$_3$+CD$_3$OD) δ7.68–7.06 (m, 6H, indole, thiazole), 6.84 (d, J=3.7 Hz, 1H, thiazole), 4.02 (t, J=7 Hz, 2H, CH$_2$NH), 3.16 (t, J=6.9 Hz, 2H, CH$_2$).

$^{13}$C-NMR (CDCl$_3$+CD$_3$OD) δ177 (thiazole), 161 (thiazole), 137 (thiazole), 136 (indole), 127 (indole), (indole), 121 (indole), 118 (indole), 117 (indole), 111 (thiazole), 110 (indole), 109 (indole), 46 (CH$_2$), 26 (CH$_2$).

Example 130

N-(2-(2-hydroxyethoxy)ethyl)-N'-(2-thiazolyl)thiourea

In a manner analogous to Example 105, the product of Example 103 was condensed with 2-(2-aminoethoxy)ethanol to give the titled product.

$^1$H-NMR (CDCl$_3$) δ7.34 (d, J=3.4 Hz, 1H, thiazole), 6.84 (d, J=3.4 Hz, 1H, thiazole), 3.96 (t, J=4.9 Hz, 2H, CH$_2$NH), 3.7 6(m, 4H, CH$_2$), 3.66 (t, J=4.3 Hz, 2H, CH$_2$).

$^{13}$C-NMR (CDCl$_3$) δ177.4 (C=S), 161.8 (thiazole), 137.5 (thiazole), 111.2 (thiazole), 72.1, 68.4, 61.5, 44.9.

Example 131

N-(2-(5-Nitropyrid-2-yl)aminoethyl)-N'-(2-thiazolyl)thiourea

In a manner analogous to Example 105, the product of Example 103 was condensed with 2-(2-aminoethylamino)-5-nitropyridine to give the titled product.

$^1$H-NMR (CDCl$_3$+CD$_3$OD) δ8.95 (d, 1H, pyr), 8.12 (dd, 1H, pyr), 7.26 (d, J=3.8 Hz, 1H, thiazole), 6.86 (d, J=3.8 Hz, 1H, thiazole), 6.52 (d, 1H, pyr), 3.99 (t, 2H, CH$_2$NH), 3.78 (t, 2H, CH$_2$).

Example 132

N-(2-(1-Methylpyrrolid-2-yl)ethyl)-N'-(2-thiazolyl)thiourea

In a manner analogous to Example 105, the product of Example 103 was condensed with 2-(2-aminoethyl)-1-methylpyrrolidine to give the titled product.

$^1$H-NMR (CDCl$_3$) δ7.32 (d, J=4 Hz, 1H, thiazole), 6.83 (d, J=3.6 Hz, 1H, thiazole), 3.78 (q, 2H, CH$_2$NH), 3.08 (m, 1H, NCH(CH$_2$)$_2$), 2.34 (s, 3H, N—CH$_3$), 2.16 (m, 2H, NCH$_2$), 2.01 (m, 2H, CH$_2$), 1.7 (m, 4H, pyr).

$^{13}$C-NMR (CDCl$_3$) δ177 (C=S), 161 (thiazole), 137.5 (thiazole), 111.1 (thiazole), 64.1 (pyr), 57.1 (pyr), 43.1 (CH$_2$), 40.6 (CH$_2$), 32.1 (pyr), 30.3 (pyr), 22.2 (pyr).

Example 133

N-(2-(2,4-Dichloro)phenethyl)-N'-(2-thiazolyl)thiourea

In a manner analogous to Example 105, the product of Example 103 was condensed with 2,4-dichlorophenethylamine to give the titled product.

$^1$H-NMR (CDCl$_3$+CD$_3$OD) δ7.40 (d, 1H, thiazole), 7.41 (s, 1H, DClPh), 7.24 (m, 2H, DClPh), 6.87 (d, 1H, thiazole), 3.95 (t, 2H, CH$_2$NH), 3.14 (t, 2H, CH$_2$).

Example 134

N-(1,1-(2-p-hydroxyphenyl)methoxycarbonylethyl)-N'-(2-thiazolyl thiourea

In a manner analogous to Example 105, the product of Example 103 was condensed with tyrosine methylester to give the titled product.

$^1$H-NMR (CDCl$_3$) δ7.25 (d, J=3.3 Hz, 1H, thiazole), 7.02 (d, J=8.2 Hz, 2H, Tyr), 6.82 (d, J=3.4 Hz, 1H, thiazole), 6.74 (d, J=8.2 Hz, 2H, Tyr), 5.29 (t, 1H, CH), 3.73 (s, 3H, CH$_3$), 3.19 (d, 2H, CH$_2$).

$^{13}$C-NMR (CDCl$_3$) δ177.4 (C=S), 171.5 (CO$_2$Me), 161.2 (thiazole), 155.4 (Tyr), 136.9 (thiazole), 130.0 (Tyr), 126.2 (Tyr), 115.0 (Tyr), 111.1 (thiazole), 59.0 (CH), 51.9 (CH$_3$), 3 6.4 (CH$_2$).

Example 135

1-(2-Thiazolyl)-4-(p-hydroxybenzyl)-2-thiohydantoin

The titled produce was obtained as a by product during the preparation of the product described in Example 134.

$^1$H-NMR (CDCl$_3$+CD$_3$oD) δ7.78 (d, 1H, thiazole), 7.50 (d, 1H, thiazole), 7.07 (d, 2H, Tyr), 6.78 (d, 2H, Tyr), 4.50 (t, 1H, CH), 3.15 (m, 2H, CH$_2$).

Example 136

N-(2-trans-phenylcyclopropyl)-N'-2-(thiazolyl)thiourea

In a manner analogous to Example 105 the product of Example 103 was condensed with trans-2-phenylcyclopropylamine to give the titled product.

$^1$H-NMR (CDCl$_3$+CD$_3$OD) δ7.32 (d, J=3.8 Hz, 1H, thiazole), 7.23 (m, 5H, Ph), 3.38 (m, 1H, CHNH), 2.27 (m, 1H, CH), 1.91 (m, 2H, CH$_2$).

$^{13}$C-NMR (CDCl$_3$+CD$_3$OD) δ179.2 (C=S), 161.7 (thiazole), 139.8 (Ph), 137.3 (thiazole), 128.2 (Ph), 126.5 (Ph), 126.0 (Ph), 111.2 (thiazole), 36.1 (CH), 35.1 (CH), 16.1 (CH$_2$).

Example 137

N-(4-Methyl-3-pentenyl)-N'-(2-thiazolyl)thiourea

The starting material, 4-methyl-3-pentenylamine, was prepared from 5-bromo-2-methyl-2-pentene.

4-Methyl-3-pentenylamine

LiN$_3$ (1 g, 20 mmol) was added to a solution of 5-bromo-2-methyl-2-pentene (1.63 g, 10 mmol) in 5 ml DMF. The solution was stirred at room temperature for two days. The reaction mixture was poured into a mixture of hexanes and sat. NH$_4$Cl-solution. The organic phase was washed with sat. NH$_4$Cl-solution, brine and water. After drying, the solvent was removed and the crude azide was reacted with LiAlH$_4$ (380 mg, 10 mmol) in ether at 0° C. After 2 h the reaction was quenched by the addition of 380 μl H$_2$O, 380 μl 15% NaOH-solution and 1.14 ml H$_2$O, respectively. After filtration the solvent was evaporated and the residue was distilled in vacuo to give 0.42 g of the title amine.

B.p. 50° C./40 mm.

$^1$H-NMR (CDCl$_3$) δ1.5 (broad s, 2H), 1.60 (d, 3H), 1.70 (d, 3H), 2.68 (q, 2H), 5.05–5.15 (m, 1H).

$^{13}$C-NMR (CDCl$_3$) δ17.70, 18.39, 25.66, 32.22, 42.03, 121.64, 133.50.

In a manner analogous to Example 105, the product of Example 103 was condensed with 4-methyl-3-pentenylamine to give the titled product.

Mp: 87.5°–88.5° C.

Analyses: Calculated: C 49.76, H 6.26, N 17.41. Found: C 49.35, H 6.20, N 17.15.

$^1$H-NMR (CDCl$_3$) δ1.65 (s, 3H), 1.75 (s, 3H), 2.40 (q, 2H), 3.73 (q, 2H), 5.1–5.25 (m, 1H), 6.83 (d, 1H), 7.29 (d, 1H).

$^{13}$C-NMR (CDCl$_3$) δ17.93, 25.88, 27.31, 45.54, 111.22, 120.40, 135.10, 137.51, 161.94, 177.21.

Example 138

N-(Trans-3-hexenyl)-N'-(2-thiazolyl)thiourea

The starting material, trans-3-hexenylamine, was prepared from trans-3-hexen-1-ol.

Trans-3-hexenylamine

To a stirred solution of trans-3-hexen-1-ol (5.0 g, 0.050 mol), Et$_3$N (7.65 ml, 0.055 mol) and CH$_2$Cl$_2$ (70 ml) at −30° C. was added 4.33 ml (0.055 mol) methanesulfonyl chloride. The solution was stirred at about −20° C. for 2 h. After addition of CH$_2$Cl$_2$, the organic phase was washed with sat. NaHCO$_3$ solution, sat. NH$_4$Cl-solution and water, dried (Na$_2$SO$_4$) and concentrated in vacuo. This gave a crude mesylate which was dissolved in DMF (30 ml) and LiN$_3$ (5 g, 100 mmol) was added. The reaction mixture was stirred overnight and poured into a mixture of ether and brine. The ether phase was washed with brine (×2) and dried (Na$_2$SO$_4$). The ether solution was concentrated to about 100 ml and cooled to 0° C., whereafter 1.9 g (50 mmol) of LiAl$_4$ was added. After 1 h the reaction was quenched with 1.9 ml H$_2$O, 1.9 ml 15% NaOH-solution and 5.7 ml H$_2$O, respectively. After filtration, the solvent was evaporated and the residue was distilled in vacuo to give 2.35 g of the titled amine.

B.p. 34° C./20 mm $^1$H-NMR (CDCl$_3$) δ0.92 –1.05 (m, 3H), 1.75 (broad s, 2H), 1.95–2.20 (m, 4H), 2.68–2.75 (m, 2H), 5.27–5.63 (m, 2H).

$^{13}$C-NMR (CDCl$_3$) δ13.80, 25.55, 36.62, 41.56, 126.10, 134.48.

In a manner analogous to Example 105, the product of Example 103 was condensed with trans-3-hexenylamine to give the titled product.

Mp: 116.0°–117.0° C.

Analyses: Calculated: C 49.76, H 6.26, N 17.41. Found: C 49.6, H 6.3, N 17.4.

$^1$H-NMR (CDCl$_3$) δ0.98 (t, 3H), 2.0–2.1 (m, 2H), 2.41 (q, 2H), 3.76 (q, 2H), 5.4–5.7 (m, 2H), 6.83 (d, 1H), 7.29 (d, 1H), 10.8 (broad s, 1H), 11.35 (broad s, 1H).

$^{13}$C-NMR (CDCl$_3$) δ13.72, 25.65, 45.42, 111.25, 124.97, 135.56, 137.50, 161.95, 177.14.

Example 139

N-[2-(Cyclo-2-penten-1-yl)ethyl]-N'-(2-thiazolyl)thiourea

The starting material 2-(cyclo-2-penten-1-yl)ethylamine was prepared from 2-cyclopenten-1-yl acetic acid.

2-(Cyclo-2-penten-1-yl)ethylamine

2-Cyclopenten-1-ylacetic acid (5 ml, 0.042 mol) was dissolved in ether (100 ml). LiAl$_4$ (2.4 g, 0.063 mol) was added in portions. After the addition, the reaction mixture was stirred for 2 h at room temperature. The reaction mixture was quenched with 2.4 g H$_2$O, 2.4 g 15% NaOH-solution and 7.2 ml H$_2$O, respectively. Filtration and evaporation of the solvent gave 4.45 g of crude 2-(cyclo-2-penten-1-yl)ethanol. This alcohol was transformed to the title amine by a procedure analogous to Example 138.

$^1$H-NMR (CDCl$_3$) δ1.4–1.8 (m, 4H), 2.0–2.15 (m, 1H), 2.2–2.4 (m, 3H), 2.6–2.8 (m, 3H), 5.6–5.8 (m, 2H).

$^{13}$C-NMR (CDCl$_3$) δ29.68, 31.78, 40.00, 40.64, 42.97, 130.29, 134.61.

In a manner analogous to Example 105, the product of Example 103 was condensed with 2-(cyclo-2-penten-1-yl)ethylamine to give the titled product.

Mp: 139.0°–140.0° C.

Analyses: Calculated: C 52.14, H 5.97, N 16.58. Found: C 52.20, H 6.05, N 16.35.

$^1$H-NMR (CDCl$_3$) δ1.42–1.58 (m, 1H), 1.62–1.92 (m, 2H), 2.06–2.45 (m, 3H), 2.72–2.86 (m, 1H), 3.71–3.84 (m, 2H), 5.70–5.80 (m, 2H), 6.85 (d, 1H), 7.32 (d, 1H), 10.9 (broad s, 1H), 10.95 (broad s, 1H).

$^{13}$C-NMR (CDCl$_3$) δ29.71, 32.01, 34.77, 43.23, 44.31, 111.15, 131.19, 134.13, 137.66, 161.99, 177.28.

Example 140

N-(2-(trans-3-pentenyl))-N'-(2-thiazolyl)thiourea

The starting material trans-3-penten-1-ol was prepared by reduction of 3-pentyn-1-ol with lithium aluminium hydride in refluxing tetrahydrofuran and the titled product was then prepared in a manner analogous to Examples 106 and 112

¹H-NMR (250 MHz, CDCl₃) δ7.28 (d, 1H, CH=CH), 6.83 (d, 1H, CH=CH), 5.66–5.38 (m, 2H, trans-CH=CH), 3.67 (q, 2H, CH₂—NH), 2.37 (q, 2H, CH₂—CH=CH), 1.72 (dd, 3H, CH=CH—CH₃).

¹³C-NMR (250 MHz, CDCl₃) δ177, 162, 138, 129, 127, 111, 46, 32, 18.

Mp: 129°–129.5° C.

Anal. Calcd. for C₉H₁₃N₃S₂: C, 47.5; H, 5.7; N, 18.5. Found: C, 47.9; H, 5.8; N, 17.8.

Example 141

N-(2-(cis-3-pentenyl))-N'-(2-thiazolyl)thiourea

The starting material cis-3-penten-1-ol was prepared by reduction of 3-pentyn-1-ol with hydrogen in acetone at about 5 psi for 20 minutes using palladium on calcium carbonate as a catalyst (Lindlar catalyst), and the titled product was then prepared in a manner analogous to Examples 106 and 112.

¹H-NMR (250 MHz, CDCl₃) δ7.30 (d, 1H, CH=CH), 6.83 (d, 1H, CH=CH), 5.73–5.34 (m, 2H, cis-CH=CH), 3.76 (q, 2H, CH₂—NH), 2.48 (q, 2H, CH=CH—CH₂), 1.66 (d, 3H, CH=CH—CH₃).

¹³C-NMR (250 MHz, CDCl₃) δ177, 162, 138, 127, 126, 111, 45, 26.

Mp: 76.5° C.

Example 142

N-(2-(2-Methyl)-phenethyl)-N'-(2-thiazolyl)thiourea

The starting material 1-methylphenethanol was prepared by reduction of o-tolylacetic acid with lithium aluminium hydride in refluxing tetrahydrofuran and the titled product was then prepared analogous to Examples 106 and 112.

Mp: 143°–144° C.

Example 143

N-(2-(3,4,5-trimethoxy)phenethyl)-N'-(2-thiazolyl)thiourea

The starting material 2-(3,4,5-trimethoxy)phenethylamine was prepared by reduction of 3,4,5-trimethoxyphenylacetonitrile with cobalt chloride and sodium borohydride, according to the general method described by L. S. Heinzman in *J. Am. Chem. Soc.* 104, p. 6801 (1982).

3,4,5-Trimethoxybenzonitrile (965 mg, 5 mmole) and cobalt chloride (2,37 g, 10 mmole) were dissolved in methanol (70 ml). To the solution was added sodium borohydride (1.89 g, 50 mmole). After 3 hours, the reaction mixture was filtered through celite, and concentrated to small volume. It was then taken up in chloroform and extracted with 1N HCl (100 ml). The organic phase was discarded. The aqueous solution was basified with aqueous ammonia, and extracted with chloroform. The organic phase was dried over magnesium sulfate, and dried in vacuo to yield 2-(3,4,5-trimethoxy)phenethylamine (427 mg).

¹H-NMR (CDCl₃) δ6.58 (s, 2H, TMPh), 3.85 (m, 8H, 2×MeO, CH₂), 3.82 (s, 3H, OMe), 3.80 (m, 2H, CH₂).

The titled product was then prepared analogous to Example 105.

¹H-NMR (CDCl₃) δ7.26 (d, 1H, thiazole), 6.85 (d, 1H, thiazole), 6.64 (s, 2H, TMPh), 4.84 (d, J=5.7 Hz, 2H, CH₂NH), 3.86 (m, 11H, CH₂, MeO).

¹³C-NMR (CDCl₃) δ177 (C=S), 161 (thiazole), 153 (TMPh), 138 (TMPh), 137 (thiazole), 132 (TMPh), 111 (thiazole), 104.8 (TMPh), 61 (MeO), 56.1 (MeO), 53 (CH₂), 50 (CH₂).

Example 144

N-(2-(2,4-Difluoro)phenethyl)-N'-(2-thiazolyl)thiourea

In a manner analogous to Example 143, using 2,4-difluorophenylacetonitrile, the titled product resulted.

¹H-NMR (CDCl₃) δ7.26 (m, 1H, DFPh), 7.20 (d, 1H, thiazole), 6.80 (d, 1H, thiazole), 6.75 (m, 2H, DFPh), 3.85 (q, 2H, CH₂NH), 3.04 (t, 2H, CH₂).

Example 145

N-(2-(2,6-Difluoro)phenethyl)-N'-(2-thiazolyl)thiourea

In a manner analogous to Example 143, using 2,6-difluorophenylacetonitrile, the titled product resulted.

¹H-NMR (CDCl₃) δ7.23 (d, J=3.8 Hz, 1H, thiazole), 7.26–7.12 (m, 1H, DFPh), 6.86 (m, 2H, DFPh), 6.81 (d, J=3.6 Hz, 1H, thiazole), 3.96 (q, 2H, CH₂NH), 3.11 (t, J=7 Hz, CH₂).

¹³C-NMR (CDCl₃) δ177 (C=S), 164 and 159 (dd, C-F coupling, DFPh), 162 (thiazole), 137 (thiazole), 128 (m, C-F coupling, DFPh), 111 (thiazole), 110.8 (d, C-F coupling, DFPh), 44.5 (CH₂), 21.6 (CH₂).

Example 146

N-(2-(3,4-Methylenedioxy)phenethyl)-N'-(2-thiazolyl)thiourea

In a manner analogous to Example 143, using 3,4-methylenedioxyphenylacetonitrile, the titled product resulted.

¹H-NMR (CDCl₃) δ7.24 (d, 1H, thiazole), 6.80 (m, 3H, Ph, thiazole), 6.74 (s, 1H, Ph), 5.93 (s, 2H, OCH₂O), 3.94 (q, 2H, CH₂NH), 2.93 (t, 2H, CH₂).

¹³C-NMR (CDCl₃) δ177.3 (C=S), 161.6 (thiazole), 148 (Ph), 146 (Ph), 137.4 (thiazole), 132.1 (Ph), 111.1 (thiazole), 109.2 (Ph), 108.2 (Ph), 100.7 (OCH₂O), 47.0 (CH₂), 34.4 (CH₂).

Example 147

N-(2-(4-Trifluoromethyl)phenethyl)-N'-(2-thiazolyl)thiourea

In a manner analogous to Example 143, using 4-trifluoromethylphenylacetonitrile, the titled product resulted.

¹H-NMR (CDCl₃+CD₃OD) δ7.57 (d, J=8.3 Hz, 2H, TFMPh), 7.40 (d, J=8.3 Hz, 2H, TFMPh), 7.19 (d, J=3.7 Hz, 1H, thiazole), 6.83 (d, J=3.7 Hz, 1H, thiazole), 3.95 (t, J=7.2 Hz, 2H, CH₂NH), 3.08 (t, 2H, CH₂).

Example 148

(RS)-N-(2-Methyl-2-(2,6-difluoro)phenethyl)-N'-(2-thiazolyl)thiourea 2,6-Difluorobenzyl cyanide (1.24 ml, 10 mmole) was reacted with sodium hydride (360 mg, 12 mmole) in THF (5 ml) for 2 hour. Then iodomethane was added to the reaction mixture. After 30 min, the reaction mixture was worked up and the product was isolated by silica gel column chromatography. Yield 985 mg (59%).

$^1$H-NMR (CDCl$_3$) δ (Mixture of two stereoisomers) 7.28 (m, 1H, DFPh), 6.98 (m, 2H, DFPh), 4.26 (m, 1H, CH), 1.69 and 1.66 (2×s, 3H, CH$_3$).

In a manner analogous to Example 143, using 2-methyl-2-(2,6-difluoro)phenethylamine, the titled product resulted.

$^1$H-NMR (CDCl$_3$) δ R and S stereomixture), 7.12 (m, 2H, DFPh, thiazole), 6.85 (t, 2H, DFPh), 6.77, 6.76, 6.75, 6.74 (2d, J=3.6 Hz, 1H, thiazole), 4.11 (m, 1H, CH), 4.05–3.65 (m, 2H, CH$_2$), 1.45, 1.42, (2s, 3H, CH$_3$).

Example 149

N-(2-(2-Bromo)-phenethyl)-N'-(2-thiazolyl)thiourea

In a manner analogous to Example 143, using 2-bromophenylacetonitrile, the titled product resulted.

$^1$H-NMR (DMSO-d$_6$) δ2.9 (t, PhCH$_2$, 2H), 3.05 (t, PhCH$_2$, 2H), 3.8 (q, CH$_2$N, 2H), 7.1 (d, thiazole, 1H), 7.15–7.6 (mult. o, m, p, thiazole, 5H).

Example 150

N-(2-(1-Phenyl-1-cyclopropane)ethyl)-N'-(2-thiazolyl)thiourea

In a manner analogous to Example 116, using 1-phenyl-1-cyclopropanecarbonitrile, the titled product resulted.

$^1$H-NMR (CDCl$_3$) δ1.0 (d), 3.8 (d), 6.9 (d), 7.2–7.4 (m), 7.9, 9.5 (NH).

Example 151

N-(2-(2,6-Dimethoxy)phenethyl)-N'-(2-thiazolyl)thiourea

The starting material 2,6-dimethoxyphenethylamine was prepared from 2,6-dimethoxybenzaldehyde. Reaction with nitromethane according to the procedure described in Vogel, *Textbook of Practical Organic Chemistry*, p. 176 (Longman 1978, 4th Ed.) yielded 2,6-dimethoxy-β-nitrostyrene. This compound (1.1 g, 5.3 mmole) was dissolved in diethyl ether/tetrahydrofuran (2:1, 200 ml) and lithium aluminium hydride (0.5 g, 13 mmol) was added in small portions. The mixture was refluxed for 120 minutes and then treated with 0.6 ml H$_2$O, 0.6 ml 15% NaOH (aq) and 1.8 ml H$_2$O. The mixture was filtered and purified by acid-base partitioning (NH$_4$OH (aq) HCl dil. (aq)) and evaporated. The crude product 2,6-dimethoxyphenethylamine was pure enough to be used directly in the following reaction where it was condensed with the product of Example 103, in a manner analogous to Example 105, to give the titled product.

$^1$H-NMR (DMSO-d$_6$) δ2.9 (t, PhCH$_2$, 2H), 3,7 (q, CH$_2$N, 2H), 3.8 (s, OCH$_3$, 6H), 6.7 (d, o, 2H), 7.1 (d, thiazole, 1H), 7.2 (t, p, 1H), 7.3 (d, thiazole, 1H)).

Example 152

N-(2-(3,5-Dimethoxy)phenethyl)-N'-(thiazolyl)thiourea

In a manner analogous to Example 151 the product of Example 103 was condensed with 3,5-dimethoxyphenethylamine, obtained from 3,5-dimethoxybenzaldehyde, to result in the titled product.

$^1$H-NMR (DMSO-d$_6$) δ2.8 (t, PhCH$_2$, 2H), 3.65 (s, OCH$_3$, 6H), 3.7 (q, CH$_2$N, 2H), 6.3 (t, p, 1H), 6.4 (t, o, 2H), 7.1 (d, thiazole, 1H), 7.3 (d, thiazole, 1H).

Example 153

N-(2-(3,5-Dichloro)phenethyl)-N'-(2-thiazolyl)thiourea

In a manner analogous to Example 151, the product of Example 103 was condensed with 3,5-dichlorophenethylamine, obtained from 3,5-dichlorobenzaldehyde.

$^1$H-NMR (DMSO-d$_6$) δ2.9 (t, PhCH$_2$, 2H), 3.8 (q, CH$_2$N, 2H), 7.1 (d, thiazole, 1H), 7.3 (mult. o and p, 3H), 7.4 (d, thiazole, 1H).

Example 154

N-(2-(2,5-Dichloro-6-hydroxy)phenethyl)-N'-(2-thiazolyl)thiourea

In a manner analogous to Example 151, the product of Example 103 was condensed with 2,5-dichloro-6-hydroxylphenethylamine, obtained from 2,5-dichloro-6-hydroxybenzaldehyde.

$^1$H-NMR (CDCl$_3$) δ3.0 (t, PhCH2, 2H), 3.9 (q, CH$_2$N, 2H), 6.9 (d, o, 1H), 7.1 (d, thiazole, 1H), 7.2 (d, p, 1H), 7.3 (d, thiazole, 1H).

Example 155

N-(2,3,6-Trichloro)phenethyl)-N'-(2-thiazolyl)thiourea

In a manner analogous to Example 151, the product of Example 103, was condensed with 2,3,6-trichlorophenethylamine, obtained from 2,3,6-trichlorobenzaldehyde.

$^1$H-NMR (DMSO-d$_6$) δ3.3 (t, PhCH$_2$, 2H), 3.4 (q, CH$_2$N, 2H), 7.1 (d, thiazole, 1H), 7.4 (d, thiazole, 1H), 7.5–7.5 (mult., m and p, 2H).

Example 156

N-(2-(2,3,4-Trifluoro)phenethyl)-N'-(2-thiazolyl)thiourea

In a manner analogous to Example 151, the product of Example 103 was condensed with 2,3,4-trichlorophenethylamine, obtained from 2,3,4-trifluorobenzaldehyde, to result in the titled product.

$^1$H-NMR (CDCl$_3$) δ3.0 (t, PhCH$_2$, 2H), 4.0 (q, CH$_2$N, 2H), 6.8 (d, thiazole, 2H), 6.85–7.0 (mult., m and o, 2H), 7.2 (d, thiazole, 1H).

Example 157

N-(2-(2,3,5-Trichloro)phenethyl)-N'-(2-thiazolyl)thiourea

In a manner analogous to Example 151, the product of Example 103 was condensed with 2,3,5-trichlorophenethylamine, obtained from 2,3,5-trichlorobenzaldehyde.

¹H-NMR (DMSO-d₆) δ3.05 (t, PhCH₂, 2H), 3.9 (q, CH₂N, 2H), 7.1 (d, thiazole, 1H), 7.4 (d, thiazole, 1H), 7.5 (d, o, 1H), 7.7 (d, p, 1H).

Example 158

N-(2-(2,4-Dimethoxy)phenethyl)-N'-(2-thiazolyl)thiourea

In a manner analogous to Example 151, the product of Example 103 was condensed with 2,4-dimethoxyphenethylamine, obtained from 2,4-dimethoxybenzaldehyde.

¹H-NMR (CDCl₃+CD₃OD) δ7.23 (d, J=3.6 Hz, 1H, thiazole), 7.10 (d, J=7.8 Hz, 1H, DMPh), 6.81 (d, 3.6 Hz, 1H, thiazole), 6.44 (s, 1H, DMPh), 6.42 (d, 1H, DMPh), 3.87 (t, 2H, CH₂NH), 3.80 (s, 3H, OMe), 3.79 (s, 3H, OMe), 2.94 (t, 2H, CH₂).

¹³C-NMR (CDCl₃₊CD₃) δ177.3 (C=S), 161.6 (thiazole), 159.7 (DMPh), 158.4 (DMPh), 137.5 (thiazole), 130.9 (DMPh), 119.1 (DMPh ), 110.9 (thiazole), 103.8 (DMPh), 99.3 (DMPh), 55.3 (OMe), 55.1 (OMe), 45.5 (CH₂), 28.7 (CH₂).

Example 159

N-(2-(2,3-Dimethoxy)phenethyl)-N'-(2-thiazolyl)thiourea

In a manner analogous to Example 151, the product of Example 103 was condensed with 2,3-dimethoxyphenethylamine, obtained from 2,3-dimethoxybenzaldehyde.

¹H-NMR (CDCl₃) δ7.23 (d, J=3.7 Hz, 1H, thiazole), 7.02–6.83 (m, 3H, DMPh), 6.79 (d, J=3.6 Hz, 1H, thiazole), 3.99 (q, J=8.9 Hz, 2H, CH₂NH), 3.87 (s, 3H, OMe), 3.86 (s, 3H, OMe), 3.05 (t, 2H, CH₂).

¹³C-NMR (CDCl₃) δ177.3 (C=S), 161.6 (thiazole), 152.6 (DMPh), 147.3 (DMPh), 137.3 (thiazole), 132 (DMPh), 123.7 (DMPh), 122.2 (DMPh), 110.9 (thiazole), 110.8 (DMPh), 60.6 (OMe), 55.5 (OMe), 45.8 (CH₂), 28.9 (CH₂).

Example 160

N-(2-(2,3,5,6-Tetrafluoro)phenethyl)-N'-(2-thiazolyl)thiourea

In a manner analogous to Example 151, the product of Example 103, was condensed with 2,3,5,6-tetrafluorophenethylamine, obtained from 2,3,5,6-tetrafluorobenzaldehyde.

¹H-NMR (CDCl₃+CD₃OD) δ7.24 (d, J=3 Hz, 1H, thiazole), 6.98 (m, H-F coupling, 1H, TFPh), 6.83 (d, J=3 Hz, 1H, thiazole), 3.99 (t, J=6.8 Hz, 2H, CH₂NH), 3.18 (t, J=6.9 Hz, 2H, CH₂).

¹³C-NMR(CDCl₃) δ178.2(C=S), 161.5(thiazole), 147.6(m,TFPh), 143.6(m,TFPh), 137.3(thiazole), 117.6(t, TFPh), 111.1(thiazole), 104.3(t,TFPh), 53.3(CH₂), 43.7(CH₂).

Example 161

N-(2-(2-Methoxy-5-bromo)phenethyl)-N'-(2-thiazolyl)thiourea

In a manner analogous to Example 151, the product of Example 103 was condensed with 2-methoxy-5-bromophenethylamine, obtained from 2-methoxy-5-bromobenzaldehyde.

¹H-NMR (CDCl₃) δ7.34 (m, 3H, MBPh and thiazole), 6.81 (d, J=3.6 Hz, 1H, thiazole), 6.72 (d, J=8.4 Hz, 1H, MBPh), 3.95 (q, 2H, CH₂NH), 3.79 (s, 3H, OMe), 2.98 (t, J=6.8 Hz, 2H, CH₂).

Example 162

N-(2-(2-Ethoxy)phenethyl)-N'-(2-thiazolyl)thiourea

In a manner analogous to Example 151, the product of Example 103, was condensed with 2-ethoxyphenethylamine, obtained from 2-ethoxybenzaldehyde.

¹H-NMR (250 MHz, CDCl₃) δ7.37–7.16 (m, 2H, arom.), 7.22 (d, 1H, CH=CH), 6.91–6.78 (m, 2H, arom), 6.78 (d, 1H, CH=CH), 4.07–3.93 (2×q, 2×2H, CH₂—NH, CH₂—O), 3.04 (t, 2H, Ph—CH₂), 1.42 (t, 3H, OCH₂CH₃).

¹³C-NNR (250 MHz, CDCl₃) δ178, 162, 157, 138, 131, 128, 127, 120, 111, 111, 63 , 46, 30, 15.

Mp: 140° C.

Anal. Calcd. for C₁₄H₁₇N₃OS₂: C, 54.6; H, 5.5; N, 13.7. Found: C, 54.4; H, 5.6; N, 13.3:

Example 163

N-(2-(2,3-Dichloro)phenethyl)-N'-(2-thiazolyl)thiourea

In a manner analogous to Example 151, the product of Example 103 was condensed with 2,3-dichlorophenethylamine, obtained from 2,3-dichlorobenzaldehyde.

¹H-NMR (250 MHz, DMSO) δ7.55 (d, 1H, CH=CH), 7.42–7.32 (m, 3H, arom), 7.12 (d, 1H, CH=CH), 3.86 (q, 2H, CH₂—NH), 3.12 (t, 2H, Ph—CH₂).

¹³C-NMR (250 MHz, DMSO) δ178, 162, 138, 130, 129, 128, 112, 44, 33.

Example 164

N-[2-(4-chlorothenyl)ethyl]-N'-[2-(4,5-dimethyl)thiazolyl]

A solution of 1-[(2-[4,5-dimethyl]thiazolyl)thiocarbamoyl]imidazole (10 mmol) and 2-(4-chlorophenyl)ethylamine (1.55 g, 10 mmol) in N,N-dimethylformamide (30 mL) was stirred at 90° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 2.44 g (75%) of the titled product.

IR (KBr, cm⁻¹) 3170, 3024, 1550, 1510, 1260, 1212, 708;

¹H NMR (300 MHz, DMSO-d₆) δ11.45 (br s, 1H), 9.8 (br s, 1H), 7.35 (d, J=8 Hz, 2H), 7.3 (d, J=8 Hz, 2H), 3.8 (m, 2H), 2.85 (t, J=7 Hz, 2H), 2.2 (s, 3H), 2.05 (s, 3H);

MS (FD) m/e 326 (M⁺);

UV (EtOH) 297 nm (e=17467), 257 nm (e=10021), 219 nm (e=16075, 201 nm (e=22380)).

Anal. Calcd for C₁₄H₁₆N₃S₂Cl: Theory: C, 51.60; H, 4.95; N, 12.89. Found: C, 51.70; H, 5.07; N, 13.08.

Example 165

1-[(2-naptho[1,2]thiazolyl)thiocarbamoyl]imidazole

A solution of 1,1'-thiocarbonyldiimidazole (1.8 g, 20 mmol) and 2-aminonaptho[1,2]thiazole (2.0 g, 20 mmol) in acetonitrile (150 mL) was stirred at 65° C. for 24 h. The resulting precipitate was collected by filtration to provide 1.69 g (46%) of the titled product.

IR (KBr, cm$^{-1}$) 3148, 2670, 1465, 736;

$^1$H NMR (300 MHz, DMSO-d$_6$) δ9.2 (s, 1H) 8.85 (s, 1H), 8.65 (d, J=8 Hz, 1H), )8.2 (br s, 1H), 8.0–7.3 (m, 5H);

MS (FD) m/e 309 (M$^+$-H);

UV (EtOH) 383 nm (ε=8297), 244 nm (ε=15160), 226 nm (ε=17126).

Anal. Calcd for C$_{15}$H$_{10}$N$_4$S$_2$: Theory: C, 58.04; H, 3.25; N, 18.05. Found: C, 58.13; H, 3.21; N, 18.03.

Example 166

N-[2-phenylethyl]-N'-[2-naptho[1,2]thiazolyl]thiourea

A solution of 1-[(2-naptho[1,2]thiazolyl)thiocarbamoyl] imidazole (1.6 g, 5 mmol) and 2-phenylethylamine (0.62 g, 5.2 mmol) in N,N-dimethylformamide (20 mL) was stirred at 90° C. for 1 h, the reaction was cooled to room temperature and the solvent removed in vacuo. The residue was crystallized from ethyl acetate to provide 1.5 g (82%) of the titled product:

IR (KBr, cm$^{-1}$) 3171, 3027, 1581, 1521, 1213, 695;

$^1$H NMR (300 MHz, DMSO-d$_6$) δ11.7 (br s, 1H), 9.9 (br s, 1H), 8.25 (d, J=8 Hz, 1H), 8.0 (d, J=8 Hz, 2H), 7.8 (d, J=8 Hz, 1H), 7.6–7.2 (m, 7H), 3.95 (m, 2H), 3.05 (t, J=7 Hz, 2H);

MS (FD) m/e 364 (M$^+$);

UV (EtOH) 340 nm (ε=23922), 325 nm (ε=19262), 313 nm (ε=20808), 245 nm (ε=39665), 209 nm (ε=36141).

Anal. Calcd for C$_{20}$H$_{17}$N$_3$S$_2$: Theory: C, 66.09; H, 4.71; N, 11.56. Found: C, 65.86; H, 4.84; N, 11.48.

Example 167

1-[(2-[4-methyl]thiazolyl)thiocarbamoyl]imidazole

A solution of 1,1'-thiocarbonyldiimidazole (13.37 g, 75 mmol) and 2-amino-4-methylthiazole (8.55 g, 75 mmol) in acetonitrile (150 mL) was stirred at room temperature for 24 h. The resulting precipitate was collected by filtration to provide 14.22 g (85%) of the titled product:

IR (KBr, cm$^{-1}$) 3179, 2558, 1455, 1217, 737;

$^1$H NMR (300 HHz, DMSO-d$_6$) δ8.55 (s, 1H) 7.9 (s, 1H), 7.05 (s, 1H), ), 6.9 (s, 1H), 2.3 (s, 3H);

MS (FD) m/e 224 (M$^+$-H);

UV (EtOH) 359 nm (ε=10749), 291 nm (ε=8720), 202 nm (ε=20498).

Anal. Calcd for C$_8$H$_8$N$_4$S$_2$: Theory: C, 42.84; H, 3.59; N, 24.98. Found: C, 42.90; H, 3.54; N, 24.89.

Example 168

N-(2-[1-Cyclohexenyl]ethyl)-N'-[2-(4-methyl)thiazolyl]thiourea

A solution of 1-[(2-[4-methyl]thiazolyl)thiocarbamoyl] imidazole (2.24 g, 10 mmol) and 2-(1-cyclohexenyl)ethylamine (1.25 g, 10 mmol) in N,N-dimethylformamide (25 mL) was stirred at 90° C. for 4 h, the reaction was cooled to room temperature and the solvent removed in vacuo. The residue was crystallized from ethyl acetate to provide 2.4 g (86%) of the titled product:

IR (KBr, cm$^{-1}$) 3177, 2918, 1565, 1505, 1202, 717;

$^1$H NMR (300 MHz, DMSO-d$_6$) δ11.55 (br s, 1H), 9.85 (br s, 1H), 6.65 (s, 1H), 5.45 (s, 1H), 3.65 (m, 2H), 2.25 (m, 5H), 1.9 (m, 4H), 1.55 (m, 4H);

MS (FD) m/e 281 (M$^+$);

UV (EtOH) 291 nm (ε=19178), 257 nm (ε=9837), 201 nm (ε=16247).

Anal. Calcd for C$_{13}$H$_{19}$N$_3$S$_2$: Theory: C, 55.48; H, 6.80; N, 14.93. Found: C, 55.40; H, 6.82; N, 14.77.

Example 169

N-[2-(2-chlorophenyl)ethyl]-N'-[2-(4-methyl)thiazolyl]thiourea

A solution of 1-[(2-[4-methyl]thiazolyl)thiocarbamoyl] imidazole (2.24 g, 10 mmol) and 2-(2-chlorophenyl)ethylamine (1.56 g, 10 mmol) in N,N-dimethylformamide (25 mL) was stirred at 90° C. for 1.5 h, the reaction was cooled to room temperature and the solvent removed in vacuo. The residue was crystallized from ethyl acetate to provide 2.4 g (77%) of the titled product:

IR (KBr, cm$^{-1}$) 3163, 3012, 1584, 1214, 754, 706;

$^1$H NMR (300 MHz, DMSO-d$_6$) δ11.6 (br s, 1H), 9.8 (br s, 1H), 7.5–7.2 (m, 4H), 6.65 (s, 1H), 3.85 (m, 2H), 3.05 (t, J=7 Hz, 2H), 2.2 (s, 3H);

MS (FD) m/e 311 (M$^+$);

UV (EtOH) 292 nm (ε=18641), 257 nm (ε=10471), 202 nm (ε=24729).

Anal. Calcd for C$_{13}$H$_{14}$N$_3$S$_2$Cl: Theory: C, 50.07; H, 4.52; N, 13.47. Found: C, 49.99; H, 4.56; N, 13.45.

Example 170

N-[2-(3-chlorophenyl)ethyl]-N'-[2-(4-methyl)thiazolyl]thiourea

A solution of 1-[(2-[4-methyl]thiazolyl)thiocarbamoyl] imidazole (2.24 g, 10 mmol) and 2-(3-chlorophenyl)ethylamine (1.56 g, 10 mmol) in N,N-dimethylformamide (25 mL) was stirred at 90° C. for 1.5 h, the reaction was cooled to room temperature and the solvent removed in vacuo. The residue was crystallized from ethyl acetate to provide 2.67 g (86%) of the titled product:

IR (KBr, cm$^{-1}$) 3171, 3016, 1581, 1214, 761, 713;

$^1$H NMR (300 MHz, DMSO-d$_6$) δ11.6 (br s, 1H), 9.85 (br s, 1H), 7.4–7.2 (m, 4H), 6.65 (s, 1H), 3.85 (m, 2H), 2.95 (t, J=7 Hz, 2H), 2.2 (s, 3H);

MS (FD) m/e 311 (M$^+$);

UV (EtOH) 293 nm (ε=18976), 257 nm (ε=10523), 202 nm (ε=27048).

Anal. Calcd for C$_{13}$H$_{14}$N$_3$S$_2$Cl: Theory: C, 50.07; H, 4.52; N, 13.47. Found: C, 49.94; H, 4.48; N, 13.37.

Example 171

N-[2-(4-chlorophenyl)ethyl]-N'-[2-(4-methyl)thiazolyl]thiourea

A solution of 1-[(2-[4-methyl]thiazolyl)thiocarbamoyl] imidazole (2.24 g, 10 mmol) and 2-(4-chlorophenyl)ethylamine (1.56 g, 10 mmol) in N,N-dimethylformamide (25 mL) was stirred at 90° C. for 1.5 h, the reaction was cooled to room temperature and the solvent removed in vacuo. The residue was crystallized from ethyl acetate to provide 2.52 g (81%) of the titled product:

IR (KBr, cm$^{-1}$) 3170, 3022, 1562, 1215, 744, 709;

$^1$H NMR (300 MHz, DMSO-d$_6$) δ11.6 (br s, 1H), 9.85 (br s, 1H), 7.38 (d, J=8 Hz, 2H), 7.30 (d, J=8 Hz, 2H), 6.65 (s, 1H), 3.8 (m, 2H), 2.9 (t, J=7 Hz, 2H), 2.18 (s, 3H);

MS (FD) m/e 311 (M$^+$);

UV (EtOH) 292 nm ($\epsilon$=16470), 257 nm ($\epsilon$=9506), 219 nm ($\epsilon$=13695), 201 nm ($\epsilon$=20563).

Anal. Calcd for $C_{13}H_{14}N_3S_2Cl$: Theory: C, 50.07; H, 4.52; N, 13.47. Found: C, 49.94; H, 4.55; N, 13.58.

Example 172

N-[2-(2-methoxyphenyl)ethyl]-N'-[2-(4-methyl)thiazolyl]thiourea

A solution of 1-[(2-[4-methyl]thiazolyl)thiocarbamoyl]imidazole (2.24 g, 10 mmol) and 2-(2-methoxyphenyl)ethylamine (1.51 g, 10 mmol) in dimethylformamide (25 mL) was stirred at 90° C. for 2 h, the reaction was cooled to room temperature and the solvent removed in vacuo. The residue was crystallized from ethyl acetate to provide 2.2 g (73%) of the titled product:

IR (KBr, cm$^{-1}$) 3173, 3024, 1568, 1246, 1206, 750, 694;

$^1$H NMR (300 MHz, DMSO-d$_6$) $\delta$11.55 (br s, 1H), 9.85 (br s, 1H), 7.2–6.8 (m, 4H), 6.65 (s, 1H), 3.75 (m, 5H), 2.9 (t, J=7 Hz, 2H), 2.18 (s, 3H);

MS (FD) m/e 307 (M$^+$);

UV (EtOH) 291 nm ($\epsilon$=18637), 259 nm ($\epsilon$=10786), 202 nm ($\epsilon$=25565).

Anal. Calcd for $C_{14}H_{17}N_3OS_2$: Theory: C, 54.70; H, 5.57; N, 13.67. Found: C, 54.68; H, 5.50; N, 13.46.

Example 173

N-[2-(3-methoxyphenyl)ethyl]-N'-[2-(4-methyl)thiazolyl]thiourea

A solution of 1-[(2-[4-methyl]thiazolyl)thiocarbamoyl]imidazole (2.24 g, 10 mmol) and 2-(3-methoxyphenyl)ethylamine (1.51 g, 10 mmol) in N,N-dimethylformamide (25 mL) was stirred at 90° C. for 3.5 h, the reaction was cooled to room temperature and the solvent removed in vacuo. The residue was crystallized from ethyl acetate to provide 2.73 g (89%) of the titled product:

IR (KBr, cm$^{-1}$) 3170, 3029, 1586, 1213, 749, 691;

$^1$H NMR (300 MHz, DMSO-d$_6$) $\delta$11.55 (br s, 1H), 9.9 (br s, 1H), 7.2–6.8 (m, 4H), 6.65 (s, 1H), 3.8 (m, 2H), 3.72 (s, 3H), 2.85 (t, J=7 Hz, 2H), 2.18 (s, 3H);

MS (FD) m/e 307 (M$^+$);

UV (EtOH) 292 nm ($\epsilon$=16935), 258 nm ($\epsilon$=9604), 202 nm ($\epsilon$=27197).

Anal. Calcd for $C_{14}H_{17}N_3OS_2$: Theory: C, 54.70; H, 5.57; N, 13.67. Found: C, 54.97; H, 5.58; N, 13.60.

Example 174

N-[2-(4-methoxyphenyl)ethyl]-N'-[2-(4-methyl)thiazolyl]thiourea

A solution of 1-[(2-[4-methyl]thiazolyl)thiocarbamoyl]imidazole (2.24 g, 10 mmol) and 2-(4-methoxyphenyl)ethylamine (1.51 g, 10 mmol) in N,N-dimethylformamide (25 mL) was stirred at 90° C. for 3 h, the reaction was cooled to room temperature and the solvent removed in vacuo. The residue was crystallized from ethyl acetate to provide 2.35 g (76%) of the titled product:

IR (KBr, cm$^{-1}$) 3171, 3009, 1565, 1511, 1218, 720, 514;

$^1$H NMR (300 MHz, DMSO-d$_6$) $\delta$11.55 (br s, 1H), 9.9 (br s, 1H), 7.2 (d, J=8 Hz, 2H), 6.9 (d, J=8 Hz, 2H), 6.65 (s, 1H), 3.8 (m, 2H), 3.75 (s, 3H), 2.85 (t, J=7 Hz, 2H), 2.18 (s, 3H);

MS (FD) m/e 307 (M$^+$);

UV (EtOH) 292 nm ($\epsilon$=18700), 258 nm ($\epsilon$=11165), 223 nm ($\epsilon$=14043), 201 nm ($\epsilon$=25520).

Anal. Calcd for $C_{14}H_{17}N_3OS_2$: Theory: C, 54.70; H, 5.57; N, 13.67. Found: C, 54.62; H, 5.55; N, 13.69.

Example 175

N-[2-(4-methylphenyl)ethyl]-N'-[2-(4-methyl)thiazolyl]thiourea

A solution of 2-(4-methylphenyl)ethyl isothiocyanate (1.0 g, 5.64 mmol) and 2-amino-4-methylthiazole (0.644 g, 5.64 mmol) in N,N-dimethylformamide (20 mL) was heated to 90° C. for 24 h. The solvent was removed in vacuo. The resultant solid was recrystallized from ethyl acetate to provide 0.67 g (41%) of the titled product as a white solid:

IR (KBr, cm$^{-1}$) 3170, 3020, 1562, 1507, 1203, 986;

$^1$H NMR (300 MHz, DMSO-d$_6$) $\delta$11.55 (br s, 1H), 9.9 (br s, 1H), 7.18 (d, J=8 Hz, 2H), 7.18 (d, J=8 Hz, 2H), 6.65 (s, 1H), 3.8 (m, 2H), 2.85 (t, J=7 Hz, 2H), 2.26 (s, 3H), 2.18 (s, 3H);

MS (FD) m/e 291 (M$^+$);

UV (EtOH) 292 nm ($\epsilon$=18863), 257 nm ($\epsilon$=10889), 202 nm ($\epsilon$=21164).

Anal. Calcd for $C_{14}H_{17}N_3S_2$: Theory: C, 57.70; H, 5.88; N, 14.42. Found: C, 57.83; H, 5.90; N, 14.36.

Example 176

N-[2-(2-methoxyphenyl)ethyl]-N'-[2-(5-chloro)thiazolyl]thiourea

A solution of 1-[(2-[5-chloro]thiazolyl)thiocarbamoyl]imidazole (1.22 g, 5.0 mmol) and 2-(2-methoxyphenyl)ethylamine (0.77 g, 5.0 mmol) in N,N-dimethylformamide (20 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 0.86 g (53%) of the titled product:

mp 152°–156° C.;

IR (KBr, cm$^{-1}$) 3313, 2835, 1608, 1527, 1514, 1441, 1352, 1244, 1040;

$^1$H NMR (300 MHz, DMSO-d$_6$) $\delta$11.55 (br s, 1H), 8.4 (br s, 1H), 7.4 (s, 1H), 7.2–6.8 (m, 4H), 3.74 (s, 3H), 3.68 (m, 2H), 2.8 (t, J=7 Hz, 2H);

MS (FD) m/e 327 (M$^+$);

UV (EtOH) 295 nm ($\epsilon$=14366), 261 nm ($\epsilon$=12558), 203 nm ($\epsilon$=31267).

Example 177

N-[2-(3-methoxyphenyl)ethyl]-N'-[2-(5-chloro)thiazolyl]thiourea

A solution of 1-[(2-[5-chloro]thiazolyl)thiocarbamoyl]imidazole (1.22 g, 5.0 mmol) and 2-(3-methoxyphenyl)ethylamine (0.77 g, 5.0 mmol) in N,N-dimethylformamide (20 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 0.86 g (53%) of the titled product:

mp 106°–107° C.;

IR (KBr, cm$^{-1}$) 3334, 2826, 1611, 1517, 1332, 1259, 1156, 1051, 777;

$^1$H NMR (300 MHz, DMSO-d$_6$) δ11.6 (br s, 1H), 8.4 (br s, 1H), 7.4 (s, 1H), 7.18 (m, 1H), 6.77 (m, 3H), 3.7 (m, 5H), 2.8 (t, J=7 Hz, 2H);

MS (FD) m/e 327 (M$^+$);

UV (EtOH) 295 nm (ε=13695), 260 nm (ε=11987), 203 nm (ε=32295).

Anal. Calcd for C$_{13}$H$_{14}$N$_3$OS$_2$Cl: Theory: C, 47.63; H, 4.30; N, 12.81. Found: C, 47.75; H, 4.41; N, 12.65.

Example 178

N-[2-(4-methoxyphenyl)ethyl]-N'-[2-(5-chloro)thiazolyl]thiourea

A solution of 1-[(2-[5-chloro]thiazolyl)thiocarbamoyl]imidazole (1.22 g, 5.0 mmol) and 2-(4-methoxyphenyl)ethylamine (0.77 g, 5.0 mmol) in N,N-dimethylformamide (20 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 1.2 g (74%) of the titled product:

mp 156°14 158° C.;

IR (KBr, cm$^{-1}$) 3315, 2934, 1601, 1511, 1320, 1243, 1180, 1034, 745;

$^1$H NMR (300 MHz, DMSO-d$_6$) δ11.6 (br s, 1H), 8.4 (br s, 1H), 7.4 (s, 1H), 7.1 (d, J=8 Hz, 2H), 6.8 (d, J=8 Hz, 2H), 3.67 (s, 3H), 3.63 (m, 2H), 2.7 (t, J=7 Hz, 2H);

MS (FD) m/e 327 (M$^+$);

UV (EtOH) 295 nm (ε=13569), 260 nm (ε=12490), 223 nm (ε=18432), 202 nm (ε=28264).

Anal. Calcd for C$_{13}$H$_{14}$N$_3$OS$_2$Cl: Theory: C, 47.63; H, 4.30; N, 12.81. Found: C, 47.59; H, 4.34; N, 12.53.

Example 179

N-[2-(1-cyclohexenyl)ethyl]-N'-[2-(5-chloro)thiazolyl]thiourea

A solution of 1-[(2-[5-chloro]thiazolyl)thiocarbamoyl]imidazole (1.22 g, 5.0 mmol) and 2-(1-cyclohexenyl)ethylamine (0.645 g, 5.0 mmol) in N,N-dimethylformamide (20 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the residue recrystallized from methylene chloride to provide 0.83 g (55%) of the titled product:

mp 145°–147° C.;

IR (KBr, cm$^{-1}$) 3167, 2929, 1564, 1488, 1230, 1183, 1098, 1030, 685;

$^1$H NMR (300 MHz, DMSO-d$_6$) δ11.6 (br s, 1H), 8.4 (br s, 1H), 7.4 (s, 1H), 5.4 (s, 1H), 3.5 (m, 2H), 2.15 (t, J=7 Hz, 2H), 1.9 (m, 4H), 1.5 (m, 4H);

MS (FD) m/e 301 (M$^+$);

UV (EtOH) 295 nm (ε=14231), 259 nm (ε=11275), 204 nm (ε=20953).

Anal. Calcd for C$_{12}$H$_{16}$N$_3$S$_2$Cl: Theory: C, 47.75; H, 5.34; N, 13.92. Found: C, 47.90; H, 5.47; N, 14.21.

Example 180

5-Benzyl-3-phenyl-2-thiohydantoin

A solution of DL-phenylalanine (1.65 g, 10 mmol), methyl N-phenyldithiocarbamate (1.85 g, 10 mmol), and triethylamine (1.4 mL, 10 mmol) in ethanol (30 mL) was heated at reflux for 5 h, the mixture was cooled to room temperature and the solvent removed in vacuo. The residue was dissolved in ethyl acetate, washed with 1N aqueous HCl and water. The organic layer was concentrated and the residue recrystallized form ethanol to provide 2.48 g (88%) of the titled product:

mp 187°–189° C.;

MS (FD) m/e 282 (M$^+$).

Example 181

1-[(2-[5-bromo]thiazolyl)thiocarbamoyl]imidazole

A solution of 1,1'-thiocarbonyldiimidazole (9.9 g, 50 mmol) and 2-amino-5-bromothiazole (8.95 g, 50 mmol) in acetonitrile (200 mL) was stirred at 50° C. for 24 h. The resulting precipitate was collected by filtration to provide 5.38 g (37%) of the titled product:

$^1$H NMR (300 MHz, DMSO-d$_6$) δ9.3 (s, 1H), 8.25 (s, 1H), 7.63 (s, 1H), 7.43 (s, 1H);

MS (FD) m/e 288, 290 (M$^+$).

Example 182

N-[2-(2-chlorophenyl)ethyl]-N'-[2-(5-bromo)thiazolyl]thiourea

A solution of 1-[(2-[5-bromo]thiazolyl)thiocarbamoyl]imidazole (0.72 g, 2.5 mmol) and 2-(2-chlorophenyl)ethylamine (0.40 d, 2.5 mmol) in N,N-dimethylformamide (15 mL) was stirred at 100 ° C. for 1 h. The reaction was cooled to room temperature, poured into ethyl acetate, washed with water, 1N aqueous HCl, water, saturated sodium bicarbonate, and brine. The organic layer was concentrated and the residue purified by chromatography on silica gel to provide 0.06 g (5%) of the titled product:

IR (KBr, cm$^{-1}$) 3318, 2926, 1562, 1512, 1257, 1177, 1052, 749, 687;

$^1$H NMR (300 MHz, DMSO-d$_6$) δ11.6 (br s, 1H), 8.4 (br s, 1H), 7.4–7.0 (m, 5H), 3.8 (m, 2H), 2.9 (t, J=7 Hz, 2H);

MS (FD) m/e 375, 377 (M$^+$);

UV (EtOH) 291 nm (ε=15522), 258 nm (ε=11594), 202 nm (ε=28572).

Example 183

N-[2-(3-chlorophenyl)ethyl]-N'-[2-(5-bromo)thiazolyl]thiourea

A solution of 1-[(2-[5-bromo]thiazolyl)thiocarbamoyl]imidazole (0.72 g, 2.5 mmol) and 2-(3-chlorophenyl)ethylamine (0.40 g, 2.5 mmol) in N,N-dimethylformamide (15 mL) was stirred at 100° C. for 1 h. The reaction was cooled to room temperature, poured into ethyl acetate, washed with water, 1N aqueous HCl, water, saturated sodium bicarbonate, and brine. The organic layer was concentrated and the residue purified by chromatography on silica gel to provide 0.36 g (38%) of the titled product:

mp 141°–145° C.;

IR (KBr, cm$^{-1}$) 3168, 3019, 1568, 1514, 1331, 1251, 1189, 787, 686;

$^1$H NMR (300 MHz, DMSO-d$_6$) δ11.6 (br s, 1H), 8.4 (br s, 1H), 7.44 (s, 1H), 7.4–7.2 (m, 4H), 3.7 (m, 2H), 2.8 (t, J=7 Hz, 2 H);

MS (FD) m/e 377, 379 (M$^+$);

UV (EtOH) 296 nm (ε=10140), 259 nm (ε=8392), 201 nm (ε=23984).

Example 184

N-[2-(4-chlorothenyl)ethyl]-N'-[2-(5-bromo)thiazolyl]thiourea

A solution of 1-[(2-[5-bromo]thiazolyl)thiocarbamoyl] imidazole (0.72 g, 2.5 mmol) and 2-(4-chlorophenyl)ethylamine (0.40 g, 2.5 mmol) in N,N-dimethylformamide (15 mL) was stirred at 100° C. for 1 h. The reaction was cooled to room temperature, poured into ethyl acetate, washed with water, 1N aqueous HCl, water, saturated sodium bicarbonate, and brine. The organic layer was concentrated and the residue purified by chromatography on silica gel to provide 0.32 g (34%) of the titled product:

mp 147°–150° C.;

IR (KBr, cm$^{-1}$) 3170, 3020, 1608, 1507, 1348, 1180, 745, 642;

$^1$H NMR (300 MHz, DMSO-d$_6$) δ11.6 (br s, 1H), 8.4 (br s, 1H), 7.44 (s, 1H), 7.3 (d, J=8 Hz, 2H), 7.2 (d, J=8 Hz, 2H), 3.7 (m, 2H), 2.8 (t, J=7 Hz, 2H);

MS (FD) m/e 377, 379 (M$^+$);

UV (EtOH) 296 nm (ε=14604), 259 nm (ε=12656), 201 nm (ε=28845).

Example 185

N-[2-(2-methoxyphenyl)ethyl]-N'-[2-(5-bromo)thiazolyl]thiourea

A solution of 1-[(2-[5-bromo]thiazolyl)thiocarbamoyl] imidazole (0.72 g, 2.5 mmol) and 2-(2-methoxyphenyl)ethylamine (0.41 g, 2.5 mmol) in N,N-dimethylformamide (15 mL) was stirred at 100° C. for 1 h. The reaction was cooled to room temperature, poured into ethyl acetate, washed with water, 1N aqueous HCl, water, saturated sodium bicarbonate, and brine. The organic layer was concentrated and the residue purified by chromatography on silica gel to provide 0.38 g (41%) of the titled product:

IR (KBr, cm$^{-1}$) 3164, 2960, 1563, 1513, 1241, 1182, 1030, 757, 682;

$^1$H NMR (300 MHz, DMSO-d$_6$) δ11.6 (br s, 1H), 8.4 (br s, 1H), 7.43 (s, 1H), 7.4–7.0 (m, 4H), 3.73 (s, 3H), 3.7 (m, 2H), 2.9 (t, J=7 Hz, 2H);

MS (FD) m/e 371, 373 (M$^+$);

UV (EtOH) 291 nm (ε=16746), 261 nm (ε=13112), 202 nm (ε=31492).

Example 186

N-[2-(3-methoxythenyl)ethyl]-N'-[2-(5-bromo)thiazolyl]thiourea

A solution of 1-[(2-[5-bromo]thiazolyl)thiocarbamoyl] imidazole (0.72 g, 2.5 mmol) and 2-(3-methoxyphenyl)ethylamine (0.41 g, 2.5 mmol) in N,N-dimethylformamide (15 mL) was stirred at 100° C. for 1 h. The reaction was cooled to room temperature, poured into ethyl acetate, washed with water, 1N aqueous HCl, water, saturated sodium bicarbonate, and brine. The organic layer was concentrated and the residue purified by chromatography on silica gel to provide 0.53 g (57%) of the titled product:

IR (KBr, cm$^{-1}$) 3174, 1558, 1510, 1339, 1238, 1175, 1041, 785, 688;

$^1$H NMR (300 MHz, DMSO-d$_6$) δ11.6 (br s, 1H), 8.4 (br s, 1H), 7.44 (s, 1H), 7.3–6.8 (m, 4H), 3.7 (s, 3H), 3.7 (m, 2H), 2.9 (t, J=7 Hz, 2H);

MS (FD) m/e 371, 373 (M$^+$);

UV (EtOH) 294 nm (ε=15068), 260 nm (ε=12248), 202 nm (ε=35594).

Example 187

N-[2-(4-methoxyphenyl)ethyl]-N'-[2-(5-bromo)thiazolyl]thiourea

A solution of 1-[(2-[5-bromo]thiazolyl)thiocarbamoyl] imidazole (0.72 g, 2.5 mmol) and 2-(3-methoxyphenyl)ethylamine (0.41 g, 2.5 mmol) in N,N-dimethylformamide (15 mL) was stirred at 100° C. for 1 h. The reaction was cooled to room temperature, poured into ethyl acetate, washed with water, 1N aqueous HCl, water, saturated sodium bicarbonate, and brine. The organic layer was concentrated and the residue purified by chromatography on silica gel to provide 0.42 g (45%) of the tilted product:

IR (KBr, cm$^{-1}$) 3170, 1558, 1512, 1343, 1246, 1163, 1082, 824;

$^1$H NMR (300 MHz, DMSO-d$_6$) δ11.6 (br s, 1H), 8.4 (br s, 1H), 7.44 (s, 1H), 7.1 (d, J=8 Hz, 2H), 6.8 (d, J=8 Hz, 2H), 3.67 (s, 3H), 3.63 (m, 2H), 2.9 (t, J=7 Hz, 2H);

MS (FD) m/e 371, 373 (M$^+$);

UV (EtOH) 295 nm (ε=15314), 260 nm (ε=13349), 222 nm (ε=19619), 202 nm (ε=30379).

Example 188

N-[2-(1-cyclohexenyl)ethyl]-N'-[2-(5-bromo)thiazolyl]thiourea

A solution of 1-[(2-[5-bromo]thiazolyl)thiocarbamoyl] imidazole (0.72 g, 2.5 mmol) and 2-(1-cyclohexenyl)ethylamine (0.32 g, 2.5 mmol) in N,N-dimethylformamide (15 mL) was stirred at 100° C. for 1 h. The reaction was cooled to room temperature, poured into ethyl acetate, washed with water, 1N aqueous HCl, water, saturated sodium bicarbonate, and brine. The organic layer was concentrated and the residue recrystallized from methylene chloride to provide 0.157 g (18%) of the titled product:

IR (KBr, cm$^{-1}$) 3170, 2928, 1559, 1510, 1478, 1344, 1228, 1182, 1096, 834;

$^1$H NMR (300 MHz, DMSO-d$_6$) δ11.6 (br s, 1H), 8.3 (br s, 1H), 7.4 (s, 1H), 5.4 (s, 1H), 3.5 (m, 2H), 2.15 (t, J=7 Hz, 2H), 1.9 (m, 4H), 1.5 (m, 4H);

MS (FD) m/e 345, 347 (M$^+$);

UV (EtOH) 295 nm (ε=15533), 259 nm (ε=11792), 201 nm (ε=21261).

Anal. Calcd for $C_{12}H_{16}N_3S_2Br$: Theory: C, 41.62; H, 4.66; N, 12.13. Found: C, 41.87; H, 4.91; N, 12.21.

Example 189

N-[2-(1-Cyclohexenyl)ethyl]-N'-[2-(5-bromo)pyridyl]thiourea

A stirred solution of 2-(1-cyclohexenyl)ethyl isothiocyanate (1.67 g, 10 mmol) and 2-amino-5-bromopyridine 1.73 g, 10 mmol) in N-methylpyrrolidinone (20 mL) was heated to 100° C. After 17 h, the reaction was cooled to room temperature and poured into ethyl acetate. The organic phase was washed with 1N hydrochloric acid, water (2×) and brine. The organic layer was dried over sodium sulfate, filtered and concentrated. The solid obtained was purified by recrystallization from ethyl acetate to provide 1.08 g of the titled product (32%) as an off-white crystalline solid:

mp 166°–167° C.; IR (KBr, cm$^{-1}$) 3159, 2927, 1595, 1561, 1531, 1475, 1310, 1228, 1092; $^1$H NMR (300 MHZ, DMSO-d$_6$) δ11.09 (br s, 1H), 10.64 (s, 1H), 8.20 (d, J=2.4 Hz, 1H), 7.93 (dd, J=8.9, 2.4 Hz, 1H), 7.09 (d, J=9.0 Hz, 1H), 5.47 (s, 1H), 3.62–3.58 (m, 2H), 2.19 (t, J=6.7 Hz, 2H), 2.00–1.90 (m, 4H), 1.55–1.44 (m, 4H); MS (FD) m/e 339 (M+), 341 (M+2); UV (EtOH) 305 nm (ε=14037), 274 nm (ε=25281).

Anal. Calcd for $C_{14}H_{18}BrN_3S$: C, 49.42; H, 5.33; N, 12.35. Found: C, 49.22; H, 5.28; N, 12.32.

Example 190

N-(2-Phenethyl)-N'-[2-(4-methyl)pyridyl]thiourea

A stirred solution of 2-phenethyl isothiocyanate (1.63 g, 10 mmol, 1.5 mL) and 2-amino-4-methylpyridine (1.08 g, 10 mmol) in N-methylpyrrolidinone (20 mL) was heated to 100° C. After 16.75 h, the reaction was cooled to room temperature and poured into ethyl acetate. The organic phase was washed with 1N hydrochloric acid, water (3×) and brine. The organic layer was dried over sodium sulfate, filtered and concentrated. The solid obtained was purified by recrystallization from ethyl acetate/hexanes to provide 1.69 g of the titled product (62%) as a white crystalline solid:

mp 151°–153° C.; IR (KBr, cm$^{-1}$) 3225, 1616, 1534, 1486, 1313, 1192, 1037;

$^1$H NMR (300 MHZ, DMSO-d$_6$) δ11.72 (br s, 1H), 10.42 (s, 1H), 7.87 (d, J=5.3 Hz, 1H), 7.31–7.15 (m, 5H), 6.88 (s, 1H), 6.80 (d, J=5.2 Hz, 1H), 3.81–3.76 (m, 2H), 2.88 (t, J=7.0 Hz, 2H), 2.20 (s, 3H); MS (FD) m/e 271 (M+);

UV (EtOH) 290 nm (ε=15080), 266 nm (ε=15528), 247 nm (ε=13132), 202 nm (ε=21819).

Anal. Calcd for $C_{15}H_{17}N_3S$: C, 66.38; H, 6.31; N, 15.48. Found: C, 66.09; H, 6.34; N, 15.71.

Example 191

N-(2-Phenethyl)-N'-[2-(4,6-dimethyl)pyridyl]thiourea

A stirred solution of 2-phenethyl isothiocyanate (1.63 g, 10 mmol, 1.5 mL) and 2-amino-4,6-dimethylpyridine (1.22 g, 10 mmol) in N-methylpyrrolidinone (20 mL) was heated to 100° C. After 16 h, the reaction was cooled to room temperature and poured into ethyl acetate. The organic phase was washed with 1N hydrochloric acid, water (3×) and brine. The organic layer was dried over sodium sulfate, filtered and concentrated. The solid obtained was purified by recrystallization from ethyl acetate/hexanes to provide 1.81 g of the titled product (63%) as an off-white crystalline solid:

mp 165°–167° C.; IR (KBr, cm$^{-1}$) 3219, 1618, 1543, 1342, 1215;

$^1$H NMR (300 MHZ, DMSO-d$_6$) δ11.83 (br s, 1H), 10.35 (s, 1H), 7.25–7.16 (m, 5H), 6.69 (s, 1H), 6.63 (s, 1H), 3.88–3.82 (m, 2H), 2.89 (t, J=6.8 Hz, 2H), 2.14 (s, 3H), 2.09 (s, 3H); MS (FD) m/e 285 (M+);

UV (EtOH) 294 nm (ε=17405), 266 nm (ε=15904), 247 nm (ε=14348), 203 nm (ε=23896).

Anal. Calcd for $C_{16}H_{19}N_3S$: C, 67.33; H, 6.71; N, 14.72. Found: C, 67.11; H, 6.63; N, 14.71.

Example 192

N-(2-Phenethyl)-N'-[2-(3-hydroxy)pyridyl]thiourea

A stirred solution of 2-phenethyl isothiocyanate (1.63 g, 10 mmol, 1.5 mL) and 2-amino-3-hydroxypyridine (1.10 g, 10 mmol) in N-methylpyrrolidinone (20 mL) was heated to 100° C. After 65.5 h, the reaction was cooled to room temperature and poured into ethyl acetate. The organic phase was washed with 1N hydrochloric acid, water (3×) and brine. The organic layer was dried over sodium sulfate, filtered and concentrated. The solid obtained was purified by flash chromatography on silica gel (5% ethyl acetate/dichloromethane to 10% ethyl acetate) to provide 1.51 g of the titled product (55%). This material was recrystallized from ethyl acetate to provide 1.05 g of the titled product as an off-white crystalline solid:

mp 168°–169° C.;

IR (KBr, cm$^{-1}$) 3377, 1613, 1561, 1534, 1347, 1288, 1152;

$^1$H NMR (300 MHZ, DMSO-d$_6$) δ11.43 (br s, 1H), 10.94 (s, 1H), 8.32 (s, 1H), 7.54–7.52 (m, 1H), 7.28–7.14 (m, 6H), 6.90–6.86 (m, 1H), 3.84–3.77 (m, 2H), 2.90 (t, J=7.0 Hz, 2H);

MS (FD) m/e 273 (M+);

UV (EtOH) 309 nm (ε=17349), 261 nm (ε=11851), 245 nm (ε=17252), 204 nm (ε=23596).

Anal. Calcd for $C_{14}H_{15}N_3OS$: C, 61.51; H, 5.53; N, 15.37. Found: C, 61.46; H, 5.52; N, 15.35.

Example 193

N-[2-(2-Methoxyphenyl)ethyl]-N'-[2-(5-bromo)pyridyl]thiourea

A stirred solution of N-(thioimidazoyl)-2-(2-methoxyphenyl)ethyl amine (2.61 g, 10 mmol) and 2-amino-5-bromopyridine (1.73 g, 10 mmol) in N,N-dimethylformamide (25 mL) was heated to 90° C. After 65 h, the reaction was cooled to room temperature and poured into ethyl acetate. The organic phase was washed with 1N hydrochloric acid (2×), water (2×) and brine. The organic layer was dried over sodium sulfate, filtered and concentrated. The solid obtained was purified by recrystallization from ethyl acetate to provide 1.78 g of the titled product (49%) as an off-white crystalline solid:

mp 147°–148° C.;

IR (KBr, cm$^{-1}$) 3224, 1596, 1530, 1492, 1459, 1229, 1191, 1038;

$^1$H NMR (300 MHZ, DMSO-d$_6$) δ11.10 (br s, 1H), 10.63 (s, 1H), 8.11 (d, J=2.3 Hz, 1H), 7.90 (dd, J=8.9, 2.6 Hz, 1H), 7.21–7.16 (m, 2H), 7.06 (d, J=8.9 Hz, 1H), 6.94–6.83 (m, 2H), 3.78–3.73 (m, 2H), 3.72 (s, 3H), 2.86 (t, J=6.8 Hz, 2H);

MS (FD) m/e 365 (M+), 367 (M+2);

UV (EtOH) 305 nm (ε=13279), 274 nm (ε=26971), 202 nm (ε=28527).

Anal. Calcd for $C_{15}H_{16}BrN_3OS$: C, 49.19; H, 4.40; N, 11.47. Found: C, 48.97; H, 4.36; N, 11.66.

Example 194

N-[2-(2-Chlorophenyl)ethyl]-N'-[2-(5-bromo)pyridyl]thiourea

A stirred solution of N-(thioimidazoyl)-2-(2-chlorophenyl)ethyl amine (2.65 g, 10 mmol) and 2-amino-5-bromopyridine (1.73 g, 10 mmol) in N,N-dimethylformamide (20 mL) was heated to 90° C. After 64.75 h, the reaction was cooled to room temperature and poured into ethyl acetate. The organic phase was washed with water (4×) and brine. The organic layer was dried over sodium sulfate, filtered and concentrated. The solid obtained was purified by recrystallization from ethyl acetate/hexanes to provide 1.52 g of the titled product (41%) as a tan crystalline solid:

mp 160°–161° C.;

IR (KBr, cm$^{-1}$) 3220, 1594, 1562, 1534, 1474, 1338, 1222, 1165, 1088;

$^1$H NMR (300 MHZ, DMSO-d$_6$) δ11.16 (br s, 1H), 10.69 (s, 1H), 8.15 (d, J=2.2 Hz, 1H), 7.93 (dd, J=8.9, 2.4 Hz, 1H), 7.41–7.38 (m, 2H), 7.28–7.23 (m, 2H), 7.08 (d, J=8.9 Hz, 1H), 3.86–3.80 (m, 2H), 3.04 (t, J=6.9 Hz, 2H);

MS (FD) m/e 369 (M+), 371 (M+2);

UV (EtOH) 306 nm (ε=14321), 275 nm (ε=24813), 257 nm 16728), 201 nm (ε=27700).

Anal. Calcd for $C_{14}H_{13}BrClN_3S$: C, 45.36; H, 3.53; N, 11.33. Found: C, 45.13; H, 3.60; N, 11.17.

Example 195

N-(2-Phenethyl)-N'-[2-(4-n-propyl)thiazolyl]thiourea

A stirred solution of 2-phenethyl isothiocyanate (1.38 g, 8.44 mmol, 1.26 mL) and 2-amino-4-n-propylthiazole (1.2 g, 8.44 mmol) in N-methylpyrrolidinone (20 mL) was heated to 100° C. After 17 h, the reaction was cooled to room temperature and poured into ethyl acetate. The organic phase was washed with 1N hydrochloric acid (2×), water (2×) and brine. The organic layer was dried over sodium sulfate, filtered and concentrated. The solid obtained was purified by recrystallization from ethyl acetate/hexanes to provide 1.39 g of the titled product (54%) as a yellow crystalline solid:

mp 135°–137° C.;

IR (KBr, cm$^{-1}$) 3175, 3027, 1562, 1529, 1507, 1216;

$^1$H NMR (300 MHZ, DMSO-d$_6$) δ11.50 (br s, 1H), 9.93 (br s, 1H), 7.29–7.15 (m, 5H), 6.60 (s, 1H), 3.79–3.73 (m, 2H), 2.85 (t, J=6.9 Hz, 2H), 2.40 (t, J=7.4 Hz, 2H), 1.53–1.41 (m, 2H), 0.82 (t, J=7.3 Hz, 3H);

MS (FD) m/e 305 (M+);

UV (EtOH) 292 nm (ε=19216), 257 nm (ε=10283), 202 nm (ε=20314).

Anal. Calcd for $C_{15}H_{19}N_3S_2$: C, 58.98; H, 6.27; N, 13.76. Found: C, 59.17; H, 6.08; N, 13.55.

Example 196

N-(2-Phenethyl)-N'-[2-(3,5-dichloro)pyridyl]thiourea

A stirred solution of 2-phenethyl isothiocyanate (1.63 g, 10 mmol, 1.5 mL) and 2-amino-3,5-dichloropyridine (3.26 g, 20 mmol) in N-methylpyrrolidinone (20 mL) was heated to 125° C. After 16.5 h, the reaction was cooled to room temperature and poured into ethyl acetate. The organic phase was washed with water (5×) and brine. The organic layer was dried over sodium sulfate, filtered and concentrated. The solid obtained was purified by flash chromatography on silica gel (20% hexanes/dichloromethane) and then recrystallized from ethyl acetate/hexanes to provide 581 mg of the titled product (18%) as a white crystalline solid:

mp 102°–104° C.;

IR (KBr, cm$^{-1}$) 3409, 3040, 1560, 1508, 1429, 1147, 1057;

$^1$H NMR (300 MHZ, DMSO-d$_6$) δ10.66 (s, 1H), 8.71 (s, 1H), 8.27 (d, J=2.2 Hz, 1H), 8.12 (d, J=2.2 Hz, 1H), 7.32–7.19 (m, 5H), 3.82–3.76 (m, 2H), 2.90 (t, J=7.1 Hz, 2H);

MS (FD) m/e 325 (M+), 327 (M+2);

UV (EtOH) 311 nm (ε=8820), 276 nm (ε=16571), 257 nm (ε=13676), 203 nm (ε=19245).

Anal. Calcd for $C_{14}H_{13}Cl_2N_3S$: C, 51.54; H, 4.02; N, 12.88. Found: C, 51.32; H, 4.12; N, 12.69.

Example 197

N-(2-Phenethyl)-N'-[2-(4-n-butyl)thiazolyl]thiourea

A stirred solution of 2-phenethyl isothiocyanate (1.63 g, 10 mmol, 1.5 mL) and 2-amino-4-n-butylthiazole (1.56 g, 10 mmol) in N-methylpyrrolidinone (20 mL) was heated to 100° C. After 16.5 h, the reaction was cooled to room temperature and poured into ethyl acetate. The organic phase was washed with 1 N hydrochloric acid (2×), water (2×) and brine. The organic layer was dried over sodium sulfate, filtered and concentrated. The solid obtained was purified by recrystallization from ethyl acetate/hexanes to provide 1.63 g of the titled product (51%) as a yellow crystalline solid:

mp 100°–102° C.;

IR (KBr, cm$^{-1}$) 3027, 1560, 1529, 1262, 1212;

$^1$H NMR (300 MHZ, DMSO-d$_6$) δ11.52 (br s, 1H), 9.89 (br s, 1H), 7.29–7.15 (m, 5H), 6.59 (s, 1H), 3.79–3.73 (m, 2H), 2.86 (t, J=6.9 Hz, 2H), 2.45–2.40 (m, 2H), 1.50–1.40 (m, 2H), 1.29–1.19 (m, 2H), 0.84 (t, J=7.3 Hz, 3H);

MS (FD) m/e 319 (M+);

UV (EtOH) 292 nm (ε=19193), 258 nm (ε=10262), 203 nm (ε=20024).

Anal. Calcd for $C_{16}H_{21}N_3S_2$: C, 60.15; H, 6.62; N, 13.15. Found: C, 59.86; H, 6.62; N, 12.99.

Example 198

N-[2-(1-Cyclohexenyl)ethyl]-N'-[2-(4-n-propyl)thiazolyl]thiourea

A stirred solution of 2-(1-cyclohexenyl)ethyl isothiocyanate (1.67 g, 10 mmol) and 2-amino-4-n-propylthiazole (1.42 g, 10 mmol) in N-methylpyrrolidinone (20 mL) was heated to 100° C. After 40.5 h, the reaction was cooled to room temperature and poured into ethyl acetate. The organic phase was washed with 1N hydrochloric acid (2×), water (2×) and brine. The organic layer was dried over sodium sulfate, filtered and concentrated. The solid obtained was purified by recrystallization from ethyl acetate/hexanes to provide 1.26 g of the titled product (41%) as a yellow crystalline solid:

mp 152°–153° C.;

IR (KBr, cm$^{-1}$) 3175, 2930, 1561, 1529, 1507, 1203;

$^1$H NMR (300 MHZ, DMSO-d$_6$) δ11.49 (br s, 1H), 9.90 (br s, 1H), 6.63 (s, 1H), 5.42 (s, 1H), 3.60–3.54 (m, 2H), 2.49–2.45 (m, 2H), 2.16 (t, J=6.5 Hz, 2H), 1.95–1.88 (m, 4H), 1.60–1.43 (m, 6H), 0.84 (t, J=7.3 Hz, 3H);

MS (FD) m/e 309 (M+);

UV (EtOH) 292 nm, 257 nm, 201 nm.

Anal. Calcd for C$_{15}$H$_{23}$N$_3$S$_2$: C, 58.21; H, 7.49; N, 13.58. Found: C, 58.29; H, 7.58; N, 13.37.

Example 199

N-[2-(1-Cyclohexenyl)ethyl]-N'-[2-(4-n-butyl)thiazolyl]thiourea

A stirred solution of 2-(1-cyclohexenyl)ethyl isothiocyanate (1.67 g, 10 mmol) and 2-amino-4-n-butylthiazole (1.56 g, 10 mmol) in N-methylpyrrolidinone (20 mL) was heated to 100° C. After 18 h, the reaction was cooled to room temperature and poured into ethyl acetate. The organic phase was washed with 1N hydrochloric acid (2×), water (2×) and brine. The organic layer was dried over sodium sulfate, filtered and concentrated. The solid obtained was purified by recrystallization from ethyl acetate/hexanes to provide 1.02 g of the titled product (32%) as a yellow crystalline solid:

mp 92°–94° C.;

IR (KBr, cm$^{-1}$) 3174, 2927, 1583, 1532, 1507, 1466, 1203;

$^1$H NMR (300 MHZ, DMSO-d$_6$) δ11.73 (br s, 1H), 10.14 (br s, 1H), 6.86 (s, 1H), 5.65 (s, 1H), 3.83–3.78 (m, 2H), 2.75–2.70 (m, 2H), 2.42–2.38 (m, 2H), 2.18–2.10 (m, 4H), 1.81–1.65 (m, 6H), 1.55–1.43 (m, 2H), 1.08 (t, J=7.3 Hz, 3H);

MS (FD) m/e 323 (M+);

UV (EtOH) 292 nm (ε=19266), 257 nm (ε=9555), 201 nm (ε=15788).

Anal. Calcd for C$_{16}$H$_{25}$N$_3$S$_2$: C, 59.40; H, 7.79; N, 12.99. Found: C, 59.56; H, 7.94; N, 13.00.

Example 200

N-[2-(1-Cyclohexenyl)ethyl]-N'-[2-(4-i-propyl)thiazolyl]thiourea

A stirred solution of 2-(1-cyclohexenyl)ethyl isothiocyanate (1.67 g, 10 mmol) and 2-amino-4-i-propylthiazole (1.42 g, 10 mmol) in N-methylpyrrolidinone (20 mL) was heated to 100° C. After 15.75 h, the reaction was cooled to room temperature and poured into ethyl acetate. The organic phase was washed with 1N hydrochloric acid (2×), water (2×) and brine. The organic layer was dried over sodium sulfate, filtered and concentrated. The solid obtained was purified by recrystallization from ethyl acetate/hexanes to provide 1.01 g of the titled product (33%) as a pale yellow crystalline solid:

mp 110°–112° C.;

IR (KBr, cm$^{-1}$) 3164, 2936, 1562, 1525, 1463, 1321, 1214;

$^1$H NMR (300 MHZ, DMSO-d$_6$) δ11.50 (br s, 1H), 9.84 (br s, 1H), 6.61 (s, 1H), 5.41 (s, 1H), 3.61–3.55 (m, 2H), 2.82–2.76 (m, 1H), 2.17 (t, J=6.4 Hz, 2H), 1.94–1.88 (m, 4H), 1.56–1.41 (m, 4H), 1.14 (d, J=6.8 Hz, 6H);

MS (FD) m/e 309 (M+);

UV (EtOH) 291 nm (ε=20249), 256 nm (ε=9969), 201 nm (ε=15880).

Anal. Calcd for C$_{15}$H$_{23}$N$_3$S$_2$: C, 58.21; H, 7.49; N, 13.58. Found: C, 58.50; H, 7.63; N, 13.38.

Example 201

N-(2-Phenethyl)-N'-[2-(4-i-propyl)thiazolyl]thiourea

A stirred solution of 2-phenethyl isothiocyanate (1.63 g, 10 mmol, 1.5 mL) and 2-amino-4-i-propylthiazole (1.42 g, 10 mmol) in N-methylpyrrolidinone (20 mL) was heated to 100° C. After 17 h, the reaction was cooled to room temperature and poured into ethyl acetate. The organic phase was washed with N/10 hydrochloric acid (2×), water (2×) and brine. The organic layer was dried over sodium sulfate, filtered and concentrated. The solid obtained was purified by recrystallization from ethyl acetate/hexanes to provide 1.42 g of the titled product (46%) as a yellow crystalline solid:

mp 155°–156° C.;

IR (KBr, cm$^{-1}$) 3172, 2962, 1581, 1525, 1467, 1350, 1290, 1210;

$^1$H NMR (300 MHZ, DMSO-d$_6$) δ11.52 (br s, 1H), 9.89 (br s, 1H), 7.29–7.14 (m, 5H), 6.58 (s, 1H), 3.80–3.74 (m, 2H), 2.87 (t, J=6.9 Hz, 2H), 2.76–2.71 (m, 1H), 1.07 (d, J=6.8 Hz, 6H);

MS (FD) m/e 305 (M+);

UV (EtOH) 292 nm (ε=19882), 257 nm (ε=10580), 203 nm (ε=20047).

Anal. Calcd for C$_{15}$H$_{19}$N$_3$S$_2$: C, 58.98; H, 6.27; N, 13.76. Found: C, 58.95; H, 6.39; N, 13.72.

Example 202

N-(2-Phenethyl)-N'-[2-((4-glyoxylic acid)thiazolyl)]thiourea

A solution of N-(2-phenethyl)-N'-[2-((4-ethylglyoxylate)thiazolyl)]thiourea (1.30 g, 3.58 mmol) in ethanol (30 mL) was treated with 1 N sodium hydroxide and heated to reflux. After 1 h, the reaction was cooled to room temperature, diluted with water and washed with ethyl acetate (2×). The aqueous layer was acidified to pH 1 with hydrochloric acid and extracted with dichloromethane (2×). The organic layers were combined, washed with brine, dried over sodium sulfate, filtered and concentrated. The solid obtained was purified by triturating with ethyl acetate to yield 390 mg of the titled product (32%) as a light brown solid:

mp >170° C. (d);

IR (KBr, cm$^{-1}$) 3024, 1705, 1669, 1565, 1323, 1146;

$^1$H NMR (300 MHZ, DMSO-d$_6$) δ12.2 (br s, 1H), 9.07 (s, 1H), 8.01 (s, 1H), 7.28–7.14 (m, 5H), 3.71–3.64 (m, 2H), 2.84 (t, J=7.3 Hz, 2H);

MS (FD) m/e 336 (M+1);

HRMS (FAB) m/e (M+1) calcd 336.0477, obs 336.0474;

UV (EtOH) 284 nm (ε=17301), 203 nm (ε=18110).

Example 203

N-(2-Phenethyl)-N'-[2-(4-methoxybenzothiazolyl)]thiourea

A solution of 2-phenethyl isothiocyanate (3.26 g, 20 mmol, 3.0 mL) and 2-amino-4-methoxybenzothiazole (3.60 g, 20 mmol) in N,N-dimethylformamide (50 mL) was heated to 100° C. After 64 h, the reaction was cooled to room temperature and poured into ethyl acetate. The organic phase was washed with 1N hydrochloric acid, saturated sodium bicarbonate solution, water (2×), and brine. The organic layer was filtered directly to provide 3.87 g of the titled product (56%) as a white solid:

mp 209°–211° C.;

IR (KBr, cm$^{-1}$) 3171, 2938, 1570, 1527, 1331, 1191, 1044;

$^1$H NMR (300 MHZ, DMSO-d$_6$) δ11.88 (s, 1H), 9.86 (s, 1H), 7.49–6.93 (m, 8H), 3.86 (s, 3H), 3.77–3.70 (m, 2H), 2.89 (t, J=7.1 Hz, 2H);

MS (FD) m/e 343 (M+);

HRMS (FAB) m/e (M+1) calcd 344.0891, obs 344.0884;

UV (EtOH) 290 nm, 248 nm, 210 nm.

Example 204

N-(2-Phenethyl)-N'-[2-((5-trifluoromethyl)-1,3,4-thiadiazolyl)]thiourea

A solution of 2-phenethyl isothiocyanate (3.26 g, 20 mmol, 3.0 mL) and 2-amino-5-trifluoromethyl-1,3,4-thiadiazole (3.38 g, 20 mmol) in N,N-dimethylformamide (50 mL) was heated to 100° C. After 40 h, the reaction was cooled to room temperature and poured into ethyl acetate. The organic phase was washed with water (3×) and brine (2×). The organic layer was dried over sodium sulfate, filtered and concentrated. The solid obtained was purified by flash chromatography on silica gel (5% ethyl acetate in dichloromethane) and then recrystallized from ethyl acetate to provide 171 mg of the titled product (3%) as a white solid:

mp 212°–213° C.;

IR (KBr, cm$^{-1}$) 3336, 2788, 1629, 1534, 1494, 1398, 1327, 1148, 1038;

$^1$H NMR (300 MHZ, DMSO-d$_6$) δ12.6 (br s, 1H), 8.51 (s, 1H), 7.30–7.15 (m, 5H), 3.73–3.66 (m, 2H), 2.85 (t, J=7.3 Hz, 2H);

MS (FD) m/e 332 (M+);

UV (EtOH) 322 nm (ε=5240), 261 nm (ε=11025), 204 nm (ε=28776).

Anal. Calcd for $C_{12}H_{11}F_3N_4S_2$: C, 43.36; H, 3.34; N, 16.86. Found: C, 43.20; H, 3.44; N, 16.86.

Example 205

N-(2-Phenethyl)-N'-[2-((4-carboxylic acid)thiazolyl)]thiourea

A solution of N-(2-phenethyl)-N'-[2-(4-cyano)thiazolyl]thiourea (250 mg, 0.867 mmol) in glacial acetic acid (10 mL) and 5N hydrochloric acid (10 mL) was heated to reflux. After 16 h, the reaction was cooled to room temperature, diluted with acetonitrile and concentrated to dryness (2×). The solid obtained was purified by flash chromatography on silica gel (2% acetic acid in ethyl acetate) and then recrystallized from methanol/ethyl acetate to provide 13 mg of the titled product. The mother liquor was concentrated and triturated with ethyl acetate to provide another 34 mg of the titled product, for a total yield of 47 mg (18%) as a white solid:

mp >230° C.;

IR (KBr,cm$^{-1}$) 3275, 1603, 1531, 1394, 1268;

$^1$H NMR (300 MHZ, DMSO-d$_6$) δ7.26–7.14 (m, 6H), 3.71–3.65 (m, 2H), 2.87 (t, J=7.2 Hz, 2H);

MS (FD) m/e 307 (M+);

HRMS (FAB) m/e (M+1) calcd 309.0527, obs 309.0528;

UV (EtOH) 288 nm, 260 nm, 206 nm.

Example 206

N-(2-(1-Cyclohexenyl)ethyl)-N'-[2-(6-fluorobenzothiazolyl)]thiourea

A solution of 2-(1-cyclohexenyl)ethyl isothiocyanate (1.66 g, 9.93 mmol) and 2-amino-6-fluorobenzothiazole (1.67 g, 9.93 mmol) in dimethyl sulfoxide (10 mL) was heated to 125° C. After 20 h, the reaction was cooled to room temperature and poured into ethyl acetate. The organic phase was washed with 1N hydrochloric acid, water (3×), and brine. The organic layer was dried over sodium sulfate, filtered and concentrated. The solid obtained was purified by flash chromatography on silica gel (1% ethyl acetate in dichloromethane) and then recrystallized from ethyl acetate to provide 1.04 g of the titled product (31%) as a yellow crystalline solid:

mp 200°–201° C.;

IR (KBr, cm$^{-1}$) 3451, 3177, 3044, 2924, 2832, 1560, 1533, 1462, 1215, 1198;

$^1$H NMR (300 MHZ, CDCl$_3$) δ10.83 (s, 1H), 10.33 (br s, 1H), 7.61–7.56 (m, 1H), 7.41–7.37 (m, 1H), 7.17–7.10 (m, 1H), 5.65 (s, 1H), 3.87–3.81 (m, 2H), 2.38 (t, J=6.5 Hz, 2H), 2.03–2.00 (m, 4H), 1.67–1.52 (m, 4H);

MS (FD) m/e 335 (M+);

UV (EtOH) 301 nm, 218 nm, 201 nm.

Anal. Calcd for $C_{16}H_{18}FN_3S_2$: C, 57.29; H, 5.41; N, 12.53. Found: C, 57.58; H, 5.44; N, 12.42.

Example 207

N-(2-Phenethyl)-N'-[2-(5-chlorothiazolyl)]thiourea

2-Amino-5-chlorothiazole hydrochloride (1.71 g, 10 mmol) was slurried with dichloromethane and shaken with a slight excess of sodium hydroxide solution. The layers were separated and the aqueous washed with dichloromethane. The combined organics were dried over sodium sulfate, filtered and concentrated. To the resulting solid was added 2-phenethyl isothiocyanate (1.63 g, 10 mmol, 1.5 mL) and N-methyl-pyrrolidinone (20 mL). The resulting solution was heated to 100° C. After 20 h, the reaction was cooled to room temperature and poured into ethyl acetate. The organic phase was washed with 1N hydrochloric acid, water (4×), and brine. The organic layer was dried over sodium sulfate, filtered and concentrated. The solid obtained was purified by flash chromatography on silica gel (2% ethyl acetate in dichloromethane) and then recrystallized twice from 1:1 ethyl acetate/hexanes to provide 187 mg of the titled product (6%) as a light brown crystalline solid:

mp 163°–164° C.;

IR (KBr, cm$^{-1}$) 3312, 3028, 2925, 1607, 1527, 1513, 1438, 1377, 1348, 1314, 1026;

$^1$H NMR (300 MHZ, DMSO-d$_6$) δ11.60 (br s, 1H), 8.41 (s, 1H), 7.39 (s, 1H), 7.30–7.15 (m, 5H), 3.70–3.63 (m, 2H), 2.82 (t, J=7.2 Hz, 2H);

MS (FD) m/e 297 (M+), 299 (M+2);

UV (EtOH) 296 nm (ε=14487), 260 nm (ε=12442), 206 nm (ε=27427).

Anal. Calcd for $C_{12}H_{12}ClN_3S_2$: C, 48.40; H, 4.06; N, 14.11. Found: C, 48.40; H, 4.16; N, 13.85.

Example 208

N-[2-(1-Cyclohexenyl)ethyl]-N'-[2-((4-trifluoromethyl)thiazolyl)]thiourea

A solution of 2-(1-cyclohexenyl)ethyl isothiocyanate (1.67 g, 10 mmol) and 2-amino-4-trifluoromethylthiazole (1.68 g, 10 mmol ) in N-methylpyrrolidinone (20 mL) was heated to 125° C. After 20 h, the reaction was cooled to room temperature and poured into ethyl acetate. The organic phase was washed with 1N hydrochloric acid (2×), water (3×), and brine. The organic layer was dried over sodium sulfate, filtered and concentrated. The solid obtained was purified by flash chromatography on silica gel (1% ethyl acetate in dichloromethane) and then recrystallized from 1:1 ethyl acetate/hexanes to provide 139 mg of the titled product (4%) as an off-white solid:

mp 153°–154° C.;

IR (KBr,cm$^{-1}$) 3168, 2932, 1562, 1513, 1472, 1438, 1219, 1175, 1081;

$^1$H NMR (300 MHZ, DMSO-d$_6$) δ11.95 (s, 1H), 8.21 (s, 1H), 7.71 (s, 1H), 5.41 (s, 1H), 3.55–3.49 (m, 2H), 2.14 (t, J=6.7 Hz, 2H), 1.93–1.83 (m, 4H), 1.56–1.41 (m, 4H);

MS (FD) m/e 335 (M+);

HRMS (FAB) m/e (M+1) calcd 336.0816, obs 336.0842;

UV (EtOH) 285 nm (ε=15215), 258 nm (ε=12868), 203 nm (ε=20271).

Example 209

N-[2-(2-Chlorophenyl)ethyl]-N'-[2-((4-trifluoromethyl)thiazolyl)]thiourea

A solution of 2-(2-chlorophenyl)ethyl amine (1.56 g, 10 mmol, 1.41 mL) and N-(thioimidazoyl)-2-amino-4-trifluoromethylthiazole (3.0 g, 10.8 mmol) in N,N-dimethylformamide (20 mL) was heated to 90°–100° C. After 2 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by flash chromatography on silica gel (1% ethyl acetate in dichloromethane) and then recrystallized from 1:1 ethyl acetate/hexanes to provide 870 mg of the titled product (24%) as a white crystalline solid:

mp 187°–188° C.;

IR (KBr,cm$^{-1}$) 3169, 3018, 1569, 1512, 1245, 1220, 1154, 1133, 1080;

$^1$H NMR (300 MHZ, DMSO-d$_6$) δ11.92 (s, 1H), 8.32 (s, 1H), 7.71 (s, 1H), 7.41–7.22 (m, 4H), 3.76–3.69 (m, 2H), 2.97 (t, J=7.1 Hz, 2H);

MS (FD) m/e 365 (M+);

UV (EtOH) 285 nm (ε=13758), 257 nm (ε=14164), 202 nm (ε=30204).

Anal. Calcd for C$_{13}$H$_{11}$F$_3$ClN$_3$S$_2$: C, 42.68; H, 3.03; N, 11.49. Found: C, 42.82; H, 3.14; N, 11.68.

Example 210

N-[2-(4-Chlorophenyl)ethyl]-N'-[2-((4-trifluoromethyl)thiazolyl)]thiourea

A solution of 2-(4-chlorophenyl)ethyl amine (1.56 g, 10 mmol, 1.40 mL) and N-(thioimidazoyl)-2-amino-4-trifluoromethylthiazole (3.0 g, 10.8 mmol) in N,N-dimethylformamide (20 mL) was heated to 90°–100° C. After 2 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by flash chromatography on silica gel (1% ethyl acetate in dichloromethane) and then recrystallized from 1:1 ethyl acetate/hexanes to provide 570 mg of the titled product (16%) as a white crystalline solid:

mp 196°–197° C.;

IR (KBr, cm$^{-1}$) 3167, 3021, 1562, 1516, 1469, 1445, 1184, 1173, 1126, 1083;

$^1$H NMR (300 MHZ, DMSO-d$_6$) δ11.91 (s, 1H), 8.27 (s, 1H), 7.71 (s, 1H), 7.32 (d, J=8.4 Hz, 2H), 7.23 (d, J=8.4 Hz, 2H), 3.72–3.65 (m, 2H), 2.83 (t, J=7.0 Hz, 2H);

MS (FD) m/e 365 (M+);

UV (EtOH) 286 nm (ε=11309), 257 nm (ε=11445), 202 nm (ε=21815).

Anal. Calcd for C$_{13}$H$_{11}$F$_3$ClN$_3$S$_2$: C, 42.68; H, 3.03; N, 11.49. Found: C, 42.87; H, 3.05; N, 11.46.

Example 211

N-[2-(3-Chlorophenyl)ethyl]-N'-[2-((4-trifluoromethyl)thiazolyl)]thiourea

A solution of 2-(3-chlorophenyl)ethyl amine (1.56 g, 10 mmol, 1.40 mL) and N-(thioimidazoyl)-2-amino-4-trifluoromethylthiazole (3.0 g, 10.8 mmol) in N,N-dimethylformamide (20 mL) was heated to 90°–100° C. After 2 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by flash chromatography on silica gel (1% ethyl acetate in dichloromethane) and then recrystallized from 1:1 ethyl acetate/hexanes to provide 407 mg of the titled product (11% ) as a white crystalline solid:

mp 159°–160° C.;

IR (KBr, cm$^{-1}$) 3176, 3017, 1567, 1517, 1224, 1133, 1080;

$^1$H NMR (300 MHZ, DMSO-d$_6$) δ11.93 (s, 1H), 8.28 (s, 1H), 7.72 (s, 1H), 7.33–7.17 (m, 4H), 3.73–3.67 (m, 2H), 2.85 (t, J=7.0 Hz, 2H);

MS (FD) m/e 365 (M+), 367 (M+2);

UV (EtOH) 285 nm (ε=14175), 257 nm (ε=14293), 202 nm (ε=31514).

Anal. Calcd for C$_{13}$H$_{11}$F$_3$ClN$_3$S$_2$: C, 42.68; H, 3.03; N, 11.49. Found: C, 42.72; H, 3.09; N, 11.79.

Example 212

N-[2-(2-Methoxyphenyl)ethyl]-N'-[2-((4-trifluoromethyl)thiazolyl)]thiourea

A solution of 2-(2-methoxyphenyl)ethyl amine (1.51 g, 10 mmol, 1.46 mL) and N-(thioimidazoyl)-2-amino-4-trifluoromethylthiazole (3.0 g, 10.8 mmol) in N,N-dimethylformamide (20 mL) was heated to 90°–100° C. After 2 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by flash chromatography on silica gel (2% ethyl acetate in dichloromethane) and then recrystallized from 1:1 ethyl acetate/hexanes to provide 872 mg of the titled product (24%) as a white crystalline solid:

mp 184°–184.5° C.;

IR (KBr, cm$^{-1}$) 3168, 2973, 1571, 1514, 1244, 1221, 1168, 1127, 1077;

$^1$H NMR (300 NMZ, DMSO-d$_6$) δ11.87 (s, 1H), 8.24 (s, 1H), 7.71 (s, 1H), 7.18–7.10 (m, 2H), 6.94–6.82 (m, 2H), 3.74 (s, 3H), 3.68–3.61 (m, 2H), 2.80 (t, J=7.0 Hz, 2H);

MS (FD) m/e 361 (M+);

UV (EtOH) 280 nm (ε=16781), 259 nm (ε=15202), 203 nm (ε=32863).

Anal. Calcd for C$_{14}$H$_{14}$F$_3$N$_3$OS$_2$: C, 46.53; H, 3.90; N, 11.63. Found: C, 46.52; H, 3.94; N, 11.52.

Example 213

N-[2-(3-Methoxythenyl)ethyl]-N'-[2-((4-trifluoromethyl)thiazolyl)]thiourea

A solution of 2-(3-methoxyphenyl)ethyl amine (1.51 g, 10 mmol, 1.45 mL) and N-(thioimidazoyl)-2-amino-4-trifluoromethylthiazole (3.0 g, 10.8 mmol) in N,N-dimethylformamide (20 mL) was heated to 90°–100° C. After 2 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by flash chromatography on silica gel (2% ethyl acetate in dichloromethane) and then recrystallized from 1:1 ethyl acetate/hexanes to provide 1.32 g of the titled product (36%) as a white solid:

mp 139°–140° C.;

IR (KBr, cm$^{-1}$) 3215, 3018, 1598, 1582, 1544, 1490, 1299, 1242, 1180, 1081;

$^1$H NMR (300 MHZ, DMSO-d$_6$) δ11.93 (s, 1H), 8.26 (s, 1H), 7.71 (s, 1H), 7.18 (t, J=8.0 Hz, 1H), 6.79–6.74 (m, 3H), 3.73–3.66 (m, 2H), 3.69 (s, 3H), 2.80 (t, J=7.0 Hz, 2H);

MS (FD) m/e 361 (M+);

UV (EtOH) 281 nm (ε=15384), 258 nm (ε=14389), 202 nm (ε=35020).

Anal. Calcd for C$_{14}$H$_{14}$F$_3$N$_3$OS$_2$: C, 46.53; H, 3.90; N, 11.63. Found: C, 46.76; H, 3.91; N, 11.52.

Example 214

N-[2-(4-Methoxyphenyl)ethyl]-N'-[2-((4-trifluoromethyl)thiazolyl)]thiourea

A solution of 2-(4-methoxyphenyl)ethyl amine (1.51 g, 10 mmol, 1.46 mL) and N-(thioimidazoyl)-2-amino-4-trifluoromethylthiazole (3.0 g, 10.8 mmol) in N,N-dimethylformamide (20 mL) was heated to 90°–100° C. After 2 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by flash chromatography on silica gel (2% ethyl acetate in dichloromethane) and then recrystallized from 1:1 ethyl acetate/hexanes to provide 893 mg of the titled product (25%) as a white crystalline solid:

mp 169°–170° C.;

IR (KBr, cm$^{-1}$) 3173, 3025, 1565, 1515, 1240, 1181, 1127, 1083;

$^1$H NMR (300 MHZ, DMSO-d$_6$) δ11.90 (s, 1H), 8.26 (s, 1H), 7.71 (s, 1H), 7.12 (d, J=8.5 Hz, 2H), 6.83 (d, J=8.5 Hz, 2H), 3.67 (s, 3H), 3.67–3.61 (m, 2H), 2.76 (t, J=7.1 Hz, 2H);

MS (FD) m/e 361 (M+);

UV (EtOH) 284 nm (ε=15865), 258 nm (ε=14872), 224 nm (ε=16821), 201 nm (ε=29323).

Anal. Calcd for C$_{14}$H$_{14}$F$_3$N$_3$OS$_2$: C, 46.53; H, 3.90; N, 11.63. Found: C, 46.70; H, 3.89; N, 11.50.

Example 215

N-[2-(1-Cyclohexenyl)ethyl]-N'-[2-((4,5-dimethyl)thiazolyl)]thiourea

2-Amino-4,5-dimethylthiazole hydrochloride (1.65 g, 10 mmol) was slurried with dichloromethane and shaken with a mixture of sodium hydroxide/saturated sodium bicarbonate solution. The organics were washed with brine, dried over sodium sulfate, filtered and concentrated. To the resulting solid was added 2-(1-cyclohexenyl)ethyl isothiocyanate (1.67 g, 10 mmol) and N-methylpyrrolidinone (20 mL). The resulting solution was heated to 105° C. After 20 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by recrystallization from 2:1 ethyl acetate/hexanes to provide 1.57 g of the titled product (53%) as a light yellow crystalline solid:

mp 162°–164° C.;

IR (KBr, cm$^{-1}$) 3170, 2917, 1583, 1554, 1514, 1433, 1325, 1255, 1215;

$^1$H NMR (300 MHZ, DMSO-d$_6$) δ11.35 (s, 1H), 9.83 (br s, 1H), 5.43 (s, 1H), 3.58–3.52 (m, 2H), 2.17–2.11 (m, 5H), 2.07 (s, 3H), 1.94–1.89 (m, 4H), 1.57–1.44 (m, 4H)

MS (FD) m/e 295 (M+)

UV (EtOH) 297 nm (ε=18557), 256 nm (ε=9443), 201 nm (ε=16880).

Anal. Calcd for C$_{14}$H$_{21}$N$_3$S$_2$: C, 56.91; H, 7.16; N, 14.22. Found: C, 57.10; H, 7.28; N, 14.36.

Example 216

N-[2-(3-Ethoxy-4-methoxyphenyl)ethyl]-N'-(2-thiazolyl)thiourea

A solution of 2-(3-ethoxy-4-methoxyphenyl)ethyl amine (1.00 g, 5.12 mmol) and N-(thioimidazoyl)-2-aminothiazole (1.08 g, 5.12 mmol) in N,N-dimethylformamide (20 mL) was heated to 90°–100° C. After 16 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by recrystallization from dichloromethane/ethyl acetate to provide 471 mg of the titled product (27%) as an off-white solid:

mp 150°–152° C.;

IR (KBr, cm$^{-1}$) 3176, 3112, 3040, 1575, 1514, 1469, 1261, 1235, 1140, 1042;

¹H NMR (300 MHZ, DMSO-d₆) δ11.51 (s, 1H), 9.73 (br s, 1H), 7.28 (d, J=3.6 Hz, 1H), 7.07 (s, 1H), 6.90–6.78 (m, 2H), 6.72 (d, J=8.2 Hz, 1H), 4.00–3.88 (m, 2H), 3.80–3.67 (m, 5H), 2.76 (t, J=6.9 Hz, 2H), 1.25 (t, J=6.9 Hz, 3H);

MS (FD) m/e 337 (M+);

UV (EtOH) 287 nm (ε=21828), 259 nm (ε=11770), 205 nm (ε=35881).

Anal. Calcd for $C_{15}H_{19}N_3O_2S_2$: C, 53.39; H, 5.67; N, 12.45. Found: C, 53.10; H, 5.64; M, 12.22.

Example 217

N-[2-(3-Methoxy-4-isopropoxyphenyl)ethyl]-N'-(2-thiazolyl)thiourea

A solution of 2-(3-methoxy-4-isopropoxy-phenyl)ethyl amine (1.00 g, 4.78 mmol) and N-(thioimidazoyl)-2-aminethiazole (1.00 g, 4.78 mmol) in N,N-dimethylformamide (20 mL) was heated to 90°–95° C. After 24 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by recrystallization from ethyl acetate no provide 891 mg of the titled product (53%) as yellowish needles. A sample was recrystallized a second time from ethyl acetate:

mp 140°–141° C.;

IR (KBr, cm⁻¹) 3165, 2971, 1560, 1516, 1466, 1266, 1182, 1144;

¹H NMR (300 MHZ, DMSO-d₆) δ11.53 (s, 1H), 9.71 (br s, 1H), 7.28 (d, J=3.6 Hz, 1H), 7.06 (s, 1H), 6.84–6.81 (m, 2H), 6.71–6.68 (m, 1H), 4.45–4.37 (m, 1H), 3.74–3.66 (m, 5H), 2.77 (t, J=7.0 Hz, 2H), 1.17 (d, J=6.0 Hz, 6H);

MS (FD) m/e 351 (M+);

UV (EtOH) 286 nm, 258 nm, 204 nm.

Anal. Calcd for $C_{16}H_{21}N_3O_2S_2$: C, 54.68; H, 6.02; N, 11.96. Found: C, 54.79; H, 6.11; N, 12.21.

Example 218

N-[2-(3,4-dichlorothenyl)ethyl]-N'-(2-thiazolyl)thiourea 2-(3,4-Dichlorophenyl)ethyl amine hydrochloride (1.00 g, 4.41 mmol) was slurried in dichloromethane and shaken with a slight excess of sodium hydroxide solution. The layers were separated and the organics were dried over sodium sulfate, filtered and concentrated. N-(thioimidazoyl)-2-aminothiazole (928 mg, 4.41 mmol) and N,N-dimethylformamide (20 mL) were added to the resulting oil. This solution was heated to 90°–100° C. After 18 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by flash chromatography on silica gel (2% ethyl acetate/dichloromethane) to provide 1.0 g of 3 (68%) as a white solid. This solid was recrystallized from ethyl acetate to provide 700 mg of the titled product as a white crystalline solid:

mp 159.5°–160° C.;

IR (KBr, cm⁻¹) 3175, 1577, 1515, 1472, 1328, 1190, 1029;

¹H NMR (300 MHZ, DMSO-d₆) δ11.55 (s, 1H), 9.63 (br s, 1H), 7.54–7.48 (m, 2H), 7.30–7.21 (m, 2H), 7.06 (s, 1H), 3.77–3.70 (m, 2H), 2.87 (t, J=6.9 Hz, 2H);

MS (FD) m/e 331 (M+);

UV (EtOH) 289 nm (ε=19623), 265 nm (ε=11818), 204 nm (ε=36059).

Anal. Calcd for $C_{12}H_{11}Cl_2N_3S_2$: C, 43.38; H, 3.34; N, 12.65. Found: C, 43.14; H, 3.36; N, 12.63.

Example 219

N-[2-(2-methyl-3-trifluoromethylphenyl)ethyl]-N'-(2-thiazolyl)thiourea 2-(2-Methyl-3-trifluoromethylphenyl)ethyl amine hydrochloride (1.00 g, 4.17 mmol) was slurried in dichloromethane and shaken with a slight excess of sodium hydroxide solution. The layers were separated and the organics were dried over magnesium sulfate, filtered and concentrated. N-(thioimidazoyl)-2-aminothiazole (877 mg, 4.17 mmol) and N,N-dimethylformamide (20 mL) were added to the resulting oil. This solution was heated to 90°–100° C. After 65 h, the reaction was cooled to room temperature and poured into ethyl acetate. The organic phase was washed with 1N hydrochloric acid (2×), water, and brine. The organic layer was dried over sodium sulfate, filtered and concentrated. The solid obtained was purified by flash chromatography on silica gel (2% ethyl acetate/dichloromethane) and then recrystallized from ethyl acetate (1st crop) or 1:1 ethyl acetate/hexanes (2nd crop) to provide 581 mg of the titled product (40%) as a white solid:

mp 158°–159° C.;

IR (KBr,cm⁻¹) 3178, 3130, 2994, 1566, 1514, 1473, 1321, 1161, 1120;

¹H NMR (300 MHZ, DMSO-d₆) δ11.60 (s, 1H), 9.76 (br s, 1H), 7.52–7.47 (m, 2H), 7.33–7.28 (m, 2H), 7.07 (s, 1H), 3.75–3.68 (m, 2H), 2.98 (t, J=7.4 Hz, 2H), 2.40 (s, 3H);

MS (FD) m/e 345 (M+);

UV (EtOH) 289 nm (ε=19176), 258 nm (ε=11507), 203 nm (ε=21953).

Anal. Calcd for $C_{14}H_{14}F_3N_3S_2$: C, 48.68; H,4.08; N,12.16. Found: C,48.89; H,4.06; N,12.14.

Example 220

N-[2-(3-(3,3,3-trifluoro)propylphenyl)ethyl]-N'-(2-thiazolyl)thiourea 2-(3-(3,3,3-trifluoro)propylphenyl) ethyl amine tosylate (1.00 g, 2.57 mmol) was slurried in dichloromethane and shaken with a slight excess of sodium hydroxide solution. The layers were separated and the aqueous was extracted with dichloromethane. The combined organics were dried over magnesium sulfate, filtered and concentrated. N-(thioimidazoyl)-2-aminothiazole (540 mg, 2.57 mmol) and N,N-dimethylformamide (20 mL) were added to the resulting oil. This solution was heated to 90°–95° C. After 1 h, the reaction was cooled to room temperature and poured into ethyl acetate. The organic phase was washed with 1N hydrochloric acid (2×), water (2×), and brine. The organic layer was dried over sodium sulfate, filtered and concentrated. The solid obtained was purified by recrystallization from 40% ethyl acetate/hexanes to provide 508 mg of the titled product (55%) as an off-white crystalline solid:

mp 138°–139° C.;

IR (CHCl$_3$, cm$^{-1}$) 3192, 3058, 2979, 1567, 1514, 1259, 1139;

$^1$H NMR (300 MHZ, DMSO-d$_6$) δ11.53 (s, 1H), 9.73 (br s, 1H), 7.29–7.06 (m, 6H), 3.75–3.69 (m, 2H), 2.83 (t, J=7.0 Hz, 2H), 2.77–2.71 (m, 2H), 2.57–2.45 (m, 2H);

MS (FD) m/e 359 (M+);

UV (EtOH) 288 nm (ε=19255), 257 nm (ε=11152), 203 nm (ε=21782).

Anal. Calcd for C$_{15}$H$_{16}$F$_3$N$_3$S$_2$: C, 50.13; H, 4.49; N, 11.69. Found: C, 50.36; H, 4.45: N, 11.46.

Example 221

N-(2-(1-Cyclohexenyl)ethyl)-N'-[2-pyridyl]thiourea

A solution of 2-(1-cyclohexenyl)ethyl isothiocyanate (1.67 g, 10 mmol) and 2-aminopyridine (941 mg, 10 mmol) in N-methylpyrrolidinone (20 mL) was heated to 100° C. After 16.5 h, the reaction was cooled to room temperature and poured into ethyl acetate. The organic phase was washed with water (4×) and brine. The organic layer was dried over sodium sulfate, filtered and concentrated. The solid obtained was purified by recrystallization from ethyl acetate to provide 1.31 g of the titled product (50%) as a white crystalline solid:

mp 153°–155° C.;

IR (KBr, cm$^{-1}$) 3219, 2921, 1605, 1569, 1537, 1481, 1319, 1235, 1181, 1092;

$^1$H NMR (300 MHZ, DMSO-d$_6$) δ11.55 (s, 1H), 10.47 (s, 1H), 8.09 (d, J=3.9 Hz, 1H), 7.74–7.68 (m, 1H), 7.09 (d, J=8.3 Hz, 1H), 7.00–6.96 (m, 1H), 5.47 (s, 1H), 3.65–3.59 (m, 2H), 2.19 (t, J=6.6 Hz, 2H), 1.94–1.90 (m, 4H), 1.55–1.43 (m, 4H);

MS (FD) m/e 261 (M+);

UV (EtOH) 292 nm (ε=15926), 265 nm (ε=17724), 247 nm (ε=15198).

Anal. Calcd for C$_{14}$H$_{19}$N$_3$S: C, 64.33; H, 7.33; N, 16.08. Found: C, 64.12; H, 7.33; N, 15.89.

Example 222

N-(2-phenethyl)-N'-[2-(5-bromo)pyridyl]thiourea

A solution of 2-phenethyl isothiocyanate (1.63 g, 10 mmol, 1.5 mL) and 2-amino-5-bromopyridine (1.73 g, 10 mmol) in N-methylpyrrolidinone (20 mL) was heated to 100° C. After 22 h, the reaction was cooled to room temperature and poured into ethyl acetate. The organic phase was washed with 1N hydrochloric acid (2×), water (2×) and brine. The organic layer was dried over sodium sulfate, filtered and concentrated. The solid obtained was purified by recrystallization from ethyl acetate/hexanes to provide 1.20 g of the titled product (36%) as a white crystalline solid:

mp 160°–162° C.;

IR (KBr, cm$^{-1}$) 3028, 1595, 1559, 1531, 1475, 1311, 1228, 1092;

$^1$H NMR (300 MHZ, DMSO-d$_6$) δ11.16 (s, 1H), 10.65 (s, 1H), 8.11 (d, J=2.1 Hz, 1H), 7.93–7.90 (m, 1H), 7.29–7.18 (m, 5H), 7.05 (d, J=8.8 Hz, 1H), 3.82–3.77 (m, 2H), 2.88 (t, J=7.0 Hz, 2H);

MS (FD) m/e 335 (M+), 337 (M+2);

UV (EtOH) 305 nm (ε=14171), 275 nm (ε=24881), 201 nm (ε=21601).

Anal. Calcd for C$_{14}$H$_{14}$BrN$_3$S: C, 50.01; H, 4.20; N, 12.50. Found: C, 49.93; H, 4.19; N, 12.52.

Example 223

N-[2-(1-Cyclohexenyl)ethyl]-N'-[2-(5-cyano)pyridyl]thiourea

A stirred solution of 2-(1-cyclohexenyl)ethyl isothiocyanate (1.36 g, 8.14 mmol) and 2-amino-5-cyanopyridine (0.97 g, 8.14 mmol) in N-methylpyrrolidinone (20 mL) was heated to 100° C. After 5 days, the reaction was cooled to room temperature and poured into EtOAc. The organic phase was washed with H$_2$O (4×) and brine. The organic layer was dried over Na$_2$SO$_4$, filtered and concentrated. The solid obtained was purified by flash chromatography on silica gel (2% EtOAc/CH$_2$Cl$_2$), followed by recrystallization with EtOAc/hexanes to provide 78 mg of the titled product (3%) as an off-white solid:

mp 195°–197° C.;

IR (KBr, cm$^{-1}$) 2927, 2224, 1605, 1570, 1533, 1487, 1369, 1228, 1165;

$^1$H NMR (300 MHZ, DMSO-d$_6$) δ11.17 (br s, 1H), 10.96 (s, 1H), 8.57 (d, J=1.9 Hz, 1H), 8.12 (dd, J=8.8, 2.1 Hz, 1H), 7.20 (d, J=8.8 Hz, 1H), 5.47 (s, 1H), 3.66–3.59 (m, 2H), 2.20 (t, J=6.6 Hz, 2H), 1.94–1.89 (m, 4H), 1.54–1.43 (m, 4H);

MS (FD) m/e 286 (M+);

UV (EtOH) 308 nm, 202 nm.

Anal. Calcd for C$_{15}$H$_{18}$N$_4$S: C, 62.91; H, 6.34; N, 1956.Found: C, 62.70; H, 6.42; N, 19.42.

Example 224

N-(2-phenethyl)-N'-[2-(4-(4-biphenyl)thiazolyl]thiourea

A solution of 2-phenethyl isothiocyanate (0.82 g, 5 mmol, 0.75 mL) and 2-amino-4-(4-biphenyl)thiazole (1.26 g, 5 mmol) in N,N-dimethylformamide (12.5 mL) was heated to 100° C. After 19.5 h, the reaction was cooled to room temperature and poured into ethyl acetate. The organic solution was washed with 1N hydrochloric acid. The mixture was filtered and the filtrate was separated and the organic phase washed with saturated sodium bicarbonate solution, water (4×) and brine. The organic layer was dried over sodium sulfate, filtered and concentrated. The material was purified by flash chromatography on silica gel (1% ethyl acetate in dichloromethane to 2% ethyl acetate in dichloromethane) to provide 372 mg of the titled product (18%). The yellow solid was recrystallized from ethyl acetate:

mp 208.5°–209° C.;

IR (KBr, cm$^{-1}$) 3437, 3172, 3029, 1570, 1553, 1511, 1211, 1060, 738;

$^1$H NMR (300 MHz, DMSO-d$_6$) δ11.72 (s, 1H), 9.54 (br s, 1H), 7.86–7.80 (m, 2H), 7.78–7.68 (m, 4H), 7.58 (s, 1H), 7.52–7.44 (m, 2H), 7.41–7.35 (m, 1H), 7.34–7.29 (m, 4H), 7.27–7.20 (m, 1H), 3.92–3.84 (m, 2H), 2.98 (t, J=3 Hz, 2H);

MS (FD) m/e 415 (M+);

UV (EtOH) 293 nm, 212 nm.

Anal. Calcd for C$_{24}$H$_{21}$N$_3$S$_2$: C, 69.36; H, 5.09; N, 10.11. Found: C, 69.08; H, 5.10; N, 9.99.

Example 225

N-(2-Phenethyl)-N'-2-[4-(4-pyridyl)thiazolyl]thiourea

2-Amino-4-(4-pyridyl)thiazole hydrobromide was slurried with methylene chloride and shaken with saturated sodium bicarbonate solution. The layers were separated and the aqueous washed with methylene chloride and ethyl acetate. The combined organic layers were concentrated. To the solid (1.0 g, 5.6 mmol) was added 2-phenethyl isothiocyanate (0.91 g, 5.6 mmol, 0.83mL) in N,N-dimethylformamide (12.5 mL). The resulting suspension was heated to 100° C. After 20.5 h, the reaction was cooled to room temperature and poured into ethyl acetate. The organic phase was washed with water (4×) and brine. The organic layer was dried over sodium sulfate, filtered and concentrated. The resulting solid was recrystallized from ethyl acetate (3×) to provide 133 mg (7%) of the titled product:

mp 196.5° C.;

IR (KBr, cm$^{-1}$) 3250, 2939, 1723, 1604, 1506, 1223, 670, 664;

$^1$H NMR (300 MHz, DMSO-d$_6$) δ11.72 (s, 1H), 9.21 (br s, 1H), 8.54 (d, J=6 Hz, 2H), 7.82 (s, 1H), 7.63 (d, J=6 Hz, 2H), 7.30–7.15 (m, 5H), 3.84–3.77 (m, 2H), 2.89 (t, J=7 Hz, 2H);

MS (FD) m/e 340 (M+);

HRMS (FAB) m/e (M+) calcd 341.0895, obs 341.0909;

UV (EtOH) 294 nm (ε=23935), 231 nm (ε=16356), 203 nm (ε=25793).

Example 226

N-(2-Phenethyl)-N'-2-[4-(1-(1-ethoxycarbonyl)-3-t-butoxycarbonylmethoxy)imino)thiazoyl]thiourea 2-Amino-4-(1-(1-ethoxycarbonyl)-3-t-butoxycarbonylmethoxy)imino)thiazole (2.64 g, 8 mmol) and 2-phenethyl isothiocyanate (1.31 g, 8 mmol, 1.2 mL) in N,N-dimethylformamide (20 mL) were heated to 100° C. After 24 h, the reaction was cooled to room temperature and poured into ethyl acetate. The organic phase was washed with 1N hydrochloric acid, saturated sodium bicarbonate solution, water (3×) and brine. The organic layer was dried over sodium sulfate, filtered and concentrated. The resulting solid was triturated with ethyl acetate to provide 801 mg (20%) of the titled product:

mp 188.5° C.;

IR (KBr, cm$^{-1}$) 3293, 2975, 1749, 1594, 1543, 1453, 1382, 1231, 1154, 1054, 748, 698;

$^1$H NMR (300 MHz, DMSO-d$_6$) δ11.85 (s, 1H), 8.46 (br s,1H), 7.29–7.17 (m, 5H), 4.59 (s, 2H), 4.31–4.24 (q, J=7.1 Hz, 2H), 3.70–3.64 (m, 2H), 2.82 (t, J=7.1 Hz, 2H), 1.36 (s, 9H), 1.23 (t, J=7.1 Hz, 3H);

MS (FD) m/e 492 (M$^+$);

UV (EtOH) 292 nm, 257 nm (ε=16356), 203 nm.

Anal. Calcd for C$_{22}$H$_{28}$N$_4$O$_5$S$_2$: C, 53.64; H, 5.73; N, 11.37. Found: C, 53.67; H, 5.83; N, 11.34.

Example 227

N-(2-Phenethyl)-N'-2-[4-t-butyl-5-methylthiazolyl]thiourea

2-Amino-4-t-butyl-5-methylthiazole (1.87 g, 11 mmol) and 2-phenethyl isothiocyanate (1.80 g, 11 mmol, 1.64 mL) in N,N-dimethylformamide (25 mL) were heated to 100° C.

After 18.5 h, the reaction was cooled to room temperature and poured into ethyl acetate. The organic phase was washed with 1N hydrochloric acid, saturated sodium bicarbonate solution, water (3×) and brine. The organic layer was dried over sodium sulfate, filtered and concentrated. The resulting solid was triturated with ether to provide 1.02 g (28%) of the titled product:

mp 153°–153.5° C.;

IR (KBr, cm$^{-1}$) 3171, 2966, 1474, 1534, 1510, 1455, 1346, 1221, 1186, 755, 704;

$^1$H NMR (300 MHz, DMSO-d$_6$) δ11.28 (BR S, 1H), 9.90 (BR S, 1H), 7.28–7.14 (M, 5H), 3.78–3.34 (M, 2H), 2.84 (T, J=7 Hz, 2H), 2.27 (s, 3H), 1.16 (s, 9H);

MS (FD) m/e 333 (M$^+$);

UV (EtOH) 297 nm (ε=19835), 257 nm (ε=9954), 202 nm (ε=21059).

Anal. Calcd for C$_{17}$H$_{23}$N$_3$S$_2$: C, 61.22; H, 6.95; N, 12.60. Found: C, 61.42; H, 6.92; N, 12.55.

Example 228

N-(2-Phenethyl)-N'-2-[4-(4-bromophenyl)-5-ethylthiazolyl]thiourea

2-Amino-4-(4-bromophenyl)-5-ethylthiazole (848 mg, 3 mmol) and 2-phenethyl isothiocyanate (490 mg, 3 mmol, 0.45 mL) in N,N-dimethylformamide (7.5 mL) were heated to 100° C. After 22.5 h, the reaction was cooled to room temperature and poured into ethyl acetate. The organic phase was washed with 1N hydrochloric acid, saturated sodium bicarbonate solution, water (3×) and brine. The organic layer was dried over sodium sulfate, filtered and concentrated. The resulting solid was recrystallized from ethyl acetate and toulene to provide 146 mg (11%) of the titled product:

mp 169°–170° C.;

IR (KBr, cm$^{-1}$) 3169, 3025, 2969, 2930, 1581, 1558, 1520, 1234, 1168, 1009;

$^1$H NMR (300 MHz, DMSO-d$_6$) δ11.54 (s, 1H), 9.40 (br s, 1H), 7.57 (d, J=8.3 Hz, 2H), 7.36 (d, J=8.3 Hz, 2H), 7.21–7.14 (m, 5H), 3.75–3.73 (m, 2H), 2.87–2.82 (m, 2H), 2.80 (q, J=7.8 Hz, 2H), 1.17 (t, J=7.8 Hz, 3H);

MS (FD) m/e 445 (M+), 447 (M+2);

UV (EtOH) 291 nm, 263 nm, 237 nm, 203 nm.

Anal. Calcd for C$_{20}$H$_{20}$BrN$_3$S$_2$: C, 53.81; H, 4.52; N, 9.41; Found: C, 53.71; H, 4.61; N, 9.39.

Example 229

N-(2-phenethyl)-N'-[2-pyridino[2,3-d]thiazolyl thiourea

A solution of 2-phenethyl isothiocyanate (1.33 g, 8.13 mmol, 1.21 mL) and 2-aminopyridion[2,3-d]thiazole (1.23 g, 8.13 mmol) in N,N-dimethylformamide (15 mL) was heated to 105° C. After 46.5 h, the reaction was cooled to room temperature and poured into ethyl acetate. The organic solution was washed with water (6×) and brine. The organic layer was dried over sodium sulfate, filtered and concentrated. The material was purified by flash chromatography on silica gel (5% ethyl acetate in dichloromethane to 10% ethyl acetate in dichloromethane) to provide 330 mg of the titled product (13%). The white powder was recrystallized from ethyl acetate:

mp 202°–202.5° C.;

IR (KBr, cm$^{-1}$) 3445, 3171, 3025, 1565, 1551, 1510, 1382, 1201, 1150;

$^1$H NMR (300 MHz, DMSO-d$_6$) δ11.91 (br s, 1H), 9.76 (br s, 1H), 8.37 (m, 1H), 7.88 (m, 1H), 7.43 (dd, J=3 and 6 Hz, 1H), 7.33–7.20 (m, 5H), 3.82–3.79 (m, 2H), 2.89 (t, J=7 Hz, 2H);

MS (FAB) m/e 315 (M+1);

UV (EtOH) 312 nm (ε=22468), 211 nm (ε=19194).

Anal. Calcd for $C_{15}H_{14}N_4S_2$: C, 57.30; H, 4.49; N, 17.82. Found: C, 57.20; H, 4.49; N, 17.66.

Example 230

N-(2-Phenethyl)-N'-[2-(3-ethyl)pyridyl]thiourea

A) 2-t-Butoxycarbonylamino-3-ethylpyridine 2-t-Butoxycarbonylaminopyridine (10 g, 51.5 mmol) was dissolved in tetrahydrofuran (80 mL), and cooled to −78° C. N-butyllithium (80 mL of 1.49M in hexanes, 120 mmol) was added dropwise over a period of 1 h. After stirring for an additional 15 min at −78° C. and then for 2.5 hours at −10° C., the solution was then recooled back down to −78° C. and iodoethane (77.2 mmol, 6.18 mL) was added dropwise over a period of 15 min via syringe. The solution was allowed to warm to room temperature. The reaction was quenched with 100 mL of a saturated ammonium chloride and extracted with ethyl acetate (3×). The organic layers were collected, dried over magnesium sulfate, and concentrated. The resulting solid was purified by flash chromatography on silica gel (25% ethyl acetate/hexanes) to provide the 4.9 g (43%) of the titled product as a light brown solid:

mp 101°–102° C.;

IR (KBr,cm$^{-1}$) 3174, 2968, 1725, 1594, 1519, 1442, 1278, 1249, 1156;

$^1$H NMR (300 MHZ, DMSO-d$_6$) δ8.98 (s, 1H), 8.17 (m, 1H), 7.61 (m, 1H), 7.15 (m, 1H), 2.52 (q, J=7.5 Hz, 2H), 1.39 (s, 9H), 1.08 (t, J=7.5 Hz, 3H);

MS (FD) m/e 222 (M+);

UV (EtOH) 270 nm (ε=4398), 223 nm (ε=6745).

Anal. Calcd for $C_{12}H_{18}N_2O_2$: C, 64.84; H, 8.16; N, 12.60. Found: C, 64.91; H, 8.34; N, 12.42.

B) Preparation of 3-Ethyl-2-aminopyridine.

2-t-Butoxycarbonylamino-3-ethylpyridine (4.9 g, 19.8 mmol) was dissolved in 90 ml of 3N HCl/Acetic acid and stirred for two hours. The sloution was neutralized with 2N NaOH to pH 7 and then extracted with ethyl acetate (2×400 ml). The organics were dried over magnesium sulfate and concentrated giving 2.3 g (95%) of a yellowish solid. This solid was used in the next reaction without further purification.

C) N-(2-Phenethyl)-N'-[2-(3-ethyl)pyridyl]thiourea

A solution of phenethyl isothiocyanate (3.61 g, 18.8 mmol, 3.3 mL) and 2-amino-3-ethylpyridine (2.3 g, 18.8 mmol) in N,N-dimethylformamide (20 mL) was stirred at 90°–95° C. for 3 h. The solution was cooled to room temperature, poured into ethyl acetate (150 mL), and washed with 0.1N hydrochloric acid (2×), water (3×), and brine. The organics were dried over sodium sulfate, filtered, and concentrated. The resulting solid was purified by flash chromatography on silica gel (1.5% ethyl acetate/dichloromethane) and then recrystallized (30% ethyl acetate/hexanes) to give 1.1 g (21%) of the titled product as a white solid:

mp 57°–58° C.;

IR (KBr, cm$^{-1}$) 3433, 2932, 1561, 1516, 1452, 1433, 1328, 1237, 760;

$^1$H NMR (300 MHZ, DMSO-d$_6$) δ11.58 (br s, 1H), 8.66 (s, 1H), 7.92–7.90 (m, 1H), 7.6–7.58 (m, 1H), 7.30–7.15 (m, 5H), 7.02–6.98 (m, 1H), 3.83–3.77 (m, 2H), 2.89 (t, J=6 Hz, 2H), 2.64 (q, J=7.5 Hz, 2H), 1.09 (t, J=7.5 Hz, 3H);

MS (FD) m/e 285 (M+);

UV (EtOH) 293 nm (ε=16632), 265 nm (ε=14930), 244 nm (ε=16594), 202 nm (ε=21127).

Anal. Calcd for $C_{16}H_{19}N_3S$: C, 67.33; H, 6.71; N, 14.72. Found: C, 67.17; H, 6.88; N, 14.51.

Example 231

N-(2-Phenethyl)-N'-[2-(3-bromo)pyridyl]thiourea

A) 2-t-Butoxycarbonylamino-3-bromopyridine 2-t-Butoxycarbonylaminopyridine (10 g, 51.5 mmol) was dissolved in tetrahydrofuran (80 mL), and cooled to −78° C. N-butyllithium (120 mmol, 80 mL of 1.49M in hexanes) was added dropwise over a period of 1 h. After stirring for an additional 15 min at −78° C. and then for 2.5 h at −10° C., the solution was recooled back down to −78° C. and 1,2-dibromoethane (77.2 mmol, 6.65 mL) was added dropwise over a period of 15 min via syringe. The solution was allowed to warm to room temperature. The reaction was quenched with 100 mL of saturated ammonium chloride and was extracted with ethyl acetate (3×). The organic layers were collected, dried over magnesium sulfate, filtered, and concentrated. The resulting solid was purified by flash chromatography on silica gel (25% ethyl acetate/hexanes) giving 4.5 g (32%) of the titled product as a light brown solid:

mp 120°–121° C.;

IR (KBr, cm$^{-1}$) 3191, 2980, 1729, 1521, 1442, 1365, 1272, 1166, 1032;

$^1$H NMR (300 MHZ, DMSO-d$_6$) δ9.28 (s, 1H), 8.34 (m, 1H), 8.05 (m, 1H), 7.15 (m, 1H), 1.39 (s, 9H);

MS (FD) m/e 272 (M+), 274 (M+2);

UV (EtOH) 280 nm (ε=4047), 230 nm (ε=9067), 204 nm (ε=16385).

B) Preparation of 3-Bromo-2-aminopyridine.

3-Bromo-2-t-butoxycarbonylaminopyridine (3.8 g, 13.9 mmol) was dissolved up in 70 ml of 3N HCl/Acetic acid and stirred for two hours. The solution was neutralized with 2N NaOH to pH 7 and then extracted with ethyl acetate (3×300 ml). The organics were dried over magnesium sulfate and concentrated giving a brown oil. This was put on vacuum overnight giving 2.4 g (100%) solid crystals. This was used in the next reaction without further purification:

mp 57°–59° C.;

$^1$H NMR (300 MHZ, DMSO-d$_6$) δ7.9 (m, 1H), 7.65 (m, 1H), 6.5–6.4 (m, 1H), 6.2–6.1(s, 2H).

C) N-(2-Phenethyl)-N'-[2-(3-bromo)pyridyl]thiourea

A solution of phenethyl isothiocyanate (1.89 g, 11.6 mmol, 1.73 mL) and 2-amino-3-bromopyridine (2.0 g, 11.6 mmol) in N,N-dimethylformamide was stirred at 90°–95° C. for 3 h. The solution was cooled to room temperature, poured into ethyl acetate (150 mL), and washed with 0.1N hydrochloric acid (2×), water (3×), and brine. The organics were dried over sodium sulfate, filtered, and concentrated. The resulting solid was purified by flash chromatography on silica gel (30% ethyl acetate/hexanes) to yield 0.5 g (13%) of the titled product as a white solid:

mp 95°–96° C.;

IR (KBr, cm$^{-1}$) 3403, 3021, 1591, 1564, 1548, 1514, 1435, 1150, 750, 700;

$^1$H NMR (300 MHZ, DMSO-d$_6$) δ11.2 (s, 1H), 8.45 (s, 1H), 8.13–8.06 (m, 2H), 7.29–7.18 (m, 5H), 7.04–7.0 (m, 1H), 3.86–3.8 (m, 2H), 2.91 (t, J=6 Hz, 2H);

MS (FD) m/e 335 (M+), 337 (M+2);

UV (EtOH) 298 nm (ε=13404), 272 nm (ε=16029), 250 nm (ε=17186), 203 nm (ε=22974).

Anal. Calcd for $C_{14}H_{14}N_3S_2Br$: C, 50.01; H, 4.20; N, 12.50. Found: C, 49.77; H, 4.21; N, 12.37.

Example 232

N-(4-Bromophenethyl)-N'-[2-(4-ethyl)thiazolyl]thiourea

4-Bromophenethylamine hydrochloride (1 g, 4.22 mmol) was slurried with dichloromethane and water. Sodium hydroxide (0.17 g, 4.22 mmol) dissolved in water was added to this mixture and stirred. The organics were separated, washed with brine, dried over sodium sulfate, filtered, and concentrated. The resulting solid was added to N-(thioimidazoyl)-2-amino-4-ethylthiazole (1.0 g, 4.22 mmol) in N,N-dimethyl-formamide (20 mL) and stirred for 3 h at 90°–95° C. The solution was cooled to room temperature and added to 150 mL of ethyl acetate, washed with 0.1N hydrochloric acid (2×), water (3×), and brine. The organics were dried over sodium sulfate, filtered, and concentrated. The solid was recrystallized (50% ethyl acetate/hexanes) providing 0.7 g (45%) of the titled product as a yellow solid:

mp 156°–157° C.;

IR (KBr, cm$^{-1}$) 2963, 1560, 1527, 1259, 1212, 1011, 802, 743;

$^1$H NMR (300 MHZ, CDCl$_3$) δ10.94 (br s, 1H), 9.77 (br s, 1H), 7.41 (d, J=8.3 Hz, 2H), 7.24 (d, J=8.2 Hz, 2H), 6.33 (s, 1H), 4.03–3.97 (m, 2H), 2.97 (t, J=6.8 Hz, 2H), 2.49 (q, J=7.5 Hz, 2H), 1.13 (t, J=7.5 Hz, 3H);

MS (FD) m/e 369 (M+), 371 (M+2);

UV (EtOH) 292 nm (ε=10803), 257 nm (ε=6300).

Anal. Calcd for C$_{14}$H$_{16}$N$_3$SBr: C, 45.41; H, 4.35; N, 11.35. Found: C, 45.53; H, 4.42; N, 11.49.

Example 233

N-(3-Phenoxyphenethyl)-N'-[2-(4-ethyl)thiazolyl]thiourea

3-Phenoxyphenethylamine hydrochloride (1.0 g, 4.0 mmol) was slurried with dichloromethane and water. Sodium hydroxide (0.16 g, 4.0 mmol) dissolved in water was added and stirred. The organics were separated, washed with brine, dried over sodium sulfate, filtered, and concentrated. The resulting solid was added to N-(thioimidazoyl)-2-amino-4-ethylthiazole (1.0 g, 4.22 mmol) in N,N-dimethyl-formamide (20 mL) and stirred for 3 h at 90°–95° C. The solution was cooled to room temperature, added to 150 mL of ethyl acetate and washed with 0.1N hydrochloric acid (2×), water (3×), and brine. The organics were dried over sodium sulfate, filtered, and concentrated. The oil was put on vacuum overnight and recrystallized (50% ethyl acetate/hexanes) providing 0.6 g (42%) of the titled product as a white solid:

mp 124° C.;

IR (KBr, cm$^{-1}$) 3177, 2966, 1563, 1534, 1509, 1491, 1446, 1349, 1287, 1260, 1218, 1158, 773;

$^1$H NMR (300 MHZ, CDCl$_3$) δ10.99 (br s, 1H), 9.87 (br s, 1H), 7.31–7.23 (m, 3H), 7.09–6.84 (m, 6H), 6.32 (s, 1H), 4.03–3.97 (m, 2H), 2.99 (t, J=6.8 Hz, 2H), 2.53 (q, J=7.5 Hz, 2H), 1.14 (t, J=7.5 Hz, 3H);

MS (FD) m/e 383 (M+);

UV (EtOH) 293 nm (ε=19262), 258 nm (ε=11356), 205 nm (ε=37212).

Anal. Calcd for C$_{20}$H$_{21}$N$_3$OS$_2$: C, 62.63; H, 5.52; N, 10.96. Found: C, 62.69; H, 5.61; N, 11.06.

Example 234

N-(2-Nitrophenethyl)-N'-[2-(4-ethyl)thiazolyl]thiourea

2-Nitrophenethylamine tosylate (0.97 g, 3.0 mmol) was slurried with dichloromethane and water. Sodium hydroxide (0.12 g, 3 mmol) dissolved in water was added and stirred. The organics were separated, washed with brine, dried over sodium sulfate, filtered, and concentrated. The resulting solid was added to N-(thioimidazoyl)-2-amino-4-ethylthiazole [BK8-6TT-074] (0.71 g, 3 mmol) in N,N-dimethylformamide (20 mL) and stirred for 3 h at 90°–95° C. The solution was allowed to cool to room temperature and then was added to 150 mL of ethyl acetate and washed with 0.1N hydrochloric acid (2×), water (3×), and brine. The organics were dried over sodium sulfate, filtered, and concentrated. The solid was recrystallized (50% ethyl acetate/hexanes) providing 0.5 g (54%) of the titled product as a white solid:

mp 132°–133° C.;

IR (KBr, cm$^{-1}$) 3171, 2966, 1586, 1531, 1509, 1341, 1215;

$^1$H NMR (300 MHZ, CDCl$_3$) δ11.06 (br s, 1H), 9.76 (br s, 1H), 7.98 (d, J=8.1 Hz, 1H), 7.56–7.35 (m, 3H), 6.35 (s, 1H), 4.13–4.02 (m, 2H), 3.33 (t, J=7 Hz, 2H), 2.56 (q, J=7.4 Hz, 2H), 1.16 (t, J=7.4 Hz, 3H);

MS (FD) m/e 336 (M+);

UV (EtOH) 292 nm (ε=20546), 258 nm (ε=14748), 203 nm (ε=24932).

Anal. Calcd for C$_{14}$H$_{16}$N$_4$O$_2$S$_2$: C, 49.98; H, 4.79; N, 16.65. Found: C, 49.95; H, 4.86; N, 16.59.

Example 235

N-[6-(2-phenylbenzoxazole)]ethyl]-N'-[2-ethylthiazolyl]thiourea

2-[6-(2-phenylbenzoxazole)]ethylamine hydrochloride (0.88 g, 3.2 mmol) was slurried with dichloromethane and water. Sodium hydroxide (0.13 g, 3.2 mmol) dissolved in water was added and stirred. The organics were separated, washed with brine, dried over sodium sulfate, filtered, and concentrated. The resulting solid was added to N-(thioimidazoyl)-2-amino-4-ethylthiazole (0.71 g, 3 mmol) in N,N-dimethylformamide (20 mL) and stirred for 3 h at 90°–95° C. The solution was cooled to room temperature, added to 150 mL of ethyl acetate and washed with 0.1N hydrochloric acid (2×), water (3×), and brine. The organics were dried over sodium sulfate, filtered, and concentrated. The solid was recrystallized (50% ethyl acetate/hexanes) providing 0.64 g (49%) of the titled product as a white solid:

mp 183° C.;

IR (KBr, cm$^{-1}$) 3178, 3035, 1578, 1533, 1506, 1253, 1214, 701;

$^1$H NMR (300 MHZ, CDCl$_3$) δ10.96 (br s, 1H), 9.7 (br s, 1H), 8.25–8.21 (m, 2H), 7.69 (d, J=8.1 Hz, 1H), 7.53–7.48 (m, 4H), 7.29 (m, 1H), 6.28 (s, 1H), 4.13–4.06 (m, 2H), 3.17 (t, J=6.6 Hz, 2H), 2.39 (q, J=7.5 Hz, 2H), 1.0 (t, J=7.5 Hz, 3H);

MS (FD) m/e 408 (M+);

UV (EtOH) 294 nm (ε=12603), 201 nm (ε=14517).

Anal. Calcd for C$_{21}$H$_{20}$N$_4$OS$_2$: C, 61.74; H, 4.93; N, 13.71. Found: C, 61.99; H, 5.18; N, 13.85.

Example 236

N-(2-Phenoxyphenethyl]-N'-[2-(ethyl)thiazolyl]thiourea

2-Phenoxyphenethylamine hydrochloride (0.97 g, 3.9 mmol) was slurried with dichloromethane and water. Sodium hydroxide (0.13 g, 3.9 mmol) dissolved in water was added and stirred. The organics were separated, washed with brine, dried over sodium sulfate, filtered, and concentrated. The resulting solid was added to N-(thioimidazoyl)-

2-amino-4-ethylthiazole (0.929 g, 3.9 mmol) in N,N-dimethylformamide (20 mL) and stirred for 3 h at 90°–95° C. The solution was cooled to room temperature, added to 150 mL of ethyl acetate and washed with 0.1N hydrochloric acid (2×), water (3×), and brine. The organics were dried over sodium sulfate, filtered, and concentrated. The resulting solid was recrystallized (50% ethyl acetate/hexanes) providing 0.73 g (49%) of the titled product as a white solid:

mp 168° C.;

IR (KBr, cm$^{-1}$) 3168, 3013, 1581, 1532, 1487, 1237, 1209, 753;

$^1$H NMR (300 MHZ, CDCl$_3$) δ10.93 (br s, 1H), 9.67 (br s, 1H), 7.35–7.24 (m, 3H), 7.21–7.16 (m, 1H), 7.08–7.02 (m, 2H), 6.94–6.86 (m, 3H), 6.31 (s, 1H), 4.05–4.0 (m, 2H), 3.05 (t, J=6.9 Hz, 2H), 2.5 (q, J=7.5 Hz, 2H), 1.12 (t, J=7.5 Hz, 3H);

MS (FD) m/e 383 (M+);

UV (EtOH) 292 nm (ε=19052), 258 nm (ε=11450), 204 nm (ε=38534).

Anal. Calcd for C$_{20}$H$_{21}$N$_3$OS$_2$: C, 62.63; H, 5.52; N, 10.96. Found: C, 62.91; H, 5.67; N, 11.22.

Example 237

N-[[(4-methyl-2-thiazolyl)amino]thioxomethyl]-DL-phenylalanine methyl ester

A solution of 1-[(2-[4-methyl]thiazolyl)thiocarbamoyl] imidazole (0.45 g, 5.0 mmol) and DL-phenylalanine methyl ester hydrochloride (0.43 g, 2.0 mmol) in N,N-dimethylformamide (50 mL) was heated at 110° C. for 12 h. The reaction was cooled to room temperature, solvent removed under reduced pressure, recrystallized from ethyl ether-hexanes to provide 118 mg (18%) of the titled product:

mp 131°–132° C.;

IR (KBr, cm$^{-1}$) 3179, 3027, 1578, 1579, 1533,1224;

$^1$H NMR (300 MHz, DMSO-d$_6$) δ11.80 (br s, 1H), 10.20 (br s, 1H), 7.20–7.38 (m, 5H), 6.63 (s, 1H), 5.10 (q, 1H), 3.63 (s, 3H), 3.03–3.22 (m, 2H), 2.12 (s, 3H);

MS (FD) m/e 335 (M$^+$);

UV (EtOH) 294 nm (ε=18428), 257 nm (ε=9852), 202 nm (ε=21796).

Anal. Calcd for C$_{15}$H$_{17}$N$_3$O$_2$S$_2$: C, 53.71; H, 5.11; N, 12.53. Found: C, 53.47; H, 5.11; N, 12.75.

Example 238

(±)-3-(4-methyl-2-thiazolyl)-5-(phenylmethyl)-2-thioxo-4-imidazolidinone

A solution of N-[[(4-methyl-2-thiazolyl)amino]thioxomethyl]-DL-phenylalanine methyl ester (0.94 g, 2.80 mmol) and p-toluene sulfonic acid hydrate (0.20 g 1.05 mmol) in toluene (80 mL) was refluxed with a Dean-Stark trap for 24 h. The reaction was cooled to room temperature, solvent removed under reduced pressure, residue taken up in ethyl acetate, washed with saturated sodium bicarbonate and saturated sodium chloride, dried over magnesium sulfate, and concentrated under reduced pressure. The resulting product was recrystallized from ethyl acetate-hexanes to provide 216.1 mg (25%) of the titled product:

mp 169°–171° C.;

IR (KBr, cm$^{-1}$) 3153, 1776, 1539, 1280, 1195, 744, 303;

$^1$H NMR (300 MHz, DMSO-d$_6$) δ10.85 (s, 1H), 7.40 (d, 1H), 7.30(m, 3H), 7.11(m, 2H), 4.83 (t, 1H), 3.50 (d, 2H), 2.35 (s, 3H);

MS (FD) m/e 303 (M$^+$);

UV(EtOH) 265 nm (ε=16902), 203 nm (ε=17971).

Anal. Calcd for C$_{14}$H$_{13}$N$_3$OS$_2$: C, 55.42; H, 4.32; N, 13.85. Found: C, 55.63; H, 4.45; N, 13.91.

Example 239

N-[(2-thiazolylamino)thioxomethyl]-DL-phenylalanine methyl ester

A solution of 1-[(2-thiazolyl)thiocarbamoyl]imidazole (4.21 g, 20.0 mmol) and DL-phenylalanine methyl ester hydrochloride (4.31 g, 20.0 mmol) in N,N-dimethylformamide (150 mL) was heated at 90° C. for 3 h. The reaction was cooled to room temperature, solvent removed under reduced pressure, recrystalllized from ether-hexanes to provide 3.26 g (51%) of the titled product:

IR (KBr, cm$^{-1}$) 3184, 3029, 1735 1569, 1510, 1223,1189;

$^1$H NMR (300 MHz, DMSO-d$_6$) δ11.90 (s, 1H), 7.40 (d, 1H), 7.20–7.38 (m, 5H), 7.17 (d, 1H), 5.30 (q, 1H), 3.63 (s, 3H), 3.02–3.22 (m, 2H);

MS (FD) m/e 321(M$^+$);

UV (mtOH) 291 nm (ε=18235), 255 nm (ε=10773), 202 nm (ε=20575).

Anal. Calcd for C$_{14}$H$_{15}$N$_3$O$_2$S$_2$: C, 52.31; H, 4.70; N, 13.07. Found: C, 52.24; H, 4.61; N, 13.18.

Example 240

DL-5-(phenylmethyl)-3-(2-thiazolyl)-2-thioxo-4-thiazolidinone

A solution of N-[(2-thiazolylamino)thioxomethyl]-DL-phenylalanine methyl ester (0.47 g, 2.23 mmol) and p-toluene sulfonic acid hydrate (0.20 g 1.05 mmol) in toluene (50 mL) was refluxed with a Dean-Stark trap for 12 h. The reaction was cooled to room temperature, solvent removed under reduced pressure, residue taken up in ethyl acetate, washed with saturated sodium bicarbonate and saturated sodium chloride, dried over magnesium sulfate, and concentrated under reduced pressure. The resulting product was recrystallized from ethyl ether-hexanes to provide 0.243 g (58%) of the titled product:

mp 164°–165° C.;

IR (KBr, cm$^{-1}$) 3099, 2985, 2873, 1775,1532, 1440, 1398, 1329, 1251, 1208, 737;

$^1$H NMR (300 MHz, DMSO-d$_6$) δ10.90 (s, 1H), 7.83 (d, 1H), 7.80 (d, 1H), 7.50 (m, 3H), 7.20 (m, 2H), 4.90 (t, 1H), 3.17 (d, 2H);

MS (FD) m/e 289 (M$^+$);

UV (EtOH) 264 nm (ε=16108), 202 nm (ε=17275).

Anal. Calcd for C$_{13}$H$_{11}$N$_3$OS$_2$: C, 53.96; H, 3.83; N, 14.52. Found: C, 54.22; H, 3.96; N, 14.30.

EXAMPLE 241

N-[(2-benzothiazolylamino)thioxomethyl]-DL-phenylalanine methyl ester

A solution of 1-[(2-benzothiazolyl)thiocarbamoyl]imidazole (1.30 g, 5.0 mmol) and DL-phenylalanine methyl ester hydrochloride (1.08 g, 5.0 mmol) in N,N-dimethylformamide (50 mL) was heated at 90° C. for 3 h. The reaction was cooled to room temperature, solvent removed under reduced pressure, recrystalllized from ethyl ether-hexanes to provide 1.31 g (70%) of the titled product:

mp 168°–169° C.; IR (KBr, cm$^{-1}$) 3168, 3030, 1732, 1548, 1525, 1206,1193;

$^1$H NMR (300 MHz, DMSO-d$_6$) δ10.30 (br s, 1H), 7.88 (d, 1H), 7.62 (d, 1H), 7.32 (t, 1H), 7.20–7.29 (m, 6H), 5.18 (q, 1H), 3.70 (s, 3H), 3.22 (m, 2H);

MS (FD) m/e 371 (M$^+$);

UV (EtOH) 303 nm (ε=25329), 247 nm (ε=12095), 203 nm (ε=28990).

Anal. Calcd for C$_{18}$H$_{17}$N$_3$O$_2$S$_2$: C, 58.20; H, 4.61; N, 11.31. Found: C, 58.19; H, 4.70; N, 11.30.

Example 242

DL-3-(2-benzothiazolyl)-5-(phenylmethyl)-2-thioxo-4-thiazolidinone

A solution of N-[(2-benzothiazolylamino)thioxomethyl]-DL-phenylalanine methyl ester (1.0 g, 2.69 mmol) and p-toluene sulfonic acid hydrate (0.20 g 1.05 mmol) in toluene (80 mL) was refluxed with a Dean-Stark trap for 36 h. The reaction was cooled to room temperature, solvent removed under reduced pressure, residue taken up in ethyl acetate, washed with saturated sodium bicarbonate and saturated sodium chloride, dried over magnesium sulfate, and concentrated under reduced pressure. The resulting product was recrystallized from ethyl acetate-hexanes to provide 74.9 mg (8%) of the titled product:

mp 187°–189° C.;

IR (KBr, cm$^{-1}$) 3250, 1766, 1522, 1489;

$^1$H NMR (300 MHz, DMSO-d$_6$) δ11.00 (s, 1H), 8.18 (d, 1H), 8.02 (d, 1H), 7.08–8.00 (m, 2H), 7.37 (m, 3H), 7.23 (d, 2H), 4.97 (t, 1H), 3.18 (d, 2H);

MS (FD) m/e 339 (M$^+$);

UV (EtOH) 300 nm (ε=7355), 265 nm (ε=19454), 217 nm (ε=26558), 203 nm (ε=31150).

Anal. Calcd for C$_{17}$H$_{13}$N$_3$OS$_2$: C, 60.16; H, 3.86; N, 12.38. Found: C, 60.33; H, 4.14; N, 12.25.

Example 243

N-[[(6-fluoro-2-benzothiazolyl)amino]thioxomethyl]-DL-phenylalanine methyl ester A solution of 1-[(2-[6-fluoro]benzothiazolyl)thiocarbamoyl]imidazole (1.40 g, 5.0 mmol) and DL-phenylalanine methyl ester hydrochloride (1.08 g, 5.0 mmol) in N,N-dimethylformamide (175 mL) was heated at 90° C. for 3 h. The reaction was cooled to room temperature, solvent removed under reduced pressure, recrystalllized from ethyl ether-hexanes to provide 900 mg (46%) of the titled product:

$^1$H NMR (300 MHz, DMSO-d$_6$) δ10.03 (br s, 1H), 7.82 (q, 1H), 7.60 (m, 1H), 7.20–7.32 (m, 6H), 5.10 (q, 1H), 3.63 (s, 3H), 3.20 (t, 2H); MS (FD) m/e 389 (M$^+$).

Example 244

DL-3-(6-fluoro-2-benzothiazolyl)-5-(phenylmethyl)-2-thioxo-4-imidazolidinone

A solution of N-[[(6-fluoro-2-benzothiazolyl)amino]thioxomethyl]-DL-phenylalanine methyl ester (0.90 g, 2.31 mmol) and p-toluene sulfonic acid hydrate (0.20 g 1.05 mmol) in toluene (80 mL) was refluxed with a Dean-Stark trap for 48 h. The reaction was cooled to room temperature, solvent removed under reduced pressure, residue taken up in ethyl acetate, washed with saturated sodium bicarbonate and saturated sodium chloride, dried over magnesium sulfate, and concentrated under reduced pressure. The resulting product was recrystallized from ethyl ether-hexanes to provide 251 mg (31%) of the titled product:

mp 223°–224° C.;

IR (KBr, cm$^{-1}$) 3173, 1767, 1538, 1453, 1388, 1267;

$^1$H NMR (300 MHz, DMSO-d$_6$) δ11.02 (s, 1H), 8.00–8.12 (m, 2H), 7.40–7.50 (m, 1H), 7.20–7.39 (m, 5H), 4.97 (t, 1H), 3.20 (d, 2H);

MS (FD) m/e 357 (M$^+$);

UV (EtOH) 265 nm (ε=15680), 223 nm (ε=19505), 201 nm (ε=23665).

Anal. Calcd for C$_{17}$H$_{12}$FN$_3$OS$_2$: C, 57.13; H, 3.38; N, 11.76. Found: C, 56.89; H, 3.43; N, 11.60.

Example 245

N-[[(4,5-dimethyl-2-thiazolyl)amino]thioxomethyl]-DL-phenylalanine methyl ester

A solution of 1-[(2-[4,5-dimethyl]thiazolyl)thiocarbamoyl]imidazole (1.80 g, 7.5 mmol) and DL-phenylalanine methyl ester hydrochloride (1.60 g, 7.5 mmol) in N,N-dimethylformamide (50 mL) was heated at 90° C. for 4 h. The reaction was cooled to room temperature, solvent removed under reduced pressure, recrystalllized from ether-hexanes to provide 1.91 g (72%) of the titled product:

IR (KBr, cm$^{-1}$) 3178, 3029, 1756, 1552, 1505, 1219;

$^1$H NMR (300 MHz, DMSO-d$_6$) δ11.65 (br s, 1H), 7.20–7.38 (m, 5H), 5.10 (q, 1H), 3.65 (s, 3H), 3.05–3.21 (m, 2H), 2.20 (s, 3H), 2.08 (s, 3H);

MS (FD) m/e 349 (M$^+$);

UV (EtOH) 300 nm (ε=17248), 257 nm (ε=9202), 203 nm (ε=22444).

Anal. Calcd for C$_{16}$H$_{19}$N$_3$O$_2$S$_2$: C, 54.99; H, 5.48; N, 12.02. Found: C, 55.16; H, 5.57; N, 12.01.

Example 246

DL-3-(4,5-dimethyl-2-thiazolyl)-5-(phenylmethyl)-2-thiooxo-4-imidazolidinone

A solution of N-(4,5-dimethyl-2-thiazolyl)amino]thioxomethyl]-DL-phenylalanine (1.00 g, 2.86 mmol) and p-toluene sulfonic acid hydrate (0.20 g, 1.05 mmol) in toluene (50 mL) was refluxed with a Dean-Stark trap for 48 h. The reaction was cooled to room temperature, solvent removed under reduced pressure, residue taken up in ethyl acetate, washed with saturated sodium bicarbonate and saturated sodium chloride, dried over magnesium sulfate, and concentrated under reduced pressure. The resulting product was recrystallized from ethyl ether-hexanes to provide 0.545 g (60%) of the titled product:

mp 205°–207° C.;

IR (KBr, cm$^{-1}$) 3161, 1783, 1527, 1287, 1164;

$^1$H NMR (300 MHz, DMSO-d$_6$) δ10.80 (s, 1H), 7.30 (m, 3H), 7.20 (m, 2H), 4.83 (t, 1H), 3.10 (d, 2H), 2.32 (s, 3H), 2.21 (s, 3H));

MS (FD) m/e 317 (M$^+$);

UV (EtOH) 266 nm (ε=16921), 201 nm (ε=17995).

Example 247

N-[[(4-cyano-2-thiazolyl)amino]thioxomethyl]-DL-phenylalanine methyl ester

A solution of 1-[(2-[4-cyano]thiazolyl)thiocarbamoyl]imidazole (1.76 g, 7.5 mmol) and DL-phenylalanine methyl ester hydrochloride (1.62 g, 7.5 mmol) in N,N-dimethylformamide (50 mL) was heated at 90° C. for 5 h. The reaction was cooled to room temperature, solvent removed under reduced pressure, recrystallized from ethyl ether-hexanes to provide 1.42 g (55%) of the titled product:

IR (KBr, cm$^{-1}$) 3011, 2220, 1742, 1672, 1586, 1455, 1372;

$^1$H NMR (300 MHz, DMSO-d$_6$) δ7.12–7.38 (m, 5H), 7.40 (s, 1H), 5.05 (q, 1H), 3.63 (s, 3H), 3.03–3.22 (m, 2H); MS (FD) m/e 346 (M$^+$);

UV (EtOH) 287 nm (ε=7404), 257 nm (ε=12260), 206 nm (ε=30014).

Anal. Calcd for C$_{15}$H$_{15}$N$_3$OS$_2$: C, 56.76; H, 4.76; N, 13.24. Found: C, 56.53; H, 4.94; N, 13.49.

Example 248

DL-3-(4-cyano-2-thiazolyl)-5-(phenylmethyl)-2-thioxo-4-imidazolidinone

A solution of N-[[(4-cyano-2-thiazolyl)amino]thioxomethyl]-DL-phenylalanine methyl ester (1.42 g, 4.10 mmol) and p-toluene sulfonic acid hydrate (0.20 g 1.05 mmol) in toluene (80 mL) was refluxed with a Dean-Stark trap for 24 h. The reaction was cooled to room temperature, solvent removed under reduced pressure, residue taken up in ethyl acetate, washed with saturated sodium bicarbonate and saturated sodium chloride, dried over magnesium sulfate, and concentrated under reduced pressure. The resulting product was recrystallized from ethyl ether-hexanes to provide 170.1 mg (10%) of the titled product:

mp 214°–216° C.; IR (KBr, cm$^{-1}$) 3294, 3092, 2246, 1781, 1505, 1381, 1325, 1244;

$^1$H NMR (300 MHz, DMSO-d$_6$) δ11.08 (s, 1H), 8.90 (s, 1H), 7.22–7.80 (m, 3H), 7.20–7.22 (m, 2H), 4.83 (t, 1H), 3.17 (d, 2H);

MS (FD) m/e 314(M$^+$);

UV (EtOH) 259 nm (ε=15097), 205 nm (ε=26419).

Anal. Calcd for C$_{14}$H$_{10}$N$_4$OS$_2$: C, 53.49; H, 3.21; N, 17.82. Found: C, 53.75; H, 3.43; N, 17.62.

Example 249

N-[[(4-trifluoromethyl-2-thiazolyl)amino]thioxomethyl]-DL-phenylalanine methyl ester A solution of 1-[(2-[4-trifluoromethyl]thiazolyl)thiocarbamoyl]imidazole (1.60 g, 5.8 mmol) and DL-phenylalanine methyl ester hydrochloride (1.24 g, 5.8 mmol) in N,N-dimethylformamide (50 mL) was heated at 90° C. for 5 h. The reaction was cooled to room temperature, solvent removed under reduced, recrystallized ethyl ether-hexanes to provide 2.22 g (99%) of the titled product:

IR (CHCl$_3$, cm$^{-1}$) 3000, 1744, 1672, 1554, 1523, 1226;

$^1$H NMR (300 MHz, DMSO-d$_6$) δ8.64 (d, 1H), 7.82 (s, 1H), 7.21–7.38 (m, 3H), 7.19–7.21 (d, 2H), 5.05 (q, 1H), 3.63 (s, 3H), 3.02–3.22 (m, 2H);

MS (FD) m/e 389 (M$^+$);

UV (EtOH) 287 nm (ε=11327), 256 nm (ε=11674), 203 nm (ε=24532).

Anal. Calcd for C$_{15}$H$_{14}$F$_3$N$_3$O$_2$S$_2$: C, 46.27; H, 3.62; N, 10.79. Found: C, 46.55; H, 3.57; N, 11.06.

Example 250

DL-3-(4-trifluoromethyl-2-thiazolyl)-5-(phenylmethyl)-2-thioxo-4-imidazolidinone A solution of N-[[(4-trifluoromethyl-2-thiazolyl)amino]thioxomethyl]-DL-phenylalanine methyl ester (2.09 g, 5.38 mmol) and p-toluene sulfonic acid hydrate (0.20 g 1.05 mmol) in toluene (80 mL) was refluxed with a Dean-Stark trap for 48 h. The reaction was cooled to room temperature, solvent removed under reduced pressure, residue taken up in ethyl acetate, washed with saturated sodium bicarbonate and saturated sodium chloride, dried over magnesium sulfate, and concentrated under reduced pressure. The resulting product was recrystallized from ethyl ether-hexanes to provide 1.01 g (53%) of the titled product:

mp 187°–189° C.;

IR (CHCl$_3$, cm$^{-1}$) 3431, 3008, 1782, 1495, 1369, 1328, 1242, 1178, 1149, 1085;

$^1$H NMR (300 MHz, DMSO-d$_6$) δ11.02 (s, 1H), 8.59 (s, 1H), 7.22–7.80 (m, 3H), 7.20–7.22 (m, 2H), 4.83 (t, 1H), 3.17 (d, 2H);

MS (FD) m/e 357 (M$^+$);

UV (EtOH) 263 nm (ε=13898), 202 nm (ε=19355).

Anal. Calcd for C$_{14}$H$_{10}$F$_3$N$_3$OS$_2$: C, 47.05; H, 2.82; N, 11.76. Found: C, 47.33; H, 2.86; N, 11.67.

Example 251

N-(2-[1-cyclohexenyl]ethyl)-N'-[2-(6-bromo)pyridinyl]thiourea

A solution of 2-(1-cyclohexenyl)ethyl isothiocyanate (1.67 g, 10 mmol) and 2-amino-6-bromopyridine (1.73 g, 10 mmol) in N,N-dimethylformamide (100 mL) was heated at 100° C. for 96 h. The reaction was cooled to room temperature, solvents removed under reduced pressure, taken up in ethyl acetate washed with 1N HCl. The organic layer was concentrated and the residue purified by HPLC (elution with hexanes-EtOAc) to afford 70.1 mg (2.1%) of the titled product:

mp 174°–175° C.;

IR (CHCl$_3$, cm$^{-1}$) 2936, 1592, 1512, 1448, 1203;

$^1$H NMR (300 MHz, DMSO-d$_6$) δ10.79 (s,1H), 10.65 (m, 1H), 7.70 (t, 1H), 7.28 (d, 1H), 7.19 (d, 1H), 5.60 (s, 1H), 3.70 (q, 2H), 2.23 (t, 2H), 1.95 (s, 4H), 1.62–1.42 (m, 4H);

MS (FD) m/e 341 (M$^+$);

UV (EtOH) 303 nm (ε=19786), 269 nm (ε=18279), 252 nm (ε=18006), 201 nm (ε=17992).

Anal. Calcd for C$_{14}$H$_{18}$BrN$_3$S: C, 49.42 H, 5.33; N, 12.35. Found: C, 49.69; H, 5.36; N, 12.09.

Example 252

N-(2-[1-cyclohexenyl]ethyl)-N'-[(4-isopropyl)pyridinyl]thiourea

A solution of 2-(1-cyclohexenyl)ethyl isothiocyanate (0.36 g, 2.2 mmol) and 2-amino-4-isopropylpyridine (0.36 g, 2.2 mmol) in N,N-dimethylformamide (20 mL) was heated at 100° C. for 96 h. The reaction was cooled to room temperature, solvents removed under reduced pressure, taken up in ethyl acetate, washed with 1N aqueous HCl. The organic layer was concentrated and the residue purified by HPLC (elution with hexanes-EtOAc) to afford 169 mg (5.6%) of the titled product:

mp 105°–106° C.;

IR (KBr, cm$^{-1}$) 3215, 2931, 1614 1556, 1534, 1487, 1199;

$^1$H NMR (300 MHz, DMSO-d$_6$) δ11.65 (t, 1H), 10.40 (s, 1H), 8.30 (d, 1H), 7.20 (s, 1H), 6.93 (d, 1H), 5.52 (s, 1H), 3.63 (q, 2H), 2.80 (m, 1H), 2.22 (t, 2H), 1.95 (m, 4H), 1.62–1.42 (m, 4H), 1.18 (d, 6H);

MS (FD) m/e 303 (M$^+$);

UV (EtOH) 290 nm (ε=17565), 266 nm (ε=18863), 247 nm (ε=15125), 203nm(ε=23091).

Anal. Calcd for C$_{17}$H$_{25}$N$_3$S: C, 67.28; H, 8.30; N, 13.85. Found: C, 67.55; H, 8.48; N, 13.94.

Example 253

N-(2-[1-cyclohexenyl]ethyl)-N'-(2-[6-methylthio]benzothiazolyl]thiourea

A solution of 2-(1-cyclohexenyl)ethyl isothiocyanate (1.67 g, 10 mmol) and 2-amino-6-methylthiobenzothiazole (1.96 g, 10 mmol) in N,N-dimethylformamide (20 mL) was heated at 100° C. for 96 h. The reaction was cooled to room temperature, a precipitate formed, collected, washed with ethyl acetate to provide 1.22 g (54%) of the titled product:

mp 186°–187° C.;

IR (KBr, cm$^{-1}$) 3171, 3036, 2918, 1548, 1522, 1251, 1214;

$^1$H NMR (300 MHz, DMSO-d$_6$) δ11.82 (br s, 1H), 10.20 (br s, 1H), 7.88 (s, 1H), 7.6–7.5 (m, 1H), 7.4–7.3 (q, 1H), 5.55 (s, 1H), 3.67 (q, 2H), 2.4 (s, 3H), 2.25 (t, 2H), 1.95 (s, 4H), 1.62–1.42 (m, 4H);

MS (FD) m/e 363 (M$^+$);

UV (EtOH) 318 nm (ε=14538), 256 nm (ε=6742), 224 nm (ε=13749), 201 nm (ε=11940).

Anal. Calcd for C$_{17}$H$_{21}$N$_3$S$_3$: C, 56.16; H, 5.82; N, 11.56. Found: C, 56.40; H, 5.94; N, 11.76.

Example 254

N-(2-[1-cyclohexenyl]ethyl)-N'-[2-(4-[4-bromophenyl)thiazolyl]thiourea

A solution of 2-(1-cyclohexenyl)ethyl isothiocyanate (1.67 g, 10 mmol) and 2-amino-[4-(4-bromophenyl)]thiazole (2.55 g, 10 mmol) in N,N-dimethylformamide (20 mL) was heated at 100° C. for 72 h. The reaction was cooled to room temperature, solvent removed under reduced, recrystallized from ethyl acetate-hexanes to provide 455 mg (11%) of the titled product:

mp 219°–220° C.;

IR (KBr, cm$^{-1}$) 3171, 2927, 1566, 1516, 1301, 1211, 1071, 1110;

$^1$H NMR (300 MHz, DMSO-d$_6$) δ11.70 (s, 1H), 9.30 (br s, 1H), 7.80 (d, 2H), 7.60 (m, 3H), 5.43 (s, 1H), 3.67 (q, 2H), 2.25 (t, 2H), 1.95 (s, 4H), 1.62–1.42 (m, 4H);

MS (FD) m/e 421 (M$^+$);

UV (EtOH) 285 nm (ε=27781), 245 nm (ε=17426), 202 nm (ε=31192).

Anal. Calcd for C$_{18}$H$_{20}$BrN$_3$S$_2$: C, 51.18; H, 4.77; N, 9.95. Found: C, 51.08; H, 4.47; N, 9.91.

Example 255

N-(2-[1-cyclohexenyl]ethyl)-N'-[2-(4-[2-(hexadecyloxy)phenyl])thiazolyl]thiourea A solution of 2-(1-cyclohexenyl)ethyl isothiocyanate (840 mg, 5 mmol) and 2-amino-4-(2-[hexadecyloxy]phenyl)thiazole (2.10 g, 5 mmol) in N,N-dimethylformamide (20 mL) was heated at 100° C. for 72 h. The reaction was cooled to room temperature, solvent removed under reduced, recrystallized from ethyl acetate-hexanes to provide 900 mg (31%) of the titled product:

mp 98°–99° C.;

IR (KBr, cm$^{-1}$) 2919, 1567, 1473, 1222,1062, 681;

$^1$H NMR (300 MHz, DMSO-d$_6$) δ11.62 (s, 1H), 9.62 (br s, 1H), 7.95 (d, 1H), 7.56 (s, 1H), 7.30 (t, 1H), 7.12 (d, 1H), 7.0 (t, 1H), 5.43 (s, 1H), 4.10 (t, 2H), 3.65 (q, 2H), 2.25 (t, 2H), 1.95 (br s, 2H), 1.83 (t, 3H), 1.94–1.73 (m, 4H), 1.40–1.38 (m, 2H), 1.23 (s, 28H);

MS (FD) m/e 583 (M$^+$);

UV (EtOH) 299 nm (ε=21244), 263 nm (ε=21549), 202 nm (ε=30773).

Anal. Calcd for C$_{34}$H$_{53}$N$_3$OS$_2$: C, 69.93; H, 9.15; N, 7.19. Found: C, 69.70; H, 8.99; N, 7.28.

Example 256

N-[(2-thiazolyl)amino]thioxomethyl-DL-2-fluorophenylalanine methyl ester

A solution of 1-[(2-thiazolyl)thiocarbamoyl]imidazole (3.15 g, 15 mmol) and DL-2-fluorophenylalanine methyl ester hydrochloride (3.51 g, 15 mmol) in N,N-dimethylformamide (100 mL) was heated at 80° C. for 8 h. The reaction was cooled to room temperature, the solvent removed under reduced pressure, and the residue recrystallized from ethyl ether-hexanes to provide 1.89 g (37%) of the titled product:

IR (KBr, cm$^{-1}$) 3187, 3122, 3090, 3037, 2950, 1739, 1566, 1495, 1209, 1182;

$^1$H NMR (300 MHz, DMSO-d$_6$) δ11.81 (br s, 1H), 7.39 (d, 1H), 7.26 (m, 2H), 7.18 (m, 3H), 5.16 (q, 1H), 3.64 (s, 3H), 3.28 (m, 2H);

MS (FD) m/e 339 (M$^+$);

UV (EtOH) 290 nm (ε=18548), 256 nm (ε=10899), 203 nm (ε=19927).

Anal. Calcd for C$_{14}$H$_{14}$FN$_3$O$_2$S$_2$: C, 49.67; H, 3.87; N, 12.42. Found: C, 49.45; H, 4.07; N, 12.40.

Example 257

DL-3-(2-thiazolyl)-5-[(2-fluoro)phenylmethyl]-2-thioxo-4-imidazolidinone

A solution of N-[(2-thiazolyl)amino]thioxomethyl-DL-2-fluorophenylalanine methyl ester (1.0 g, 2.95 mmol) and p-toluenesulfonic acid hydrate (0.20 g 1.05 mmol) in toluene (100 mL) was refluxed with a Dean-Stark trap for 48 h. The reaction was cooled to room temperature, solvent removed under reduced pressure, residue taken up in ethyl acetate, washed with saturated sodium bicarbonate and saturated sodium chloride, dried over magnesium sulfate, and concentrated under reduced pressure. The resulting product was recrystallized from ethyl acetate-hexanes to provide 305 mg (23%) of the titled product:

IR (KBr, cm$^{-1}$) 3104, 2870, 1781, 1531, 1438, 1330, 1255, 1204;

¹H NMR (300 MHz, DMSO-d₆) δ10.95 (br s, 1H), 7.85 (d, 1H), 7.78 (d, 1H), 7.30 (m, 2H), 7.18 (m, 2H), 4.83 (t, 1H), 3.18 (d, 2H);

MS (FD) m/e 307 (M⁺);

UV (EtOH) 397 (ε=586), 263 nm (ε=16615), 201 nm (ε=15980)

Anal. Calcd for $C_{13}H_{10}N_2FOS_2$: C, 50.80; H, 3.28; N, 13.67. Found: C, 50.84; H, 3.33; N, 13.38.

Example 258

N-[(2-thiazolyl)amino]thioxomethyl-DL-3,5-bis(trifluoromethyl)phenylalanine methyl ester A solution of 1-[(2-thiazolyl)thiocarbamoyl]imidazole (0.46 g, 2.19 mmol) and DL-3,5-ditrifluoromethylphenylalanine methyl ester hydrochloride (0.77 g, 2.19 mmol) in N,N-dimethylformamide (75 mL) was heated at 80° C. for 7 h. The reaction was cooled to room temperature, the solvent removed under reduced pressure, and the residue recrystallized from ethyl ether-hexanes to provide 203 mg (20%) of the titled product:

IR (KBr, cm⁻¹) 3179, 3022, 1745, 1568, 1379, 1291, 1212;

¹H NMR (300 MHz, DMSO-d₆) δ11.82 (br s, 1H), 7.98 (s, 3H), 7.10 (m, 1H), 5.12 (m, 1H), 3.31 (s, 3H), 3.08 (m, 2H);

MS (FD) m/e 457 (M⁺);

UV (EtOH) 291 (ε=18895), 255 nm (ε=10490), 202 nm (ε=19571)

Anal. Calcd for $C_{16}H_{13}F_6N_3O_2S_2$: C, 42.01; H, 2.86; N, 9.19. Found: C, 41.90; H, 2.74; N, 9.36.

Example 259

DL-3-(2-thiazolyl)-5-[(3,5-bis[trifluoromethyl])phenylmethyl]-2-thioxo-4-imidazolidinone A solution of N-[(2-thiazolyl)amino]thioxomethyl-DL-3,5-bistrifluoromethylphenylalanine methyl ester (0.15 g, 0.32 mmol) and p-toluene sulfonic acid hydrate (0.10 g 0.53 mmol) in toluene (65 mL) was refluxed with a Dean-Stark trap for 48 h. The reaction was cooled to room temperature, the solvent removed under reduced pressure, and the residue taken up in ethyl acetate, washed with saturated sodium bicarbonate ana saturated sodium chloride, dried over magnesium sulfate, concentrated under reduced pressure to provide 39 mg (29%) of the titled product.

IR (KBr, cm⁻¹) 3105, 1771, 1535, 1500, 1444, 1380, 1278, 1217;

¹H NMR (300 MHz, DMSO-d₆) δ10.93 (br s, 1H), 8.03 (s, 1H), 7.96 (s, 2H), 7.89 (d, 1H), 7.80 (d, 1H), 5.01 (t, 1H), 3.37 (d, 2H);

MS (FD) m/e 425 (M⁺);

UV (EtOH) 440 nm (ε=1169), 264 nm (ε=14109).

Anal. Calcd for $C_{15}H_9F_6N_3OS_2$: C, 42.35; H, 2.13; N, 9.88. Found: C, 42.60; H, 2.33; N, 9.63.

Example 260

N-[(2-thiazolyl)amino]thioxomethyl-DL-2-chlorophenylalanine methyl ester

A solution of 1-[(2-thiazolyl)thiocarbamoyl]imidazole (1.5 g, 7.1 mmol) and DL-2-chlorophenylalanine methyl ester hydrochloride (1.78 g, 7.1 mmol) in N,N-dimethylformamide (65 mL) was heated at 80° C. for 7 h. The reaction was cooled to room temperature, the solvent removed under reduced pressure, and the residue recrystallized from ethyl ether-hexanes to provide 280 mg (12%) of the titled product:

¹H NMR (300 MHz, DMSO-d₆) δ7.38 (m, 3H), 7.23 (m, 2H), 7.08 (br s, 1H), 5.17 (q, 1H), 3.62 (s, 3H), 3.21 (m, 2H);

MS (FD) m/e 355 (M⁺).

Example 261

N-[(2-thiazolyl)amino]thioxomethyl-DL-4-chlorophenylalanine methyl ester

A solution of 1-[(2-thiazolyl)thiocarbamoyl]imidazole (1.5 g, 7.1 mmol) and DL-4-chlorophenylalanine methyl ester hydrochloride (1.78 g, 7.1 mmol) in dimethylformamide (65 mL) was heated at 80° C. for 6 h. The reaction was cooled to room temperature, the solvent removed under reduced pressure, and the residue recrystallized from ethyl ether-hexanes to provide 840 mg (20%) of the titled product:

IR (KBr, cm⁻¹) 3176, 3025, 1735, 1562, 1510, 1493, 1467, 1452, 1387, 1353, 1306, 1202, 1191;

¹H NMR (300 MHz, DMSO-d₆) δ11.81 (br s, 1H), 7.39 (m, 3H), 7.26 (d, 2H), 7.18 (br s, 1H), 5.09 (q, 1H), 3.64 (s, 3H), 3.18 (m, 2H);

MS (FD) m/e 355 (M⁺);

UV (EtOH) 291 nm (ε=18545), 255 nm (ε=11222), 220 nm (ε=16171), 201 (ε=18545).

Anal. Calcd for $C_{12}H_{14}ClN_3O_2S_2$: C, 47.25; H, 3.96; N, 11.81. Found: C, 47.28; H, 3.94; N, 11.88.

Example 262

DL-3-(2-thiazolyl)-5-[(4-chloro)phenylmethyl]-2-thioxo-4-imidazolidinone

A solution of N-[(2-thiazolyl)amino]thioxomethyl-DL-4-chlorophenylalanine methyl ester (0.84 g, 2.36 mmol) and p-toluene sulfonic acid hydrate (0.20 g, 1.05 mmol) in toluene (100 mL) was refluxed with a Dean-Stark trap for 48 h. The reaction was cooled to room temperature, the solvent removed under reduced pressure, residue taken up in ethyl acetate, washed with saturated sodium bicarbonate and saturated sodium chloride, dried over magnesium sulfate, and concentrated under reduced pressure. The resulting product was recrystallized from ethyl acetate-hexanes to provide 176 mg (23%) of the titled product:

¹H NMR (300 MHz, DMSO-d₆) δ7.83 (d, 1H), 7.78 (d, 1H), 7.38 (d, 2H), 7.22 (d, 2H), 4.85 (t, 1H), 3.11 (d, 2H);

MS (FD) m/e 323 (M⁺).

Example 263

N-[(2-thiazolyl)amino]thioxomethyl-DL-4-trifluoromethylphenylalanine methyl ester A solution of 1-[(2-thiazolyl)thiocarbamoyl]imidazole (1.03 g, 4.1 mmol) and DL-4-trifluoromethylphenylalanine methyl ester hydrochloride (1.15 g, 4.1 mmol) in N,N-dimethylformamide (75 mL) was heated at 80° C. for 6 h. The reaction was cooled to room temperature, the solvent removed under reduced pressure, and the residue recrystallized from ethyl ether-hexanes to provide 389 mg (24%) of the titled product:

IR (KBr, cm⁻¹) 3178, 3020, 1747, 1577, 1509, 1325, 1278, 1185;

¹H NMR (300 MHz, DMSO-d₆) δ11.82 (br s, 1H), 9.82 (br s, 1H), 7.63 (d, 2H), 7.39 (d, 2H), 7.35 (d, 1H), 7.13 (s, 1H), 5.18 (q, 1H), 3.62 (s, 3H), 3.31 (m, 2H);

MS (FD) m/e 389 (M⁺);

UV (EtOH) 291 nm (ε=18127), 255 nm (ε=10867), 201 nm (ε=20712).

Anal. Calcd for $C_{15}H_{14}N_3F_3O_2S_2$: C, 46.26; H, 3.62; N, 10.79. Found: C, 46.21; H, 3.69; N, 11.00.

Example 264

DL-3-(2-thiazolyl)-5-[(4-trifluoromethyl)phenylmethyl]-2-thioxo-4-imidazolidinone A solution of N-[(2-thiazolyl)amino]thioxomethyl-DL-4-trifluoromethylphenylalanine methyl ester (0.34 g, 0.87 mmol) and p-toluene sulfonic acid hydrate (0.20 g 0.106 mmol) in toluene (100 mL) was refluxed with a Dean-Stark trap for 48 h. The reaction was cooled to room temperature, the solvent removed under reduced pressure, and the residue taken up in ethyl acetate, washed with saturated sodium bicarbonate and saturated sodium chloride, dried over magnesium sulfate, concentrated under reduced pressure to provide 145 mg (46%) of the titled product.

IR (KBr, cm⁻¹) 3176, 1779, 1619, 1532, 1508, 1432, 1327, 1270, 1194, 1129;

¹H NMR (300 MHz, DMSO-d₆) δ10.90 (br s, 1H), 7.83 (d, 1H), 7.79 (d, 1H), 7.65 (d, 2H), 7.41 (d, 2H), 4.88 (t, 1H), 3.22 (d, 2H);

MS (FD) m/e 357 (M⁺);

UV (EtOH) 264 nm (ε=15626), 201 nm (ε=16341).

Anal. Calcd for $C_{14}H_{10}F_3N_3OS_2$: C, 47.05; H, 2.82; N, 11.76. Found: C, 47.17; H, 2.82; N, 11.53.

Example 265

N-[(2-thiazolyl)amino]thioxomethyl-DL-2,6-difluorophenylalanine methyl ester

A solution of 1-[(2-thiazolyl)thiocarbamoyl]imidazole (0.65 g, 3.08 mmol) and DL-2,6-difluorophenylalanine methyl ester hydrochloride (0.78 g, 3.08 mmol) in N,N-dimethylformamide (75 mL) was heated at 80° C. for 7 h. The reaction was cooled to room temperature, the solvent removed under reduced pressure, and the residue recrystallized from ethyl ether-hexanes to provide 413 mg (38%) of the titled product:

IR (KBr, cm⁻¹) 3205, 3036, 1737, 1625, 1554, 1511, 1468, 1442, 1388, 1265;

¹H NMR (300 MHz, DMSO-d₆) δ11.83 (br s, 1H), 7.37 (q, 2H), 7.08 (m, 2H), 5.21 (q, 1H), 3.62 (s, 3H), 3.31 (m, 2H);

MS (FD) m/e 357 (M⁺);

UV (EtOH) 291 nm (ε=18495), 256 nm (ε=10699), 202 nm (ε=20082).

Anal. Calcd for $C_{14}H_{13}F_2N_3O_2S_2$: C, 47.05; H, 3.67; N, 11.76. Found: C, 47.08; H, 3.76; N, 11.93.

Example 266

N-[2-(1-cyclohexenyl)ethyl]-N'-[4,5,6,7-tetrahydrobenzothiazolyl]thiourea

A solution of 2-(1-cyclohexenyl)ethyl isothiocyanate (1.67 g, 10 mmol) and 2-amino-4,5,6,7-tetrahydrobenzothiazole (1.54 g, 10 mmol) in N,N-dimethylformamide (100 mL) was heated at 100° C. for 120 h. The reaction was cooled to room temperature, the solvent removed under reduced pressure, the residue taken up in ethyl acetate and washed with 1N HCl. The organic layer was concentrated and the residue recrystallized from ethyl acetate-hexanes to provide 426 mg (13%) of the titled product:

IR (KBr, cm⁻¹) 3169, 3031, 2931, 1580, 1258, 1198;

¹H NMR (300 MHz, DMSO-d₆) δ11.41 (br s, 1H), 10.05 (br s, 1H), 5.43 (s, 1H), 3.58 (m, 2H), 2.6–1.9 (m, 10H), 1.7 (m, 4H), 1.5 (m, 4H);

MS (FD) m/e 321 (M⁺);

UV (EtOH) 298 nm (ε=12157), 257 nm (ε=6569), 201 nm (ε=12172).

Anal. Calcd for $C_{16}H_{23}N_3S_2$: C, 59.97 H, 7.21; N, 13.07. Found: C, 60.06; H, 6.95; N, 12.82.

Example 267

N-[2-(1-cyclohexenyl)ethyl]-N'-[2-(5-chloro)pyrazinyl]thiourea

A solution of 2-(1-cyclohexenyl)ethyl isothiocyanate (2.30 g, 13.7 mmol) and 2-amino-5-chloropyrazine (1.75 g, 13.7 mmol) in N,N-dimethylformamide (40 mL) was heated at 100° C. for 192 h. The reaction was cooled to room temperature, the solvent removed under reduced pressure, and the residue taken up in ethyl acetate and washed with 1N aqueous HCl. The organic layer was concentrated and the resulting product was recrystallized from ethyl acetate-hexanes to provide 64 mg (1.6%) of the titled product:

IR (KBr, cm⁻¹) 3192, 2931, 1588, 1515, 1457, 1320, 1251, 1153;

¹H NMR (300 MHz, DMSO-d₆) δ11.01 (br s, 1H), 10.45 (t, 1H), 8.38 (d, 1H), 8.29 (d, 1H), 5.50 (br s, 1H), 3.63 (q, 2H), 2.21 (t, 2H), 1.95 (m, 4H), 1.52 (m, 4H);

MS (FD) m/e 296 (M⁺);

UV (EtOH) 330 nm (ε=9176), 273 nm (ε=21432), 201 nm (ε=10972).

Anal. Calcd for $C_{13}H_{17}N_4SCl$: C, 67.28; H, 8.30; N, 13.85. Found: C, 67.55; H, 8.48; N, 13.94.

Example 268

N-[2-(1-cyclohexenyl)ethyl]-N'-(2-[4-(3,4-dichlorophenyl)]thiazolyl)thiourea

A solution of 2-(1-cyclohexenyl)ethyl isothiocyanate (1.67 g, 10 mmol) and 4-(3,4-dichlorophenyl)-2-thiazolamine (2.45 g, 10 mmol) in N,N-dimethylformamide (50 mL) was heated at 100° C. for 120 h. The reaction was cooled to room temperature, the solvent removed under reduced pressure, and the residue taken up in ethyl acetate and washed with 1N HCl. The organic layer was concentrated and the residue recrystallized from ethyl acetate-hexanes to provide 933 mg (2.3%) of the titled product:

IR (KBr, cm⁻¹) 3169, 2927, 1573, 1558, 1523, 1460, 1393, 1295, 1214;

¹H NMR (300 MHz, DMSO-d₆) δ11.72 (br s, 1H), 9.11 (br s, 1H), 8.07 (d, 1H), 7.83 (m, 1H), 7.62 (m, 2H), 5.45 (m, 1H), 3.60 (m, 2H), 2.21 (m, 2H), 1.85 (m, 4H), 1.43 (m, 4H);

MS (FD) m/e 411 (M⁺);

UV (MeOH) 287 nm (ε=25040), 241 nm (ε=16142), 205 nm (ε=29362).

Anal. Calcd for $C_{18}H_{19}N_3S_2Cl_2$: C, 52.42; H, 4.64; N, 10.19. Found: C, 52.63; H, 4.48; N, 10.21.

Example 269

1-(2-[2-methoxyphenyl]ethyl)thiocarbamoyl imidazole

A solution of 1,1'-thiocarbonyldiimidazole (1.78 g, 10 mmol) and 2-methoxyphenethylamine (1.51 g, 10 mmol) in acetonitrile (25 mL) was stirred at room temperature for 20 h. The resulting precipitate was collected by filtration to provide 1.40 g (53%) of the titled product:

IR (KBr, cm$^{-1}$) 2944, 1563, 1493, 1409, 1282, 1246, 1031, 755;

$^1$H NMR (300 MHz, DMSO-d$_6$) δ12.0 (br s, 1H), 7.65 (s, 1H), 7.25 (m, 2H), 7.05–6.9 (m, 4H), 3.8 (m, 2H), 3.8 (s, 3H), 2.95 (t, J=7 Hz, 2H);

MS (FD) m/e 261 (M$^+$);

UV (EtOH) 278 nm (ε=7083), 216 nm (ε=12683), 203 nm (ε=22221).

Example 270

N-[2-(2-methoxyphenyl)ethyl]-N'-(2-pyridyl)thiourea

A solution of 1-(2-[2-methoxyphenyl]ethyl)thiocarbamoyl imidazole (0.52 g, 2 mmol) and 2-aminopyridine (0.19 g, 2 mmol) in N,N-dimethylformamide (5 mL) was stirred at 90° C. for 4 h, the reaction was cooled to room temperature and the solvent removed in vacuo. The residue was crystallized from ethyl acetate to provide 0.25 g (44%) of the titled product: IR (KBr, cm$^{-1}$) 3219, 3048, 1607, 1557, 1236, 1036, 756;

$^1$H NMR (300 MHz, DMSO-d$_6$) δ11.65 (m, 1H), 10.55 (br s, 1H), 8.1 (m, 1H), 7.75 (m, 1H), 7.3–6.9 (m, 6H), 3.8 (m, 2H), 3.78 (s, 3H), 2.9 (t, J=7 Hz, 2H);

MS (FD) m/e 287 (M$^+$); UV (EtOH) 290 nm (ε=10141), 267 nm (ε=13121), 247 nm (ε=10959), 202 nm (ε=24078).

Example 271

N-[2-(1-cyclohexenyl)ethyl]-N'-[2-(6-methyl)pyridyl]thiourea

A solution of 2-(1-cyclohexenyl)ethyl isothiocyanate (1.67 g, 10.0 mmol) and 2-amino-6-methylpyridine (1.08 g, 10.0 mmol) in N,N-dimethylformamide (25 mL) was heated at 90° C. for 20 h. The reaction was cooled to room temperature and the solvent removed under reduced pressure. The resulting product was recrystallized from ethyl acetate-hexanes to provide 1.04 g (38%) of the titled product:

IR (KBr, cm$^{-1}$) 3230, 2920, 1608, 1572, 1540, 1457, 1378, 1317, 1235, 1164;

$^1$H NMR (300 MHz, DMSO-d$_6$) δ11.7 (br t, 1H), 10.45 (s, 1H), 7.62 (t, 1H), 6.95 (d, 1H), 6.90 (d, 1H), 5.50 (br s, 1H), 3.7 (q, 2H), 2.4 (s, 3H), 2.25 (t, 2H), 1.95 (m, 4H), 1.55 (m, 4H);

MS (FD) m/e 275 (M$^+$);

UV (EtOH) 296 nm (ε=17669), 265 nm (ε=16667), 247 nm (ε=15266).

Anal. Calcd for C$_{15}$H$_{21}$N$_3$S: C, 65.42; H, 7.69; N, 15.26. Found: C, 65.42; H, 7.75; N, 15.20.

Example 272

N-[2-(1-cyclohexenyl)ethyl]-N'-[2-(5-methyl)pyridyl]thiourea

A solution of 2-(1-cyclohexenyl)ethyl isothiocyanate (1.67 g, 10.0 mmol) and 2-amino-5-methylpyridine (1.08 g, 10.0 mmol) in N,N-dimethylformamide (25 mL) was heated at 90° C. for 20 h. The reaction was cooled to room temperature and the solvent removed under reduced pressure. The resulting product was recrystallized from ethyl acetate-hexanes to provide 1.06 g (39%) of the titled product:

IR (KBr, cm$^{-1}$) 3225, 2933, 1596, 1569, 1532, 1494, 1344, 1311, 1232, 827;

$^1$H NMR (300 MHz, DMSO-d$_6$) δ11.55 (br t, 1H), 10.45 (s, 1H), 7.95 (br s, 1H), 7.6 (dd, 1H), 7.05 (d, 1H), 5.5 (br s, 1H), 3.7 (q, 2H), 2.3 (m, 5H), 1.95 (m, 4H), 1.55 (m, 4H);

MS (FD) m/e 275 (M$^+$);

UV (EtOH) 298 nm (ε=13663), 268 nm (ε=21631), 249 nm (ε=14893).

Anal. Calcd for C$_{15}$H$_{21}$N$_3$S: C, 65.42; H, 7.69; N, 15.26. Found: C, 65.15; H, 7.75; N, 15.33.

Example 273

N-[2-(1-cyclohexenyl)ethyl-]N'-[2-(4-methyl)pyridyl]thiourea

A solution of 2-(1-cyclohexenyl)ethyl isothiocyanate (1.67 g, 10.0 mmol) and 2-amino-4-methylpyridine (1.08 g, 10.0 mmol) in N,N-dimethylformamide (25 mL) was heated at 90° C. for 16 h. The reaction was cooled to room temperature and the solvent removed under reduced pressure. The resulting product was purified by HPLC to provide 1.67 g (61%) of the titled product;

IR (KBr, cm$^{-1}$) 3220, 2935, 1617, 1535, 1487, 1322, 1188, 866;

$^1$H NMR (300 MHz, DMSO-d$_6$) δ11.65 (br t, 1H), 10.45 (s, 1H), 8.0 (d, 1H), 6.95 (s, 1H), 6.85 (d, 1H), 5.5 (br s, 1H), 3.65 (q, 2H), 2.3 (m, 5H), 1.95 (m, 4H), 1.55 (m, 4H);

MS (FD) m/e 275 (M$^+$);

UV (EtOH) 289 nm (ε=16865), 266 nm (ε=17870), 247 nm (ε=14179), 202 nm (ε=20105).

Anal. Calcd for C$_{15}$H$_{21}$N$_3$S: C, 65.42; H, 7.69; N, 15.26. Found: C, 65.16; H, 7.55; N, 15.30.

Example 274

N-[2-(1-cyclohexenyl)ethyl]-N'-[2-(3-methyl)pyridyl]thiourea

A solution of 2-(1-cyclohexenyl)ethyl isothiocyanate (1.67 g, 10.0 mmol) and 2-amino-3-methylpyridine (1.08 g, 10.0 mmol) in N,N-dimethylformamide (25 mL) was heated at 90° C. for 16 h. The reaction was cooled to room temperature and the solvent removed under reduced pressure. The resulting product was purified by HPLC to provide 1.8 g (65%) of the titled product;

IR (KBr, cm$^{-1}$) 3220, 2931, 1589, 1513, 1462, 1325, 1164;

$^1$H NMR (300 MHz, DMSO-d$_6$) δ11.6 (br t, 1H), 8.65 (s, 1H), 8.05 (d, 1H), 7.65 (d, 1H), 7.05 (dd, 1H), 5.5 (br s, 1H), 3.65 (q, 2H), 2.3 (s, 3H), 2.25 (t, 2H), 1.95 (m, 4H), 1.55 (m, 4H);

MS (FD) m/e 275 (M$^+$);

UV (EtOH) 293 nm (ε=16693), 264 nm (ε=14464), 244 nm (ε=14762), 201 nm (ε=16723).

Example 275

N-[2-(1-cyclohexenyl)ethyl]-N'-[2-(6-ethyl)pyridyl]thiourea

A solution of 2-(1-cyclohexenyl)ethyl isothiocyanate (1.67 g, 10.0 mmol) and 2-amino-6-ethylpyridine (1.22 g, 10.0 mmol) in N,N-dimethylformamide (25 mL) was heated at 90° C. for 20 h. The reaction was cooled to room temperature and the solvent removed under reduced pressure. The resulting product was purified by HPLC to provide 1.55 g (54%) of the titled product;

IR (KBr, cm$^{-1}$) 3230, 2930, 1604, 1533, 1450, 1211, 1157;

$^1$H NMR (300 MHz, DMSO-d$_6$) δ11.8 (br t, 1H), 10.45 (s, 1H), 7.62 (t, 1H), 6.95 (d, 1H), 6.90 (d, 1H), 5.45 (br s, 1H), 3.7 (q, 2H), 2.7 (q, 2H), 2.25 (m, 2H), 1.95 (m, 4H), 1.55 (m, 4H), 1.2 (t, 3H);

MS (FD) m/e 289 (M$^+$);

UV (EtOH) 296 nm (ε=17903), 265 nm (ε=16556), 247 nm (ε=14932), 201 nm (ε=14174).

Anal. Calcd for C$_{16}$H$_{23}$N$_3$S: C, 66.40; H, 8.01; N, 14.52. Found: C, 66.40; H, 8.00; N, 14.75.

Example 276

N-[2-(1-cyclohexenyl)ethyl]-N'-[2-(4-ethyl)pyridyl]thiourea

A solution of 2-(1-cyclohexenyl)ethyl isothiocyanate (1.67 g, 10.0 mmol) and 2-amino-4-ethylpyridine (1.22 g, 10.0 mmol) in N,N-dimethylformamide (25 mL) was heated at 90° C. for 16 h. The reaction was cooled to room temperature and the solvent removed under reduced pressure. The resulting product was purified by HPLC to provide 1.2 g (42%) of the titled product;

IR (KBr, cm$^{-1}$) 3215, 2931, 1615, 1535, 1407, 1334, 1198, 843;

$^1$H NMR (300 MHz, DMSO-d$_6$) δ11.68 (br t, 1H), 10.45 (s, 1H), 8.0 (d, 1H), 7.0 (s, 1H), 6.9 (d, 1H), 5.5 (br s, 1H), 3.65 (q, 2H), 2.6 (q, 2H), 2.25 (t, 2H), 1.95 (m, 4H), 1.55 (m, 4H), 1.15 (t, 3H);

MS (FAB) m/e 290 (M$^+$H);

UV (EtOH) 289 nm (ε=17378), 266 nm (ε=18654), 247 nm (ε=14847), 202 nm (ε=23101).

Anal. Calcd for C$_{16}$H$_{23}$N$_3$S: C, 66.40; H, 8.01; N, 14.52. Found: C, 66.45; H, 7.99; N, 14.26.

Example 377

N-[2-(1-cyclohexenyl)ethyl]-N'-[2-(5-trifluoromethyl)pyridyl]thiourea

A solution of 2-(1-cyclohexenyl)ethyl isothiocyanate (1.67 g, 10.0 mmol) and 2-amino-5-trifluoromethylpyridine (1.62 g, 10.0 mmol) in N,N-dimethylformamide (25 mL) was heated ac 90° C. for 72 h. The reaction was cooled to room temperature and the solvent removed under reduced pressure. The resulting product was purified by HPLC to provide 0.33 g (10%) of the titled product;

IR (KBr, cm$^{-1}$) 3220, 2929, 1618, 1551, 1500, 1324, 1238, 1132, 1078, 828;

$^1$H NMR (300 MHz, DMSO-d$_6$) δ11.4 (br t, 1H), 10.95 (s, 1H), 8.5 (br s, 1H), 8.15 (dd, 1H), 7.3 (d, 1H), 5.55 (br s, 1H), 3.7 (q, 2H), 2.3 (t, 2H), 1.95 (m, 4H), 1.55 (m, 4H);

MS (FD) m/e 329 (M$^+$);

UV (EtOH) 296 nm (ε=17058), 255 nm (ε=14250).

Anal. Calcd for C$_{15}$H$_{18}$N$_3$F$_3$S: C, 54.70; H, 5.51; N, 12.76. Found: C, 54.98; H, 5.67; N, 12.59.

Example 278

N-(2-[cyclohexanyl]ethyl)-N'-[2-(4-methyl)thiazolyl]thiourea

A solution of 1-[(2-[4-methyl]thiazolyl)thiocarbamoyl] imidazole (1.0 g, 4.46 mmol) and 2-cyclohexanylethylamine (0.567 g, 4.46 mmol) in N,N-dimethylformamide (25 mL) was stirred at 90° C. for 16 h, the reaction was cooled to room temperature and the solvent removed in vacuo. The residue was crystallized from ethyl acetate to provide 0.72 g (57%) of the titled product:

IR (KBr, cm$^{-1}$) 3220, 2922, 1565, 1505, 1227, 1168;

$^1$H NMR (300 MHz, DMSO-d$_6$) δ11.5 (br s, 1H), 9.9 (br s, 1H), 6.65 (s, 1H), 3.55 (m, 2H), 2.25 (s, 3H), 1.8–0.8 (m, 13H);

MS (FD) m/e 283 (M$^+$);

UV (EtOH) 291 nm (ε=5315), 257 nm (ε=2711).

Anal. Calcd for C$_{13}$H$_{21}$N$_3$S$_2$: C, 55.09 H, 7.47; N, 14.82. Found: C, 55.29; H, 7.60; N, 14.64.

Example 279

N-[2-(2-methoxyphenyl)ethyl]-N'-2-(5-methyl)pyridyl]thiourea

A solution of 1-(2-[2-methoxyphenyl]ethyl)thiocarbamoyl imidazole (0.7 g, 2.68 mmol) and 2-amino-5-methylpyridine (0.29 g, 2.68 mmol) in N,N-dimethylformamide (5 mL) was stirred at 90° C. for 16 h, the reaction was cooled to room temperature and the solvent removed in vacuo. The residue was crystallized from ethyl acetate to provide 0.62 g (77%) of the titled product:

IR (KBr, cm$^{-1}$) 3227, 2932, 1612, 1534, 1493, 1273, 1037;

$^1$H NMR (300 MHz, DMSO-d$_6$) δ11.55 (br t, 1H), 10.45 (s, 1H), 7.9 (br s, 1H), 7.6 (m, 1H), 7.2–6.9 (m, 5H), 3.8 (m, 5H), 2.9 (t, J=7 Hz, 2H), 2.2 (s, 3H);

MS (FAB) m/e 302 (M$^+$H);

UV (EtOH) 298 nm (ε=13316), 268 nm (ε=23132), 249 nm (ε=15574), 202 nm (ε=25460).

Anal. Calcd for C$_{16}$H$_{19}$N$_3$OS: C, 63.76; H, 6.35; N, 13.94. Found: C, 63.71; H, 6.34; N, 13.79.

Example 280

1-[2-(2-chlorophenyl)ethyl]-thiocarbamoyl imidazole

A solution of 1,1'-thiocarbonyldiimidazole (1.8 g, 10 mmol) and 2-(2-chlorophenyl)ethyl amine (1.56 g, 10 mmol) in acetonitrile (100 mL) was stirred at room temperature for 3 h. The solution was concentrated to about 50 ml and was placed in the freezer for 4 days. The resulting crystals were collected by filtration to provide 2.37 g (89%) of crude title product.

mp 74°–78° C.

IK (KBr, cm$^{-1}$) 3134, 2924, 1564, 1529, 1474, 1448, 1411, 1353, 1287, 1215;

MS (FD)m/e 266 (M$^+$);

UV (EtOH) 278 nm ($\epsilon$=5421), 247 nm ($\epsilon$=5655), 202 nm ($\epsilon$=22240).

Example 281

N-[2-(2-chlorophenyl)ethyl]-N'-[2-(5-methyl)pyridyl]thiourea

A solution of 1-(2-[2-chlorophenyl]ethyl)thiocarbamoyl imidazole (1.0 g, 3.76 mmol) and 2-amino-5-methylpyridine (0.41 g, 3.76 mmol) in N,N-dimethylformamide (10 mL) was stirred at 90° C. for 16 h, the reaction was cooled to room temperature and the solvent removed in vacuo. The residue was crystallized from ethyl acetate to provide 0.92 g (80%) of the titled product:

IR (KBr, cm$^{-1}$) 3226, 1597, 1532, 1491, 1273, 1050;

$^1$H NMR (300 MHz, DMSO-d$_6$) $\delta$11.6 (br t, 1H), 10.5 (s, 1H), 7.9 (br s, 1H), 7.6–7.0 (m, 6H), 3.9 (q, 2H), 3.1 (t, J=7 Hz, 2H), 2.2 (s, 3H);

MS (FD) m/e 305 (M$^+$);

UV (EtOH) 298 nm ($\epsilon$=14145), 268 nm ($\epsilon$=21034), 249 nm ($\epsilon$=15757), 202 nm ($\epsilon$=23053).

Anal. Calcd for C$_{15}$H$_{16}$N$_3$ClS: C, 58.91; H, 5.27; N, 13.74. Found: C, 58.65; H, 5.39; N, 13.77.

Example 282

1-[(2-(4-ethyl)thiazolyl)thiocarbamoyl]imidazole

A solution of 1,1'-thiocarbonyldiimidazole (11.9 g, 60 mmol) and 2-amino(4-ethyl)thiazole (8.0 g, 60 mmol) in acetonitrile (250 mL) was stirred at room temperature for about 5 h. The resulting precipitate was collected by filtration to provide 12.0 g (85%) of the titled product.

mp. 198°–200° C.; IR (KBr, cm$^{-1}$) 2970, 2637, 1609, 1529, 1461, 1398, 1357, 1226, 1262;

$^1$H NMR (300 MHz, DMSO-d$_6$) $\delta$8.6 (s, 1H), 7.9 (s, 1H), 7.0 (s, 1H), 6.9 (s, 1H), 2.6 (q, J=7 Hz, 2H), 1.2 (t, J=7 Hz, 3H);

MS (FD) m/e 238 (M$^+$);

UV (EtOH) 361 nm ($\epsilon$=11223), 290 nm ($\epsilon$=8828), 203 nm ($\epsilon$=20303).

Anal. Calcd for C$_9$H$_{10}$N$_4$S$_2$: C, 45.36 H, 4.23; N, 23.51. Found: C, 45.51; H, 4.20; N, 23.53.

Example 283

N-(2-[2-pyridyl]ethyl)-N'-[2-(4-ethyl)thiazolyl]thiourea

A solution of 1-[(2-[4-ethyl]thiazolyl)thiocarbamoyl]imidazole (1.00 g, 4.2 mmol) and 2-(2-aminoethyl)pyridine (0.51 g, 4.2 mmol) in N,N-dimethylformamide (25 mL) was stirred at 90° C. for 3 h, the reaction was cooled to room temperature and the solvent removed in vacuo. The residue was crystallized from ethyl acetate to provide 0.75 g (61%) of the titled product:

IR (KBr, cm$^{-1}$) 3163, 1557, 1524, 1222, 757;

$^1$H NMR (300 MHz, DMSO-d$_6$) $\delta$11.3 (br s, 1H), 10.0 (br s, 1H), 8.5 (m, 1H), 7.7 (m, 1H), 7.25 (m, 2H), 6.6 (s, 1H), 3.9 (m, 2H), 3.05 (m, 2H), 2.45 (q, J=7 Hz, 2H), 1.05 (t, J=7 Hz, 3H); MS (FD) m/e 292 (M$^+$);

UV (EtOH) 292 nm ($\epsilon$=17803), 261 nm ($\epsilon$=12919), 201 nm ($\epsilon$=17809).

Anal. Calcd for C$_{13}$H$_{16}$N$_4$S$_2$: C, 53.40 H, 5.51; N, 19.16. Found: C, 53.64; H, 5.51; N, 19.02.

Example 284

N-(2-[1-cyclohexenyl]ethyl)-N'-[2-(4-ethyl)thiazolyl]thiourea

A solution of 1-[(2-[4-ethyl]thiazolyl)thiocarbamoyl]imidazole (0.75 g, 3.15 mmol) and 2-(1-cyclohexenyl)ethylamine (0.39 g, 3.15 mmol) in N,N-dimethylformamide (15 mL) was stirred at 90° C. for 4 h, the reaction was cooled to room temperature and the solvent removed in vacuo. The residue was crystallized from ethyl acetate to provide 0.77 g (83%) of the titled product:

MP 155°–156° C.; IR (KBr, cm$^{-1}$) 3172, 2914, 1560, 1507, 1202, 710;

$^1$H NMR (300 MHz, DMSO-d$_6$) $\delta$11.5 (br s, 1H), 9.8 (br s, 1H), 6.6 (s, 1H), 5.42 (s, 1H), 3.56 (q, J=7 Hz, 2H), 2.45 (m, 2H), 2.16 (m, 2H), 1.9 (m, 4H), 1.5 (m, 4H), 1.12 (t, J=7 Hz, 3H);

MS (FD) m/e 295 (M$^+$);

UV (EtOH) 291 nm ($\epsilon$=19227), 257 nm ($\epsilon$=9628), 201 nm ($\epsilon$=15736).

Anal. Calcd for C$_{14}$H$_{21}$N$_3$S$_2$: C, 56.91 H, 7.16; N, 14.22. Found: C, 57.20; H, 7.22; N, 14.16.

Example 285

N-[2-(2-chlorophenyl)ethyl]-N'-[2-(4-ethyl)thiazolyl]thiourea

A solution of 1-[(2-[4-ethyl]thiazolyl)thiocarbamoyl]imidazole (0.75 g, 3.15 mmol) and 2-(2-chlorophenyl)ethylamine (0.49 g, 3.15 mmol) in N,N-dimethylformamide (15 mL) was stirred at 90° C. for 2 h, the reaction was cooled to room temperature and the solvent removed in vacuo. The residue was crystallized from ethyl acetate to provide 0.85 g (83%) of the titled product:

MP 153°–155° C.; IR (KBr, cm$^{-1}$) 3167, 3018, 1570, 1505, 1215, 749, 699;

$^1$H NMR (300 MHz, DMSO-d$_6$) $\delta$11.65 (br s, 1H), 9.85 (br s, 1H), 7.5–7.2 (m, 4H), 6.65 (s, 1H), 3.85 (m, 2H), 3.05 (t, J=7 Hz, 2H), 2.55 (q, J=7 Hz, 2H), 1.1 (t, J=7 Hz, 3H);

MS (FD) m/e 325 (M$^+$);

UV (EtOH) 292 nm ($\epsilon$=19154), 257 nm ($\epsilon$=10451), 202 nm ($\epsilon$=24308).

Anal. Calcd for C$_{14}$H$_{16}$N$_3$S$_2$Cl: C, 51.60; H, 4.95; N, 12.87. Found: C, 51.75; H, 4.98; N, 12.79.

Example 286

N-[2-(2-methoxyphenyl)ethyl]-N'-[2-(4-ethyl)thiazolyl]thiourea

A solution of 1-[(2-[4-ethyl]thiazolyl)thiocarbamoyl]imidazole (0.70 g, 2.94 mmol) and 2-(2-methoxyphenyl)ethylamine (0.44 g, 2.94 mmol) in N,N-dimethylformamide (15 mL) was stirred at 95° C. for 2 h, the reaction was cooled to room temperature and the solvent removed in vacuo. The residue was crystallized from ethyl acetate to provide 0.67 g (71%) of the titled product:

MP 166°–167.5° C.; IR (KBr, cm$^{-1}$) 3173, 3025, 1528, 1248, 1209, 755, 677;

¹H NMR (300 MHz, DMSO-d$_6$) δ11.5 (br s, 1H), 9.85 (br s, 1H), 7.2–6.8 (m, 4H), 6.57 (s, 1H), 3.7 (m, 5H), 2.82 (t, J=7 Hz, 2H), 2.4 (q, J=7 Hz, 2H), 1.06 (t, J=7 Hz, 3H);

MS (FD) m/e 321 (M$^+$);

UV (EtOH) 291 nm (ε=12114), 259 nm (ε=6792), 201 nm (ε=18914).

Anal. Calcd for C$_{15}$H$_{19}$N$_3$OS$_2$: C, 56.04; H, 5.96; N, 13.07. Found: C, 55.83; H, 6.00; N, 13.08.

Example 287

N-[2-(3-methoxyphenyl)ethyl]-N'-[2-(4-ethyl)thiazolyl]thiourea

A solution of 1-[(2-[4-ethyl]thiazolyl)thiocarbamoyl]imidazole (0.70 g, 2.94 mmol) and 2-(3-methoxyphenyl)ethylamine (0.44 g, 2.94 mmol) in N,N-dimethylformamide (15 mL) was stirred at 90° C. for 2 h, the reaction was cooled to room temperature and the solvent removed in vacuo. The residue was crystallized from ethyl acetate to provide 0.76 g (80%) of the titled product:

MP 123°–125° C.;

IR (KBr, cm$^{-1}$) 3167, 3027, 1587, 1207, 699;

¹H NMR (300 MHz, DMSO-d$_6$) δ11.5 (br s, 1H), 9.9 (br s, 1H), 7.2–6.8 (m, 4H), 6.58 (s, 1H), 3.75 (m, 2H), 3.67 (s, 3H), 2.84 (t, J=7 Hz, 2H), 2.45 (q, J=7 Hz, 2H), 1.05 (t, J=7 Hz, 3H);

MS (FD) m/e 321 (M$^+$);

UV (EtOH) 292 nm (ε=19113), 258 nm (ε=10607), 202 nm (ε=29289).

Anal. Calcd for C$_{15}$H$_{19}$N$_3$OS$_2$: C, 56.04; H, 5.96; N, 13.07. Found: C, 56.08; H, 5.96; N, 13.16.

Example 288

1-[(2-[4-cyano]thiazolyl)thiocarbamoyl]imidazole

A solution of 1,1'-thiocarbonyldiimidazole (3.2 g, 16 mmol) and 2-amino-4-cyanothiazole (2.0 g, 16 mmol) in acetonitrile (40 mL) was stirred at room temperature for 72 h and heated at 60° C. for 24 h. The resulting precipitate was collected by filtration to provide 2.74 g (73%) of the titled product:

IR (KBr, cm$^{-1}$) 3097, 2230;

¹H NMR (300 MHz, DMSO-d$_6$) δ11.99 (br s, 1H), 8.76 (s, 1H), 8.67 (s, 1H), 8.07 (s, 1H), 7.92 (s, 1H);

MS (FAB) m/e 236 (M+H).

Example 289

N-[2-(2-chlorophenyl)ethyl]-N'-[2-(4-cyano)thiazolyl]thiourea

A solution of 1-[(2-[4-cyano]thiazolyl)thiocarbamoyl]imidazole (0.66 g, 2.8 mmol) and 2-(2-chlorophenyl)ethylamine (0.45 g, 2.8 mmol) in N,N-dimethylformamide (15 mL) was stirred at 100° C. for 2 h. The reaction was cooled to room temperature, poured into ethyl acetate, washed with water, 1N aqueous HCl, water, saturated sodium bicarbonate, and brine. The organic layer was concentrated and the residue purified by chromatography on silica gel to provide 0.24 g (26%) of the titled product:

mp 165°–168° C.; IR (KBr, cm$^{-1}$) 3119, 2955, 2232, 1577, 1505, 1461, 1328, 1299, 1221, 1053, 826;

¹H NMR (300 MHz, DMSO-d$_6$) δ11.8 (br s, 1H), 8.5 (br s, 1H), 8.1 (s, 1H), 7.2–7.4 (m, 4H), 3.74 (m, 2H), 2.98 (t, J=7 Hz, 2H);

MS (FD) m/e 322 (M$^+$);

UV (EtOH) 287 nm (ε=10082), 258 nm (ε=15462), 205 nm (ε=31601).

Example 290

N-[2-(3-chlorophenyl)ethyl]-N'-[2-(4-cyano)thiazolyl]thiourea

A solution of 1-[(2-[4-cyano]thiazolyl)thiocarbamoyl]imidazole (0.66 g, 2.8 mmol) and 2-(3-chlorophenyl)ethylamine (0.44 g, 2.8 mmol) in N,N-dimethylformamide (15 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated. The resultant solid was crystallized from methylene chloride to provide 0.21 g (23 %) of the titled product as a tan solid:

mp 180°–185° C.; IR (KBr, cm$^{-1}$) 2955, 2239, 1559, 1522, 1331, 1251, 1206, 1168, 823;

¹H NMR (300 MHz, DMSO-d$_6$) δ11.8 (br s, 1H), 8.4 (br s, 1H), 8.1 (s, 1H), 7.1–7.3 (m, 4H), 3.71 (m, 2H), 2.86 (t, J=7 Hz, 2H);

MS (FD) m/e 322 (M$^+$), 324;

UV (EtOH) 287 nm (ε=10684), 258 nm (ε=16406), 207 nm (ε=33 113).

Example 291

N-[2-(2-methoxyphenyl)ethyl]-N'-[2-(4-cyano)thiazolyl]thiourea

A solution of 1-[(2-[4-cyano]thiazolyl)thiocarbamoyl]imidazole (0.66 g, 2.8 mmol) and 2-(2-methoxyphenyl)ethylamine (0.46 g, 2.8 mmol) in N,N-dimethylformamide (15 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the residue purified by chromatography on silica gel to provide 0.21 g (23%) of the titled product as a yellow solid:

mp 159°–161° C.;

IR (KBr, cm$^{-1}$) 2937, 2235, 1566, 1454, 1301, 1243, 1208, 1173, 754;

¹H NMR (300 MHz, DMSO-d$_6$) δ11.8 (br s, 1H), 8.4 (br s, 1H), 8.1 (s, 1H), 6.8–7.2 (m, 4H), 3.73 (s, 3H), 3.66 (m, 2H), 2.81 (t, J=7 Hz, 2H);

MS (FD) m/e 318 (M$^+$);

UV (EtOH) 279 nm (ε=12102), 259 nm (ε=16281), 203 nm (ε=33347).

Example 292

N-[2-(3-methoxyphenyl)ethyl]-N'-[2-(4-cyano)thiazolyl]thiourea

A solution of 1-[(2-[4-cyano]thiazolyl)thiocarbamoyl]imidazole (0.66 g, 2.8 mmol) and 2-(3-methoxyphenyl)ethylamine (0.44 g, 2.8 mmol) in N,N-dimethylformamide (15 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the residue purified by chromatography on silica gel to provide 0.21 g (23%) of the titled product as a yellow solid:

mp 151°–153° C.;

IR (KBr, cm$^{-1}$) 3065, 2235, 1564, 1515, 1295, 1250, 1209, 1155, 1058, 874, 768, 748, 684;

$^1$H NMR (300 MHz, DMSO-d$_6$) δ11.8 (br s, 1H), 8.4 (br s, 1H), 8.1 (s, 1H), 7.18 (m, 1H), 6.77 (m, 3H), 3.68 (m, 5H), 2.80 (t, J=7 Hz, 2H);

MS (FD) m/e 318 (M$^+$);

UV (EtOH) 280 nm (ε=11770), 258 nm (ε=16613), 204 nm (ε=34785).

Example 293

N-[2-(1-cyclohexenyl)ethyl]-N'-[2-(4-cyano)thiazolyl]thiourea

A solution of 1-[(2-[4-cyano]thiazolyl)thiocarbamoyl]imidazole (0.82 g, 3.5 mmol) and 2-(1-cyclohexenyl)ethylamine (0.45 g, 3.5 mmol) in N,N-dimethylformamide (15 mL) was stirred at 90° C. for 1.5 h. The reaction was cooled to room temperature, poured into ethyl acetate, washed with water, 1N aqueous HCl, water, saturated sodium bicarbonate, and brine. The organic layer was concentrated and the resultant solid was purified by chromatography on silica gel to provide 0.27 g (26%) of the titled product as a pale yellow solid:

mp 176°–178° C.;

IR (KBr, cm$^{-1}$) 3169, 3075, 2924, 2233, 1556, 1513, 1330, 1298, 1260, 1217, 1200, 1167, 1145, 983, 922;

$^1$H NMR (300 MHz, DMSO-d$_6$) δ11.87 (br s, 1H), 8.40 (br s, 1H), 8.11 (s, 1H), 5.42(br s, 1H), 3.52 (m, 2H), 2.14 (t, J=7 Hz, 2H), 1.90 (m, 4H), 1.49 (m, 4H);

MS (FD) m/e 292 (M$^+$);

UV (EtOH) 288 nm (ε=11250), 258 nm (ε=16113), 206 nm (ε=25473)

Anal. Calcd for C$_{13}$H$_{16}$N$_4$S$_2$: C, 53.40; H, 5.52; N, 19.16. Found: C, 53.10; H, 5.55; N, 18.96.

Example 294

1-[(2-[4-(3-chlorophenyl]thiazolyl)thiocarbamoyl]imidazole

A solution of 1,1'-thiocarbonyldiimidazole (2.52 g, 12 mmol) and 4-(3-chlorophenyl)-2-thiazoleamine (2.14 g, 12 mmol) in acetonitrile (35 mL) was stirred at room temperature for 30 hours. The resulting precipitate was collected by filtration to provide 2.77 g (72%) of the titled product:

MS (FAB) m/e 321 (M+H).

Example 295

N-[2-(2-chlorophenyl)ethyl]-N'-[2-[4-(3-chlorophenyl)]]thiazolyl thiourea

A solution of 1-[(2-[4-(3-chlorophenyl]thiazolyl)thiocarbamoyl]imidazole (0.92 g, 2.86 mmol) and 2-(2-chlorophenyl)ethylamine (0.46 g, 2.86 mmol) in N,N-dimethylformamide (15 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 1.0 g (86%) of the titled product as yellow needles:

mp 193°–195° C.;

IR (KBr, cm$^{-1}$) 3018, 1560, 1515, 1470, 1291, 1210, 1065, 935, 785, 757, 716;

$^1$H NMR (300 MHz, DMSO-d$_6$) δ11.66 (br s, 1H), 9.29 (br s, 1H), 7.79 (s, 1H), 7.63 (m, 2H), 7.35 (m, 4H), 7.23 (m, 2H), 3.83 (m, 2H), 3.02 (t, J=7 Hz, 2H);

MS (FD) m/e 407 (M$^+$), 409 (M+2);

UV (EtOH) 285 nm (ε=22709), 266 nm (ε=20608), 202 nm (ε=37861).

Anal. Calcd for C$_{18}$H$_{15}$N$_3$S$_2$Cl$_2$: C, 52.94; H, 3.70; N 10.29. Found: C, 52.96; H, 3.74; N, 10.49.

Example 296

N-[2-(3-methoxyphenyl)ethyl]-N'-[2-[4-(3-chlorophenyl)]]thiazolyl thiourea

A solution of 1-[(2-[4-(3-chlorophenyl]thiazolyl)thiocarbamoyl]imidazole (0.92 g, 2.86 mmol) and 2-(3-methoxyphenyl)ethylamine (0.45 g, 2.86 mmol) in N,N-dimethylformamide (15 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.85 g (74%) of the titled product as a white solid:

mp 183°–185° C.;

IR (KBr, cm$^{-1}$)3172, 3024, 1569, 1515, 1466, 1319, 1287, 1260, 1220, 1067, 996, 775, 728, 604;

$^1$H NMR (300 MHz, DMSO-d$_6$) δ11.66 (br s, 1H), 9.20 (br s, 1H), 7.81 (s, 1H), 7.63 (m, 2H), 7.35 (m, 2H), 7.16 (m, 1H), 6.73 (m, 3H), 3.77 (m, 2H), 3.64 (s, 3H), 2.86 (t, J=7 Hz, 2H);

MS (FD) m/e 403 (M$^+$), 405 (M+2);

UV (EtOH) 280 nm (ε=23880), 202 nm (ε=42912).

Anal. Calcd for C$_{19}$H$_{18}$N$_3$OS$_2$Cl: C, 56.49; H, 4.49; N, 10.40. Found: C, 56.62; H, 4.50; N, 10.58.

Example 297

N-[2-(1-cyclohexenyl)ethyl]-N'-[2-[4-(3-chlorophenyl)]]thiazolyl thiourea

A solution of 1-[(2-[4-(3-chlorophenyl]thiazolyl)thiocarbamoyl]imidazole (0.92 g, 2.86 mmol) and 2-(1-cyclohexenyl)ethylamine (0.37 g, 2.86 mmol) in N,N-dimethylformamide (15 mL) was stirred at 90° C. for 0.5 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.7 g (65%) of the titled product as a white solid:

mp 196°–197° C.;

IR (KBr, cm$^{-1}$) 2939, 1557, 1514, 1469, 1287, 1202, 1062, 881, 784, 719, 661;

$^1$H NMR (300 MHz, DMSO-d$_6$) δ11.66 (br s, 1H), 9.17 (br s, 1H), 7.85 (s, 1H), 7.76 (m, 1H), 7.61 (s, 1H), 7.37 (m, 2H), 5.41(br s, 1H), 3.60 (m, 2H), 2.20 (t, J=7 Hz, 2H), 1.87 (m, 4H), 1.46 (m, 4H);

MS (FD) m/e 377 (M$^+$), 379 (M+2);

UV (EtOH) 285 nm (ε=23385), 232 nm (ε=18756), 202 nm (ε=31779)

Anal. Calcd for $C_{18}H_{20}N_3S_2Cl$: C, 57.20; H, 5.33; N, 11.12. Found: C, 57.04; H, 5.32; N, 11.09.

Example 298

1-[(2-[4-(3-nitrophenyl]thiazolyl)thiocarbamoyl]imidazole

A solution of 1,1'-thiocarbonyldiimidazole (0.41 g, 2.3 mmol) and 4-(3-nitrophenyl)-2-thiazoleamine (0.5 g, 2.3 mmol) in acetonitrile (25 mL) was stirred at room temperature for 72 h and heated at 60° C. for 72 h. The resulting precipitate was collected by filtration to provide 0.51 g (68%) of the titled product:

MS (FAB) m/e 332 (M+H).

Anal. Calcd for $C_{13}H_9N_5O_2S_2$: C, 47.12; H, 2.73; N, 21.13. Found: C, 47.35; H, 2.69; N, 21.03.

Example 299

N-[2-(1-cyclohexenyl)ethyl]-N'-[2-[4-(3-nitrophenyl)]]thiazolyl thiourea

A solution of 1-[(2-[4-(3-nitrophenyl]thiazolyl)thiocarbamoyl]imidazole (0.5 g, 1.5 mmol) and 2-(1-cyclohexenyl)ethylamine (0.19 g, 1.5 mmol) in N,N-dimethylformamide (15 mL) was stirred at 90° C. for 0.75 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.37 g (63%) of the titled product as a yellow solid:

mp 218°–221° C.;

IR (KBr, cm$^{-1}$) 3165, 3017, 2922, 1569, 1513, 1465, 1352, 1265, 1216, 1167, 1065, 877, 788, 713, 676;

$^1$H NMR (300 MHz, DMSO-d$_6$) δ11.76 (s, 1H), 8.85 (br s, 1H), 8.61 (s, 1H), 8.25 (d, J=8 Hz, 1H), 8.11 (d, J=8 Hz, 1H), 7.77 (s, 1H), 7.67 (m, 1H), 5.42(br s, 1H), 3.58 (m, 2H), 2.20 (m, J=7 Hz, 2H), 1.89 (m, 4H), 1.46 (m, 4H); MS (FD) m/e 388 (M$^+$);

UV (EtOH) 286 nm (ε=22903), 265 nm (ε=23582), 237 nm (ε=17806), 202 nm (ε=24107)

Anal. Calcd for $C_{18}H_{20}N_4O_2S_2$: C, 55.65; H, 5.19; N, 14.42. Found: C, 55.45; H, 5.14; N, 14.51.

Example 300

N-[2-(4-chlorophenyl)ethyl]-N'-[2-(4-cyano)thiazolyl]thiourea

A solution of 1-[(2-[4-cyano]thiazolyl)thiocarbamoyl] imidazole (0.71 g, 3.0 mmol) and 2-(4-chlorophenyl)ethylamine (0.48 g, 3.0 mmol) in N,N-dimethylformamide (20 mL) was stirred am 90° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.4 g (41%) of the titled product as a tan solid:

mp 188°–190° C.;

IR (KBr, cm$^{-1}$) 3396, 3110, 2226, 1586, 1518, 1490, 1353, 1248, 1087, 808, 766, 649, 517;

$^1$H NMR (300 MHz, DMSO-d$_6$) δ11.8 (s, 1H), 8.43 (br s, 1H), 8.12 (s, 1H), 7.33 (d, J=8Hz, 2H), 7.24 (d, J=8Hz, 2H), 3.69 (m, 2H), 2.84 (t, J=7 Hz, 2H);

MS (FD) m/e 322 (M$^+$);

UV (EtOH) 287 nm (ε=10775), 257 nm (ε=17025), 206 nm (ε=3 1350).

Example 301

N-[2-(4-methoxyphenyl)ethyl]-N'-[2-(4-cyano)thiazolyl]thiourea

A solution of 1-[(2-[4-cyano]thiazolyl)thiocarbamoyl] imidazole (0.9 g, 3.8 mmol) and 2-(4-methoxyphenyl)ethylamine (0.59 g, 3.8 mmol) in N,N-dimethylformamide (25 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.66 g (55%) of the titled product as a yellow solid:

mp 185°–190° C.;

IR (KBr, cm$^{-1}$) 3208, 3064, 2236, 1547, 1514, 1259, 1201, 1164, 1033, 886, 775, 748, 680;

$^1$H NMR (300 MHz, DMSO-d$_6$) δ11.8 (br s, 1H), 8.4 (br s, 1H), 8.1 (s, 1H), 7.13 (d, J=9Hz, 2H), 6.83 (d, J=9Hz, 2H), 3.68 (s, 3H), 3.64 (m, 2H), 2.77 (t, J=7 Hz, 2H);

MS (FD) m/e 318 (M$^+$);

UV (EtOH) 284 nm (ε=12158), 258 nm (ε=17248), 204 nm (ε=30994).

Example 302

1-[(2-benzimidazolyl)thiocarbamoyl]imidazole

A solution of 1,1'-thiocarbonyldiimidazole (8.91 g, 50 mmol) and 2-aminobenzimidazole (6.66 g, 50 mmol) in acetonitrile (50 mL) was stirred at room temperature for 19 hours. The resulting precipitate was collected by filtration to provide 8.92 g (73%) of the titled product:

IR (KBr, cm$^{-1}$) 3058, 2621, 1623, 1580, 1509, 1469, 1445, 1355, 1290, 1252, 1212, 1153, 1099, 1081, 1048, 925, 898, 746, 659;

$^1$H NMR (300 MHz, DMSO-d$_6$) δ13.24 (br s, 2H), 8.52 (s, 1H), 7.87 (s, 1H), 7.57 (m, 2H), 7.33 (m, 2H), 6.96 (s, 1H);

MS (FAB) m/e 244 (M+1);

UV (EtOH) 351 nm (ε=18204), 283 nm (ε=13099), 227 nm (ε=17339), 204 nm (ε=31915).

Example 303

N-[2-(2-chlorophenyl)ethyl]-N'-(2-benzimidazolyl)thiourea

A solution of 1-[(2-benzimidazolyl)thiocarbamoyl]imidazole (1.22 g, 5.0 mmol) and 2-(2-chlorophenyl)ethylamine (0.81 g, 5.0 mmol) in N,N- dimethylformamide (20 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.67 g (40%) of the titled product as a white solid:

mp 166°–169° C.;

IR (KBr, cm$^{-1}$) 3235, 1656, 1554, 1459, 1248, 1224, 1192, 754, 737, 629;

¹H NMR (300 MHz, DMSO-d₆) δ11.95 (br s, 1H), 10.82 (br s, 1H), 7.42 (m, 5H), 7.25 (m, 2H), 7.12 (m, 2H), 3.83 (m, 2H), 3.05 (t, J=7 Hz, 2H);

MS (FD) m/e 330 (M⁺);

UV (EtOH) 301 nm (ε=18044), 293 nm (ε=18559), 266 nm (ε=11113), 260 nm (ε=10441), 239 nm (ε=8428), 206 nm (ε=27620).

Example 304

N-[2-(3-chlorothenyl)ethyl]-N'-(2-benzimidazolyl)thiourea

A solution of 1-[(2-benzimidazolyl)thiocarbamoyl]imidazole (1.22 g, 5.0 mmol) and 2-(3-chlorophenyl)ethylamine (0.79 g, 5.0 mmol) in N,N-dimethylformamide (20 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.24 g (14%) of the titled product as a white solid:

mp 171°–177° C.;

IR (KBr, cm⁻¹) 3387, 1574, 1539, 1461, 1426, 1237, 1175, 734, 699, 477;

¹H NMR (300 MHz, DMSO-d₆) δ11.18 (m, 2H), 7.28 (m, 8H), 7.06 (m, 1H), 3.83 (m, 2H), 2.94 (t, J=7 Hz, 2H);

MS (FD) m/e 330 (M⁺);

UV (EtOH) 293 nm (ε=17219), 266 nm (ε=9969), 260 nm (ε=9196), 240 nm (ε=8196), 203 nm (ε=27483).

Example 305

N-[2-(4-chlorophenyl)ethyl]-N'-(2-benzimidazolyl)thiourea

A solution of 1-[(2-benzimidazolyl)thiocarbamoyl]imidazole (!.22 g, 5.0 mmol) and 2-(4-chlorophenyl)ethylamine (0.79 g, 5.0 mmol) in N,N-dimethylformamide (20 mL) was stirred at 90 ° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 1.31 g (79%) of the titled product as a white solid:

mp 173°–182° C.;

IR (KBr, cm⁻¹) 3168, 3031, 1668, 1562, 1494, 1470, 1327, 1221, 1174, 1090, 817, 777, 742, 657, 526, 457;

¹H NMR (300 MHz, DMSO-d₆) δ12.18 (br s, 1H), 10.36 (br s, 1H), 7.52 (m, 2H), 7.22–7.38 (m, 7H), 3.76 (m, 2H), 2.89 (t, J=7 Hz, 2H);

MS (FD) m/e 330 (M⁺), 332 (M+2);

UV (EtOH) 301 nm (ε=21672), 293 nm (ε=22296), 266 nm (ε=13408), 260 nm (ε=12591), 206 nm (ε=29310).

Example 306

N-[2-(2-methoxyphenyl)ethyl]-N'-(2-benzimidazolyl)thiourea

A solution of 1-[(2-benzimidazolyl)thiocarbamoyl]imidazole (1.22 g, 5.0 mmol) and 2-(2-methoxyphenyl)ethylamine (0.82 g, 5.0 mmol) in N,N-dimethylformamide (20 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.62 g (38%) of the titled product as a white solid:

mp 176°–184° C.;

IR (KBr, cm⁻¹) 3035, 1644, 1539, 1495, 1463, 1331, 1246, 1203, 1025, 750, 454;

¹H NMR (300 MHz, DMSO-d₆) δ11.95 (br s, 1H}, 10.32 (br s, 1H), 7.52 (m, 2H), 7.20 (m, 5H), 6.88 (m, 2H), 3.75 (s, 3H) 3.70 (m, 2H), 2.88 (t, J=7 Hz, 2H);

MS (FD) m/e 326 (M⁺);

UV (EtOH) 301 nm (ε=20950), 293 nm (ε=21508), 265 nm (ε=14212), 239 nm (ε=9552), 204 nm (ε=30277).

Example 307

N-[2-(3-methoxyphenyl)ethyl]-N'-(2-benzimidazolyl)thiourea

A solution of 1-[(2-benzimidazolyl)thiocarbamoyl]imidazole (1.22 g, 5.0 mmol) and 2-(3-methoxyphenyl)ethylamine (0.78 g, 5.0 mmol) in N,N-dimethylformamide (20 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the resultant solid was purified by chromatography on silica gel to provide 1.2 g (73%) of the titled product as a white solid:

mp 161°–167° C.;

IR (KBr, cm⁻¹) 2932, 1574, 1541, 1460, 1230, 1152, 1016, 737, 694, 577, 461;

¹H NMR (300 MHz, DMSO-d₆) δ11.14 (br s, 1H), 10.95 (br s, 1H), 7.30 (m, 2H), 7.16 (m, 1H), 7.06(m, 2H), 6.87 (m, 2H), 6.75 (m, 2H), 3.83 (m, 2H) 3.80 (s, 3H), 2.89 (t, J=7 Hz, 2H);

MS (FD) m/e 326 (M⁺);

UV (EtOH) 301 nm (ε=23757), 293 nm (ε=24495), 265 nm (ε=16068), 260 nm (ε=14682), 239 nm (ε=11477), 204 nm (ε=36963).

Example 308

N-[2-(4-methoxyphenyl)ethyl]-N'-(2-benzimidazolyl)thiourea

A solution of 1-[(2-benzimidazolyl)thiocarbamoyl]imidazole (1.22 g, 5.0 mmol) and 2-(4-methoxyphenyl)ethylamine (0.77 g, 5.0 mmol) in N,N-dimethylformamide (20 mL) was stirred at 90° C. for 1 h. The reaction was cooled to room temperature, poured into ethyl acetate, washed with water, 1N aqueous HCl, water, saturated sodium bicarbonate, and brine. The organic layer was concentrated and the resultant solid was purified by chromatography on silica gel to provide 1.1 g (67%) of the titled product as a white solid:

mp 166°–172° C.;

IR (KBr, cm⁻¹) 3416, 3195, 3065, 1575, 1543, 1511, 1464, 1243, 1176, 1037, 747, 442;

¹H NMR (300 MHz, DMSO-d₆) δ11.11 (br s, 1H), 10.95 (br s, 1H), 7.36 (m, 2H), 7.20 (d, J=8 Hz, 2H), 7.08(m, 3H), 6.82 (d, J=8 Hz, 2H), 3.78 (m, 2H) 3.67 (s, 3H), 2.85 (t, J=7 Hz, 2H);

MS (FD) m/e 326 (M⁺);

UV (EtOH) 301 nm (ε24618), 293 nm (ε=25247), 265 nm (ε=16716), 260 nm (ε=15557), 203 nm (ε=35060).

Example 309

N-[2-(1-cyclohexenyl)ethyl]-N'-(2-benzimidazolyl)thiourea

A solution of 1-[(2-benzimidazolyl)thiocarbamoyl]imidazole (1.22 g, 5.0 mmol) and 2-(1-cyclohexenyl)ethylamine (0.64 g, 5.0 mmol) in N,N-dimethylformamide (20 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.82 g (55%) of the titled product as yellow needles:

mp 178°–180° C.;

IR (KBr, cm$^{-1}$) 3182, 2922, 1576, 1540, 1421, 1271, 1232, 1033, 740, 450;

$^1$H NMR (300 MHz, DMSO-d$_6$) δ11.08 (br s, 1H), 11.07 (br s, 1H), 11.02 (br s, 1H), 7.36 (m, 2H), 7.06(m, 2H), 5.51 (s, 1H), 3.66 (m, 2H), 2.21 (t, J=7 Hz, 2H), 1.93 (m, 4H), 1.51 (m, 4H);

MS (FD) m/e 300 (M$^+$);

UV (EtOH) 301 nm (ε=25279), 292 nm (ε=26214), 265 nm (ε=15965), 259 nm (ε=14734), 239 nm (ε=11012), 206 nm (ε=30007).

Anal. Calcd for $C_{16}H_{20}N_4S$: C, 63.97; H, 6.71; N, 18.65. Found: C, 64.25; H, 6.99; N, 18.63.

Example 310

1-[(2-pyridyl)thiocarbamoyl]imidazole

A solution of 1,1'-thiocarbonyldiimidazole (9.9 g, 50 mmol) and 2-aminopyridine (4.75 g, 50 mmol) in acetonitrile (50 mL) was stirred at room temperature for 72 h. The resulting solution was evaporated to a black oil and triturated with hexane. The remaining oily residue was placed under vacuum to provide 13.6 g of crude titled product as a black solid:

$^1$H NMR (300 MHz, DMSO-d$_6$) δ8.89 (br s, 1H), 8.58 (m, 1H), 8.35 (m, 1H), 7.80 (m, 2H), 7.40 (m, 1H), 7.15 (m, 1H), 6.95 (m, 1H);

MS (FAB) m/e 204 (M+, weak)

Example 311

N-[2-(2-chlorothenyl)ethyl]-N'-(2-pyridyl)thiourea

A solution of 1-[(2-pyridyl)thiocarbamoyl]imidazole (1.02 g, 5.0 mmol) and 2-(2-chlorophenyl)ethylamine (0.81 g, 5.0 mmol) in N,N-dimethylformamide (20 mL) was stirred am 90° C. for 24 h. The reaction was cooled to room temperature, poured into ethyl acetate, washed with water, 1N aqueous HCl, water, saturated sodium bicarbonate, and brine. The organic layer was concentrated and the resultant oil was purified by chromatography on silica gel to provide 0.21 g (14%) of the titled product as a yellow solid:

mp 116°–122° C.;

IR (KBr, cm$^{-1}$) 3235, 1606, 1592, 1558, 1537, 1477, 1439, 1332, 1259, 1234, 1212, 1185, 1150, 1088, 1057, 861;

$^1$H NMR (300 MHz, DMSO-d$_6$) δ11.63 (m, 1H), 10.53 (s, 1H), 8.03 (m, 1H), 7.68 (m, 1H), 7.41 (m, 2H), 7.30 (m, 2H), 7.07 (m, 1H), 6.96 (m, 1H), 3.84 (m, 2H), 3.04 (t, J=7 Hz, 2H);

MS (FD) m/e 291 (M$^+$);

UV (EtOH) 293 nm (ε=14959), 266 nm (ε=15723), 246 nm (ε=15174), 201 nm (ε=23340).

Example 312

2-(2,6-Difluorophenyl)ethylamine 2,6-Difluorophenylacetonitrile (15.8 g, 100 mmol) was dissolved in tetrahydrofuran (75 mL) at room temperature. The solution was cooled in an ice bath and borane.THF complex (100mL, 100 mmol) was added dropwise over 15 minutes under nitrogen atmosphere. The ice bath was removed after borane addition was complete and the mixture was stirred at room temperature for 23 hours under nitrogen atmosphere. Saturated aqueous ammonium chloride solution (20 mL) was added dropwise with stirring over 30 minutes. The reaction mixture was filtered through diatomaceous earth, concentrated to an oil, redissolved in ethyl acetate/water, and adjusted to pH 1.0 with concentrated hydrochloric acid. The mixture was filtered through diatomaceous earth and the ethyl acetate layer extracted with 1N hydrochloric acid (4×10 mL). The combined acidic aqueous extracts were washed with ethyl acetate (2×50 ml). Solid sodium chloride was added to the acidic aqueous extracts, adjusted to pH 9.0 with solid sodium bicarbonate and 5N sodium hydroxide solution, and the mixture extracted with methylene chloride (7×50 mL). The combined methylene chloride extracts were washed with brine solution, dried over anhydrous sodium sulfate, filtered, and concentrated to yield 10.6 g (68%) of the titled product as a nearly colorless oil:

IR (KBr, cm$^{-1}$) 2967, 2876, 1626, 1590, 1469, 1265, 1236, 1213, 1157, 1128, 1085, 1051, 1016, 956, 843;

$^1$H NMR (300 MHz, CDCl$_3$) δ7.13 (m, 1H), 6.83 (m, 2H), 2.89 (m, 2H), 2.80 (t, J=7 Hz, 2H), 1.19 (s, 2H);

MS (FD) m/e 157 (M+, weak);

UV (EtOH) 265 nm (ε=650), 260 nm (ε=674), 204 nm (ε=7922);

TITRATION (66% DMF/H$_2$O) pKa 9.06

Anal. Calcd for $C_8H_9F_2N$: C, 61.14; H, 5.77; N, 8.91. Found: C, 60.88; H, 5.88; N, 8.63.

Example 313

N-[2-(2,6-difluorophenyl)ethyl]-N'-[2-(4-ethyl)thiazolyl]thiourea

A solution of 2-(2,6-difluorophenyl)ethylamine (0.16 g, 1 mmol) and 1-[(2-[4-ethyl]thiazolyl)thiocarbamoyl]imidazole (0.24 g, 1 mmol) in N,N-dimethylformamide (15 mL) was stirred at 90° C. for 2 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.29 g (89%) of the titled product as a pale yellow solid:

mp 157°–158° C.;

IR (KBr, cm$^{-1}$) 3178, 2972, 1584, 1502, 1469, 1340, 1351, 1293, 1267, 1212, 1075, 1014, 953, 787, 726, 672;

$^1$H NMR (300 MHz, DMSO-d$_6$) δ11.54 (br s, 1H), 9.75 (br s, 1H), 7.29 (m, 1H), 7.01 (m, 2H), 6.58 (s, 1H), 3.77 (m, 2H), 2.92 (t, J=7 Hz, 2H), 2.45 (q, J=8 Hz, 2H), 1.05 (t, J=8 Hz, 3H);

MS (FD) m/e 327 (M$^+$);

UV (EtOH) 292 nm (ε=18786), 257 nm (ε=10109), 202 nm (ε=19042)

Anal. Calcd for $C_{14}H_{15}F_2N_3S_2$: C, 51.36; H, 4.62; N, 12.83. Found: C, 51.60; H, 4.78; N, 13.08.

Example 314

N-[2-(2,6-difluorophenyl)ethyl]-N'-(2-pyridyl)thiourea

A solution of 2-(2,6-difluorophenyl)ethylamine (0.43 g, 2.7 mmol) and 1-[(2-pyridyl)thiocarbamoyl]imidazole (0.55 g, 2.7 mmol) in N,N-dimethylformamide (20 mL) was stirred at 90° C. for 27 h. The reaction was cooled to room temperature, poured into ethyl acetate, washed with water, 1N aqueous HCl, water, saturated sodium bicarbonate, and brine. The organic layer was concentrated and the resultant oil was purified by chromatography on silica gel to provide 0.08 g (10%) of the titled product as a pale yellow solid:

mp 157°–160° C.;

IR (KBr, cm$^{-1}$) 3226, 1605, 1539, 1466, 1332, 1260, 1236, 1188, 1100, 974, 899, 861, 774, 725, 635, 516;

$^1$H NMR (300 MHz, DMSO-d$_6$) δ11.68 (br s, 1H), 10.53 (br s, 1H), 7.99 (m, 1H), 7.70 (m, 1H), 7.28 (m, 1H), 7.04 (m, 4H), 3.82 (m, 2H), 2.97 (t, J=7 Hz, 2H);

MS (FD) m/e 293 (M$^+$);

UV (EtOH) 292 nm (ε=15506), 266 nm (ε=16020), 245 nm (ε=14709)

Example 315

1-[(2-(2,6-difluorophenyl)ethyl)thiocarbamoyl]imidazole

A solution of 1,1'-thiocarbonyldiimidazole (9.5 g, 48 mmol) and 2-(2,6-difluorophenyl)ethylamine (7.54 g, 48 mmol) in acetonitrile (100 mL) was stirred at room temperature for 20 h. The solution was concentrated under reduced pressure and the resulting precipitate was collected by filtration and triturated with hexane to provide 16 g of crude titled product as a brown solid:

IR (KBr, cm$^{-1}$) 3129, 1565, 1468, 1355, 1259, 1203, 1120, 1065, 1031, 937, 900, 827, 787, 751, 664, 621, 499;

$^1$H NMR (300 MHz, DMSO-d$_6$) δ10.50 (br s, 1H), 8.29 (s, 1H), 7.71 (s, 1H), 7.35 (m, 1H), 7.04 (m, 3H), 3.85 (m, 2H), 3.0 (m, 2H);

MS (FAB) m/e 268 (M+H);

UV (EtOH) 280 nm (ε=4068), 250 nm (ε=4341), 201 nm (ε=15062)

Example 316

N-[2-(1-cyclohexenyl)ethyl]-N'-[2-(6-chloro)pyrazinyl]thiourea

A solution of 2-amino-6-chloropyrazine (2.59 g, 20 mmol) and 2-(1-cyclohexenyl)ethylisothiocyanate (3.34 g, 20 mmol) in N,N-dimethylformamide (25 mL) was stirred at 95° C. for 27 h. The reaction was cooled to room temperature, poured into ethyl acetate, washed with water, 1N aqueous HCl, water, saturated sodium bicarbonate, and brine. The organic layer was concentrated and the resultant solid was purified by chromatography on silica gel and crystallized from EtOAc to provide 0.44 g (7%) of the titled product as white needles:

mp 170°–171° C.;

IR (KBr, cm$^{-1}$) 3207, 2926, 1584, 1514, 1414, 1295, 1161, 1005, 866, 714, 459;

$^1$H NMR (300 MHz, DMSO-d$_6$) δ11.08 (br s, 1H), 10.02 (br s, 1H), 8.49 (s, 1H), 8.29 (s, 1H), 5.48 (br s, 1H), 3.64 (m, 2H), 2.21 (t, J=7 Hz, 2H), 1.90 (m, 4H), 1.49 (m, 4H);

MS (FD) m/e 296 (M$^+$), 298 (M+2);

UV (EtOH) 327 nm (ε=12429), 266 nm (ε=17577)

Anal. Calcd for $C_{13}H_{17}N_4SCl$: C, 52.60; H, 5.77; N, 18.87. Found: C, 52.89; H, 5.89; N, 19.11.

Example 317

N-[2-(2,6-difluorophenyl)ethyl]-N'-[2-(6-methyl)pyridyl]thiourea

A solution of 1-[(2-(2,6-difluorophenyl)ethyl)thiocarbamoyl]imidazole (0.53 g, 2 mmol) and 2-amino-6-methylpyridine (0.22 g, 2 mmol) in N,N-dimethylformamide (20 mL) was stirred at 90° C. for 3 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.14 g (23%) of the titled product as nearly colorless prisms:

mp 187°–189° C.;

IR (KBr, cm$^{-1}$) 3195, 1612, 1544, 1468, 1451, 1380, 1293, 1269, 1230, 1192, 1160, 1072, 950, 788, 722, 635, 501;

$^1$H NMR (300 MHz, DMSO-d$_6$) δ11.83 (br s, 1H), 10.44 (br s, 1H), 7.56 (t, J=8 Hz, 1H), 7.26 (m, 1H), 6.98 (m, 2H), 6.87 (d, J=8 Hz, 1H), 6.79 (d, J=8 Hz, 1H), 3.87 (m, 2H), 2.94 (t, J=7 Hz, 2H), 2.11 (s, 3H);

MS (FD) m/e 307 (M$^+$);

UV (EtOH) 296 nm (ε=12052), 265 nm (ε=10578), 246 nm (ε=10257)

Anal. Calcd for $C_{15}H_{15}F_2N_3S$: C, 58.62; H, 4.92; N, 13.67. Found: C, 58.35; H, 4.98; N, 13.39.

Example 318

H-[2-(1-cyclohexenyl)ethyl]-N'-[2-(3,5-dimethyl)pyrazinyl]thiourea

A solution of 2-amino-3,5-dimethylpyrazine (0.62 g, 5 mmol) and 2-(1-cyclohexenyl)ethylisothiocyanate (0.84 g, 5 mmol) in N,N-dimethylformamide (20 mL) was stirred at 90° C. for 24 h. The reaction was cooled to room temperature, poured into ethyl acetate, washed with water, 1N aqueous HCl, water, saturated sodium bicarbonate, and brine. The organic layer was concentrated and the resultant oil was purified by chromatography on silica gel to provide 0.27 g (19%) of the titled product as an off-white solid:

mp 100°–103° C.;

IR (KBr, cm$^{-1}$) 3387, 2929, 1515, 1329, 1214, 1164, 1014, 966, 907;

$^1$H NMR (300 MHz, DMSO-d$_6$) δ10.57 (br s, 1H), 9.12 (br s, 1H), 7.91 (s, 1H), 5.44 (br s, 1H), 3.61 (m, 2H), 2.47 (s, 3H), 2.35 (s, 3H), 2.18 (t, J=7 Hz, 2H), 1.90 (m, 4H), 1.48 (m, 4H);

MS (FD) m/e 290 (M$^+$);

UV (EtOH) 320 nm (ε=11659), 265 nm (ε=16153), 201 nm (ε=11795)

Anal. Calcd for $C_{15}H_{22}N_4S$: C, 62.03; H, 7.63; N, 18.29. Found: C, 62.06; H, 7.65; N, 18.58.

Example 319

N-[2-(2,6-difluorophenyl)ethyl]-N'-[2-(5-trifluoromethyl)pyridyl]thiourea

A solution of 1-[(2-(2,6-difluorophenyl)ethyl)thiocarbamoyl]imidazole (1.07 g, 4 mmol) and 2-amino-5-trifluoromethylpyridine (0.65 g, 4 mmol) in N,N-dimethylformamide (20 mL) was stirred at 95° C. for 25 h. The reaction was cooled to room temperature, poured into ethyl acetate, washed with water, 1N aqueous HCl, water, saturated sodium bicarbonate, and brine. The organic layer was concentrated and the resultant solid was purified by chromatography on silica gel to provide 0.26 g (18%) of the titled product as a white solid:

mp 148°–152° C.;

IR (KBr, cm$^{-1}$) 3165, 3033, 1619, 1600, 1548, 1470, 1332, 1248, 1189, 1160, 1138, 1106, 1079, 964, 886, 776, 669, 603, 435;

$^1$H NMR (300 MHz, DMSO-d$_6$) δ11.42 (br s, 1H), 10.94 (br s, 1H), 8.36 (s, 1H), 8.08 (m, 1H), 7.28 (m, 2H), 7.02 (m, 2H), 3.82 (m, 2H), 2.98 (t, J=7 Hz, 2H);

MS (FD) m/e 361 (M$^+$);

UV (EtOH) 297 nm (ε=18455), 253 nm (ε=14782), 201 nm (ε=15765)

Anal. Calcd for C$_{15}$H$_{12}$F$_5$N$_3$S: C, 49.86; H, 3.35; N, 11.63. Found: C, 49.59; H, 3.28; N, 11.35

Example 320

N-[2-(2,6-difluorophenyl)ethyl]-N'-[2-(5-chloro)pyridyl]thiourea

A solution of 1-[(2-(2,6-difluorophenyl)ethyl)thiocarbamoyl]imidazole (1.07 g, 4 mmol) and 2-amino-5-chloropyridine (0.53 g, 4 mmol) in N,N-dimethylformamide (20 mL) was stirred at 90° C. for 22 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.65 g (50%) of the titled product as a tan solid:

mp 172°–175° C.;

IR (KBr, cm$^{-1}$) 3233, 1597, 1557, 1529, 1468, 1340, 1308, 1265, 1231, 1190, 1112, 1072, 950, 857, 834;

$^1$H NMR (300 MHz, DMSO-d$_6$) δ11.19 (m, 1H), 10.67 (s, 1H), 8.03 (s, 1H), 7.82 (m, 1H), 7.30 (m, 1H), 7.13 (m, 1H), 7.03 (m, 2H), 3.79 (m, 2H), 2.96 (t, J=7 Hz, 2H);

MS (FD) m/e 327 (M$^+$), 329 (M+2);

UV (EtOH) 304 nm (ε=13180), 274 nm (ε=23154), 253 nm (ε=15998), 201 nm (ε=19019)

Example 321

N-[2-(2,6-difluorophenyl)ethyl]-N'-[2-(5-methyl)pyridyl]thiourea

A solution of 1-[(2-(2,6-difluorophenyl)ethyl)thiocarbamoyl]imidazole (1.33 g, 5 mmol) and 2-amino-5-methylpyridine (0.54 g, 5 mmol) in N,N-dimethylformamide (20 mL) was stirred at 90° C. for 7 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.83 g (86%) of the titled product as yellow crystals:

mp 195°–196° C.;

IR (KBr, cm$^{-1}$) 3230, 1611, 1535, 1492, 1468, 1334, 1274, 1236, 1190, 1111, 1065, 957, 821, 777, 716, 657, 608, 513;

$^1$H NMR (300 MHz, DMSO-d$_6$) δ11.59 (br s, 1H), 10.44 (br s, 1H), 7.83 (br s, 1H), 7.53 (d, J=8 Hz, 1H), 7.30 (m, 1H), 7.02 (m, 3H), 3.80 (m, 2H), 2.96 (t, J=7 Hz, 2H), 2.16 (s, 3H);

MS (FD) m/e 307 (M$^+$);

UV (EtOH) 297 nm (ε=5129), 268 nm (ε=7508), 247 nm (ε=5383)

Anal. Calcd for C$_{15}$H$_{15}$F$_2$N$_3$S: C, 58.62; H, 4.92; N, 13.67. Found: C, 58.36; H, 4.98; N, 13.73.

Example 322

N-[2-(2,6-difluorophenyl)ethyl]-N'-[2-(5-bromo)pyrazinyl]thiourea

A solution of 1-[(2-(2,6-difluorophenyl)ethyl)thiocarbamoyl]imidazole (1.33 g, 5 mmol) and 2-amino-5-bromopyrazine (0.87 g, 5 mmol) in N,N-dimethylformamide (20 mL) was stirred at 95° C. for 26 h. The reaction was cooled to room temperature, poured into ethyl acetate, washed with water, 1N aqueous HCl, water, saturated sodium bicarbonate, and brine. The organic layer was concentrated and the resultant solid was purified by chromatography on silica gel to provide 0.31 g (17%) of the titled product as a white solid:

mp 175°–178° C.;

IR (KBr, cm$^{-1}$) 3200, 1596, 1560, 1526, 1469, 1441, 1324, 1259, 1179, 1161, 1114, 1012, 962, 899, 874, 788, 780, 667, 601;

$^1$H NMR (300 MHz, DMSO-d$_6$) δ10.98 (br s, 1H), 10.51 (br s, 1H), 8.33 (s, 1H), 8.24 (s, 1H), 7.31 (m, 1H), 7.04 (m, 2H), 3.81 (m, 2H), 2.97 (t, J=7 Hz, 2H);

MS (FD) m/e 372 (M$^+$), 374 (M+2);

UV (EtOH) 333 nm (ε=10125), 275 nm (ε=22570), 201 nm (ε=16801)

Anal. Calcd for C$_{13}$H$_{11}$BrF$_2$N$_4$S: C, 41.84; H, 2.97; N, 15.01. Found: C, 42.10; H, 3.12; N, 14.73.

Example 323

N-[2-(2,6-difluorophenyl)ethyl]-N'-[2-(6-ethyl)pyridyl]thiourea

A solution of 1-[(2-(2,6-difluorophenyl)ethyl)thiocarbamoyl]imidazole (1.33 g, 5 mmol) and 2-amino-6-ethylpyridine (0.61 g, 5 mmol) in N,N-dimethylformamide (20 mL) was stirred at 95° C. for 21 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.63 g (39%) of the titled product as dense yellow crystals:

mp 147°–148° C.;

IR (KBr, cm$^{-1}$) 2972, 1609, 1541, 1468, 1344, 1292, 1265, 1225, 1155, 1073, 951, 804, 786, 727, 692, 635, 501;

$^1$H NMR (300 MHz, DMSO-d$_6$) δ11.97 (m, 1H), 10.48 (br s, 1H), 7.59 (t, J=8 Hz, 1H), 7.27 (m, 1H), 6.98 (m, 2H), 6.89 (d, J=8 Hz, 1H), 6.80 (d, J=8 Hz, 1H), 3.87 (m, 2H), 2.95 J=7 Hz, 2H), 2.44 (q, J=8 Hz, 2H), 0.93 (t, J=8 Hz, 3H);

MS (FD) m/e 321 (M$^+$);

UV (EtOH) 296 nm (ε=17512), 266 nm (ε=15047), 246 nm (ε=14627), 201 nm (ε=16211)

Anal. Calcd for $C_{16}H_{17}F_2N_3S$: C, 59.80; H, 5.33; N, 13.07. Found: C, 60.04; H, 5.38; N, 13.22.

Example 324

N-[2-(2,6-difluorothenyl)ethyl]-N'-[2-(6-chloro)pyrazinyl]thiourea

A solution of 1-[(2-(2,6-difluorophenyl)ethyl)thiocarbamoyl]imidazole (4.0 g, 15 mmol) and 2-amino-6-chloropyrazine (1.96 g, 15 mmol) in N,N-dimethylformamide (25 mL) was stirred at 95° C. for 18 h. The reaction was cooled to room temperature, poured into ethyl acetate, washed with water, 1N aqueous HCl, water, saturated sodium bicarbonate, and brine. The organic layer was concentrated and the resultant solid was purified by chromatography on silica gel to provide 0.7 g (14%) of the titled product as a light yellow solid:

mp 175°–180° C.;

IR (KBr, cm$^{-1}$) 3232, 1588, 1512, 1468, 1414, 1296, 1240, 1163, 1097, 1004, 981, 869, 777, 714, 659, 459;

$^1$H NMR (300 MHz, DMSO-d$_6$) δ11.07 (br s, 1H), 10.07 (br s, 1H), 8.50 (s, 1H), 8.28 (s, 1H), 7.28 (m, 1H), 7.00 (m, 2H), 3.85 (m, 2H), 2.95 (C, J=7 Hz, 2H);

MS (FD) m/e 328 (M$^+$), 330 (M+2);

UV (EtOH) 327 nm (ε=10851), 265 nm (ε=14817), 201 nm (ε=16442)

Example 325

N-[2-(2-pyridyl)ethyl]-N'-[2-(4-cyano)thiazolyl]thiourea

A solution of 1-[(2-[4-cyano]thiazolyl)thiocarbamoyl]imidazole (2.35 g, 10 mmol) and 2-(2-pyridyl)ethylamine (1.29 g, 10 mmol) in N,N-dimethylformamide (25 mL) was stirred at 95° C. for 2 h. The reaction was cooled to room temperature, poured into ethyl acetate, washed with water, saturated sodium bicarbonate, and brine. The organic layer was concentrated and the residue purified by chromatography on silica gel to provide 0.4 g (14%) of the titled product as a yellow solid:

mp 160° C.;

IR (KBr, cm$^{-1}$) 3165, 3100, 2996, 2234, 1540, 1489, 1433, 1305, 1266, 1219, 1159, 1132, 999, 904, 817, 758, 574, 435;

$^1$H NMR (300 MHz, DMSO-d$_6$) δ11.88 (br s, 1H), 8.67 (br s, 1H), 8.49 (d, J=4 Hz, 1H), 8.11 (s, 1H), 7.69 (m, 1H), 7.23 (m, 2H), 3.87 (m, 2H), 3.01 (t, J=7 Hz, 2H);

MS (FD) m/e 289 (M$^+$);

UV (EtOH) 288 nm (ε=10826), 257 nm (ε=19925), 205 nm (ε=28658).

Example 326

N-[2-(2,6-difluorophenyl)ethyl]-N'-[2-(4-methyl)pyridyl]thiourea

A solution of 1-[(2-(2,6-difluorophenyl)ethyl)thiocarbamoyl]imidazole (1.33 g, 5 mmol) and 2-amino-4-methylpyridine (0.54 g, 5 mmol) in N,N-dimethylformamide (20 mL) was stirred at 90° C. for 3 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.49 g (32%) of the titled product as yellow needles:

mp 168°–170° C.;

IR (KBr, cm$^{-1}$) 3233, 1616, 1536, 1465, 1335, 1262, 1191, 1104, 959, 815, 783, 719, 653, 442;

$^1$H NMR (300 MHz, DMSO-d$_6$) δ11.74 (br s, 1H), 10.44 (br s, 1H), 7.85 (d, J=5 Hz, 1H), 7.27 (m, 1H), 7.02 (m, 2H), 6.88 (s, 1H), 6.80 (d, J=5 Hz, 1H), 3.80 (m, 2H), 2.96 (t, J=7 Hz, 2H), 2.20 (s, 3H);

MS (FD) m/e 307 (M$^+$);

UV (EtOH) 290 nm (ε=16210), 266 nm (ε=15920), 246 nm (ε=13211), 202 nm (ε=13211)

Example 327

N-[2-(2,6-difluorophenyl)ethyl]-N'-[2-ethyl)pyridyl]thiourea

A solution of 1-[(2-(2,6-difluorophenyl)ethyl)thiocarbamoyl]imidazole (1.33 g, 5 mmol) and 2-amino-4-ethylpyridine (0.61 g, 5 mmol) in N,N-dimethylformamide (20 mL) was stirred at 95° C. for 3 h. The reaction was cooled to room temperature, poured into ethyl acetate, washed with water, 1N aqueous HCl, water, saturated sodium bicarbonate, and brine. The organic layer was concentrated and the resultant solid was crystallized from EtOAc to provide 0.32 g (20%) of the titled product as a light brown solid:

mp 140°–142° C.;

IR (KBr, cm$^{-1}$) 2939, 1616, 1590, 1536, 1469, 1341, 1267, 1189, 1104, 1064, 960, 868, 826, 781, 759, 721, 668, 652;

$^1$H NMR (300 MHz, DMSO-d$_6$) δ11.74 (br s, 1H), 10.42 (br s, 1H), 7.87 (d, J=5 Hz, 1H), 7.29 (m, 1H), 6.99 (m, 2H), 6.85 (s, 1H), 6.84 (d, J=5 Hz, 1H), 3.81 (m, 2H), 2.95 (t, J=7 Hz, 2H), 2.49 (q, J=8 Hz, 2H), 1.09 (t, J=8 Hz, 3H);

MS (FD) m/e 321 (M$^+$);

UV (EtOH) 290 nm (ε=18247), 266 nm (ε=18045), 246 nm (ε=15212), 202 nm (ε=27817)

Anal. Calcd for $C_{16}H_{17}F_2N_3S$: C, 59.79; H, 5.33; N, 13.07. Found: C, 59.50; H, 5.31; N, 12.87.

Example 328

1-[(2-(2-pyridyl)ethyl)thiocarbamoyl]imidazole

A solution of 1,1'-thiocarbonyldiimidazole (9.9 g, 50 mmol) and 2-(2-pyridyl)ethylamine (6.43 g, 50 mmol) in acetonitrile (120 mL) was stirred at room temperature for 24 h. The solution was concentrated under reduced pressure and the resulting brown oil was triturated with ethyl ether. The remaining oil was placed under vacuum to provide 10.7 g of crude titled product as a black solid:

IR (KBr, cm$^{-1}$) 3125, 2930, 2098, 1548, 1477, 1437, 1363, 1329, 1284, 1221, 1098, 1063, 1030, 925, 828, 750, 661, 620;

$^1$H NMR (300 MHz, DMSO-d$_6$) δ10.35 (br s, 1H), 8.48 (m, 1H), 8.33 (s, 1H), 7.76 (s, 1H), 7.72 (m, 2H), 7.25 (m, 2H), 3.95 (m, 2H), 3.1 (m, 2H);

MS (FAB) m/e 233 (M+H);

UV (EtOH) 267 nm (ε=5516), 261 nm (ε=6306), 256 nm (ε=6220), 203 nm (ε=14929)

Example 329

N-[2-(2-pyridyl)ethyl]-N'-[2-(5-bromo)pyrazinyl]thiourea

A solution of 1-[(2-(2-pyridyl)ethyl)thiocarbamoyl]imidazole (1.16 g, 5 mmol) and 2-amino-5-bromopyrazine (0.87 g, 5 mmol) in N,N-dimethylformamide (20 mL) was stirred at 95° C. for 27 h. The reaction was cooled to room temperature, poured into ethyl acetate, washed with water, saturated sodium bicarbonate, and brine. The organic layer was concentrated and the residue purified by chromatography on silica gel and crystallized from EtOAc no provide 0.13 g (7%) of the titled product as a tan solid:

mp 185°–190° C.;

IR (KBr, cm$^{-1}$) 3186, 1588, 1558, 1517, 1479, 1439, 1356, 1325, 1289, 1268, 1220, 1185, 1156, 1100, 1083, 1013, 996, 900, 876, 800, 760, 716, 569, 511, 431;

$^1$H NMR (300 MHz, DMSO-d$_6$) δ10.93 (br s, 1H), 10.74 (br s, 1H), 8.54 (d, J=5 Hz, 1H), 8.31 (s, 1H), 8.28 (s, 1H), 7.69 (m, 1H), 7.28 (m, 1H), 7.21 (m, 1H), 3.96 (m, 2H), 3.05 J=7 Hz, 2H);

MS (FD) m/e 337 (M$^+$), 339 (M+2);

UV (EtOH) 333 nm (ε=10984), 270 nm (ε=25064).

Anal. Calcd for C$_{12}$H$_{12}$BrN$_5$S: C, 42.61; H, 3.58; N, 20.71. Found: C, 42.41; H, 3.83; N, 20.54

Example 330

N-[2-(2,6-difluorophenyl)ethyl]-N'-[2-(5-chloro)pyrazinyl]thiourea

A solution of 1-[(2-(2,6-difluorophenyl)ethyl)thiocarbamoyl]imidazole (1.33 g, 5 mmol) and 2-amino-5-chloropyrazine (0.65 g, 5 mmol) in N,N-dimethylformamide (20 mL) was stirred at 95° C. for 24 h. The reaction was cooled to room temperature, poured into ethyl acetate, washed with water, 1N aqueous HCl, water, saturated sodium bicarbonate, and brine. The organic layer was concentrated and the resultant solid was purified by chromatography on silica gel and crystallized from EtOAc to provide 0.1 g (6%) of the titled product as a white solid:

mp 170°–171° C.;

IR (KBr, cm$^{-1}$) 3199, 3070, 1593, 1563, 1529, 1468, 1443, 1418, 1327, 1263, 1184, 1166, 1128, 1016, 779;

$^1$H NMR (300 MHz, DMSO-d$_6$) δ11.00 (br s, 1H), 10.53 (br s, 1H), 8.33 (s, 1H), 8.19 (s, 1H), 7.30 (m, 1H), 7.04 (m, 2H), 3.81 (m, 2H), 2.96 (t, J=7 Hz, 2H);

MS (FD) m/e 328 (M$^+$), 330 (M+2);

UV (EtOH) 332 nm (ε=10097), 274 nm (ε=22879)

Anal. Calcd for C$_{13}$H$_{11}$ClF$_2$N$_4$S: C, 47.49; H, 3.37; N, 17.04. Found: C, 47.54; H, 3.45; N, 17.19.

Example 331

1-[(2-(5-ethoxy carbonyl)thiazolyl)thiocarbamoyl]imidazole

A solution of 1,1'-thiocarbonyldiimidazole (8.9 g, 50 mmol) and 2-amino(5-ethoxy carbonyl)thiazole (8.9 g, 50 mmol) in acetonitrile (600 mL) was stirred at 50° C. for 20 h. The resulting precipitate was collected by filtration to provide 6.5 g (40%) of the titled product.

mp 208°–210° C. (d).

IR (KBr, cm$^{-1}$) 3205, 3176, 3146, 3115, 1708, 1557, 1470, 1352, 1298, 1244, 1225;

$^1$H NMR (300 MHz, DMSO-d$_6$) δ13.2 (br s, 1H), 8.1 (s, 1H), 7.9 (s, 1H), 7.6 (s, 1H), 7.1 (s, 1H), 4.2 (q, 2H), 1.3 (t, 3H);

MS (FD) m/e (no correct pk) (M$^+$);

UV (EtOH) 349 nm (ε=4746), 269 nm (ε=8713), 209 nm (ε=21033).

Anal. Calcd for C$_{10}$H$_{10}$N$_4$O$_2$S$_2$: C, 42.54 H, 3.57; N, 19.84. Found: C, 42.37; H, 3.55; N, 19.59.

Example 332

N-[2-(1-cyclohexenyl)ethyl]-N'-[2-(5-ethoxy carbonyl)thiazolyl]thiourea

A solution of 1-[(2-[5-ethoxy carbonyl]thiazolyl)thiocarbamoyl]imidazole (1.12 g, 4.0 mmol) and 2-(1-cyclohexenyl)ethylamine (0.5 g, 4.0 mmol) in N,N-dimethylformamide (40 mL) was stirred at 90 ° C. for 1 h. The reaction was cooled to room temperature, poured into ethyl acetate, washed with water, 1N aqueous HCl, water, saturated sodium bicarbonate, and brine. The organic layer was concentrated and the residue recrystallized from ethyl acetate to provide 0.790 g (56%) of the titled product:

mp. 197°–198° C.;

IR (KBr, cm$^{-1}$) 3243, 3121, 3044, 2991, 2925, 1707, 1582, 1543, 1458, 1190;

$^1$H NMR (300 MHz, DMSO-d$_6$) δ12.0 (br s, 1H), 8.5 (br s, 1H), 7.9 (s, 1H), 5.5 (s, 1H), 4.3 (q, 2H), 3.6 (m, 2H), 2.2 (t, J=7 Hz, 2H), 1.9 (m, 4H), 1.5 (m, 4H), 1.3 (t, J=7 Hz, 3H);

MS (FD)m/e 339 (M$^+$);

UV (EtOH) 262 nm (ε=17510), 205 nm (ε=19237).

Anal. Calcd for C$_{15}$H$_{21}$N$_3$O$_2$S$_2$: C, 53.07; H, 6.23; N, 12.38. Found: C, 53.31; H, 6.44; N, 12.42.

Example 333

N-(2-phenethyl)-N'-[2-(5-ethoxy carbonyl)thiazolyl]thiourea

A solution of 1-[(2-[5-ethoxy carbonyl]thiazolyl)thiocarbamoyl]imidazole (1.1 g, 4.0 mmol) and 2-(1-phenyl)ethylamino (0.6 g, 4.0 mmol) in N,N-dimethylformamide (40 mL) was stirred at 90° C. for 1 h. The reaction was cooled to room temperature, poured into ethyl acetate, washed with water, 1N aqueous HCl, water, saturated sodium bicarbonate, and brine. The organic layer was concentrated and the residue crystallized from ethyl acetate to provide 1.07 g (80%) of the titled product:

mp. 174°–175° C.;

IR (KBr, cm$^{-1}$) 3340, 3253, 3124, 3056, 1707, 1682, 1579, 1537, 1454, 1252, 1222;

$^1$H NMR (300 MHz, DMSO-d$_6$) δ12.0 (br s, 1H), 8.7 (br s, 1H), 7.9 (s, 1H), 7.3 (m, 5H), 4.3 (q, 2H), 3.8 (m, 2H), 2.9 (t, J=7 Hz, 2H), 1.3 (t, J=7 Hz, 3H);

MS (FD) m/e 335 (M$^+$);

UV (EZOH) 262 nm (ε=19184), 206 nm (ε=26117).

Anal. Calcd for C$_{15}$H$_{17}$N$_3$O$_2$S$_2$: C, 53.71; H, 5.11; N, 12.53. Found: C, 53.48; H, 5.10; N, 12.68.

Example 334

N-[2-(1-cyclohexenyl)ethyl]-N'-[2-(5-chloro)pyridyl]thiourea

A solution of 2-amino-5-chloropyridine (1.28 g, 10.0 mmol) and 2-(1-cyclohexenyl)ethylisothiocyanate (1.67 g, 10.0 mmol) in N,N-dimethylformamide (30 mL) was stirred at 90° C. for 1 h. The reaction was cooled to room temperature, concentrated under vacuum to remove solvent. The residue was purified by HPLC to provide 0.560 g (19%) of the titled product:

mp. 166°–167° C.;

IR (KBr, cm$^{-1}$) 3455,3159, 1599, 1555, 1534, 1476;

$^1$H NMR (300 MHz, DMSO-d$_6$) δ11.1 (br s, 1H), 10.7 (s, 1H), 8.2 (d, 1H), 7.9 (m, 1H), 7.2 (d, 1H), 5.5 (s, 1H), 3.6 (m, 2H), 2.2 (t, J=7 Hz, 2H), 1.9 (m, 4H), 1.5 (m, 4H);

MS (FD) m/e 295 (M$^+$);

UV (EtOH) 305 nm (ε=12139), 273 nm (ε=15905), 244 nm (ε=25052).

Anal. Calcd for C$_{14}$H$_{18}$N$_3$SCl C, 56.84; H, 6.13; N, 14.20. Found: C, 56.59; H, 6.00; N, 14.09.

Example 335

N-[2-(2-chlorophenyl)ethyl]-N'-[2-(5-chloro)pyridyl]thiourea

A solution of N-[2-(2-chlorophenyl)ethyl]-N'-thiocarbamoyl imidazole (1.3 g, 5.0 mmol) and 2-amino-5-chloro pyridine (0.65 g, 5.0 mmol) in N,N-dimethylformamide (25 mL) was stirred at 100° C. for 1 h. The reaction was cooled to room temperature, poured into ethyl acetate, washed with water and brine. The organic layer was concentrated and the residue triturated with hexane to provide 0.83 g (55%) of the titled product:

mp 178°–179° C.;

$^1$H NMR (300 MHz, DMSO-d$_6$) δ11.2 (m, 1H), 10.7 (s, 1H), 8.1 (m, 1H), 7.5 (m, 1H), 7.4 (m, 2H), 7.2 (m, 2H), 7.1 (d, 1H), 3.8 (m, 2H), 3.1 (t, J=7 Hz, 2H);

MS (FD) m/e 325 (M$^+$);

UV (EtOH) 305 nm (ε=12931), 273 nm (ε=22583), 253 nm (ε=16558) 201 nm (ε=25277).

Anal. Calcd for C$_{14}$H$_{13}$N$_3$SCl: C, 51.54; H, 4.02; N, 12.88. Found: C, 51.26; H, 3.99; N, 12.79.

Example 336

N-[2-(1-cyclohexenyl)ethyl]-N'-[3-(6-chloro)pyridazinyl]thiourea

A solution of 3-amino-6-chloropyridazine (1.3 g, 10.0 mmol) and 2-(1-cyclohexenyl)ethylisothiocyanate (1.67 g, 10.0 mmol) in N,N-dimethylformamide (20 mL) was stirred at 90° C. for 1.5 h. The reaction was cooled to room temperature and concentrated under vacuum to remove solvent. The residue was purified by HPLC to provide 0.220 g (7.5%) of the titled product:

mp. 149°–153° C.;

pKa in (66% DMF) 12.8;

IR (KBr, cm$^{-1}$) 3203, 3072, 2935, 1599, 1565, 1520, 1424, 1351, 1308, 1280, 1184, 1147, 1073;

$^1$H NMR (300 MHz, DMSO-d$_6$) δ11.1 (m, 1H), 10.9 (s, 1H), 7.8 (d, 1H), 7.6 (d, 1H), 5.5 (s, 1H), 3.7 (m, 2H), 2.2 (t, J=7 Hz, 2H), 1.9 (m, 4H), 1.5 (m, 4H);

MS (FD) m/e 296 (M$^+$);

UV (EtOH) 275 nm (ε=23066).

Anal. Calcd for C$_{13}$H$_{17}$N$_4$SCl C, 52.60; H, 5.77; N, 18.87. Found: C, 52.85; H, 5.84; N, 19.15.

Example 337

N-[2-(2,6-difluorophenyl)ethyl]-N'-[3-(6-chloro)pyridazinyl]thiourea

A solution of N-[2-(2,6-difluorophenyl)ethyl]-N'-thiocarbamoyl imidazole (1.33 g, 5.0 mmol) and 3-amino-6-chloropyridazine (0.65 g, 5.0 mmol) in N,N-dimethylformamide (20 mL) was stirred at 80° C. for 19 h. The reaction was cooled to room temperature, poured into ethyl acetate, washed with water and brine. The organic layer was concentrated and the residue was purified by HPLC to provide 0.12 g (7.5%) of the titled product:

mp 187°–189° C.;

IR (KBr, cm$^{-1}$) 3199, 3055, 1626, 1593, 1555, 1522, 1469, 1425, 1348,1313, 1263;

$^1$H NMR (300 MHz, DMSO-d$_6$) δ11.2 (m, 1H), 10.9 (s, 1H), 7.9 (d, 1H), 7.6 (d, 1H), 7.3 (m, 1H), 7.1 (m, 2H), 3.9 (m, 2H), 3.0 (t, J=7 Hz, 2H);

MS (FD) m/e 328 (M$^+$);

pKa in (66% DMF) 12.73;

UV (mtOH) 277 nm (ε=20141), 252 nm (ε=12935), 201 nm (ε=17891).

Example 338

N-[2-(2,6-difluorophenyl)ethyl]-N'-[3-(6-methoxy)pyridazinyl]thiourea

A solution of N-[2-(2,6-difluorophenyl)ethyl]-N'-thiocarbamoyl imidazole (0.8 g, 3.0 mmol) and 3-amino-6-methoxy pyridazine (0.4 g, 3.0 mmol) in N,N-dimethylformamide (20 mL) was stirred at 70° C. for 19 h. The reaction was cooled to room temperature, poured into ethyl acetate, washed with water and brine. The organic layer was concentrated and the residue was precipitated with diethyl ether to provide 0.235 g (24%) of the titled product:

mp 193°–196° C.;

IR (KBr, cm$^{-1}$) 3222, 3084, 1628, 1586, 1560, 1531, 1468, 1423, 1356, 1310, 1266;

$^1$H NMR (300 MHz, DMSO-d$_6$) δ11.45 (m, 1H), 10.7 (s, 1H), 7.42 (d, J=10 Hz, 1H), 7.28 (m, 1H), 7.21 (d, J=10 Hz, 1H), 7.0 (t, J=8 Hz, 2H), 3.9 (s, 3H), 3.85 (m, 2H), 3.0 (t, J=7 Hz, 2H);

MS (FD) m/e 324 (M$^+$);

UV (EtOH) 269 nm (ε=18845), 235 nm (ε=10636), 201 nm (ε=16622).

Example 339

N-[2-(2-pyridyl)ethyl]-N'-[3-(6-chloro)pyridazinyl]thiourea

A solution of 1,1'-thiocarbonyldiimidazole (1.83 g, 10.0 mmol) and 3-amino-6-chloro pyridazine (1.3 g, 10.0 mmol) in acetonitrile (100 mL) was stirred at room temperature for 288 h. To this solution was added 2-(2-aminoethyl)pyridine (1.22 g, 10 mmol) and the resultant mixture stirred at room temperature for 48 h. The solvent was removed in vacuo and the residue purified by HPLC to provide 0.300 g (10.0%) of the titled product:

mp 197°–199° C.;

IR (KBr, cm$^{-1}$) 3172, 3045, 1583, 1562, 1511, 1478, 1428, 1345, 1313, 1280;

$^1$H NMR (300 MHz, DMSO-d$_6$) δ11.3 (m, 1H), 10.9 (s, 1H), 8.6 (d, J=5 Hz, 1H), 7.8 (d, J=10 Hz, 1H), 7.7 (m, 1H), 7.55 (d, J=10 Hz, 1H), 7.3 (d, J=8 Hz, 1H), 7.2 (m, 1H), 4.0 (m, 2H), 3.1 (t, j=7 Hz, 2H);

MS (FD) m/e 293 (M$^+$);

pka (66% DMF) is 4.17, 12.32;

UV (EtOH) 275 nm (ε=21715), 270 nm (ε=21836), 221 nm (ε=9867).

Anal. Calcd for C$_{12}$H$_{12}$N$_5$SCl$_2$: C, 49.06; H, 4.12; N, 23.84. Found: C, 48.91; H, 4.14; N, 23.76.

Example 340

N-[2-(2,6-Difluorophenyl)ethyl]-N'-[2-(5-bromo)pyridyl]thiourea

A stirred solution of N-(thioimidazoyl)-2-(2,6-difluorophenyl)ethyl amine (2.67 g, 10 mmol) and 2-amino-5-bromopyridine (1.73 g, 10 mmol) in 1-methyl-2-pyrrolidinone (20 mL) was heated to 90° C. After 16.5 h, the reaction was cooled to room temperature and poured into ethyl acetate. The organic phase was washed with H$_2$O (2×), 1N HCl, H$_2$O and brine. The organic layer was dried over Na$_2$SO$_4$, filtered and concentrated. The solid obtained was purified by recrystallization from 1:1 EtOAc/hexanes to provide 1.6 g (43%) of the titled product. This material was recrystallized again from 70% EtOAc/hexanes to provide 1.16 g of the titled product as a light brown crystalline solid:

mp 174°–175° C.;

IR (KBr, cm$^{-1}$) 3229, 1593, 1558, 1529, 1468, 1265, 1188, 1071, 832;

$^1$H NMR (300 MHZ, DMSO-d$_6$) δ11.20 (s, 1H), 10.68 (s, 1H), 8.11 (s, 1H), 7.95–7.91 (m, 1H), 7.33–7.28 (m, 1H), 7.09–7.01 (m, 3H), 3.83–3.77 (m, 2H), 2.98–2.94 (m, 2H);

MS (FD) m/e 371 (M$^+$), 373 (M+2);

UV (EtOH) 306 nm (ε=12790), 275 nm (ε=22096), 257 nm (ε=14120), 201 nm (ε=17270).

Anal. Calcd for C$_{14}$H$_{12}$BrF$_2$N$_3$S: C, 45.17; H, 3.25; N, 11.29. Found: C, 44.96; H, 3.29; N, 11.21.

Example 341

2-cyanomethyl-3-ethoxypyridine

A solution of thionyl chloride (3.26 g, 27.4 mmol, 2.0 mL) in CH$_2$Cl$_2$ (10 mL) was added dropwise with stirring to a solution of 2-ethoxy-3-hydroxymethylpyridine (3.0 g, 19.6 mmol) in CH$_2$Cl$_2$ (20 mL) at 0° C. The ice bath was removed and the reaction stirred 2 h at RT. The reaction was concentrated in vacuo and redissolved in MeOH (30 mL). Potassium cyanide (3.82 g, 58.7 mmol) was dissolved in H$_2$O (10 mL) and added to the reaction in one amount. The reaction was heated to reflux and stirred for 66 h, then quenched with saturated Na$_2$CO$_3$ solution. The reaction was diluted with H$_2$O and extracted with Et$_2$O (3×). The combined organic extracts were washed with brine, dried over Na$_2$SO$_4$, filtered and concentrated to yield 2.84 g (89%) of the titled product as a brownish oil. A small sample was further purified by flash chromatography (40% EtOAc/hexanes) to provide a clear, colorless oil:

IR (KBr, cm$^{-1}$) 3020, 2988, 2936, 1579, 1450, 1397, 1282, 1122, 1041;

$^1$H NMR (300 MHZ, CDCl$_3$) δ8.17–8.15 (m, 1H), 7.25–7.15 (m, 2H), 4.09 (q, J=7 Hz, 2H), 3.90 (s, 2H), 1.47 (t, J=7 Hz, 3H);

MS (FD) m/e 162 (M+);

UV (EtOH) 278 nm (ε=5241), 220 nm (ε=7490).

Example 342

N-[2-(3-ethoxypyridyl)ethyl]-N'-[2-(5-bromo)pyridyl]thiourea

A solution of 2-cyanomethyl-3-ethoxypyridine (22.03 g, 136 mmol) in EtOH (475 mL) and 5N HCl (3 mL) was treated with PtO$_2$ catalyst (4.5 g) under 60 psi of H$_2$. The reaction was stirred overnight at RT, then filtered. The crude reaction was concentrated and redissolved in H$_2$O and EtOAc. The aqueous layer was made basic with 5N NaOH and extracted with EtOAc. The organic layer was washed with brine, dried on Na$_2$SO$_4$, filtered and concentrated to give 16.89 g of a yellow oil. This crude product was dissolved in 1-methyl-2-pyrrolidinone (175 mL) and N-(thioimidazoyl)-2-amino-5-bromopyridine (36 g, 127 mmol) was added. The reaction was heated to 100° C. and stirred for 68 h. The crude reaction was cooled and poured into EtOAc. The organic layer was washed with H$_2$O (4×), brine, dried on Na$_2$SO$_4$, filtered and concentrated. The resulting solid was again dissolved in EtOAc and extracted with 1N HCl (3×). The acid extracts were stirred with CH$_2$Cl$_2$, made basic with 5N NaOH and extracted with CH$_2$Cl$_2$ (2×). The CH$_2$Cl$_2$ extracts were combined, washed with brine, dried on MgSO$_4$, filtered and concentrated. The crude product was purified by flash chromatography (10% EtOAc/CH$_2$Cl$_2$), followed by trituration with 1:1 EtOAc/hexanes to provide 3.76 g of the titled product (7%) as a white crystalline solid:

mp 170°–172° C.;

$^1$H NMR (300 MHZ, DMSO-d$_6$) δ11.39 (s, 1H), 10.59 (s, 1H), 8.13–8.11 (m, 2H), 7.92–7.87 (m, 1H), 7.30 (d, J=8.1 Hz, 1H), 7.22–7.18 (m, 1H), 7.05 (d, J=8.9 Hz, 1H), 4.05–3.95 (m, 4H), 3.00 (t, J=6.3 Hz, 2H), 1.29 (t, J=6.9 Hz, 3H);

MS (FD) m/e 380 (M+), 382 (M+2);

UV (EtOH) 305 nm (ε=16291), 276 nm (ε=36829).

Example 343

N-[2-(3-ethoxypyridyl)ethyl]-N'-[2-(5-bromo)pyridyl]thiourea hydrochloride

N-[2-(3-ethoxypyridyl)ethyl]-N'-[2-(5-bromo)pyridyl]thiourea (5.17 g, 13.5 mmol) was dissolved in a saturated solution of methanolic HCl (100 mL) with stirring. After complete dissolution, a precipitate started to form. The solution was poured into Et$_2$O (400 mL) with stirring, and the resulting white solid was filtered. The crude product was triturated with 10% MeOH/EtOAc to provide 5.47 g of the titled product (97%) as a white solid:

mp 203°–205° C. (d);

IR (KBr, cm$^{-1}$) 3226, 3007, 2306, 1593, 1565, 1530, 1472, 1290, 1197, 1172;

$^1$H NMR (300 MHZ, DMSO-d$_6$) δ11.24–11.20 (m, 1H), 10.65 (s, 1H), 8.29 (d, J=5.3 Hz, 1H), 8.17 (d, J=2.3 Hz, 1H), 7.96–7.88 (m, 2H), 7.73–7.68 (m, 2H), 7.08 (d, J=8.9 Hz, 1H), 4.10–4.03 (m, 4H), 3.24 (t, J=6.0 Hz, 2H), 1.27 (t, J=6.9 Hz, 3H);

MS (FD) m/e 380 (M$^+$), 382 (M+2);

UV (EtOH) 304 nm (ε=13635), 276 nm (ε=28876).

Anal. Calcd for $C_{15}H_{18}BrClN_4OS$: C, 43.13; H, 4.34; N, 13.41. Found: C, 42.90; H, 4.36; N, 13.11.

Example 344

1-[(2-amino-5-bromopyridyl)thiocarbamoyl]imidazole

A solution of 1,1'-thiocarbonyldiimidazole (17.8 G, 0.1 m) and 2-amino-5-bromopyridine (17.3 g, 0.1 m) in acetonitrile (150 mL) was stirred at room temperature for 2 hours. To this suspension was added the material described below.

Example 345

N-[2-(2-pyridyl)ethyl)]-N'-(2-amino-5-bromopyridyl)thiourea

To the above solution of 1-[(2-amino-5-bromopyridyl)thiocarbamoyl]imidazole was added 2-(2-aminoethyl)pyridine (14.7 g, 0.12 m) stirred at r.t. for 2 hours and at 50° C. 12 hours. The reaction was cooled to room temperature, filtered, washed with acetonitrile. The resultant solid was dissolved in methanol, filtered, hydrogen chloride gas was bubbled into this solution with cooling. Solvents removed under reduced pressure and the resulting residue was recrystallized from methanol ethyl ether to provide 24.8 g (76%) of the titled product as a white solid:

mp 215°–216° C.;

IR (KBr, cm$^{-1}$) 3015, 2576, 1634, multiple peaks between (1633–400);

$^1$H NMR (300 MHz, DMSO-d$_6$) δ11.30 (s, 1H), 10.75 (s, 1H), 10.78 (s,1H), 8.80 (d, 1H), 8.40 (t, 1H), 8.22 (s, 1H), 7.97–8.00 (q, 1H), 7.82–7.90 (d, 1H), 7.80 (t, 1H), 7.10 (d, 1H), 4.10(q,2H), 3.35(t, 2H);

MS (FD) m/e 338 (M$^+$);

UV (EtOH) 305 nm (ε=13565), 274 nm (ε=24201), 201 nm (ε=17628).

Anal. Calcd for $C_{13}H_{14}N_4BrClS$: C, 41.78; H, 3.78; N, 14.99. Found: C, 42.02; H, 3.86; N, 15.16.

Example 346

N-[2-((3-Methoxy)pyridyl)ethyl]-N'-[2-(5-bromo)pyridyl]thiourea hydrochloride

A) Preparation of 2-Hydroxymethyl-3-methoxy pyridine

Potassium hydroxide (41.66 g, 0.744 mol) was ground under nitrogen and stirred in DMSO (130 ml, anhydrous) for 20 min. 3-Hydroxy-2-hydroxymethyl pyridine hydrochloride [Aldrich] (47 g, 0.248 mol) was added and stirred for 30 rain in an ice bath. Methyl iodide (35.2 g, 0.248 mol, 15.43 ml) in DMSO (20 ml) was added dropwise to the solution and then allowed to stir overnight at room temperature. 5N HCl was added to pH 1 and the solution was extracted with dichloromethane (5×500 ml). The aqueous was then basified with 5N NaOH to pH 14 and extracted with dichloromethane (3×500 ml). The organics (base wash) were dried over sodium sulfate, and concentrated leaving tan colored crystals. The solid was recrystallized (50% ethyl acetate/hexanes) providing 10.8 g (32%) of the titled product as light tan crystals:

mp 72° C.;

IR (KBr, cm$^{-1}$) 3080, 1575, 1459, 1424, 1278, 1218, 1066, 809;

$^1$H NMR (300 MHZ, DMSO-d$_6$) δ8.5 (d,J=4.5 Hz,1H), 7.3 (d,J=8.3 Hz,1H), 7.25 (dd,J=8.2,4.6 Hz,1H), 4.77 (t,J=5.74 Hz,1H), 4.48 (d,J=5.6 Hz,2H), 3.77 (s,3H);

MS (FD) m/e 139 (M+);

UV (EtOH) 278 nm (ε=4909), 220 nm (ε=6984).

Anal. Calcd for $C_7H_9NO_2$: C, 60.42; H, 6.52; N, 10.07. Found: C, 60.32; H, 6.54; N, 10.23.

B) Preparation of 2-[(3-methoxy)pyridyl]acetonitrile

Thionylchloride (100 ml) was added dropwise to 2-Hydroxymethyl-3-methoxy pyridine (13.9 g, 0.1 mol) while stirring in an ice bath. After initial fuming subsided, the thionyl chloride was added more rapidly. The solution was then heated to reflux for 2 h. After cooling, the thionyl chloride was removed under reduced pressure leaving brown crystals. The solid was taken up in 190 ml methanol and potassium cyanide (19.4 g, 0.298 mol) dissolved in 80 ml of water was added to the methanolic solution. This solution was heated to reflux and allowed to reflux overnight. The solution was cooled down and 150 ml of saturated sodium carbonate was added and then poured into diethyl ether (500 ml). The solution was extracted 3 more times with 500 ml diethyl ether. The collected organics were washed with brine and saturated sodium bicarbonate. The organics were dried over sodium sulfate and concentrated giving 12.1 g (81.7%) of brown crystalline solid. This solid was used in the reduction without further purification:

mp 71° C.;

IR (KBr, cm$^{-1}$) 3074, 2949, 2253, 1578, 1459, 1286, 1017, 821;

$^1$H NMR (300 MHZ, DMSO-d$_6$) δ8.07 (m,1H), 7.43 (m,1H), 7.35 (m,1H), 4.0 (s,2H), 3.8 (s,3H);

MS (FD) m/e 148 (M+);

UV (EtOH) 278 nm (ε=5407), 219 nm (ε=7435).

Anal. Calcd for $C_8H_8N_2O$: C, 64.85; H, 5.44; N, 18.91. Found: C, 64.62; H, 5.50; N, 19.0.

C) Preparation of 2-Ethylamine-3-methoxypyridine

2-[(3-methoxy)pyridyl]acetonitrile (2.0 g, 13 mmol) in 25 ml ethanol was reduced at room temperature under 60 p.s.i. for 24 h using platinum oxide (0.5 g) and 5N HCl (0.2 ml) as catalyst. The organics were concentrated and then taken up in ethyl acetate and water. 1N NaOH was added to pH 12 and the amine was extracted out (2×300 ml ethyl acetate). The organics were then washed with brine and saturated sodium bicarbonate and then dried over sodium sulfate. The solution is filtered and concentrated giving 1.5 g of oily material. This is used without further purification.

D) Preparation of N-[2-((3-Methoxy)pyridyl)ethyl]-N'-[2-(5-bromo)pyridyl]thiourea Thiocarbonyldiimidazole (5 g, 28 mmol) was taken up in acetonitrile (50 ml, anhydrous) and stirred. 2-Amino-5-bromopyridine [Aldrich] (4.85 g, 28 mmol) and 30 ml acetonitrile was added to the solution. The solution was allowed to stir overnight forming a precipitate. The cream colored solid was filtered off and used in the next reaction without further purification. (6.89 g, 87%)

The cream colored solid (2.88 g, 10.3 mmol) was taken up in 1-methyl-2-pyrrolidinone [Aldrich]. 2-Ethylamine-3-methoxypyridine was added and the solution was heated to 100° C. overnight. The solution was poured into ethyl acetate and washed with water and saturated sodium bicarbonate (3×200 ml). The organics were then dried over sodium sulfate and concentrated. The crude material was purified by flash chromatography on silica gel using 40% ethyl acetate/hexanes, giving 100 mg (3%) of needle-like crystals:

mp 178° C.;

IR (KBr, cm$^{-1}$) 3157, 3037, 1595, 1562, 1534, 1314, 1275, 1178, 1023, 825;

$^1$H NMR (300 MHZ, DMSO-d$_6$) δ11.53 (s,1H), 8.5 (s,1H), 8.17–8.12 (m,2H), 7.68–7.65 (dd, J=8.75, 8.73 Hz, 1H), 4.24–4.18 (m,2H), 3.8 (s,3H), 3.2–3.17 (t, J=6.63 Hz, 2H);

MS (FD) m/e 366 (M+), 368(M+1), 369(M+2);

UV (EtOH) 305 nm (ε=13005), 275 nm (ε=28998)

Anal. Calcd for C$_{14}$H$_{15}$N$_4$OSBr: C, 45.78; H, 4.12; N, 15.25. Found: C, 45.85; H, 4.12; N, 15.12.

E) Preparation of N-[2-((3-Methoxy)pyridyl)ethyl]-N'-[2-(5-bromo)pyridyl]thiourea hydrochloride N-[2-((3-Methoxy)pyridyl)ethyl]-N'-[2-(5-bromo)pyridyl]thiourea (70 mg, 0.02 mmol) was taken up in a solution of methanol saturated with HCl. The solid immediately went into solution and then came back out as a white solid. More of the solid was crashed out with diethyl ether. This solid was filtered providing 65 mg (84%) of the hydrochloride salt.

Example 347

N-(2-(2-Fluoro-6-methoxy)phenethyl)-N'-(2-thiazolyl)thiourea

3-Fluoro-anisole (10 ml, 88 mmol) was dissolved in dry THF (200 ml). The solution was cooled to −750° C. and n-BuLi (52 ml, 105 mmol) was added slowly. The pale yellow solution was stirred at −70° C. for 10 minutes. DMF (20 ml) was added and the solution was warmed to ambient temperature. Toluene (200 ml) was added and the solution was washed with water and evaporated to dryness. The product formed crystals. The aldehyde was transformed into the corresponding titled thiazolyl-thiourea product according to the procedure in Example 151.

$^1$H NMR,CDCl$_3$ δ2.9–3.0 (2H, t) 3.7–3.9 (2H, t) 6.7–6.9 (2H, q, m) 7–7.1 (1H, d,) 7.15–7.3 (1H, q) 7.4 (1H, d).

Example 348

Cis-(D,L)-2-phenylcyclopropylamine

Styrene (100 ml, 873 mmol), CuI (10 mg, 0.05 mmol) and Pd (OAc) 2 (10 mg, 0.045 mmol) in 1,2-dichloroethane (100 ml) was heated to reflux. Ethyl diazoacetate (50 ml, 475 mmol) in styrene (100 ml, 873 mmol) was added over 30 minutes. The solution was refluxed for an additional 5 minutes. The solution was cooled and filtered through a short column of alumina which was eluted with ethyl acetate/hexane (1:9). The solvents including styrene were evaporated. The residual oil contained a cis-trans mixture (3:7). The oil was dissolved in methanol (200 ml), and potassium hydroxide (30 g, 535 mmol) in water (50 ml) was added. The solution was refluxed for 2 hours. The solution was cooled and diluted with toluene (100 ml) and water (100 ml).

The water-phase was separated and acidified with hydrochloric acid. The solution was extracted with toluene. The organic phase was dried with sodium sulphate, filtered and evaporated, yielding a pale brown solid. The solid (70 g, 430 mmol) was dissolved in acetone (400 ml) with mechanical stirring under an atmosphere of N$_2$-gas. Triethylamine (70 ml, 502 mmol) was added. The solution was cooled to 5° C. and ethyl chloroformate (41 ml, 430 mmol) was added during 20 minutes. The solution was stirred for an additional 5 minutes. Sodium azide (30 g, 460 mmol) in water (100 ml) was added and the solution was stirred for 30 minutes. Toluene (400 ml) was added and a thick, white precipitate formed. The solution was decanted to remove the precipitate and dried with sodium sulphate (50 g). The solution was evaporated to ¼ of the original volume. The solution was diluted with 1,2-dichloro-ethane (400 ml) and was refluxed for 3 hours with evolution of nitrogen gas.

To the solution was added a mixture of hydrochloric acid (conc. aq.) (100 ml), water (100 ml) and dioxane (200 ml). The solution was refluxed for 3 hours with evolution of CO$_2$ gas. The solution was diluted with water (200 ml), the water-phase was separated and washed with 1,2-dichloroethane, basified with ammonia (conc. aq.) and extracted with dichloromethane (3×100 ml). The organic-phase was washed with water (100 ml), dried with sodium-sulphate, filtered and evaporated.

50 g of the residual oil was separated on 1000 ml silica-gel, by elution with ethyl acetate, the product (cis) is the faster-eluting component. The pure cis-fractions were evaporated to yield an oil (14 g).

$^1$H-NMR CDCl$_3$ δ ppm 0.8–0.9 (1H, CH$_2$, m) 1.1–1.2 (1H, CH$_2$, m) 2.–2.1 (1H, PhCH, q) 2.6–2.7 (1H, C HNH$_2$m.) 7.1–7.4 (5H, Ph.).

Example 349

N-(cis-(D,L)-2-thenylcyclopropyl)-N'-(2-thiazolyl)thiourea

The product cis-(D,L)-2-phenylcyclopropylamine from Example 348 was transformed into the titled product according to the procedure in Example 151.

$^1$H-NMR CDCl$_3$ δ ppm 1.2–1.3 (1H, CH$_2$, m) 1.5–1.6 (1H, m) 2.4–2.5 (1H, q, PhCH) 3.6–3.7 (1H, m) 6.6–6.7 (1H, d) 6.8–6.9 (1H, d) 7.2–7.4 (5H, m)

Example 350

N-(cic-(D,L)-2-phenylcyclobutyl)-N'-(2-thiazolyl)thiourea

A cis/trans mixture of 2-phenylcyclobutylamine (C. Beard, A. Burger, JOC, 27, 1647 (1962)) (0.150 g, 1 mmol) was condensed with 165 mg of the product of Example 103 according to the procedure of Example 105. The solution was put into a refrigerator (−10° C.) over night and the crystals were collected on a filter and washed with CH$_3$CN. The stereochemistry was determined with NOE-difference NMR. The crystals were pure cis.

$^1$H-NMR CDCl$_3$ δ ppm 2.2–2.4 (3H, m) 2.6–2.7 (1H, m) 3.9–4.0 (1H, q) 5.1–5.2 (1H, q) 6.6–6.7 (1H, d, thiazole) 6.8–6.9 (1H, d, thiazole) 7.3–7.5 (5H, m, Ph).

Example 351

N-(cis=(D,L)-2-methyl-2-phenyl-cyclopropyl)-N'-(4-chlorophenyl)thiourea a-Methylstyrene (Aldrich) was transformed into the corresponding amine as a cis-trans mixture according to the procedure of Example 348. The amine (300 mg, 2.04 mmol) and 4-chloro-phenylisothiocyanate were refluxed in $CH_3CN$ (5 ml) for 60 minutes. The solution was evaporated and final purification was made by flash-chromatography on silica-gel by elution with ethyl acetate/n-hexane (1:4). The collected fractions were pure cis as determined by NOE-difference NMR.

$^1$H-NMR $CDCl_3$ δ1.1–1.2 (2H, m, $CH_2$) 1.4–1.5 (3H, s, C$H_3$), 3.2–3.4 (1H, m, CHN), 6.4–6.5 (1H, b.s., NH), 7.0–7.1 (2H, Ph), 7.3–7.5 (7H, s, +m, Ph), 7.9–8.1 (1H, b.s., NH).

Example 352

N-(2-(2,6-difluorophenyl)ethyl)-N'-(2-pyrazinyl)-thiourea 2,6-Difluorophenethylamine (1.0 g, 6.4 mmol), 2-aminopyrazine (0.61 g, 6.4 mmol) and N,N-thiocarbonyl-diimidazole (1.13 g, 6.4 mmol) were condensed according to the procedure of Example 93 to give the titled compound as crystals.

$^1$H-NMR $CDCl_3$ δ ppm 3.1–3.2 (2H, m, PhC$H_2$), 3.9–4.0 (2H, t, C$H_2$N), 6.8–6.9 (2H, t, Ph), 7.1–7.3 (1H, m, Ph), 7.9–8.0 (1H, s, pyr), 8.1–8.2 (1H, d, pyr), 8.3–8.4 (1H, s, pyr), 9.3–9.4 (1H, b.s., NH), 11.0–11.2 (1H, b.s., NH).

Example 353

N-(2-(2,6-difluoro-3-carboxamidomethyl phenyl)ethyl)-N'-(2-(5-bromopyridyl)-thiourea 2,6-Difluorobenzaldehyde (10 g, 70.4 mmol), ethylene glycol (20 ml), triethyl-orthoformate (10 ml) and para-toluene sulphonic acid in 1,2-dichloroethane were heated to 80° C. for 2 hours. The solution was neutralized with sodium hydrogen carbonate, washed with water, dried with sodium sulfate, filtered and evaporated. The residual oil was dissolved in tetrahydrofurane (700 ml) under nitrogen-atmosphere. The solution was stirred and cooled to −70° C. and n-BuLi (48 ml, 1.6M) was added slowly. The solution was stirred for 20 minutes. Dry-ice (20 g, 455 mmol) was added as quickly as possible (foaming).

The solution was slowly brought up to ambient temperature. Water was added and the solution was washed with ethyl acetate, acidified with acetic acid and extracted with ethyl acetate.

The organic phase was dried with sodium sulfate, filtered and evaporated. 1 g of the residual solid (4.35 mmol) and N,N-diisopropylamine (2.0 ml) were dissolved in dichloromethane (50 ml) and the solution was cooled to 0° C.

Thionylchloride (0.50 ml, 6.9 mmol) was added and the solution was slowly heated to ambient temperature. Methylamine (3 ml) was added. The solution was stirred for 30 minutes and was washed with water, dried with sodium sulfate, filtered and evaporated.

The residue was dissolved in a mixture of water and dioxane (1:2, 20 ml) and para-toluene sulphonic acid (0.5 g, 2.63 mmol) was added. The solution was stirred and heated to 60° C. for 2 hours. The solution was neutralized with sodium hydrogen carbonate, extracted with ethyl acetate, dried with sodium sulfate, filtered and evaporated.

The residue was dissolved in toluene and benzyloxycarbonylmethyl triphenyl-phosphorane (1.5 g, 3.7 g) was added. The solution was stirred for 30 minutes at 50° C. The solution was put onto a silica-gel column. The column was eluted with ethyl acetate-hexane (1:2) and the collected fractions were evaporated. 0.15 g of the residue was hydrogenated in methanol (50 ml) and acetic acid (5 ml) with Pd/C (10 %, 100 mg) and hydrogen gas, using a Parr apparatus at 1.5 bar for 1 hour.

The solution was filtered through Celite and evaporated. A part of the residue (50 mg, 0.26 mmol) was dissolved in acetone at 0° C.

Triethylamine (50 ml, 0.36 mmol) was added followed by ethyl chloroformate (30 ml, 0.32 mmol). The solution was stirred for 15 minutes and sodium azide (30 mg, 0.46 mmol) in water (2 ml) was added. The solution was stirred for 15 minutes, diluted with ethyl acetate, washed with water, dried with sodium sulfate, filtered and evaporated.

The residue was dissolved in toluene (20 ml) and was stirred and heated at 90° C. for 1 hour. The solution was evaporated and dissolved in a dioxane-water-hydrochloric acid (conc. aq.) mixture (1:3:1). The solution was stirred at ambient temperature for 20 minutes. The solution was evaporated and the residual 2-(2,6-difluoro-3-carboxamidomethyl phenyl)ethylamine hydrochloride was condensed with 1-(2-amino-5-bromopyridyl)-1'-(imidazolyl)thiocarbonyl using the procedure of Example 94.

The reaction mixture was evaporated and the residue was purified by flash chromatography on silica-gel by elution with ethyl acetate-hexane (1:1). Evaporation of the collected fractions yielded the titled product.

$^1$H-NMR $CDCl_3$ δ ppm 2.9–3.0 (3H, s, $CH_3$), 3.1–3.2 (2H, t, PhC$H_2$), 4.0–4.1 (2H, t, C$H_2$N), 6.8–6.9 (1H, d), 6.9–7.0 (2H, t), 7.7–7.8 (2H, m), 8.0–8.1 (1H, s).

Example 354

N-(2-(3-acetamidomethyl-2,6-difluorophenyl)-ethyl)-N'-(2-(5-bromopyridyl))-thiourea Under an atmosphere of nitrogen-gas, 2,4-difluorobenzonitrile (Aldrich) (4.6 g, 33 mmol) was dissolved in tetrahydrofurane (200 ml) with stirring under an atmosphere of nitrogen gas. The solution was cooled to −75° C. and lithium-diisopropylamide (25 ml, 1.5M solution) was added. The solution was stirred for 15 minutes and dimethylformamide (10 ml) was added. The cooling was withdrawn and the solution was diluted with toluene (200 ml), washed with water, dried with sodium sulfate, filtered and evaporated. The residue (4.76 g, 28.5 mmol) was dissolved in 250 ml toluene and benzyloxycarbonylmethyl triphenyl-phosphorate (14 g, 34 mmol) was added.

The solution was stirred for 40 minutes at 35° C. (slightly exothermic reaction), and then put onto a column of silica gel. The column was eluted with ethyl acetate-hexane 1:4, and the collected fractions were evaporated. A small part of the residue (0.5 g) was dissolved in methanol (50 ml) and acetic acid (6 ml) and 5%—Pd/C (300 mg) was added. The mixture was hydrogenated in a Parr apparatus at 1.5 bar for 1 hour.

The solution was filtered through celite and evaporated. The residue was dissolved in acetic anhydride and the solution was stirred and heated to 50° C. for 20 minutes. Excess reagent was evaporated and the residue was dissolved in water. The solution was heated to 60° C. for 20 minutes under stirring. The residue (0.29 g, 1.14 mmol) was dissolved in acetone at 0° C.

Triethylamine (0.315 ml, 2.3 mmol) was added, followed by ethyl chloroformate (0.16 ml, 1.7 mmol). The solution was stirred for 15 minutes and sodium azide (220 mg, 3.3 mmol) in water (2 ml) was added. The solution was stirred for 15 minutes, diluted with ethyl acetate, washed with water, dried with sodium sulfate, filtered and evaporated.

The residue was dissolved in toluene (20 ml) and was stirred and heated at 90° C. for 1 hour. The solution was evaporated and dissolved in a dioxane-water-hydrochloric acid (conc. aq.) mixture (50:10:1, 50 ml). The solution was stirred at ambient temperature for 20 minutes. The solution was evaporated and the residual amine-hydrochloride was condensed with 1-(2-amino-5-bromopyridyl)-1'-(imidazolyl)thiocarbonyl using the procedure of Example 94.

The reaction-mixture was evaporated and the residue was purified by flash chromatography on silica-gel by elution with ethyl acetate-hexane (1:1). The collected fractions were evaporated to yield the titled product as crystals.

$^1$H-NMR CDCl$_3$ δ ppm 1.9–2.0 (3H, s, C$\underline{H}_3$CON), 3.0–3.1 (2H, b.s., PhC$\underline{H}_2$CH$_2$N), 3.9–4.1 (2H, b.s., PhCH$_2$C$\underline{H}_2$N), 4.3–4.4 (2H, s, PhC$\underline{H}_2$N), 6.8–6.9 (2H, m), 7.2–7.4 (1H, ml, 7.7–7.8 (1H, d), 8.1–8.2 (1H, s).

Example 355

N-(4-methyl-3-pentenyl)-N'-(4-methyl-2-thiazolyl)thiourea

4-Methyl-3-pentenylamine and an activated derivative of 2-amino-4-methylthiazole, i.e. 1-(2-amino-4-methylthiazole)-1'-imidazole thiocarbonyl, were condensed according to the procedures of Example 105 to give the titled product.

Mp.: 164.5°–165.5° C.

Analyses: Calculated C 51.73, H 6.71, N 16.45; Found C 52.0, H 6.9, N 16.7.

$^1$H-NMR (CDCl$_3$ d): 1.65 (s, 3H), 1.73 (d, 3H), 2.29 (d, 3H), 2.40 (q, 2H), 3.70–3.78 (m, 2H), 5.16–5.22 (m, 1H), 6.36 (q, 1H), 10.14 (broad s, 1H), 10.90 (broad s, 1H).

$^{13}$C NMR (CDCl$_3$d): 17.16, 17.93, 25.83, 27.28, 45.69, 105.04, 120.53, 134.84, 147.99, 160.79, 177.28.

Example 356

N-(2-(2,6-difluoro)-phenethyl)-N'-(2-benzimidazolyl)thiourea 2,6-Difluorphenetylamine and 2-aminobenzimidazole were reacted according to the procedures of Examples 93 and 94, using 2-aminobenzimidazole instead of 2-aminothiazole, to give the titled product. p Mp: 195°–7° C. (dec)

$^1$H-NMR (DMSO-d$_6$ d): 3.16 (t, 2H), 4.02 (q, 2H), 7.14–7.24 (m, 4H), 7.43–7.49 (m, 3H), 11.13 (broad s, 1H), 11.40 (broad s, 1H).

Example 357

N-(2-(3-hydroxy)-phenethyl)-N'-(5-bromo-2-pyridinyl)thiourea

3-Hydroxyphenethylamine and 5-bromo-2-aminopyridine were reacted according to the procedures of Examples 93 and 94, using 4-bromo-2-aminopyridine instead of 2-aminothiazole, to give the titled product.

Yield: 35%.

Mp: 176.5°–178.0° C.

$^1$H-NMR (DMSO-d$_6$ d): 2.95 (t, 2H), 3.90 (q, 2H), 6.73–6.85 (m, 3H), 7.20–7.27 (m, 2H), 8.08 (dd, 1H), 8.32 (d, 1H), 9.49 (s, 1H), 10.84 (s, H), 11.33 (t, 1H).

$^{13}$C-NMR (DMSO-d$_6$ d): 34.01, 46.30, 111.70, 113.26, 114.41, 115.70, 119.32, 129.35, 140.41, 141.29, 145.79, 152.29, 157.34, 179.07.

Example 358

N-(2-(1-methyl)-2-pyrrolylethyl)-N'(5-chloro-2-pyridinyl)thiourea 2-(Aminoethyl)-1-methylpyrrole and an isothiocyanate of 5-chloro-2-aminopyridine were condensed analogous to the procedures described in Example 105, to give the titled product.

Yield: 78%.

Mp: 169.5°–170.0° C.

$^1$H-NMR (DMSO-d$_6$ d): 3.01 (t, 2H), 3.67 (s, 3H), 3.93 (q, 2H), 6.00–6.02 (m, 2H), 6.74 (s, 1H), 7.32 (d, 1H), 7.97 (dd, 1H), 8.27 (d, 1H), 10.76 (s, 1H), 11.36 (broad s, 1H).

$^{13}$C-NMR (DMSO-d$_6$ d): 24.97, 33.19, 44.37, 106.22, 106.39, 114.02, 121.58, 123.70, 129.32, 138.70, 143.61, 152.05, 179.31.

Example 359

N-(2-(3-Methyl)phenethyl)-N'-(2-thiazolyl)thiourea (3-Methyl-phenyl)acetic acid was reduced with lithium aluminum hydride in tetrahydrofurane under reflux to 2-(3-methyl-phenyl)ethanol, which was further transformed to 2-(3-methyl-phenyl)ethylamine by the procedure described in Example 106. Condensation of this amine with the product of Example 103 and using the procedure described in Example 105, gave the titled product.

$^{13}$C-NMR (250 MHz, CDCl$_3$): δ178, 162, 138, 137, 137, 130, 128, 127, 126, 102, 47, 35, 22.

Mp: 145°–146° C.

Example 360

N-(2-(2-Ethoxy)phenethyl)-N'-(2(4-methyl)thiazolyl)thiourea

In a manner analogous to Example 105, 2-(2-ethoxyphenyl)ethylamine was condensed with 1-(2-amino-4-methylthiazolyl)-1'-imidazole thiocarbonyl, which was made in a similar way as described in Example 103, to give the titled product.

$^1$H-NMR (250 MHz, DMSO): δ7.32–6.73 (m, 5H, phenyl, thiazole), 4.09 (q, 2H, OCH$_2$CH$_3$), 3.86 (q, 2H, CH$_2$NH), 2.97 (t, 2H, Ph—C$\underline{H}_2$), 2.25 (s, 3H, thiazole-CH$_3$), 1.43 (t, 3H, OCH$_2$C$\underline{H}_3$).

$^{13}$C-NMR (250 MHz, DMSO): δ176, 162, 157, 130, 128, 127, 120, 112, 107, 106, 63, 44, 29, 17, 15.

Mp: 188°–189° C.

Example 361

N-(2-(3-Ethoxy)phenethyl)-N'-(2-thiazolyl)thiourea

3-Hydroxybenzaldehyde (3.0 g, 24.6 mmol), ethyl iodide (5.9 ml, 73.8 mmol) and $K_2CO_3$ (3.4 g, 24.6 mmol) in 50 ml of acetone was stirred at +40° C. for 6 h and at RT overnight. The mixture was filtered and evaporated. The product was purified by silica gel column chromatography (EtOAc/petroleum ether 15:100) to give 3-ethoxybenzaldehyde.

Yield 2.91 g (79%).

$^1$H-NMR (250 MHz, $CDCl_3$): 9.97 (s, 1H, CHO), 7.45–7.14 (m, 4H, phenyl), 4.10 (q, 2H, $CH_2CH_3$), 1.44 (t, 3H, $CH_2CH_3$).

By using the procedure of Example 151, 3-ethoxybenzaldehyde was transformed to 2-(3-ethoxyphenyl)ethylamine, which was reacted with the product of Example 103, following the procedure of Example 105 to give the titled product.

$^1$H-NMR (250 MHz, DMSO):δ7.60 (d, 1H, thiazole), 7.30–6.93 (m, 4H, phenyl), 4.08 (q, 2H, $OCH2CH_3$), 3.87 (q, 2H, $CH_2$—NH), 2.96 (t, 2H, phenyl-$CH_2$), 1.42 (t, 3H, $OCH_2\underline{CH}_3$).

Mp: 169°–170° C.

Example 362

N-(2-(2-Ethoxy-6-fluoro)phenethyl)-N'-(2-thiaozolyl)thiourea 1) 3-Fluorophenol (20.0 g, 178.4 mmol), ethyl iodide (83.5 g, 535.2 mmol) and $K_2CO_3$ (49.3 g, 356.8 mmol) in 250 ml of acetone were stirred at 50° C. overnight. The mixture was filtered and evaporated to give 1-ethoxy-3-fluorobenzene.

Yield 19.84 g (79%).

$^1$H-NMR (250 MHz, $CDCl_3$): δ7.20 (q, 1H, phenyl), 6.69–6.57 (m, 3H, phenyl), 4.00 (q, 2H, $CH_2CH_3$), 1.40 (t, 3H, $CH_2CH_3$).

2) 1.6M Butyl lithium in hexane (24 ml, 38.4 mmol) was added slowly (0.5 h) to a solution of 1-ethoxy-3-fluorobenzene (5.0 g, 35.7 mmol) in 100 ml of dry THF at –65° C. under nitrogen. The solution was stirred at –65° C. for 25 min. DMF (5.22 g, 71.4 mmol) was added dropwise to the solution. The mixture was allowed to warm to room temperature. 300 ml of ice was poured to this mixture and it was extracted with diethyl ether. Diethyl ether was washed with brine, dried over $Na_2SO_4$ and evaporated. The product was purified by silica gel column chromatography (EtOAc/petroleum ether 10:100) to give 2-ethoxy-6-fluorobenzaldehyde.

Yield: 3.69 g (61%).

$^1$H-NMR (250 MHz, $CDCl_3$): δ7.52–7.40, 6.80–6.64 (m, 3H, phenyl), 4.18 (q, 2H, $CH_2CH_3$), 1.50 (t, 3H, $CH_2CH_3$).

$^{13}$C-NMR (250 MHz, $CDCl_3$): 5188, 165, 161, 136, 109, 108, 65, 14.

3) Following the procedure of Example 151, this aldehyde was transformed to 2-(2-ethoxy-6-fluorophenyl)ethylamine, which was condensed with the product of Example 103, using the procedure of Example 105 to give the titled product.

$^1$H-NMR (250 MHz, DMSO): δ7.32–6.72 (m, 5H, phenyl, thiazole), 4.00 (q, 2H, $CH_2CH_3$), 3.78 (q, 2H, $CH_2$—NH), 2.92 (t, phenyl-$CH_2$), 1.33 (t, 3H, $CH_2CH_3$).

Example 363

N-(2-(3-Isopropoxy)phenethyl)-N'-(2-thiazolyl)thiourea

3-Isopropoxybenzaldehyde was prepared from 3-hydroxybenzaldehyde and isopropyl iodide analogous to the procedure described in Example 361. By using the procedure of Example 151 this aldehyde was transformed to 2-(3-isopropoxyphenyl)ethylamine, which was reacted with the product of Example 103, following the procedure of Example 105 to give the titled product.

$^1$H-NMR (250 MHz, DMSO): δ7.44–6.84 (m, 6H, phenyl, thiazole), 4.69–4.64 (m, 1H, isopropoxy-CH), 3.87 (q, 2H, $CH_2NH$), 2.96 (t, 2H, phenyl-$CH_2$), 1.36–1.32 (m, 6H, $2CH_3$).

Example 364

N-(2-(5-Bromo-2-ethoxy)phenethyl-N'-(2-thiazolyl)thiourea 1) 5-Bromo-2-hydroxybenzylalcohol (5.0 g, 24.6 mmol), ethyl iodide (11.5 g, 73.8 mmol) and $K_2CO_3$ (3.4 g, 24.6 mmol) in 50 ml of acetone was stirred at +50° C. overnight. The mixture was filtered and evaporated. The product was purified by silica gel column chromatography (EtOAc/petroleum ether 30:100) to give 5-bromo-2-ethoxybenzyl alcohol.

Yield: 5.24 g (92%).

$^1$H-NMR (250 MHz, $CDCl_3$): δ7.42–7.31 (m, 2H, phenyl), 6.73 (d, 1H, phenyl), 4.67 (d, 2H, $\underline{CH}_2$—OH), 4.07 (q, 2H, $\underline{CH}_2CH_3$), 1.60 (s, 1H, OH), 1.43 (t, 3H, $CH_2\underline{CH}_3$).

2) 5-Bromo-2-ethoxybenzyl alcohol (2.78 g, 12.0 mmol) and pyridinium dichromate (4.51 g, 12.0 mmol) in 120 ml of $CH_2Cl_2$ was stirred at RT for 6 h. The mixture was filtered, washed with $H_2O$, 0.5 N HCl and brine and dried over $Na_2SO_4$. The product was purified by silica gel column chromatography (EtOAc/petroleum ether 10:100) to give 5-bromo-2-ethoxybenzaldehyde.

Yield: 2.33 g (85%).

$^1$H-NMR (250 MHz, $CDCl_3$): δ10.4 (s, 1H, CHO), 7.91 (d, 1H, phenyl), 7.60 (dd, 1H, phenyl), 6.88 (d, 1H, phenyl), 4.14 (q, 2H, $CH_2CH_3$), 1.51 (t, 3H, $CH_2CH_3$).

3) Following the procedure of Example 151, the aldehyde was transformed to 2-(5-bromo-2-ethoxyphenyl)ethylamine, which was condensed with the product of Example 103, using the procedure of Example 105, to give the titled product.

$^1$H-NMR (250 MHz, DMSO): δ7.10–6.62 (m, 5H, phenyl, thiazole), 3.73 (q, 2H, $CH_2CH_3$), 3.52 (q, 2H, $CH_2NH$), 2.62 (t, 2H, phenyl-$CH_2$), 1.07 (t, 3H, $CH_2CH_3$).

Example 365

N-(2-(2,5-Dimethoxy)phenethyl)-N'-(2-pyridyl)thiourea 2,5-Dimethoxy phenethylamine (0.3 6 g, 2.0 mmol) in 7 ml of DMF was added to a solution of 1,1-thiocarbonyldiimidazole (0.36 g, 2.0 mmol) in 7 ml of DMF at 0° C. After 5 minutes 2-aminopyridine (0.19 g, 2.0 mmol) in 7 ml of DMF was added at 0° C.

This mixture was refluxed at 150° C. for 4 hours. After cooling to room temperature it was poured into ice-water and extracted with diethyl ether, dried over $Na_2SO_4$ and the solvent was evaporated. The product was purified by silica gel column chromatography (EtOAc/petroleum ether 15:100).

Yield: 0.24 g (39%).

$^1$H-NMR (250 MHz, CDCl$_3$): δ8.41 (broad s, 1H, NH), 8.04 (d, 1H, pyridine), 7.61 (t, 1H, pyridine), 6.94–6.67 (m, 5H, phenyl, pyridine), 4.03 (q, 2H, CH$_2$NH), 3.78 (s, 3H, CH$_3$O), 3.73 (s, 3H, CH$_3$O), 3.00 (t, 2H, phenyl-CH$_2$).

Example 366

N-(2-(2-Ethoxy)phenethyl)-N'-(2-(5-bromo)pyridyl)thiourea

In a manner analogous to Example 151, 2-ethoxy phenethylamine was obtained from 2-ethoxybenzaldehyde.

2-Ethoxy phenethylamine (1.1 g, 6.7 mmol) in 20 ml of acetonitrile was added slowly to a mixture of 1,1-thiocarbonyldiimidazole (1.32 g, 7.4 mmol) in 20 ml of acetonitrile at 0° C. The mixture was warmed to RT and evaporated. 2-Amino-5-bromo-pyridine (1.63 g, 9.4 mmol) and this crude reaction mixture in 30 ml of DMF were refluxed for 6 h at 140° C. After cooling to room temperature the reaction mixture was poured into ice-water and extracted with diethyl ether, dried over Na$_2$SO$_4$ and the solvent was evaporated. The product was purified by silica gel column chromatography (EtOAc/petroleum ether 15/100).

$^1$H-NMR (250 MHz, CDCl$_3$) δ8.73 (broad s, 1H, NH), 8.00 (d, 1H, pyridine), 7.68 (dd, 1H, pyridine), 7.26–7.16 (m, 2H, phenyl), 6.96–6.82 (m, 2H, phenyl), 6.68 (d, 1H, pyridine), 4.03 (q, 2H, CH$_2$CH$_3$), 4.03 (q, 2H, CH$_2$NH), 3.02, (t, 2H, phenyl-CH$_2$), 1.42 (t, 3H, CH$_2$CH$_3$).

$^{13}$C-NMR (250 MHz, CDCl$_3$) δ179, 157, 152, 146, 141, 131, 128, 127, 120, 113, 112, 111, 63, 46, 30, 15.

Example 367

N-(2-(2-Ethoxy-6-fluoro)phenethyl)-N'-(2-pyridyl)thiourea

The starting material 2-(2-ethoxy-6-fluorophenyl)ethylamine was prepared as described in Example 362. Following the condensation procedure described in Example 366, and using 2-aminopyridine instead of 2-amino-5-bromopyridine, the titled product resulted.

$^1$H-NMR (250 MHz, CDCl$_3$) δ8.00 (d, 1H, pyridine), 7.58 (t, 1H, pyridine), 7.14 (q, 1H, pyridine), 6.91–6.59 (m, 4H, phenyl, pyridine), 3.95 (q, 2H, CH$_2$CH$_3$), 3.95 (q, 2H, CH$_2$—NH), 3.09 (t, 2H, phenyl-CH$_2$), 1.39 (t, 3H, CH$_2$CH$_3$).

$^{13}$C-NMR (250 MHz, CDCl$_3$) δ179, 164, 153, 145, 138, 128, 128, 117, 112, 108, 107, 107, 64, 45, 22, 15.

Example 368

N-2-(2-Methoxy)phenethyl)-N'-(2-thiazolyl)methylthioether

Methyl iodide (0.425 g, 3.0 mmol) was added to a solution of N-(2-(2-methoxy)phenethyl)-N'-(2-thiazolyl)thiourea, (Example 94), (0.3 g 1.0 mmol) in 15 ml of DMF. The mixture was stirred at RT for 8 h. Methyl iodide was evaporated and the mixture was poured to ice, extracted with methylene chloride, dried over Na$_2$SO$_4$ and evaporated. The product was purified by silica gel column chromatography (EtOAc/petroleum ether 10:100).

$^1$H-NMR (250 MHz, CDCl$_3$): δ7.25 (d, 1H, thiazole), 7.24–7.16 (m, 2H, phenyl), 6.92–6.81 (m, 2H, phenyl), 6.70 (d, 1H, thiazole), 3.79 (s, 3H, CH$_3$O), 3.57 (q, 2H, CH$_2$NH), 2.95 (t, 2H, phenyl-CH$_2$), 2,46, (s, 3H, SCH$_3$).

$^{13}$C-NMR (250 MHz, CDCl$_3$): δ173, 162, 157, 137, 130, 127, 126, 120, 111, 110, 55, 43, 30, 13.

Example 369

N-(2-(2-Ethoxy-6-fluoro)phenethyl)-N'-(2-(5-methyl)pyridyl)thiourea

The starting material 2-(2-ethoxy-6-fluorophenyl)ethylamine was prepared as described in Example 362. Following the condensation procedure described in Example 366 and using 2-amino-5-methylpyridine instead of 2-amino-5-bromopyridine, the titled product resulted.

$^1$H-NMR (250 MHz, CDCl$_3$): δ8.65 (broad s, 1H, NH), 7.83 (s, 1H, pyridine), 7.41 (d, 1H, pyridine), 7.22–7.05 (q, 1H, phenyl), 6.73–6.58 (m, 3H, phenyl, pyridine), 3.98 (q, 2H, CH$_2$CH$_3$), 3.98 (q, 2H, CH$_2$NH), 3.07 (t, 2H, phenyl-CH$_2$), 2.25 (s, 3H, CH$_3$), 1.40 (t, 3H, CH$_2$CH$_3$).

$^{13}$C-NMR (250 MHz, CDCl$_3$): δ179, 168, 152, 145, 139, 127, 127, 126, 111, 108, 108, 107, 63, 44, 22, 17, 14.

Example 370

N-Phenethyl-N'-(2-(5-chloro)pyridyl)thiourea

The product from example 374 (0.3 g, 1.76 mmol) and phenethylamine (0.22 ml, 1.76 mmol) in 8 ml of acetonitrile was stirred at RT for 0.5 h. The mixture was filtered. The precipitate was dried and recrystallized from acetonitrile.

Mp: 152°–153° C.

$^1$H-NMR (250 MHz, DMSO): δ8.20 (d, 1H, pyridine), 7.98 (dd, 1H, pyridine), 7.45–7.40 (m, 5H, phenyl), 7.27 (d, 1H, pyridine), 3.94 (q, 2H, CH$_2$NH), 3.04 (t, 2H, phenyl-CH$_2$).

$^{13}$C-NMR (250 MHz, DMSO): δ179, 152, 143, 139, 139, 129, 128, 126, 124, 114, 46, 34.

Example 371

N-(cis-(D,L)-2-Phenylcyclopropyl)-N'-(2-pyridyl)thiourea cis-(D,L)-2-Phenylcyclopropylamine (Example 348) and 2-aminopyridine were reacted according to the procedures of Examples 93 and 94, using 2-aminopyridine instead of 2-aminothiazole, to give the titled product.

$^1$H-NMR: 1.19–1.27 (m, 1H), 1.45–1.55 (m, 1H), 2.50 (q, 1H), 3.67–3.78 (m, 1H), 6.73–6.78 (m, 2H), 7.27–7.34 (m, 5H), 7.41–7.53 (m, 2H), 1.08 (broad s, 1H).

$^{13}$C-NMR: 12.4, 21.9, 34.6, 111.8, 117.3, 126.5, 128.2, 129.1, 136.5, 138.2, 145.1, 153.0, 180.3.

Mp: 184.5°–186.0° C.

Example 372

N-(5-Chloro-2-pyridyl)-N'-(cis-(D,L)-2-phenylcyclopropyl)thiourea cis-(D,L)-2-Phenylcyclopropylamine (Example 348) and an activated derivative of 2-amino-5-chloropyridine, i.e. 1-(2-amino-5-chloropyridine)-1'-imidazole-thiocarbonyl, were condensed using the procedures of Example 105 to give the titled product.

¹H-NMR (CDCl₃): 1.19–1.26 (m, 1H), 1.46–1.55 (m, 1H), 2.51 (q, 1H), 3.64–3.74 (m, 1H), 6.74 (dd, 1H), 7.30–7.40 (m, 6H), 7.47 (dd, 1H), 9.2 (broad s, 1H), 10.9 (broad s, 1H).

¹³C-NMR (CDCl₃): 12.4, 22.0, 34.7, 112.7, 124.7, 126.8, 128.4, 129.2, 136.5, 138.3, 143.9, 151.1, 180.2.

Mp: 194°–195.5° C.

Example 373

N-(5-Bromo-2-pyridyl)-N'-(cis-(D,L)-2-phenylcyclopropyl)thiourea cis-(D,L)-2-Phenylcyclopropylamine (Example 348) and 2-amino-5-bromopyridine were reacted according to the procedures of Examples 93 and 94, using 2-amino-5-bromopyridine instead of 2-aminothiazole, to give the titled product.

¹H-NMR (CDCl₃): 1.19–1.26 (m, 1H), 1.47–1.55 (m, 1H), 2.52 (q, 1H), 3.66–3.75 (m, 1H), 6.66 (dd, 1H), 7.27–7.41 (m, 5H), 7.47 (d, 1H), 7.60 (dd, 1H), 8.98 (broad s, 1H), 10.88 (broad s, 1H).

¹³C-NMR (CDCl₃): 12.4, 22.0, 34.7, 112.3, 113.1, 126.8, 128.4, 129.2, 136.5, 140.9, 146.2, 151.3, 180.2.

Mp: 204°–205° C.

Anal. calcd. for $C_{15}H_{14}BrN_3S$: C, 51.7; H, 4.05; N, 12.07. Found C, 51.5; H, 4.0; N, 12.0.

Example 374

5-Chloropyrid-2-ylisothiocyanate

2-Amino-5-chloropyridine (10.28 g) was added in portions, with stirring, over a period of 25 minutes to a solution of thiocarbonyl diimidazole (14.26 g) in acetonitrile (100 ml) at ambient temperature. The stirring was continued and the solution/suspension was left at ambient temperature for a few hours. The precipitate was filtered and washed with acetonitrile (3×25 ml). The solid residue was dissolved in hot acetone and filtered. The acetone solution was evaporated in vacuo, the residue was dissolved in hot ethyl acetate and filtered through a pad of silica (diam. 7 cm×3 cm). The silica was washed with another portion of hot ethyl acetate. The combined solutions were evaporated in vacuo to yield a crude product (5 g) of the titled product.

¹H-NMR (DMSO): 7.54 (d, J=8.7 Hz, 1H), 8.17 (dd, J=2.7, 8.7 Hz, 1H), 8.63 (d, J=2.7 Hz, 1H).

¹³C-NMR (DMSO): 121.4, 130.1, 139.4, 140.7, 143.9, 148.6.

Example 375

N-cis-(D,L)-(2-(3-Methoxy)-phenylcyclopropyl)-N'-(2-thiazolyl)thiourea

The starting material, 3-methoxystyrene, was prepared in following manner: To a mixture of 26.2 g (73.4 mmol) of methyl triphenylphosphonium bromide in 200 ml of THF cooled to 0° C., was added 42 ml (2M in THF, 82 mmol) of a lithium diisopropyl amide solution over 30 min. The mixture was stirred for an additional 2 hours then 10 g (73.4 mmol) 3-methoxybenzaldehyde was added dropwise over 25 min. The reaction mixture was stirred for one hour at room temperature and then heated under reflux for 14 hours. After cooling the solvent was evaporated in vacuo, the residue was diluted with 200 ml diethyl ether and the precipitate was removed by filtration. The ether solution was washed with water, dried with $Na_2SO_4$ and evaporated in vacuo. The product was purified by silica gel column chromatography (diethyl ether/cyclohexane).

Yield: 2.83 g (29%).

¹H-NMR (CDCl₃)d: 7.24 (t, J=8.1 Hz, 1H, Ph), 7.21–6.98 (m, 1H, Ph), 6.95 (t, J=2.3 Hz, 1H, Ph), 6.81 (ddd, J=8.1 Hz, 2.3 Hz, 0.9 Hz, 1H, Ph), 6.69 (dd, J=17.6 Hz, 10.8 Hz, 1H, CH), 5.74 (dd, J=17.6 Hz, 0.9 Hz, 1H, CH₂), 5.25 (dd, J=10.8 Hz, 0.9 Hz, 1H, CH₂), 3.81 (s, 3H, CH₃).

¹³C-NMR (CDCl₃)d: 159.81 (C-3), 139.04 (C-1), 136.79 (C-a), 129.51 (C-5), 118.92 (C-6), 114.15 (C-4), 113.46 (C-2), 111.53 (C-b), 55.22 (O—CH₃).

The titled compound was prepared in a manner analogous to the procedures described in Examples 348 and 349, using 3-methoxystyrene instead of styrene.

¹H-NMR (CDCl₃)d: 7.26–7.19 (t and d, 2H, o and thiazole), 6.90–6.69 (m, 4H, o, m, p, thiazole), 3.76 (s, 3H, OMe), 3.65 (broad s, 1H, NH—CH—), 2.50 (q, 1H, Ph—CH—), 1.22 (m, 2H, Cyclopropyl).

¹³C -NMR (CDCl₃)d: 178.6 (C=S), 161.3 (thiazole), 159.8 (C—OMe), 137.8 (Ph), 137.7 (thiazole), 129.5 (Ph), 121.6 (Ph), 114.5 (Ph), 112.8 (Ph), 111.0 (thiazole), 55.2 (O—CH₃), 44.0 (CH—NH), 22.0 (CH—Ph), 12.1 (CH₂).

Example 376

N-cis-(D,L)-(2-(2-Fluorophenyl)cyclopropyl)-N'-(2-thiazoyl thiourea

In a manner analogous to the procedures described in Examples 348 and 349 and using 2-fluorostyrene instead of styrene, the titled product was prepared.

¹H-NMR (CDCl₃)d: 7.32–7.05 (m, 4H), 6.91–6.64 (m, 2H), 3.68 (broad s, 1H, CH—NH), 2.57 (q, 1H, CH—Ph), 1.70–1.40 (m, 3H), 1.31–1.18 (m, 1H).

¹³C-NMR (CDCl₃)d: 178.8 (C=S), 162.5 and 160.5 (C—F, Ph), 161.2 (thiazole), 137.4 (thiazole), 129.9 (Ph), 128.5 and 128.4 (m to F,Ph), 124.0 (p to F, Ph) 115.4 and 115.1 (o to F, Ph), 111.8 (thiazole), 33.8 (CH—NH), 16.4 (CH—Ph), 12.2 (CH₂).

Example 377

N-(2-[3-(6-Chloro-2-methoxy)pyridyl]ethyl)-N'-(2-(5-bromo)pyridyl)thiourea

The starting material, 3-(2-aminoethyl)-6-chloro-2-methoxypyridine, was prepared in following manner:

To a solution of 1.0 g (7.0 mmol) of 2-chloro-6-methoxypyridine in 20 ml of dry THF cooled to −78° C. was added 10.9 ml (1.6M in hexanes, 17.4 mmol) n-BuLi under an atmosphere of nitrogen. The temperature of the mixture was allowed to raise to −40° C. before an addition of 4 ml ethylene oxide in 6 ml ether. The mixture was warmed to room temperature, 50 ml water was added and the aqueous layer was separated and extracted with 2×100 ml EtOAc. The organic extracts were combined, washed once with water, dried with $Na_2SO_4$, and concentrated in vacuo. The crude material was purified by dry column flash chromatography (hexane/EtOAc) to afford 0.22 g of 3-(2-hydroxyethyl)-6-chloro-2-methoxypyridine as a yellowish oil.

To a solution of 0.20 g (0.8 mmol) of 3-(2-hydroxyethyl)-6-chloro-2-methoxypyridine in 10 ml of dry $CH_2Cl_2$ cooled to −50° C. was added 0.18 ml (0.8 mmol) trifluoromethanesulfonic anhydride under an atmosphere of nitrogen. The mixture was stirred for 30 min at this temperature and an additional 10 min at −78° C. before a rapid addition of 30 ml of cold (−78° C.) NH₃ (l). The mixture was stirred for 15 min at room temperature, and then concentrated in vacuo to afford 1.0 g of crude 3-(2-aminoethyl)-6-chloro-2-methoxypyridine as a trifluoromethanesulfonic acid salt.

$^1$H-NMR (CD₃OD)d: 7.66 (d, 1H, Py), 7.03 (d, 1H, Py), 4.04 (s, 3H, CH₃—O), 3.24 (t, 2H, CH₂—N), 3.03 (t, 2H, CH₂—Py).

The crude 3-(2-aminoethyl)-6-chloro-2-methoxypyridine was condensed with N-(2-(5-bromo)pyridyl-N'-(1-imidazolyl)thiourea in a manner analogous to Example 103, to give the titled product.

$^1$H-NMR (CD₃OD)d: 11.25 (broad s, 1H, N—H), 10.82 (broad s, 1H, N—H), 8.31 (s, 1H, Br—Py), 8.08 (d, 1H, Br—Py), 7.89 (d, 1H, Cl—Py), 7.21 (m, 2H, Cl— and Br—Py), 3.96 (m, 5H, CH₂—N, and CH₃—O), 3.03 (t, 2H, CH₂—Py).

$^{13}$C-NMR (CD₃OD)d: 179.45 (C=S), 161.43 (Cl—C in Py), 152.41 (Br—C in Py), 145.92 (Cl—Py), 145.14 (MeO—C—Py), 141.89 (Br—Py), 141.51 (Br—Py), 120.32 (Cl—Py), 116.48 (Cl—Py), 114.60 (Br—Py), 111.95 (Br—Py), 55.10 (CH₃—O), 43.76 (CH₂—NH), 27.89 (CH₂—Ph).

Example 378

N-(2-[3-(2-Fluoro)pyridyl]ethyl)-N'-(2-(5-bromo)pyridyl)thiourea

The starting material, 3-(2-aminoethyl)-2-fluoropyridine, was prepared in following manner:

A solution of 2.0 g (20.6 mmol) of 2-fluoropyridine in 25 ml of dry THF was cooled to −78° C. was added 25 ml (1.6M in hexanes, 41.6 mmol) n-BuLl under an atmosphere of nitrogen. The mixture was stirred at this temperature for 2 hours before an addition of 4 ml ethylene oxide in 7 ml ether. The mixture was warmed to room temperature, 150 ml ether and 25 ml acetone was added. The precipitate was removed by filtration, and the filtrate was concentrated to ⅓ of volume in vacuo. The remainder was washed once with brine, dried with Na₂SO₄, and concentrated in vacuo. The crude material was purified by dry column flash chromatography (hexane/EtOAc) to afford 0.42 g of 3-(2-hydroxyethyl)-2-fluoropyridine as a brown oil.

To a solution of 0.20 g (1.42 mmol) of 3-(2-hydroxyethyl)-2-fluoropyridine in 8 ml of dry CH₂Cl₂ cooled to −40° C. was added 0.18 ml (0.8 mmol) trifluoromethanesulfonic anhydride under an atmosphere of nitrogen. After stirring for 30 min at −40° C., 30 ml of cold (−78° C.) NH₃ (l) was added. The mixture was stirred for 30 min at −40° C., and then concentrated in vacuo to afford 1.03 g of crude salt which was washed twice with 20 ml diethyl ether to yield 0.82 g of 3-(2-aminoethyl)-2-fluoropyridine as a trifluoromethanesulfonic acid salt.

$^1$H-NMR (CD₃OD)d: 8.23 (d, 1H, Py), 7.98 (t, 1H, Py), 7.40 (m, 1H, Py), 3.30 (t, 2H, CH₂—N), 3.12 (t, 2H, CH₂—Py).

The crude 3-(2-aminoethyl)-2-fluoropyridine was condensed with N-(2-(5-bromo)pyridyl-N'-(1-imidazolyl)thiourea in a manner analogous to example 103, to give the titled product.

$^1$H-NMR (CD₃OD)d: 8.31 (d, 1H, Br—Py), 8.23 (m, 1H, F—Py), 8.06 (m, 2H, Br— and F—Py), 7.45 (m, 1H, F—Py), 7.23 (d, 1H, Br—Py), 4.00 (q, 2H, CH₂—N), 3.14 (m, 2H, CH₂—Py).

$^{13}$C-NMR (CD₃OD)d: 179.59 (C=S), 163.53 and 159.78 (F—C in Py), 152.39 (Br—Py), 145.87 (F—Py), 145.63 and 142.38 (F—Py), 142.28 (Br—Py),141.54 (Br—Py), 122.31 and 122.26 (F—Py), 120.94 and 120.45 (F—Py), 114.59 (Br—Py), 111.97 (Br—Py), 44.29 (CH₂—NH), 27.32 (CH₂—Ph).

Example 379

N-(2-(2,6-difluoro)phenethyl)-N'-(2-benzothiazolyl)thiourea

In a manner analogous to Example 105, 2,6-difluorophenethylamine was condensed with 1-(2-aminobenzothiazole)-1'-imidazole thiocarbonyl which was made in similar way as described in Example 103. The titled compound crystallized from methylene chloride.

$^1$H-NMR (CDCl₃+CD₃OD) d: 7.64 (m, 2H, benzo), 7.3 8 (m, 3H, DFPh, benzo), 7.24 (t, 2H, DFPh), 4.04 (t, 2H, CH₂), 3.15 (t, 2H, CH₂).

Example 380

N-(2-(2,6-difluoro)phenethyl)-N'-(2-(4,5-dimethyl)thiazolyl)thiourea

In a manner analogous to Example 105, 2,6-difluorophenethylamine was condensed with 1-(2-amino-4,5-dimethylthiazole)-1'-imidazole thiocarbonyl which was made in a similar way as described in Example 103. The titled compound crystallized from methylene chloride.

$^1$H-NMR (CDCl₃) d: 7.21 (m, 1H, DFPh), 7.15 (t, 2H, DFPh), 4.00 (q, 2H, CH₂), 3.09 (t, 2H, CH₂), 2.22 (d, J=0.5 Hz, 3H, Me), 2.08 (d, J=0.6 Hz, 3H, Me).

Example 381

N-(2-(2-fluoro)phenethyl)-N'-(2-(6-fluorobenzothiazolyl)thiourea

In a manner analogous to Example 105, 2-fluorophenethylamine was condensed with 1-(2-amino-6-fluorobenzothiazole)-1'-imidazole thiocarbonyl which was made in a similar way as described in Example 103. The titled compound crystallized from methylene chloride.

$^1$H-NMR(CDCl₃+CD₃OD) d: 7.53–7.06 (m, 7H, benzo, FPh), 4.04 (t, 2H, CH₂), 3.10 (t, 2H, CH₂).

Example 382

N-(2-(2,6-difluoro)phenethyl)-N'-(2-(6-fluorobenzothiazolyl)thiourea

In a manner analogous to Example 105, 2,6-difluorophenethylamine was condensed with 1-(2-amino-6-fluorobenzothiazole)-1'-imidazole thiocarbonyl which was made in a similar way as described in Example 103. The titled compound crystallized from methylene chloride.

$^1$H-NMR (CDCl₃+CD₃OD) d: 7.52 (m, 1H, benzo), 7.40 (m, 1H, benzo), 7.14 (m, 2H, DFPh, benzo), 6.88 (m, 2H, DFPh), 4.02 (t, 2H, CH₂), 3.14 (t, 2H, CH₂).

Example 383

N-(2-(2-fluoro)phenethyl)-N'-(2-benzothiazolyl)thiourea

In a manner analogous to Example 105, 2-fluorophenethylamine was condensed with 1-(2-aminobenzothiazole)-1'-imidazolyl thiocarbonyl which was made in a similar way as described in Example 103. The titled compound crystallized from methylene chloride.

$^1$H-NMR (CDCl$_3$+CD$_3$OD) d: 7.63 (q, 2H, benzo), 7.32 (m, 4H, benzo, FPh), 7.10 (q, 2H, FPh), 4.06 (t, 2H, CH$_2$), 3.11 (t, 2H, CH$_2$).

Example 384

N-(2-(2-fluoro)phenethyl)-N'-(2-(4-methylthiazolyl)thiourea

In a manner analogous to Example 105, 2-fluorophenethylamine was condensed with 1-(2-amino-4-methylthiazole)-1'-imidazole thiocarbonyl which was made in a similar way as described in Example 103. The titled compound crystallized from methylene chloride.

$^1$H-NMR (CDCl$_3$+CD$_3$OD) d: 7.23 (m, 2H, FPh), 7.06 (m, 2H, FPh), 6.34 (d, J=1 Hz, 1H, thiazole), 3.99 (t, 2H, CH$_2$), 3.05 (m, 2H, CH$_2$), 2.20 (d, J=0.9 Hz, 3H, Me).

Example 385

N-(2-(2,6-difluoro)phenethyl)-N'-(2-(4-methylthiazolyl)thiourea

In a manner analogous to Example 105, 2,6-difluorophenethylamine was condensed with 1-(2-amino-4-methylthiazole)-1'-imidazole thiocarbonyl which was made in a similar way as described in Example 103. The titled compound crystallized from methylene chloride.

$^1$H-NMR (CDCl$_3$+CD$_3$OD) d: 7.19 (m, 1H, DFPh), 6.87 (t, 2H, DFPh), 6.35 (s, 1H, thiazole), 3.98 (t, 2H, CH$_2$), 3.09 (t, 2H, CH$_2$), 2.22 (s, 3H, Me).

Example 386

N-(2,2-dimethyl-2-(2-chloro-6-fluoro)phenethyl)-N'-(2-thiazolyl)thiourea

A solution of 2-chloro-6-fluorophenyl acetonitrile (1.69 g, 10 mmole) in dry THF (70 ml) was cooled to −60° C., and lithium diisopropylamide (5.25 ml, 10.5 mmole) was added. After 30 min, methyl iodide (0.68 ml, 11 ml) was added into the reaction mixture, and the reaction was slowly warmed to 0° C., and kept at 0° C. for 1 hr. Then it was cooled to −60° C. again, and more lithium diisopropylamide (6 ml, 12 mmole) was added. After 30 min, methyl iodide (1.87 ml, 30 mmole) was added. The reaction mixture was allowed to warm to room temperature and kept there for 2 hr after which it was poured into a sodium hydrogen carbonate solution, and extracted with chloroform. The organic phase was washed with water, dried, and the solvent was evaporated in vacuo. The product 2,2-dimethyl-2(2-chloro-6-fluorophenyl)acetonitrile (1.07 g) was isolated by silica gel column chromatography.

$^1$H-NMR (CDCl$_3$) d: 7.25 (m, 2H, Ph), 7.03 (m, 1H, Ph), 1.98 (s, 3H, Me), 1.96 (s, 3H, Me).

The 2,2-dimethyl-2-(2-chloro-6-fluorophenyl)ethylamine was obtained by reduction of 2,2-dimethyl-2(2-chloro-6-fluorophenyl)acetonitrile with cobalt chloride and sodium borohydride according to the method described by L. S. Heizman in *J. Am. Chem. Soc.*, 104, p. 6801, (1980). It was then condensed with 1-(2-aminothiazole)-1'-imidazole thiocarbonyl in the analogous manner to Example 105. The titled compound was isolated by silica gel column chromatography.

$^1$H-NMR (CDCl$_3$) d: 7.35–7.09 (m, 3H, Ph), 6.95 (d, 1H, thiazole), 6.73 (d, 1H, thiazole), 4.09 (d, 2H, CH$_2$), 1.50 (s, 6H, Me).

Example 387

N-(2-(5-bromo-2-methoxy)phenethyl)-N'-(2-(4-methylthiazolyl)thiourea

In a manner analogous to Example 105, 5-bromo-2-methoxyphenethylamine was condensed with 1-(2-amino-4-methylthiazole)-1'-imidazole thiocarbonyl which was made in a similar way as described in Example 103. The titled compound crystallized from methylene chloride.

$^1$H-NMR (CDCl$_3$+CD3OD) d: 7.31 (d, 1H, Ph), 7.29 (s, 1H, Ph), 6.72 (d, 1H, Ph), 6.34 (s, 1H, thiazole), 3.95 (t, 2H, CH$_2$), 3.79 (s, 3H, MeO), 2.96 (t, 2H, CH$_2$), 2.23 (s, 3H, Me).

Example 388

N-(2-(5-bromo-2-methoxy)phenethyl)-N'-(2-(4-cyanothiazolyl)thiourea

In a manner analogous to Example 105, 5-bromo-2-methoxyphenethyl-amine was condensed with 1-(2-amino-4-cyanothiazole)-1'-imidazole thiocarbonyl which was made in a similar way as described in Example 103. The titled compound was purified by silica gel column chromatography.

$^1$H-NMR (CDCl$_3$+CD$_3$OD) d: 7.51 (thiazole), 7.32 (d, 1H, Ph), 7.27 (s, 1H, Ph), 6.76 (d, 1H, Ph), 3.90 (t, 2H, CH$_2$), 3.83 (s, 3H, MeO), 2.97 (t, 2H, CH$_2$).

Example 389

N-(2-(2,6-difluoro)phenethyl)-N'-(2-(4-cyanothiazolyl)thiourea

In a manner analogous to Example 105, 2,6-difluorophenethylamine was condensed with 1-(2-amino-4-cyanothiazole)-1'-imidazole thiocarbonyl which was made in a similar way as described in Example 103. The titled compound crystallized from methylene chloride.

(CDCl$_3$+CD$_3$OD) d: 7.51 (s, 1H, thiazole), 7.22 (m, 1H, DFPh), 6.90 (t, 2H, DFPh), 3.93 (t, 2H, CH$_2$), 3.08 (s, 2H, CH$_2$).

Example 390

N-(2-(2,6-difluoro)phenethyl)-N'-(2-imidazolyl)thiourea

In a manner analogous to Example 93, using 2,6-difluorophenethylamine and 2-aminoimidazole, the titled compound was obtained.

$^1$H-NMR (DMSO+D$_2$O) d: 7.28 (m, 1H, DFPh), 7.02 (t, 2H, DFPh), 6.78 (broad, 1H, imidazole), 6.62 (broad, 1H, imidazole), 3.79 (t, 2H, CH$_2$), 2.97 (t, 2H, CH$_2$).

Example 391

N-(1-amine-2-(5-imidazolyl)-ethyl)-N'-(2-(5-methyl)thiazolyl)thiourea 1-(2-(5-methyl)-aminothiazole-1'-imidazolethiocarbonyl (prepared as described in Example 103, using 2-amino-5-methylthiazole instead of 2-aminothiazole) (4.06 mmol, 910 mg) and histamine (4.05 mmol, 450 mg) in dimethylformamide (10 ml) was heated to 50° C. for 3 hrs. The mixture was concentrated and partitioned between ethyl acetate and saturated aqueous sodium bicarbonate. The organic layer was dried over MgSO$_4$ and concentrated to give the titled compound in 43% yield (463 mg).

$^1$H NMR (250 MHz, DMSO-d$_6$) δ2.18 (s, 3 H), 2.80 (m, 2H), 6.57 (s, 1 H), 6.90 (s, 1 H), 7.60 (s, 1 H).

Example 392

1-(2-Amino-5-bromopyridyl)-1'-(imidazolyl)thiocarbonyl

A mixture of 2-amino-5-bromopyridine, 97% (25.0 g, 140 mmol) and 1,1'-thiocarbonyldiimidazole, 90% (27.72 g, 140 mmol) in 300 mol of acetonitrile was stirred at ambient temperature overnight and then filtered. The precipitate was dried in vacuo to give the titled compound as a crude product which was stored and used for further condensations with various phenethylamines.

Yield: 37.5 g (95%).

Example 393

1-(5-chloropyrid-2-yl-thiocarbamoyl)imidazole

In a 500 ml reaction-flask, N,N-thiocarbonyl-diimidazole (60.0 g, 337 mmol) was dissolved in acetonitrile (400 ml) at 50° C. with stirring. The solution was then cooled to 20° C. 2-Amino-5-chloropyridine (43 g, 337 mmol) was then added.

The solution was stirred for 35 minutes and kept at ambient temperature over night. The solution was filtered and the crystalline mass consisted of a mixture of needles and pellets. The pellets were separated mechanically and purified by fluidization with a hair-dryer to give the titled product.

$^1$H-NMR DMSO-d$_6$ δ ppm 7.1–7.2 (2H, s, imid) 7.5–7.6 (1H, d, orto-coupling, pyr.) 7.9–8.0 (1H, s, imid.) 8.1–8.2 (1H, d,d, pyr.) 8.6–8.7 (1H, d, meta-coupling, pyr.)

Example 394

N-2-(2,5-dimethoxyphenylethyl)-N'-(2-(6-fluorobenzothiazolyl))thiourea 450 mg 2,5-dimethoxyphenethylamine (2.5 mmol) and 740 mg 1-((2-(6-fluoro)benzothiazolyl)thiocarbamoyl)imidazole (2.5 mmol) (Example 80) in 5 ml acetonitrile were refluxed for one half hour. The mixture was cooled, and crystals were filtered off. Recrystallization from a mixture of ethanol and dimethylformamide gave 640 mg of the pure product as very fine needles.

Mp: 1960° C.

$^1$H-NMR: 3.00 2H (t), 3.77 3H (s), 3.84 3H (s), 3.91 2H (m), 6.91–7.03 3H (m), 7.38 1H (m), 7.70 1H (m), 7.94 1H (m), 9.9 1H broad singlet, 12.0 1H broad singlet Analysis C$_{18}$H$_{18}$FN$_3$O$_2$S$_2$: calculated C 55.22 H 4.63 N 10.73; found: C 55.3 H 4.70 N 10.75

Example 395

N-2-(-2,5-dimethoxyphenylethyl)-N'-(2-(4-methylthiazolyl))thiourea 1000 mg (4.46 mmol) 1-(2-(4-methylthiazolyl)thiocarbamoyl)imidazole (prepared analogously to 1-(2-thiazolyl)thiocarbamoyl)imidazole described in Example 103) and 800 mg 2,5-dimethoxyphenethylamine (4.42 mmol) in 7 ml acetonitrile were refluxed for one half hour. The mixture was cooled to 0° C., crystals were filtered off, rinsed with acetonitrile and dried. Recrystallization from ethanol-dimethylformamide gave 1.42 g of the pure product.

Mp: 210° C.

$^1$H-NMR (DMSO-d$_6$): 2.27 3H (s), 2.96 2H (t), 3.78 3H (s), 3.83 3H (s), 3.84 2H (m), 6.73 1H (s), 6.85–7.04 3H (m)

Analysis C$_{15}$H$_{19}$N$_3$O$_2$S$_2$: calculated C 53.39 H 5.67 N 12.45; found: C 53.1 H 5.65 N 12.35

Example 396

N-2-(-2,5-dimethoxyphenethyl)-N'-(2-(2-benzothiazolyl))thiourea 556 mg 1-(2-benzothiazolyl)thiocarbamoyl)imidazole (2 mmol) (Example 66) and 362 mg 2,5-dimethoxyphenethylamine (2 mmol) in 5 ml acetonitrile were refluxed for one half hour. Recrystallization from ethanol-dimethylformamide gave 565 mg pure product.

$^1$H-NMR (DMSO-d$_6$): 3.02 2H (t), 3.77 3H (s), 3.85 3H (s), 3.93 2H (m), 6.92–7.04 3H (m), 7.38 1H (m), 7.53 1H (m), 7.70 1H (m), 8.01 1H (m)

Analysis C$_{18}$H$_{19}$N$_3$O$_2$S$_2$: calculated C 57.88 H 5.13 N 11.25; found: C 57.95 H 5.15 N 11.25

Example 397

N-2-(2,6-dichlorophenylethyl)-N'-(2-thiazolyl)thiourea 9.3 g 2,6-Dichlorophenylacetonitrile (50 mmol) in 50 ml diethylether was added dropwise to a mixture of 5 g lithium aluminum hydride in 200 ml ether. The mixture was heated to reflux, and reaction was allowed to take place for 2 hours. The mixture was cooled to room temperature, and 5 ml water was added dropwise, followed by 5 ml 25% sodium hydroxide in water. 10 ml water was then added, and the mixture was filtered. 10 ml acetic acid was added rapidly to the stirred filtrate. The 2,6-dichlorophenethylammonium acetate that precipitated was filtered off and dried. 500 mg 2,6-dichlorophenethylammonium acetate (2 mmol), 0.42 g 1-(2-aminothiazole)-1'-imidazole thiocarbonyl (Example 103) and 0.5 g diisopropylethylamine were mixed in 5 ml acetonitrile and refluxed for 30 minutes. The mixture was then kept at 0° C. for 17 hours and the crystals were filtered off. Recrystallization from acetonitrile gave 265 mg of the titled product.

$^1$H-NMR (DMSO-d$_6$): 3.3 2H (t), 3.9 2H (m), 7.2 1H (d), 7.35–7.6 4H (m).

Example 398

N-2-(2,6-dichlorophenylethyl)-N'-(2-(4-methylthiazolyl))thiourea 500 mg 2,6-dichlorophenylethylammonium acetate (2 mmol) (Example 397), 0.48 g 1-(2-(4-methylthiazolyl)thiocarbamoyl)imidazole (prepared analogously to 1-(2-thiazolyl)thiocarbamoyl)imidazole described in Example 103) (2 mmol) and 0.5 g diisopropylethylamine were mixed in 5 ml acetonitrile and refluxed for 30 minutes. The mixture was cooled and crystals were filtered off. Recrystallization from acetonitrile gave 598 mg of the titled product.

$^1$H-NMR (DMSO-d$_6$): 2.2 3H (s), 3.3 2H (t), 4.0 2H (m), 6.7 1H (S), 7.4 1H (m), 7.5 2H (m), 9.8 1H broad singlet, 11.7 1H broad singlet Analysis $C_{13}H_{13}Cl_2N_3S_2$: calculated C 45.09 H 3.78 N 12.13; found: C 45.45 H 3.9 N 12.55

Example 399

N-(-2-(2,6-dichlorophenyl)ethyl)-N'-(2-benzothiazolyl)thiourea 500 mg 2,6-dichlorophenylethylammonium acetate (2 mmol) (Example 397), 0.55 g 1-(2-benzothiazolyl)thiocarbamoyl)imidazole (2 mmol) (Example 66) and 0.5 g diisopropyl-ethylamine were mixed in 5 ml acetonitrile and refluxed for 30 minutes. The mixture was cooled and crystals were filtered off. Recrystallization from acetonitrile gave 497 mg of the titled product.

$^1$H-NMR (DMSO-$d_6$) 3.3 2H (t), 4.0 2H (m), 7.3–7.7 6H (m), 8.0 1H (d), 10.0 1H broad peak, 12.11H broad peak.

Analysis $C_{16}H_{13}Cl_2N_3S_2$: calculated C 50.26 H 3.43 N 10.99; found: C 50.3 H 3.45 N 11.1

Example 400

N-(2-(2,6-dichlorophenyl)ethyl)-N'-(2-(6-(fluorobenzothiazolyl))thiourea 500 mg 2,6-dichlorophenylethylammonium acetate (2 mmol) (Example 397), 0.59 g 1-((2-(6-fluoro)benzothiazolyl)thiocarbamoyl)imidazole (2 mmol) (Example 80) and 0.5 g diisopropylethylamine were mixed in 5 ml acetonitrile and refluxed for 30 minutes. The mixture was cooled and crystals were filtered off. Recrystallization from acetonitrile gave 548 mg of the titled product.

$^1$H-NMR (DMSO-$d_6$): 3.4 2H (t), 4.0 2H (m), 7.3–7.4 2H (m), 7.5–7.7 2H (m), 8.0 1H (m), 9.8 1H broad peak, 12.0 1H broads peak.

Analysis $C_{16}H_{12}Cl_2FN_3S_2$: calculated C 48.00 H 3.02 N 10.50; found: C 48.25 H 3.1 N 10.6

Example 401

N-(2-(2,6-difluoro-3-methoxyphenyl)ethyl)-N'-(-2-thiazolyl)thiourea 6.25 ml 1.6M n-butyl lithium in hexane was added dropwise to a solution of 10 mmol 2,4-difluoroanisole in 30 ml diethyl ether. The mixture was kept at –65° C. during the addition. 3 ml Dimethylformamide was then added, and the mixture was slowly (1 h) allowed to warm to room temperature. The mixture was poured into a separation funnel containing 50 ml ice-water. The ether layer was separated, washed with 50 ml water and dried (Na$_2$SO$_4$). The solvent was evaporated, and the residue was redissolved in 50 ml ethanol. 2 g Ammonium acetate and 3 ml nitromethane were added and the mixture was refluxed for 3 hours. The solvent was evaporated, and the residue was partitioned between 50 ml dichloromethane and 50 ml water. The organic layer was dried, and the solvent was evaporated. Crystallization from cold ethanol gave 480 mg brown crystals of 1-nitro-2(2,6-difluoro-3-methoxyphenyl)ethene.

$^1$H-NMR (CDCl$_3$): 3.9 3H (s), 6.9–7.12H (m), 7.8 1H (d), 8.11H (d).

420 mg 1-nitro-2-(2,6-difluoro-3-methoxyphenyl)ethene was dissolved in 50 ml tetrahydrofurane and added dropwise under stirring to a solution of 2 g lithium aluminum hydride in 50 ml tetrahydrofurane. The mixture was refluxed for 3 hours. The product amine was worked-up by the dropwise addition of 2 ml water followed by 2 ml 25% sodium hydroxide in water followed by 4 ml water.

The mixture was then filtered. The filtrate was extracted with 2×20 ml 1M HCl. The aqueous layer was made basic by the addition of 50 ml 45% sodium hydroxide solution, and then extracted with 3×50 ml dichloro-methane. The 2-(2,6-difluoro-3-methoxyphenyl)ethyl-amine obtained by the evaporation of solvent was pure enough for use in the next step.

$^1$H-NMR: 1.2 2H broad singlet, 2.6 2H (m), 2.7 2H (m), 3.65 3H (s), 6.4–6.6 2H (m)

172 mg 2-(2,6-difluoro-3-methoxyphenyl)ethylamine (1.0 mmol) and 2 10 mg 1-(2-aminothiazole)-1'-imidazole thiocarbonyl (1.0 mmol) in 5 ml acetonitrile were refluxed for one hour. The solution was cooled, and crystallization was allowed for overnight. Solid material was filtered off, and recrystallized from acetonitrile to give 138 mg of the titled product.

$^1$H-NMR (DMSO-$d_6$): 3.1 2H (t), 3.8–4.0 5H (m), 6.9–7.2 3H (m), 7.4 1H (d), 9.8 1H broad peak, 11.7 1H broad peak Analysis $C_{13}H_{13}F_2N_3OS_2$: calculated C 47.40% H 3.98% N 12.76%; found: C 47.6% H 4.1% N 12.75%

Example 402

N-(2-(-2-Benzotriazolyl)ethyl)-N'-(2-thiazolyl)thiourea 59.5 g benzotriazole (0.50 mol) was dissolved in 700 ml dimethylformamide. 160 g Sodium carbonate (1.5 mol) was added and then dropwise 73.5 g ethyl chloroacetate (0.60 mol). The stirred mixture was slowly heated to 40° C., and kept ac that temperature for 17 h. The solvent was evaporated and the residue was extracted with ethyl acetate. GC showed one major and one minor product. The minor product ethyl-2-(2-benzotriazolyl)acetate was isolated by fractional crystallization from cold mixtures of ethanol and ethyl acetate.

7.1 g Of this minor product (40 mmol) was dissolved in 50 ml diethyl ether-tetrahydrofurane 1:1 and 1.5 g of lithium borohydride was added. The reaction mixture was stirred for 17 h at room temperature. The solvent was removed and replaced with 50 ml butanol. 5 ml Water was added and the temperature was slowly raised to about 50° C. After 4 h at this temperature the solvent was removed and the residue was partitioned between dichloromethane and water. The organic layer was dried, and the product 2-(2-benzotriazolyl)ethanol was isolated by crystallization from cold ethanol.

4.70 g Of the 2-(2-benzotriazolyl)ethanol (28.8 mmol) was dissolved in 200 ml diethyl ether and 2.28 g pyridine (28.8 mmol) was added. The mixture was cooled to –50° C., and 8.18 g triflic anhydride (29 mmol) was added. The mixture was removed from the cooling bath, and was allowed to reach room temperature. The mixture was filtered under dry conditions and added to a cold –40° C. solution of ca 150 ml ammonia in 50 ml diethyl ether. This mixture was allowed to reach room temperature, and ether was removed. 50 ml 2M HCl was added, and this mixture was washed with methylene chloride. The aqueous phase was made basic by addition of 50 ml 25% sodium hydroxide and extracted with 3×25 ml methylene chloride. Evaporation of the solvent gave 2.10 g 2-(2-benzotriazolyl)ethylamine (12.9 mol). This amine was used in the next step without further purification.

324 mg 2-(2-benzotriazolyl)ethylamine (2 mmol) and 420 mg 1-(2-aminothiazole)-1'-imidazole thiocarbonyl (2 mmol) were mixed in 3 ml acetonitrile. The mixture was slowly heated to reflux, and was then cooled to allow the product to crystallize. Repeated crystallization from acetonitrile gave 234 mg pure N-(2-(-2-benzotriazolyl)ethyl)N'-(2-thiazolyl)thiourea.

$^1$H-NMR (DMSO-d$_6$): 4.5 2H (m), 5.1 2H (m), 6.75 1H (d), 7.05 1H (d), 7.4 2H (m), 7.9 2H (m).

$^{13}$C-NMR 47, 56, 112, 119, 127, 145, 180.

Analysis C$_{12}$H$_{12}$N$_6$S$_2$: calculated C 47.35% H 3.97% N 27.61%; found: C 47.3% H 3.95% N 27.2%

Example 403 cis/trans N-(2-(2-ethoxyphenylcyclopropanyl))-N'-(2-pyridyl)thiourea 28.56 g methyl triphenylphosphonium bromide (80 mmol) in 500 ml tetrahydrofurane was cooled to −50° C. 50 ml n-Butyllithium in hexane (about 1.6M, 80 mmol) was added dropwise under stirring. The mixture was slowly warmed to room temperature, and kept there for two hours. The mixture was then cooled to −30°, and 12 g 2-ethoxybenzaldehyde (80 mmol) was added. The mixture was warmed to room temperature, and most of the solvent was removed and the residue was mixed with 400 ml ether and filtered. The solvent was evaporated and ethyl acetate was added to residue. The solution was passed through a pad of silica gel. This crude 2-ethoxystyrene was dissolved in 50 ml dichloroethane and used as such in the next reaction step:

0.1 g CuI was added, and the mixture was heated to reflux temperature. 8.80 g Ethyl diazoacetate in 30 ml dichloroethane was then added dropwise over a period of 1 hour. GC-analysis showed the formation of two products in a about 1:2 ratio. The two isomeric products were separated from other material by column chromatography (silica-gel, mixtures of hexane-ethyl acetate). This gave 3.1 g of a cis/trans mixture of 2-(2-ethoxyphenyl)-1-carboxyethyl cyclopropanes. The product mixture was hydrolysed in a refluxing mixture of 50 ml ethanol+10 ml water+4 g sodium hydroxide (2 hours). The solvent was evaporated and the residue was made acidic with 100 ml 2M hydrochloric acid and extracted with 2×50 ml dichloromethane. The organic layers were dried and solvent was evaporated. 50 ml Toluene was added followed by 6 g thionyl chloride. The mixture was heated to 80° C. for one hour and the solvent was then removed. 100 ml Acetone was added, the solution was cooled in an ice-bath and 4 g sodium azide in 20 ml water and 100 ml toluene was added after which the mixture was washed with 3×50 ml water. The organic layer was dried (Na$_2$SO$_4$), the solvent was evaporated and the residue was dissolved in 100 ml dioxane. The dioxane solution was heated slowly to reflux, and kept at reflux 30 min. 25 ml Concentrated hydrochloric acid was added and the mixture was refluxed for 2 hours. The solvent was removed and the residue was partitioned between 50 ml dichloromethane and 50 ml 2M hydrochloric acid. The aqueous layer was made basic by the addition of 50 ml 25% sodium hydroxide solution, and extracted with 3×50 ml dichloromethane. The dichloromethane solvent was evaporated and the residue was purified by column chromatography (silica-gel, mixtures of ethanol and ethyl acetate to give about 1:1 mixture of cis/trans 2-(2-ethoxyphenyl)cyclopropyl-amines. 0.24 g 2-Aminopyridine (2.6 mmol) and 0.46 g thiocarbonyldiimidazole (2.6 mmol) were stirred in 5 ml acetonitrile for 2 hours. 0.41 g (2.6 mmol) of the mixture of cyclopropylamines was added, and the reaction mixture was heated slowly to 70° C. and stirred at that temperature for 17 hours.

The solvent was evaporated, and the titled product was isolated by column chromatography (silica-gel, mixtures of hexane-ethyl acetate.

$^1$H-NMR: 1.15–1.25 5H (m), 2.50 1H (m), 3.42 0.55H (m), 3.73 0.45% (m), 4.0–4.1 2H (q), 6.7–8.15 8H (m)

Example 404

N-(2-(2-pyridylethyl))-N'-(2-(5-chloropyridyl))thiourea 1.73 g 2-Amino-5-chloropyridine (10 mmol) and 1.78 g thiocarbonyl diimidazole (10 mmol) were stirred for 2 hours in 15 ml acetonitrile. 1.47 g 2-(2-Aminoethyl)pyridine (12 mmol) was added, and the mixture was stirred at room temperature for 2 hours. The reaction mixture was then heated to 50° C. and was stirred for 17 hours. Crystals were collected by filtration after cooling of the mixture. Recrystallization from acetonitrile gave pure titled product.

$^1$H-NMR (DMSO-d$_6$): 3.2 2H (t), 4.1 2H (m), 7.2–7.5 3H (m), 7.8–8.0 2H (m), 8.2 1H (d), 8.7 1H (m), 18.0 1H (s), 11.5 1H (s)

Example 405

N-(2-(2-pyridylethyl))-N'-(2-(5-bromopyridyl))thiourea 1.28 g 2-Amino-5-bromopyridine (10 mmol) and 1.78 g thiocarbonyl diimidazole (10 mmol) were stirred for 2 hours in 15 ml acetonitrile. 1.47 g 2-(2-Aminoethyl)pyridine (12 mmol) was added, and the mixture was stirred at room temperature for 2 hours. The reaction mixture was then heated to 50° C. and was stirred for 17 hours. Crystals were collected by filtration after cooling of the mixture. Recrystallization from acetonitrile gave pure titled product.

$^1$H-NMR (DMSO-d$_6$): 3.5 2H (t), 4.2 2H (m), 7.2 2H (d), 7.9–8.1 3H (m), 8.3 1H (d), 8.6 1H (m), 8.9 1H (d) 10.9 1H (s), 11.4 1H (t)

Example 406

N-(2-(2-pyridylethyl))-N'-(2-(5-nitropyridyl))thiourea 1.39 g 2-Amino-5-nitropyridine (10 mmol) was dissolved in 20 ml tetrahydrofurane. 0.68 g (10 mmol) Sodium ethoxide (10 mmol) was added. The mixture was heated to 50° C. and stirred for 30 minutes. The mixture was cooled, and most of the liquid was decanted from the formed red precipitate. The precipitate was taken up in 20 ml acetonitrile, and added to 1.78 g thiocarbonyl diimidazole in 10 ml acetonitrile. This mixture was stirred for 10 minutes at room temperature. 1.22 g 2-(2-Amino-ethyl)pyridine was added and the mixture was stirred for one hour. 1 ml Acetic acid was added, and the solvent was evaporated. The residue was washed with water. Repeated crystallizations from acetonitrile gave 1.28 g yellow crystals of the titled product.

$^1$H-NMR (DMSO-d$_6$): 3.1 2H (t), 3.2 2H (t), 7.2 1H (m), 7.3 3H (m), 7.7 1H (m), 8.4 1H (m), 8.5 1H (m), 8.9 1H (d)

Example 407

N-(2-(2-pyridylethyl))-N'-(2-(5-methylpyridyl))thiourea 1.78 g thiocarbonyl diimidazole (10 mmol) and 1.58 g 2-amino-5-methylpyridine (10 mmol) in 15 ml acetonitrile were stirred for 1 h at room temperature. 1.22 g 2-(2-Aminoethyl)-pyridine was added. The mixture was stirred 1 h at room temperature, and then 17 h at 50° C. The mixture was cooled and crystals were collected by filtration. Recrystallization from acetonitrile gave 1.30 g pure titled product.

$^1$H-NMR (DMSO-d$_6$): 2.2 3H (s), 3.1 2H (t), 4.0 2H (m), 7.0 1H (d), 7.2 1H (m), 7.3 1H (d), 7.6 1H (m), 7.7 1H (m), 7.8 1H (m), 8.6 1H (m)

$^{13}$C-NMR: 17.3, 36.3, 44.0, 112.1, 121.7, 123.5, 126.7, 136.6, 139.7, 144.6, 149.2, 151.8, 159.0, 179.2

Example 408

(N-(2-(2-pyridylethyl))-N'-(2-(5-bromopyridyl))thiourea HCl salt)

100 mg N-(2-(2-pyridylethyl))-N'-(2-(5-bromopyridyl))thiourea (Example 405) was added to about 10 ml water. The suspension was heated to about 90° C. and pH was adjusted to about 3 by addition of hydrochloric acid. The titled product was isolated by freeze-drying.

$^1$H-NMR (DMSO-d$_6$): 3.6 2H (t), 4.2 2H (m), 7.2 2H (d), 7.9–8.1 3H (m), 8.3 1H (d), 8.6 1H (m), 8.9 1H (d) 10.9 1H (s), 11.4 1H (t)

Example 409

(N-(2-(2-pyridylethyl))-N'-(2-chloropyridyl))thiourea HCl salt)

100 mg N-(2-(2-pyridylethyl))-N'-(2-(5-chloropyridyl))thiourea (Example 404) was added to about 10 ml water. The suspension was heated to about 90° C. and pH was adjusted to about 3 by addition of hydrochloric acid. The titled product was isolated by freeze-drying.

$^1$H-NMR (DMSO-d$_6$): 3.6 2H (t), 4.2 2H (m), 7.3 1H (d), 8.0–8.2 3H (m), 8.3 1H (m), 8.6 1H (m), 9.0 1H (m), 10.9 1H (s), 11.4 1H (t).

Example 410

N-(2-(-2-Benzotriazolyl)ethyl)N'-(2-(5-bromopyridyl))thiourea 356 mg Thiocarbonyl diimidazole (2 mmol) and 346 mg 2-amino-5-bromopyridine (2 mmol) in 2 ml acetonitrile were stirred for 1 h at room temperature. 324 mg 2-(2-Benzotriazolyl)ethylamine (Example 402) (2 mmol) was then added. This mixture was stirred for 10 min, and was then heated to reflux. After 20 min 5 ml more acetonitrile and 3 ml dimethylformamide were added to give a clear solution. The solution was cooled and the resulting precipitate was collected after centrifugation. Recrystallization from acetonitrile-dimethylformamide gave 310 mg of the pure titled product.

$^1$H-NMR (DMSO-d$_6$): 4.44 2H (m), 5.15 2H (m), 7.18 1H (d), 7.56 2H (m), 7.90 1H (d), 8.04 3H (m), 10.93 1H (s), 11.41 1H (s)

$^{13}$C-NMR: 44, 55, 114, 118, 118, 127, 142, 144, 146, 152, 180 PPM

Example 411

N-(2-(2,6-difluoro-3-methoxyphenyl)ethyl)-N'-(2-(5-bromopyridyl))thiourea 334 mg 2-(-2,6-difluoro-3-methoxyphenyl)ethylamine (Example 401) (mw 167, 2 mmol) and 566 mg 1-(2-(5-bromopyridyl)thiocarbamoyl)imidazole (Example 392) (mw 283.15) (2 mmol) were mixed in 3 ml acetonitrile. The mixture was slowly heated to reflux, and was then cooled to crystallize. Repeated crystallization from acetonitrile gave 238 mg of the pure titled product.

$^1$H-HNMR: (DMSO) 3.12 2H (t), 3.86 3H (s), 4.00 2H (m), 6.82 3H (m), 7.68–7.72 1H (m), 8.12 1H (d), 9.16 1H (s), 11.35 1H (s)

Example 412

N-(2-(3,4,5-trimethoxy)-benzyl)-N'-(2-thiazolyl)thiourea

The starting material 3,4,5-trimethoxybenzylamine was prepared by reduction of 3,4,5-trimethoxybenzonitrile with cobalt chloride and sodium borohydride, according to the general method described by L. S. Heinzman in *J. Am. Chem. Soc.*, 104, p. 6801 (1980).

3,4,5-trimethylbenzonitrile (965 mg, 5 mmole) and cobolt chloride (2.37 g, 10 mmole) were dissolved in methanol (70 ml). To the solution was added sodium borohydride (1.89 g, 50 mmole). After 3 hrs, the reaction mixture was filtered through Celite, and concentrated to small volume. It was then taken up in chloroform and extracted with 1N HCl (100 ml). The organic phase was discarded. The aqueous phase was basified with aqueous ammonia, and extracted with chloroform. The organic phase was dried over magnesium sulfate, and evaporated in vacuo to yield 3,4,5-trimethoxy-benzylamine (427 mg).

$^1$H-NMR(CDCl$_3$)d: 6.58 (s, 2H, TMPh), 3.85 (m, 6H, 2×MeO), 3.82 (s, 3H, MeO), 3.80 (m, 2H, CH$_2$).

The titled compound was prepared analogous to Example 105.

$^1$H-NMR (CDCl$_3$)d: 7.26 (d, 1H, thiazole), 6.85 (d, 1H, thiazole), 6.64 (s, 2H, TMPh), 4.84 (d, J=5.7 Hz, 2H, CH$_2$), 3.86 (m,6H, MeO), 3.85 (s, 3H, MeO).

$^{13}$C-NMR(CDCl$_3$)d: 177 (C=S), 161 (thiazole), 153 (TMPh), 138 (TMPh), 137 (thiazole), 132 (TMPh), 111 (thiazole), 104 (TMPh), 61 (MeO), 56 (MeO), 50 (CH$_2$).

Example 413

2-Formyl-3-fluoropyridine

Dry ethyl ether (500 mL), n-BuLi (1.6$\underline{M}$ in hexane, 62.5 mL, 0.1 mol), and dry 1,4-diazabicyclo[2.2.2]octane (DABCO) (11.56 g, 0.1 mol) were introduced into a 1 L flask under a dry N$_2$ stream at −60° C. and the resulting cloudy solution was stirred for 1 hour at −20° C. The mixture was then cooled to −75° C. and an ethyl ether (50 mL) solution of 3-fluoropyridine (9.81 g, 0.1 mol) was added dropwise and stirring continued for 1½ hours at −60° C. The mixture was recooled to −75° C., dry N,N-dimethylformamide (8.52 mL, 0.11 mol) dissolved in ethyl ether (50 mL) was added dropwise and the mixture stirred for 2 hours at −75° C. Water (175 mL) was introduced slowly at −10° C., the aqueous layer extracted with ethyl acetate (5×200 mL), and the combined extracts were dried over anhydrous sodium sulfate. Solvent removal produced a dark brown oil which after vacuum distillation and purification by chromatography on silica gel provided 4.4 g (35%) of the titled product as an off-white crystalline solid:

mp 48°–49° C.;

IR (CHCl$_3$, cm$^{-1}$) 3071, 3020, 2873, 2842, 1720, 1588, 1461, 1441;

$^1$H NMR (300 MHz, CDCl$_3$) δ10.21 (s, 1H), 8.62 (m, 1H), 7.57 (m, 2H);

MS (FD) m/e 125 (M$^+$);

UV (EtOH) 263 nm (ε=1551), 201 nm (ε=2188)

Example 414

2-Hydroxymethyl-3-fluoropyridine

A solution of 2-formyl-3-fluoropyridine (4.0 g, 32 mmol) and sodium borohydride (309 mg, 8 mmol) in absolute ethanol (40 mL) was stirred at 0° C. for 15 minutes and at room temperature for 1 hour. The reaction was quenched with saturated aqueous ammonium chloride (5 mL) and filtered through diatomaceous earth to remove solids. The filtrate was evaporated and the resultant white solid was dissolved in ethyl acetate and water. The aqueous layer was extracted with ethyl acetate (5×30 mL) and the combined extracts were dried over anhydrous sodium sulfate. Solvent removal provided 3.78 g (93%) of the titled product as a pale yellow oil:

IR (CHCl$_3$, cm$^{-1}$) 3607, 3439, 3019, 1607, 1576, 1451, 1416, 1312, 1257, 1218, 1209, 1167, 1105, 1053, 857, 803;

$^1$H NMR (300 MHz, CDCl$_3$) δ8.38 (m, 1H), 7.39 (m, 1H), 7.26 (m, 1H), 4.83 (s, 2H), 3.73 (br s, 1H);

MS (FD) m/e 127 (M$^+$);

UV (EtOH) 263 nm (ε=2796), 201 nm (ε=3651)

Anal. Calcd for C$_6$H$_6$FNO: C, 56.69; H, 4.76; N, 11.02. Found: C, 56.45; H, 4.97; N, 10.89

Example 415

2-chloromethyl-3- fluoropyridine hydrochloride

To a solution of 2-hydroxymethyl-3-fluoropyridine (3.43 g, 27 mmol) in dichloromethane (30 mL) cooled to −10° C. was added neat thionyl chloride (4.4 mL, 60 mmol) dropwise over 5 minutes. The resultant pale green solution was stirred at −10° C. for 3 hours followed by evaporation to dryness to provide 4.66 g (.95%) of the titled product as an off-white crystalline solid:

IR (CHCl$_3$, cm$^{-1}$) 2984, 1732, 1551, 1470, 1452, 1333, 1286, 1273, 1237, 1219, 1208, 1193, 1094, 905, 863, 806;

$^1$H NMR (300 MHz, CDCl$_3$) δ8.69 (m, 1H), 8.06 (m, 1H), 7.89 (m, 1H), 5.09 (s, 2H);

MS (FD) m/e 145 (M$^+$ free base), 147 (M+2 free base)

Example 416

2-cyanomethyl-3-fluoropyridine

A solution of 2-chloromethyl-3-fluoropyridine hydrochloride (4.85 g, 26.7 mmol) and potassium cyanide (3.47 g, 53.4 mmol) in methanol (50 mL) and water (20 mL) was stirred am approximately 55° C. for 17 hours. The resultant black solution was concentrated to an oil under reduced pressure, redissolved in ethyl acetate and water, and adjusted to pH 11.5 with solid sodium carbonate. The aqueous layer was salted with sodium chloride, extracted with ethyl acetate (7×40 mL), and the combined extracts were dried over anhydrous sodium sulfate. Solvent removal provided 3.6 g (99%) of (4) as a black solid:

IR (CHCl$_3$, cm$^{-1}$) 3019, 3011, 2977, 1708, 1603, 1578, 1454, 1412, 1259, 1222, 1219, 1215, 1161, 1097, 1047, 804;

$^1$H NMR (300 MHz, CDCl$_3$) δ8.43 (m, 1H), 7.42 (m, 1H), 7.33 (m, 1H), 3.97 (s, 1H), 3.96 (s, 1H); MS (FD) m/e 136 (M$^+$); UV (EtOH) 263 nm (ε=3719), 203 nm (ε=3707)

Example 417

2-aminoethyl-3-fluoropyridine

To a solution of 2-cyanomethyl-3-fluoropyridinein absolute ethanol (75 mL) and 5$\underline{N}$ hydrochloric acid (0.3 mL) was added platinum oxide catalyst (0.64 g) and the mixture was hydrogenated at 60 psig for 1 hour in a Paar hydrogenation apparatus. Filtered off the catalyst, concentrated the filtrate under reduced pressure to a brown oil, dissolved the oil in water (40 mL) and ethyl acetate (10 mL) and adjusted to pH 0.9 with concentrated hydrochloric acid. Separated the layers, extracted the ethyl acetate layer with 1$\underline{N}$ HCl (1×10 mL), combined the acidic aqueous extracts and washed them with ethyl acetate (4×30 mL). Adjusted the aqueous layer to pH 10.8, extracted with dichloromethane (6×30 mL), and the combined extracts were dried over anhydrous sodium sulfate. Solvent removal provided 1.58 g (70%) of the titled product as a brown oil:

IR (CHCl$_3$, cm$^{-1}$) 2969, 2873, 1632, 1602, 1575, 1550, 1450, 1414, 1359, 1246, 1219, 1212, 1203, 1169, 1093;

$^1$H NMR (300 MHz, CDCl$_3$) δ8.31 (m, 1H), 7.29 (m, 1H), 7.13 (m, 1H), 3.03 (m, 4H), 1.80 (br s, 2H);

MS (FD) m/e 140 (M$^+$);

Titration (66% DMF/H$_2$O) pKa 9.56

Example 418

1-[(2-[5-chloro]pyridyl)thiocarbamoyl]imidazole

A solution of 1,1'-thiocarbonyldiimidazole (4.95 g, 25 mmol) and 2-amino-5-chloropyridine (3.28 g, 25 mmol) in acetonitrile (75 mL) was stirred at room temperature for 23 hours. The resulting precipitate was collected by filtration to provide 3.42 g (57%) of the titled product:

IR (KBr, cm$^{-1}$) 3218, 3090, 1599, 1572, 1551, 1529, 1471, 1455, 1390, 1375, 1340, 1310, 1228, 1183, 1109, 1053, 939, 831;

$^1$H NMR (300 MHz, DMSO-d$_6$) δ8.58 (m, 1H), 8.25 (m, 1H), 8.05 (br s, 1H), 8.03 (m, 1H), 7.65 (m, 1H), 7.15 (d, J=8 Hz, 1H), 6.80 (s, 1H);

MS (FAB) m/e 239 (M+1);

UV (EtOH) 305 nm (ε=15141), 273 nm (ε=14730), 226 nm (ε=11407), 203 nm (ε=16456).

Example 419

1-[(2-[5-bromo]pyridyl)thiocarbamoyl]imidazole

A solution of 1,1'-thiocarbonyldiimidazole (4.95 g, 25 mmol) and 2-amino-5-bromopyridine (4.46 g, 25 mmol) in acetonitrile (75 mL) was stirred at room temperature for 23 hours. The resulting precipitate was collected by filtration to provide 5.42 g (76%) of the titled product:

IR (KBr, cm$^{-1}$) 3218, 3088, 1594, 1565, 1550, 1465, 1387, 1370, 1340, 1309, 1251, 1196, 1182, 1096, 1053, 938, 828;

$^1$H NMR (300 MHz, DMSO-d$_6$) δ8.57 (m, 1H), 8.30 (m, 1H), 8.15 (m, 1H), 8.03 (br s, 1H), 7.75 (m, 1H), 7.15 (d, J=8 Hz, 1H), 6.80 (s, 1H); MS (FAB) m/e 284 (M+1); UV (EtOH) 304 nm (ε=13932), 274 nm (ε=13051), 230 nm (ε=11098), 204 nm (ε=17821).

Example 420

N-[2-(2-[3-fluoro]pyridyl)ethyl]-N'-[2-(5-bromo)pyridyl]thiourea

A solution of 1-[(2-[5-bromo]pyridyl)thiocarbamoyl]imidazole (7) (1.42 g, 5 mmol) and 2-aminoethyl-3-fluoropyridine (5) (0.7 g, 5 mmol) in N,N-dimethylformamide (20 mL) was stirred at 95° C. for 3 hours. The reaction was cooled to room temperature, poured into ethyl acetate, and washed with water, saturated aqueous sodium bicarbonate, and brine. The organic layer was dried over anhydrous sodium sulfate, concentrated and the resultant solid was purified by chromatography on silica gel to provide 0.33 g (19%) of the titled product as a white solid:

mp 184°–187° C.;

IR (KBr, cm$^{-1}$) 3161, 3023, 1597, 1579, 1555, 1524, 1488, 1473, 1447, 1364, 1342, 1315, 1236, 1221, 1172, 1142, 1087, 833;

$^1$H NMR (300 MHz, DMSO-d$_6$) δ11.38 (m, 1H), 10.64 (s, 1H), 8.41 (m, 1H), 8.14 (d, J=2 Hz, 1H), 7.91 (m, 1H), 7.63 (m, 1H), 7.33 (m, 1H), 7.06 (d, J=9 Hz, 1H), 4.01 (m, 2H), 3.10 (t, J=6 Hz, 2H);

MS (FD) m/e 355 (M$^+$), 357 (M+2);

UV (EtOH) 305 nm (ε=13169), 273 nm (ε=25811), 201 nm (ε=17493).

Example 421

N-[2-(2-[3-fluoro]pyridyl)ethyl]-N'-[2-(5-chloro)pyridyl]thiourea

A solution of 1-[(2-[5-chloro]pyridyl)thiocarbamoyl]imidazole (2.39 g, 10 mmol) and 2-aminoethyl-3-fluoropyridine (1.4 g, 10 mmol) in N,N-dimethylformamide (25 mL) was stirred at 95° C. for 3 hours. The reaction was cooled to room temperature, poured into ethyl acetate, and washed with water, saturated aqueous sodium bicarbonate, and brine. The organic layer was dried over anhydrous sodium sulfate, concentrated and the resultant solid was purified by chromatography on silica gel to provide 0.96 g (31%) of the titled product as an off-white solid:

mp 170°–173° C.;

IR (KBr, cm$^{-1}$) 3167, 3022, 1603, 1583, 1554, 1524, 1492, 1474, 1449, 1367, 1342, 1317, 1238, 1222, 1173, 1142, 1087, 835, 803;

$^1$H NMR (300 MHz, DMSO-d$_6$) δ11.39 (m, 1H), 10.65 (s, 1H), 8.42 (m, 1H), 8.07 (d, J=2 Hz, 1H), 7.81 (m, 1H), 7.63 (m, 1H), 7.33 (m, 1H), 7.11 (d, J=9 Hz, 1H), 4.01 (m, 2H), 3.10 (t, J=6 Hz, 2H);

MS (FD) m/e 310 (M$^+$), 312 (M+2);

UV (EtOH) 305 nm (ε=11338), 272 nm (ε=23394).

Example 422

(+) and (−) N-(cis-2-phenylcyclopropyl)-S-α-methoxy phenylacetamide

S-α-methoxyphenylacetic acid (2.0 g, 12 mmol) was dissolved in dichloro-methane (100 ml) and oxalylchloride (1.36 ml, 16 mmol) was added together with 2 drops of N,N-dimethylformamide. The solution was stirred under an atmosphere of nitrogen gas at ambient temperature for 120 minutes. The solvent and excess reagent were removed on a rotavapor. The oily residue was dissolved in 100 ml dichloromethane and D,L-cis-phenylcyclopropylamine (Example 202) (2.0 g, 15 mmol) in pyridine (5.0 ml) was added. The solution was stirred for 15 minutes and diethyl ether (200 ml) was added. The precipitate was filtered off and the solution was evaporated. The residual crystalline diastereoisomerical mixture was purified by flash-chromathography by elution with ethyl acetate-toluene-dichloroethane (1:2:2). The fractions containing the faster eluting product were evaporated to yield product A. The slower eluting fractions were evaporated to yield product B.

A] $^1$H-NMR (35 mg in 0.6 ml CDCl$_3$, 294K) 0.99–1.06 (1H, m), 1.29–1.38 (1H, m), 2.29–2.38 (1H, q), 3.00 (3H, s), 3.07–3.17 (m), 4.41 (1H, s), 6.3 (1H), 7.16–7.32 (10H, m).

$^{13}$C-NMR: 11.18, 21.83, 27.82, 57.11, 83.68, 126.34, 126.43, 128.08, 128.18, 128.26, 128.78, 136.15, 136.85, 171.75, 171.75.

calc for C$_{18}$H$_{19}$N: C 76.84%, H 6.80%, N 4.99%

Mp. 136.7°–137.1° C.

B] $^1$H-NMR (same conditions as for A): 1.09–1.16 (1H, q), 1.32–1.41 (1H, q), 2.24–2.38 (1H, q), 3.10–3.20 (4H, m), 4.45, (1H, s), 6.4 (1H), 6.95–6.99 (2H, m), 7.15–7.27 (7H, m).

$^{13}$C-NMR: 10.69, 21.82, 27.85, 56.87, 83.63, 126.35, 126.87, 128.00, 128.13, 128.19, 128.83, 135.88, 136.54, 171.55.

Calc for C$_{18}$H$_{19}$N: C 76.84%, H 6.80%, N 4.99%

Mp. 143.6°–144.7° C.

Example 423

(−) cis-2-phenylcyclopropylamine

Compound A (1.2 g) was refluxed in a mixture of water-dioxane-hydrochloric acid conc. aq. (1:1:1) for 4 hours. The solution was diluted with water, washed with dichloromethane, basified with ammonium hydroxide (conc. aq.), extracted with dichloromethane, dried with sodium sulfate, filtered and evaporated to yield the titled product as an oil.

$^1$H-NMR CDCl$_3$ δ ppm 0.8–0.9 (1H, CH$_2$, m), 1.1–1.2 (1H, CH$_2$, m), 2.–2.1 (1H, PhCH, q), 2.6–2.7 (1H, CHNH$_2$, m), 7.1–7.4 (5H, Ph).

Example 424

(+) cis-2-phenylcyclopropylamine

Compound B (1.2 g) was refluxed in a mixture of water-dioxane-hydrochloric acid conc. aq. (1:1:1) for 4 hours. The solution was diluted with water, washed with dichloromethane, basified with ammonium hydroxide (conc. aq.), extracted with dichloromethane, dried with sodiumsulfate, filtered and evaporated to yield the titled product as an oil.

$^1$H-NMR CDCl$_3$ δ ppm 0.8–0.9 (1H, CH$_2$, m), 1.1–1.2 (1H, CH$_2$, m), 2.0–2.1 (1H, PhCH, q), 2.6–2.7 (1H, CHNH$_2$, m), 7.1–7.4 (5H, Ph). D

[a]=+62.7° (C 1, CHCl$_3$) 20

Example 425

(−)-N-(cis-2-phenylcyclopropyl)-N'-(5-chloropyrid-2-yl)-thiourea (+)-N-cis-2-phenylcyclopropylamine (0.23 g, 1.7 mmol) from Example 424 was condensed with 1-(5-chloropyrid-2-yl-thiocarbamoyl)-imidazole (0.4 g, 1.7 mmol) according to the procedure of Example 372 to yield the titled product as crystals.

$^1$H-NMR CDCl$_3$ δ ppm 1.2–1.3 (1H, m, CH$_2$), 1.5–1.6 (1H, m, CH$_2$), 2.5–2.6 (1H, q, PhCH), 3.7–3.8 (CHN), 6.6–6.7 (1H, d, pyr), 7.2–7.5 (7H, Ph, pyr), 8.9–9.0 (1H, NH), 10.8–10.9 (1H, NH).

Mp. 189.6–191.3° C. D

[a]=−62.7° (C 1, CHCl$_3$)

Example 426

(+)-N-(cis-2-phenylcyclopropyl)-N'-(5-chloropyrid-2-yl)thiourea (−)-N-cis-2-phenylcyclopropylamine (0.23 g, 1.7 mmol) from Example 423 was condensed with 1-(5-chloropyrid-2-yl-thiocarbamoyl)-imidazole (0.4 g, 1.7 mmol) according to the procedure of Example 372 to yield the titled product as crystals.

$^1$H-NMR CDCl$_3$ δ ppm 1.2–1.3 (1H, m, CH$_2$), 1.5–1.6 (1H, m, CH$_2$), 2.5–2.6 (1H, q, PhCH), 3.7–3.8 (CHN), 6.6–6.7 (1H, d, pyr), 7.2–7.5 (7H, Ph, pyr), 8.9–9.0 (1H, NH), 10.8–10.9 (1H, NN).

Mp. 189.2°–191.8° C. D

[a]=+59.3° (C 1, CHCl$_3$) 20

Example 427

(−)-N-(cis-2-phenylcyclopropyl)-N'-(5-bromopyrid-2-yl)thiourea (+)-N-cis-2-phenylcyclopropylamine from Example 424 and 2-amino-5-bromopyridine were reacted according to the procedures of Examples 93 and 94 using 2-amino-5-bromopyridine instead of 2-aminothiazole, to give the titled product as crystals.

$^1$H-NMR (CDCl$_3$): 1.19–1.26 (m, 1H), 1.47–1.55 (m, 1H), 2.52 (q, 1H), 3.66–3.75 (m, 1H), 6.66 (dd, ! H), 7.27–7.41 (m, 5H), 7.47 (d, 1H), 7.60 (dd, 1H), 8.98 (broad s., 1H), 10.88 (broad s., 1H).

Mp=192.0°–193.0° C. D

[a]=−52.8° (C 1, CHCl$_3$) 20

Example 428

(+)-N-(cis-2-phenylcyclopropyl)-N'-(5-bromopyrid-2-yl)thiourea (−)-N-cis-2-phenylcyclopropylamine from Example 423 and 2-amino-5-bromopyridine were reacted according to the procedures of Examples 93 and 94 using 2-amino-5-bromopyridine instead of 2-aminothiazole, to give the titled product as crystals.

$^1$H-NMR (CDCl$_3$): 1.19–1.26 (m, 1H), 1.47–1.55 (m, 1H), 2.52 (q, 1H), 3.66–3.75 (m, 1H), 6.66 (dd, 1H), 7.27–7.41 (m, 5H), 7.47 (d, 1H), 7.60 (dd, 1H), 8.98 (broad s., 1H), 10.88 (broad s., 1H).

Mp=195.5°–196.5° C. D

[a]=+50° (C 1, CHCl$_3$) 20

Example 429

N-(2(2,6-difluoro-3-methoxymethyl)phenethyl)-N'-(2-amino-5-bromopyridyl thiourea A) Preparation of 2,6-Difluoro-1-(1,3-propylendioxan-2-yl)benzene To 7.05 g (50 mmol) of 2,6-difluorobenzaldehyde in 300 ml toluene was added 50 mg p-toluenesulfonic acid monohydrate and 20 ml propylene glycol. The reaction mixture was refluxed with stirring, and the water formed was removed by Dean-Stark trap. After 2 hours the mixture was cooled, washed with 50 ml saturated NaHCO$_3$. Toluene layer was dried over anhydrous Na$_2$SO$_4$, and solvent was removed under reduced pressure giving 9.08 g (92%) o the titled compound as a pale oil.

$^1$H-NMR (CDCl$_3$) 67.23 (m, 1H), 6.87 (t,2H), 6.38 and 6.25 (s,1H), 4.47, 4.30 and 4.18 (m,m and t, 3H), 3.63 and 3.51 and t, 1H) 1.39 and 1.31 (dd, 3H)

$^{13}$C-NMR(CDCl$_3$) δ16.95, 17.55, 70.98, 72,14, 72.70, 73.96, 96.07, 96.13, 96.22, 96.46, 96.54, 96.60, 111.31, 111.43, 111.58, 111.71, 114.40, 130.51, 130.68, 130.84, 131.01, 159.27, 159.41, 159.53, 163.30, 163.43, 163.56.

B) Preparation of 2,6-Difluoro-3-methoxymethyl-2-(1,3-propylendioxan-2-yl)benzene 7.0 g (34.6 mmol) of 2,6-Difluoro-1(1,3-propylendioxan-2-yl)benzene was dissolved in 100 ml dry THF. The solution was cooled to −70° C. under nitrogen, and 16.8 ml n-butyllithium (2.5M) was added dropwise under 10 minutes. After stirring for 10 minutes, 7.0 ml chloromethylmethyl ether was added under 2 minutes. The mixture reached room temperature during 18 hours, poured into 50 ml water and 50 ml ammonia solution (25%), and extracted into (3×50 ml) ether. The combined ether layers were washed with brine, dried over anhydrous Na$_2$SO$_4$, and solvent was removed under reduced pressure giving 7.8 g of crude product as a pale yellow oil which was purified by dry column flash chromatography (DCF) on silica gel (5×100 ml hexane and 5×100 ml 1:10 ether-hexane)—to yield 4.0 g of the titled compound as a pale oil.

$^1$H-NMR(CDCl$_3$) δ7.34 (m, 1H), 6.88 (t, 1H), 6.35 and 6.25 (s, 1H) 4.43 (s, 2H), 4.43, 4.30 and 4.10 (m, m and t, 3H) 3.62 and 3.52 (t and t, 1H), 3.36 (s, 3H) 1.39 and 1.31 (dd, 3H)

$^{13}$C-NMR (CDCl$_3$) δ17.06, 17.40, 58.02, 67.28, 71.08, 72.27, 72.79, 74.07, 95.98, 96.23, 96.31, 96.64, 96.70, 96.77, 110.53, 110.78, 110.86, 111.18, 111.49, 111.53, 130.69, 130.80, 130.95, 131.07, 157.10, 158.86, 161.12, 162.87.

C) Preparation of 2,6-Difluoro-3-methoxymethylbenzaldehyde

To 0.23 g (0.94 mmol) 2,6-Difluoro-3-methoxymethyl-1l-(1,3-propylendioxan-2-yl)benzene in 30 ml dioxane was added 20 ml of 2M HCl (aq.) at room temperature. The mixture was stirred 76 h at this temperature, poured into 50 ml water, and extracted into (3×50 ml) ether. The combined ether layers were washed with brine, dried over anhydrous Na$_2$SO$_4$, and solvent was removed under reduced pressure yielding 0.15 g of the titled pruct as a pale oil.

$^1$H-NMR(CDCl$_3$) δ7.34 (m, 1H),10.31 (s, 1H), 7.63 (m, 1H), 6.97 (t, 1H), 4.48 (s, 2H), 3.42 (s, 3H)

$^{13}$C-NMR(CDCl$_3$) δ58.17, 58.37,66.67, 66.73, 111.89, 111.95, 112.22, 112.27, 122.31, 123.35, 135.83, 135.96, 140.00, 136.12, 158.21, 158.30, 160.16, 160.24, 162.38, 162.50, 164.33, 164.42, 184.47.

D) Preparation of N-(2(2,6-Difluoro-3-methoxymethyl)phenethyl)-N'-(2-amino-5-bromopyridyl)thiourea The starting material, 0.050 g 2,6-Difluoro-3-methoxymethylphenethylamine, was prepared from 2,6-difluoro-3-methoxymethylbenzaldehyde in a manner analogous to Example 151, and was condensed with product of Example 344 in 3 ml acetonitrile. The stirred mixture was refluxed 30 minutes, cooled, poured into 10 ml water and extracted into (3×20 ml) ether. The combined ether layers were washed with brine, dried over anhydrous Na₂SO₄, and solvent was removed under reduced pressure giving 0.079 g of crude product as a brownish solid which was purified by flash chromatography on silaca gel (1:1 ether-hexane) to afford 0.040 g of titled product as white crystals:
mp. 141.9°–142.9° C.

¹H-NMR(CDCl₃) δ11.31 (broad s, 1H), 8.78 (broad s, 1H), 8.15 (d, 1H), 7.72 (dd, 1H), 7.28 (m, 1H), 6.88 (t, 1H), 6.69 (m,1H), 4.44 (s,2H), 4.00(m,2H), 3.36 (s,3H), 3.10 (s,2H).

¹³C-NMR(CDCl₃) δ21.67, 44.94, 58.29, 67.71, 67.74, 110.65, 110.96, 111.00, 111.49, 112.63, 128.54, 128.69, 128.80, 141.13, 146.42, 151.45, 179.53.

We claim:

1. A method for inhibiting the replication of HIV which comprises contacting a compound of the formula below

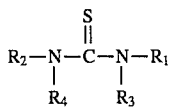

in which R₁ is a cyclo(C₃–C₈)alkyl, cyclo (C₃–C₈) alkenyl; isothiazolyl, substituted isothiazolyl, tetrazolyl, substituted tetrazolyl, triazolyl, substituted triazolyl, pyridyl, substituted pyridyl, imidazolyl, substituted imidazolyl, phenyl, substituted phenyl, naphthyl, substituted naphthyl, benzoxazolyl, substituted benzoxazolyl, benzimidazolyl, substituted benzimidazolyl, thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thiadiazolyl, substituted thiadiazolyl, benzotriazolyl, substituted benzotriazolyl, pyrrolyl, substituted pyrrolyl, indolyl, substituted indolyl, benzothienyl, substituted benzothienyl, thienyl, substituted thienyl, benzofuryl, substituted benzofuryl, furyl, substituted furyl, quinolinyl, substituted quinolinyl, isoquinolinyl, substituted isoquinolinyl, pyrazolyl, and substituted pyrazolyl;

R₂ is a group of the formula

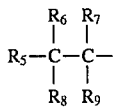

wherein

R₅ is R₁ as defined above; or R₅ is a group of the formula

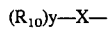

wherein y is 1 or 2; X is N, S, O and R₁₀ is R₁ as defined; or R₁₀ is hydrogen, C₁–C₆ alkyl, C₂–C₆ alkenyl, or C₂–C₆ alkynyl; or R₅ is hydrogen, halo, cyano, carboxy, amino, thio, hydroxy, C₁–C₄ alkoxy, C₁–C₆ alkyl, C₂–C₈ alkenyl, C₂–C₈ alkynyl, or C₂–C₈ alkenoxy;

R₆, R₇, R₈, and R₉ are independently C₃–C₈ cycloalkyl, hydrogen, C₁–C₆ alkyl, C₂–C₆ alkenyl, C₂–C₆ alkynyl, halo, amino, nitro, cyano, C₁–C₅ alkoxy, hydroxy, carboxy, hydroxymethyl, aminomethyl, carboxymethyl, C₁–C₄ alkylthio, C₁–C₄ alkanoyloxy, carbamoyl, or a halo substituted C₁–C₆ alkyl; or two of which, along with the carbons to which they are attached, combine to form a stable, saturated or unsaturated, substituted or unsubstituted, 3 to 7 membered organic monocylic ring having 0 to 4 hetero atoms selected from S, O, or N; or R₆ and R₈, or R₇ and R₉, along with the carbon to which they are attached, form a stable, saturated or unsaturated, substituted or unsubstituted, 3 to 7 membered organic monocylic ring having 0 to 4 hetero atoms selected from S, O, or N;

R₃ and R₄ are independently hydrogen, hydroxy, C₁–C₆ alkyl, C₂–C₆ alkenyl, C₂–C₆ alkynyl, amine, cyano, nitro, C₁–C₅ alkoxy, carboxy, hydroxymethyl, aminomethyl, carboxymethyl, C₁–C₄ alkylthio, C₁–C₄ alkanoyloxy, halo-substituted (C₁–C₆) alkyl, or carbamoyl; or salts thereof, with HIV.

2. The method of claim 1 wherein R₁ and R₅ are independently cyclo(C₃–C₈)alkyl, cyclo (C₃–C₈) alkenyl; isothiazolyl, substituted isothiazolyl, tetrazolyl, substituted tetrazolyl, triazolyl, substituted triazolyl, pyridyl, substituted pyridyl, imidazolyl, substituted imidazolyl, phenyl, substituted phenyl, naphthyl, substituted naphthyl, benzoxazolyl, substituted benzoxazolyl, benzimidazolyl, substituted benzimidazolyl,thiazolyl, substituted thiazolyl, oxazolyl, substituted oxazolyl, benzothiazolyl, substituted benzothiazolyl, pyrazinyl, substituted pyrazinyl, pyridazinyl, substituted pyridazinyl, thiadiazolyl, substituted thiadiazolyl, benzotriazolyl, substituted benzotriazolyl, pyrrolyl, substituted pyrrolyl, indolyl, substituted indolyl, benzothienyl, substituted benzothienyl, thienyl, substituted thienyl, benzofuryl, substituted benzofuryl, furyl, substituted furyl, quinolinyl, substituted quinolinyl, isoquinolinyl, substituted isoquinolinyl, pyrazolyl, and substituted pyrazolyl.

3. The method of claim 1 wherein R₃, R₄, R₆, R₇, R₈, and R₉ are all hydrogen.

4. The method as recited in claim 3 wherein R₅ is phenyl, substituted phenyl, naphthyl, substituted naphthyl, pyridyl, substituted pyridyl, or cyclohexenyl.

5. The method as recited in claim 3 R₁ is thiazolyl, substituted thiazolyl, benzothiazolyl, substituted benzothiazolyl, pyrazinyl, substituted pyrazinyl, pyridyl, substituted pyridyl, pyridazinyl, substituted pyridazinyl, thiadiazolyl, or substituted thiadiazolyl.

6. The method as recited in claim 1 wherein said compound is selected from:

N-(2-(2-methoxyphenyl)ethyl)-N'-[2-(4-cyano)thiazolyl]thiourea

N-(2-(2-methoxyphenyl)ethyl)-N'-[2-(4-trifluoromethyl)thiazolyl]thiourea

N-(2-(2-methoxyphenyl)ethyl)-N'-[2-(4-ethyl)thiazolyl]thiourea

N-(2-(2-methoxyphenyl)ethyl)-N'-[2-(5-bromo)pyridyl]thiourea

N-(2-(2-methoxyphenyl)ethyl)-N'-[2-(5-chloro)pyridyl]thiourea

N-(2-(3-methoxyphenyl)ethyl)-N'-[2-(4-cyano)thiazolyl]thiourea

N-(2-(3-methoxyphenyl)ethyl)-N'-[2-(4-trifluoromethyl)thiazolyl]thiourea

N-(2-(3-methoxyphenyl)ethyl)-N'-[2-(4-ethyl)thiazolyl]thiourea

N-(2-(3-methoxyphenyl)ethyl)-N'-[2-(5-bromo)pyridyl]thiourea

N-(2-(3-methoxyphenyl)ethyl)-N'-[2-(5-chloro)pyridyl]thiourea

N-(2-(2-ethoxyphenyl)ethyl)-N'-[2-(5-bromo)pyridyl]thiourea

N-(2-(2-ethoxyphenyl)ethyl)-N'-[2-(5-chloro)pyridyl]thiourea

N-(2-(2,6-difluorophenyl)ethyl)-N'-[2-(4-cyano)thiazolyl]thiourea

N-(2-(2,6-difluorophenyl)ethyl)-N'-[2-(4-trifluoromethyl)thiazolyl]thiourea

N-(2-(2,6-difluorophenyl)ethyl)-N'-[2-(4-ethyl)thiazolyl]thiourea

N-(2-(2,6-difluorophenyl)ethyl)-N'-[2-(5-bromo)pyridyl]thiourea
N-(2-(2,6-difluorophenyl)ethyl)-N'-[2-(5-chloro)pyridyl]thiourea
N-(2-(2,6-difluorophenyl)ethyl)-N'-[2-(5-bromo)pyrazinyl]thiourea
N-(2-(2,6-difluorophenyl)ethyl)-N'-[3-(6-chloro)pyridazinyl)]thiourea
N-(2-(2-fluoro-6-methoxyphenyl)ethyl)-N'-[2-(5-bromo)pyridyl]thiourea
N-(2-(2-fluoro-6-methoxyphenyl)ethyl)-N'-[2-(5-chloro)pyridyl]thiourea
N-(2-(2-chlorophenyl)ethyl)-N'-[2-(4-cyano)thiazolyl]thiourea
N-(2-(2-chlorophenyl)ethyl)-N'-[2-(4-ethyl)thiazolyl]thiourea
N-(2-(2-chlorophenyl)ethyl)-N'-[2-(5-bromo)pyridyl]thiourea
N-(2-(2-chlorophenyl)ethyl)-N'-[2-(5-chloro)pyridyl]thiourea
N-(2-(3-chlorophenyl)ethyl)-N'-[2-(4-cyano)thiazolyl]thiourea
N-(2-(3-chlorophenyl)ethyl)-N'-[2-(4-ethyl)thiazolyl]thiourea
N-(2-(3-chlorophenyl)ethyl)-N'-[2-(5-bromo)pyridyl]thiourea
N-(2-(3-chlorophenyl)ethyl)-N'-[2-(5-chloro)pyridyl]thiourea
N-(2-(1-cyclohexenyl)ethyl)-N'-[2-(4-cyano)thiazolyl]thiourea
N-(2-(1-cyclohexenyl)ethyl)-N'-[2-(4-trifluoromethyl)thiazolyl]thiourea
N-(2-(1-cyclohexenyl)ethyl)-N'-[2-(4-ethyl)thiazolyl]thiourea
N-(2-(1-cyclohexenyl)ethyl)-N'-[2-(5-bromo)pyridyl]thiourea
N-(2-(1-cyclohexenyl)ethyl)-N'-[2-(5-chloro)pyridyl]thiourea
N-(2-(1-cyclohexenyl)ethyl)-N'-[(3-(6-chloro)pyridazinyl)]thiourea
N-(2-(2,5-dimethoxyphenyl)ethyl)-N'-[2-(5-chloro)pyrazinyl]thiourea
N-(2-(2,5-dimethoxyphenyl)ethyl)-N'-[2-(5-bromo)pyrazinyl]thiourea
N-(2-cis-phenylcyclopropyl)-N'-[2-(5-bromo)pyridyl]thiourea
N-(2-cis-phenylcyclopropyl)-N'-[2-(5-chloro)pyridyl]thiourea
N-[2-(2-pyridyl)ethyl]-N'-[2-(5-bromo)pyridyl]thiourea
N-[2-(2-pyridyl)ethyl]-N'-[2-(5-chloro)pyridyl]thiourea
N-[2-(2-pyridyl)ethyl]-N'-[2-(5-trifluoromethyl)pyridyl]thiourea
N-[2-(2-pyridyl)ethyl]-N'-[2-(5-ethyl)pyridyl]thiourea
N-[2-(2-pyridyl)ethyl]-N'-[2-(5-methyl)pyridyl]thiourea
N-[2-(2-(6-methoxy)pyridyl)ethyl]-N'-[2-(5-bromo)pyridyl]thiourea
N-[2-(2-(6-methoxy)pyridyl)ethyl]-N'-[2-(5-chloro)pyridyl]thiourea
N-[2-(2-(6-ethoxy)pyridyl)ethyl]-N'-[2-(5-bromo)pyridyl]thiourea
N-[2-(2-(6-ethoxy)pyridyl)ethyl]-N-[2-(5-chloro)pyridyl]thiourea
N-[2-(2-(6-fluoro)pyridyl)ethyl]-N-[2-(5-bromo)pyridyl]thiourea
N-[2-(2-(6-fluoro)pyridyl)ethyl]-N-[2-(5-chloro)pyridyl]thiourea
N-[2-(2-(3-fluoro)pyridyl)ethyl]-N-[2-(5-bromo)pyridyl]thiourea
N-[2-(2-(3-fluoro)pyridyl)ethyl]-N-[2-(5-chloro)pyridyl]thiourea
N-[2-(2-(6-chloro)pyridyl)ethyl]-N-[2-(5-bromo)pyridyl]thiourea
N-[2-(2-(6-chloro)pyridyl)ethyl]-N-[2-(5-chloro)pyridyl]thiourea
N-[2-(2-(3-methoxy-6-fluoro)pyridyl)ethyl]-N'-[2-(5-bromo)pyridyl]thiourea
N-[2-(2-(3-methoxy-6-fluoro)pyridyl)ethyl]-N'-[2-(5-chloro)pyridyl]thiourea
N-[2-(2-(5-ethoxy-6-fluoro)pyridyl)ethyl]-N'-[2-(5-bromo)pyridyl]thiourea
N-[2-(2-(5-ethoxy-6-fluoro)pyridyl)ethyl]-N'-[2-(5-chloro)pyridyl]thiourea
N-[2-(2-(3-ethoxy-6-fluoro)pyridyl)ethyl]-N'-[2-(5-bromo)pyridyl]thiourea
N-[2-(2-(3-ethoxy-6-fluoro)pyridyl)ethyl]-N'-[2-(5-chloro)pyridyl]thiourea
N-[2-(2-(3,6-difluoro)pyridyl)ethyl]-N'-[2-(5-bromo)pyridyl]thiourea
N-[2-(2-(3,6-difluoro)pyridyl)ethyl]-N'-[2-(5-chloro)pyridyl]thiourea
N-[2-(cis-2-pyridyl)cyclopropyl]-N'-[2-(5-bromo)pyridyl]thiourea
N-[2-(cis-2-pyridyl)cyclopropyl]-N'-[2-(5-chloro)pyridyl]thiourea
N-[2-(cis-2-(6-fluoro)pyridyl)cyclopropyl]-N'-[2-(5-bromo)pyridyl]thiourea
N-[2-(cis-2-6-fluoro)pyridyl)cyclopropyl]-N'-[2-(5-chloro)pyridyl]thiourea
N-[2-(cis-2-(6-methoxy)pyridyl)cyclopropyl]-N'-[2-(5-bromo)pyridyl]thiourea
N-[2-(cis-2-6-methoxy)pyridyl)cyclopropyl]-N'-[2-(5-chloro)pyridyl]thiourea
N-[2-(cis-2-(6-ethoxy)pyridyl)cyclopropyl]-N'-[2-(5-bromo)pyridyl]thiourea
N-[2-(cis-2-6-ethoxy)pyridyl)cyclopropyl]-N'-[2-(5-chloro)pyridyl]thiourea
N-[2-(2,6-difluoro-3-methoxyphenyl)ethyl]-N'-[2-(5-bromo)pyridyl]thiourea; and salts thereof.

7. The method as recited in claim 1 further comprising also contacting at least one other anti-HIV agent with said HIV.

8. The method as recited in claim 7 wherein said agent is selected from ddI, ddC, or AZT.

9. The method according to claim 1 wherein $R_1$ is thiazolyl, substituted thiazolyl, pyridyl, substituted pyridyl, pyridazinyl, substituted pyridazinyl, pyrazinyl, or substituted pyrazinyl; $R_5$ is pyridyl, substituted pyridyl, phenyl, or substituted phenyl; and $R_8$ and $R_9$, along with the carbons to which they are attached form cyclopropyl.

* * * * *